United States Patent
Kim et al.

(10) Patent No.: US 10,494,355 B2
(45) Date of Patent: Dec. 3, 2019

(54) OXADIAZOLE AMINE DERIVATIVE COMPOUNDS AS HISTONE DEACETYLASE 6 INHIBITOR, AND THE PHARMACEUTICAL COMPOSITION COMPRISING THE SAME

(71) Applicant: Chong Kun Dang Pharmaceutical Corp., Seoul (KR)

(72) Inventors: Yuntae Kim, Yongin-si (KR); Chang Sik Lee, Yongin-si (KR); Jung Taek Oh, Yongin-si (KR); Hyeseung Song, Yongin-si (KR); Jin Choi, Yongin-si (KR); Jaeyoung Lee, Yongin-si (KR)

(73) Assignee: Chong Kun Dang Pharmaceutical Corp. (KR)

(*) Notice: Subject to any disclaimer, the term of this patent is extended or adjusted under 35 U.S.C. 154(b) by 0 days.

(21) Appl. No.: 15/763,972

(22) PCT Filed: Oct. 11, 2016

(86) PCT No.: PCT/KR2016/011355
§ 371 (c)(1),
(2) Date: Mar. 28, 2018

(87) PCT Pub. No.: WO2017/065473
PCT Pub. Date: Apr. 20, 2017

(65) Prior Publication Data
US 2018/0273495 A1   Sep. 27, 2018

(30) Foreign Application Priority Data
Oct. 12, 2015   (KR) .................. 10-2015-0142014

(51) Int. Cl.
| | |
|---|---|
| C07D 271/10 | (2006.01) |
| C07D 413/04 | (2006.01) |
| C07D 413/14 | (2006.01) |
| A61K 31/4245 | (2006.01) |
| A61P 31/00 | (2006.01) |
| A61P 1/00 | (2006.01) |
| A61P 25/00 | (2006.01) |
| A61P 11/00 | (2006.01) |
| A61P 3/00 | (2006.01) |
| A61P 21/00 | (2006.01) |
| A61P 9/00 | (2006.01) |
| A61P 35/00 | (2006.01) |
| A61P 17/00 | (2006.01) |
| A61P 5/00 | (2006.01) |
| A61P 27/02 | (2006.01) |

(52) U.S. Cl.
CPC ........ *C07D 271/10* (2013.01); *A61K 31/4245* (2013.01); *A61P 1/00* (2018.01); *A61P 3/00* (2018.01); *A61P 5/00* (2018.01); *A61P 9/00* (2018.01); *A61P 11/00* (2018.01); *A61P 17/00* (2018.01); *A61P 21/00* (2018.01); *A61P 25/00* (2018.01); *A61P 27/02* (2018.01); *A61P 31/00* (2018.01); *A61P 35/00* (2018.01); *C07D 413/04* (2013.01); *C07D 413/14* (2013.01)

(58) Field of Classification Search
CPC combination set(s) only.
See application file for complete search history.

(56) References Cited

U.S. PATENT DOCUMENTS

| | | |
|---|---|---|
| 4,871,753 A | 10/1989 | Rorh |
| 8,981,084 B2 | 3/2015 | Baloglu et al. |
| 9,670,193 B2 | 6/2017 | Hebach et al. |
| 2005/0288282 A1 | 12/2005 | Delorme et al. |
| 2006/0058298 A1 | 3/2006 | Delorme et al. |
| 2007/0293530 A1 | 12/2007 | Smil et al. |

(Continued)

FOREIGN PATENT DOCUMENTS

| | | |
|---|---|---|
| CN | 104744446 A | 7/2015 |
| JP | 2005513123 | 5/2005 |

(Continued)

OTHER PUBLICATIONS

Chemical Abstract Service STN Registry No. 1436149-02-8 [Entered STN: Jun. 9, 2013] (Year: 2013).*
Chemical Abstract Service STN Registry No. 1384673-31-7 [Entered STN: Jul. 27, 2012] (Year: 2012).*
U.S. Appl. No. 15/747,952, filed Jan. 26, 2018, Lee et al.
U.S. Appl. No. 15/747,850, filed Jan. 26, 2018, Lee et al.
U.S. Appl. No. 15/748,081, filed Jan. 26, 2018, Lee et al.
U.S. Appl. No. 15/750,067, filed Feb. 2, 2018, Lee et al.
U.S. Appl. No. 15/763,972, filed Mar. 28, 2018, Kim et al.
AU Office Action for AU App No. 2016299484, dated Aug. 28, 2018 (6 pages).
AU Office Action for AU App No. 2016299486, dated Jul. 31, 2018 (5 pages).

(Continued)

*Primary Examiner* — Amanda L Aguirre
(74) *Attorney, Agent, or Firm* — Fish & Richardson P.C.

(57) ABSTRACT

The present disclosure relates to novel compounds having histone deacetylase 6 (HDAC6) inhibitory activity, stereoisomers thereof or pharmaceutically acceptable salts thereof, the use thereof for the preparation of therapeutic medicaments, pharmaceutical compositions containing the same, a method for treating diseases using the composition, and methods for preparing the novel compounds. The novel compounds, stereoisomers thereof or pharmaceutically acceptable salts thereof according to the present disclosure have histone deacetylase (HDAC) inhibitory activity and are effective for the prevention or treatment of HDAC6-mediated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities.

11 Claims, No Drawings

(56) References Cited

U.S. PATENT DOCUMENTS

| | | | |
|---|---|---|---|
| 2012/0027874 A1 | 2/2012 | Charrier et al. | |
| 2012/0289495 A1 | 11/2012 | Baloglu et al. | |
| 2013/0059883 A1 | 3/2013 | Baloglu et al. | |
| 2014/0005133 A1 | 1/2014 | Trivedi et al. | |
| 2014/0142105 A1 | 5/2014 | Hebach et al. | |
| 2014/0329825 A1 | 11/2014 | Hebach et al. | |
| 2017/0015809 A1 | 1/2017 | Hawkins et al. | |
| 2018/0230114 A1* | 8/2018 | Lee | C07D 413/14 |
| 2018/0251437 A1* | 9/2018 | Lee | C07D 413/12 |

FOREIGN PATENT DOCUMENTS

| | | |
|---|---|---|
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2014520794 | 8/2014 |
| JP | 2014524922 | 9/2014 |
| JP | 2014533721 | 12/2014 |
| JP | 2014533734 | 12/2014 |
| KR | 100265385 | 11/2000 |
| KR | 100903743 | 6/2009 |
| KR | 20147017436 | 11/2012 |
| KR | 101262870 | 5/2013 |
| KR | 101320198 | 10/2013 |
| KR | 20130112911 | 10/2013 |
| KR | 20140097459 | 8/2014 |
| KR | 101561860 | 10/2015 |
| RU | 2515611 | 8/2012 |
| WO | WO 2003/028729 | 4/2003 |
| WO | WO 2007011626 | 1/2007 |
| WO | WO 2007-032445 A1 | 3/2007 |
| WO | WO 2007/107758 | 9/2007 |
| WO | WO 2009/010479 | 1/2009 |
| WO | WO 2010/123933 | 10/2010 |
| WO | WO 2010/126002 | 11/2010 |
| WO | WO 2011/088181 | 7/2011 |
| WO | WO 2011/088192 | 7/2011 |
| WO | WO 2011/104680 | 9/2011 |
| WO | WO 2011-133888 A1 | 10/2011 |
| WO | WO 2012/013716 | 2/2012 |
| WO | WO 2013/066833 | 5/2013 |
| WO | WO 2013/066835 | 5/2013 |
| WO | WO 2013/066839 | 5/2013 |
| WO | WO 2013/080120 | 6/2013 |
| WO | WO 2015/033301 | 3/2015 |
| WO | WO 2015/087151 | 6/2015 |
| WO | WO 2016082930 | 6/2016 |
| WO | WO 2017/018803 | 2/2017 |
| WO | WO 2017/018804 | 2/2017 |
| WO | WO 2017/018805 | 2/2017 |
| WO | WO 2017/023133 | 2/2017 |
| WO | WO 2017/065473 | 4/2017 |

OTHER PUBLICATIONS

Chen, J.J. et al., Discovery of 2-methylpyridine-based biaryl amides as γ-secretase modulators for the treatment of Alzheimer's disease, Bioorganic & Medicinal Chemistry letters, 2013, 23(23):6447-6454.

International Preliminary Report on Patentability and Written Opinion for Intl. App. No. PCT/KR2016/008214 dated Jan. 30, 2018 (8 pages).

International Preliminary Report on Patentability and Written Opinion for Intl. App. No. PCT/KR2016/008216 dated Jan. 30, 2018 (9 pages).

International Preliminary Report on Patentability and Written Opinion for Intl. App. No. PCT/KR2016/008218 dated Jan. 30, 2018 (8 pages).

International Preliminary Report on Patentability and Written Opinion for Intl. App. No. PCT/KR2016/008622 dated Feb. 6, 2018 (8 pages).

International Search Report of ISA/KR for PCT/KR2016/008214, dated Nov. 24, 2016 (5 pages).

International Search Report of ISA/KR for PCT/KR2016/008216, dated Nov. 21, 2016 (4 pages).

International Search Report of ISA/KR for PCT/KR2016/008218 dated Nov. 21, 2016 (5 pages).

International Search Report of ISA/KR for PCT/KR2016/008622, dated Feb. 17, 2017 (5 pages).

Japan Office Action for JP App No. 2018-505725 dated Sep. 12, 2018 (3 pages).

Korea Office Action for KR Application No. 10-2016-0095332, dated Sep. 5, 2017 (15 pages).

Korea Office Action for KR Application No. 10-2016-0095334, dated Sep. 5, 2017 (17 pages).

Korea Office Action for KR Application No. 10-2016-0099508, dated Sep. 5, 2017 (20 pages).

Korea Office Action for KR Application No. 10-2016-0131245, dated Sep. 5, 2017 (7 pages).

Manku, et al., Synthesis and evaluation of lysine derived sulfamides as histone deacetylase inhibitors, Bioorganic & Medicinal Chemistry Letters 19, 1866-1870 (2009).

Pal et al., Hydroxamic acid—A novel molecule for anticancer therapy, Journal of Advanced Pharmaceutical Technology & Research, 3(2), 92-99 (Apr.-Jun. 2012).

STN Express; Chemical Abstract compound RN: 1355844-43-7 (Feb. 8, 2012).

STN Express; Chemical Abstract compound RN: 1708354-35-1 (May 20, 2015).

STN Express; Chemical Abstract compound RN: 1790675-44-3 (Jun. 29, 2015).

STN Express; Chemical Abstract compound RN: 1798074-73-3 (Jul. 9, 2015).

STN Express; Chemical Abstract compound RN: 904653-20-9 (Aug. 25, 2006).

Wiest et al., Computational exploration of zinc binding groups for HDAC inhibition, J. Org. Chem. 78, 5051-5055 (2013).

Taiwan Office Action for TW App No. 105132939 dated Nov. 2, 2017 (with English translation) (8 pages).

Cancer [online], [retrieved on Jul. 6, 2007]. Retrieved from the internet, URL http://www.nlm.nih.gov/mededlineplus/cancer.html (10 pages).

Golub et al., Molecular Classification of Cancer: Class Discovery and Class Prediction by Gene Expression Monitoring, Science 286:531-537 (1999).

Lala et al., Role of nitric oxide in tumor progression: Lessons from experimental tumors, Cancer and Metastasis Reviews 17(1):91-106 (1998).

AU Office Action for AU App No. 2016299484, dated Dec. 18, 2018 (3 pages).

AU Office Action for AU App No. 2016299485, dated Sep. 13, 2018 (7 pages).

CA Office Action for CA App No. 2987570, dated Oct. 18, 2018 (5 pages).

EP Extended Search Report for EP App No. 16830836.9, dated Dec. 19, 2018 (7 pages).

EP Extended Search Report for EP App No. 16830837.7, dated Dec. 17, 2018 (9 pages).

EP Extended Search Report for EP App No. 16830838.5, dated Nov. 19, 2018 (7 pages).

JP Office Action for App No. JP 2018-503804, dated Dec. 18, 2018 (with English Translation) (4 pages).

JP Office Action for JP App No. 2018-504096, dated Dec. 18, 2018 (with English Translation) (5 pages).

Rossi et al., 4-N-Hydroxy-4-[ 1-( sulfonyl )piperidin-4-yl ]-butyramides as HDAC inhibitors, Bioorganic & Medicinal Chemistry Letters, 21:6767-6769 (2011).

RU Office Action for App No. RU2018106877, dated Oct. 18, 2018 (with English translation) (16 pages).

RU Office Action for RU App. No. 2018106904, dated Sep. 20, 2018 (with English translation) (14 pages).

(56) References Cited

OTHER PUBLICATIONS

CA Office Action for CA App No. 2993918, dated Dec. 4, 2018 (5 pages).
CAS Registry No. 904529-79-9 (Aug. 25, 2006).
CAS Registry No. 904541-56-6 (Aug. 25, 2006).
CAS Registry No. 904541-91-9 (Aug. 25, 2006).
CAS Registry No. 904548-90-9 (Aug. 25, 2006).
CAS Registry No. 904549-01-5 (Aug. 25, 2006).
CAS Registry No. 904549-10-3 (Aug. 25, 2006).
CAS Registry No. 904556-59-8 (Aug. 25, 2006).
CAS Registry No. 904568-68-9 (Aug. 25, 2006).
CAS Registry No. 904568-84-9 (Aug. 25, 2006).
CAS Registry No. 904569-62-6 (Aug. 25, 2006).
CAS Registry No. 904635-15-0 (Aug. 25, 2006).
CAS Registry No. 904635-23-0 (Aug. 25, 2006).
CAS Registry No. 904635-49-0 (Aug. 25, 2006).
CAS Registry No. 904635-57-0 (Aug. 25, 2006).
CAS Registry No. 904635-61-6 (Aug. 25, 2006).
CAS Registry No. 904635-67-2 (Aug. 25, 2006).
CAS Registry No. 904644-90-2 (Aug. 25, 2006).
CAS Registry No. 904644-93-5 (Aug. 25, 2006).
CAS Registry No. 904645-01-8 (Aug. 25, 2006).
CAS Registry No. 904645-03-0 (Aug. 25, 2006).
CAS Registry No. 904645-27-8 (Aug. 25, 2006).
CAS Registry No. 904645-29-0 (Aug. 25, 2006).
CAS Registry No. 904645-35-2 (Aug. 25, 2006).
CAS Registry No. 904645-35-8 (Aug. 25, 2006).
CAS Registry No. 904645-37-0 (Aug. 25, 2006).
CAS Registry No. 904645-47-2 (Aug. 25, 2006).
CAS Registry No. 904652-55-1 (Aug. 25, 2006).
CAS Registry No. 904652-68-2 (Aug. 25, 2006).
CAS Registry No. 904653-05-0 (Aug. 25, 2006).
CAS Registry No. 904653-11-8 (Aug. 25, 2006).
CAS Registry No. 904653-15-2 (Aug. 25, 2006).
CAS Registry No. 904653-17-4 (Aug. 25, 2006).
CAS Registry No. 904653-21-0 (Aug. 25, 2006).
CAS Registry No. 904653-22-1 (Aug. 25, 2006).
JP Office Action for App No. JP 2018-504720, dated Jan. 8, 2019 (English Translation) (4 pages).
NZ Office Action for App No. NZ739211, dated Jun. 14, 2019 (3 pages).
RU Office Action for RU App. No. 2018106914, dated Nov. 15, 2018 (with English translation) (14 pages).
Bolden et al., *Anticancer activities of histone deacetylase inhibitors*, Nat. Rev. Drug Discov., 5(9):769-784 (2006).
Hassig et al., *Nuclear histone acetylases and deacetylases and transcriptional regulation: HATS off to HDACs*, Curr. Opin. Chem. Biol. 1:300-308 (1997).
Hu et al., *HDAC6 a-tubulin deacetylase: A potential therapeutic target in neurodegenerative diseases*, J. Neurol. Sci. 304:1-8 (2011).
International Preliminary Report on Patentability and Written Opinion for Intl. App. No. PCT/KR2016/011355 dated Apr. 17, 2018 (6 pages).
International Search Report for Int. App. No. PCT /KR2016/ 011355, dated Jan. 26, 2017 (5 pages).

Matthias et al., *Mice Lacking Histone Deacetylase 6 Have Hyperacetylated Tubulin but Are Viable and Develop Normally*, Mol. Cell. Biol. 28:1688-1701 (2008).
Methot et al., *Exploration of the internal cavity of histone deacetylase (HDAC) with selective HDAC1/HDAC2 inhibitors (SHI-1: 2)*, Bioorg. Med. Chem. Lett. 18:973-978 (2008).
Piekarz et al., *Clinical Toxicities of Histone Deacetylase Inhibitors*, Pharmaceuticals, 3:2751-2767 (2010).
Rajak et al., *2,5-Disubstituted-1,3,4-oxadiazoles/thiadiazole as 1-10, 12 surface recognition moiety: Design and synthesis of novel hydroxamic acid based hi stone deacetylase inhibitors*, Bioorganic & Medicinal Chemistry Letters, 21:5735-5738 (2011).
Santo et al., *Preclinical activity, pharmacodynamic, and pharmacokinetic properties of a selective HDAC6 inhibitor,ACY-1215, in combination with bortezomib in multiple myeloma*, Blood 119:2579-2589 (2012).
Vishwakarma et al., *Tubastatin, a selective histone deacetylase 6 inhibitor shows anti-inflammatory and anti-rheumatic effects*, International Immunopharmacology, 16:72-78 (2013).
Warrell et al, *Therapeutic Targeting of Transcription in Acute Promyelocytic Leukemia by Use of an Inhibitor of Histone Deacetylase*, J. Natl. Cancer Inst. 90:1621-1625 (1998).
Witt et al., *HDAC family: What are the cancer relevant targets?* Cancer Letters, 277:8-21 (2009).
Woster et al., *Discovery of a new class of histone deacetylase inhibitors with a novel zinc binding group*, Med. Chem. Commun., online publication (2015).
Yao et al., *Regulation of the Dynamics of hsp90 Action on the Glucocorticoid Receptor by Acetylation/Deacetylation of the Chaperone*, Mol. Cell, 18:601-607 (2005).
CAS Registry No. 904548-10-3 (Aug. 25, 2006).
AU Office Action for App No. AU2016303891, dated Nov. 16, 2018 (7 pages).
CA Office Action for App No. CA 2993929, dated Dec. 4, 2018 (4 pages).
CAS Registry No. 904645-39-2 Database Registry [Online] retrieved from STN, dated Nov. 14, 2018.
CAS Registry No. 904652-59-1 Database Registry [Online] retrieved from STN, dated Nov. 14, 2018.
CAS Registry No. 904635-69-4 (Aug. 25, 2006).
CAS Registry No. 904652-71-7 (Aug. 25, 2006).
CAS Registry No. 904653-13-0 (Aug. 25, 2006).
EP Suppl Search Report for App No. EP 16833369, dated Apr. 1, 2019 (6 pages).
Gamal El-Din. et, al, European Journal of Medicinal Chemistry, 90:45-52, (Jan. 27, 2015).
IN Office Action for App No. 201727037873, dated May 21, 2019 (7 pages).
IN Office Action for App No. 201817006324, dated Jun. 27, 2019 (6 pages).
Othman et al., *1,3,4-Oxadiazole, 1,3,4-thiadiazole* and *1,2,4-triazole derivatives as potential antibacterial agents*, Arabian Journal of Chemistry (2014) https://doi.org/10.1016/j.arabjc.2014.09.003 (16 pages).

* cited by examiner

OXADIAZOLE AMINE DERIVATIVE COMPOUNDS AS HISTONE DEACETYLASE 6 INHIBITOR, AND THE PHARMACEUTICAL COMPOSITION COMPRISING THE SAME

TECHNICAL FIELD

The present disclosure relates to oxadiazole amine derivative compounds having histone deacetylase 6 (HDAC6) inhibitory activity, stereoisomers thereof, or pharmaceutically acceptable salts thereof; uses thereof for the preparation of therapeutic medicaments; methods of treating diseases using the same; pharmaceutical compositions comprising the same; and methods for preparing the same.

BACKGROUND ART

Post-translational modifications such as acetylation are very crucial regulatory modules at the heart of biological processes in the cells and are tightly regulated by a multitude of enzymes. Histones are the chief protein components of chromatin and act as spools around which DNA strands. Also, the balance of histone acetylation and deacetylation is a critical role in the regulation of gene expression.

Histone deacetylases (HDACs) are enzymes that remove acetyl groups from lysine residues on histone proteins of chromatin, and are known to be associated with gene silencing and induce cell cycle arrest, angiogenic inhibition, immune regulation, cell death, etc. (Hassig et al., Curr. Opin. Chem. Biol. 1997, 1, 300-308). In addition, it was reported that the inhibition of enzymatic function of HDACs induces the apoptosis of cancer cells in vivo by reducing the activity of cancer cell survival-associated factors and activating cancer cell apoptosis-associated factors (Warrell et al, J. Natl. Cancer Inst. 1998, 90, 1621-1625).

In humans, 18 HDACs have been identified and are subdivided into four classes based on their homology to yeast HDACs. Among them, 11 HDACs use zinc as a cofactor and can be divided into three groups: Class I (HDAC1, 2, 3 and 8), Class II (IIa: HDAC4, 5, 7 and 9; IIb: HDAC6 and 10), Class IV (HDAC 11). Additionally, 7 HDACs of Class III (SIRT 1-7) require NAD$^+$ instead of zinc as a cofactor (Bolden et al., Nat. Rev. Drug Discov. 2006, 5(9), 769-784).

Various HDAC inhibitors are in preclinical or clinical development, but to date, only non-selective HDAC inhibitors have been identified as anticancer agents, and only vorinostat (SAHA) and romidepsin (FK228) have been approved for the treatment of cutaneous T-cell lymphoma. However, non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC6, a member of Class IIb HDACs, is present mainly in the cytoplasm and is involved in the deacetylation of a number of non-histone substrates (HSP90, cortactin, etc.), including tubulin, (Yao et al., Mol. Cell 2005, 18, 601-607). HDAC6 has two catalytic domains, and the zinc finger domain of C-terminal can bind to ubiquitinated proteins. It is known that HDAC6 has a number of non-histone proteins as substrates, and thus plays an important role in various diseases, including cancer, inflammatory diseases, autoimmune diseases, neurological diseases and neurodegenerative disorders (Santo et al., Blood 2012 119: 2579-258; Vishwakarma et al., International Immunopharmacology 2013, 16, 72-78; Hu et al., J. Neurol. Sci. 2011, 304, 1-8).

The common structural characteristic of various HDAC inhibitors is a structure consisting of a cap group, a linker and a zinc-binding group (ZBG), as shown in the following Vorinostat structure. Many researchers have conducted studies on enzyme inhibitory activity and selectivity by structurally modifying the cap group and the linker. Among these groups, the zinc-binding group is known to play a more important role in enzyme inhibitory activity and selectivity (Wiest et al., J. Org. Chem. 2013 78: 5051-5065; Methot et al., Bioorg. Med. Chem. Lett. 2008, 18, 973-978).

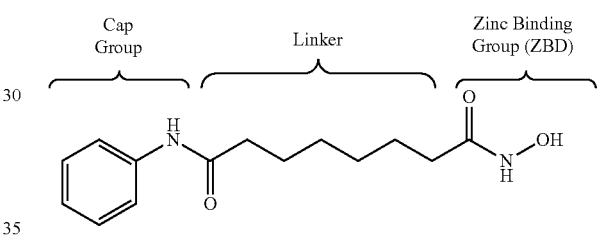

The zinc-binding group is generally a hydroxamic acid or benzamide derivative. Herein, the hydroxamic acid derivative exhibits a potent HDAC inhibitory effect, but has problems of low bioavailability and severe off-target activity. In addition, the benzamide derivative has a problem in that it can produce toxic metabolites in vivo, because it contains aniline (Woster et al., Med. Chem. Commun. 2015, online publication).

Accordingly, there is a need for the development of selective HDAC 6 inhibitors for treatment of diseases such as cancer, inflammatory diseases, autoimmune diseases, neurological diseases and neurodegenerative disorders, which have a zinc-binding group with improved bioavailability and, at the same time, cause no side effects, unlike non-selective inhibitors that cause side effects.

DISCLOSURE OF INVENTION

Technical Problem

It is an object of the present disclosure to provide oxadiazole amine derivative compounds having selective HDAC6 inhibitory activity, stereoisomers thereof, or pharmaceutically acceptable salts thereof.

Another object of the present disclosure is to provide pharmaceutical compositions comprising oxadiazole amine derivative compounds having selective HDAC6 inhibitory activity, stereoisomers thereof, or pharmaceutically acceptable salts thereof.

Still another object of the present disclosure is to provide methods for preparing the novel compounds.

Still another object of the present disclosure is to provide pharmaceutical compositions for prevention or treatment of HDAC6 activity-associated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculo-skeletal system and connective tissue; or congenital malformations, deformations and chromosomal abnormalities, which contain the above compound.

Still another object of the present disclosure is to provide the use of the compounds for the preparation of therapeutic medicaments against HDAC6 activity-associated diseases.

Yet another object of the present disclosure is to provide methods for treating HDAC6 activity-associated diseases, which comprise administering a therapeutically effective amount of the pharmaceutical compositions containing the compounds.

Solution to Problem

The present inventors have discovered oxadiazole amine derivative compounds, which have histone deacetylase 6 (HDAC6) inhibitory activity, and have found that these compounds can be used for the inhibition or treatment of histone deacetylase 6 (HDAC6) activity-associated diseases, thereby completing the present disclosure.

As used herein, the term "—($C_1$-$C_2$ alkyl)-" refers to —$CH_2$— or —$CH_2CH_2$—.

As used herein, the term "—($C_1$-$C_4$ alkyl) or —($C_1$-$C_6$ alkyl)" refers to a straight- or branched-chain $C_1$-$C_4$ or $C_1$-$C_6$ saturated hydrocarbon, for example, methyl, ethyl, propyl, isopropyl, butyl, isobutyl, pentyl, or hexyl.

As used herein, the term "—($C_2$-$C_4$ alkenyl)" refers to a straight- or branched-chain unsaturated hydrocarbon having at least one double bond, for example, ethenyl, propenyl or butenyl.

As used herein, the term "heterocycloalkyl" refers to a saturated cyclic compound containing 1 to 3 heteroatoms selected from N, O and S as a ring member.

As used herein, the term "heteroaryl" refers to an aromatic cyclic compound containing 1 to 3 heteroatoms selected from N, O and S as a ring member.

Oxadiazole Amine Derivative Compounds

To achieve the above objects, the present disclosure provides an oxadiazole amine derivative compound represented by the following formula I, a stereoisomer thereof, or a pharmaceutically acceptable salt thereof:

[Formula I]

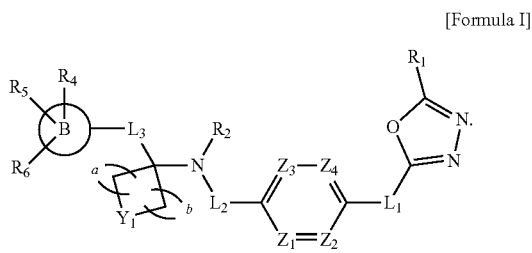

wherein $R_1$ is —$CF_2H$ or —$CF_3$;

$L_1$ and $L_2$ are each independently —($C_1$-$C_2$ alkyl)- or null;

$Z_1$ to $Z_4$ are each independently N or $CR^Z$ {wherein three or more of $Z_1$ to $Z_4$ cannot be N at the same time}, wherein $R^Z$ is —H, —F, —Cl, —Br, —I or —O($C_1$-$C_4$ alkyl);

$R_2$ is —H or —($C_1$-$C_4$ alkyl);

$Y_1$ is —$CH_2$—, —$NR^C$—, —O—, —C(=O)— or —S(=O)$_2$—, wherein $R^C$ is —H, —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —C(=O)—O($C_1$-$C_4$ alkyl)-aryl, —($C_1$-$C_4$ alkyl)-C(=O)—O($C_1$-$C_4$ alkyl), —($C_1$-$C_4$ alkyl)-$NR^AR^B$, —S(=O)$_2$—($C_1$-$C_4$ alkyl), aryl, —($C_1$-$C_4$ alkyl)-aryl, —($C_2$-$C_4$ alkenyl)-aryl, heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl), {wherein at least one H of the —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —C(=O)—O($C_1$-$C_4$ alkyl)-aryl, —($C_1$-$C_4$ alkyl)-C(=O)—O($C_1$-$C_4$ alkyl), —($C_1$-$C_4$ alkyl)-$NR^AR^B$, —S(=O)$_2$—($C_1$-$C_4$ alkyl), aryl, —($C_1$-$C_4$ alkyl)-aryl, ($C_2$-$C_4$ alkenyl)-aryl, heteroaryl, —($C_1$-$C_4$ alkyl)-heteroaryl, —C(=O)—($C_3$-$C_7$ cycloalkyl), —$C_2$-$C_6$ heterocycloalkyl or —($C_1$-$C_4$ alkyl)-C(=O)—($C_2$-$C_6$ heterocycloalkyl) may be substituted with —X (namely, —F, Cl, Br or I)};

a and b are each independently an integer of 0, 1, 2, 3 or 4 {wherein the a and b cannot all be 0};

$L_3$ is —($C_1$-$C_2$ alkyl)-, —$SO_2$—, —($C_1$-$C_2$ alkyl)-$SO_2$—, or null;

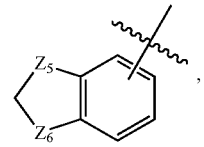

is -aryl, -heteroaryl,

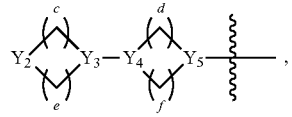

or heterocycloalkyl, wherein $Z_5$ and $Z_6$ are each independently —$CH_2$— or —O—; and $R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, heterocycloalkyl {wherein the heterocycloalkyl may be unsubstituted or substituted with $C_1$-$C_4$ alkyl or heterocycloalkyl}, O-aryl, —$CF_2H$, —C(=O)—($C_1$-$C_4$ alkyl), —C(=O)—O($C_1$-$C_4$ alkyl), —$NR^AR^B$, —C(=O)—$NR^AR^B$ or —S(=O)$_2$—($C_1$-$C_4$ alkyl), wherein $Y_2$ is —$CH_2$—, —$NR^C$—, —O—, —C(=O)— or —S(=O)$_2$—, $Y_3$ to $Y_5$ are each independently —CH— or —N—, and c to f are each independently an integer of 0, 1, 2, 3 or 4 {wherein c and e cannot all be 0, and d and f cannot all be 0}, wherein $R^A$ and $R^B$ are each independently —H or —($C_1$-$C_4$ alkyl) {wherein at least one H of the —($C_1$-$C_4$ alkyl) may be substituted with —X (namely, —F, Cl, Br or I) or —OH}.

According to preferable embodiment of the present disclosure,
wherein $R_1$ is —$CF_2H$ or —$CF_3$;
$L_1$ and $L_2$ are null;
$Z_1$ and $Z_3$ are N;
$Z_2$ and $Z_4$ are $CR^Z$, wherein $R^Z$ is —H, —F, —Cl, —Br, —I or —$O(C_1$-$C_4$ alkyl);
$R_2$ is —H or —($C_1$-$C_4$ alkyl);
$Y_1$ is —$CH_2$— or —$NR^c$—, wherein $R^C$ is —H, or —C(=O)—O($C_1$-$C_4$ alkyl)-aryl {wherein at least one H of the —C(=O)—O($C_1$-$C_4$ alkyl)-aryl may be substituted with —X};
a and b are each independently an integer of 0, 1, 2 or 3 {wherein the a and b cannot all be 0};
$L_3$ is —($C_1$-$C_2$ alkyl)-, ($C_1$-$C_2$ alkyl)-$SO_2$—, or null;

(B)

is phenyl, pyridine, benzo[d][1,3]dioxol, thiophene, pyrimidine, pyrazine or pyridazine; and
$R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, piperidine, morpholino, piperazine or pyrrolidine {wherein the piperidine, morpholino, piperazine or pyrrolidine may be unsubstituted or substituted

[structure]

wherein $Y_2$ is —O—, $Y_3$ and $Y_5$ are —CH—, $Y_4$ is —N—, c and e are each independently an integer of 0, 1 or 2 {wherein c and e cannot all be 0}, and d and f are each independently an integer of 0, 1, 2 or 3 {wherein d and f cannot all be 0}.

Preferably, the oxadiazole amine derivative compound represented by the above Formula I may be a compound represented by the following Formula II:

[Formula II]

[structure]

wherein $R_1$ is —$CF_2H$ or —$CF_3$;
$R_2$ is —H;
$Y_1$ is —$CH_2$— or —$NR^c$—, wherein $R^c$ is —H, or —C(=O)—O($C_1$-$C_4$ alkyl)-aryl;
a and b are each independently an integer of 0, 1, 2 or 3 {wherein a and b cannot all be 0, preferably, a ring formed by $Y_1$, a and b is a 3- to 7-membered saturated cycloalkyl when $Y_1$ is -$CH_2$—, or a ring formed by $Y_1$, a and b is a 3- to 7-membered saturated heterocycloalkyl containing one N when Y1 is —$NR^c$—};

$L_3$ is —($C_1$-$C_2$ alkyl)-, ($C_1$-$C_2$ alkyl)-$SO_2$—, or null;

(B)

is phenyl, pyridine, benzo[d][1,3]dioxol and thiophene; and
$R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, piperidine, morpholino {wherein the piperidine may be unsubstituted or substituted with $C_1$-$C_4$ alkyl}, or

[structure]

According to more preferable embodiment of the present disclosure,
wherein $R_1$ is —$CF_2H$ or —$CF_3$;
$R_2$ is —H;
$Y_1$ is —$CH_2$— or —$NR^c$—, wherein $R^C$ is —H, or

[structure]

a and b are each independently an integer of 0, 1, 2 or 3 {wherein the a and b cannot all be 0, and a ring formed by $Y_1$, a and b is a 3- to 7-membered saturated cycloalkyl when $Y_1$ is —$CH_2$— or a ring formed by $Y_1$, a and b is a 3- to 7-membered saturated heterocycloalkyl containing one N when $Y_1$ is —$NR^c$—};
$L_3$ is —$CH_2$—, —$CH_2$—$SO_2$—, or null;

(B)

is phenyl, pyridine, benzo[d][1,3]dioxol and thiophene; and
$R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, morpholino,

[structures] or

[structure]

wherein $R_7$ is —H or —($C_1$-$C_4$ alkyl).
According to one embodiment, the compound represented by formula I may be a compound represented by formula I-1:

[Formula I-1]

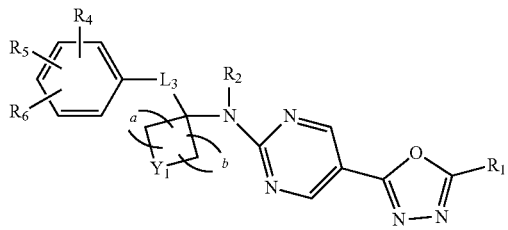

wherein $R_1$ is —$CF_2H$ or —$CF_3$;
$R_2$ is —H;
$Y_1$ is —$CH_2$—, —NH—, or

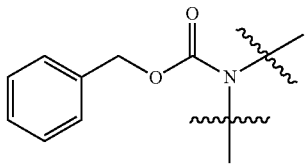 [SMILES: *N(*)C(=O)OCc1ccccc1]

a and b are each independently an integer of 0, 1, 2 or 3 {wherein the a and b cannot all be 0, and a ring formed by $Y_1$, a and b is a 3- to 7-membered saturated cycloalkyl when $Y_1$ is-$CH_2$— or a ring formed by $Y_1$, a and b is a 3- to 7-membered saturated heterocycloalkyl containing one N when $Y_1$ is —$NR^c$—};

$L_3$ is —($C_1$-$C_2$ alkyl)-, —($C_1$-$C_2$ alkyl)-$SO_2$—, or null; and $R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, morpholino, piperidine {wherein the piperidine may be unsubstituted or substituted with $C_1$-$C_4$ alkyl}, or

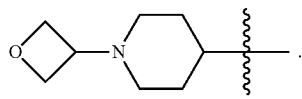

Preferably, the piperidine is

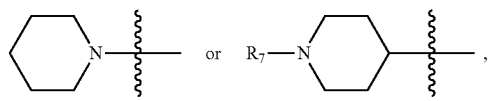

and $R_7$ is —H or —($C_1$-$C_4$ alkyl).

According to another embodiment of the present disclosure, the compound represented by formula I may be a compound represented by the following formula I-2:

[Formula I-2]

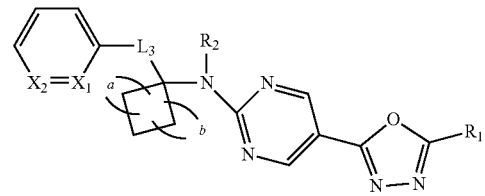

wherein $R_1$ is —$CF_2H$ or —$CF_3$;
$R_2$ is —H;
a and b are each independently an integer of 0, 1, 2 or 3 {wherein the a and b cannot all be 0, and a ring formed by a and b is a 3- to 7-membered saturated cycloalkyl};
$L_3$ is —($C_1$-$C_2$ alkyl)-, —($C_1$-$C_2$ alkyl)-$SO_2$—, or null; and
$X_1$ and $X_2$ are each independently N or C {wherein both $X_1$ and $X_2$ cannot be N at the same time}.

According to still another embodiment of the present disclosure, the compound represented by formula I may be a compound represented by the following formula I-3:

[Formula I-3]

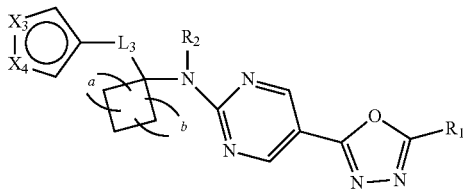

wherein $R_1$ is —$CF_2H$ or —$CF_3$;
$R_2$ is —H;
a and b are each independently an integer of 0, 1, 2 or 3 {wherein the a and b cannot all be 0, and a ring formed by a and b is a 3- to 7-membered saturated cycloalkyl};
$L_3$ is —($C_1$-$C_2$ alkyl)-, —($C_1$-$C_2$ alkyl)-$SO_2$—, or null; and
$X_3$ and $X_4$ are each independently S or C {wherein $X_3$ and $X_4$ cannot be S or C at the same time}.

According to yet another embodiment of the present disclosure, the compound represented by formula I may be a compound represented by the following formula I-4:

[Formula I-4]

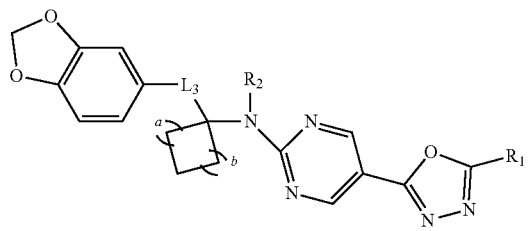

wherein $R_1$ is —$CF_2H$ or —$CF_3$;
$R_2$ is —H;
a and b are each independently an integer of 0, 1, 2 or 3 {wherein the a and b cannot all be 0, and a ring formed by a and b is a 3- to 7-membered saturated cycloalkyl}; and
$L_3$ is —($C_1$-$C_2$ alkyl)-, —($C_1$-$C_2$ alkyl)-$SO_2$—, or null.

The specific compounds represented by formula I are shown in Table 1 below:
TABLE 1
| Compound | Structure |
|---|---|
| 1524 | 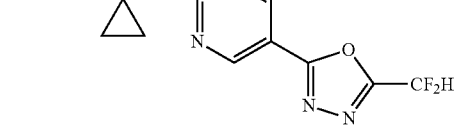 |
| 1526 | 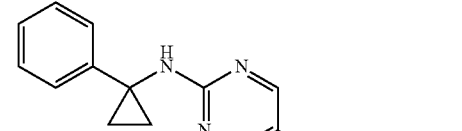 |
| 1559 | 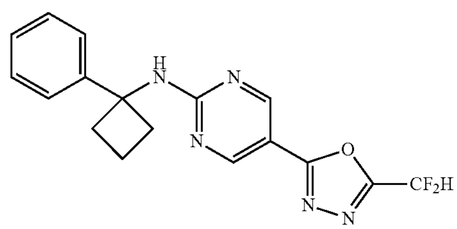 [SMILES: FC(F)c1nnc(-c2cnc(NC3(c4ccccc4)CCC3)nc2)o1] |
| 1579 | 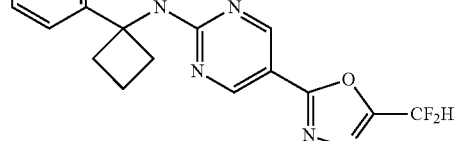 |
| 1580 | 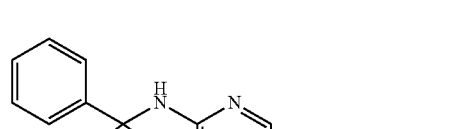 |
| 1581 | 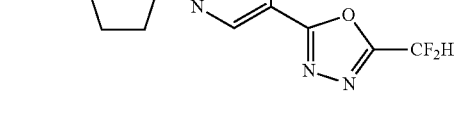 |

TABLE 1-continued

| Compound | Structure |
|---|---|
| 1582 | (phenyl-cyclohexyl)-NH-pyrimidine-oxadiazole-CF₃ |
| 1603 | (4-methoxyphenyl-cyclobutyl)-NH-pyrimidine-oxadiazole-CF₂H |
| 1604 | (4-methoxyphenyl-cyclobutyl)-NH-pyrimidine-oxadiazole-CF₃ |
| 1605 | (3-methoxyphenyl-cyclobutyl)-NH-pyrimidine-oxadiazole-CF₂H |
| 1606 | (3-methoxyphenyl-cyclobutyl)-NH-pyrimidine-oxadiazole-CF₃ |
| 1607 | (3-fluorophenyl-cyclobutyl)-NH-pyrimidine-oxadiazole-CF₂H |

TABLE 1-continued

| Compound | Structure |
|---|---|
| 1608 | 3-F-C6H4-C(cyclobutyl)(NH)-pyrimidine-5-(1,3,4-oxadiazole)-CF3 |
| 1609 | 2-F-C6H4-C(cyclobutyl)(NH)-pyrimidine-5-(1,3,4-oxadiazole)-CF2H |
| 1610 | 2-F-C6H4-C(cyclobutyl)(NH)-pyrimidine-5-(1,3,4-oxadiazole)-CF3 |
| 1611 | 4-F-C6H4-C(cyclobutyl)(NH)-pyrimidine-5-(1,3,4-oxadiazole)-CF2H |
| 1612 | 4-F-C6H4-C(cyclobutyl)(NH)-pyrimidine-5-(1,3,4-oxadiazole)-CF3 |
| 1614 | 2-Cl-C6H4-C(cyclobutyl)(NH)-pyrimidine-5-(1,3,4-oxadiazole)-CF2H |

TABLE 1-continued
| Compound | Structure |
|---|---|
| 1615 | 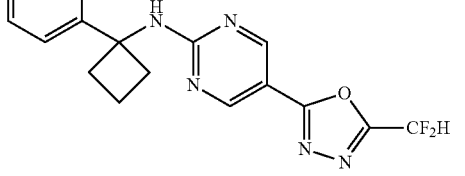 |
| 1616 | 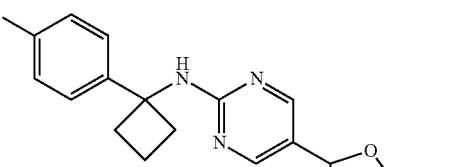 |
| 1617 | 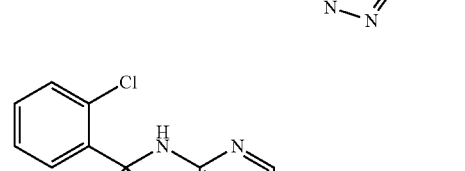 |
| 1618 | 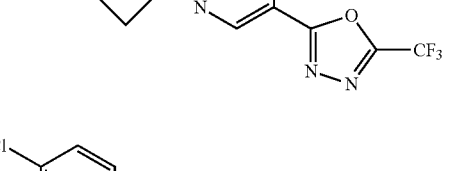 |
| 1640 | 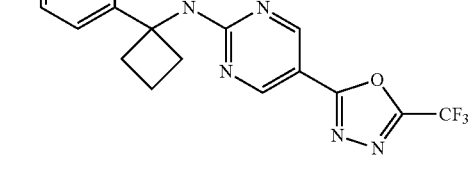 |
| 1641 | 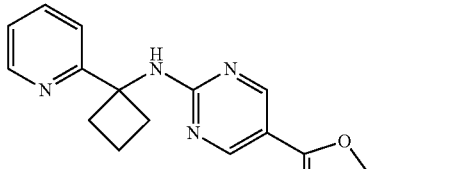 |

TABLE 1-continued
| Compound | Structure |
|---|---|
| 1642 | 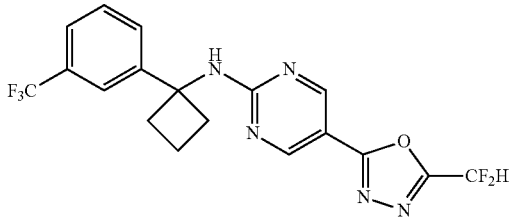 [SMILES: FC(F)c1nnc(-c2cnc(NC3(c4cccc(C(F)(F)F)c4)CCC3)nc2)o1] |
| 1670 | 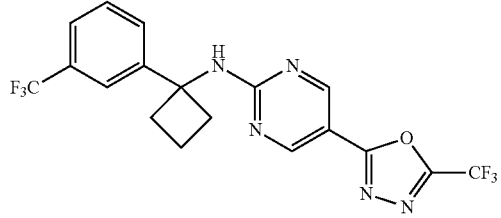 [SMILES: FC(F)(F)c1cccc(C2(Nc3ncc(-c4nnc(C(F)(F)F)o4)cn3)CCC2)c1] |
| 1671 | 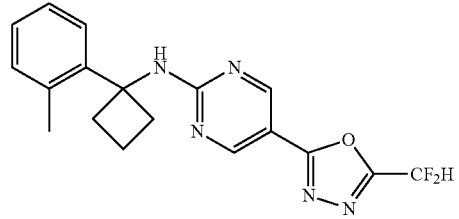 [SMILES: Cc1ccccc1C1(Nc2ncc(-c3nnc(C(F)F)o3)cn2)CCC1] |
| 1672 | 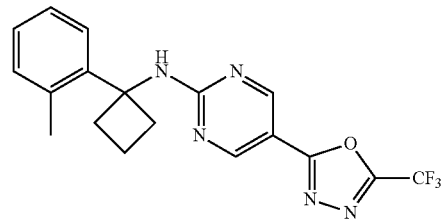 [SMILES: Cc1ccccc1C1(Nc2ncc(-c3nnc(C(F)(F)F)o3)cn2)CCC1] |
| 1673 | 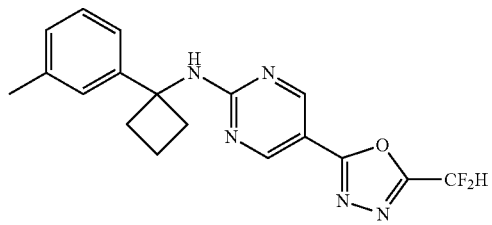 [SMILES: Cc1cccc(C2(Nc3ncc(-c4nnc(C(F)F)o4)cn3)CCC2)c1] |
| 1674 | 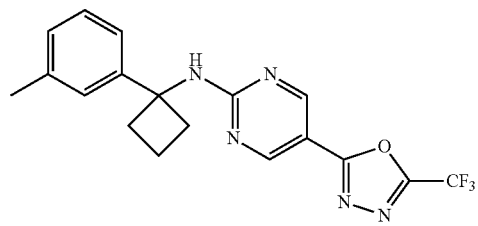 [SMILES: Cc1cccc(C2(Nc3ncc(-c4nnc(C(F)(F)F)o4)cn3)CCC2)c1] |

TABLE 1-continued

| Compound | Structure |
|---|---|
| 1675 | 1-(p-tolyl)cyclobutyl-NH-pyrimidine-5-(1,3,4-oxadiazole)-CF₂H |
| 1676 | 1-(p-tolyl)cyclobutyl-NH-pyrimidine-5-(1,3,4-oxadiazole)-CF₃ |
| 1677 | 4-phenyl-1-Cbz-piperidin-4-yl-NH-pyrimidine-5-(1,3,4-oxadiazole)-CF₂H |
| 1678 | 4-phenyl-piperidin-4-yl-NH-pyrimidine-5-(1,3,4-oxadiazole)-CF₂H |
| 1683 | 1-(2-fluorophenyl)cyclopropyl-NH-pyrimidine-5-(1,3,4-oxadiazole)-CF₂H |
| 1711 | 1-(4-fluorophenyl)cyclopropyl-NH-pyrimidine-5-(1,3,4-oxadiazole)-CF₂H |

TABLE 1-continued
| Compound | Structure |
|---|---|
| 1712 | 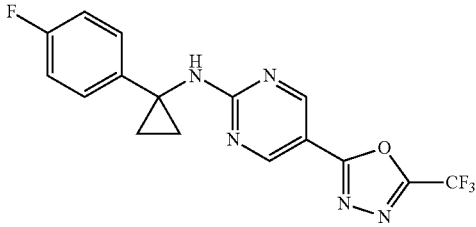 [SMILES: Fc1ccc(C2(Nc3ncc(-c4nnc(C(F)(F)F)o4)cn3)CC2)cc1] |
| 1713 | 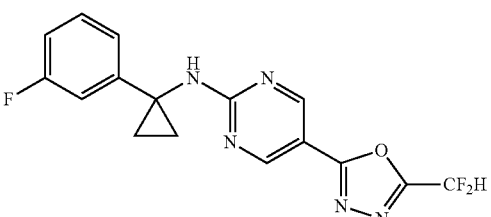 |
| 1714 | 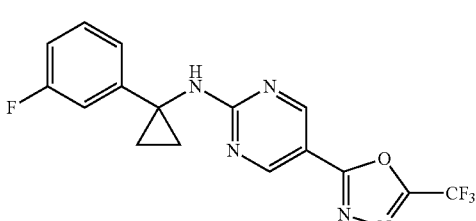 |
| 1722 | 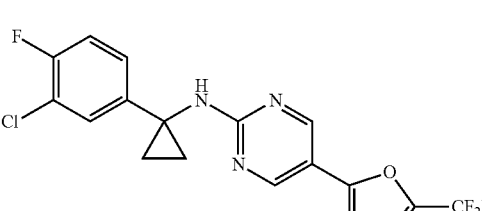 |
| 1723 | 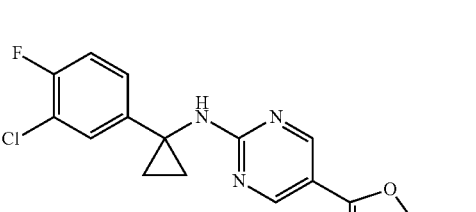 |
| 1738 | 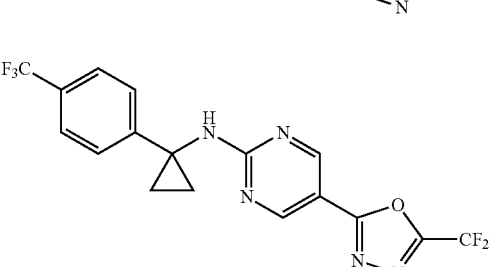 |

TABLE 1-continued

| Compound | Structure |
|---|---|
| 1740 | 3-(CF₃)-phenyl-C(cyclopropyl)-NH-pyrimidin-2-yl-5-(1,3,4-oxadiazol-2-yl)-CF₂H |
| 1741 | 3-(CF₃)-phenyl-C(cyclopropyl)-NH-pyrimidin-2-yl-5-(1,3,4-oxadiazol-2-yl)-CF₃ |
| 1742 | 4-(CF₃)-phenyl-C(cyclopropyl)-NH-pyrimidin-2-yl-5-(1,3,4-oxadiazol-2-yl)-CF₃ |
| 1761 | 3-(HO)-phenyl-C(cyclobutyl)-NH-pyrimidin-2-yl-5-(1,3,4-oxadiazol-2-yl)-CF₂H |
| 1779 | 3,4-difluorophenyl-C(cyclopropyl)-NH-pyrimidin-2-yl-5-(1,3,4-oxadiazol-2-yl)-CF₂H |
| 1780 | 3,4-difluorophenyl-C(cyclopropyl)-NH-pyrimidin-2-yl-5-(1,3,4-oxadiazol-2-yl)-CF₃ |

TABLE 1-continued

| Compound | Structure |
|---|---|
| 1817 | 3-chloro-4-fluorophenyl cyclobutyl-NH-pyrimidine-oxadiazole-CF₂H |
| 1818 | 3-chloro-4-fluorophenyl cyclobutyl-NH-pyrimidine-oxadiazole-CF₃ |
| 1819 | 3,5-difluorophenyl cyclobutyl-NH-pyrimidine-oxadiazole-CF₂H |
| 1820 | benzo[1,3]dioxol-5-yl cyclobutyl-NH-pyrimidine-oxadiazole-CF₂H |
| 1821 | 2,5-difluorophenyl cyclobutyl-NH-pyrimidine-oxadiazole-CF₂H |
| 1822 | 4-trifluoromethoxyphenyl cyclobutyl-NH-pyrimidine-oxadiazole-CF₂H |

TABLE 1-continued

| Compound | Structure |
|---|---|
| 1826 | 2,4,5-trifluorophenyl-cyclobutyl-NH-pyrimidin-2-yl, 5-(5-(CF₂H)-1,3,4-oxadiazol-2-yl) |
| 1827 | 2,3-difluorophenyl-cyclobutyl-NH-pyrimidin-2-yl, 5-(5-(CF₂H)-1,3,4-oxadiazol-2-yl) |
| 1828 | 2,6-difluorophenyl-cyclobutyl-NH-pyrimidin-2-yl, 5-(5-(CF₂H)-1,3,4-oxadiazol-2-yl) |
| 1832 | 2,3-dichlorophenyl-cyclobutyl-NH-pyrimidin-2-yl, 5-(5-(CF₂H)-1,3,4-oxadiazol-2-yl) |
| 1833 | 2,3-dichlorophenyl-cyclobutyl-NH-pyrimidin-2-yl, 5-(5-(CF₃)-1,3,4-oxadiazol-2-yl) |
| 1834 | 3,4-dichlorophenyl-cyclobutyl-NH-pyrimidin-2-yl, 5-(5-(CF₂H)-1,3,4-oxadiazol-2-yl) |

TABLE 1-continued

| Compound | Structure |
|---|---|
| 1835 | 3,4-dichlorophenyl-cyclobutyl-NH-pyrimidine-oxadiazole-CF3 |
| 1836 | 2,4-dichlorophenyl-cyclobutyl-NH-pyrimidine-oxadiazole-CF2H |
| 1837 | 2,4-dichlorophenyl-cyclobutyl-NH-pyrimidine-oxadiazole-CF3 |
| 1838 | 2,6-dichlorophenyl-cyclobutyl-NH-pyrimidine-oxadiazole-CF2H |
| 1913 | 3-pyridyl-cyclobutyl-NH-pyrimidine-oxadiazole-CF2H |
| 1959 | 2-chloro-4-fluorophenyl-cyclobutyl-NH-pyrimidine-oxadiazole-CF2H |

TABLE 1-continued
| Compound | Structure |
|---|---|
| 1960 | 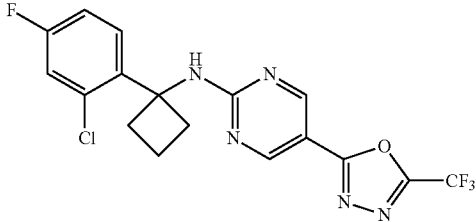 [SMILES: Fc1ccc(C2(Nc3ncc(-c4nnc(C(F)(F)F)o4)cn3)CCC2)c(Cl)c1] |
| 1961 | 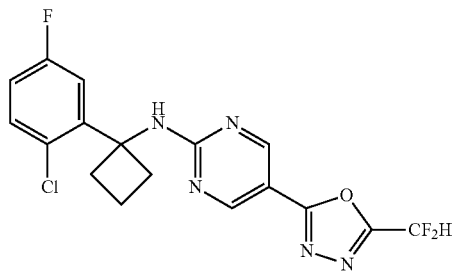 [SMILES: Fc1ccc(Cl)c(C2(Nc3ncc(-c4nnc(C(F)F)o4)cn3)CCC2)c1] |
| 1962 | 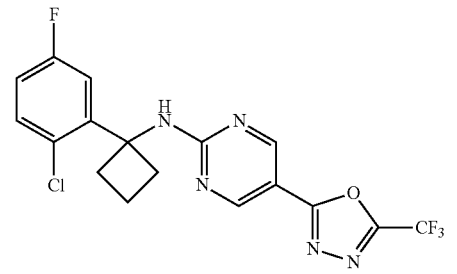 [SMILES: Fc1ccc(Cl)c(C2(Nc3ncc(-c4nnc(C(F)(F)F)o4)cn3)CCC2)c1] |
| 1963 | 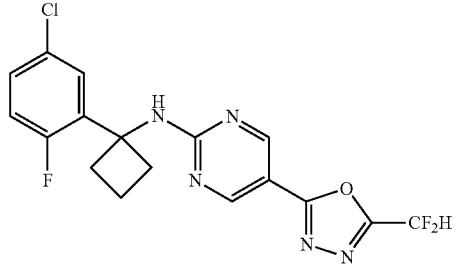 [SMILES: Fc1ccc(Cl)cc1C1(Nc2ncc(-c3nnc(C(F)F)o3)cn2)CCC1] |
| 1964 | 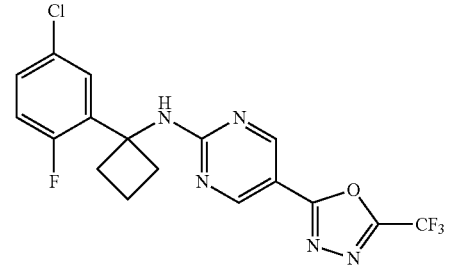 [SMILES: Fc1ccc(Cl)cc1C1(Nc2ncc(-c3nnc(C(F)(F)F)o3)cn2)CCC1] |
| 1965 | 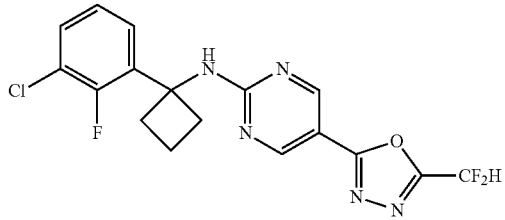 [SMILES: Fc1c(Cl)cccc1C1(Nc2ncc(-c3nnc(C(F)F)o3)cn2)CCC1] |

TABLE 1-continued

| Compound | Structure |
|---|---|
| 1966 | 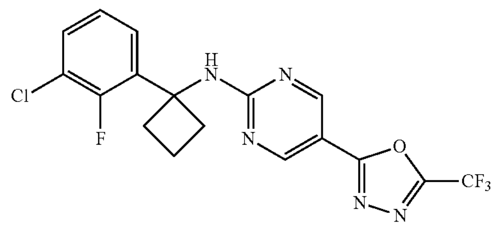 [SMILES: Fc1c(Cl)cccc1C1(Nc2ncc(-c3nnc(C(F)(F)F)o3)cn2)CCC1] |
| 2023 | 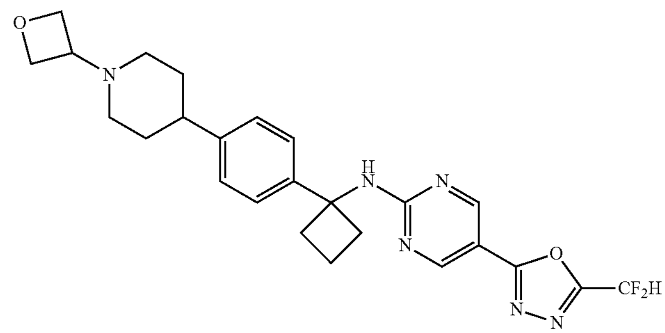 [SMILES: FC(F)c1nnc(-c2cnc(NC3(c4ccc(C5CCN(C6COC6)CC5)cc4)CCC3)nc2)o1] |
| 2026 | 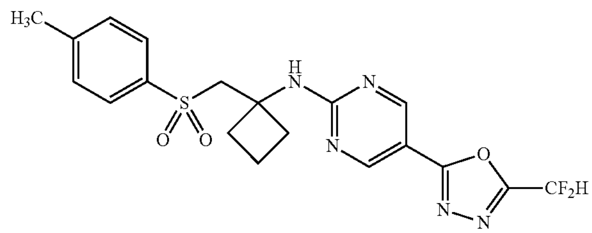 [SMILES: Cc1ccc(S(=O)(=O)CC2(Nc3ncc(-c4nnc(C(F)F)o4)cn3)CCC2)cc1] |
| 2027 | 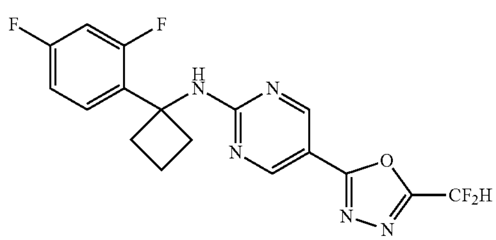 [SMILES: Fc1ccc(C2(Nc3ncc(-c4nnc(C(F)F)o4)cn3)CCC2)c(F)c1] |
| 2028 | 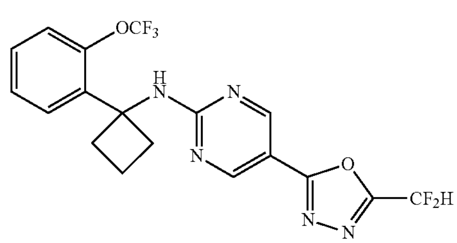 [SMILES: FC(F)c1nnc(-c2cnc(NC3(c4ccccc4OC(F)(F)F)CCC3)nc2)o1] |
| 2030 | 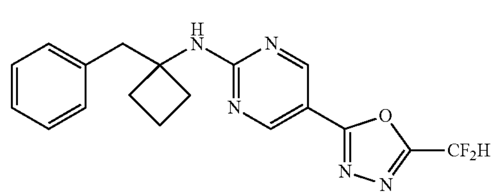 [SMILES: FC(F)c1nnc(-c2cnc(NC3(Cc4ccccc4)CCC3)nc2)o1] |

TABLE 1-continued

| Compound | Structure |
|---|---|
| 2033 | 2-OCF3-phenyl-cyclobutyl-NH-pyrimidin-5-yl-1,3,4-oxadiazol-2-yl-CF3 |
| 2034 | 2,4-difluorophenyl-cyclobutyl-NH-pyrimidin-5-yl-1,3,4-oxadiazol-2-yl-CF3 |
| 2035 | 1-methylpiperidin-4-yl-phenyl-cyclobutyl-NH-pyrimidin-5-yl-1,3,4-oxadiazol-2-yl-CF2H |
| 2036 | 1-ethylpiperidin-4-yl-phenyl-cyclobutyl-NH-pyrimidin-5-yl-1,3,4-oxadiazol-2-yl-CF2H |
| 2037 | 1-isopropylpiperidin-4-yl-phenyl-cyclobutyl-NH-pyrimidin-5-yl-1,3,4-oxadiazol-2-yl-CF2H |

TABLE 1-continued

| Compound | Structure |
|---|---|
| 2038 | (3-thienyl)-cyclobutyl-NH-pyrimidine-oxadiazole-CF₂H |
| 2040 | (2-thienyl)-cyclopropyl-NH-pyrimidine-oxadiazole-CF₂H |
| 2041 | (4-piperidinylphenyl)-cyclobutyl-NH-pyrimidine-oxadiazole-CF₂H |
| 2042 | (2-CF₃-phenyl)-cyclobutyl-NH-pyrimidine-oxadiazole-CF₂H |
| 2043 | (4-CF₃-phenyl)-cyclobutyl-NH-pyrimidine-oxadiazole-CF₂H |
| 2044 | (4-CF₃-phenyl)-cyclobutyl-NH-pyrimidine-oxadiazole-CF₃ |

TABLE 1-continued

| Compound | Structure |
|---|---|
| 2045 | 1-(3,4-difluorophenyl)cyclobutyl linked via NH to pyrimidine-2-yl, pyrimidine-5 substituted with 5-(difluoromethyl)-1,3,4-oxadiazol-2-yl |
| 2046 | 1-(4-fluoro-3-morpholinophenyl)cyclobutyl linked via NH to pyrimidine-2-yl, pyrimidine-5 substituted with 5-(difluoromethyl)-1,3,4-oxadiazol-2-yl |
| 2047 | 1-(2-methoxyphenyl)cyclopropyl linked via NH to pyrimidine-2-yl, pyrimidine-5 substituted with 5-(difluoromethyl)-1,3,4-oxadiazol-2-yl |
| 2048 | 1-(3-methoxyphenyl)cyclopropyl linked via NH to pyrimidine-2-yl, pyrimidine-5 substituted with 5-(difluoromethyl)-1,3,4-oxadiazol-2-yl |
| 2049 | 1-(4-methoxyphenyl)cyclopropyl linked via NH to pyrimidine-2-yl, pyrimidine-5 substituted with 5-(difluoromethyl)-1,3,4-oxadiazol-2-yl |
| 2050 | 1-(3-chlorophenyl)cyclopropyl linked via NH to pyrimidine-2-yl, pyrimidine-5 substituted with 5-(difluoromethyl)-1,3,4-oxadiazol-2-yl |

TABLE 1-continued

| Compound | Structure |
|---|---|
| 2051 | 3-chlorophenyl-cyclopropyl-NH-pyrimidin-5-yl-[1,3,4-oxadiazol-2-yl]-CF₃ |
| 2052 | 4-chlorophenyl-cyclopropyl-NH-pyrimidin-5-yl-[1,3,4-oxadiazol-2-yl]-CF₂H |
| 2053 | 4-chlorophenyl-cyclopropyl-NH-pyrimidin-5-yl-[1,3,4-oxadiazol-2-yl]-CF₃ |
| 2054 | 4-chloro-3-fluorophenyl-cyclopropyl-NH-pyrimidin-5-yl-[1,3,4-oxadiazol-2-yl]-CF₂H |
| 2055 | 2-methylphenyl-cyclopropyl-NH-pyrimidin-5-yl-[1,3,4-oxadiazol-2-yl]-CF₂H |
| 2056 | 4-chloro-2-fluorophenyl-cyclopropyl-NH-pyrimidin-5-yl-[1,3,4-oxadiazol-2-yl]-CF₂H |

TABLE 1-continued

| Compound | Structure |
|---|---|
| 2057 | 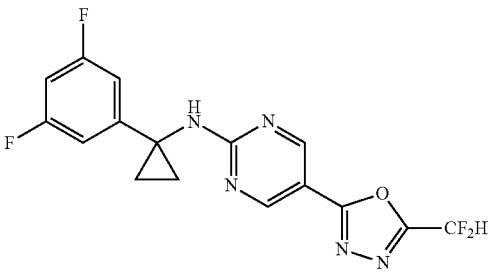 [SMILES: Fc1cc(F)cc(C2(Nc3ncc(-c4nnc(C(F)F)o4)cn3)CC2)c1] |
| 2058 | 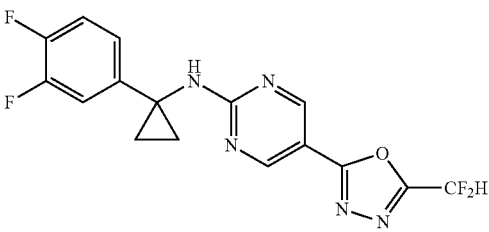 [SMILES: Fc1ccc(C2(Nc3ncc(-c4nnc(C(F)F)o4)cn3)CC2)cc1F] |
| 2060 | 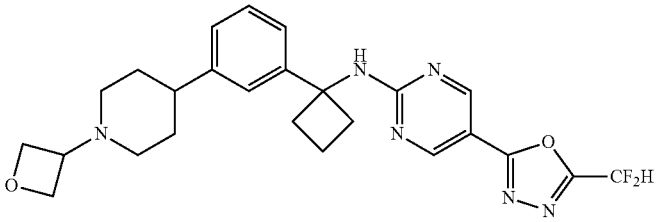 [SMILES: FC(F)c1nnc(-c2cnc(NC3(c4cccc(C5CCN(C6COC6)CC5)c4)CCC3)nc2)o1] |
| 2061 | 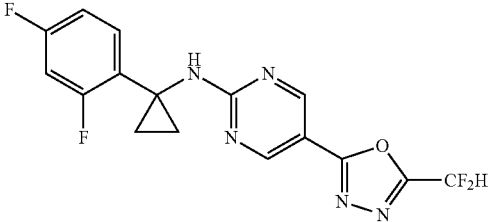 [SMILES: Fc1ccc(C2(Nc3ncc(-c4nnc(C(F)F)o4)cn3)CC2)c(F)c1] |
| 2062 | 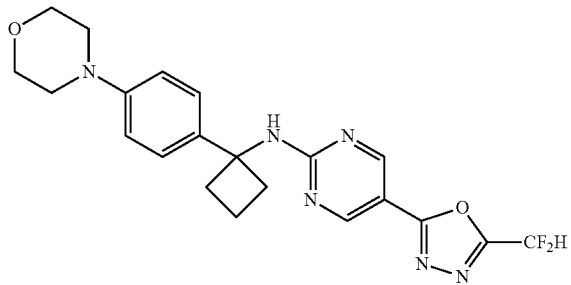 [SMILES: FC(F)c1nnc(-c2cnc(NC3(c4ccc(N5CCOCC5)cc4)CCC3)nc2)o1] |

The specific compound names represented by formula I are shown in Table 2 below:

TABLE 2

| Exam. | Compound | Compound name |
|---|---|---|
| 1 | 1524 | 5-(5-(difluoromethyl)-1,3,4-oxadiazol-2-yl)-N-(1-phenylcyclopropyl)pyrimidin-2-amine |
| 2 | 1526 | N-(1-phenylcyclopropyl)-5-(5-(trifluoromethyl)-1,3,4-oxadiazol-2-yl)pyrimidin-2-amine |
| 3 | 1559 | 5-(5-(difluoromethyl)-1,3,4-oxadiazol-2-yl)-N-(1-phenylcyclobutyl)pyrimidin-2-amine |
| 4 | 1579 | 5-(5-(difluoromethyl)-1,3,4-oxadiazol-2-yl)-N-(1-phenylcyclopentyl)pyrimidin-2-amine |
| 5 | 1580 | N-(1-phenylcyclopentyl)-5-(5-(trifluoromethyl)-1,3,4-oxadiazol-2-yl)pyrimidin-2-amine |
| 6 | 1581 | 5-(5-(difluoromethyl)-1,3,4-oxadiazol-2-yl)-N-(1-phenylcyclohexyl)pyrimidin-2-amine |

TABLE 2-continued

| Exam. | Compound | Compound name |
|---|---|---|
| 7 | 1582 | N-(1-phenylcyclohexyl)-5-(5-(trifluoromethyl)-1,3,4-oxadiazol-2-yl)pyrimidin-2-amine |
| 8 | 1603 | 5-(5-(difluoromethyl)-1,3,4-oxadiazol-2-yl)-N-(1-(4-methoxyphenyl)cyclobutyl)pyrimidin-2-amine |
| 9 | 1604 | N-(1-(4-methoxyphenyl)cyclobutyl)-5-(5-(trifluoromethyl)-1,3,4-oxadiazol-2-yl)pyrimidin-2-amine |
| 10 | 1605 | 5-(5-(difluoromethyl)-1,3,4-oxadiazol-2-yl)-N-(1-(3-methoxyphenyl)cyclobutyl)pyrimidin-2-amine |
| 11 | 1606 | N-(1-(3-methoxyphenyl)cyclobutyl)-5-(5-(trifluoromethyl)-1,3,4-oxadiazol-2-yl)pyrimidin-2-amine |
| 12 | 1607 | 5-(5-(difluoromethyl)-1,3,4-oxadazol-2-yl)-N-(1-(3-fluorophenyl)cyclobutyl)pyrimidin-2-amine |
| 13 | 1608 | N-(1-(3-fluorophenyl)cyclobutyl)-5-(5-(trifluoromethyl)-1,3,4-oxadiazol-2-yl)pyrimidin-2-amine |
| 14 | 1609 | 5-(5-(difluoromethyl)-1,3,4-oxadazol-2-yl)-N-(1-(2-fluorophenyl)cyclobutyl)pyrimidin-2-amine |
| 15 | 1610 | N-(1-(2-fluorophenyl)cyclobutyl)-5-(5-(trifluoromethyl)-1,3,4-oxadiazol-2-yl)pyrimidin-2-amine |
| 16 | 1611 | 5-(5-(difluoromethyl)-1,3,4-oxadiazol-2-yl)-N-(1-(4-fluorophenyl)cyclobutyl)pyrimidin-2-amine |
| 17 | 1612 | N-(1-(4-fluorophenyl)cyclobutyl)-5-(5-(trifluoromethyl)-1,3,4-oxadiazol-2-yl)pyrimidin-2-amine |
| 18 | 1614 | N-(1-(2-chlorophenyl)cyclobutyl)-5-(5-(difluoromethyl)-1,3,4-oxadiazol-2-yl)pyrimidin-2-amine |
| 19 | 1615 | N-(1-(3-chlorophenyl)cyclobutyl)-5-(5-(difluoromethyl)-1,3,4-oxadiazol-2-yl)pyrimidin-2-amine |
| 20 | 1616 | N-(1-(4-chlorophenyl)cyclobutyl)-5-(5-(difluoromethyl)-1,3,4-oxadiazol-2-yl)pyrimidin-2-amine |
| 21 | 1617 | N-(1-(2-chlorophenyl)cyclobutyl)-5-(5-(trifluoromethyl)-1,3,4-oxadazol-2-yl)pyrimidin-2-amine |
| 22 | 1618 | N-(1-(4-chlorophenyl)cyclobutyl)-5-(5-(trifluoromethyl)-1,3,4-oxadiazol-2-yl)pyrimidin-2-amine |
| 23 | 1640 | 5-(5-(difluoromethyl)-1,3,4-oxadiazol-2-yl)-N-(1-(pyridin-2-yl)cyclobutyl)pyrimidin-2-amine |
| 24 | 1641 | N-(1-(pyridin-2-yl)cyclobutyl)-5-(5-(trifluoromethyl)-1,3,4-oxadazol-2-yl)pyrimidin-2-amine |
| 25 | 1642 | 5-(5-(difluoromethyl)-1,3,4-oxadiazol-2-yl)-N-(1-(3-(trifluoromethyl)phenyl)cyclobutyl)pyrimidin-2-amine |
| 26 | 1670 | 5-(5-(trifluoromethyl)-1,3,4-oxadiazol-2-yl)-N-(1-(3-(trifluoromethyl)phenyl)cyclobutyl)pyrimidin-2-amine |
| 27 | 1671 | 5-(5-(difluoromethyl)-1,3,4-oxadiazol-2-yl)-N-(1-(o-tolyl)cyclobutyl)pyrimidin-2-amine |
| 28 | 1672 | N-(1-(o-tolyl)cyclobutyl)-5-(5-(trifluoromethyl)-1,3,4-oxadiazol-2-yl)pyrimidin-2-amine |
| 29 | 1673 | 5-(5-(difluoromethyl)-1,3,4-oxadiazol-2-yl)-N-(1-(m-tolyl)cyclobutyl)pyrimidin-2-amine |
| 30 | 1674 | N-(1-(m-tolyl)cyclobutyl)-5-(5-(trifluoromethyl)-1,3,4-oxadiazol-2-yl)pyrimidin-2-amine |
| 31 | 1675 | 5-(5-(difluoromethyl)-1,3,4-oxadiazol-2-yl)-N-(1-(p-tolyl)cyclobutyl)pyrimidin-2-amine |
| 32 | 1676 | N-(1-(p-tolyl)cyclobutyl)-5-(5-(trifluoromethyl)-1,3,4-oxadiazol-2-yl)pyrimidin-2-amine |
| 33 | 1677 | Benzyl 4-((5-(5-(difluoromethyl)-1,3,4-oxadiazol-2-yl)pyrimidin-2-yl)amino)-4-phenylpiperidine-1-carboxylate |
| 34 | 1678 | 5-(5-(difluoromethyl)-1,3,4-oxadiazol-2-yl)-N-(4-phenylpiperidin-4-yl)pyrimidin-2-amine |
| 35 | 1683 | 5-(5-(difluoromethyl)-1,3,4-oxadiazol-2-yl)-N-(1-(2-fluorophenyl)cyclopropyl)pyrimidin-2-amine |
| 36 | 1711 | 5-(5-(difluoromethyl)-1,3,4-oxadiazol-2-yl)-N-(1-(4-fluorophenyl)cyclopropyl)pyrimidin-2-amine |
| 37 | 1712 | N-(1-(4-fluorophenyl)cyclopropyl)-5-(5-(trifluoromethyl)-1,3,4-oxadiazol-2-yl)pyrimidin-2-amine |
| 38 | 1713 | 5-(5-(difluoromethyl)-1,3,4-oxadiazol-2-yl)-N-(1-(3-fluorophenyl)cyclopropyl)pyrimidin-2-amine |
| 39 | 1714 | N-(1-(3-fluorophenyl)cyclopropyl)-5-(5-(trifluoromethyl)-1,3,4-oxadiazol-2-yl)pyrimidin-2-amine |
| 40 | 1722 | N-(1-(3-chloro-4-fluorophenyl)cyclopropyl)-5-(5-(difluoromethyl)-1,3,4-oxadiazol-2-yl)pyrimidin-2-amine |
| 41 | 1723 | N-(1-(3-chloro-4-fluorophenyl)cyclopropyl)-5-(5-(trifluoromethyl)-1,3,4-oxadiazol-2-yl)pyrimidin-2-amine |
| 42 | 1738 | 5-(5-(difluoromethyl)-1,3,4-oxadiazol-2-yl)-N-(1-(4-(trifluoromethyl)phenyl)cyclopropyl)pyrimidin-2-amine |
| 43 | 1740 | 5-(5-(difluoromethyl)-1,3,4-oxadiazol-2-yl)-N-(1-(3-(trifluoromethyl)phenyl)cyclopropyl)pyrimidin-2-amine |
| 44 | 1741 | 5-(5-(trifluoromethyl)-1,3,4-oxadiazol-2-yl)-N-(1-(3-(trifluoromethyl)phenyl)cyclopropyl)pyrimidin-2-amine |
| 45 | 1742 | 5-(5-(trifluoromethyl)-1,3,4-oxadiazol-2-yl)-N-(1-(4-(trifluoromethyl)phenyl)cyclopropyl)pyrimidin-2-amine |
| 46 | 1761 | 3-(1-((5-(5-(difluoromethyl)-1,3,4-oxadiazol-2-yl)pyrimidin-2-yl)amino)cyclobutyl)phenol |
| 47 | 1779 | 5-(5-(difluoromethyl)-1,3,4-oxadiazol-2-yl)-N-(1-(3,4-difluorophenyl)cyclopropyl)pyrimidin-2-amine |
| 48 | 1780 | N-(1-(3,4-difluorophenyl)cyclopropyl)-5-(5-(trifluoromethyl)-1,3,4-oxadiazol-2-yl)pyrimidin-2-amine |
| 49 | 1817 | N-(1-(3-chloro-4-fluorophenyl)cyclobutyl)-5-(5-(difluoromethyl)-1,3,4-oxadiazol-2-yl)pyrimidin-2-amine |
| 50 | 1818 | N-(1-(3-chloro-4-fluorophenyl)cyclobutyl)-5-(5-(trifluoromethyl)-1,3,4-oxadiazol-2-yl)pyrimidin-2-amine |

TABLE 2-continued

| Exam. | Compound | Compound name |
|---|---|---|
| 51 | 1819 | 5-(5-(difluoromethyl)-1,3,4-oxadiazol-2-yl)-N-(1-(3,5-difluorophenyl)cyclobutyl)pyrimidin-2-amine |
| 52 | 1820 | N-(1-(benzo[d][1,3]dioxol-5-yl)cyclobutyl)-5-(5-(difluoromethyl)-1,3,4-oxadiazol-2-yl)pyrimidin-2-amine |
| 53 | 1821 | 5-(5-(difluoromethyl)-1,3,4-oxadazol-2-yl)-N-(1-(2,5-difluorophenyl)cyclobutyl)pyrimidin-2-amine |
| 54 | 1822 | 5-(5-(difluoromethyl)-1,3,4-oxadiazol-2-yl)-N-(1-(4-(trifluoromethoxy)phenyl)cyclobutyl)pyrimidin-2-amine |
| 55 | 1826 | 5-(5-(difluoromethyl)-1,3,4-oxadiazol-2-yl)-N-(1-(2,4,5-trifluorophenyl)cyclobutyl)pyrimidin-2-amine |
| 56 | 1827 | 5-(5-(difluoromethyl)-1,3,4-oxadiazol-2-yl)-N-(1-(2,3-difluorophenyl)cyclobutyl)pyrimidin-2-amine |
| 57 | 1828 | 5-(5-(difluoromethyl)-1,3,4-oxadiazol-2-yl)-N-(1-(2,6-difluorophenyl)cyclobutyl)pyrimidin-2-amine |
| 58 | 1832 | N-(1-(2,3-dichlorophenyl)cyclobutyl)-5-(5-(difluoromethyl)-1,3,4-oxadiazol-2-yl)pyrimidin-2-amine |
| 59 | 1833 | N-(1-(2,3-dichlorophenyl)cyclobutyl)-5-(5-(trifluoromethyl)-1,3,4-oxadiazol-2-yl)pyrimidin-2-amine |
| 60 | 1834 | N-(1-(3,4-dichlorophenyl)cyclobutyl)-5-(5-(difluoromethyl)-1,3,4-oxadiazol-2-yl)pyrimidin-2-amine |
| 61 | 1835 | N-(1-(3,4-dichlorophenyl)cyclobutyl)-5-(5-(trifluoromethyl)-1,3,4-oxadiazol-2-yl)pyrimidin-2-amine |
| 62 | 1836 | N-(1-(2,4-dichlorophenyl)cyclobutyl)-5-(5-(difluoromethyl)-1,3,4-oxadiazol-2-yl)pyrimidin-2-amine |
| 63 | 1837 | N-(1-(2,4-dichlorophenyl)cyclobutyl)-5-(5-(trifluoromethyl)-1,3,4-oxadiazol-2-yl)pyrimidin-2-amine |
| 64 | 1838 | N-(1-(2,6-dichlorophenyl)cyclobutyl)-5-(5-(difluoromethyl)-1,3,4-oxadazol-2-yl)pyrimidin-2-amine |
| 65 | 1913 | 5-(5-(difluoromethyl)-1,3,4-oxadiazol-2-yl)-N-(1-(pyridin-3-yl)cyclobutyl)pyrimidin-2-amine |
| 66 | 1959 | N-(1-(2-chloro-4-fluorophenyl)cyclobutyl)-5-(5-(difluoromethyl)-1,3,4-oxadazol-2-yl)pyrimidin-2-amine |
| 67 | 1960 | N-(1-(2-chloro-4-fluorophenyl)cyclobutyl)-5-(5-(trifluoromethyl)-1,3,4-oxadiazol-2-yl)pyrimidin-2-amine |
| 68 | 1961 | N-(1-(2-chloro-5-fluorophenyl)cyclobutyl)-5-(5-(difluoromethyl)-1,3,4-oxadazol-2-yl)pyrimidin-2-amine |
| 69 | 1962 | N-(1-(2-chloro-5-fluorophenyl)cyclobutyl)-5-(5-(trifluoromethyl)-1,3,4-oxadiazol-2-yl)pyrimidin-2-amine |
| 70 | 1963 | N-(1-(5-chloro-2-fluorophenyl)cyclobutyl)-5-(5-(difluoromethyl)-1,3,4-oxadiazol-2-yl)pyrimidin-2-amine |
| 71 | 1964 | N-(1-(5-chloro-2-fluorophenyl)cyclobutyl)-5-(5-(trifluoromethyl)-1,3,4-oxadiazol-2-yl)pyrimidin-2-amine |
| 72 | 1965 | N-(1-(3-chloro-2-fluorophenyl)cyclobutyl)-5-(5-(difluoromethyl)-1,3,4-oxadazol-2-yl)pyrimidin-2-amine |
| 73 | 1966 | N-(1-(3-chloro-2-fluorophenyl)cyclobutyl)-5-(5-(trifluoromethyl)-1,3,4-oxadiazol-2-yl)pyrimidin-2-amine |
| 74 | 2023 | 5-(5-(difluoromethyl)-1,3,4-oxadiazol-2-yl)-N-(1-(4-(1-(oxetan-3-yl)piperidin-4-yl)phenyl)cyclobutyl)pyrimidin-2-amine |
| 75 | 2026 | 5-(5-(difluoromethyl)-1,3,4-oxadiazol-2-yl)-N-(1-(tosylmethyl)cyclobutyl)pyrimidin-2-amine |
| 76 | 2027 | 5-(5-(difluoromethyl)-1,3,4-oxadiazol-2-yl)-N-(1-(2,4-difluorophenyl)cyclobutyl)pyrimidin-2-amine |
| 77 | 2028 | 5-(5-(difluoromethyl)-1,3,4-oxadiazol-2-yl)-N-(1-(2-(trifluoromethoxy)phenyl)cyclobutyl)pyrimidin-2-amine |
| 78 | 2030 | N-(1-benzylcyclobutyl)-5-(5-(difluoromethyl)-1,3,4-oxadiazol-2-yl)pyrimidin-2-amine |
| 79 | 2033 | N-(1-(2-(trifluoromethoxy)phenypcyclobutyl)-5-(5(trifluoromethyl)-1,3,4-oxadiazol-2-yl)pyrimidin-2-amine |
| 80 | 2034 | N-(1-(2,4-difluorophenyl)cyclobutyl)-5-(5-(trifluoromethyl)-1,3,4-oxadiazol-2-yl)pyrimidin-2-amine |
| 81 | 2035 | 5-(5-(difluoromethyl)-1,3,4-oxadiazol-2-yl)-N-(1-(4-(1-methylpiperidin-4-yl)phenyl)cyclobutyl)pyrimidin-2-amine |
| 82 | 2036 | 5-(5-(difluoromethyl)-1,3,4-oxadiazol-2-yl)-N-(1-(4-(1-ethylpiperidin-4-yl)phenyl)cyclobutyl)pyrimidin-2-amine |
| 83 | 2037 | 5-(5-(difluoromethyl)-1,3,4-oxadiazol-2-yl)-N-(1-(4-(1-isopropylpiperidin-4-yl)phenyl)cyclobutyl)pyrimidin-2-amine |
| 84 | 2038 | 5-(5-(difluoromethyl)-1,3,4-oxadiazol-2-yl)-N-(1-(thiophen-3-yl)cyclobutyl)pyrimidin-2-amine |
| 85 | 2040 | 5-(5-(difluoromethyl)-1,3,4-oxadiazol-2-yl)-N-(1-(thiophen-2-yl)cyclopropyl)pyrimidin-2-amine |
| 86 | 2041 | 5-(5-(difluoromethyl)-1,3,4-oxadiazol-2-yl)-N-(1-(4-(piperidin-1-yl)phenyl)cyclobutyl)pyrimidin-2-amine |
| 87 | 2042 | 5-(5-(difluoromethyl)-1,3,4-oxadiazol-2-yl)-N-(1-(2-(trifluoromethyl)phenyl)cyclobutyl)pyrimidin-2-amine |
| 88 | 2043 | 5-(5-(difluoromethyl)-1,3,4-oxadiazol-2-yl)-N-(1-(4-(trifluoromethyl)phenyl)cyclobutyl)pyrimidin-2-amine |
| 89 | 2044 | 5-(5-(trifluoromethyl)-1,3,4-oxadiazol-2-yl)-N-(1-(4-(trifluoromethyl)phenyl)cyclobutyl)pyrimidin-2-amine |
| 90 | 2045 | 5-(5-(difluoromethyl)-1,3,4-oxadiazol-2-yl)-N-(1-(3,4-difluorophenyl)cyclobutyl)pyrimidin-2-amine |

TABLE 2-continued

| Exam. | Compound | Compound name |
|---|---|---|
| 91 | 2046 | 5-(5-(difluoromethyl)-1,3,4-oxadiazol-2-yl)-N-(1-(4-fluoro-3-morpholinophenyl)cyclobutyl)pyrimidin-2-amine |
| 92 | 2047 | 5-(5-(difluoromethyl)-1,3,4-oxadiazol-2-yl)-N-(1-(2-methoxyphenyl)cyclopropyl)pyrimidin-2-amine |
| 93 | 2048 | 5-(5-(difluoromethyl)-1,3,4-oxadiazol-2-yl)-N-(1-(3-methoxyphenyl)cyclopropyl)pyrimidin-2-amine |
| 94 | 2049 | 5-(5-(difluoromethyl)-1,3,4-oxadiazol-2-yl)-N-(1-(4-methoxyphenyl)cyclopropyl)pyrimidin-2-amine |
| 95 | 2050 | N-(1-(3-chlorophenyl)cyclopropyl)-5-(5-(difluoromethyl)-1,3,4-oxadiazol-2-yl)primidin-2-amine |
| 96 | 2051 | N-(1-(3-chlorophenyl)cyclopropyl)-5-(5-(trifluoromethyl)-1,3,4-oxadiazol-2-yl)pyrimidin-2-amine |
| 97 | 2052 | N-(1-(4-chlorophenyl)cyclopropyl)-5-(5-(difluoromethyl)-1,3,4-oxadiazol-2-yl)pyrimidin-2-amine |
| 98 | 2053 | N-(1-(4-chlorophenyl)cyclopropyl)-5-(5-(trifluoromethyl)-1,3,4-oxadazol-2-yl)pyrimidin-2-amine |
| 99 | 2054 | N-(1-(4-chloro-3-fluorophenyl)cyclopropyl)-5-(5-(difluoromethyl)-1,3,4-oxadiazol-2-yl)pyrimidin-2-amine |
| 100 | 2055 | 5-(5-(difluoromethyl)-1,3,4-oxadiazol-2-yl)-N-(1-(o-tolyl)cyclopropyl)pyrimidin-2-amine |
| 101 | 2056 | N-(1-(4-chloro-2-fluorophenyl)cyclopropyl)-5-(5-(difluoromethyl)-1,3,4-oxadazol-2-yl)pyrimidin-2-amine |
| 102 | 2057 | 5-(5-(difluoromethyl)-1,3,4-oxadiazol-2-yl)-N-(1-(3,5-difluorophenyl)cyclopropyl)pyrimidin-2-amine |
| 103 | 2058 | 5-(5-(difluoromethyl)-1,3,4-oxadiazol-2-yl)-N-(1-(3,4-difluorophenyl)cyclopropyl)pyrimidin-2-amine |
| 104 | 2060 | 5-(5-(difluoromethyl)-1,3,4-oxadiazol-2-yl)-N-(1-(3-(1-(oxetan-3-yl)piperidin-4-yl)phenyl)cyclobutyl)pyrimidin-2-amine |
| 105 | 2061 | 5-(5-(difluoromethyl)-1,3,4-oxadiazol-2-yl)-N-(1-(2,4-difluorophenyl)cyclopropyl)pyrimidin-2-amine |
| 106 | 2062 | 5-(5-(difluoromethyl)-1,3,4-oxadiazol-2-yl)-N-(1-(4-morpholinophenyl)cyclobutyl)pyrimidin-2-amine |

Preferably, the compounds represented by formula I, stereoisomers thereof or pharmaceutically acceptable salts thereof may be selected from the group consisting of compounds 1524, 1559, 1579, 1603, 1605, 1607, 1609, 1611, 1614, 1615, 1616 and 1640. More preferably, the compounds represented by formula I, stereoisomers thereof or pharmaceutically acceptable salts thereof may be selected from the group consisting of compounds 1559, 1607, 1609, 1614, 1615 and 1640.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid or the like, salts with sulfonic acids such as methanesulfonic acid, ethanesulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

In the present disclosure, preferred salts include salts with hydrochloric acid, phosphoric acid, sulfuric acid, trifluoroacetic acid, citric acid, bromic acid, maleic acid, tartaric acid or the like.

The compounds represented by formula I may contain one or more asymmetrical carbon atoms, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, stereoisomers of the compounds of formula I may be synthesized by stereospecific synthesis using optically pure starting materials and/or reagents of known configuration.

Methods for Preparation of Oxadiazole Amine Derivative Compounds

The present disclosure provides methods for the preparation of the oxadiazole amine derivative compounds presented by formula I, stereoisomers thereof, or pharmaceutically acceptable salts thereof.

Preferred methods for the preparation of the oxadiazole amine derivative compounds presented by formula I, stereoisomers thereof, or pharmaceutically acceptable salts thereof are as shown in reaction schemes 1 to 6 below, and also include modifications obvious to those skilled in the art.

In reaction schemes 1 to 6 below, $R_3$ denotes

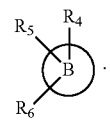

Reaction scheme 1 below shows a method for preparing an intermediate for preparation of the oxadiazole amine derivative compound represented by formula I, an optical isomer thereof, or a pharmaceutically acceptable salt thereof.

[Reaction Scheme 1]

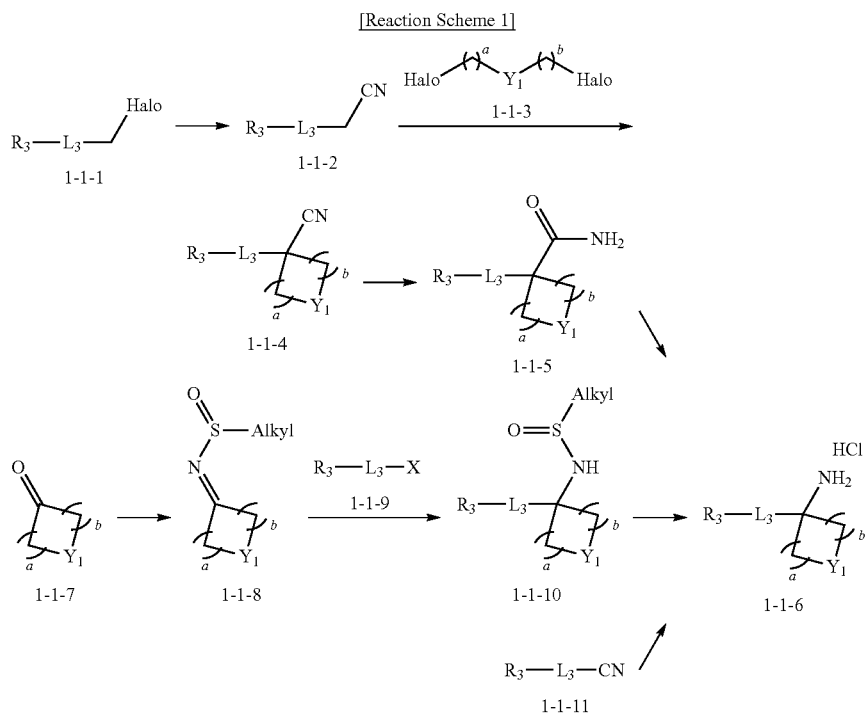

Reaction scheme 1 above shows a method for preparation of a compound having a primary amine structure. As shown in reaction scheme 1, compounds of formula 1-1-6, which have various structures, are prepared from the respective starting materials by the following three methods.

1. A compound of formula 1-1-1 is reacted with potassium cyanide to yield a compound of formula 1-1-2. The compound of formula 1-1-2 is subjected to a substitution reaction with a compound of formula 1-1-3 to yield a compound of formula 1-1-4. The nitrile of the compound of formula 1-1-4 is hydrolyzed to produce a compound of formula 1-1-5 having an amide structure, which is then subjected to a Hofmann rearrangement reaction, thereby preparing a compound of formula 1-1-6 having an amine structure.

2. Ellman's sulfinamide is added to a compound of formula 1-1-7 to yield an amine compound of formula 1-1-8, which is then reacted with a compound of formula 1-1-9, which is a nucleophile, thereby preparing a compound of formula 1-1-10. The compound of formula 1-1-10 is treated with hydrochloric acid to remove the alkylsulfinyl (e.g., butylsulfinyl), thereby preparing an ammonium salt compound of formula 1-1-6 having an amine structure.

3. Using a compound of formula 1-1-11, a compound of formula 1-1-6, which has cyclopropane introduced therein, is prepared (Kulinkovich-Szymoniak Reaction, J. Org. Chem., 2002, 67, 3965.).

[Reaction scheme 2]

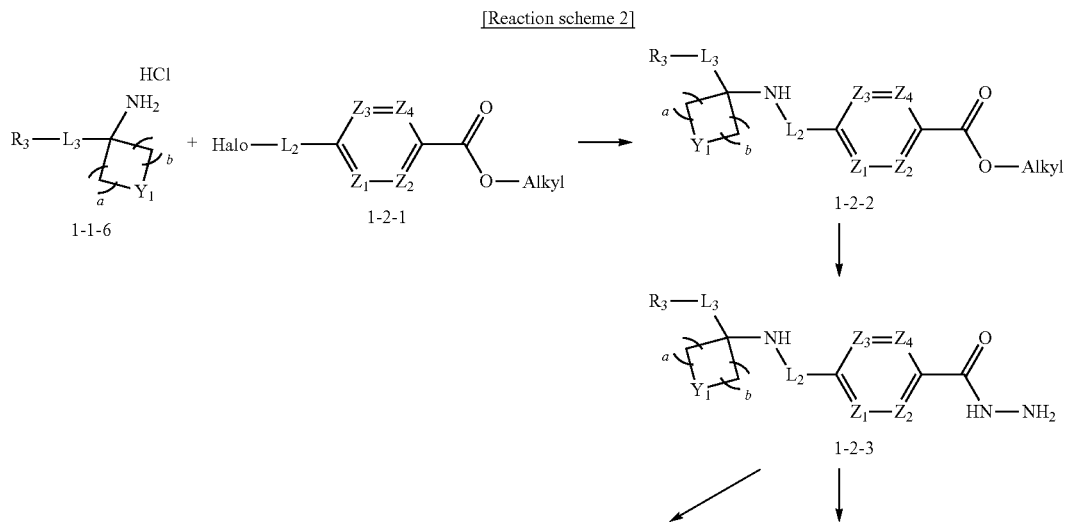

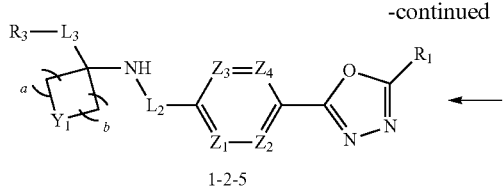

1-2-5

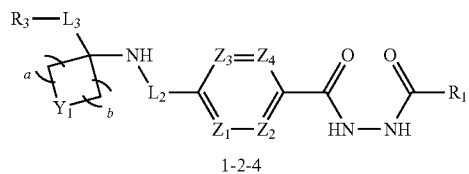

1-2-4

Reaction scheme 2 above shows a method for synthesis of a compound having a 1,3,4-oxadiazole structure. As shown therein, the compound of formula 1-1-6, prepared according to reaction scheme 1 above, is subjected to a substitution reaction with a compound of formula 1-2-1 to yield a compound of formula 1-2-2. The ester moiety of the compound of formula 1-2-2 is substituted with hydrazine, and then reacted with trifluoroacetic acid anhydride or difluoroacetic acid anhydride to thereby prepare a compound of formula 1-2-5. Alternatively, in the case of a compound of formula 1-2-4, which has no oxadiazole ring formed therein, it is reacted with 1-methoxy-N-(triethylammoniosulfonyl)-methaneimidate (Burgess reagent) to thereby prepare a compound of formula 1-2-5, which has a 1,3,4-oxadiazole structure.

In the present disclosure, compounds which are prepared according to the above reaction scheme include compounds 1524, 1526, 1559, 1579, 1580, 1581, 1582, 1603, 1604, 1605, 1606, 1607, 1608, 1609, 1610, 1611, 1612, 1614, 1615, 1616, 1617, 1618, 1640, 1641, 1642, 1670, 1671, 1672, 1673, 1674, 1675, 1676, 1711, 1712, 1713, 1714, 1722, 1723, 1738, 1740, 1741, 1742, 1761, 1779, 1780, 1817, 1818, 1819, 1820, 1821, 1822, 1826, 1827, 1828, 1832, 1833, 1834, 1835, 1836, 1837, 1838, 1913, 1959, 1960, 1961, 1962, 1963, 1964, 1965, 1966, 2026, 2027, 2028, 2030, 2033, 2034, 2038, 2040, 2042, 2043, 2044, 2045, 2047, 2048, 2049, 2050, 2051, 2052, 2053, 2054, 2055, 2056, 2057, 2058 and 2061.

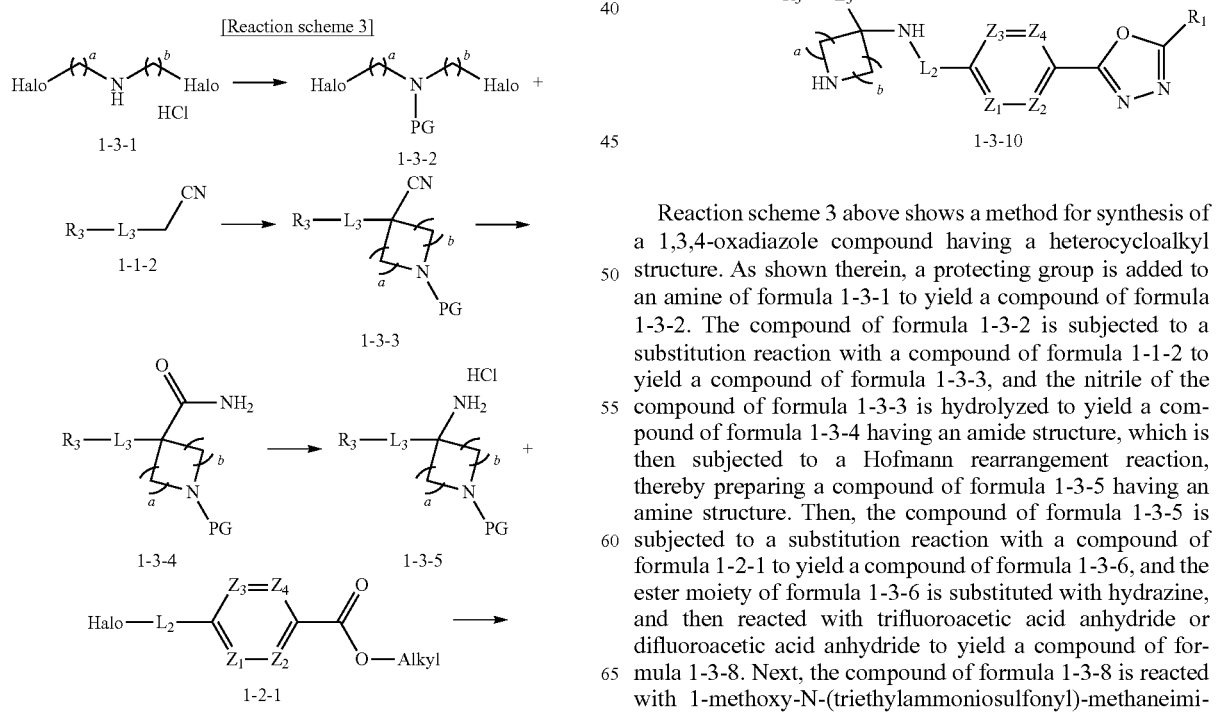

Reaction scheme 3 above shows a method for synthesis of a 1,3,4-oxadiazole compound having a heterocycloalkyl structure. As shown therein, a protecting group is added to an amine of formula 1-3-1 to yield a compound of formula 1-3-2. The compound of formula 1-3-2 is subjected to a substitution reaction with a compound of formula 1-1-2 to yield a compound of formula 1-3-3, and the nitrile of the compound of formula 1-3-3 is hydrolyzed to yield a compound of formula 1-3-4 having an amide structure, which is then subjected to a Hofmann rearrangement reaction, thereby preparing a compound of formula 1-3-5 having an amine structure. Then, the compound of formula 1-3-5 is subjected to a substitution reaction with a compound of formula 1-2-1 to yield a compound of formula 1-3-6, and the ester moiety of formula 1-3-6 is substituted with hydrazine, and then reacted with trifluoroacetic acid anhydride or difluoroacetic acid anhydride to yield a compound of formula 1-3-8. Next, the compound of formula 1-3-8 is reacted with 1-methoxy-N-(triethylammoniosulfonyl)-methaneimidate (Burgess reagent) to yield a compound of formula 1-3-9

(for example, compound 1677), which has a 1,3,4-oxadiazole structure. Then, the protecting group is removed, thereby preparing a compound of formula 1-3-10 (for example, compound 1678).

[Reaction scheme 4]

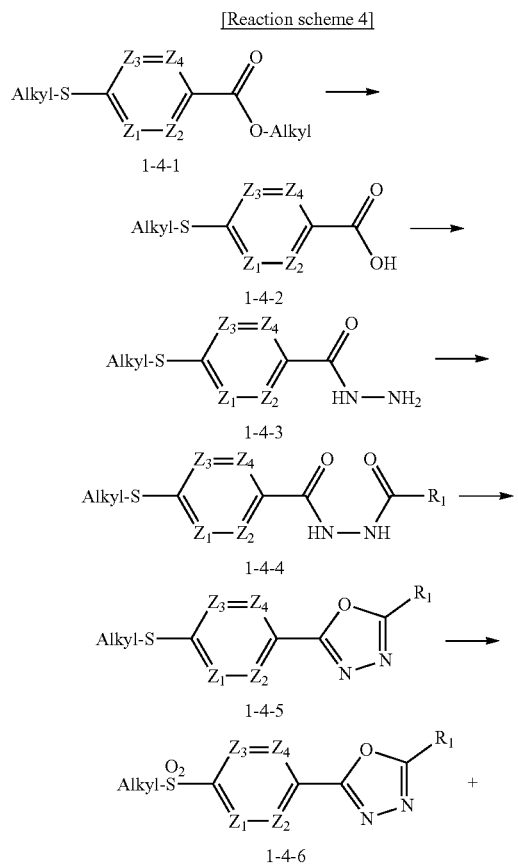

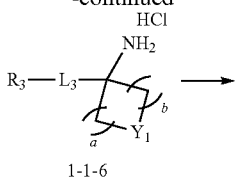

1-1-6

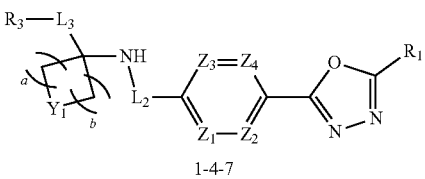

1-4-7

Reaction scheme 4 above shows a method for synthesis of a compound having a 1,3,4-oxadiazole structure. As shown therein, a compound of formula 1-4-1 is hydrolyzed to yield a compound of formula 1-4-2, which is then subjected to an amide coupling reaction to yield a compound of formula 1-4-3. Then, the compound of formula 1-4-3 is reacted with trifluoroacetic acid anhydride or difluoroacetic acid anhydride to yield a compound of formula 1-4-4, which is then reacted with 1-methoxy-N-(triethylammoniosulfonyl)-methaneimidate (Burgess reagent), thereby preparing a compound of formula 1-4-5, which has a 1,3,4-oxadiazole structure. The compound of formula 1-4-5 is subjected to an oxidation reaction to yield a compound of formula 1-4-6, which is then subjected to a substitution reaction with a compound of formula 1-1-6, thereby preparing a compound of formula 1-4-7 (for example, compound 1683).

[Reaction scheme 5]
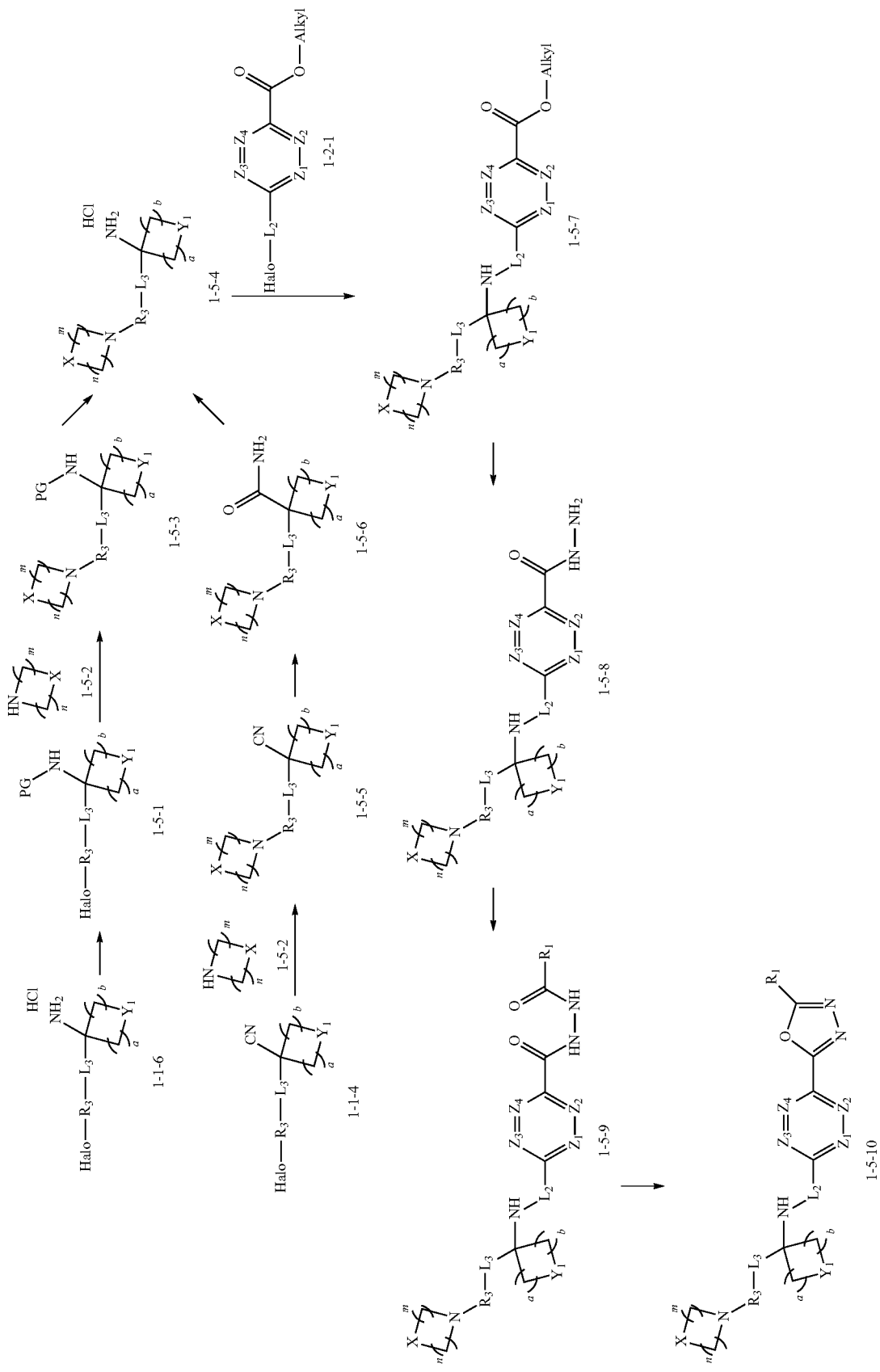

Reaction scheme 5 above shows a method for synthesis of a compound which includes a heterocyclic amine derivative and which has a 1,3,4-oxadiazole structure. As shown therein, a protecting group is added to an amine of formula 1-1-6 to yield a compound of formula 1-5-1. Then, the compound of formula 1-5-1 is subjected to a C—N coupling reaction (Buchwald reaction) with a compound of formula 1-5-2, which is a heterocyclic amine derivative, thereby preparing a compound of formula 1-5-3. Then, the protecting group is removed to yield a compound of formula 1-5-4. In reaction scheme 5 above, X is —CH$_2$—, —NH—, —O—, —C(=O)— or —S(=O)$_2$—, and n and m are each independently an integer of 0, 1, 2 or 3, provided that n and m cannot all be 0.

Furthermore, the compound of formula 1-5-4 is subjected to a C—N coupling reaction (Buchwald reaction) with a compound of formula 1-5-2 to yield a compound of formula 1-5-5. Then, the nitrile of the compound of formula 1-5-5 is hydrolyzed to yield a compound of formula 1-5-6 having an amide structure, which is then subjected to a Hofmann rearrangement reaction, thereby preparing a compound of formula 1-5-4.

The compound of formula 1-5-4 is subjected to a substitution reaction with a compound of formula 1-2-1 to yield a compound of formula 1-5-7. The ester moiety of the compound of formula 1-5-7 is substituted with hydrazine, and then reacted with trifluoroacetic acid anhydride or difluoroacetic acid anhydride to yield a compound of formula 1-5-9, which is then reacted with 1-methoxy-N-(triethylammoniosulfonyl)-methaneimidate (Burgess reagent), thereby preparing a compound of formula 1-5-10, which includes a heterocyclic amine derivative and has a 1,3,4-oxadiazole structure.

In the present disclosure, compounds which are prepared according to the above reaction scheme include compounds 2041, 2062 and 2046.

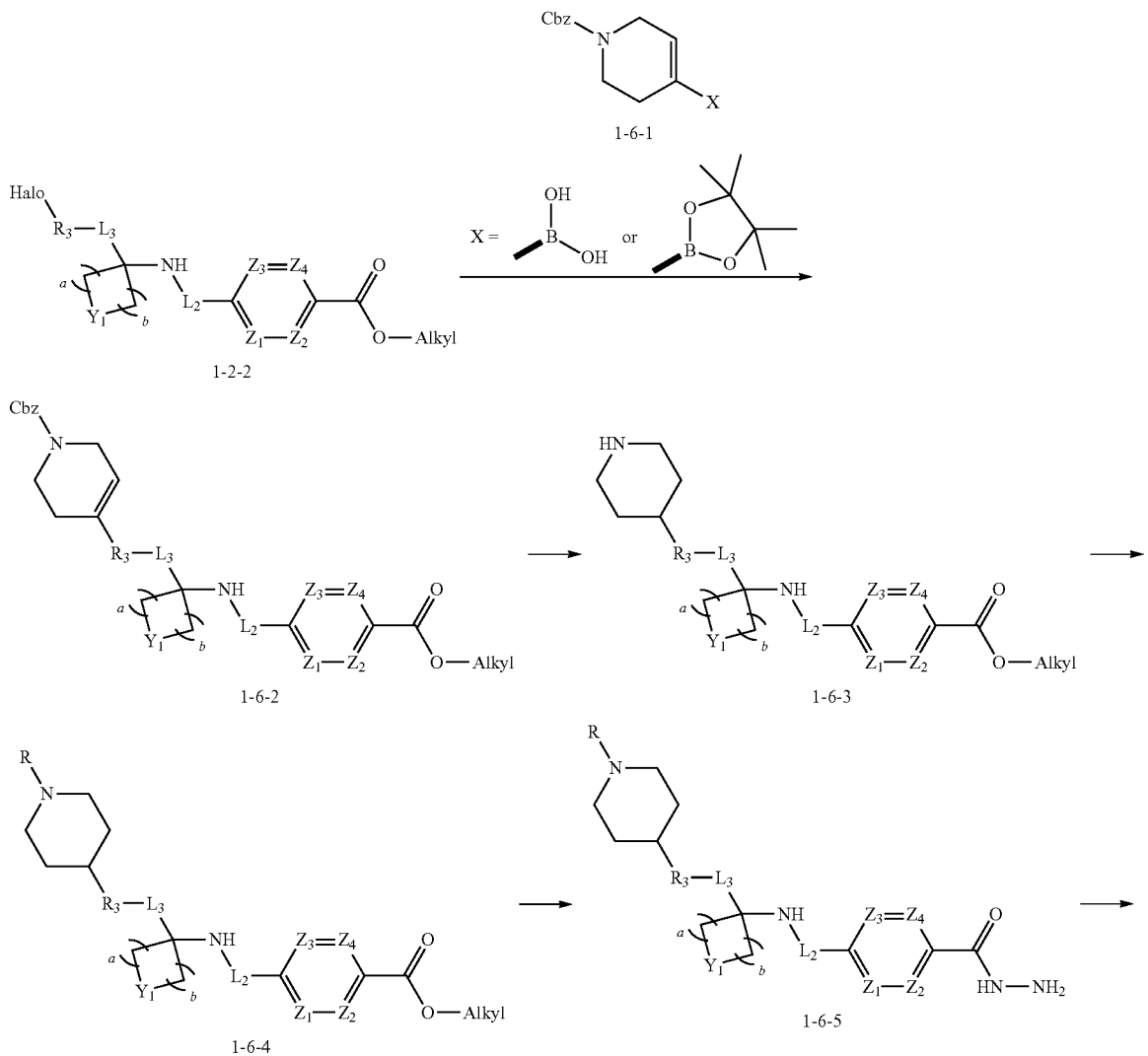

[Reaction scheme 6]

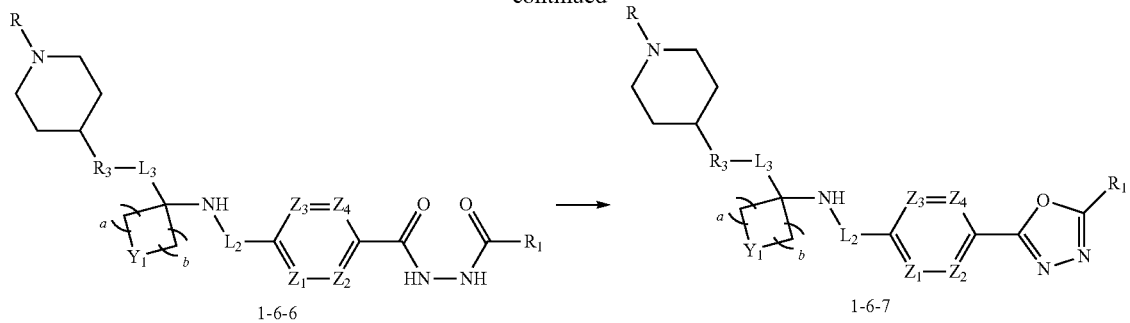

Reaction scheme 6 above shows a method for synthesis of a compound which includes a heterocyclic amine derivative and which has a 1,3,4-oxadiazole structure. As shown therein, an amine of formula 1-2-2 is subjected to a C—C coupling reaction (Suzuki reaction) with a protected compound of formula 1-6-1 to yield a compound of formula 1-6-2. Next, the compound of formula 1-6-2 is hydrogenated to yield a compound of formula 1-6-3, which is then subjected to reductive amination and substitution reactions to thereby prepare a compound of formula 1-6-4. The ester moiety of the compound of formula 1-6-4 is substituted with hydrazine, and then reacted with trifluoroacetic acid anhydride or difluoroacetic acid anhydride to yield a compound of formula 1-6-6, which is then reacted with 1-methoxy-N-(triethylammoniosulfonyl)-methaneimidate (Burgess reagent) to thereby prepare a compound of formula 1-6-7, which includes a heterocyclic amine derivative and has a 1,3,4-oxadiazole structure. In reaction scheme 6 above, R is either

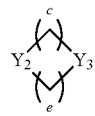

of the substituent group defined as

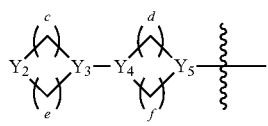

in formula I, or —(C1-C4 alkyl).

In the present disclosure, compounds which are prepared according to the above reaction scheme include compounds 2023, 2035, 2036, 2037 and 2060.

Compositions Comprising Oxadiazole Amine Derivative Compounds, the Use Thereof and the Method of Treating Diseases The present disclosure provides a pharmaceutical composition comprising a compound represented by the following formula I, a stereoisomer thereof or a pharmaceutically acceptable salt thereof:

[Formula I]

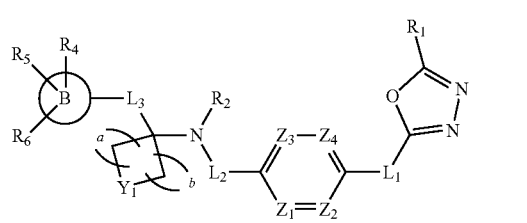

wherein formula I is as defined above.

The present disclosure provides a pharmaceutical composition for preventing or treating histone deacetylase 6 (HDAC6) activity-associated diseases comprising a compound represented by the following formula I, a stereoisomer thereof or a pharmaceutically acceptable salt thereof:

[Formula I]

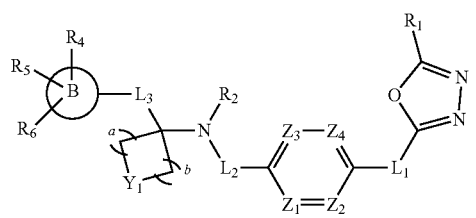

wherein formula I is as defined above.

The pharmaceutical composition according to the present disclosure exhibits a remarkable effect on the prevention or treatment of histone deacetylase 6 (HDAC6) activity-associated diseases by selectively inhibiting histone deacetylase 6 (HDAC6).

The histone deacetylase 6 (HDAC6) activity-associated diseases include infectious diseases such as prion disease; neoplasms such as benign tumor (e.g. myelodysplastic syndrome) or malignant tumor (e.g. multiple myeloma, lymphoma, leukemia, lung cancer, rectal cancer, colon cancer, prostate cancer, urothelial carcinoma, breast cancer, melanoma, skin cancer, liver cancer, brain cancer, gastric cancer, ovarian cancer, pancreatic cancer, head and neck cancer, oral cancer, or glioma); endocrine, nutritional and metabolic diseases such as Wilson's disease, amyloidosis or diabetes; mental and behavioral disorders such as depression or Rett's syndrome, and the like; neurological diseases such as atrophy of central nervous system (e.g. Huntington's disease, spinal muscular atrophy (SMA), spinocerebellar ataxia (SCA)), neurodegenerative disease (e.g. Alzheimer's disease), movement disorder (e.g. Parkinson's disease), neuropathy (e.g. hereditary neuropathy (Charcot-Marie-Tooth disease), sporadic neuropathy, inflammatory neuropathy, drug-induced neuropathy), motor neuron diseases (amyotrophic lateral sclerosis (ALS)), or demyelinating diseases of the central nervous system (e.g. multiple sclerosis (MS)), and the like; diseases of the eye and adnexa, such as uveitis; cardiovascular diseases such as atrial fibrillation or stroke and the like; respiratory diseases such as asthma; digestive diseases such as alcoholic liver disease, inflammatory bowel disease, Crohn's disease or ulcerative bowel disease, and the like; diseases of the skin and subcutaneous tissue, such as psoriasis; diseases of the musculoskeletal system and connective tissue, such as rheumatoid arthritis, osteoarthritis or systemic lupus erythematosus (SLE), and the like; or congenital malformations, deformations and chromosomal abnormalities, such as autosomal dominant polycystic kidney disease, as well as disorders or diseases associated with the abnormal function of histone deacetylase.

The pharmaceutically acceptable salt is as described above with respect to a pharmaceutically acceptable salt of the compound represented by formula I according to the present disclosure.

For administration, the pharmaceutical composition according to the present disclosure may further contain at least one pharmaceutically acceptable carrier in addition to the compound of formula I, an isomer thereof or a pharmaceutically acceptable salt thereof. The pharmaceutically acceptable carrier that is used in the present disclosure may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition can be formulated into injectable formulations such as solutions, suspensions, turbid fluid, etc, pills, capsules, granules or tablets using a diluent, a dispersing agent, a surfactant, a binder and a lubricant. Thus, the composition of the present disclosure may be in the form of patches, liquids, pills, capsules, granules, tablets, suppositories, etc. These formulations can be prepared either by conventional methods that are used for formulation in the art or by the method disclosed in Remington's Pharmaceutical Science (the latest edition), Mack Publishing Company, Easton Pa.

The pharmaceutical composition of the present disclosure may be administered orally or parenterally (e.g., intravenously, subcutaneously, intraperitoneally or topically) depending on the intended use. The dose of the pharmaceutical composition varies depending on the patient's weight, age, sex, health conditions and diet, the time of administration, the mode of administration, excretion rate, the severity of the disease, and the like. The daily dose of the compound of formula I according to the present disclosure may be about 1 to 1000 mg/kg, preferably 5 to 100 mg/kg, and may be administered once to several times a day.

The pharmaceutical composition of the present disclosure may further contain, in addition to the compound represented by formula I, a stereoisomer thereof or a pharmaceutically acceptable salt thereof, one or more active ingredients that exhibit medicinal efficacy identical or similar thereto.

The present disclosure also provides a method for preventing or treating a histone deacetylase-mediated disease, which comprises administering a therapeutically effective amount of the compound represented by formula I, a stereoisomer thereof or a pharmaceutically acceptable salt thereof.

As used herein, the term "therapeutically effective amount" refers to the amount of the compound represented by formula I, which is effective for the prevention or treatment of histone deacetylase 6 activity-associated diseases.

The present disclosure also provides a method of selectively inhibiting HDAC6, which comprises administering the compound of formula I, a stereoisomer thereof or a pharmaceutically acceptable salt thereof to mammals including humans.

The method of preventing or treating histone deacetylase 6 activity-associated disease according to the present disclosure includes inhibiting or averting the disease as well as addressing the disease itself, prior to the onset of symptoms by administering the compound represented by formula I. In the management of diseases, the magnitude of a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens can be readily selected by those skilled in the art with due consideration of such factors. In addition, the method of preventing or treating histone deacetylase 6 activity-associated disease according to the present disclosure may further comprise administering a therapeutically effective amount of an additional active agent helpful for the treatment of the disease together with the compound represented by formula I, in which the additional active agent can exhibit a synergistic effect with the compound of formula I or an assistant effect.

The present disclosure is also intended to provide the use of the compound represented by formula I, a stereoisomer thereof or a pharmaceutically acceptable salt thereof, for the preparation of a medicament for treating histone deacetylase 6 activity-associated disease. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present disclosure may be appropriately combined unless contradictory to one another.

Advantageous Effects of Invention

The compounds represented by formula I, stereoisomers thereof or pharmaceutically acceptable salts thereof can selectively inhibit HDAC6, and thus exhibit excellent effects on the prevention or treatment of histone deacetylase 6 activity-associated diseases.

MODE FOR THE INVENTION

Hereinafter, preferred examples will be presented to assist in the understanding of the present disclosure. However, these examples are provided only for a better understanding of the present disclosure and are not intended to limit the scope of the present disclosure.

Preparation of Oxadiazole Amine Derivative Compounds

Specific methods for preparing the compounds of formula I are as follows.

Example 1: Compound 1524, 5-(5-(difluoromethyl)-1,3,4-oxadiazol-2-yl)-N-(1-phenylcyclopropyl)pyrimidin-2-amine

[Step 1] Ethyl 2-((1-phenylcyclopropyl)amino)pyrimidine-5-carboxylate

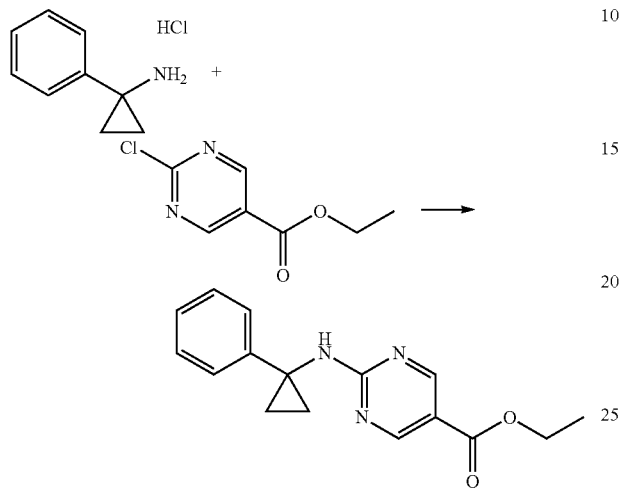

A solution of 1-phenylcyclopropan-1-amine hydrochloride (1.000 g, 5.894 mmol), ethyl 2-chloropyrimidine-5-carboxylate (1.155 g, 6.189 mmol) and N,N-diisopropylethylamine (2.265 mL, 12.968 mmol) in 1,4-dioxane (20 mL) prepared at the room temperature was stirred at the same temperature and the reaction mixture was concentrated under the reduced pressure to remove the solvent. The crude product was crystallized at the room temperature using ethyl acetate (5 mL) and hexane (50 mL). The resulting precipitates were filtered, washed by hexane, and dried to give ethyl 2-((1-phenylcyclopropyl)amino)pyrimidine-5-carboxylate as pale orange solid (0.900 g, 53.9%).

[Step 2] 2-((1-phenylcyclopropyl)amino)pyrimidine-5-carbohydrazide

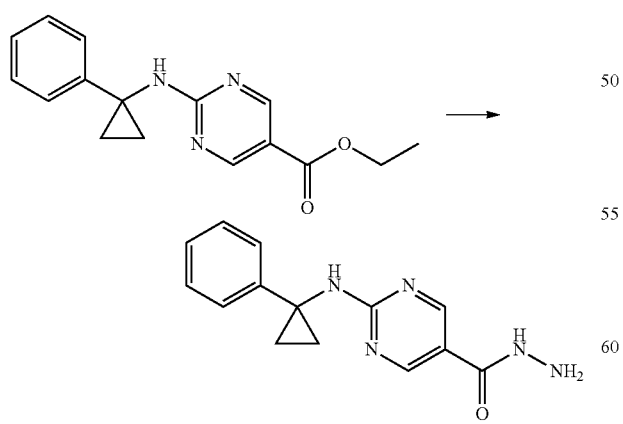

Ethyl 2-((1-phenylcyclopropyl)amino)pyrimidine-5-carboxylate (0.400 g, 1.412 mmol) and hydrazine monohydrate (1.372 mL, 28.236 mmol) in ethanol (10 mL) was mixed at the room temperature, heated at 120° C. under the microwaves for 1 hr, and cooled down to the room temperature to terminal reaction. The reaction mixture was concentrated under the reduced pressure to remove the solvent. The precipitates were collected by filtration, washed by ethanol, and dried to give 2-((1-phenylcyclopropyl)amino)pyrimidine-5-carbohydrazide as white solid (0.367 g, 96.5%).

[Step 3] N'-(2,2-difluoroacetyl)-2-((1-phenylcyclopropyl)amino)pyrimidine-5-carbohydrazide

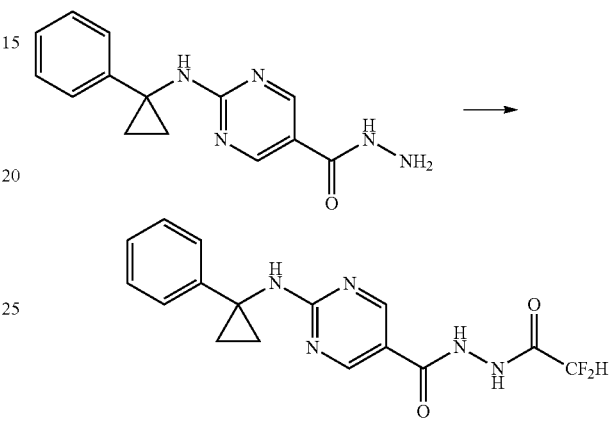

A solution of 2-((1-phenylcyclopropyl)amino)pyrimidine-5-carbohydrazide (0.200 g, 0.743 mmol) and triethylamine (0.155 mL, 1.114 mmol) in dichloromethane (10 mL) was mixed at the room temperature with 2,2-difluoroacetic anhydride (0.083 mL, 0.668 mmol), and stirred at the same temperature for 1 hr. The reaction mixture was concentrated under the reduced pressure to remove the solvent. The precipitates were collected by filtration, washed by dichloromethane, and dried to give N'-(2,2-difluoroacetyl)-2-((1-phenylcyclopropyl)amino)pyrimidine-5-carbohydrazide as white solid (0.144 g, 55.8%).

[Step 4] Compound 1524

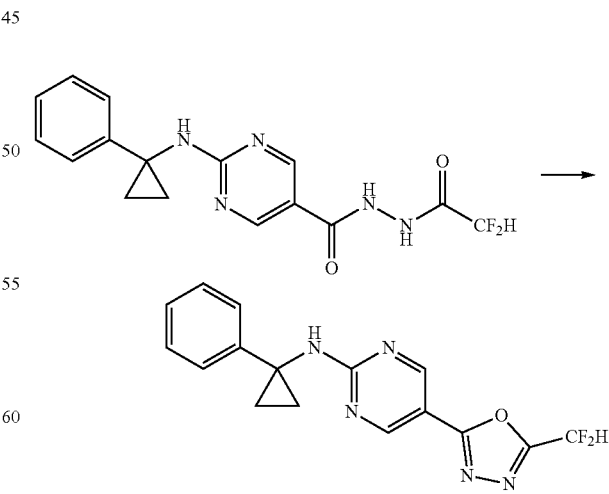

N'-(2,2-difluoroacetyl)-2-((1-phenylcyclopropyl)amino)pyrimidine-5-carbohydrazide (0.268 g, 0.772 mmol) and 1-methoxy-N-triethylammoniosulfonyl-methanimidate (Burgess reagent, 0.276 g, 1.157 mmol) in tetrahydrofuran (4 mL) was mixed at the room teN'-(2,2-difluoroacetyl)-2-((1-phenylcyclopropyl)amino)pyrimidine-5-carbohydrazide (0.268 g, 0.772 mmol) and 1-methoxy-N-triethylammoniosulfonyl-methanimidate (Burgess reagent, 0.276 g, 1.157 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=30% to 60%) to give 5-(5-(difluoromethyl)-1,3,4-oxadiazol-2-yl)-N-(1-phenylcyclopropyl)pyrimidin-2-amine as white solid (0.031 g, 12.2%).

$^1$H NMR (400 MHz, CDCl$_3$) δ 9.02 (s, 1H), 8.96 (s, 1H), 7.33-7.27 (m, 4H), 7.24-7.20 (m, 1H), 6.91 (t, J=51.7 Hz, 1H), 6.71 (s, 1H), 1.50-1.40 (m, 4H); LRMS (ES) m/z 330.3 (M$^+$+1).

Example 2: Compound 1526, N-(1-phenylcyclopropyl)-5-(5-(trifluoromethyl)-1,3,4-oxadiazol-2-yl)pyrimidin-2-amine

[Step 1] 2-((1-phenylcyclopropyl)amino)-N'-(2,2,2-trifluoroacetyl)pyrimidine-5-carbohydrazide

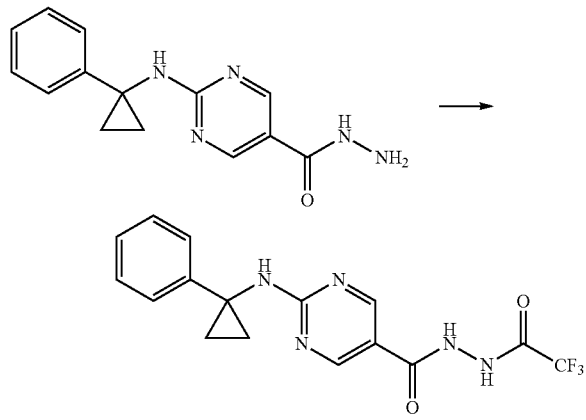

A solution of 2-((1-phenylcyclopropyl)amino)pyrimidine-5-carbohydrazide (0.200 g, 0.743 mmol) and triethylamine (0.155 mL, 1.114 mmol) in dichloromethane (10 mL) was mixed at the room temperature with trifluoroacetic anhydride (0.093 mL, 0.668 mmol), and stirred at the same temperature for 1 hr, concentrated under the reduced pressure to remove the solvent Then, water was added to the reaction mixture, followed by extraction with dichlorimethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=30% to 100%) to give 2-((1-phenylcyclopropyl)amino)-N'-(2,2,2-trifluoroacetyl)pyrimidine-5-carbohydrazide as white solid (0.051 g, 18.8%).

[Step 2] Compound 1526

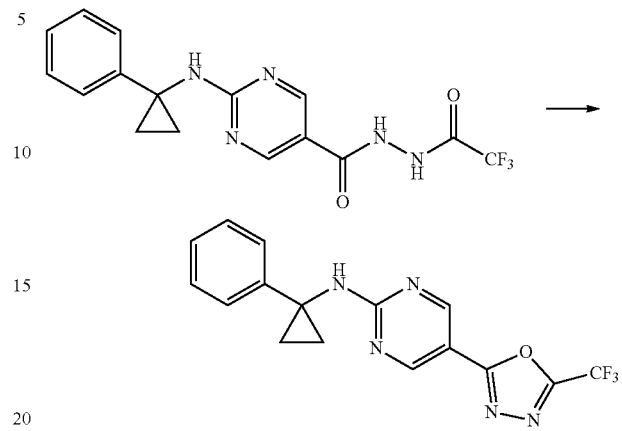

2-((1-phenylcyclopropyl)amino)-N'-(2,2,2-trifluoroacetyl)pyrimidine-5-carbohydrazide (0.097 g, 0.266 mmol) and 1-methoxy-N-triethylammoniosulfonyl-methanimidate (Burgess reagent, 0.095 g, 0.398 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=30% to 60%) to give N-(1-phenylcyclopropyl)-5-(5-(trifluoromethyl)-1,3,4-oxadiazol-2-yl)pyrimidin-2-amine as white solid (0.003 g, 3.3%).

$^1$H NMR (400 MHz, CDCl$_3$) δ 9.00 (s, 1H), 8.97 (s, 1H), 7.33-7.20 (m, 5H), 6.48 (s, 1H), 1.47-1.46 (m, 2H), 1.43-1.42 (m, 2H); LRMS (ES) m/z 348.1 (M$^+$+1).

Example 3: Compound 1559, 5-(5-(difluoromethyl)-1,3,4-oxadiazol-2-yl)-N-(1-phenylcyclobutyl)pyrimidin-2-amine

[Step 1] Ethyl 2-((1-phenylcyclobutyl)amino)pyrimidine-5-carboxylate

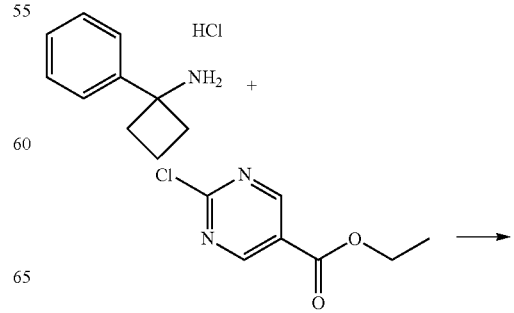

-continued

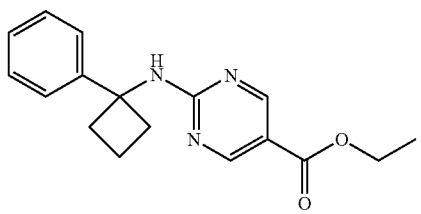

1-Phenylcyclobutan-1-amine hydrochloride (0.353 g, 1.922 mmol), ethyl 2-chloropyrimidine-5-carboxylate (0.377 g, 2.018 mmol) and N,N-diisopropylethylamine (1.343 mL, 7.687 mmol) were mixed at the room temperature in 1,4-dioxane (10 mL), and then suspension was stirred at 100° C. for 17 hr, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 10%) to give ethyl 2-((1-phenylcyclobutyl)amino)pyrimidine-5-carboxylate as yellow solid (0.277 g, 48.5%).

[Step 2] 2-((1-Phenylcyclobutyl)amino)pyrimidine-5-carbohydrazide

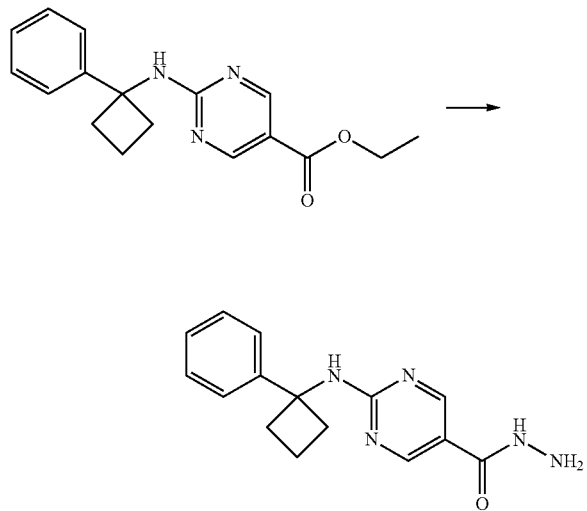

Ethyl 2-((1-phenylcyclobutyl)amino)pyrimidine-5-carboxylate (0.277 g, 0.932 mmol) and hydrazine mono hydrate (0.905 mL, 18.631 mmol) were mixed at the room temperature in ethanol (5 mL), stirred at 120° C. for 17 hr, and then cooled down to the room temperature to terminate the reaction. The reaction mixture was concentrated under the reduced pressure to remove the solvent. And then, the precipitates were collected by filtration, washed by ethanol, and dried to give 2-((1-phenylcyclobutyl)amino)pyrimidine-5-carbohydrazide as white solid (0.163 g, 61.8%).

[Step 3] N'-(2,2-difluoroacetyl)-2-((1-phenylcyclobutyl)amino)pyrimidine-5-carbohydrazide

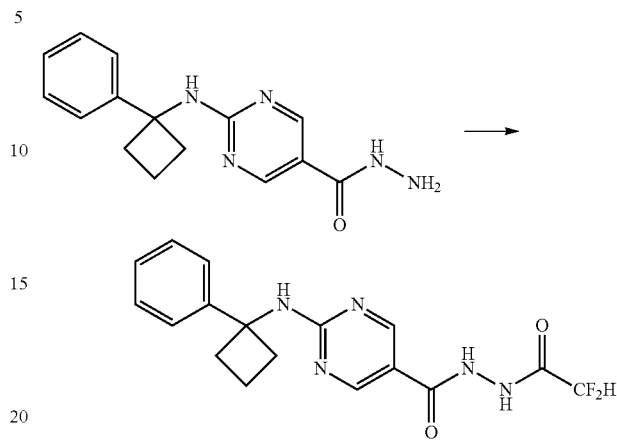

A solution of 2-((1-phenylcyclobutyl)amino)pyrimidine-5-carbohydrazide (0.163 g, 0.575 mmol) and triethylamine (0.120 mL, 0.863 mmol) in dichloromethane (5 mL) was mixed at the room temperature with 2,2-difluoroacetic anhydride (0.056 mL, 0.518 mmol), and stirred at the same temperature for 1 hr. The reaction mixture was concentrated under the reduced pressure to remove the solvent. And then, the concentrate was purified and concentrated by column chromatography (SiO$_2$, 4 g cartridge; ethyl acetate/hexane=10% to 50%) to give N'-(2,2-difluoroacetyl)-2-((1-phenylcyclobutyl)amino)pyrimidine-5-carbohydrazide as white solid (0.128 g, 61.6%).

[Step 4] Compound 1559

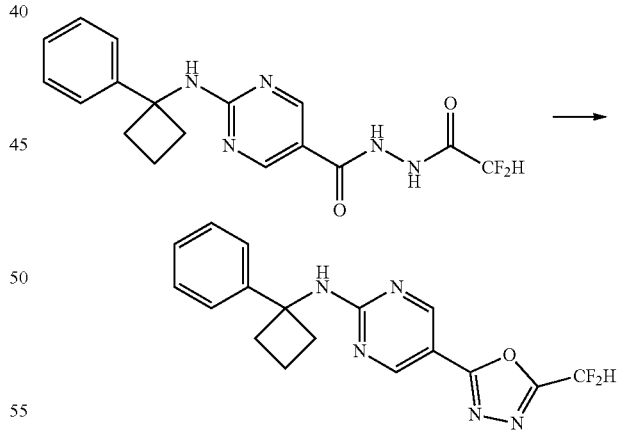

N'-(2,2-difluoroacetyl)-2-((1-phenylcyclobutyl)amino)pyrimidine-5-carbohydrazide (0.128 g, 0.354 mmol) and 1-methoxy-N-triethylammoniosulfonyl-methanimidate (Burgess reagent, 0.127 g, 0.531 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; ethyl acetate/hexane=0% to 20%) to give 5-(5-(difluoromethyl)-1,3,4-oxadiazol-2-yl)-N-(1-phenylcyclobutyl)pyrimidin-2-amine as white solid (0.029 g, 23.8%).

$^1$H NMR (400 MHz, CDCl₃) δ 8.89 (s, 2H), 7.53 (d, J=8.9 Hz, 2H), 7.35 (t, J=7.6 Hz, 2H), 7.25-7.23 (m, 1H), 6.89 (t, J=51.7 Hz, 1H), 6.46 (s, 1H), 2.80-2.73 (m, 2H), 2.66-2.59 (m, 2H), 2.24-2.17 (m, 1H), 2.07-2.00 (m, 1H); LRMS (ES) m/z 344.3 (M⁺+1).

Example 4: Compound 1579, 5-(5-(difluoromethyl)-1,3,4-oxadiazol-2-yl)-N-(1-phenylcyclopentyl)pyrimidin-2-amine

[Step 1] 1-Phenylcyclopentane-1-carbonitrile

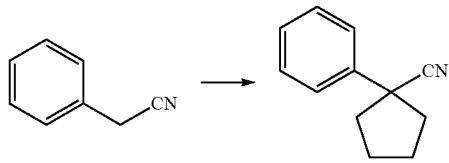 [SMILES: N#CCc1ccccc1 ; N#CC1(c2ccccc2)CCCC1]

A solution of phenylacetonitrile (2.000 g, 17.085 mmol) and 1,4-dibromobutane (2.325 mL, 17.085 mmol) in N,N-dimethylformamide (100 mL) was stirred at 0° C. for 30 min, and mixed with sodium hydride (60.00%, 1.504 g, 37.588 mmol). The reaction mixture was stirred at 50° C. for additional 17 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. 1-Phenylcyclopentane-1-carbonitrile was used without further purification (3.830 g, 121.0%, brown oil).

[Step 2] 1-Phenylcyclopentane-1-carboxamide

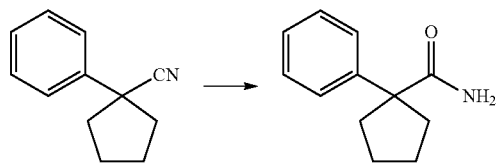 [SMILES: N#CC1(c2ccccc2)CCCC1 ; NC(=O)C1(c2ccccc2)CCCC1]

A solution of 1-phenylcyclopentane-1-carbonitrile (1.530 g, 8.935 mmol) and poly phosphoric acid (115.00%, 5 mL) was mixed at the room temperature, stirred at 110° C. for additional 17 hr, and cooled down to the room temperature to terminate the reaction. And then, the mixture was added to the saturated aqueous sodium bicarbonate solution (300 mL), followed by extraction with ethyl acetate. The organic layer was washed with aqueous saturated sodium chloride solution, dried with anhydrous MgSO₄ filtered, and concentrated in vacuo. The concentrate was diluted with ethyl acetate (10 mL) and stirred at the ambient temperature. The resulting precipitates were collected by filtration, washed by ethyl acetate, and dried to give 1-phenylcyclopentane-1-carboxamide as white solid (1.340 g, 79.2%).

[Step 3] 1-Phenylcyclopentan-1-amine hydrochloride

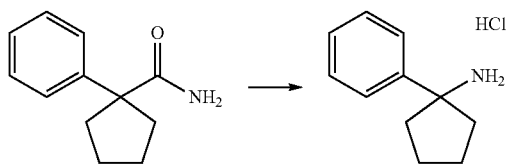 [SMILES: NC(=O)C1(c2ccccc2)CCCC1 ; NC1(c2ccccc2)CCCC1 ; Cl]

A solution of 1-phenylcyclopentane-1-carboxamide (1.350 g, 7.248 mmol) and sodium hydroxide (3.00 M solution in water, 6.765 mL, 20.294 mmol) in 1-butanol (30 mL) was stirred at 0° C. for 1 hr, and mixed with sodium hypochlorite (11.00% solution, 5.675 mL, 10.147 mmol). The reaction mixture was stirred at the room temperature for additional 17 hr. And then, water added to the concentrate, followed by extraction with ethyl acetate The organic layer was washed with aqueous saturated sodium chloride solution, dried with anhydrous MgSO₄, filtered, and concentrated in vacuo. The concentrate was diluted with ethyl acetate and hydrochloric acid (4.00 M solution, 2.718 mL, 10.872 mmol) and stirred at the ambient temperature. 1-phenylcyclopentan-1-amine hydrochloride were collected by filtration and dried to give 1-phenylcyclopentan-1-amine hydrochloride as white solid (0.753 g, 53.4%).

[Step 4] Ethyl 2-((1-phenylcyclopentyl)amino)pyrimidine-5-carboxylate

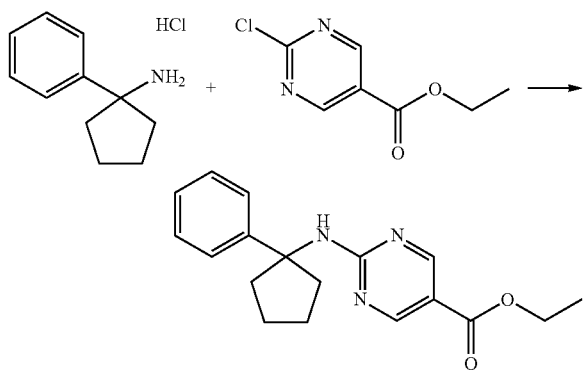

1-phenylcyclopentan-1-amine hydrochloride (0.753 g, 3.809 mmol), ethyl 2-chloropyrimidine-5-carboxylate (0.746 g, 3.999 mmol) and N,N-diisopropylethylamine (3.317 mL, 19.043 mmol) were mixed at the room temperature in 1,4-dioxane (10 mL), stirred at 90° C. for 17 hr, and cooled down to the room temperature to terminate the reaction. Saturated water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=5% to 15%) to give ethyl 2-((1-phenylcyclopentyl)amino)pyrimidine-5-carboxylate as yellow oil (0.345 g, 29.1%).

[Step 5] 2-((1-phenylcyclohexyl)amino)pyrimidine-5-carbohydrazide

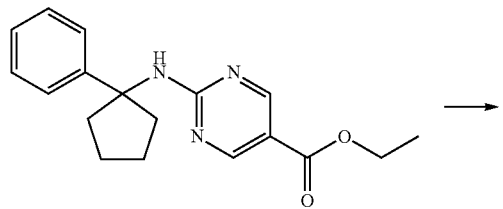

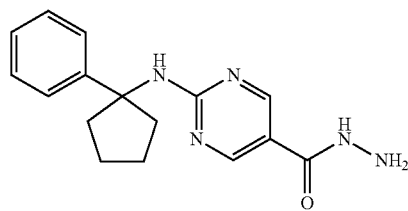

Ethyl 2-((1-phenylcyclopentyl)amino)pyrimidine-5-carboxylate (0.345 g, 1.108 mmol) and hydrazine monohydrate (1.077 mL, 22.159 mmol) in ethanol (3 mL) was mixed at the room temperature, heated at 120° C. under the microwaves for 1 hr, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-phenylcyclohexyl)amino)pyrimidine-5-carbohydrazide was used without further purification (0.303 g, 92.0%, pale yellow solid).

[Step 6] N'-(2,2-difluoroacetyl)-2-((1-phenylcyclopentyl)amino)pyrimidine-5-carbohydrazide

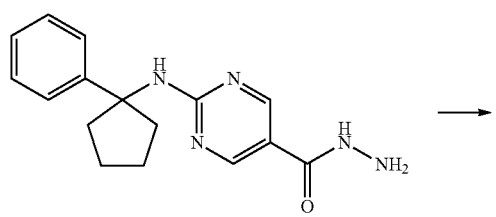

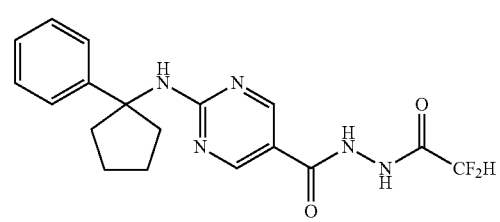

A solution of 2-((1-phenylcyclohexyl)amino)pyrimidine-5-carbohydrazide (0.150 g, 0.504 mmol) and triethylamine (0.105 mL, 0.757 mmol) in dichloromethane (4 mL) was mixed at the room temperature with 2,2-difluoroacetic anhydride (0.049 mL, 0.454 mmol). The reaction mixture was stirred at the same temperature. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 60%) to give N'-(2,2-difluoroacetyl)-2-((1-phenylcyclopentyl)amino)pyrimidine-5-carbohydrazide as white solid (0.183 g, 96.6%).

[Step 7] Compound 1579

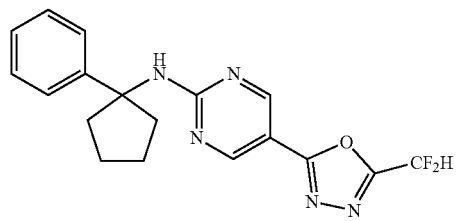

N'-(2,2-difluoroacetyl)-2-((1-phenylcyclopentyl)amino)pyrimidine-5-carbohydrazide (0.192 g, 0.511 mmol) and 1-methoxy-N-triethylammoniosulfonyl-methanimidate (Burgess reagent, 0.183 g, 0.767 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give 5-(5-(difluoromethyl)-1,3,4-oxadiazol-2-yl)-N-(1-phenylcyclopentyl)pyrimidin-2-amine as white solid (0.047 g, 25.7%).

$^1$H NMR (400 MHz, CDCl$_3$) δ 8.90 (s, 1H), 8.80 (s, 1H), 7.45 (d, J=9.0 Hz, 2H), 7.31 (t, J=7.7 Hz, 2H), 7.22 (t, J=7.3 Hz, 1H), 6.88 (t, J=51.7 Hz, 1H), 6.17 (s, 1H), 2.48-2.44 (m, 2H), 2.26-2.23 (m, 2H), 1.94-1.90 (m, 4H); LRMS (ES) m/z 358.5 (M$^+$+1).

Example 5: Compound 1580, N-(1-phenylcyclopentyl)-5-(5-(trifluoromethyl)-1,3,4-oxadiazol-2-yl)pyrimidin-2-amine

[Step 1] 2-((1-phenylcyclopentyl)amino)-N'-(2,2,2-trifluoroacetyl)pyrimidine-5-carbohydrazide

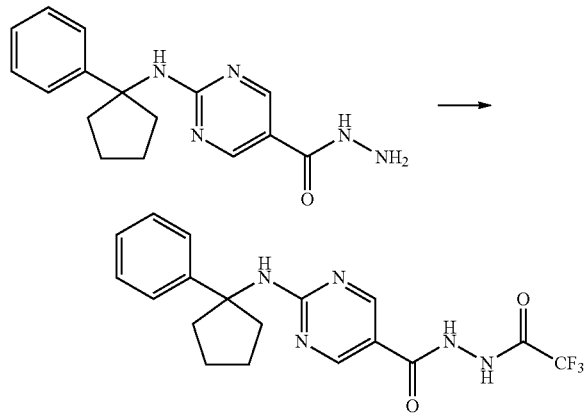

A solution of 2-((1-phenylcyclohexyl)amino)pyrimidine-5-carbohydrazide (0.150 g, 0.504 mmol) and triethylamine (0.105 mL, 0.757 mmol) in dichloromethane (4 mL) was mixed at the room temperature with trifluoroacetic anhydride (0.064 mL, 0.454 mmol). The reaction mixture prepared at the room temperature was stirred at the same temperature. And then saturated aqueous sodium bicarbonate was added to the filtrate, followed by extraction with dichloromethane The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 60%) to give 2-((1-phenylcyclopentyl)amino)-N'-(2,2,2-trifluoroacetyl)pyrimidine-5-carbohydrazide as white solid (0.145 g, 73.1%).

[Step 2] Compound 1580

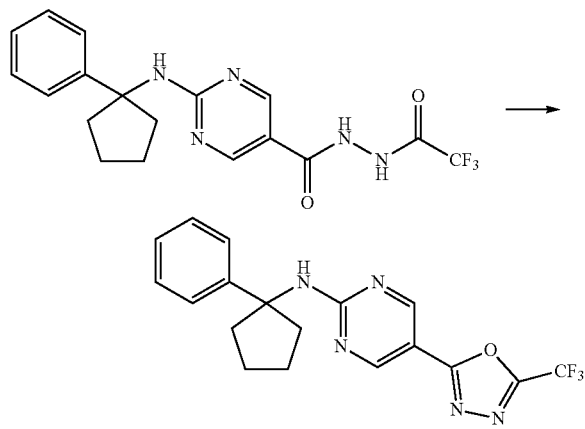

2-((1-phenylcyclopentyl)amino)-N'-(2,2,2-trifluoroacetyl)pyrimidine-5-carbohydrazide (0.150 g, 0.385 mmol) and 1-methoxy-N-triethylammoniosulfonyl-methanimidate (Burgess reagent, 0.138 g, 0.578 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-phenylcyclopentyl)-5-(5-(trifluoromethyl)-1,3,4-oxadiazol-2-yl)pyrimidin-2-amine as white solid (0.010 g, 6.9%).

$^1$H NMR (400 MHz, CDCl$_3$) δ 8.89 (s, 1H), 8.79 (s, 1H), 7.46-7.43 (m, 2H), 7.33-7.29 (m, 2H), 7.25-2.21 (m, 1H), 6.23 (s, 1H), 2.48-2.43 (m, 2H), 2.27-2.23 (m, 2H), 1.92-1.90 (m, 4H); LRMS (ES) m/z 376.5 (M$^+$+1).

Example 6: Compound 1581, 5-(5-(difluoromethyl)-1,3,4-oxadiazol-2-yl)-N-(1-phenylcyclohexyl)pyrimidin-2-amine

[Step 1] 1-Phenylcyclohexane-1-carbonitrile

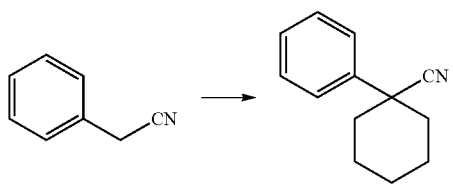 [SMILES: N#CCc1ccccc1 ; N#CC1(c2ccccc2)CCCCC1]

A solution of phenylacetonitrile (2.000 g, 17.072 mmol) and 1,5-dibromopentane (2.036 mL, 17.072 mmol) in N,N-dimethylformamide (100 mL) was stirred at 0° C. for 30 min, and mixed with sodium hydride (60.00%, 1.502 g, 37.559 mmol). The reaction mixture was stirred at 50° C. for additional 17 hr, cooled down to the room temperature, and partitioned between ethyl acetate and water. The organic layer was washed with aqueous saturated sodium chloride solution, dried with anhydrous MgSO$_4$ filtered, and concentrated in vacuo. 1-phenylcyclohexane-1-carbonitrile was used without further purification (3.370 g, 115.3%, brown oil).

[Step 2] 1-Phenylcyclohexane-1-carboxamide

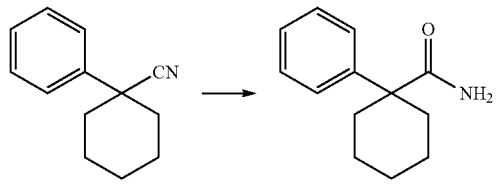 [SMILES: N#CC1(c2ccccc2)CCCCC1 ; NC(=O)C1(c2ccccc2)CCCCC1]

A neat mixture of 1-phenylcyclohexane-1-carbonitrile (1.660 g, 8.960 mmol) and poly phosphoric acid (5 mL) was stirred at the room temperature and then at 110° C. for additional 17 hr, cooled down to the room temperature to terminate the reaction. And then, the mixture slowly poured to saturated aqueous sodium bicarbonate solution (300 mL) at 0° C., and then extraction with ethyl acetate. The organic layer was washed with aqueous saturated sodium chloride solution, dried with anhydrous MgSO₄, filtered, and concentrated in vacuo. The concentrate was diluted with ethyl acetate (10 mL) and stirred at the ambient temperature. The resulting precipitates were collected by filtration, washed by ethyl acetate and dried to give 1-phenylcyclohexane-1-carboxamide as white solid (1.090 g, 59.8%).

[Step 3] 1-Phenylcyclohexan-1-amine hydrochloride

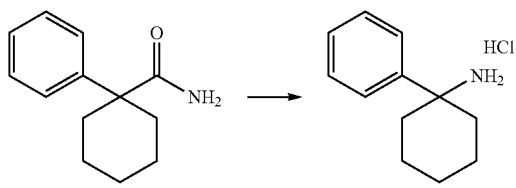 [SMILES: NC(=O)C1(c2ccccc2)CCCCC1 ; NC1(c2ccccc2)CCCCC1 ; Cl]

A solution of 1-phenylcyclohexane-1-carboxamide (1.090 g, 5.362 mmol) and sodium hydroxide (3.00 M solution in water, 5.004 mL, 15.013 mmol) in 1-butanol (30 mL) was stirred at 0° C. for 1 hr, and mixed with sodium hypochlorite (11.00%, 5.080 g, 7.507 mmol). The reaction mixture was stirred at the room temperature for additional 17 hr. And then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was diluted with ethyl acetate and hydrochloric acid (4.00 M solution, 2.011 mL, 8.043 mmol) and stirred at the ambient temperature. The resulting precipitates were collected by filtration, washed by ethyl acetate and dried to give 1-phenylcyclohexan-1-amine hydrochloride as white solid (0.536 g, 47.2%).

[Step 4] Ethyl 2-((1-phenylcyclohexyl)amino)pyrimidine-5-carboxylate

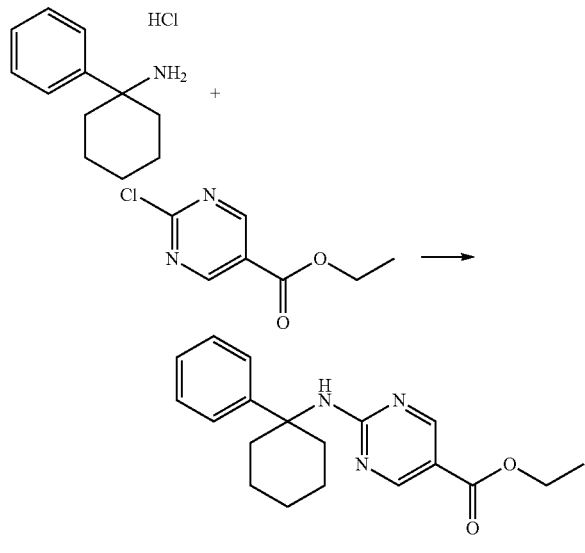

1-phenylcyclohexan-1-amine hydrochloride (0.536 g, 2.532 mmol), ethyl 2-chloropyrimidine-5-carboxylate (0.496 g, 2.658 mmol) and N,N-diisopropylethylamine (2.205 mL, 12.658 mmol) were mixed at the room temperature in 1,4-dioxane (10 mL) and then stirred at 90° C. for 17 hr, and cooled down to the room temperature to terminate the reaction. And then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=5% to 15%) to give ethyl 2-((1-phenylcyclohexyl)amino)pyrimidine-5-carboxylate as yellow oil (0.372 g, 45.2%).

[Step 5] 2-((1-phenylcyclohexyl)amino)pyrimidine-5-carbohydrazide

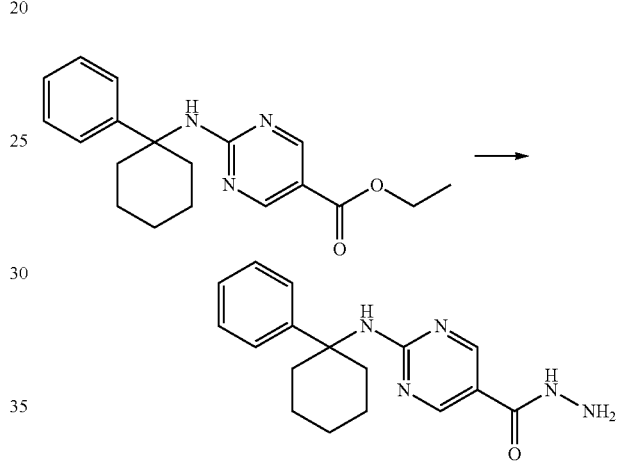

Ethyl 2-((1-phenylcyclohexyl)amino)pyrimidine-5-carboxylate (0.372 g, 1.143 mmol) and hydrazine monohydrate (1.111 mL, 22.863 mmol) in ethanol (3 mL) was mixed at the room temperature, heated at 120° C. under the microwaves for 1 hr, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-phenylcyclohexyl)amino)pyrimidine-5-carbohydrazide was used without further purification (0.342 g, 96.1%, pale yellow solid).

[Step 6] N'-(2,2-difluoroacetyl)-2-((1-phenylcyclohexyl)amino)pyrimidine-5-carbohydrazide

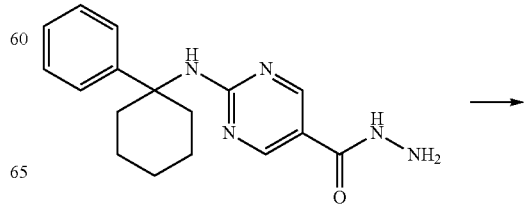

-continued

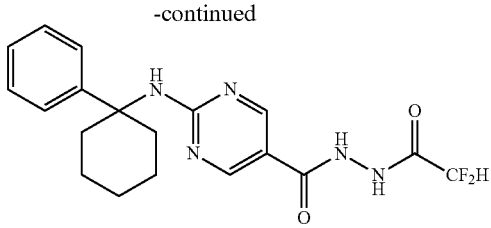

A solution of 2-((1-phenylcyclohexyl)amino)pyrimidine-5-carbohydrazide (0.170 g, 0.546 mmol) and triethylamine (0.114 mL, 0.819 mmol) in dichloromethane (4 mL) was mixed at the room temperature with 2,2-difluoroacetic anhydride (0.086 g, 0.491 mmol). The reaction mixture was stirred at the same temperature for 1 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 60%) to give N'-(2,2-difluoroacetyl)-2-((1-phenylcyclohexyl)amino)pyrimidine-5-carbohydrazide as white solid (0.205 g, 96.4%).

[Step 7] Compound 1581

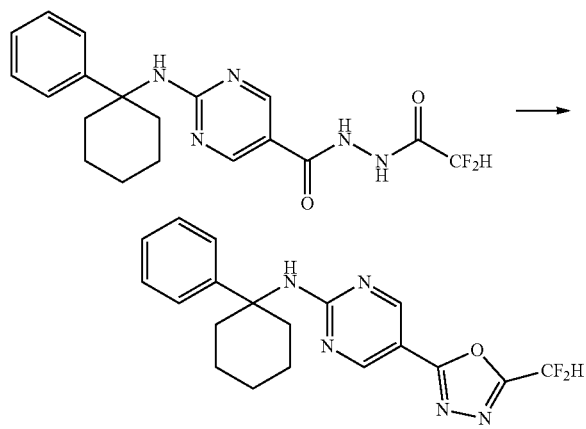

N'-(2,2-difluoroacetyl)-2-((1-phenylcyclohexyl)amino)pyrimidine-5-carbohydrazide (0.215 g, 0.552 mmol) and 1-methoxy-N-triethylammoniosulfonyl-methanimidate (Burgess reagent, 0.197 g, 0.828 mmol) in tetrahydrofuran (4 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give 5-(5-(difluoromethyl)-1,3,4-oxadiazol-2-yl)-N-(1-phenylcyclohexyl)pyrimidin-2-amine as white solid (0.065 g, 31.7%).

$^1$H NMR (400 MHz, CDCl$_3$) δ 8.92 (s, 1H), 8.73 (s, 1H), 7.46-7.43 (m, 2H), 7.33-7.28 (m, 2H), 7.25-7.21 (m, 1H), 7.01-6.75 (m, 1H), 6.11 (s, 1H), 2.54 (d, J=13.5 Hz, 2H), 1.94 (td, J=13.1, 3.7 Hz, 2H), 1.81-1.60 (m, 5H), 1.42-1.29 (m, 1H); LRMS (ES) m/z 372.3 (M$^+$+1).

Example 7: Compound 1582, N-(1-phenylcyclohexyl)-5-(5-(trifluoromethyl)-1,3,4-oxadiazol-2-yl)pyrimidin-2-amine

[Step 1] 2-((1-phenylcyclohexyl)amino)-N'-(2,2,2-trifluoroacetyl)pyrimidine-5-carbohydrazide

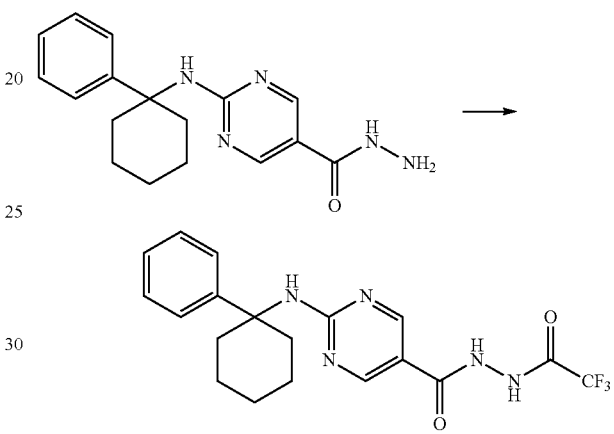

A solution of 2-((1-phenylcyclohexyl)amino)pyrimidine-5-carbohydrazide (0.170 g, 0.546 mmol) and triethylamine (0.114 mL, 0.819 mmol) in dichloromethane (4 mL) was mixed at the room temperature with trifluoroacetic anhydride (0.069 mL, 0.491 mmol). The reaction mixture was stirred at the same temperature for 1 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 60%) to give 2-((1-phenylcyclohexyl)amino)-N'-(2,2,2-trifluoroacetyl)pyrimidine-5-carbohydrazide as white solid (0.180 g, 80.9%).

[Step 2] Compound 1582

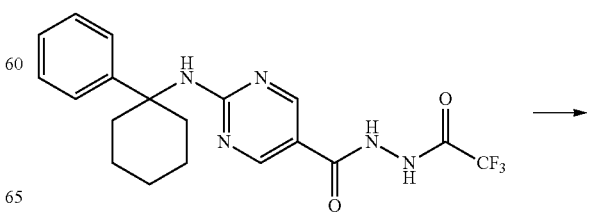

-continued

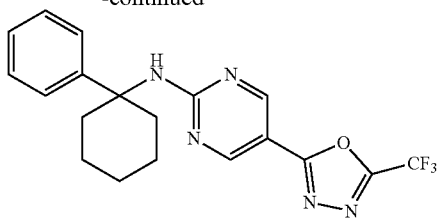

2-((1-phenylcyclohexyl)amino)-N'-(2,2,2-trifluoroacetyl)pyrimidine-5-carbohydrazide (0.180 g, 0.442 mmol) and 1-methoxy-N-triethylammoniosulfonyl-methanimidate (Burgess reagent, 0.158 g, 0.663 mmol) in tetrahydrofuran (4 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-phenylcyclohexyl)-5-(5-(trifluoromethyl)-1,3,4-oxadiazol-2-yl)pyrimidin-2-amine as pale yellow solid (0.020 g, 11.6%).

$^1$H NMR (400 MHz, CDCl$_3$) δ 8.91 (s, 1H), 8.73 (s, 1H), 7.44 (d, J=9.4 Hz, 2H), 7.32 (t, J=7.7 Hz, 2H), 7.25-7.21 (m, 1H), 6.15 (s, 1H), 2.54 (d, J=13.7 Hz, 2H), 1.94 (td, J=13.1, 3.7 Hz, 2H), 1.81-1.60 (m, 5H), 1.43-1.36 (m, 1H); LRMS (ES) m/z 390.3 (M$^+$+1).

Example 8: Compound 1603, 5-(5-(difluoromethyl)-1,3,4-oxadiazol-2-yl)-N-(1-(4-methoxyphenyl)cyclobutyl)pyrimidin-2-amine

[Step 1]
1-(4-methoxyphenyl)cyclobutane-1-carbonitrile

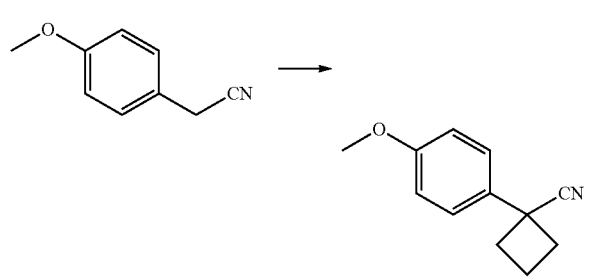

A solution of 2-(4-methoxyphenyl)acetonitrile (5.000 g, 33.972 mmol) and sodium hydride (60.00%, 2.989 g, 74.738 mmol) in N,N-dimethylformamide (100 mL) was mixed at 0° C. with 1,3-dibromopropane (3.447 mL, 33.972 mmol), stirred at the room temperature for 17 hr, and quenched at the room temperature by the addition of saturated aqueous sodium bicarbonate solution (10 mL, 10 min stirring). The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 5%) to give 1-(4-methoxyphenyl)cyclobutane-1-carbonitrile as white solid (1.760 g, 27.7%).

[Step 2]
1-(4-methoxyphenyl)cyclobutane-1-carboxamide

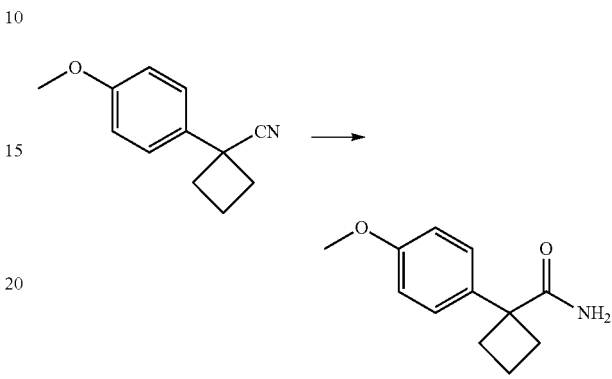

A solution of 1-(4-methoxyphenyl)cyclobutane-1-carbonitrile (1.760 g, 9.400 mmol), sodium hydroxide (25.00%, 0.376 g, 2.350 mmol), hydrogen peroxide (30.00%, 3.197 g, 28.199 mmol) and tetra-n-butylammonium bromide (0.030 g, 0.094 mmol) in methanol (150 mL) prepared at the room temperature was stirred at the same temperature for 17 hr Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(4-methoxyphenyl)cyclobutane-1-carboxamide was used without further purification (1.810 g, 93.8%, white solid).

[Step 3] 1-(4-methoxyphenyl)cyclobutan-1-amine hydrochloride

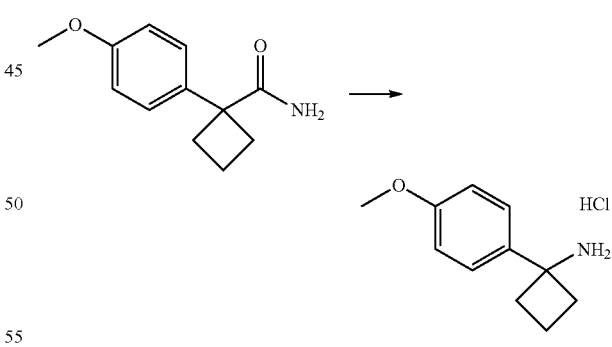

A solution of 1-(4-methoxyphenyl)cyclobutane-1-carboxamide (1.810 g, 8.818 mmol), sodium hypochlorite (11.00% solution, 6.904 mL, 12.345 mmol) and sodium hydroxide (3.00 M solution in water, 8.230 mL, 24.691 mmol) in 1-butanol (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and hydrochloric acid (4.00 M solution in 1,4-dioxane, 3.307 mL, 13.227 mmol) and stirred at the ambient temperature. The resulting precipitates were collected by filtration, washed by ethyl acetate and dried to give 1-(4-methoxyphenyl)cyclobutan-1-amine hydrochloride as white solid (0.546 g, 29.0%).

[Step 4] Ethyl 2-((1-(4-methoxyphenyl)cyclobutyl)amino)pyrimidine-5-carboxylate

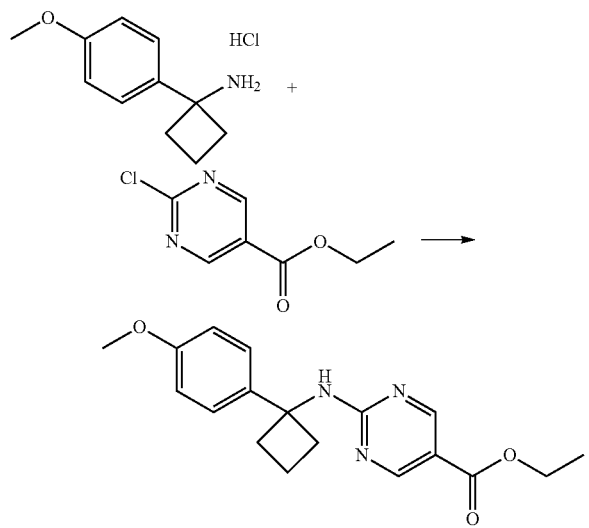

1-(4-methoxyphenyl)cyclobutan-1-amine hydrochloride (0.546 g, 2.555 mmol), ethyl 2-chloropyrimidine-5-carboxylate (0.501 g, 2.683 mmol) and N,N-diisopropylethylamine (2.225 mL, 12.774 mmol) were mixed at the room temperature in 1,4-dioxane (10 mL), stirred at 110° C. for 17 hr, and then cooled down to the room temperature to terminate the reaction. The reaction mixture was concentrated under the reduced pressure to remove the solvent. And then the concentrate was purified and concentrated by column chromatography (SiO$_2$, 12 g cartridge; ethyl acetate/hexane=0% to 10%) to give ethyl 2-((1-(4-methoxyphenyl)cyclobutyl)amino)pyrimidine-5-carboxylate as yellow solid (0.239 g, 28.6%).

[Step 5] 2-((1-(4-methoxyphenyl)cyclobutyl)amino)pyrimidine-5-carbohydrazide

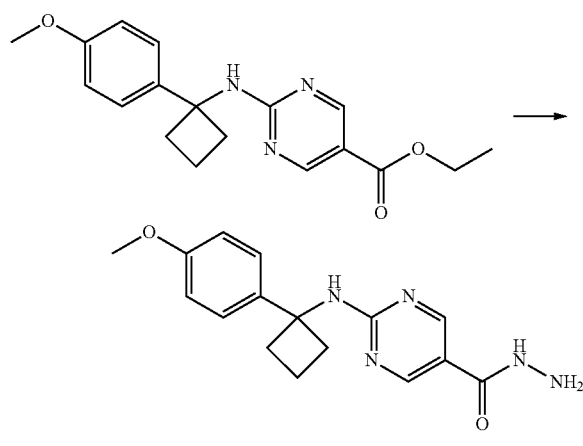

Ethyl 2-((1-(4-methoxyphenyl)cyclobutyl)amino)pyrimidine-5-carboxylate (0.478 g, 1.460 mmol) and hydrazine monohydrate (1.419 mL, 29.202 mmol) were mixed at the room temperature in ethanol (4 mL), stirred at 120° C. for 17 hr, and cooled down to the room temperature to terminate the reaction. The reaction mixture was concentrated under the reduced pressure to remove the solvent. And then, the precipitates were collected by filtration, washed by ethanol, and dried to give 2-((1-(4-methoxyphenyl)cyclobutyl)amino)pyrimidine-5-carbohydrazide as white solid (0.433 g, 94.6%).

[Step 6] N'-(2,2-difluoroacetyl)-2-((1-(4-methoxyphenyl)cyclobutyl)amino)pyrimidine-5-carbohydrazide

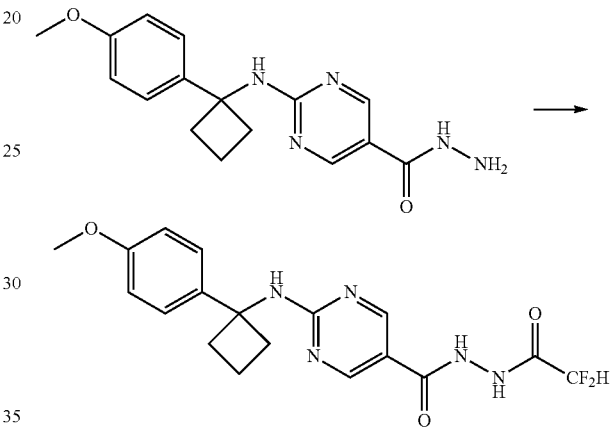

A solution of 2-((1-(4-methoxyphenyl)cyclobutyl)amino)pyrimidine-5-carbohydrazide (0.100 g, 0.319 mmol) and triethylamine (0.067 mL, 0.479 mmol) in dichloromethane (10 mL) was mixed at the room temperature with 2,2-difluoroacetic anhydride (0.031 mL, 0.287 mmol), stirred at the same temperature for 48 hr. Saturated aqueous sodium bicarbonate solution was added to the concentrate, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 70%) to give N'-(2,2-difluoroacetyl)-2-((1-(4-methoxyphenyl)cyclobutyl)amino)pyrimidine-5-carbohydrazide as white solid (0.040 g, 32.0%).

[Step 7] Compound 1603

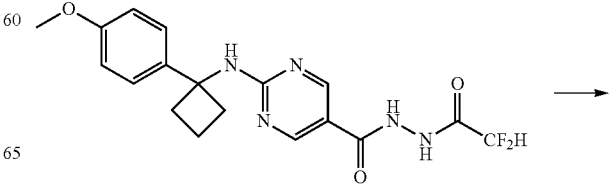

-continued

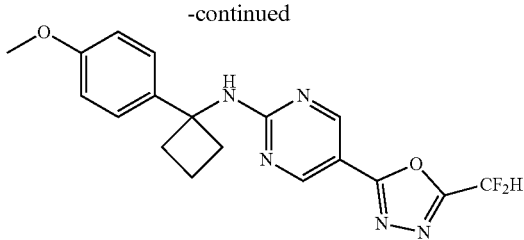

N'-(2,2-difluoroacetyl)-2-((1-(4-methoxyphenyl)cyclobutyl)amino)pyrimidine-5-carbohydrazide (0.040 g, 0.102 mmol) and 1-methoxy-N-triethylammoniosulfonyl-methanimidate (Burgess reagent, 0.037 g, 0.153 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give 5-(5-(difluoromethyl)-1,3,4-oxadiazol-2-yl)-N-(1-(4-methoxyphenyl)cyclobutyl)pyrimidin-2-amine as white solid (0.022 g, 57.7%).

$^1$H NMR (400 MHz, CDCl$_3$) δ 8.89 (s, 2H), 7.45 (d, J=8.8 Hz, 2H), 7.20-6.76 (m, 3H), 6.40 (s, 1H), 3.81 (s, 3H), 2.76-2.70 (m, 2H), 2.65-2.58 (m, 2H), 2.20-2.13 (m, 1H), 2.07-1.96 (m, 1H); LRMS (ES) m/z 374.4 (M$^+$+1).

Example 9: Compound 1604, N-(1-(4-methoxyphenyl)cyclobutyl)-5-(5-(trifluoromethyl)-1,3,4-oxadiazol-2-yl)pyrimidin-2-amine

[Step 1] 2-((1-(4-methoxyphenyl)cyclobutyl)amino)-N'-(2,2,2-trifluoroacetyl)pyrimidine-5-carbohydrazide

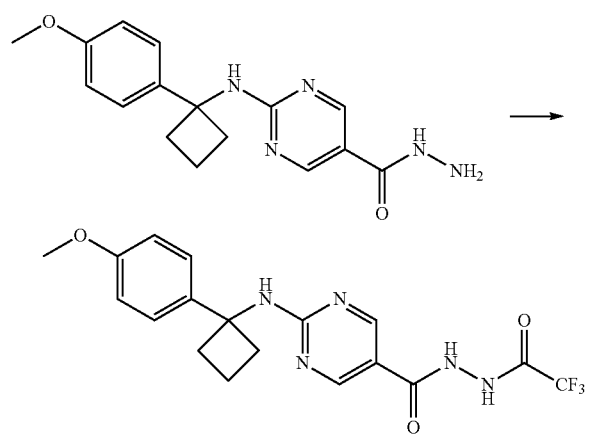

A solution of 2-((1-(4-methoxyphenyl)cyclobutyl)amino)pyrimidine-5-carbohydrazide (0.204 g, 0.651 mmol) and triethylamine (0.136 mL, 0.977 mmol) in dichloromethane (10 mL) was mixed at the room temperature with trifluoroacetic anhydride (0.083 mL, 0.586 mmol), and stirred at the same temperature for 48 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 60%) to give 2-((1-(4-methoxyphenyl)cyclobutyl)amino)-N'-(2,2,2-trifluoroacetyl)pyrimidine-5-carbohydrazide as white solid (0.057 g, 21.4%).

[Step 2] Compound 1604

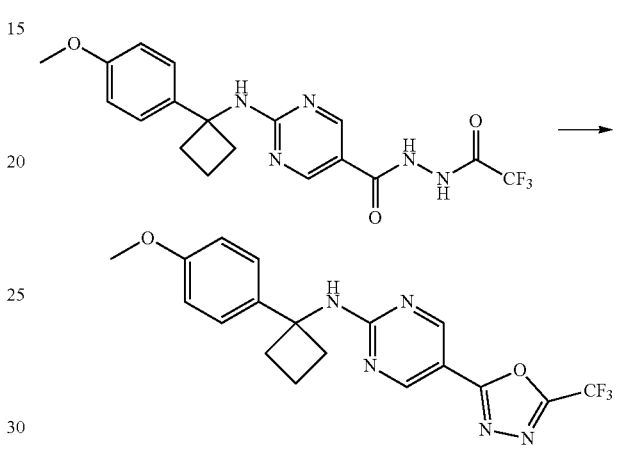

2-((1-(4-methoxyphenyl)cyclobutyl)amino)-N'-(2,2,2-trifluoroacetyl)pyrimidine-5-carbohydrazide (0.057 g, 0.139 mmol) and 1-methoxy-N-triethylammoniosulfonyl-methanimidate (Burgess reagent, 0.050 g, 0.209 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(4-methoxyphenyl)cyclobutyl)-5-(5-(trifluoromethyl)-1,3,4-oxadiazol-2-yl)pyrimidin-2-amine as white solid (0.008 g, 14.7%).

$^1$H NMR (400 MHz, CDCl$_3$) δ 8.88 (s, 2H), 7.44 (d, J=8.8 Hz, 2H), 6.88 (d, J=8.8 Hz, 2H), 6.41 (s, 1H), 3.81 (s, 3H), 2.77-2.70 (m, 2H), 2.65-2.58 (m, 2H), 2.21-2.13 (m, 1H), 2.01-1.94 (m, 1H); LRMS (ES) m/z 392.4 (M$^+$+1).

Example 10: Compound 1605, 5-(5-(difluoromethyl)-1,3,4-oxadiazol-2-yl)-N-(1-(3-methoxyphenyl)cyclobutyl)pyrimidin-2-amine

[Step 1] 1-(3-methoxyphenyl)cyclobutane-1-carbonitrile

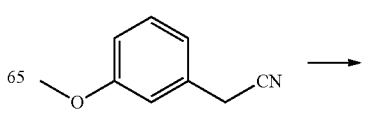

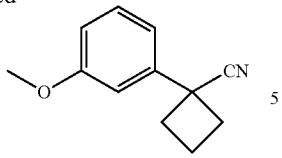

A solution of 2-(3-methoxyphenyl)acetonitrile (5.000 g, 33.972 mmol) and sodium hydride (60.00%, 2.989 g, 74.738 mmol) in N,N-dimethylformamide (100 mL) was mixed at 0° C. with 1,3-dibromopropane (3.447 mL, 33.972 mmol), stirred at the room temperature for 17 hr, and quenched at the room temperature by the addition of saturated aqueous sodium bicarbonate solution (10 mL, 10 min stirring). The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 5%) to give 1-(3-methoxyphenyl)cyclobutane-1-carbonitrile as colorless oil (2.810 g, 44.2%).

[Step 2] 1-(3-methoxyphenyl)cyclobutane-1-carboxamide

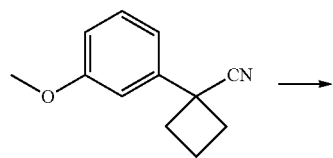

A solution of 1-(3-methoxyphenyl)cyclobutane-1-carbonitrile (2.810 g, 15.007 mmol), sodium hydroxide (25.00%, 0.600 g, 3.752 mmol), hydrogen peroxide (30.00%, 5.105 g, 45.022 mmol) and tetra-n-butylammonium bromide (0.048 g, 0.150 mmol) in methanol (150 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(3-methoxyphenyl)cyclobutane-1-carboxamide was used without further purification (1.970 g, 64.0%, white solid).

[Step 3] 1-(3-methoxyphenyl)cyclobutan-1-amine hydrochloride

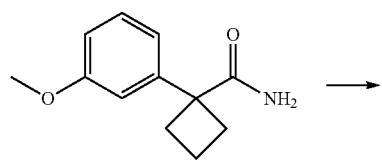

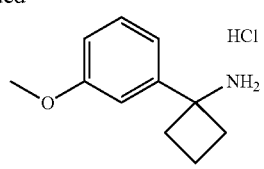

A solution of 1-(3-methoxyphenyl)cyclobutane-1-carboxamide (1.970 g, 9.598 mmol), sodium hypochlorite (11.00% solution, 7.515 mL, 13.437 mmol) and sodium hydroxide (3.00 M solution in water, 8.958 mL, 26.873 mmol) in 1-butanol (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and hydrochloric acid (4.00 M solution in 1,4-dioxane, 3.599 mL, 14.396 mmol) and stirred at the ambient temperature. The resulting precipitates were collected by filtration, washed by ethyl acetate and dried to give 1-(3-methoxyphenyl)cyclobutan-1-amine hydrochloride as white solid (1.070 g, 52.2%).

[Step 4] Ethyl 2-((1-(3-methoxyphenyl)cyclobutyl)amino)pyrimidine-5-carboxylate

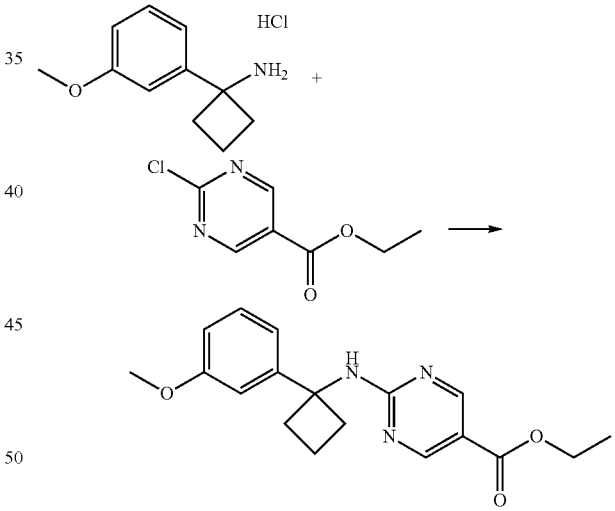

1-(3-methoxyphenyl)cyclobutan-1-amine hydrochloride (1.070 g, 5.007 mmol), ethyl 2-chloropyrimidine-5-carboxylate (0.981 g, 5.257 mmol) and N,N-diisopropylethylamine (4.360 mL, 25.034 mmol) were mixed at the room temperature in 1,4-dioxane (10 mL), stirred at 110° C. for 17 hr, and then cooled down to the room temperature to terminate the reaction. The reaction mixture was concentrated under the reduced pressure to remove the solvent. And then, the concentrate was purified and concentrated by column chromatography (SiO$_2$, 12 g cartridge; ethyl acetate/hexane=0% to 10%) to give ethyl 2-((1-(3-methoxyphenyl)cyclobutyl)amino)pyrimidine-5-carboxylate as yellow solid (1.140 g, 69.5%).

[Step 5] 2-((1-(3-methoxyphenyl)cyclobutyl)amino)pyrimidine-5-carbohydrazide

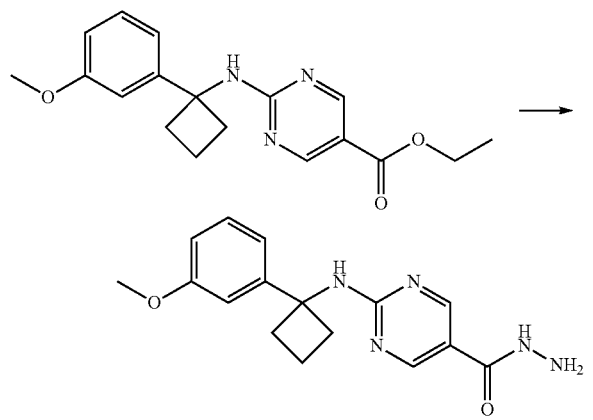

Ethyl 2-((1-(3-methoxyphenyl)cyclobutyl)amino)pyrimidine-5-carboxylate (1.140 g, 3.482 mmol) and hydrazine monohydrate (3.385 mL, 69.644 mmol) were mixed at the room temperature in ethanol (4 mL), stirred at 120° C. for 17 hr, and cooled down to the room temperature to terminate the reaction. The reaction mixture was concentrated under the reduced pressure to remove the solvent. And then, the precipitates were collected by filtration, washed by ethanol, and dried to give 2-((1-(3-methoxyphenyl)cyclobutyl)amino)pyrimidine-5-carbohydrazide as white solid (0.636 g, 58.3%).

[Step 6] N'-(2,2-difluoroacetyl)-2-((1-(3-methoxyphenyl)cyclobutyl)amino)pyrimidine-5-carbohydrazide

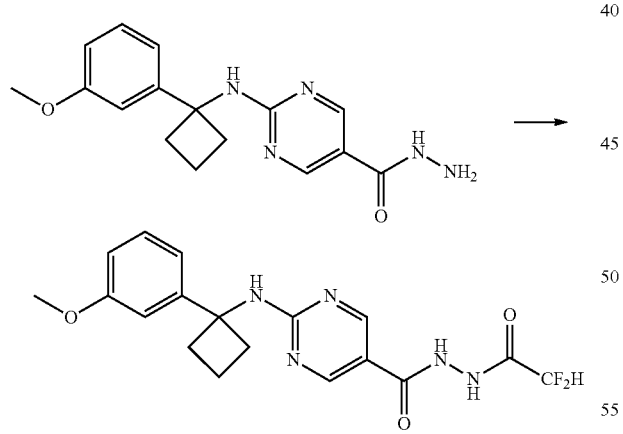

A solution of 2-((1-(3-methoxyphenyl)cyclobutyl)amino)pyrimidine-5-carbohydrazide (0.336 g, 1.072 mmol) and triethylamine (0.224 mL, 1.608 mmol) in dichloromethane (10 mL) was mixed at the room temperature with 2,2-difluoroacetic anhydride (0.105 mL, 0.965 mmol), and stirred at the same temperature for 48 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; ethyl acetate/hexane=0% to 70%) to give N'-(2,2-difluoroacetyl)-2-((1-(3-methoxyphenyl)cyclobutyl)amino)pyrimidine-5-carbohydrazide as white solid (0.103 g, 24.5%).

[Step 7] Compound 1605

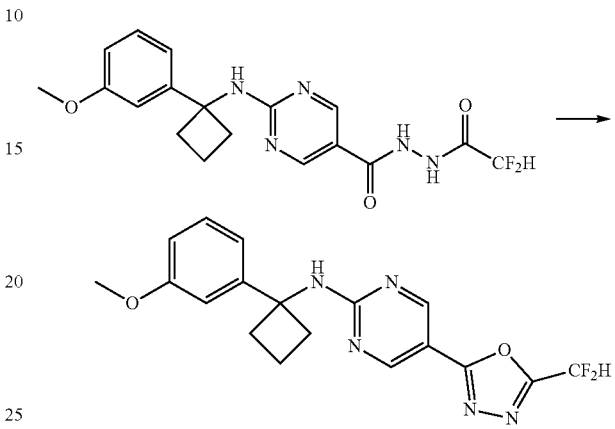

N'-(2,2-difluoroacetyl)-2-((1-(3-methoxyphenyl)cyclobutyl)amino)pyrimidine-5-carbohydrazide (0.100 g, 0.256 mmol) and hydrochloric acid (0.010 g, 0.268 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; ethyl acetate/hexane=0% to 20%) to give 5-(5-(difluoromethyl)-1,3,4-oxadiazol-2-yl)-N-(1-(3-methoxyphenyl)cyclobutyl)pyrimidin-2-amine as white solid (0.056 g, 58.7%).

¹H NMR (400 MHz, CDCl₃) δ 8.88 (s, 2H), 7.29-7.25 (m, 1H), 7.12-7.08 (m, 2H), 7.02-6.76 (m, 2H), 6.61 (s, 1H), 3.82 (s, 3H), 2.79-2.72 (m, 2H), 2.65-2.58 (m, 2H), 2.22-2.15 (m, 1H), 2.07-1.98 (m, 1H); LRMS (ES) m/z 374.4 (M⁺+1).

Example 11: Compound 1606, N-(1-(3-methoxyphenyl)cyclobutyl)-5-(5-(trifluoromethyl)-1,3,4-oxadiazol-2-yl)pyrimidin-2-amine

[Step 1] 2-((1-(3-methoxyphenyl)cyclobutyl)amino)-N'-(2,2,2-trifluoroacetyl)pyrimidine-5-carbohydrazide

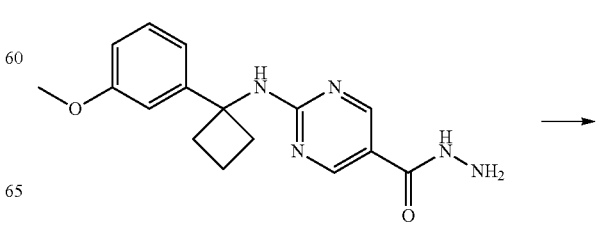

-continued

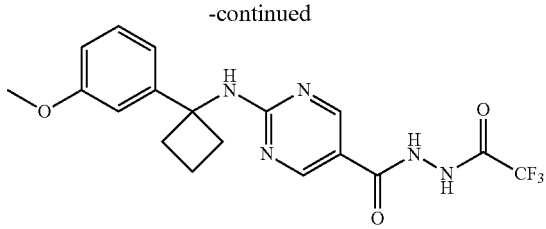

A solution of 2-((1-(3-methoxyphenyl)cyclobutyl)amino)pyrimidine-5-carbohydrazide (0.300 g, 0.957 mmol) and triethylamine (0.200 mL, 1.436 mmol) in dichloromethane (10 mL) was mixed at the room temperature with trifluoroacetic anhydride (0.122 mL, 0.862 mmol), stirred at the same temperature for 48 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 60%) to give 2-((1-(3-methoxyphenyl)cyclobutyl)amino)-N'-(2,2,2-trifluoroacetyl)pyrimidine-5-carbohydrazide as white solid (0.080 g, 20.4%).

[Step 2] Compound 1606

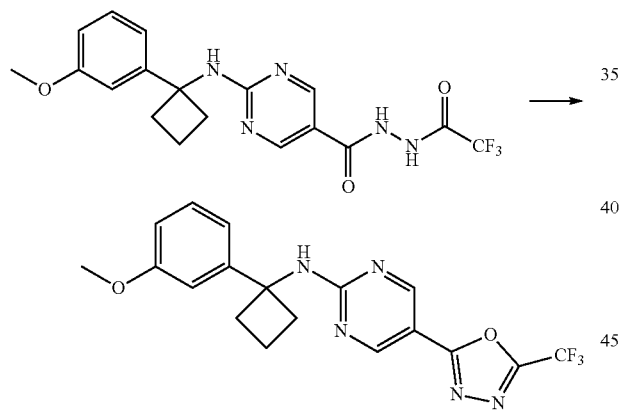

2-((1-(3-methoxyphenyl)cyclobutyl)amino)-N'-(2,2,2-trifluoroacetyl)pyrimidine-5-carbohydrazide (0.423 g, 1.033 mmol) and 1-methoxy-N-triethylammoniosulfonyl-methanimidate (Burgess reagent, 37.00%, 0.998 g, 1.550 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(3-methoxyphenyl)cyclobutyl)-5-(5-(trifluoromethyl)-1,3,4-oxadiazol-2-yl)pyrimidin-2-amine as white solid (0.049 g, 12.1%).

$^1$H NMR (400 MHz, CDCl$_3$) δ 8.88 (s, 1H), 7.29-7.25 (m, 1H), 7.11-7.07 (m, 2H), 6.81-6.78 (m, 1H), 6.48 (s, 1H), 3.82 (s, 3H), 2.79-2.72 (m, 2H), 2.65-2.58 (m, 2H), 2.20-2.00 (m, 1H); LRMS (ES) m/z 392.1 (M$^+$+1).

Example 12: Compound 1607, 5-(5-(difluoromethyl)-1,3,4-oxadiazol-2-yl)-N-(1-(3-fluorophenyl)cyclobutyl)pyrimidin-2-amine

[Step 1]
1-(3-fluorophenyl)cyclobutane-1-carbonitrile

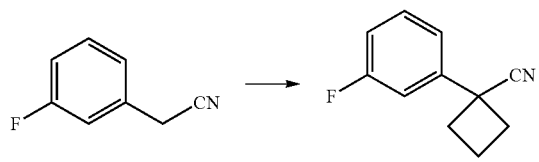 [SMILES: N#CCc1cccc(F)c1 ; N#CC1(c2cccc(F)c2)CCC1]

A solution of 2-(3-fluorophenyl)acetonitrile (6.000 g, 44.398 mmol) and sodium hydride (2.344 g, 97.676 mmol) in N,N-dimethylformamide (200 mL) was mixed at 0° C. with 1,3-dibromopropane (4.504 mL, 44.398 mmol), stirred at 50° C. for 17 hr, cooled down to the room temperature, and quenched at 0° C. by the addition of saturated aqueous sodium bicarbonate solution (10 mL, 10 min stirring). The reaction mixture was concentrated under the reduced pressure to remove the solvent. Then, water was added to the reaction mixture, followed by extraction with hexane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(3-fluorophenyl)cyclobutane-1-carbonitrile as colorless oil (4.270 g, 54.9%).

[Step 2]
1-(3-fluorophenyl)cyclobutane-1-carboxamide

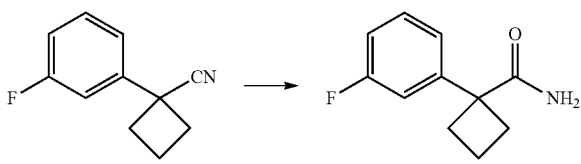 [SMILES: N#CC1(c2cccc(F)c2)CCC1 ; NC(=O)C1(c2cccc(F)c2)CCC1]

A solution of 1-(3-fluorophenyl)cyclobutane-1-carbonitrile (2.400 g, 13.698 mmol), sodium hydroxide (25.00%, 0.548 g, 3.424 mmol), hydrogen peroxide (30.00%, 4.659 g, 41.094 mmol) and tetra-n-butylammonium bromide (0.044 g, 0.137 mmol) in methanol (150 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(3-fluorophenyl)cyclobutane-1-carboxamide was used without further purification (2.200 g, 83.1%, white solid).

[Step 3] 1-(3-fluorophenyl)cyclobutan-1-amine hydrochloride

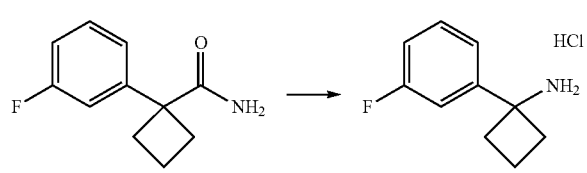 [SMILES: NC(=O)C1(c2cccc(F)c2)CCC1 ; NC1(c2cccc(F)c2)CCC1 ; Cl]

A solution of 1-(3-fluorophenyl)cyclobutane-1-carboxamide (4.200 g, 21.737 mmol), sodium hypochlorite (11.00% solution, 17.019 mL, 30.432 mmol) and sodium hydroxide (3.00 M solution in water, 20.288 mL, 60.863 mmol) in 1-butanol (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and hydrochloric acid (4.00 M solution in 1,4-dioxane, 8.151 mL, 32.605 mmol) and stirred at the ambient temperature. The resulting precipitates were collected by filtration, washed by ethyl acetate and dried to give 1-(3-fluorophenyl)cyclobutan-1-amine hydrochloride as white solid (2.390 g, 54.5%).

[Step 4] Ethyl 2-((1-(3-fluorophenyl)cyclobutyl)amino)pyrimidine-5-carboxylate

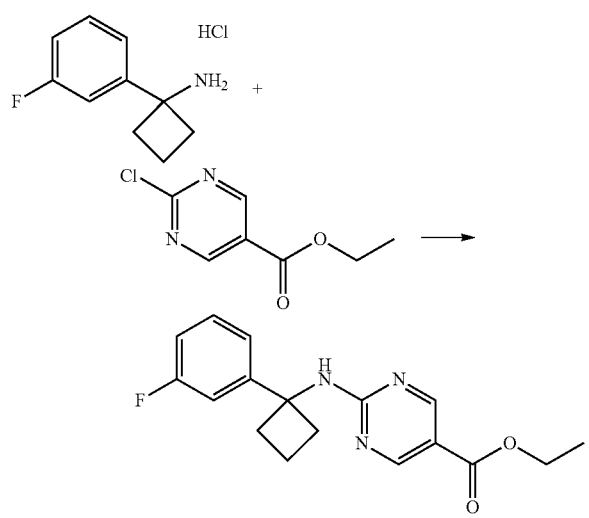

1-(3-fluorophenyl)cyclobutan-1-amine hydrochloride (0.609 g, 3.020 mmol), ethyl 2-chloropyrimidine-5-carboxylate (0.592 g, 3.171 mmol) and N,N-diisopropylethylamine (2.630 mL, 15.099 mmol) were mixed at the room temperature in 1,4-dioxane (10 mL), stirred at 110° C. for 17 hr, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=0% to 10%) to give ethyl 2-((1-(3-fluorophenyl)cyclobutyl)amino)pyrimidine-5-carboxylate as white solid (1.390 g, 146.0%).

[Step 5] 2-((1-(3-fluorophenyl)cyclobutyl)amino)pyrimidine-5-carbohydrazide

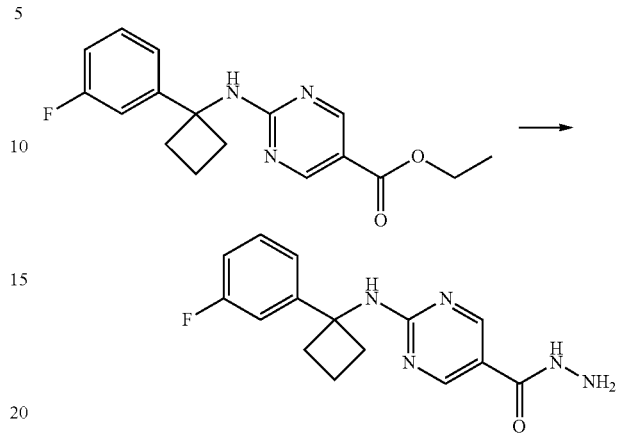

Ethyl 2-((1-(3-fluorophenyl)cyclobutyl)amino)pyrimidine-5-carboxylate (1.390 g, 4.408 mmol) and hydrazine monohydrate (4.285 mL, 88.156 mmol) were mixed at the room temperature in ethanol (4 mL), stirred at 120° C. for 17 hr, and cooled down to the room temperature to terminate the reaction. The reaction mixture was concentrated under the reduced pressure to remove the solvent. The precipitates were collected by filtration, washed by ethanol, and dried to give 2-((1-(3-fluorophenyl)cyclobutyl)amino)pyrimidine-5-carbohydrazide as white solid (0.932 g, 70.2%).

[Step 6] N'-(2,2-difluoroacetyl)-2-((1-(3-fluorophenyl)cyclobutyl)amino)pyrimidine-5-carbohydrazide

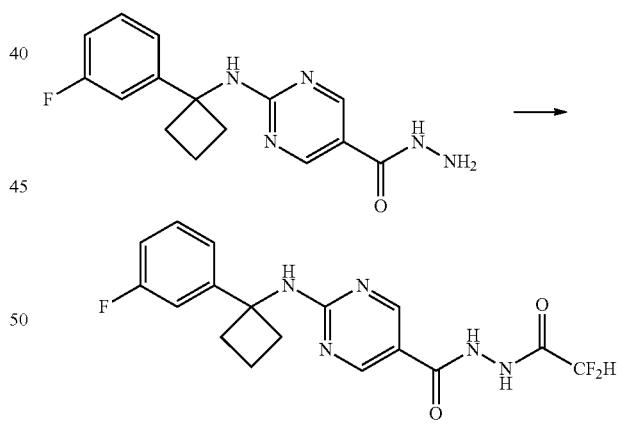

A solution of 2-((1-(3-fluorophenyl)cyclobutyl)amino)pyrimidine-5-carbohydrazide (0.500 g, 1.659 mmol) and triethylamine (0.347 mL, 2.489 mmol) in dichloromethane (10 mL) was mixed at the room temperature with 2,2-difluoroacetic anhydride (0.162 mL, 1.493 mmol), and stirred at the same temperature for 48 hr. Saturated aqueous sodium bicarbonate solution was added to the reaction mixture, followed by extraction with dichloromethane The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 70%) to give N'-(2,2-difluoroacetyl)-2-((1-(3-fluorophenyl)cyclobutyl) amino)pyrimidine-5-carbohydrazide as white solid (0.112 g, 17.8%).

[Step 7] Compound 1607

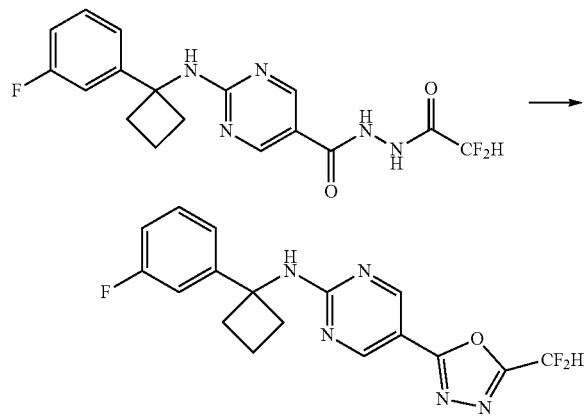

N'-(2,2-difluoroacetyl)-2-((1-(3-fluorophenyl)cyclobutyl) amino)pyrimidine-5-carbohydrazide (0.112 g, 0.295 mmol) and 1-methoxy-N-triethylammoniosulfonyl-methanimidate (Burgess reagent, 0.106 g, 0.443 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give 5-(5-(difluoromethyl)-1,3,4-oxadiazol-2-yl)-N-(1-(3-fluorophenyl)cyclobutyl)pyrimidin-2-amine as white solid (0.012 g, 11.2%).

$^1$H NMR (400 MHz, CDCl$_3$) δ 8.89 (s, 1H), 7.34-7.27 (m, 2H), 7.24-7.21 (m, 1H), 7.02-6.76 (m, 2H), 6.49 (s, 1H), 2.77-2.70 (m, 2H), 2.63-2.56 (m, 2H), 2.25-2.17 (m, 1H), 2.07-2.00 (m, 1H); LRMS (ES) m/z 362.4 (M$^+$+1).

Example 13: Compound 1608, N-(1-(3-fluorophenyl)cyclobutyl)-5-(5-(trifluoromethyl)-1,3,4-oxadiazol-2-yl)pyrimidin-2-amine

[Step 1] 2-((1-(3-fluorophenyl)cyclobutyl)amino)-N'-(2,2,2-trifluoroacetyl)pyrimidine-5-carbohydrazide

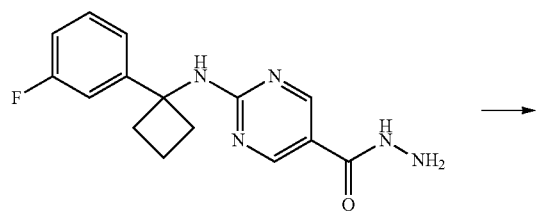

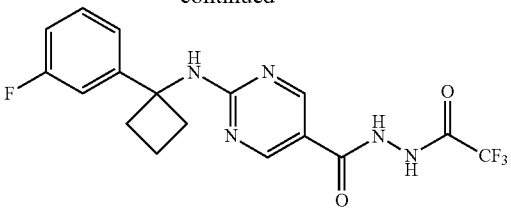

A solution of 2-((1-(3-fluorophenyl)cyclobutyl)amino) pyrimidine-5-carbohydrazide (0.432 g, 1.434 mmol) and triethylamine (0.300 mL, 2.150 mmol) in dichloromethane (10 mL) was mixed at the room temperature with trifluoroacetic anhydride (0.182 mL, 1.290 mmol), stirred at the same temperature for 48 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 60%) to give 2-((1-(3-fluorophenyl)cyclobutyl)amino)-N'-(2,2,2-trifluoroacetyl) pyrimidine-5-carbohydrazide as white solid (0.071 g, 12.5%).

[Step 2] Compound 1608

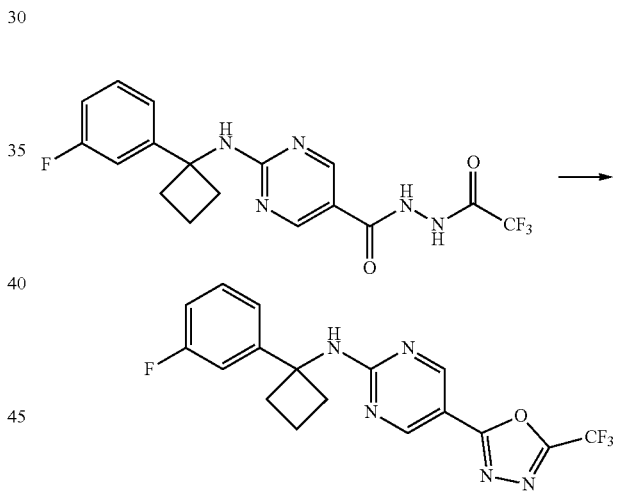

2-((1-(3-fluorophenyl)cyclobutyl)amino)-N'-(2,2,2-trifluoroacetyl)pyrimidine-5-carbohydrazide (0.071 g, 0.179 mmol) and 1-methoxy-N-triethylammoniosulfonyl-methanimidate (Burgess reagent, 0.064 g, 0.268 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(3-fluorophenyl)cyclobutyl)-5-(5-(trifluoromethyl)-1,3,4-oxadiazol-2-yl)pyrimidin-2-amine as white solid (0.040 g, 59.0%).

$^1$H NMR (400 MHz, CDCl$_3$) δ 8.92 (s, 1H), 8.87 (s, 1H), 7.32-7.27 (m, 2H), 7.24-7.21 (m, 1H), 6.97-6.92 (m, 1H), 6.42 (s, 1H), 2.78-2.71 (m, 2H), 2.63-2.56 (m, 2H), 2.25-2.17 (m, 1H), 2.07-2.00 (m, 1H); LRMS (ES) m/z 380.4 (M$^+$+1).

Example 14: Compound 1609, 5-(5-(difluoromethyl)-1,3,4-oxadiazol-2-yl)-N-(1-(2-fluorophenyl)cyclobutyl)pyrimidin-2-amine

[Step 1] 1-(2-fluorophenyl)cyclobutane-1-carbonitrile

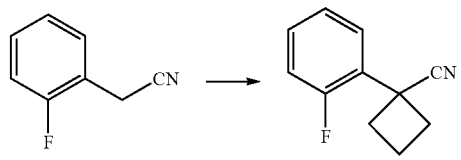 [SMILES: N#CCc1ccccc1F ; N#CC1(c2ccccc2F)CCC1]

A solution of 2-(2-fluorophenyl)acetonitrile (3.000 g, 22.199 mmol) and sodium hydride (60.00%, 1.953 g, 48.838 mmol) in N,N-dimethylformamide (150 mL) was mixed at 0° C. with 1,3-dibromopropane (2.253 mL, 22.199 mmol), stirred at 50° C. for 17 hr, cooled down to the room temperature, and quenched at 0° C. by the addition of saturated aqueous sodium bicarbonate solution (10 mL, 10 min stirring). The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(2-fluorophenyl)cyclobutane-1-carbonitrile as coloreless oil (2.000 g, 51.4%).

[Step 2] 1-(2-fluorophenyl)cyclobutane-1-carboxamide

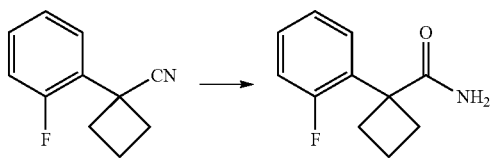 [SMILES: N#CC1(c2ccccc2F)CCC1 ; NC(=O)C1(c2ccccc2F)CCC1]

A solution of 1-(2-fluorophenyl)cyclobutane-1-carbonitrile (1.760 g, 10.045 mmol), sodium hydroxide (25.00%, 0.402 g, 2.511 mmol), hydrogen peroxide (30.00%, 3.417 g, 30.135 mmol) and tetra-n-butylammonium bromide (0.032 g, 0.100 mmol) in methanol (150 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(2-fluorophenyl)cyclobutane-1-carboxamide was used without further purification (1.760 g, 90.7%, white solid).

[Step 3] 1-(2-fluorophenyl)cyclobutan-1-amine hydrochloride

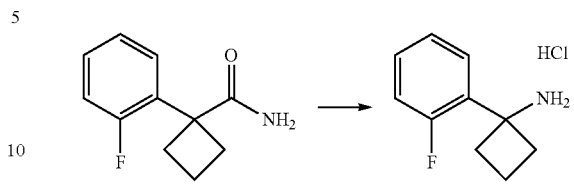

A solution of 1-(2-fluorophenyl)cyclobutane-1-carboxamide (1.760 g, 9.109 mmol), sodium hypochlorite (11.00% solution, 7.132 mL, 12.752 mmol) and sodium hydroxide (3.00 M solution in water, 8.502 mL, 25.505 mmol) in 1-butanol (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and hydrochloric acid (4.00 M solution in 1,4-dioxane, 3.416 mL, 13.663 mmol) and stirred at the ambient temperature. The resulting precipitates were collected by filtration, washed by ethyl acetate and dried to give 1-(2-fluorophenyl)cyclobutan-1-amine hydrochloride as white solid (0.609 g, 33.2%).

[Step 4] Ethyl 2-((1-(2-fluorophenyl)cyclobutyl)amino)pyrimidine-5-carboxylate

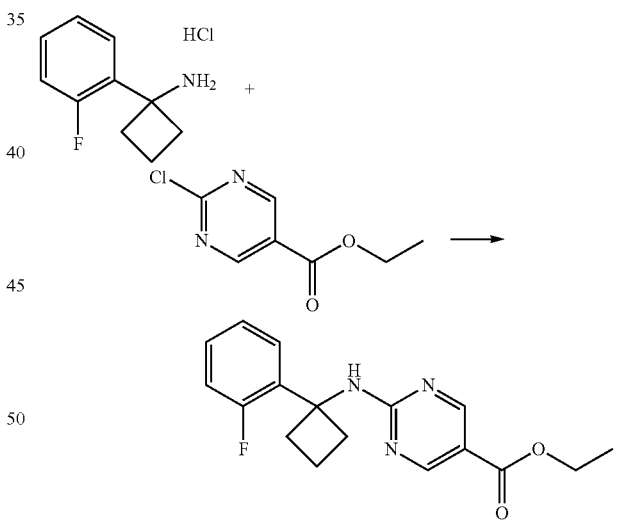

1-(2-fluorophenyl)cyclobutan-1-amine hydrochloride (0.609 g, 3.020 mmol), ethyl 2-chloropyrimidine-5-carboxylate (0.592 g, 3.171 mmol) and N,N-diisopropylethylamine (2.630 mL, 15.099 mmol) were mixed at the room temperature in 1,4-dioxane (10 mL), stirred at 110° C. for 17 hr, and then cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=0% to 10%) to give ethyl 2-((1-(2-fluorophenyl)cyclobutyl)amino)pyrimidine-5-carboxylate as white solid (0.565 g, 59.3%).

[Step 5] 2-((1-(2-fluorophenyl)cyclobutyl)amino)pyrimidine-5-carbohydrazide

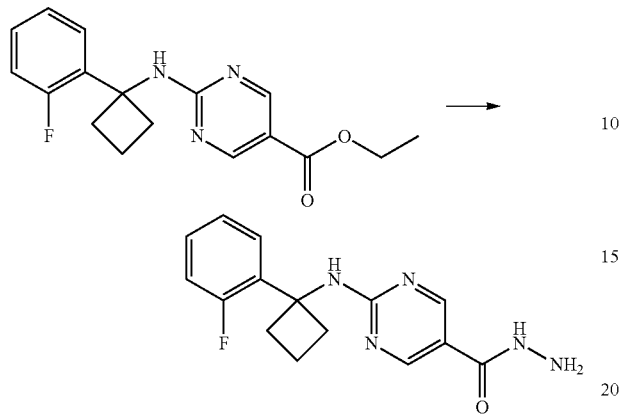

Ethyl 2-((1-(2-fluorophenyl)cyclobutyl)amino)pyrimidine-5-carboxylate (0.565 g, 1.792 mmol) and hydrazine monohydrate (1.742 mL, 35.833 mmol) were mixed at the room temperature in ethanol (4 mL), stirred at 120° C. for 17 hr, and then cooled down to the room temperature to terminate the reaction. The reaction mixture was concentrated under the reduced pressure to remove the solvent. The precipitates were collected by filtration, washed by ethanol, and dried to give 2-((1-(2-fluorophenyl)cyclobutyl)amino)pyrimidine-5-carbohydrazide as white solid (0.350 g, 64.8%).

[Step 6] N'-(2,2-difluoroacetyl)-2-((1-(2-fluorophenyl)cyclobutyl)amino)pyrimidine-5-carbohydrazide

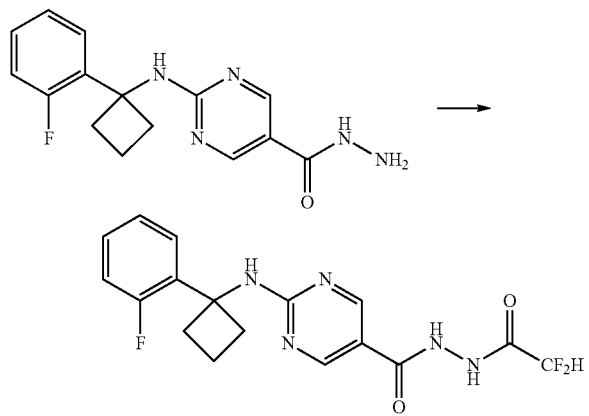

A solution of 2-((1-(2-fluorophenyl)cyclobutyl)amino)pyrimidine-5-carbohydrazide (0.200 g, 0.664 mmol) and triethylamine (0.139 mL, 0.996 mmol) in dichloromethane (10 mL) was mixed at the room temperature with 2,2-difluoroacetic anhydride (0.065 mL, 0.597 mmol), and stirred at the same temperature for 48 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 70%) to give N'-(2,2-difluoroacetyl)-2-((1-(2-fluorophenyl)cyclobutyl)amino)pyrimidine-5-carbohydrazide as white solid (0.062 g, 24.6%).

[Step 7] Compound 1609

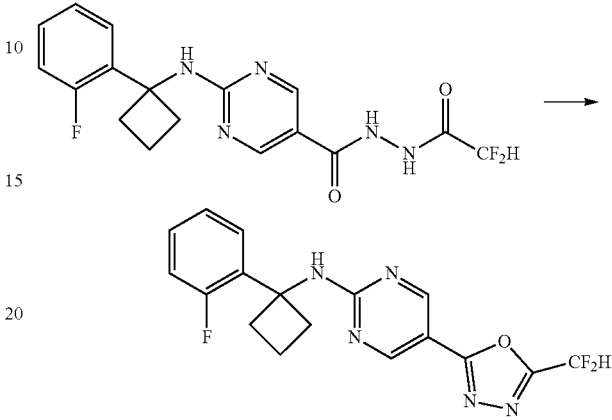

N'-(2,2-difluoroacetyl)-2-((1-(2-fluorophenyl)cyclobutyl)amino)pyrimidine-5-carbohydrazide (0.062 g, 0.163 mmol) and 1-methoxy-N-triethylammoniosulfonyl-methanimidate (Burgess reagent, 0.058 g, 0.245 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give 5-(5-(difluoromethyl)-1,3,4-oxadiazol-2-yl)-N-(1-(2-fluorophenyl)cyclobutyl)pyrimidin-2-amine as white solid (0.008 g, 13.5%).

$^1$H NMR (400 MHz, CDCl$_3$) δ 8.90 (s, 2H), 7.64 (td, J=7.9, 1.8 Hz, 1H), 7.26-7.20 (m, 1H), 7.12 (td, J=7.5, 1.3 Hz, 1H), 7.03-6.76 (m, 2H), 6.52 (s, 1H), 2.87-2.80 (m, 2H), 2.68-2.61 (m, 2H), 2.20-2.19 (m, 1H), 2.00-1.93 (m, 1H); LRMS (ES) m/z 362.4 (M$^+$+1).

Example 15: Compound 1610, N-(1-(2-fluorophenyl)cyclobutyl)-5-(5-(trifluoromethyl)-1,3,4-oxadiazol-2-yl)pyrimidin-2-amine

[Step 1] 2-((1-(2-fluorophenyl)cyclobutyl)amino)-N'-(2,2,2-trifluoroacetyl)pyrimidine-5-carbohydrazide

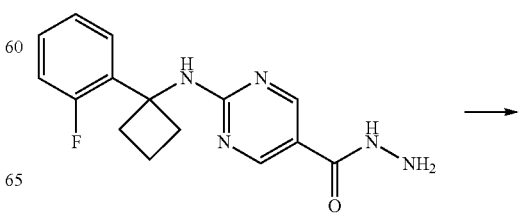

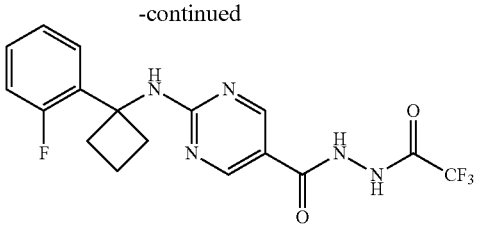

A solution of 2-((1-(2-fluorophenyl)cyclobutyl)amino)pyrimidine-5-carbohydrazide (0.150 g, 0.498 mmol) and triethylamine (0.104 mL, 0.747 mmol) in dichloromethane (10 mL) was mixed at the room temperature with trifluoroacetic anhydride (0.063 mL, 0.448 mmol), stirred at the same temperature for 48 hr Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 60%) to give 2-((1-(2-fluorophenyl)cyclobutyl)amino)-N'-(2,2,2-trifluoroacetyl)pyrimidine-5-carbohydrazide as white solid (0.037 g, 18.7%).

[Step 2] Compound 1610

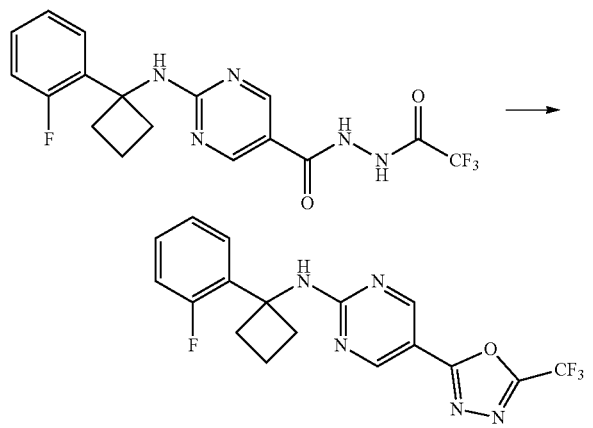

2-((1-(2-fluorophenyl)cyclobutyl)amino)-N'-(2,2,2-trifluoroacetyl)pyrimidine-5-carbohydrazide (0.037 g, 0.093 mmol) and 1-methoxy-N-triethylammoniosulfonyl-methanimidate (Burgess reagent, 0.033 g, 0.140 mmol) in tetrahydrofuran (3 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(2-fluorophenyl)cyclobutyl)-5-(5-(trifluoromethyl)-1,3,4-oxadiazol-2-yl)pyrimidin-2-amine as white solid (0.005 g, 14.2%).

$^1$H NMR (400 MHz, CDCl$_3$) δ 8.87 (s, 2H), 7.64 (td, J=8.0, 1.5 Hz, 1H), 7.24-7.20 (m, 1H), 7.12 (t, J=7.5 Hz, 1H), 7.03-6.98 (m, 1H), 2.87-2.80 (m, 2H), 2.68-2.61 (m, 2H), 2.28-2.17 (m, 1H), 2.07-1.93 (m, 1H); LRMS (ES) m/z 380.4 (M$^+$+1).

Example 16: Compound 1611, 5-(5-(difluoromethyl)-1,3,4-oxadiazol-2-yl)-N-(1-(4-fluorophenyl)cyclobutyl)pyrimidin-2-amine

[Step 1]
1-(4-fluorophenyl)cyclobutane-1-carbonitrile

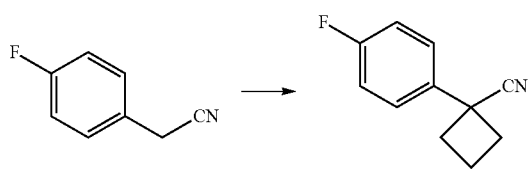 [SMILES: N#CCc1ccc(F)cc1 ; N#CC1(c2ccc(F)cc2)CCC1]

A solution of 2-(4-fluorophenyl)acetonitrile (5.000 g, 36.999 mmol) and sodium hydride (60.00%, 3.255 g, 81.397 mmol) in N,N-dimethylformamide (100 mL) was mixed at 0° C. with 1,3-dibromopropane (3.773 mL, 36.999 mmol), stirred at the room temperature for 17 hr, and quenched at the room temperature by the addition of saturated aqueous sodium bicarbonate solution (10 mL, 10 min stirring)). The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 5%) to give 1-(4-fluorophenyl)cyclobutane-1-carbonitrile as colorless oil (3.420 g, 52.8%).

[Step 2]
1-(4-fluorophenyl)cyclobutane-1-carboxamide

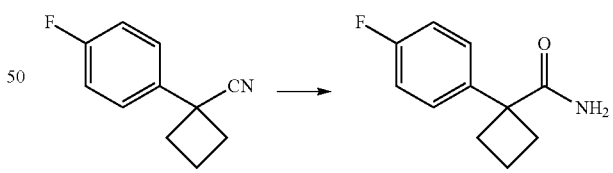

A solution of 1-(4-fluorophenyl)cyclobutane-1-carbonitrile (3.420 g, 19.519 mmol), sodium hydroxide (25.00%, 0.781 g, 4.880 mmol), hydrogen peroxide (30.00%, 6.640 g, 58.558 mmol) and tetra-n-butylammonium bromide (0.063 g, 0.195 mmol) in methanol (50 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(4-fluorophenyl)cyclobutane-1-carboxamide was used without further purification (3.190 g, 84.6%, white solid).

[Step 3] 1-(4-fluorophenyl)cyclobutan-1-amine hydrochloride

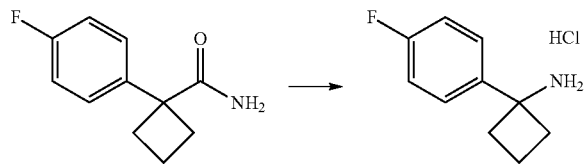 [SMILES: NC(=O)C1(c2ccc(F)cc2)CCC1 ; NC1(c2ccc(F)cc2)CCC1 ; Cl]

A solution of 1-(4-fluorophenyl)cyclobutane-1-carboxamide (3.119 g, 16.142 mmol), sodium hypochlorite (11.00% solution, 12.639 mL, 22.599 mmol) and sodium hydroxide (3.00 M solution in water, 15.066 mL, 45.198 mmol) in 1-butanol (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and hydrochloric acid (4.00 M solution in 1,4-dioxane, 6.053 mL, 24.213 mmol) and stirred at the ambient temperature. The resulting precipitates were collected by filtration, washed by ethyl acetate and dried to give 1-(4-fluorophenyl)cyclobutan-1-amine hydrochloride as white solid (2.380 g, 73.1%).

[Step 4] Ethyl 2-((1-(4-fluorophenyl)cyclobutyl)amino)pyrimidine-5-carboxylate

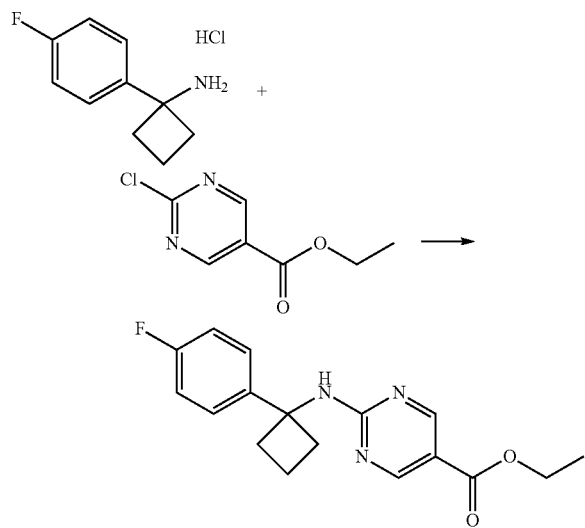

1-(4-fluorophenyl)cyclobutan-1-amine hydrochloride (1.000 g, 4.959 mmol), ethyl 2-chloroopyrimidine-5-carboxylate (0.972 g, 5.207 mmol) and N,N-diisopropylethylamine (1.296 mL, 7.438 mmol) were mixed at the room temperature in 1,4-dioxane (10 mL), stirred at 110° C. for 17 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=5% to 20%) to give ethyl 2-((1-(4-fluorophenyl)cyclobutyl)amino)pyrimidine-5-carboxylate as yellow solid (1.090 g, 69.7%).

[Step 5] 2-((1-(4-fluorophenyl)cyclobutyl)amino)pyrimidine-5-carbohydrazide

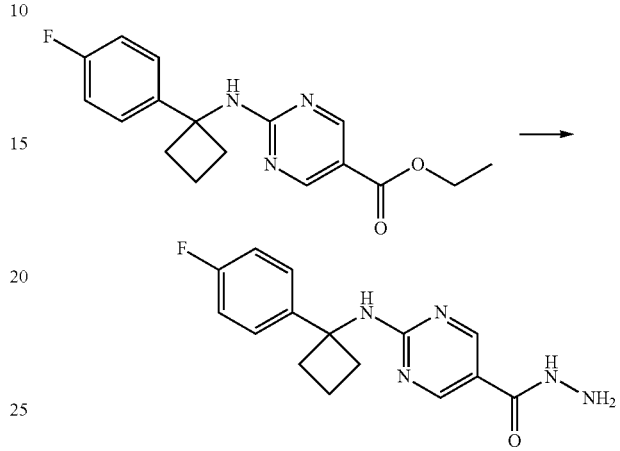

Ethyl 2-((1-(4-fluorophenyl)cyclobutyl)amino)pyrimidine-5-carboxylate (1.090 g, 3.456 mmol) and hydrazine monohydrate (3.360 mL, 69.130 mmol) in ethanol (10 mL) was mixed at the room temperature, heated at 120° C. under the microwaves for 1 hr, and cooled down to the room temperature to terminate reaction. The reaction mixture was concentrated under the reduced pressure to remove the solvent. The precipitates were collected by filtration, washed by ethanol, and dried to give 2-((1-(4-fluorophenyl)cyclobutyl)amino)pyrimidine-5-carbohydrazide as white solid (0.976 g, 93.7%).

[Step 6] N'-(2,2-difluoroacetyl)-2-((1-(4-fluorophenyl)cyclobutyl)amino)pyrimidine-5-carbohydrazide

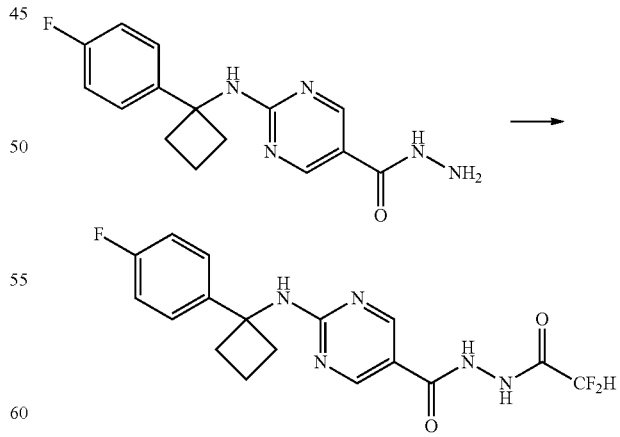

A solution of 2-((1-(4-fluorophenyl)cyclobutyl)amino)pyridine-5-carbohydrazide (0.500 g, 1.659 mmol) and triethylamine (0.347 mL, 2.489 mmol) in dichloromethane (8 mL) was mixed at the room temperature with 2,2-difluoroacetic anhydride (0.162 mL, 1.493 mmol), stirred at the same temperature for 17 hr. Saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; ethyl acetate/hexane=10% to 70%) to give N'-(2,2-difluoroacetyl)-2-((1-(4-fluorophenyl)cyclobutyl)amino)pyrimidine-5-carbohydrazide as white solid (0.226 g, 35.9%).

[Step 7] Compound 1611

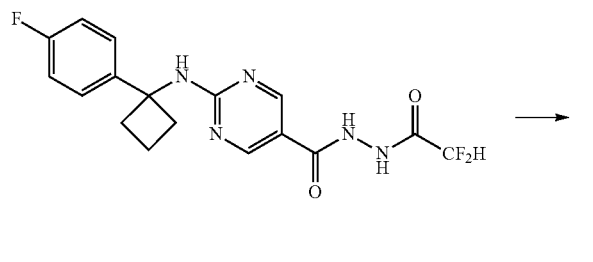

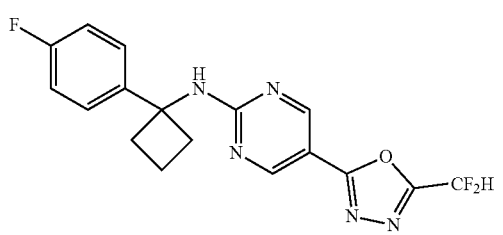

N'-(2,2-difluoroacetyl)-2-((1-(4-fluorophenyl)cyclobutyl)amino)pyrimidine-5-carbohydrazide (0.226 g, 0.596 mmol) and 1-methoxy-N-triethylammoniosulfonyl-methanimidate (Burgess reagent, 0.213 g, 0.894 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give 5-(5-(difluoromethyl)-1,3,4-oxadiazol-2-yl)-N-(1-(4-fluorophenyl)cyclobutyl)pyrimidin-2-amine as white solid (0.081 g, 37.6%).

$^1$H NMR (400 MHz, CDCl$_3$) δ 8.89 (s, 2H), 7.51-7.46 (m, 2H), 7.04-6.76 (m, 3H), 6.39 (s, 1H), 2.77-2.70 (m, 2H), 2.64-2.57 (m, 2H), 2.23-2.16 (m, 1H), 2.03-1.97 (m, 1H); LRMS (ES) m/z 362.2 (M$^+$+1).

Example 17: Compound 1612, N-(1-(4-fluorophenyl)cyclobutyl)-5-(5-(trifluoromethyl)-1,3,4-oxadiazol-2-yl)pyrimidin-2-amine

[Step 1]22-((1-(4-fluorophenyl)cyclobutyl)amino)-N'-(2,2,2-trifluoroacetyl)pyrimidine-5-carbohydrazide

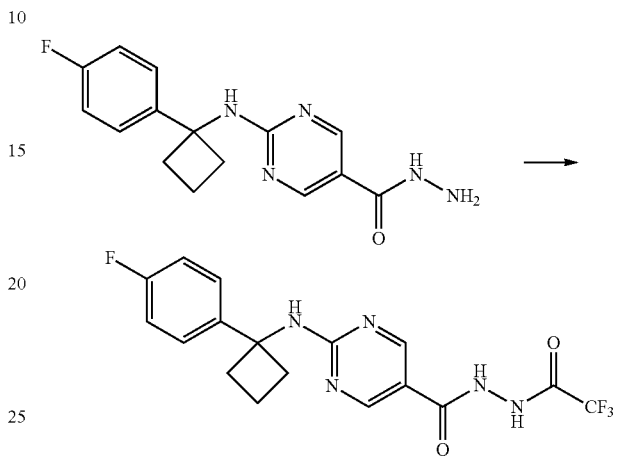

A solution of 2-((1-(4-fluorophenyl)cyclobutyl)amino)pyrimidine-5-carbohydrazide (0.476 g, 1.580 mmol) and triethylamine (0.330 mL, 2.369 mmol) in dichloromethane (8 mL) was mixed at the room temperature with trifluoroacetic anhydride (0.201 mL, 1.422 mmol), and stirred at the same temperature for 17 hr. Saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; ethyl acetate/hexane=10% to 70%) to give 2-((1-(4-fluorophenyl)cyclobutyl)amino)-N'-(2,2,2-trifluoroacetyl)pyrimidine-5-carbohydrazide as white solid (0.312 g, 49.7%).

[Step 2] Compound 1612

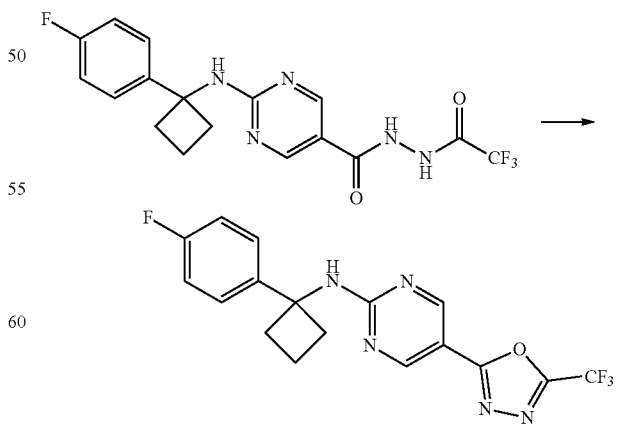

2-((1-(4-fluorophenyl)cyclobutyl)amino)-N'-(2,2,2-trifluoroacetyl)pyrimidine-5-carbohydrazide (8.000 g, 20.134 mmol) and 1-methoxy-N-triethylammoniosulfonyl-methanimidate (Burgess reagent, 7.197 g, 30.202 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(4-fluorophenyl)cyclobutyl)-5-(5-(trifluoromethyl)-1,3,4-oxadiazol-2-yl)pyrimidin-2-amine as white solid (0.062 g, 0.8%).

$^1$H NMR (400 MHz, CDCl$_3$) δ 8.88 (s, 2H), 7.50-7.47 (m, 2H), 7.02 (t, J=8.6 Hz, 2H), 6.41 (s, 1H), 7.77-7.70 (m, 2H), 2.64-2.57 (m, 2H), 2.23-2.16 (m, 1H), 2.03-1.97 (m, 1H); LRMS (ES) m/z 380.3 (M$^+$+1)

Example 18: Compound 1614, N-(1-(2-chlorophenyl)cyclobutyl)-5-(5-(difluoromethyl)-1,3,4-oxadiazol-2-yl)pyrimidin-2-amine

[Step 1]
1-(2-chlorophenyl)cyclobutane-1-carbonitrile

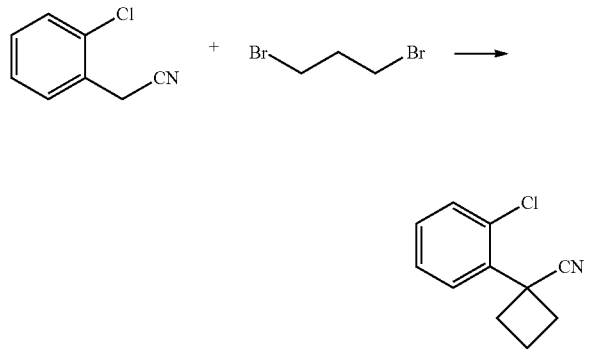

To a stirred solutTo a stirred solution of 2-(2-chlorophenyl)acetonitrile (3.000 g, 19.790 mmol) in N,N-dimethylformamide (20 mL) was added at 0° C. sodium hydride (0.950 g, 39.580 mmol). The reaction mixture was stirred at the same temperature for 30 min, treated at the room temperature with 1,3-dibromopropane (2.018 mL, 19.790 mmol), stirred for additional 12 hr. Saturated aqueous ammonium chloride solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give 1-(2-chlorophenyl)cyclobutane-1-carbonitrile as Colorless oil (1.470 g, 38.8%).

[Step 2]
1-(2-chlorophenyl)cyclobutane-1-carboxamide

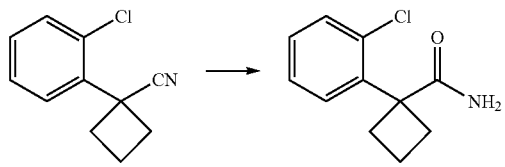 [SMILES: N#CC1(c2ccccc2Cl)CCC1 ; NC(=O)C1(c2ccccc2Cl)CCC1]

A solution of 1-(2-chlorophenyl)cyclobutane-1-carbonitrile (1.470 g, 7.670 mmol), tetra-n-butylammonium bromide (0.025 g, 0.077 mmol), sodium hydroxide (3.00 M solution, 7.670 mL, 23.009 mmol) and hydrogen peroxide (30.00% solution, 1.799 mL, 23.009 mmol) in methanol (10 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(2-chlorophenyl)cyclobutane-1-carboxamide, 1.450 g, 90.2%, White solid).

[Step 3] 1-(2-chlorophenyl)cyclobutan-1-amine hydrochloride

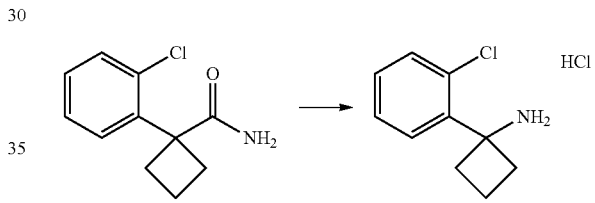

A solution of 1-(2-chlorophenyl)cyclobutane-1-carboxamide (1.450 g, 6.916 mmol), sodium hypochlorite (11.00% solution, 6.324 mL, 10.373 mmol) and sodium hydroxide (3.00 M solution, 6.916 mL, 20.747 mmol) in t-butanol (10 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with dichloromethane and then was added hydrochloric acid (4.00 M solution in Dioxane, 3.458 mL, 13.831 mmol) and stirred at the ambient temperature. The resulting precipitates were collected by filtration, washed by diethylether, and dried to give 1-(2-chlorophenyl)cyclobutan-1-amine as White solid (0.800 g, 63.7%).

[Step 4] ethyl 2-((1-(2-chlorophenyl)cyclobutyl)amino)pyrimidine-5-carboxylate

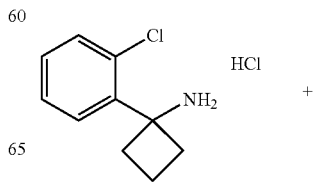

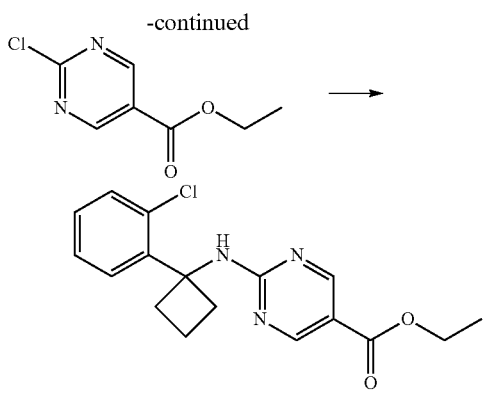

A solution of 1-(2-chlorophenyl)cyclobutan-1-amine hydrochloride (0.400 g, 2.202 mmol), ethyl 2-chloropyrimidine-5-carboxylate (0.411 g, 2.202 mmol) and N,N-diisopropylethylamine (0.767 mL, 4.404 mmol) in 1,4-dioxane (10 mL) was stirred at 80° C. for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give ethyl 2-((1-(2-chlorophenyl)cyclobutyl)amino)pyrimidine-5-carboxylate as Colorless oil (0.500 g, 68.4%).

[Step 5] 2-((1-(2-chlorophenyl)cyclobutyl)amino)pyrimidine-5-carbohydrazide

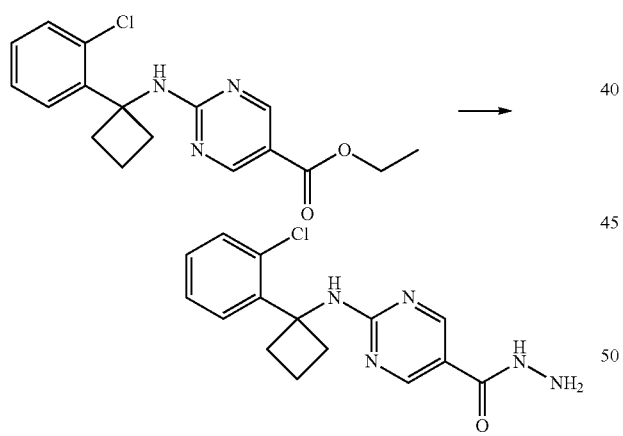

A mixture of ethyl 2-((1-(2-chlorophenyl)cyclobutyl)amino)pyrimidine-5-carboxylate (0.500 g, 1.507 mmol) and Hydrazine monohydrate (1.465 mL, 30.139 mmol) in ethanol (10 mL) was heated at 120° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (2-((1-(2-chlorophenyl)cyclobutyl)amino)pyrimidine-5-carbohydrazide, 0.250 g, 52.2%, White solid).

[Step 6] 2-((1-(2-chlorophenyl)cyclobutyl)amino)-N'-(2,2-difluoroacetyl)pyrimidine-5-carbohydrazide

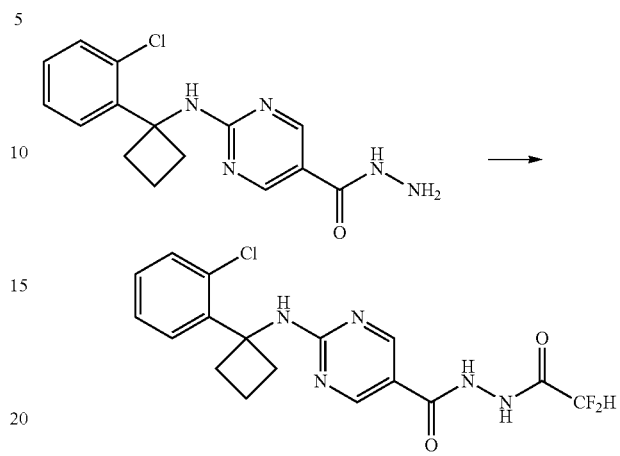

A solution of 2-((1-(2-chlorophenyl)cyclobutyl)amino)pyrimidine-5-carbohydrazide (0.127 g, 0.400 mmol), 2,2-difluoroacetic anhydride (0.039 mL, 0.360 mmol) and triethylamine (0.084 mL, 0.599 mmol) in dichloromethane (10 mL) prepared at the room temperature was stirred at the same temperature for 1 hr. And then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 100%) to give 2-((1-(2-chlorophenyl)cyclobutyl)amino)-N'-(2,2-difluoroacetyl)pyrimidine-5-carbohydrazide as Colorless oil (0.050 g, 31.6%).

[Step 7] Compound 1614

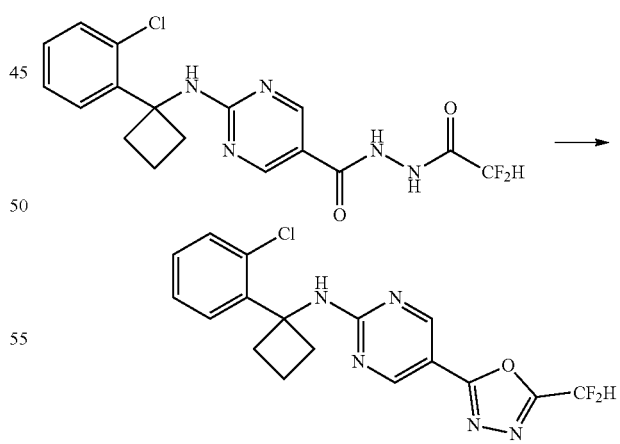

A mixture of 2-((1-(2-chlorophenyl)cyclobutyl)amino)-N'-(2,2-difluoroacetyl)pyrimidine-5-carbohydrazide (0.030 g, 0.076 mmol) and 1-methoxy-N-triethylammoniosulfonylmethanimidate (Burgess reagent, 0.027 g, 0.114 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give N-(1-(2-chlorophenyl)cyclobutyl)-5-(5-(difluoromethyl)-1,3,4-oxadiazol-2-yl)pyrimidin-2-amine as Colorless oil (0.010 g, 34.9%).

$^1$H NMR (400 MHz, CDCl$_3$) δ 8.85 (s, 2H), 7.75 (dd, J=7.8, 1.7 Hz, 1H), 7.31~7.24 (m, 2H), 7.20-7.15 (m, 1H), 7.01-6.75 (m, 2H), 2.90-2.83 (m, 2H), 2.78~2.71 (m, 2H), 2.30-2.19 (m, 1H), 1.96-1.82 (m, 1H). LRMS (ES) m/z 378.39 (M++1).

Example 19: Compound 1615, N-(1-(3-chlorophenyl)cyclobutyl)-5-(5-(difluoromethyl)-1,3,4-oxadiazol-2-yl)pyrimidin-2-amine

[Step 1]
1-(3-chlorophenyl)cyclobutane-1-carbonitrile

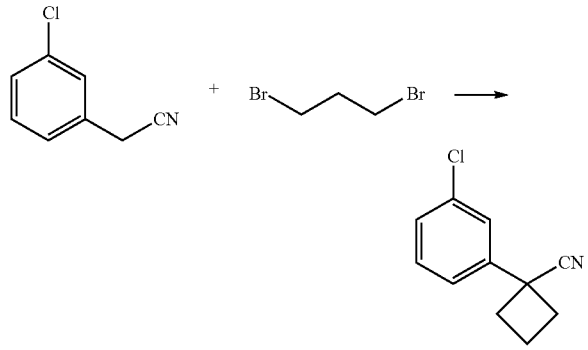

To a stirred solution of 2-(3-chlorophenyl)acetonitrile (3.000 g, 19.790 mmol) in N,N-dimethylformamide (20 mL) was added at 0° C. sodium hydride (60.00%, 1.583 g, 39.580 mmol). The reaction mixture was stirred at the same temperature for 30 min, treated at the room temperature with 1,3-dibromopropane (3.995 g, 19.790 mmol), stirred for additional 12 hr. Saturated aqueous ammonium chloride solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give 1-(3-chlorophenyl)cyclobutane-1-carbonitrile as Colorless oil (2.250 g, 59.3%).

[Step 2]
1-(3-chlorophenyl)cyclobutane-1-carboxamide

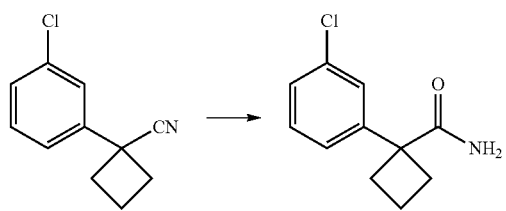 [SMILES: N#CC1(c2cccc(Cl)c2)CCC1 ; NC(=O)C1(c2cccc(Cl)c2)CCC1]

A solution of 1-(3-chlorophenyl)cyclobutane-1-carbonitrile (2.250 g, 11.740 mmol), tetra-n-butylammonium bromide (0.053 g, 0.164 mmol), sodium hydroxide (3.00 M solution, 11.740 mL, 35.219 mmol) and hydrogen peroxide (30.00%, solution, 2.754 mL, 35.219 mmol) in methanol (20 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(3-chlorophenyl)cyclobutane-1-carboxamide, 2.400 g, 97.5%, White solid).

[Step 3] 1-(3-chlorophenyl)cyclobutan-1-amine hydrochloride

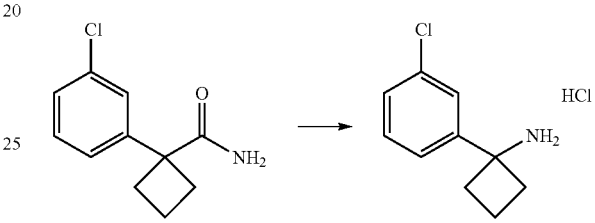

A solution of 1-(3-chlorophenyl)cyclobutane-1-carboxamide (2.400 g, 11.447 mmol), Sodium hypochlorite (11.00% solution, 10.468 mL, 17.170 mmol) and sodium hydroxide (3.00 M solution, 11.447 mL, 34.340 mmol) in t-butanol (10 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with dichloromethane (20 mL) and then was added hydrochloric acid (4.00 M solution in Dioxane, 5.723 mL, 22.893 mmol) and stirred at the ambient temperature. The resulting precipitates were collected by filtration, washed by diethyl ether, and dried to give 1-(3-chlorophenyl)cyclobutan-1-amine hydrochloride as White solid (1.200 g, 57.7%).

[Step 4] ethyl 2-((1-(3-chlorophenyl)cyclobutyl)amino)pyrimidine-5-carboxylate

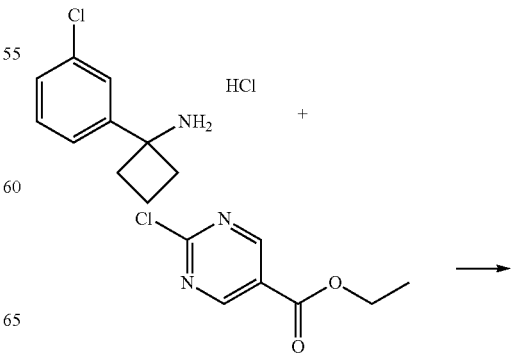

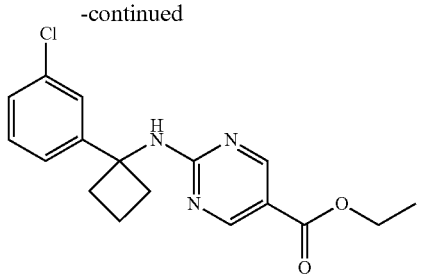

A solution of 1-(3-chlorophenyl)cyclobutan-1-amine hydrochloride (0.400 g, 2.202 mmol), ethyl 2-chloropyrimidine-5-carboxylate (0.411 g, 2.202 mmol) and N,N-diisopropylethylamine (0.767 mL, 4.404 mmol) in 1,4-dioxane (10 mL) was stirred at 80° C. for 12 hr, and cooled down to the room temperature to terminate reaction Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give ethyl 2-((1-(3-chlorophenyl)cyclobutyl)amino)pyrimidine-5-carboxylate as Colorless oil (0.420 g, 57.5%).

[Step 5] 2-((1-(3-chlorophenyl)cyclobutyl)amino)pyrimidine-5-carbohydrazide

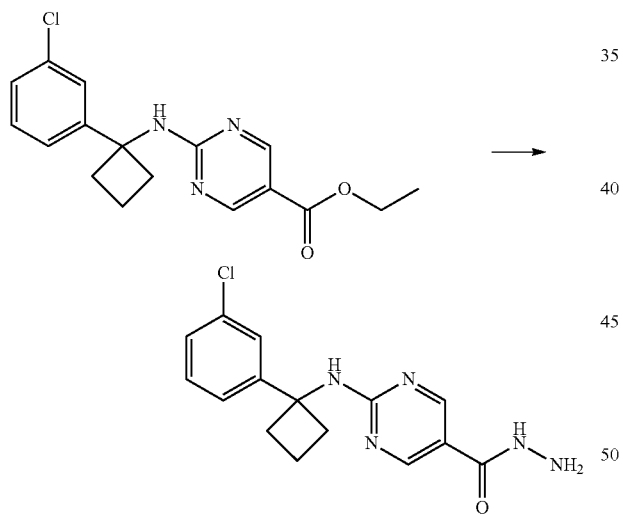

A solution of ethyl 2-((1-(3-chlorophenyl)cyclobutyl)amino)pyrimidine-5-carboxylate (0.450 g, 1.356 mmol) and Hydrazine monohydrate (1.318 mL, 27.125 mmol) in ethanol (10 mL) was heated at 120° C. for 1 hr under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (2-((1-(3-chlorophenyl)cyclobutyl)amino)pyrimidine-5-carbohydrazide, 0.110 g, 25.5%, White solid).

[Step 6] Compound 1615

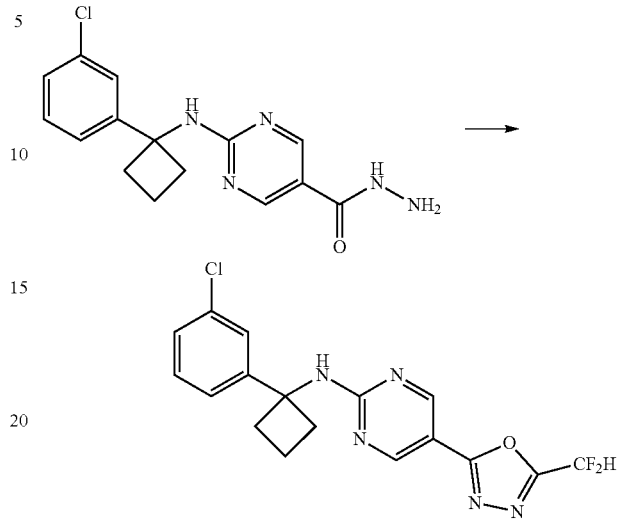

A solution of 2-((1-(3-chlorophenyl)cyclobutyl)amino)pyrimidine-5-carbohydrazide (0.110 g, 0.346 mmol), 2,2-difluoroacetic anhydride (0.034 mL, 0.312 mmol) and triethylamine (0.072 mL, 0.519 mmol) in dichloromethane (10 mL) prepared at the room temperature was stirred at the same temperature for 12 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give N-(1-(3-chlorophenyl)cyclobutyl)-5-(5-(difluoromethyl)-1,3,4-oxadiazol-2-yl)pyrimidin-2-amine as Yellow oil (0.030 g, 22.9%).

$^1$H NMR (400 MHz, CDCl$_3$) δ 8.89 (s, 2H), 7.51 (t, J=1.9 Hz, 1H), 7.41-7.40 (m, 1H), 7.40~7.38 (m, 1H), 7.29~7.25 (m, 1H), 7.23~7.20 (m, 1H), 7.02 (s, 0.25H), 6.89 (s, 0.5H), 6.77 (s, 0.25H), 6.50 (s, 1H), 2.77~2.70 (m, 2H), 2.62~2.55 (m, 2H), 2.25~2.17 (m, 1H), 2.08~1.99 (m, 1H); LRMS (ES) m/z 378.1 (M$^+$+1).

Example 20: Compound 1616, N-(1-(4-chlorophenyl)cyclobutyl)-5-(5-(difluoromethyl)-1,3,4-oxadiazol-2-yl)pyrimidin-2-amine

[Step 1] 1-(4-chlorophenyl)cyclobutane-1-carbonitrile

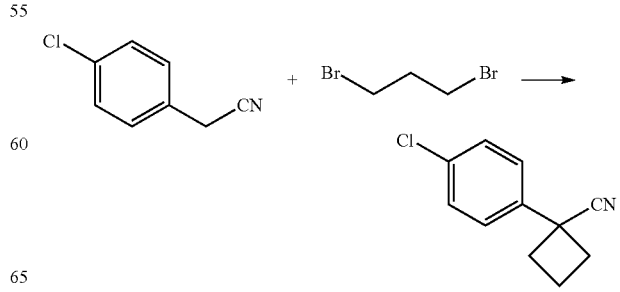

To a stirred solution of 2-(4-chlorophenyl)acetonitrile (3.000 g, 19.790 mmol) in N,N-dimethylformamide (20 mL) was added at 0° C. sodium hydride (0.950 g, 39.580 mmol). The reaction mixture was stirred at the same temperature for 30 min, treated at the room temperature with 1,3-dibromopropane (2.018 mL, 19.790 mmol), and stirred for additional 12 hr. Saturated aqueous ammonium chloride solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give 1-(4-chlorophenyl)cyclobutane-1-carbonitrile as Colorless oil (1.840 g, 48.5%).

[Step 2]
1-(4-chlorophenyl)cyclobutane-1-carboxamide

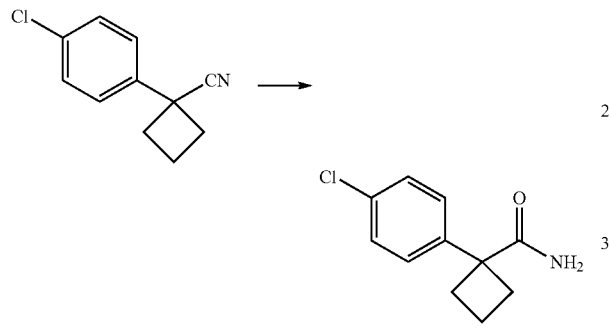

A solution of 1-(4-chlorophenyl)cyclobutane-1-carbonitrile (1.840 g, 9.600 mmol), tetra-n-butylammonium bromide (0.031 g, 0.096 mmol), sodium hydroxide (3.00 M solution, 9.600 mL, 28.801 mmol) and hydrogen peroxide (30.00% solution, 2.252 mL 28.801 mmol) in methanol (20 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(4-chlorophenyl)cyclobutane-1-carboxamide, 1.970 g, 97.9%, White solid).

[Step 3] 1-(4-chlorophenyl)cyclobutan-1-amine hydrochloride

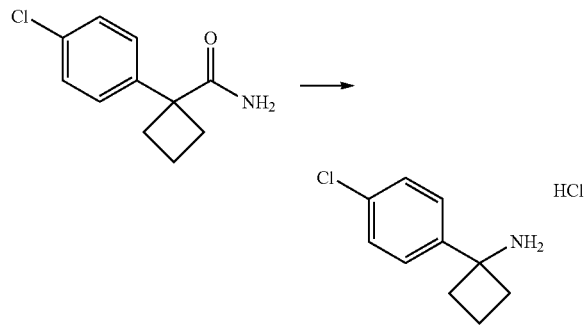

A solution of 1-(4-chlorophenyl)cyclobutane-1-carboxamide (1.970 g, 9.396 mmol), Sodium hypochlorite (11.00% solution, 8.592 mL, 14.094 mmol) and sodium hydroxide (3.00 M solution, 9.396 mL, 28.187 mmol) in t-butanol (10 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with dichloromethane (20 mL) and then was added hydrochloric acid (4.00 M solution in Dioxane, 4.698 mL, 18.791 mmol) stirred at the ambient temperature. The resulting precipitates were collected by filtration, washed by diethyl ether, and dried to give 1-(4-chlorophenyl)cyclobutan-1-amine hydrochloride as White solid (0.900 g, 52.7%).

[Step 4] ethyl 2-((1-(4-chlorophenyl)cyclobutyl)amino)pyrimidine-5-carboxylate

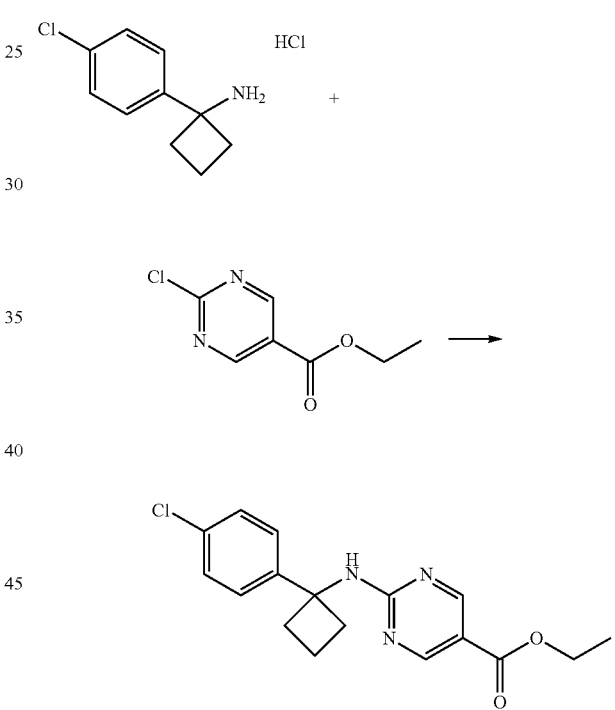

A solution of 1-(4-chlorophenyl)cyclobutan-1-amine hydrochloride (0.400 g, 2.202 mmol), ethyl 2-chloropyrimidine-5-carboxylate (0.411 g, 2.202 mmol) and N,N-diisopropylethylamine (0.767 mL, 4.404 mmol) in 1,4-dioxane (10 mL) was stirred at 80° C. for 12 hr, and then cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give ethyl 2-((1-(4-chlorophenyl)cyclobutyl)amino)pyrimidine-5-carboxylate as Colorless oil (0.420 g, 57.5%).

[Step 5] 2-((1-(4-chlorophenyl)cyclobutyl)amino)pyrimidine-5-carbohydrazide

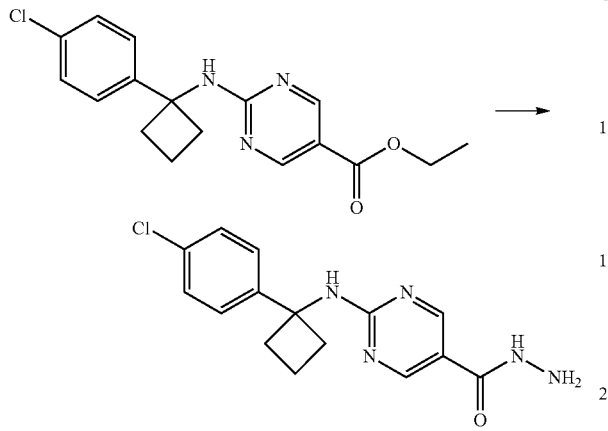

A mixture of ethyl 2-((1-(4-chlorophenyl)cyclobutyl)amino)pyrimidine-5-carboxylate (0.420 g, 1.266 mmol) and Hydrazine monohydrate (1.230 mL, 25.316 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The crude product was used without further purification (2-((1-(4-chlorophenyl)cyclobutyl)amino)pyrimidine-5-carbohydrazide, 0.310 g, 77.1%, white solid).

[Step 6] 2-((1-(4-chlorophenyl)cyclobutyl)amino)-N'-(2,2-difluoroacetyl)pyrimidine-5-carbohydrazide

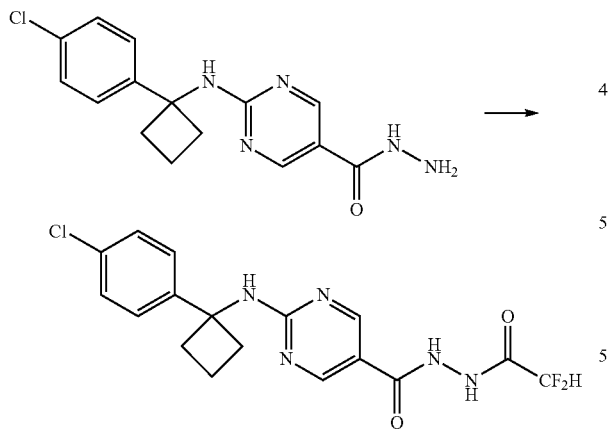

A solution of 2-((1-(4-chlorophenyl)cyclobutyl)amino)pyrimidine-5-carbohydrazide (0.176 g, 0.554 mmol), 2,2-difluoroacetic anhydride (0.054 mL, 0.498 mmol) and triethylamine (0.116 mL, 0.831 mmol) in dichloromethane (10 mL) prepared at the room temperature was stirred at the same temperature for 2 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give 2-((1-(4-chlorophenyl)cyclobutyl)amino)-N'-(2,2-difluoroacetyl)pyrimidine-5-carbohydrazide as Colorless oil (0.098 g, 44.7%).

[Step 7] Compound 1616

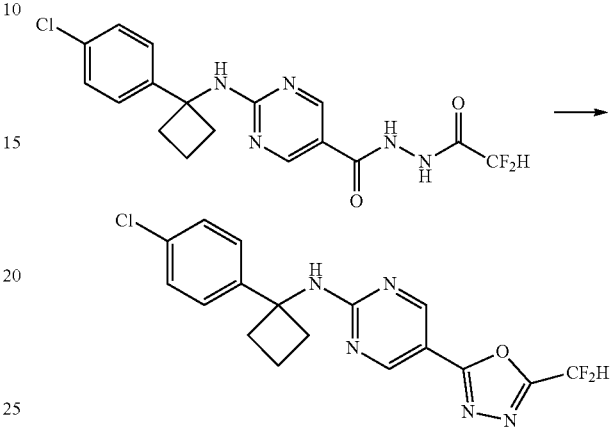

A mixture of 2-((1-(4-chlorophenyl)cyclobutyl)amino)-N'-(2,2-difluoroacetyl)pyrimidine-5-carbohydrazide (0.098 g, 0.248 mmol) and 1-methoxy-N-triethylammoniosulfonyl-methanimidate (Burgess reagent, 0.089 g, 0.371 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give N-(1-(4-chlorophenyl)cyclobutyl)-5-(5-(difluoromethyl)-1,3,4-oxadiazol-2-yl)pyrimidin-2-amine as Colorless oil (0.015 g, 16.0%).
¹H NMR (400 MHz, CDCl₃) δ 8.89 (s, 1H), 7.47~7.44 (m, 2H), 7.32~7.28 (m, 2H), 7.02 (s, 0.25H), 6.89 (s, 0.5H), 6.76 (s, 0.25H), 6.54 (s, 1H), 2.76~2.69 (m, 2H), 2.63~2.55 (m, 2H), 2.24~2.17 (m, 1H), 2.06~2.03 (m, 1H); LRMS (ES) m/z 378.1 (M⁺+1).

Example 21: Compound 1617, N-(1-(2-chlorophenyl)cyclobutyl)-5-(5-(trifluoromethyl)-1,3,4-oxadiazol-2-yl)pyrimidin-2-amine

[Step 1] 2-((1-(2-chlorophenyl)cyclobutyl)amino)-N'-(2,2,2-trifluoroacetyl)pyrimidine-5-carbohydrazide

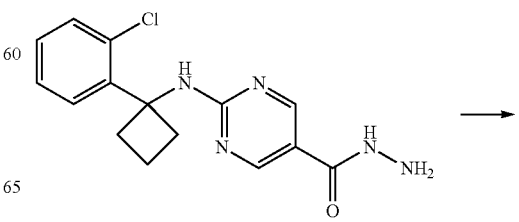

-continued

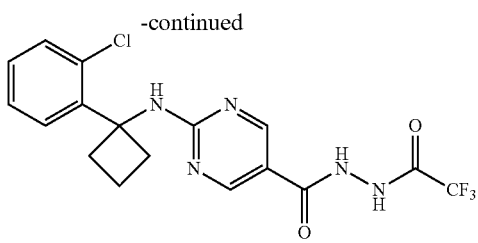

A solution of 2-((1-(2-chlorophenyl)cyclobutyl)amino)pyrimidine-5-carbohydrazide (0.106 g, 0.334 mmol), trifluoroacetic anhydride (0.042 mL, 0.300 mmol) and triethylamine (0.070 mL, 0.500 mmol) in dichloromethane (10 mL) prepared at the room temperature was stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 100%) to give 2-((1-(2-chlorophenyl)cyclobutyl)amino)-N'-(2,2,2-trifluoroacetyl)pyrimidine-5-carbohydrazide as Colorless oil (0.063 g, 45.6%).

[Step 2] Compound 1617

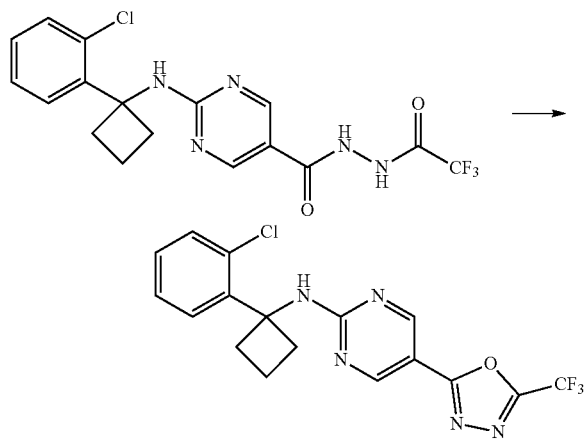

A mixture of 2-((1-(2-chlorophenyl)cyclobutyl)amino)-N'-(2,2,2-trifluoroacetyl)pyrimidine-5-carbohydrazide (0.063 g, 0.152 mmol) and 1-methoxy-N-triethylammoniosulfonyl-methanimidate (Burgess reagent, 0.054 g, 0.228 mmol) in tetrahydrofuran (10 mL) was heated at 150° C. for 30 min under the microwaves, cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give N-(1-(2-chlorophenyl)cyclobutyl)-5-(5-(trifluoromethyl)-1,3,4-oxadiazol-2-yl)pyrimidin-2-amine as Colorless oil (0.015 g, 24.9%).

$^1$H NMR (400 MHz, CDCl$_3$) δ 8.86~8.85 (m, 2H), 7.75 (dd, J=7.7, 1.6 Hz, 1H), 7.31~7.25 (m, 2H), 7.20~7.16 (m, 1H), 6.79 (s, 1H), 2.90~2.83 (m, 2H), 2.78~2.71 (m, 2H), 2.30~2.21 (m, 1H), 1.97~1.87 (m, 1H); LRMS (ES) m/z 396.37 (M$^+$+1).

Example 22: Compound 1618, N-(1-(4-chlorophenyl)cyclobutyl)-5-(5-(trifluoromethyl)-1,3,4-oxadiazol-2-yl)pyrimidin-2-amine

[Step 1] 2-((1-(4-chlorophenyl)cyclobutyl)amino)-N'-(2,2,2-trifluoroacetyl)pyrimidine-5-carbohydrazide

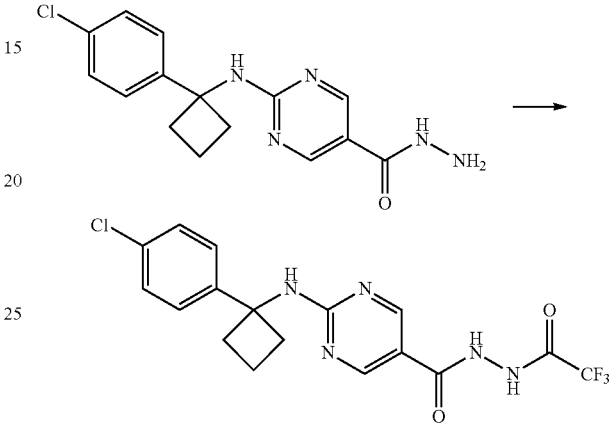

A solution of 2-((1-(4-chlorophenyl)cyclobutyl)amino)pyrimidine-5-carbohydrazide (0.098 g, 0.308 mmol), trifluoroacetic anhydride (0.039 mL, 0.278 mmol) and triethylamine (0.064 mL, 0.463 mmol) in dichloromethane (10 mL) prepared at the room temperature was stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give 2-((1-(4-chlorophenyl)cyclobutyl)amino)-N'-(2,2,2-trifluoroacetyl)pyrimidine-5-carbohydrazide as Colorless oil (0.062 g, 48.6%).

[Step 2] Compound 1618

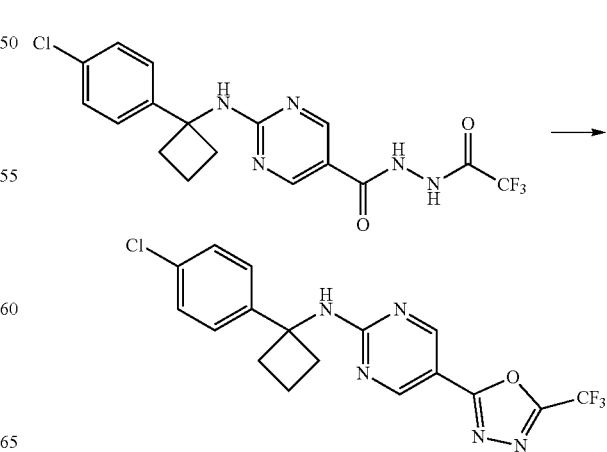

A mixture of 2-((1-(4-chlorophenyl)cyclobutyl)amino)-N'-(2,2,2-trifluoroacetyl)pyrimidine-5-carbohydrazide (0.062 g, 0.150 mmol) and 1-methoxy-N-triethylammonio-sulfonyl-methanimidate (Burgess reagent, 0.054 g, 0.225 mmol) in tetrahydrofuran (10 mL) was heated at 150° C. for 30 min under the microwaves, cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give N-(1-(4-chlorophenyl)cyclobutyl)-5-(5-(trifluoromethyl)-1,3,4-oxadiazol-2-yl)pyrimidin-2-amine as Colorless oil (0.015 g, 25.3%).

¹H NMR (400 MHz, CDCl₃) δ 8.88-8.87 (m, 2H), 7.47-7.43 (m, 2H), 7.32-7.28 (m, 2H), 6.57 (s, 1H), 2.77-2.70 (m, 2H), 2.63-2.56 (m, 2H), 2.24-2.17 (m, 1H), 2.04-2.02 (m, 1H); LRMS (ES) m/z 396.43 (M⁺+1).

Example 23: Compound 1640, 5-(5-(difluoromethyl)-1,3,4-oxadiazol-2-yl)-N-(1-(pyridin-2-yl)cyclobutyl)pyrimidin-2-amine

[Step 1] 1-(pyridin-2-yl)cyclobutane-1-carbonitrile

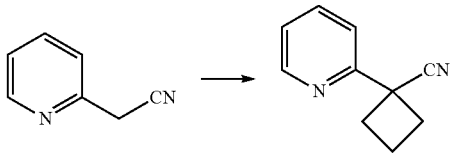 [SMILES: N#CCc1ccccn1 ; N#CC1(c2ccccn2)CCC1]

A solution of 2-(pyridin-2-yl)acetonitrile (5.000 g, 42.323 mmol) and sodium hydride (2.234 g, 93.110 mmol) in N,N-dimethylformamide (100 mL) was mixed at 0° C. with 1,3-dibromopropane (8.545 g, 42.323 mmol), and stirred at the same temperature for 1 hr. The reaction mixture was stirred at the room temperature for additional 17 hr, and quenched at 0° C. by the addition of water (10 mL, 10 min stirring) And then, water was added to the concentrate, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=5% to 40%) to give 1-(pyridin-2-yl)cyclobutane-1-carbonitrile as pale yellow oil (0.891 g, 11.4%).

[Step 2] 1-(pyridin-2-yl)cyclobutane-1-carboxamide

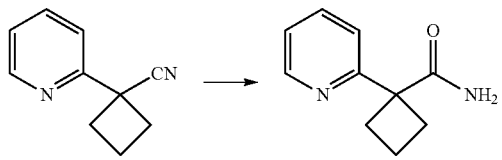 [SMILES: N#CC1(c2ccccn2)CCC1 ; NC(=O)C1(c2ccccn2)CCC1]

A solution of 1-(pyridin-2-yl)cyclobutane-1-carbonitrile (0.891 g, 5.632 mmol), sodium hydroxide (25.00%, 0.225 g, 1.408 mmol), hydrogen peroxide (30.00%, 1.916 g, 16.896 mmol) and tetra-n-butylammonium bromide (0.018 g, 0.056 mmol) in methanol (15 mL) prepared at the room temperature was stirred at the same temperature for 18 hr. And then, water was added to the concentrate, followed by extraction with ethyl acetate. The organic layer was washed with aqueous saturated sodium chloride solution, dried with anhydrous MgSO₄, filtered, and concentrated in vacuo. 1-(pyridin-2-yl)cyclobutane-1-carboxamide was used without further purification (0.384 g, 38.7%, white solid).

[Step 3] 1-(pyridin-2-yl)cyclobutan-1-amine hydrochloride

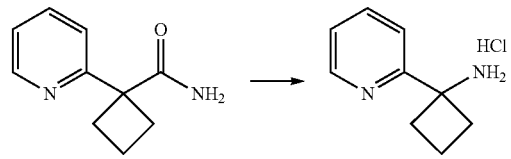 [SMILES: NC(=O)C1(c2ccccn2)CCC1 ; NC1(c2ccccn2)CCC1 ; Cl]

A solution of 1-(pyridin-2-yl)cyclobutane-1-carboxamide (0.384 g, 2.179 mmol), sodium hypochlorite (11.00% solution, 1.706 mL, 3.051 mmol) and sodium hydroxide (3.00 M solution in water, 2.034 mL, 6.101 mmol) in 1-butanol (5 mL) prepared at the room temperature was stirred at the same temperature for 18 hr. And then, water was added to the concentrate, followed by extraction with ethyl acetate. The organic layer was washed with aqueous saturated sodium chloride solution, dried with anhydrous MgSO₄, filtered, and concentrated in vacuo. The concentrate was diluted with ethyl acetate and hydrochloric acid (4.00 M solution in 1,4-dioxane, 0.817 mL, 3.269 mmol) and stirred at the ambient temperature. The resulting precipitates were collected by filtration and dried to give 1-(pyridin-2-yl)cyclobutan-1-amine hydrochloride as white solid (0.240 g, 59.6%).

[Step 4] Ethyl 2-((1-(pyridin-2-yl)cyclobutyl)amino)pyrimidine-5-carboxylate

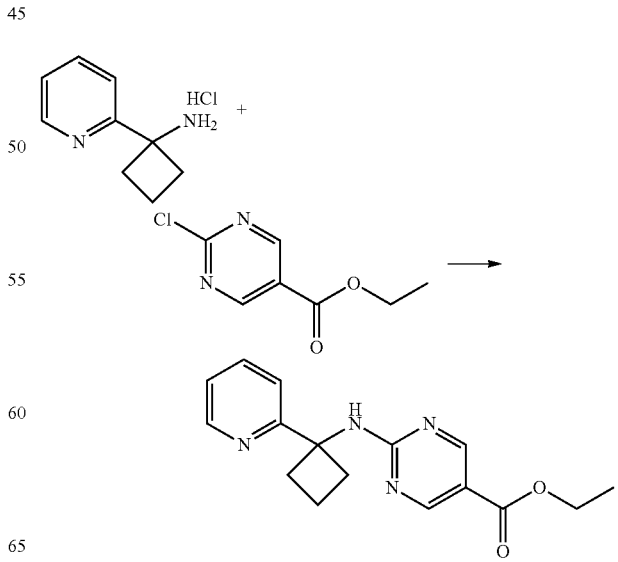

1-(pyridin-2-yl)cyclobutan-1-amine hydrochloride (0.240 g, 1.300 mmol), ethyl 2-chloropyrimidine-5-carboxylate (0.252 g, 1.365 mmol) and N,N-diisopropylethylamine (0.679 mL, 3.899 mmol) were mixed at the room temperature in 1,4-dioxane (4 mL), stirred at 110° C. for 17 hr, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=5% to 20%) to give Ethyl 2-((1-(pyridin-2-yl)cyclobutyl)amino)pyrimidine-5-carboxylate as pale yellow solid (0.243 g, 62.7%).

[Step 5] 2-((1-(pyridin-2-yl)cyclobutyl)amino)pyrimidine-5-carbohydrazide

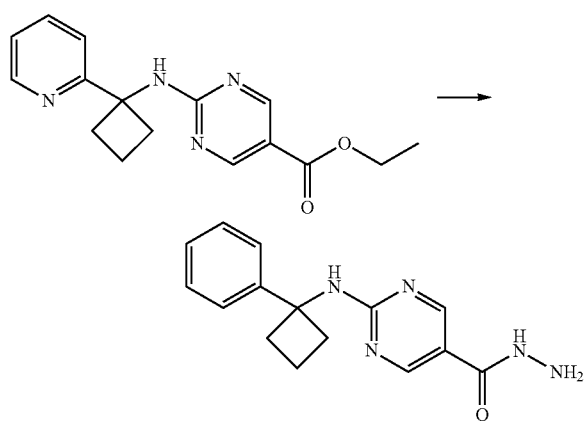

Ethyl 2-((1-(pyridin-2-yl)cyclobutyl)amino)pyrimidine-5-carboxylate (0.243 g, 0.814 mmol) and hydrazine monohydrate (0.792 mL, 16.290 mmol) were mixed at the room temperature in ethanol (4 mL), stirred at 120° C. for 17 hr, and cooled down to the room temperature to terminate the reaction. The reaction mixture was concentrated under the reduced pressure to remove the solvent. The precipitates were collected by filtration, washed by ethanol, and dried to give 2-((1-(pyridin-2-yl)cyclobutyl)amino)pyrimidine-5-carbohydrazide as white solid (0.154 g, 66.5%).

[Step 6] N'-(2,2-difluoroacetyl)-2-((1-(pyridin-2-yl)cyclobutyl)amino)pyrimidine-5-carbohydrazide

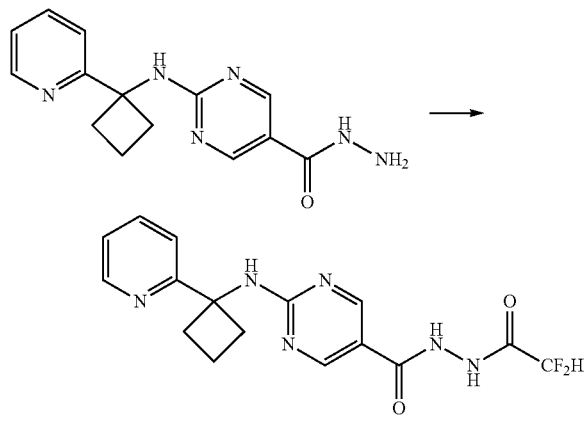

A solution of 2-((1-(pyridin-2-yl)cyclobutyl)amino)pyrimidine-5-carbohydrazide (0.080 g, 0.281 mmol) and triethylamine (0.059 mL, 0.422 mmol) in N,N-dimethylformamide (4 mL) was mixed at the room temperature with 2,2-difluoroacetic anhydride (0.028 mL, 0.253 mmol), stirred at 80° C. for 17 hr, and cooled down to the room temperature to terminate the reaction. The reaction mixture was concentrated under the reduced pressure to remove the solvent Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; ethyl acetate/hexane=5% to 70%) to give N'-(2,2-difluoroacetyl)-2-((1-(pyridin-2-yl)cyclobutyl)amino)pyrimidine-5-carbohydrazide as white solid (0.051 g, 50.0%).

[Step 7] Compound 1640

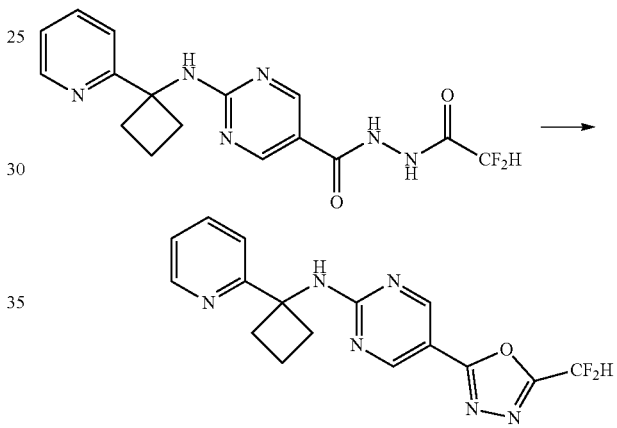

N'-(2,2-difluoroacetyl)-2-((1-(pyridin-2-yl)cyclobutyl)amino)pyrimidine-5-carbohydrazide (0.051 g, 0.141 mmol) and 1-methoxy-N-triethylammoniosulfonyl-methanimidate (Burgess reagent, 0.067 g, 0.282 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 30%) to give 5-(5-(difluoromethyl)-1,3,4-oxadiazol-2-yl)-N-(1-(pyridin-2-yl)cyclobutyl)pyrimidin-2-amine as white solid (0.046 g, 94.9%).

$^1$H NMR (400 MHz, CDCl$_3$) δ 8.95 (s, 1H), 8.85 (s, 1H), 8.64-8.62 (m, 1H), 7.69 (td, J=7.7, 1.8 Hz, 1H), 7.22-7.18 (m, 1H), 7.02-6.77 (m, 2H), 2.92-2.85 (m, 2H), 2.70-2.63 (m, 2H), 2.26-2.24 (m, 1H), 2.15-2.12 (m, 1H); LRMS (ES) m/z 345.4 (M$^+$+1).

Example 24: Compound 1641, N-(1-(pyridin-2-yl)cyclobutyl)-5-(5-(trifluoromethyl)-1,3,4-oxadiazol-2-yl)pyrimidin-2-amine

[Step 1] 2-((1-(pyridin-2-yl)cyclobutyl)amino)-N'-(2,2,2-trifluoroacetyl)pyrimidine-5-carbohydrazide

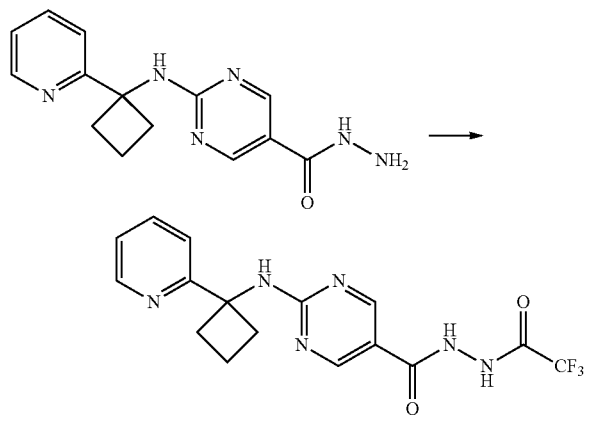

A solution of 2-((1-(pyridin-2-yl)cyclobutyl)amino)pyrimidine-5-carbohydrazide (0.074 g, 0.260 mmol) and triethylamine (0.054 mL, 0.390 mmol) in N,N-dimethylformamide (4 mL) was mixed at the room temperature with trifluoroacetic anhydride (0.033 mL, 0.234 mmol), stirred at 80° C. for 17 hr, and cooled down to the room temperature to terminate the reaction. The reaction mixture was concentrated under the reduced pressure to remove the solvent. And then, water was added to the concentrate, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; ethyl acetate/hexane=5% to 70%) to give 2-((1-(pyridin-2-yl)cyclobutyl)amino)-N'-(2,2,2-trifluoroacetyl)pyrimidine-5-carbohydrazide as white solid (0.041 g, 41.4%).

[Step 2] Compound 1641

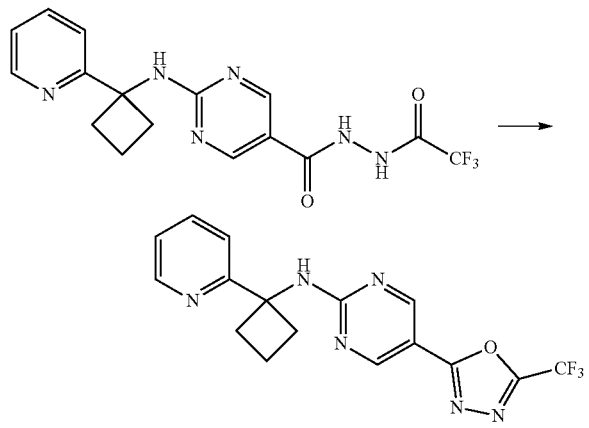

2-((1-(pyridin-2-yl)cyclobutyl)amino)-N'-(2,2,2-trifluoroacetyl)pyrimidine-5-carbohydrazide (0.041 g, 0.108 mmol) and 1-methoxy-N-triethylammoniosulfonyl-methanimidate (Burgess reagent, 0.039 g, 0.162 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give N-(1-(pyridin-2-yl)cyclobutyl)-5-(5-(trifluoromethyl)-1,3,4-oxadiazol-2-yl)pyrimidin-2-amine as white solid (0.010 g, 25.6%).

$^1$H NMR (400 MHz, CDCl$_3$) δ 8.95 (s, 1H), 8.85 (s, 1H), 8.63-8.61 (m, 1H), 7.68 (td, J=7.7, 1.8 Hz, 1H), 7.55-7.53 (m, 1H), 7.21-7.18 (m, 1H), 7.12 (s, 1H), 2.91-2.84 (m, 2H), 2.71-2.64 (m, 2H), 2.26-2.22 (m, 1H), 2.11-2.06 (m, 1H); LRMS (ES) m/z 363.4 (M$^+$+1).

Example 25: Compound 1642, 5-(5-(difluoromethyl)-1,3,4-oxadiazol-2-yl)-N-(1-(3-(trifluoromethyl)phenyl)cyclobutyl)pyrimidin-2-amine

[Step 1] 1-(3-(trifluoromethyl)phenyl)cyclobutane-1-carbonitrile

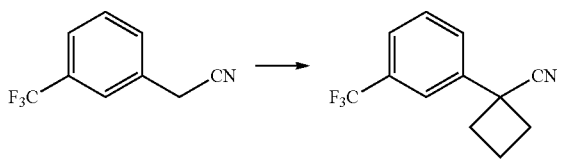 [SMILES: N#CCc1cccc(C(F)(F)F)c1 ; N#CC1(c2cccc(C(F)(F)F)c2)CCC1]

A solution of 2-(3-(trifluoromethyl)phenyl)acetonitrile (3.000 g, 16.203 mmol) and sodium hydride (60.00%, 1.426 g, 35.647 mmol) in N,N-dimethylformamide (100 mL) was mixed at 0° C. with 1,3-dibromopropane (1.731 mL, 16.203 mmol), stirred at the room temperature for 17 hr, and quenched at the room temperature by the addition of saturated aqueous sodium bicarbonate solution (10 mL, 10 min stirring)). The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 5%) to give 1-(3-(trifluoromethyl)phenyl)cyclobutane-1-carbonitrile as colorless oil (0.945 g, 25.9%).

[Step 2] 1-(3-(trifluoromethyl)phenyl)cyclobutane-1-carboxamide

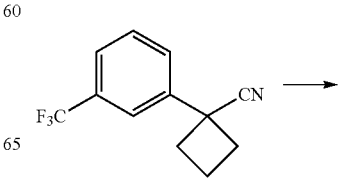

-continued

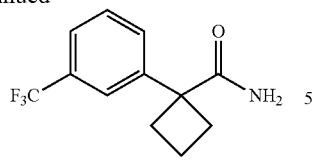

A solution of 1-(3-(trifluoromethyl)phenyl)cyclobutane-1-carbonitrile (0.945 g, 4.196 mmol), sodium hydroxide (25.00%, 0.168 g, 1.049 mmol), hydrogen peroxide (30.00%, 1.427 g, 12.588 mmol) and tetra-n-butylammonium bromide (0.014 g, 0.042 mmol) in methanol (15 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(3-(trifluoromethyl)phenyl)cyclobutane-1-carboxamide was used without further purification (1.000 g, 98.0%, colorless oil).

[Step 3] 1-(3-(trifluoromethyl)phenyl)cyclobutan-1-amine hydrochloride

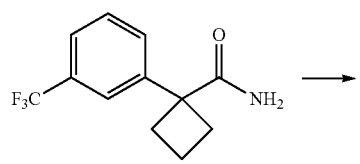

A solution of 1-(3-(trifluoromethyl)phenyl)cyclobutane-1-carboxamide (1.000 g, 4.111 mmol), sodium hypochlorite (11.00% solution, 3.219 mL, 5.756 mmol) and sodium hydroxide (3.00 M solution in water, 3.837 mL, 11.512 mmol) in 1-butanol (10 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and hydrochloric acid (4.00 M solution in 1,4-dioxane, 1.542 mL, 6.167 mmol) and stirred at the ambient temperature. The resulting precipitates were collected by filtration, washed by ethyl acetate and dried to give 1-(3-(trifluoromethyl)phenyl)cyclobutan-1-amine hydrochloride as white solid (0.519 g, 50.2%).

[Step 4] Ethyl 2-((1-(3-(trifluoromethyl)phenyl) cyclobutyl)amino)pyrimidine-5-carboxylate

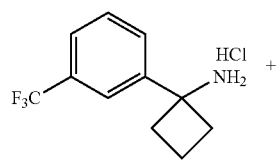

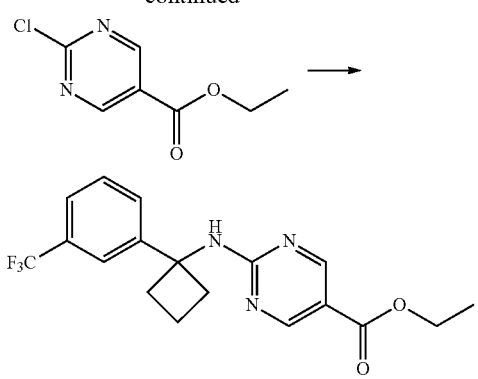

1-(3-(trifluoromethyl)phenyl)cyclobutan-1-amine hydrochloride (0.519 g, 2.062 mmol), ethyl 2-chloropyrimidine-5-carboxylate (0.404 g, 2.165 mmol) and N,N-diisopropylethylamine (1.078 mL, 6.186 mmol) were mixed at the room temperature in 1,4-dioxane (10 mL), stirred at 110° C. for 17 hr, and then cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=5% to 10%) to give ethyl 2-((1-(3-(trifluoromethyl)phenyl)cyclobutyl)amino)pyrimidine-5-carboxylate as white solid (0.338 g, 44.9%).

[Step 5] 2-((1-(3-(trifluoromethyl)phenyl)cyclobutyl)amino)pyrimidine-5-carbohydrazide

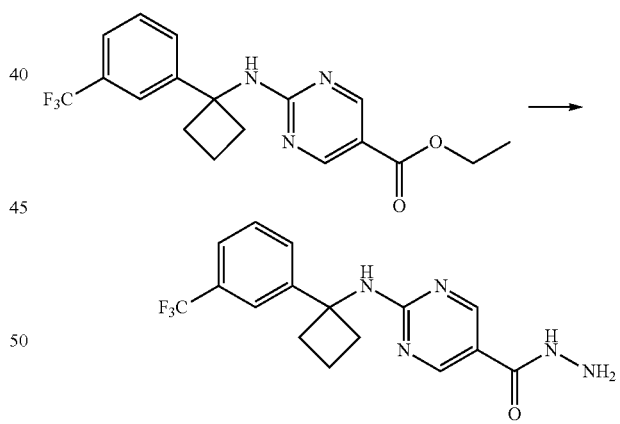

Ethyl 2-((1-(3-(trifluoromethyl)phenyl)cyclobutyl) amino)pyrimidine-5-carboxylate (0.338 g, 0.925 mmol) and hydrazine monohydrate (0.899 mL, 18.502 mmol) were mixed at the room temperature in ethanol (4 mL), stirred at 120° C. for 17 hr, and then cooled down to the room temperature to terminate the reaction. the reaction mixture was concentrated under the reduced pressure to remove the solvent. The precipitates were collected by filtration, washed by ethanol, and dried to give 2-((1-(3-(trifluoromethyl) phenyl)cyclobutyl)amino)pyrimidine-5-carbohydrazide as white solid (0.205 g, 63.1%).

[Step 6] N'-(2,2-difluoroacetyl)-2-((1-(3-(trifluoromethyl)phenyl)cyclobutyl)amino)pyrimidine-

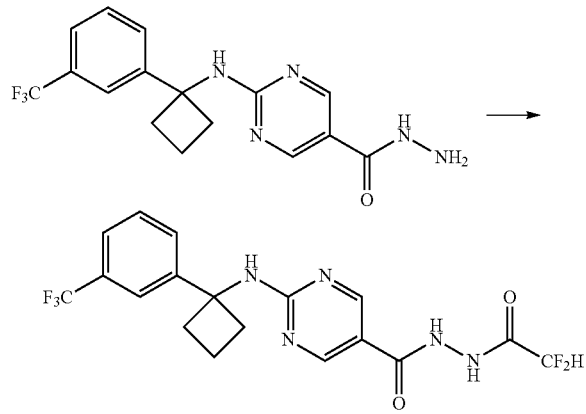

A solution of 2-((1-(3-(trifluoromethyl)phenyl)cyclobutyl)amino)pyrimidine-5-carbohydrazide (0.100 g, 0.285 mmol) and triethylamine (0.060 mL, 0.427 mmol) in N,N-dimethylformamide (4 mL) was mixed at the room temperature with 2,2-difluoroacetic anhydride (0.028 mL, 0.256 mmol), stirred at 80° C. for 17 hr, and cooled down to the room temperature to terminate the reaction. the reaction mixture was concentrated under the reduced pressure to remove the solvent. And then, water was added to the concentrate, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 70%) to give N'-(2,2-difluoroacetyl)-2-((1-(3-(trifluoromethyl)phenyl)cyclobutyl)amino)pyrimidine-5-carbohydrazide as pale yellow solid (0.060 g, 49.1%).

[Step 7] Compound 1642

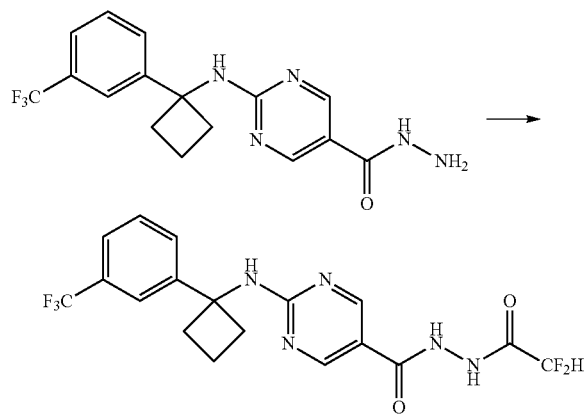

N'-(2,2-difluoroacetyl)-2-((1-(3-(trifluoromethyl)phenyl)cyclobutyl)amino)pyrimidine-5-carbohydrazide (0.060 g, 0.140 mmol) and 1-methoxy-N-triethylammoniosulfonylmethanimidate (Burgess reagent, 0.050 g, 0.210 mmol) in tetrahydrofuran (3 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 20%) to give 5-(5-(difluoromethyl)-1,3,4-oxadiazol-2-yl)-N-(1-(3-(trifluoromethyl)phenyl)cyclobutyl)pyrimidin-2-amine as white solid (0.005 g, 8.7%).

$^1$H NMR (400 MHz, CDCl$_3$) δ 8.91 (s, 1H), 8.87 (s, 1H), 7.78 (s, 1H), 7.70 (d, J=7.7 Hz, 1H), 7.52-7.44 (m, 2H), 7.02-7.76 (m, 1H), 6.50 (s, 1H), 2.81-2.74 (m, 2H), 2.65-2.58 (m, 2H), 2.28-2.21 (m, 1H), 2.07-2.01 (m, 1H); LRMS (ES) m/z 412.2 (M$^+$+1).

Example 26: Compound 1670, 5-(5-(trifluoromethyl)-1,3,4-oxadiazol-2-yl)-N-(1-(3-(trifluoromethyl)phenyl)cyclobut yl)pyrimidin-2-amine

[Step 1] 1-(3-(trifluoromethyl)phenyl)cyclobutane-1-carbonitrile

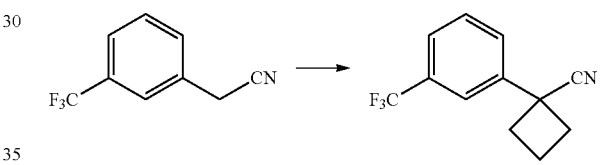

A solution of 2-(3-(trifluoromethyl)phenyl)acetonitrile (3.000 g, 16.203 mmol) and sodium hydride (60.00%, 1.426 g, 35.647 mmol) in N,N-dimethylformamide (100 mL) was mixed at 0° C. with 1,3-dibromopropane (1.731 mL, 16.203 mmol), stirred at the room temperature for 17 hr, and quenched at the room temperature by the addition of saturated aqueous sodium bicarbonate solution (10 mL, 10 min stirring). The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 5%) to give 1-(3-(trifluoromethyl)phenyl)cyclobutane-1-carbonitrile as colorless oil (0.945 g, 25.9%).

[Step 2] 1-(3-(trifluoromethyl)phenyl)cyclobutane-1-carboxamide

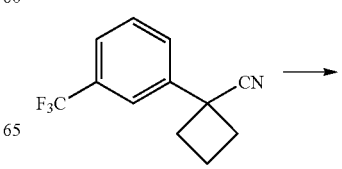

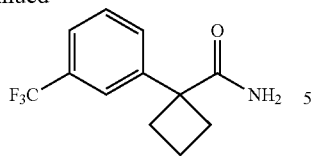

A solution of 1-(3-(trifluoromethyl)phenyl)cyclobutane-1-carbonitrile (0.945 g, 4.196 mmol), sodium hydroxide (25.00%, 0.168 g, 1.049 mmol), hydrogen peroxide (30.00%, 1.427 g, 12.588 mmol) and tetra-n-butylammonium bromide (0.014 g, 0.042 mmol) in methanol (15 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(3-(trifluoromethyl)phenyl)cyclobutane-1-carboxamide was used without further purification (1.000 g, 98.0%, colorless oil).

[Step 3]
1-(3-(trifluoromethyl)phenyl)cyclobutan-1-amine hydrochloride

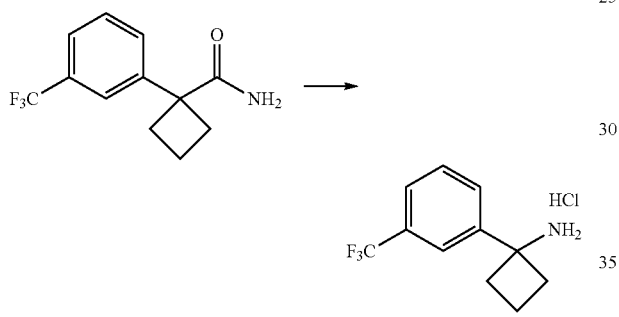

A solution of 1-(3-(trifluoromethyl)phenyl)cyclobutane-1-carboxamide (1.000 g, 4.111 mmol), sodium hypochlorite (11.00% solution, 3.219 mL, 5.756 mmol) and sodium hydroxide (3.00 M solution in water, 3.837 mL, 11.512 mmol) in 1-butanol (10 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and hydrochloric acid (4.00 M solution in 1,4-dioxane, 1.542 mL, 6.167 mmol) and stirred at the ambient temperature. The resulting precipitates were collected by filtration, washed by ethyl acetate and dried to give 1-(3-(trifluoromethyl)phenyl)cyclobutan-1-amine hydrochloride as white solid (0.519 g, 50.2%).

[Step 4] Ethyl 2-((1-(3-(trifluoromethyl)phenyl)cyclobutyl)amino)pyrimidine-5-carboxylate

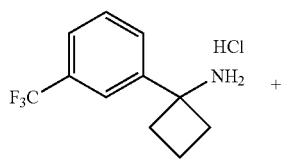 +

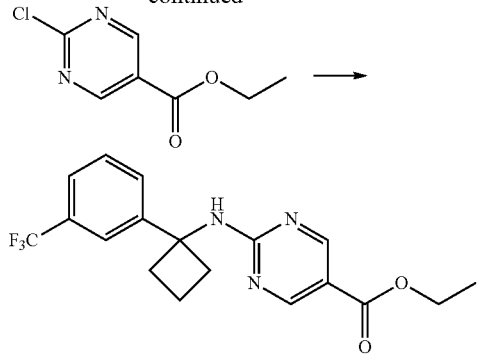

1-(3-(trifluoromethyl)phenyl)cyclobutan-1-amine hydrochloride (0.519 g, 2.062 mmol), ethyl 2-chloropyrimidine-5-carboxylate (0.404 g, 2.165 mmol) and N,N-diisopropylethylamine (1.078 mL, 6.186 mmol) were mixed at the room temperature in 1,4-dioxane (10 mL), stirred at 110° C. for 17 hr, and then cooled down to the room temperature to terminate the reaction. The reaction mixture was concentrated under the reduced pressure to remove the solvent. And then, the concentrate was purified and concentrated by column chromatography (SiO$_2$, 12 g cartridge; ethyl acetate/hexane=5% to 10%) to give ethyl 2-((1-(3-(trifluoromethyl)phenyl)cyclobutyl)amino)pyrimidine-5-carboxylate as white solid (0.338 g, 44.9%).

[Step 5] 2-((1-(3-(trifluoromethyl)phenyl)cyclobutyl)amino)pyrimidine-5-carbohydrazide

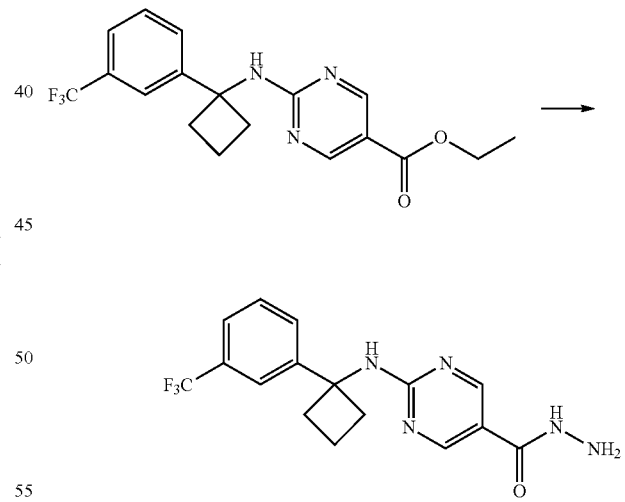

Ethyl 2-((1-(3-(trifluoromethyl)phenyl)cyclobutyl)amino)pyrimidine-5-carboxylate (0.338 g, 0.925 mmol) and hydrazine monohydrate (0.899 mL, 18.502 mmol) were mixed at the room temperature in ethanol (4 mL), stirred at 120° C. for 17 hr, and cooled down to terminate the reaction. The reaction mixture was concentrated under the reduced pressure to remove the solvent. And then, the precipitates were collected by filtration, washed by ethanol, and dried to give 2-((1-(3-(trifluoromethyl)phenyl)cyclobutyl)amino)pyrimidine-5-carbohydrazide as white solid (0.205 g, 63.1%).

[Step 6] N'-(2,2,2-trifluoroacetyl)-2-((1-(3-(trifluoromethyl)phenyl)cyclobutyl)amino)pyrimidine-5-carbohydrazide

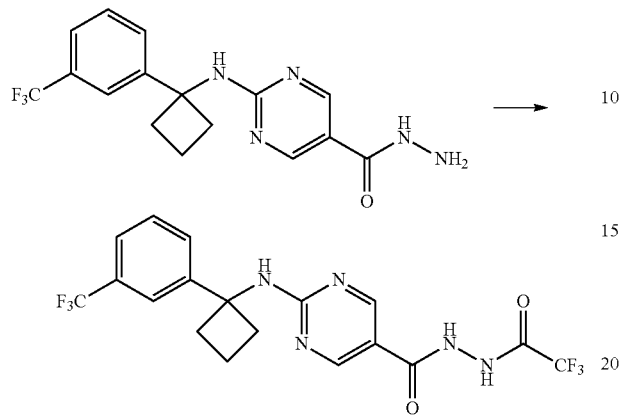

A solution of 2-((1-(3-(trifluoromethyl)phenyl)cyclobutyl)amino)pyrimidine-5-carbohydrazide (0.105 g, 0.299 mmol) and triethylamine (0.062 mL, 0.448 mmol) in N,N-dimethylformamide (4 mL) was mixed at the room temperature with trifluoroacetic anhydride (0.038 mL, 0.269 mmol), stirred at 80° C. for 17 hr, and cooled down to the room temperature to terminate the reaction. The reaction mixture was concentrated under the reduced pressure to remove the solvent. And then, water was added to the concentrate, followed by extraction with dichloromethane. The bi-phasic mixture was passed through a plastic frit to remove the solid residues and aqueous layer, and the organic layer collected was concentrated in vacuo. N'-(2,2,2-trifluoroacetyl)-2-((1-(3-(trifluoromethyl)phenyl)cyclobutyl)amino)pyrimidine-5-carbohydrazide was used without further purification (0.097 g, 72.6%, white solid).

[Step 7] Compound 1670

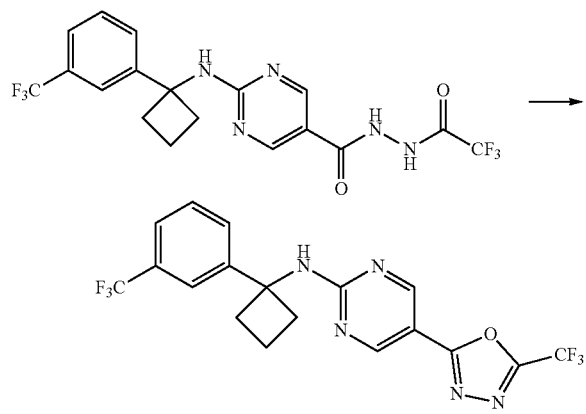

N'-(2,2,2-trifluoroacetyl)-2-((1-(3-(trifluoromethyl)phenyl)cyclobutyl)amino)pyrimidine-5-carbohydrazide (0.097 g, 0.217 mmol) and 1-methoxy-N-triethylammoniosulfonylmethanimidate (Burgess reagent, 0.078 g, 0.325 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 15%) to give the crude product which was re-chromatographed (SiO$_2$ plate, 20×20×1 mm; ethyl acetate/hexane=30%) to give 5-(5-(trifluoromethyl)-1,3,4-oxadiazol-2-yl)-N-(1-(3-(trifluoromethyl)phenyl)cyclobutyl)pyrimidin-2-amine as white solid (0.009 g, 9.7%).

$^1$H NMR (400 MHz, CDCl$_3$) δ 8.93 (s, 1H), 8.84 (s, 1H), 7.78 (s, 1H), 7.70 (d, J=7.4 Hz, 1H), 7.52-7.44 (m, 2H), 6.46 (s, 1H), 2.81-2.74 (m, 2H), 2.65-2.58 (m, 2H), 2.26-2.23 (m, 1H), 2.07-2.02 (m, 1H); LRMS (ES) m/z 430.4 (M$^+$+1).

Example 27: Compound 1671, 5-(5-(difluoromethyl)-1,3,4-oxadiazol-2-yl)-N-(1-(o-tolyl)cyclobutyl)pyrimidin-2-amine

[Step 1] 1-(o-tolyl)cyclobutane-1-carbonitrile

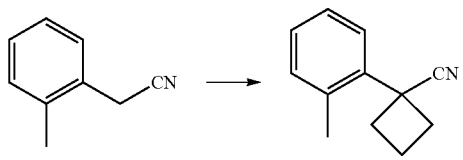

A solution of 2-(o-tolyl)acetonitrile (5.000 g, 38.116 mmol) and sodium hydride (60.00%, 3.354 g, 83.854 mmol) in N,N-dimethylformamide (100 mL) was stirred at 0° C. for 1 hr, and mixed with 1,3-dibromopropane (3.867 mL, 38.116 mmol). The reaction mixture was stirred at the room temperature for additional 3 hr and quenched at the room temperature by the addition of saturated aqueous sodium bicarbonate solution (10 mL, 10 min stirring). The reaction mixture was concentrated under the reduced pressure to remove the solvent. And then, water was added to the concentrate, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(o-tolyl)cyclobutane-1-carbonitrile as pale yellow oil (1.460 g, 22.4%).

[Step 2] 1-(o-tolyl)cyclobutane-1-carboxamide

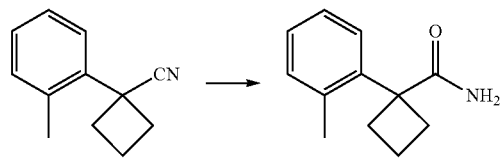

A solution of 1-(o-tolyl)cyclobutane-1-carbonitrile (1.460 g, 8.526 mmol), sodium hydroxide (25.00%, 0.341 g, 2.132 mmol), hydrogen peroxide (30.00%, 2.900 g, 25.578 mmol) and tetra-n-butylammonium bromide (0.027 g, 0.085 mmol) in methanol (70 mL) prepared at the room temperature was stirred at the same temperature for 17 hr. And then, water was added to the concentrate, followed by extraction with ethyl acetate. The organic layer was washed with aqueous saturated sodium chloride solution, dried with anhydrous MgSO₄, filtered, and concentrated in vacuo. 1-(o-tolyl) cyclobutane-1-carboxamide was used without further purification (1.560 g, 96.7%, white solid).

[Step 3] 1-(o-tolyl)cyclobutan-1-amine hydrochloride

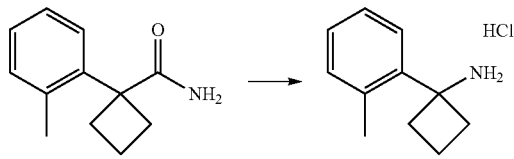

A solution of 1-(o-tolyl)cyclobutane-1-carboxamide (1.560 g, 8.243 mmol), sodium hypochlorite (8.50% solution, 8.352 mL, 11.540 mmol) and sodium hydroxide (3.00 M solution in water, 7.693 mL, 23.079 mmol) in 1-butanol (30 mL) was stirred at the room temperature. And then, water was added to the concentrate, followed by extraction with ethyl acetate. The organic layer was washed with aqueous saturated sodium chloride solution, dried with anhydrous MgSO₄, filtered, and concentrated in vacuo. The concentrate was diluted with ethyl acetate and hydrochloric acid (4.00 M solution in 1,4-dioxane, 3.091 mL, 12.364 mmol) and stirred at the ambient temperature. The resulting precipitates were collected by filtration, washed by ethyl acetate and dried to give 1-(o-tolyl)cyclobutan-1-amine hydrochloride as white solid (1.200 g, 73.6%).

[Step 4] Ethyl 2-((1-(o-tolyl)cyclobutyl)amino)pyrimidine-5-carboxylate

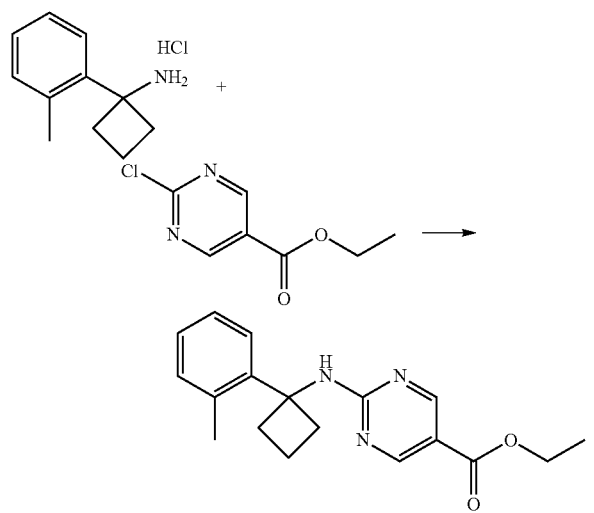

1-(o-tolyl)cyclobutan-1-amine hydrochloride (0.600 g, 3.035 mmol), ethyl 2-chloropyrimidine-5-carboxylate (0.595 g, 3.186 mmol) and N,N-diisopropylethylamine (1.586 mL, 9.104 mmol) were mixed at the room temperature in 1,4-dioxane (4 mL) and then stirred at 110° C. for 17 hr, and cooled down to the room temperature to terminate the reaction. The reaction mixture was concentrated under the reduced pressure to remove the solvent. The concentrate was purified and concentrated by column chromatography (SiO₂, 4 g cartridge; ethyl acetate/hexane=5% to 10%) to give ethyl 2-((1-(o-tolyl)cyclobutyl)amino)pyrimidine-5-carboxylate as white solid (0.355 g, 37.6%).

[Step 5] 2-((1-(o-tolyl)cyclobutyl)amino)pyrimidine-5-carbohydrazide

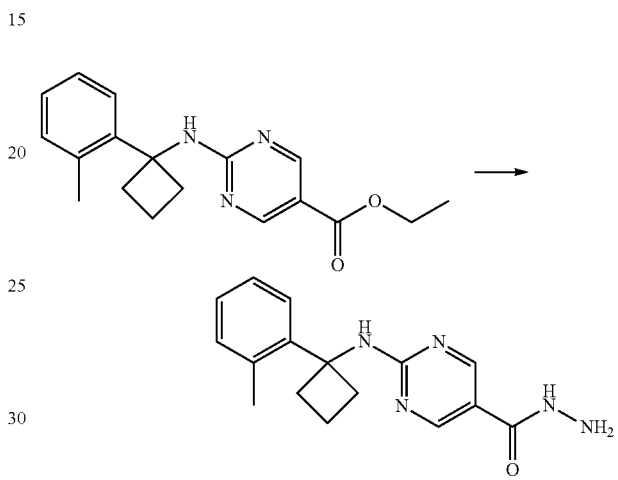

Ethyl 2-((1-(o-tolyl)cyclobutyl)amino)pyrimidine-5-carboxylate (0.355 g, 1.140 mmol) and hydrazine monohydrate (1.108 mL, 22.801 mmol) were mixed at the room temperature in ethanol (5 mL), stirred at 120° C. for 17 hr, and cooled down to the room temperature to terminate the reaction. The reaction mixture was concentrated under the reduced pressure to remove the solvent. The precipitates were collected by filtration, washed by ethanol, and dried to give 2-((1-(o-tolyl)cyclobutyl)amino)pyrimidine-5-carbohydrazide as white solid (0.200 g, 59.0%).

[Step 6] N'-(2,2-difluoroacetyl)-2-((1-(o-tolyl)cyclobutyl)amino)pyrimidine-5-carbohydrazide

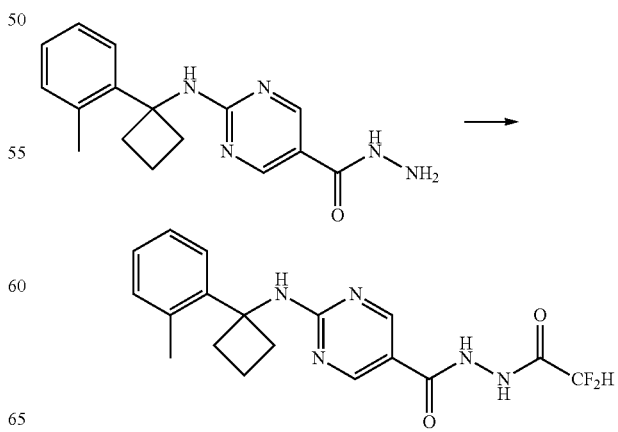

A solution of 2-((1-(o-tolyl)cyclobutyl)amino)pyrimidine-5-carbohydrazide (0.122 g, 0.410 mmol), 2,2-difluoroacetic anhydride (0.040 mL, 0.369 mmol) and triethylamine (0.086 mL, 0.615 mmol) in tetrahydrofuran (5 mL) prepared at the room temperature was stirred at the same temperature. saturated aqueous sodium bicarbonate solution was added to the concentrate, followed by extraction with dichloromethane. The bi-phasic mixture was passed through a plastic frit to remove the solid residues and aqueous layer, and the organic layer collected was concentrated in vacuo. N'-(2,2-difluoroacetyl)-2-((1-(o-tolyl)cyclobutyl)amino)pyrimidine-5-carbohydrazide was used without further purification (0.155 g, 100.6%, pale yellow solid).

[Step 7] Compound 1671

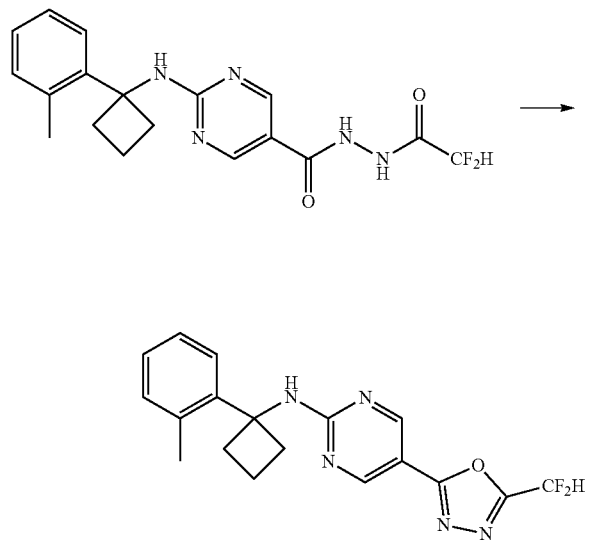

N'-(2,2-difluoroacetyl)-2-((1-(o-tolyl)cyclobutyl)amino) pyrimidine-5-carbohydrazide (0.155 g, 0.413 mmol) and 1-methoxy-N-triethylammoniosulfonyl-methanimidate (Burgess reagent, 0.148 g, 0.619 mmol) in tetrahydrofuran (5 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 15%) to give 5-(5-(difluoromethyl)-1,3,4-oxadiazol-2-yl)-N-(1-(o-tolyl)cyclobutyl)pyrimidin-2-amine as white solid (0.062 g, 42.0%).

$^1$H NMR (400 MHz, CDCl$_3$) δ 8.85 (s, 2H), 7.66 (dd, J=7.7, 1.3 Hz, 1H), 7.21 (td, J=7.5, 1.4 Hz, 1H), 7.16 (td, J=7.3, 1.5 Hz, 1H), 7.10 (d, J=7.2 Hz, 1H), 7.01-6.76 (m, 1H), 6.53 (s, 1H), 2.88-2.81 (m, 2H), 2.75-2.68 (m, 2H), 2.38 (s, 3H), 2.30-2.23 (m, 1H), 1.96-1.91 (m, 1H); LRMS (ES) m/z 358.5 (M$^+$+1).

Example 28: Compound 1672, N-(1-(o-tolyl)cyclobutyl)-5-(5-(trifluoromethyl)-1,3,4-oxadiazol-2-yl)pyrimidin-2-amine

[Step 1] 2-((1-(o-tolyl)cyclobutyl)amino)-N'-(2,2,2-trifluoroacetyl)pyrimidine-5-carbohydrazide

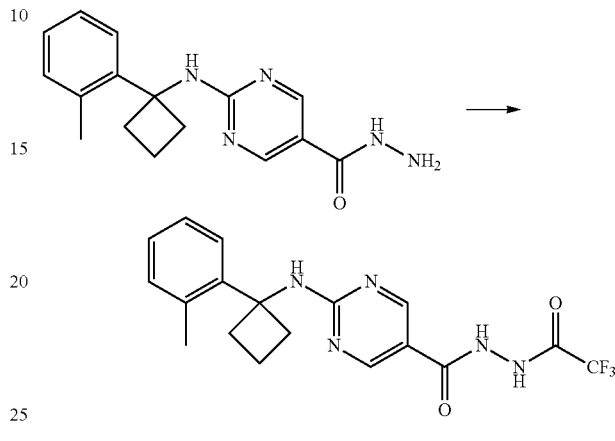

A solution of 2-((1-(o-tolyl)cyclobutyl)amino)pyrimidine-5-carbohydrazide (0.078 g, 0.262 mmol), trifluoroacetic anhydride (0.033 mL, 0.236 mmol) and triethylamine (0.055 mL, 0.393 mmol) in tetrahydrofuran (5 mL) prepared at the room temperature was stirred at the same temperature. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. 2-((1-(o-tolyl)cyclobutyl)amino)-N'-(2,2,2-trifluoroacetyl) pyrimidine-5-carbohydrazide was used without further purification (0.100 g, 96.9%, pale yellow solid).

[Step 2] Compound 1672

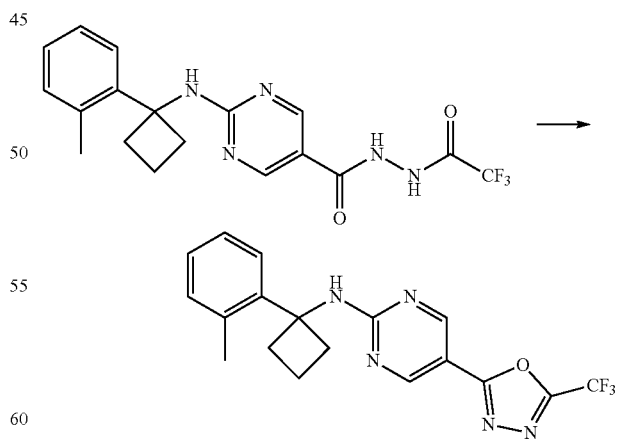

2-((1-(o-tolyl)cyclobutyl)amino)-N'-(2,2,2-trifluoroacetyl)pyrimidine-5-carbohydrazide (0.100 g, 0.254 mmol) and 1-methoxy-N-triethylammoniosulfonyl-methanimidate (Burgess reagent, 0.091 g, 0.381 mmol) in tetrahydrofuran (5 mL) was mixed at the room temperature, heated at 150°

C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(o-tolyl)cyclobutyl)-5-(5-(trifluoromethyl)-1,3,4-oxadiazol-2-yl)pyrimidin-2-amine as white solid (0.007 g, 7.3%).

$^1$H NMR (400 MHz, CDCl$_3$) δ 8.84 (s, 2H), 7.66 (d, J=7.4 Hz, 1H), 7.21 (t, J=6.9 Hz, 1H), 7.18-7.14 (m, 1H), 7.10 (d, J=7.1 Hz, 1H), 6.63 (s, 1H), 2.88-2.21 (m, 2H), 2.76-2.69 (m, 2H), 2.30-2.23 (m, 1H), 1.97-1.89 (m, 1H); LRMS (ES) m/z 376.3 (M$^+$+1).

Example 29: Compound 1673, 5-(5-(difluoromethyl)-1,3,4-oxadiazol-2-yl)-N-(1-(m-tolyl)cyclobutyl)pyrimidin-2-amine

[Step 1] 1-(m-tolyl)cyclobutane-1-carbonitrile

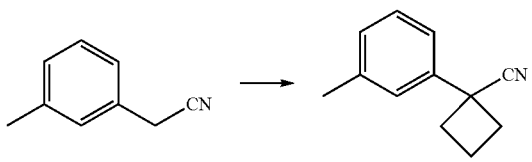

A solution of 2-(m-tolyl)acetonitrile (5.000 g, 38.116 mmol) in N,N-dimethylformamide (100 mL) was stirred at 0° C. for 1 hr, and mixed with sodium hydride (2.012 g, 83.854 mmol) and 1,3-dibromopropane (7.695 g, 38.116 mmol). The reaction mixture was stirred at the room temperature for additional 3 hr, and quenched at the room temperature by the addition of saturated aqueous sodium bicarbonate solution (10 mL, 10 min stirring). The reaction mixture was concentrated under the reduced pressure to remove the solvent. And then, water was added to the concentrate, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(m-tolyl)cyclobutane-1-carbonitrile as pale yellow oil (2.770 g, 42.4%).

[Step 2] 1-(m-tolyl)cyclobutane-1-carboxamide

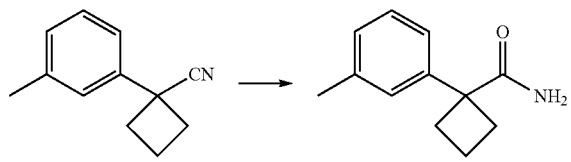

A solution of 1-(m-tolyl)cyclobutane-1-carbonitrile (2.770 g, 15.898 mmol), sodium hydroxide (25.00%, 0.636 g, 3.974 mmol), hydrogen peroxide (30.00%, 5.408 g, 47.693 mmol) and tetra-n-butylammonium bromide (0.051 g, 0.159 mmol) in methanol (70 mL) prepared at the room temperature was stirred at the same temperature for 17 hr. And then, water was added to the concentrate, followed by extraction with ethyl acetate The organic layer was washed with aqueous saturated sodium chloride solution, dried with anhydrous MgSO$_4$, filtered, and concentrated in vacuo. 1-(m-tolyl)cyclobutane-1-carboxamide was used without further purification (2.020 g, 67.1%, pale yellow oil).

[Step 3] 1-(m-tolyl)cyclobutan-1-amine hydrochloride

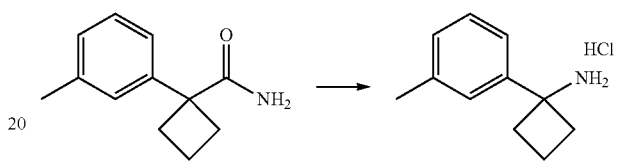

A solution of 1-(m-tolyl)cyclobutane-1-carboxamide (1.000 g, 5.284 mmol), sodium hypochlorite (8.50% solution, 5.354 mL, 7.397 mmol) and sodium hydroxide (3.00 M solution in water, 4.931 mL, 14.794 mmol) in 1-butanol (30 mL) prepared at the room temperature was stirred at the same temperature. And then, water was added to the concentrate, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and hydrochloric acid (4.00 M solution in 1,4-dioxane, 1.981 mL, 7.926 mmol) and stirred at the ambient temperature. The resulting precipitates were collected by filtration and dried to give 1-(m-tolyl)cyclobutan-1-amine hydrochloride as white solid (0.800 g, 76.6%).

[Step 4] Ethyl 2-((1-(m-tolyl)cyclobutyl)amino)pyrimidine-5-carboxylate

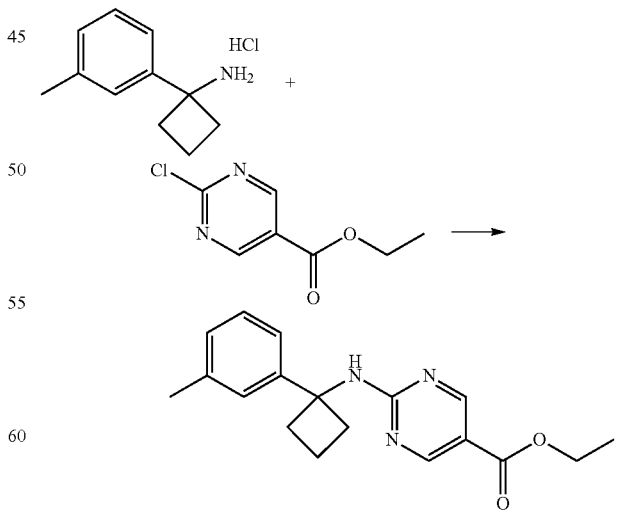

1-(m-tolyl)cyclobutan-1-amine hydrochloride (0.400 g, 2.023 mmol), ethyl 2-chloropyrimidine-5-carboxylate (0.396 g, 2.124 mmol) and N,N-diisopropylethylamine (1.057 mL, 6.069 mmol) were mixed at the room temperature in 1,4-dioxane (4 mL), stirred at 110° C. for 17 hr, and cooled down to the room temperature to terminate the reaction. The reaction mixture was concentrated under the reduced pressure to remove the solvent. The concentrate was purified and concentrated by column chromatography (SiO₂, 4 g cartridge; ethyl acetate/hexane=5% to 10%) to give ethyl 2-((1-(m-tolyl)cyclobutyl)amino)pyrimidine-5-carboxylate as white solid (0.349 g, 55.4%).

[Step 5] 2-((1-(m-tolyl)cyclobutyl)amino)pyrimidine-5-carbohydrazide

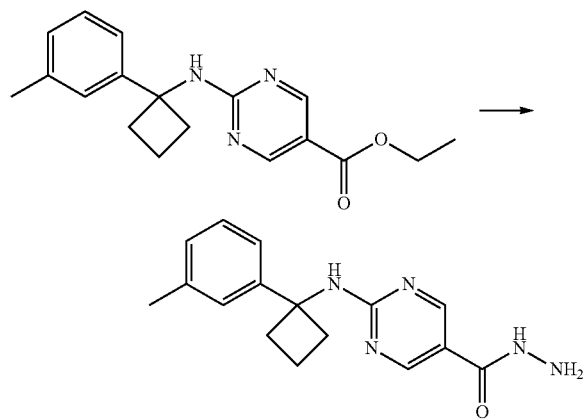

Ethyl 2-((1-(m-tolyl)cyclobutyl)amino)pyrimidine-5-carboxylate (0.349 g, 1.121 mmol) and hydrazine monohydrate (1.089 mL, 22.416 mmol) were mixed at the room temperature in ethanol (5 mL), stirred at 120° C. for 17 hr, and cooled down to the room temperature to terminate the reaction. The reaction mixture was concentrated under the reduced pressure to remove the solvent. The precipitates were collected by filtration, washed by ethanol, and dried to give 2-((1-(m-tolyl)cyclobutyl)amino)pyrimidine-5-carbohydrazide as white solid (0.278 g, 83.4%).

[Step 6] N'-(2,2-difluoroacetyl)-2-((1-(m-tolyl)cyclobutyl)amino)pyrimidine-5-carbohydrazide

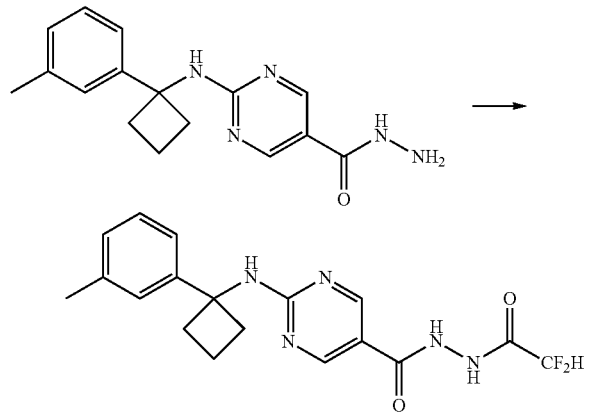

A solution of 2-((1-(m-tolyl)cyclobutyl)amino)pyrimidine-5-carbohydrazide (0.148 g, 0.498 mmol), 2,2-difluoroacetic anhydride (0.049 mL, 0.448 mmol) and triethylamine (0.104 mL, 0.747 mmol) in tetrahydrofuran (5 mL) prepared at the room temperature was stirred at the same temperature. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo.

N'-(2,2-difluoroacetyl)-2-((1-(m-tolyl)cyclobutyl)amino)pyrimidine-5-carbohydrazide was used without further purification (0.180 g, 96.3%, pale yellow solid).

[Step 7] Compound 1673

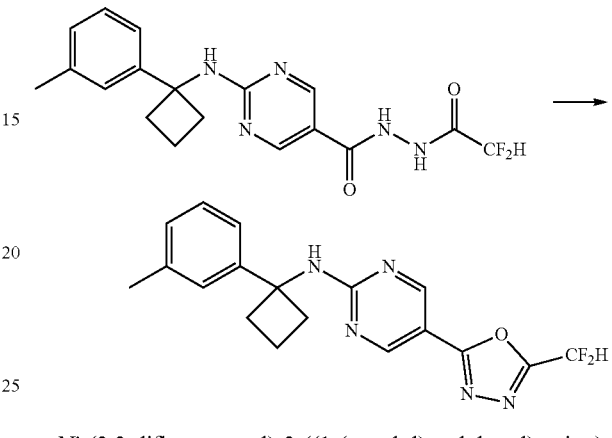

N'-(2,2-difluoroacetyl)-2-((1-(m-tolyl)cyclobutyl)amino)pyrimidine-5-carbohydrazide (0.180 g, 0.480 mmol) and 1-methoxy-N-triethylammoniosulfonyl-methanimidate (Burgess reagent, 0.171 g, 0.719 mmol) in tetrahydrofuran (5 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; ethyl acetate/hexane=0% to 15%) to give 5-(5-(difluoromethyl)-1,3,4-oxadiazol-2-yl)-N-(1-(m-tolyl)cyclobutyl)pyrimidin-2-amine as white solid (0.047 g, 27.4%).

¹H NMR (400 MHz, CDCl₃) δ 8.89 (s, 2H), 7.33-7.28 (m, 2H), 7.24 (t, J=7.9 Hz, 1H), 7.07 (d, J=7.7 Hz, 1H), 7.02-6.76 (m, 1H), 6.55 (s, 1H), 2.79-2.72 (m, 2H), 2.65-2.58 (m, 2H), 2.37 (s, 3H), 2.23-2.15 (m, 1H), 2.07-2.01 (m, 1H); LRMS (ES) m/z 358.4 (M⁺+1).

Example 30: Compound 1674, N-(1-(m-tolyl)cyclobutyl)-5-(5-(trifluoromethyl)-1,3,4-oxadiazol-2-yl)pyrimidin-2-amine

[Step 1] 2-((1-(m-tolyl)cyclobutyl)amino)-N'-(2,2,2-trifluoroacetyl)pyrimidine-5-carbohydrazide

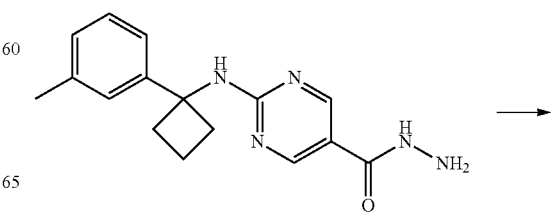

-continued

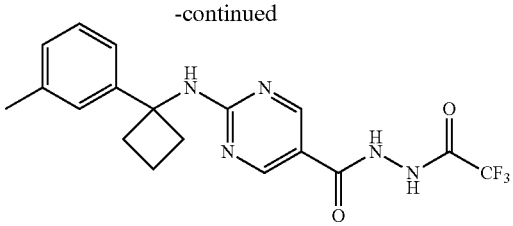

A solution of 2-((1-(m-tolyl)cyclobutyl)amino)pyrimidine-5-carbohydrazide (0.130 g, 0.437 mmol), trifluoroacetic anhydride (0.056 mL, 0.393 mmol) and triethylamine (0.091 mL, 0.656 mmol) in tetrahydrofuran (5 mL) prepared at the room temperature was stirred at the same temperature. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. 2-((1-(m-tolyl)cyclobutyl)amino)-N'-(2,2,2-trifluoroacetyl)pyrimidine-5-carbohydrazide was used without further purification (0.170 g, 98.9%, pale yellow solid).

[Step 2] Compound 1674

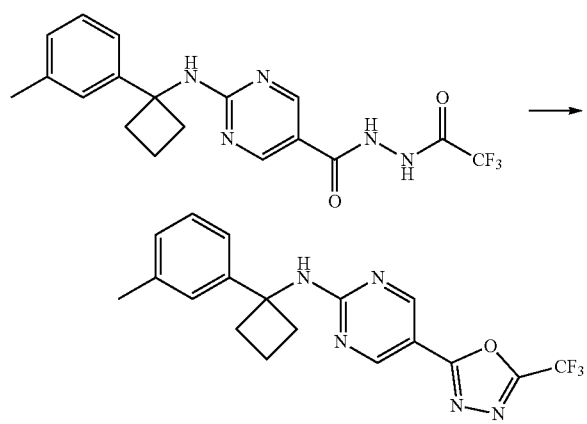

2-((1-(m-tolyl)cyclobutyl)amino)-N'-(2,2,2-trifluoroacetyl)pyrimidine-5-carbohydrazide (0.170 g, 0.432 mmol) and 1-methoxy-N-triethylammoniosulfonyl-methanimidate (Burgess reagent, 0.154 g, 0.648 mmol) in tetrahydrofuran (5 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(m-tolyl)cyclobutyl)-5-(5-(trifluoromethyl)-1,3,4-oxadiazol-2-yl)pyrimidin-2-amine as white solid (0.041 g, 25.3%).

$^1$H NMR (400 MHz, CDCl$_3$) δ 8.89 (s, 2H), 7.32-7.31 (m, 2H), 7.24 (t, J=7.9 Hz, 1H), 7.07 (d, J=7.6 Hz, 1H), 6.55 (s, 1H), 2.79-2.72 (m, 2H), 2.62-2.58 (m, 2H), 2.37 (s, 3H), 2.21-2.18 (m, 1H), 2.05-1.99 (m, 1H); LRMS (ES) m/z 376.3 (M$^+$+1).

Example 31: Compound 1675, 5-(5-(difluoromethyl)-1,3,4-oxadiazol-2-yl)-N-(1-(p-tolyl)cyclobutyl)pyrimidin-2-amine

[Step 1] 1-(p-tolyl)cyclobutane-1-carbonitrile

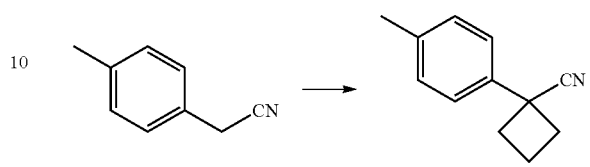

A solution of 2-(p-tolyl)acetonitrile (5.000 g, 38.116 mmol) and sodium hydride (2.012 g, 83.854 mmol) in N,N-dimethylformamide (100 mL) was stirred at 0° C. for 1 hr, and mixed with 1,3-dibromopropane (7.695 g, 38.116 mmol). The reaction mixture was stirred at the room temperature for additional 3 hr, and quenched at the room temperature by the addition of saturated aqueous sodium bicarbonate solution (10 mL, 10 min stirring). The reaction mixture was concentrated under the reduced pressure to remove the solvent. And then, water was added to the concentrate, followed by extraction with ethyl acetate The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(p-tolyl)cyclobutane-1-carbonitrile as pale yellow oil (2.640 g, 40.4%).

[Step 2] 1-(p-tolyl)cyclobutane-1-carboxamide

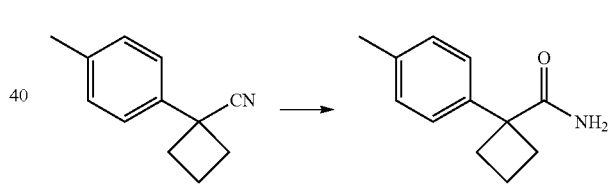

A solution of 1-(p-tolyl)cyclobutane-1-carbonitrile (2.640 g, 15.417 mmol), sodium hydroxide (25.00%, 0.617 g, 3.854 mmol), hydrogen peroxide (30.00%, 5.244 g, 46.251 mmol) and tetra-n-butylammonium bromide (0.050 g, 0.154 mmol) in methanol (70 mL) prepared at the room temperature was stirred at the same temperature 17 hr. The precipitates were collected by filtration, washed by water, and dried to give 1-(p-tolyl)cyclobutane-1-carboxamide as white solid (2.950 g, 101.1%).

[Step 3] 1-(p-tolyl)cyclobutan-1-amine hydrochloride

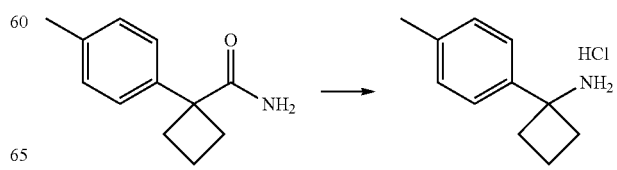

A solution of 1-(p-tolyl)cyclobutane-1-carboxamide (2.950 g, 15.587 mmol) and sodium hypochlorite (8.50% solution, 15.794 mL, 21.822 mmol) and sodium hydroxide (3.00 M solution in water, 14.548 mL, 43.644 mmol) in 1-butanol (30 mL) prepared at the room temperature was stirred at the same temperature. And then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and was added hydrochloric acid (4.00 M solution in 1,4-dioxane, 5.845 mL, 23.381 mmol) and stirred at the ambient temperature. The resulting precipitates were collected by filtration and dried to give 1-(p-tolyl)cyclobutan-1-amine hydrochloride as white solid (1.860 g, 60.4%).

[Step 4] Ethyl 2-((1-(p-tolyl)cyclobutyl)amino)pyrimidine-5-carboxylate

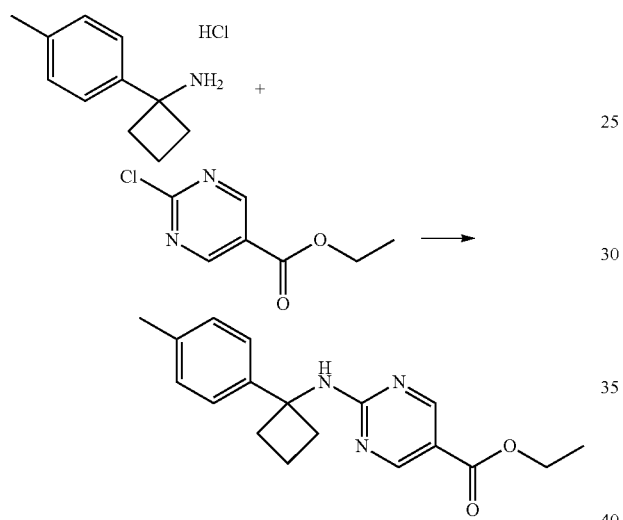

1-(p-tolyl)cyclobutan-1-amine hydrochloride (1.000 g, 5.058 mmol), ethyl 2-chloropyrimidine-5-carboxylate (0.991 g, 5.311 mmol) and N,N-diisopropylethylamine (2.643 mL, 15.174 mmol) were mixed at the room temperature in 1,4-dioxane (15 mL), stirred at 110° C. for 17 hr, and cooled down to the room temperature. The reaction mixture was concentrated under the reduced pressure to remove the solvent. The concentrate was purified and concentrated by column chromatography (SiO$_2$, 12 g cartridge; ethyl acetate/hexane=0% to 10%) to give ethyl 2-((1-(p-tolyl)cyclobutyl)amino)pyrimidine-5-carboxylate as white solid (0.706 g, 45.1%).

[Step 5] 2-((1-(p-tolyl)cyclobutyl)amino)pyrimidine-5-carbohydrazide

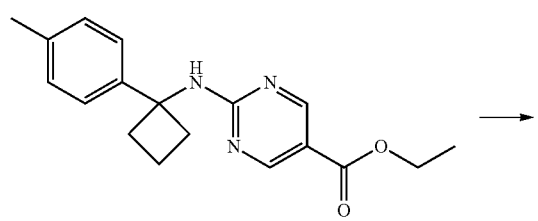

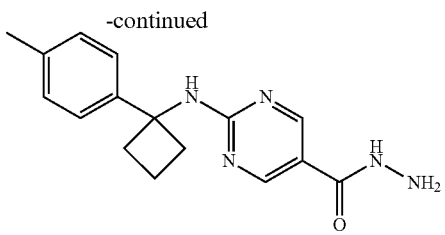

Ethyl 2-((1-(p-tolyl)cyclobutyl)amino)pyrimidine-5-carboxylate (0.706 g, 2.267 mmol) and hydrazine monohydrate (2.204 mL, 45.345 mmol) were mixed at the room temperature in ethanol (5 mL), stirred at 120° C. for 17 hr, and cooled down to the room temperature to terminate the reaction. The reaction mixture was concentrated under the reduced pressure to remove the solvent. The precipitates were collected by filtration, washed by ethanol, and dried to give 2-((1-(p-tolyl)cyclobutyl)amino)pyrimidine-5-carbohydrazide as white solid (0.537 g, 79.7%).

[Step 6] N'-(2,2-difluoroacetyl)-2-((1-(p-tolyl)cyclobutyl)amino)pyrimidine-5-carbohydrazide

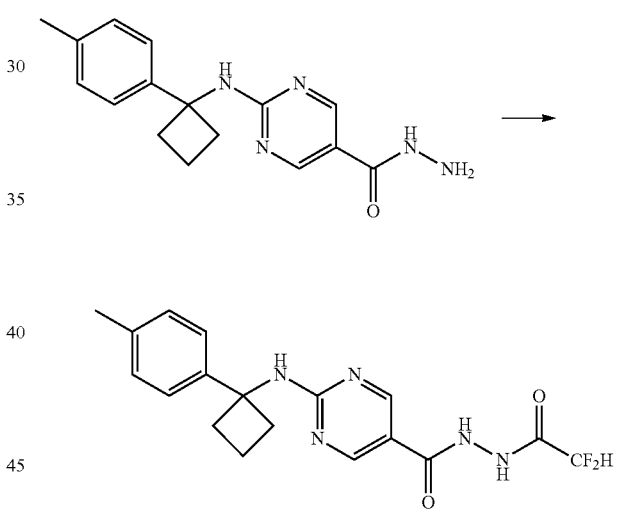

A solution of 2-((1-(p-tolyl)cyclobutyl)amino)pyrimidine-5-carbohydrazide (0.287 g, 0.965 mmol), 2,2-difluoroacetic anhydride (0.094 mL, 0.869 mmol) and triethylamine (0.202 mL, 1.448 mmol) in tetrahydrofuran (10 mL) prepared at the room temperature was stirred at the same temperature. The mixture was filtered, and then the filtrate was added saturated aqueous sodium bicarbonate solution, followed by extraction with dichloromethane. The bi-phasic mixture was passed through a plastic frit to remove the solid residues and aqueous layer, and the organic layer collected was concentrated in vacuo.

N'-(2,2-difluoroacetyl)-2-((1-(p-tolyl)cyclobutyl)amino)pyrimidine-5-carbohydrazide was used without further purification (0.360 g, 99.4%, pale yellow solid).

[Step 7] Compound 1675

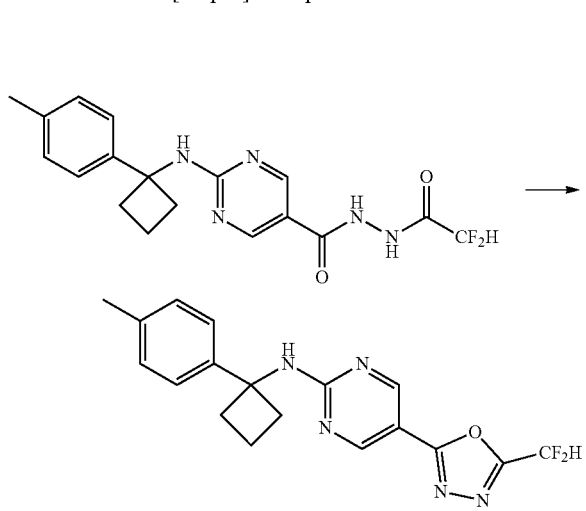

N'-(2,2-difluoroacetyl)-2-((1-(p-tolyl)cyclobutyl)amino) pyrimidine-5-carbohydrazide (0.360 g, 0.959 mmol) and 1-methoxy-N-triethylammoniosulfonyl-methanimidate (Burgess reagent, 0.343 g, 1.439 mmol) in tetrahydrofuran (5 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 15%) to give 5-(5-(difluoromethyl)-1,3,4-oxadiazol-2-yl)-N-(1-(p-tolyl)cyclobutyl)pyrimidin-2-amine as white solid (0.094 g, 27.4%).

$^1$H NMR (400 MHz, CDCl$_3$) δ 8.88 (s, 2H), 7.41 (d, J=8.2 Hz, 2H), 7.16 (d, J=7.9 Hz, 2H), 7.02-6.76 (m, 1H), 6.49 (s, 1H), 2.78-2.71 (m, 2H), 2.65-2.59 (m, 2H), 2.34 (s, 3H), 2.19-2.17 (m, 1H), 2.03-1.98 (m, 1H); LRMS (ES) m/z 376.3 (M$^+$+1).

Example 32: Compound 1676, N-(1-(p-tolyl)cyclobutyl)-5-(5-(trifluoromethyl)-1,3,4-oxadiazol-2-yl)pyrimidin-2-amine

[Step 1] 2-((1-(p-tolyl)cyclobutyl)amino)-N'-(2,2,2-trifluoroacetyl)pyrimidine-5-carbohydrazide

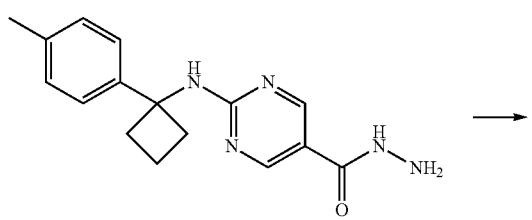

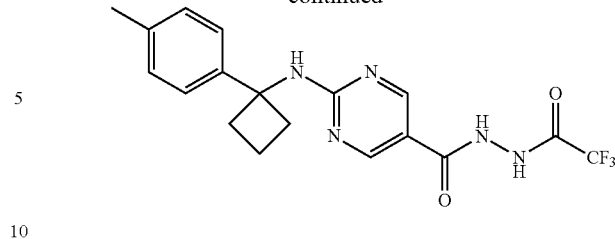

A solution of 2-((1-(p-tolyl)cyclobutyl)amino)pyrimidine-5-carbohydrazide (0.250 g, 0.841 mmol) and triethylamine (0.176 mL, 1.261 mmol) in tetrahydrofuran (10 mL) was mixed at the room temperature with trifluoroacetic anhydride (0.107 mL, 0.757 mmol). The reaction mixture prepared at the room temperature was stirred at the same temperature for 17 hr. The mixture was filtered, and then saturated aqueous sodium bicarbonate solution was added to the filtrate, followed by extraction with dichloromethane. The bi-phasic mixture was passed through a plastic frit to remove the solid residues and aqueous layer, and the organic layer collected was concentrated in vacuo. 2-((1-(p-tolyl)cyclobutyl)amino)-N'-(2,2,2-trifluoroacetyl)pyrimidine-5-carbohydrazide was used without further purification (0.330 g, 99.8%, pale yellow solid).

[Step 2] Compound 1676

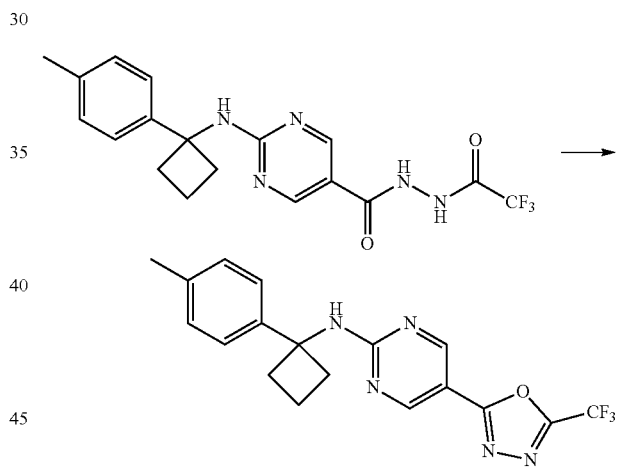

2-((1-(p-tolyl)cyclobutyl)amino)-N'-(2,2,2-trifluoroacetyl)pyrimidine-5-carbohydrazide (0.330 g, 0.839 mmol) and 1-methoxy-N-triethylammoniosulfonyl-methanimidate (Burgess reagent, 0.300 g, 1.258 mmol) in tetrahydrofuran (5 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(p-tolyl)cyclobutyl)-5-(5-(trifluoromethyl)-1,3,4-oxadiazol-2-yl)pyrimidin-2-amine as white solid (0.035 g, 11.1%).

$^1$H NMR (400 MHz, CDCl$_3$) δ 8.88 (s, 2H), 7.42 (d, J=8.2 Hz, 2H), 7.16 (d, J=7.9 Hz, 2H), 6.65 (s, 1H), 2.78-2.71 (m,

2H), 2.66-2.60 (m, 2H), 2.34 (s, 3H), 2.19-2.16 (m, 1H), 2.04-1.99 (m, 1H); LRMS (ES) m/z 376.3 (M$^+$+1).

Example 33: Compound 1677, Benzyl 4-((5-(5-(difluoromethyl)-1,3,4-oxadiazol-2-yl)pyrimidin-2-yl)amino)-4-phenylpiperidine-1-carboxylate

[Step 1] Benzyl bis(2-chloroethyl)carbamate

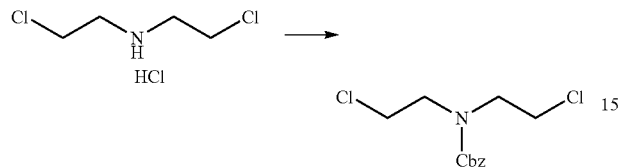

A solution of bis(2-chloroethyl)amine hydrochloride (16.000 g, 89.646 mmol) and triethylamine (31.237 mL, 224.115 mmol) in dichloromethane (300 mL) was mixed at 0° C. with benzyl chloroformate (13.437 mL, 94.128 mmol), and stirred at the same temperature for 1 hr. The reaction mixture was stirred at the room temperature for additional 17 hr. Water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 40%) to give benzyl bis(2-chloroethyl)carbamate as white solid (12.700 g, 51.3%).

[Step 2] benzyl 4-cyano-4-phenylpiperidine-1-carboxylate

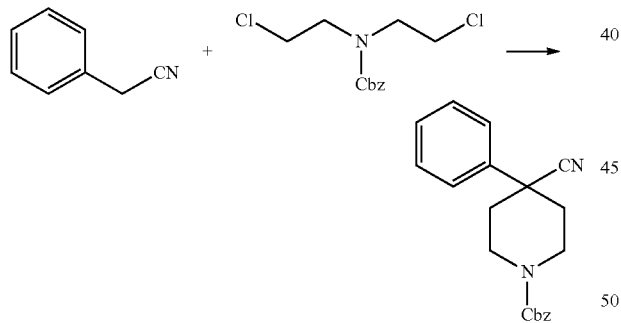

A solution of 2-phenylacetonitrile (5.000 g, 42.680 mmol) and sodium hydride (60.00%, 3.755 g, 93.897 mmol) in N,N-dimethylformamide (100 mL) was stirred at 0° C. for 30 min, and mixed with benzyl bis(2-chloroethyl)carbamate (11.787 g, 42.680 mmol). The reaction mixture was stirred at 60° C. for additional 3 hr, and cooled down to the room temperature. Water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=30% to 100%) to give benzyl 4-cyano-4-phenylpiperidine-1-carboxylate as white solid (7.500 g, 54.8%).

[Step 3] Benzyl 4-carbamoyl-4-phenylpiperidine-1-carboxylate

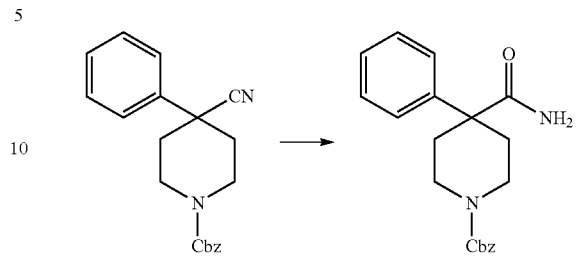

A solution of benzyl 4-cyano-4-phenylpiperidine-1-carboxylate (1.500 g, 4.682 mmol), potassium carbonate (1.941 g, 14.045 mmol) and hydrogen peroxide (30.00%, 2.654 g, 23.409 mmol) in dimethylsulfoxide (15 mL) was stirred at 0° C. for 2 hr and then for additional 17 hr at 60° C. It was cooled down to the room temperature to terminate the reaction. water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with water (200 mL) stirred at the ambient temperature. The resulting precipitates were collected by filtration, washed by water, and dried to give benzyl 4-carbamoyl-4-phenylpiperidine-1-carboxylate as white solid (1.000 g, 63.1%).

[Step 4] Benzyl 4-amino-4-phenylpiperidine-1-carboxylate hydrochloride

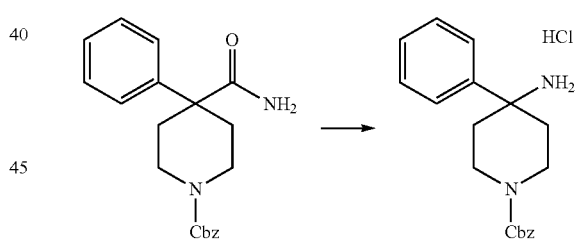

A solution of benzyl 4-carbamoyl-4-phenylpiperidine-1-carboxylate (5.960 g, 17.612 mmol), sodium hypochlorite (11.00% solution, 13.789 mL, 24.656 mmol) and sodium hydroxide (3.00 M solution in water, 16.438 mL, 49.313 mmol) in 1-butanol (100 mL) prepared at the room temperature was stirred at the same temperature for 18 hr. Water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate (20 mL) and was added hydrochloric acid (4.00 M solution in 1,4-dioxane, 6.604 mL, 26.418 mmol) and stirred at the ambient temperature. The resulting precipitates were collected by filtration and dried to give benzyl 4-amino-4-phenylpiperidine-1-carboxylate hydrochloride as white solid (4.000 g, 65.5%).

151

[Step 5] Ethyl 2-((1-((benzyloxy)carbonyl)-4-phenylpiperidin-4-yl)amino)pyrimidine-5-carboxylate

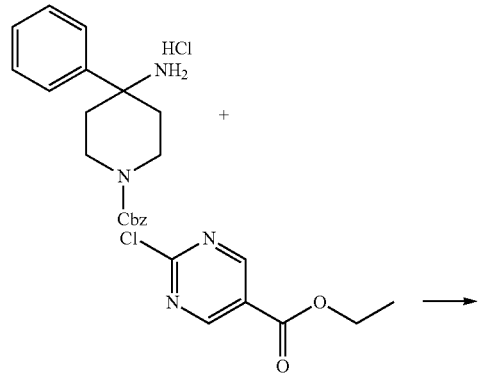

Benzyl 4-amino-4-phenylpiperidine-1-carboxylate hydrochloride (3.000 g, 8.649 mmol), ethyl 2-chloropyrimidine-5-carboxylate (1.614 g, 8.649 mmol) and N,N-diisopropylethylamine (3.465 mL, 19.893 mmol) were mixed at the room temperature in 1,4-dioxane (30 mL), stirred at 110° C. for 17 hr, and cooled down to the room temperature to terminate the reaction. The reaction mixture was concentrated under the reduced pressure to remove the solvent. The concentrate was purified and concentrated by column chromatography (SiO2, 40 g cartridge; ethyl acetate/hexane=5% to 40%) to give ethyl 2-((1-((benzyloxy)carbonyl)-4-phenylpiperidin-4-yl)amino)pyrimidine-5-carboxylate as yellow solid (1.900 g, 51.5%).

[Step 6] Benzyl 4-((5-(hydrazinocarbonyl)pyrimidin-2-yl)amino)-4-phenylpiperidine-1-carboxylate

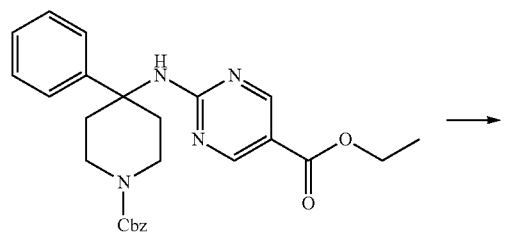

152

Ethyl 2-((1-((benzyloxy)carbonyl)-4-phenylpiperidin-4-yl)amino)pyrimidine-5-carboxylate (0.900 g, 1.954 mmol) and hydrazine monohydrate (1.900 mL, 39.085 mmol) were mixed at the room temperature in ethanol (10 mL), stirred at 120° C. for 17 hr, and cooled down to the room temperature to terminate the reaction. The reaction mixture was concentrated under the reduced pressure to remove the solvent. The concentrate was diluted with ethyl acetate (5 mL) and stirred at the ambient temperature. The resulting precipitates were collected by filtration, washed by ethyl acetate, and dried to give benzyl 4-((5-(hydrazinocarbonyl)pyrimidin-2-yl)amino)-4-phenylpiperidine-1-carboxylate as pale yellow solid (0.480 g, 55.0%).

[Step 7] Benzyl 4-((5-(2-(2,2-difluoroacetyl)hydrazine-1-carbonyl)pyrimidin-2-yl)amino)-4-phenylpiperidine-1-carboxylate

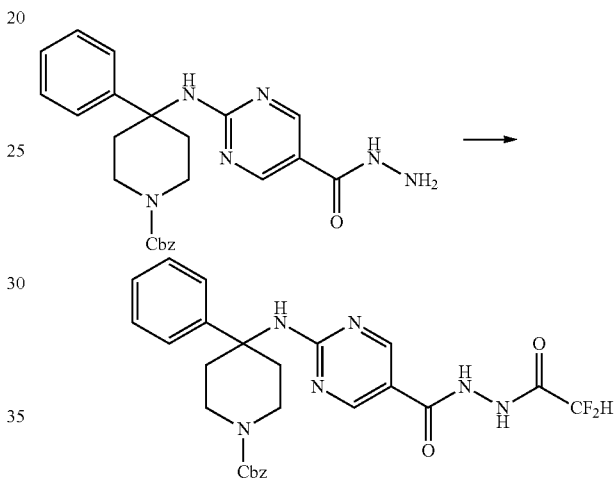

A solution of benzyl 4-((5-(hydrazinocarbonyl)pyrimidin-2-yl)amino)-4-phenylpiperidine-1-carboxylate (0.100 g, 0.224 mmol), 2,2-difluoroacetic anhydride (0.022 mL, 0.202 mmol) and triethylamine (0.047 mL, 0.336 mmol) in tetrahydrofuran (3 mL) prepared at the room temperature was stirred at the same temperature for 18 hr. Water was added to the reaction mixture, followed by extraction with dichloromethane. The bi-phasic mixture was passed through a plastic frit to remove the solid residues and aqueous layer, and the organic layer collected was concentrated in vacuo. Benzyl 4-((5-(2-(2,2-difluoroacetyl)hydrazine-1-carbonyl) pyrimidin-2-yl)amino)-4-phenylpiperidine-1-carboxylate was used without further purification (0.113 g, 96.2%, pale yellow solid).

[Step 8] Compound 1677

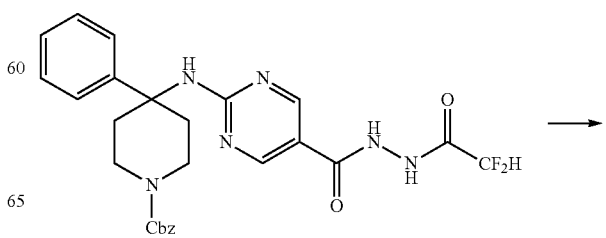

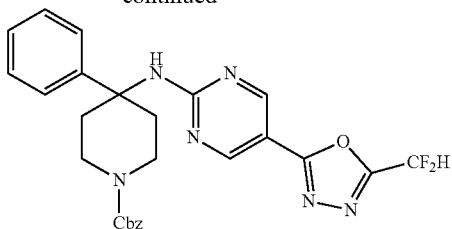

Benzyl 4-((5-(2-(2,2-difluoroacetyl)hydrazine-1-carbonyl)pyrimidin-2-yl)amino)-4-phenylpiperidine-1-carboxylate (0.113 g, 0.215 mmol) and 1-methoxy-N-triethylammoniosulfonyl-methanimidate (Burgess reagent, 0.077 g, 0.323 mmol) in tetrahydrofuran (3 mL) was mixed at the room temperature, heated at 150° C. under the microwaves for 30 hr, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=5% to 30%) to give benzyl 4-((5-(5-(difluoromethyl)-1,3,4-oxadiazol-2-yl)pyrimidin-2-yl)amino)-4-phenylpiperidine-1-carboxylate as white solid (0.070 g, 64.2%).

$^1$H NMR (400 MHz, CDCl$_3$) δ 8.92 (brs, 1H), 8.76 (brs, 1H), 7.43-7.31 (m, 9H), 7.27-7.25 (m, 1H), 6.19 (s, 1H), 4.15-4.14 (m, 2H), 3.51-3.49 (m, 2H), 2.61 (d, J=12.8 Hz, 2H), 2.21-2.15 (m, 2H); LRMS (ES) m/z 507.6 (M$^+$+1).

Example 34: Compound 1678, 5-(5-(difluoromethyl)-1,3,4-oxadiazol-2-yl)-N-(4-phenylpiperidin-4-yl)pyrimidin-2-amine

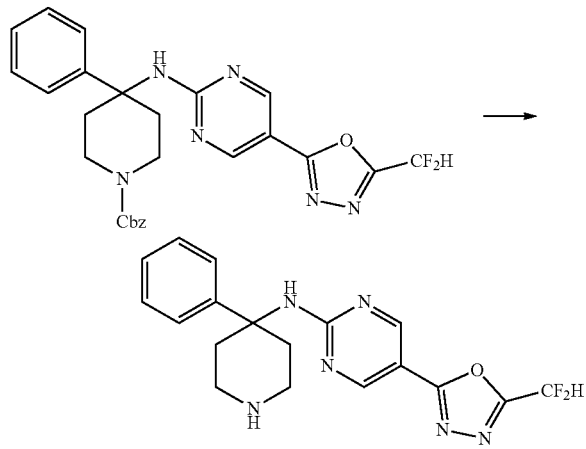

A solution of benzyl 4-((5-(5-(difluoromethyl)-1,3,4-oxadiazol-2-yl)pyrimidin-2-yl)amino)-4-phenylpiperidine-1-carboxylate (0.060 g, 0.118 mmol) in methanol (5 mL) was treated at the room temperature with 10%-Pd/C (10 mg), and stirred at the same temperature under the hydrogen atmosphere (H2 balloon) for 17 hr. The reaction mixture was filtered through a celite pad to remove solids, and concentrated under the reduced pressure to remove the solvent. The concentrate was purified and concentrated by column chromatography (SiO$_2$, 12 g cartridge; methanol/dichloromethane=0% to 30%) to give 5-(5-(difluoromethyl)-1,3,4-oxadiazol-2-yl)-N-(4-phenylpiperidin-4-yl)pyrimidin-2-amine as white solid (0.020 g, 45.3%).

$^1$H NMR (400 MHz, DMSO-d$_6$) δ 8.87 (s, 1H), 8.62 (s, 1H), 8.42 (s, 1H), 7.63-7.37 (m, 3H), 7.28 (t, J=7.6 Hz, 2H), 7.16 (t, J=7.2 Hz, 1H), 2.88-2.81 (m, 4H), 2.52-2.51 (m, 2H), 1.89-1.84 (m, 2H); LRMS (ES) m/z 373.5 (M$^+$+1).

Example 35: Compound 1683, 5-(5-(difluoromethyl)-1,3,4-oxadiazol-2-yl)-N-(1-(2-fluorophenyl)cyclopropyl)pyrimidin-2-amine

[Step 1] 2-(methylthio)pyrimidine-5-carboxylic acid

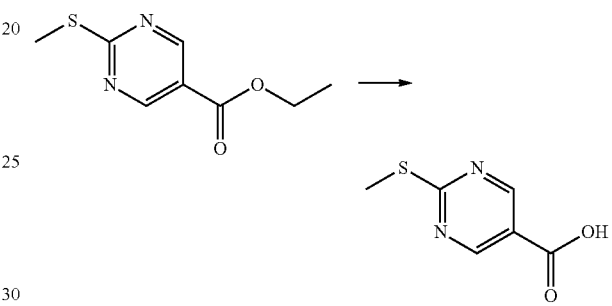

A solution of ethyl 2-(methylthio)pyrimidine-5-carboxylate (4.500 g, 22.700 mmol) and sodium hydroxide (4.539 g, 113.499 mmol) in methanol (20 mL)/water (5 mL) prepared at the room temperature was stirred at the same temperature for 1 hr. The reaction mixture was filtered through a celite pad to remove solids. Aqueous 1N-hydrochloric acid solution was added to the filtrate, followed by extraction with ethyl acetate. The organic layer was washed with aqueous saturated sodium chloride solution, dried with anhydrous MgSO$_4$, filtered, and concentrated in vacuo. The crude product was used without further purification (2-(methylthio)pyrimidine-5-carboxylic acid, 3.330 g, 86.2% white solid)

[Step 2] 2-(methylthio)pyrimidine-5-carbohydrazide

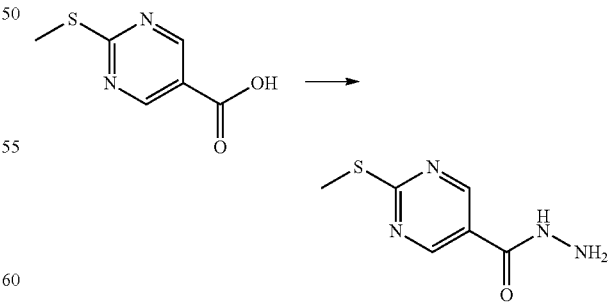

A solution of 2-(methylthio)pyrimidine-5-carboxylic acid (3.300 g, 19.390 mmol), 1,1'-Carbonyldiimidazole (3.459 g, 21.329 mmol) and Hydrazine monohydrate (4.712 mL, 96.950 mmol) in tetrahydrofuran (20 mL) prepared at the room temperature was stirred at the same temperature for 4 hr. Water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (2-(methylthio)pyrimidine-5-carbohydrazide, 1.000 g, 28.0%, White solid).

[Step 3] N'-(2,2-difluoroacetyl)-2-(methylthio)pyrimidine-5-carbohydrazide

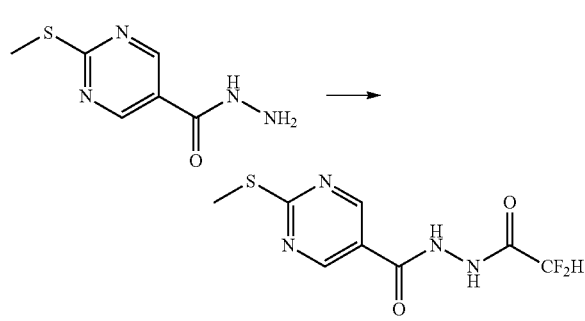

A solution of 2-(methylthio)pyrimidine-5-carbohydrazide (1.000 g, 5.428 mmol), 2,2-difluoroacetic anhydride (0.675 mL, 5.428 mmol) and triethylamine (1.135 mL, 8.142 mmol) in dichloromethane (10 mL) prepared at the room temperature was stirred at the same temperature for 2 hr. Water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N'-(2,2-difluoroacetyl)-2-(methylthio)pyrimidine-5-carbohydrazide as White solid (1.200 g, 84.3%).

[Step 4] 2-(difluoromethyl)-5-(2-(methylthio)pyrimidin-5-yl)-1,3,4-oxadiazole

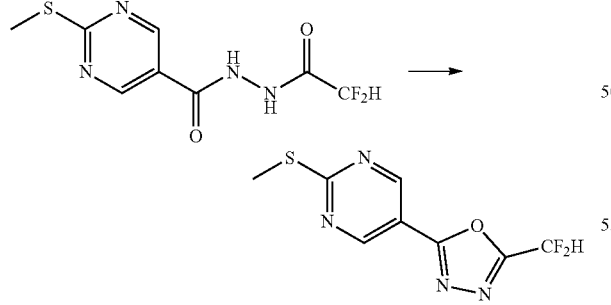

A mixture of N'-(2,2-difluoroacetyl)-2-(methylthio)pyrimidine-5-carbohydrazide (0.410 g, 1.564 mmol) and 1-methoxy-N-triethylammoniosulfonyl-methanimidate (Burgess reagent, 0.559 g, 2.345 mmol) in tetrahydrofuran (10 mL) was heated at 150° C. for 30 min under the microwaves and cooled down to the room temperature. Water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 2-(difluoromethyl)-5-(2-(methylthio)pyrimidin-5-yl)-1,3,4-oxadiazole as White solid (0.192 g, 50.3%).

[Step 5] 2-(difluoromethyl)-5-(2-(methylsulfonyl)pyrimidin-5-yl)-1,3,4-oxadiazole

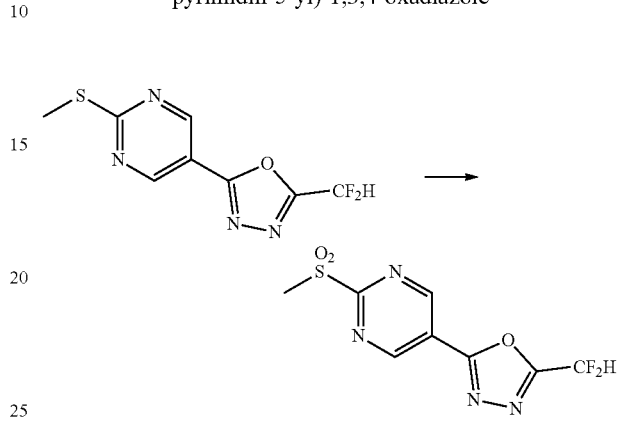

A solution of 2-(difluoromethyl)-5-(2-(methylthio)pyrimidin-5-yl)-1,3,4-oxadiazole (0.192 g, 0.786 mmol) and 3-chloroperbenzoic acid (0.407 g, 2.359 mmol) in dichloromethane (10 mL) prepared at the room temperature was stirred at the same temperature for 18 hr. Saturated aqueous sodium thiosulfate (Na$_2$S$_2$O$_3$) solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give 2-(difluoromethyl)-5-(2-(methylsulfonyl)pyrimidin-5-yl)-1,3,4-oxadiazole as White solid (0.100 g, 46.0%)

[Step 6] Compound 1683

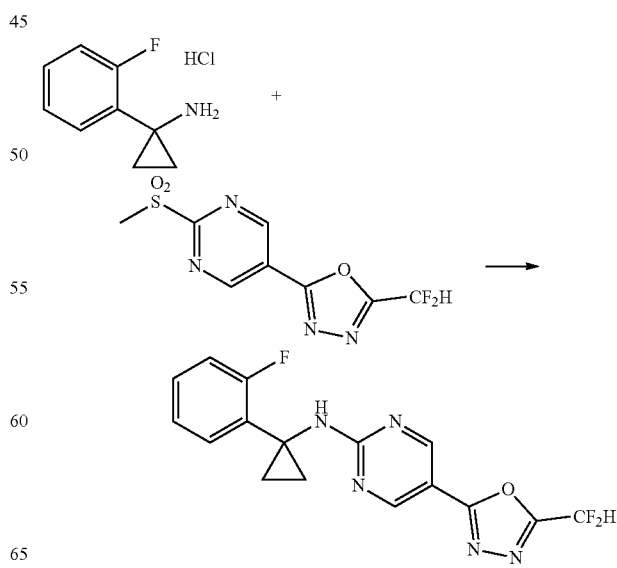

A solution of 1-(2-fluorophenyl)cyclopropan-1-amine hydrochloride (0.034 g, 0.181 mmol), 2-(difluoromethyl)-5-(2-(methylsulfonyl)pyrimidin-5-yl)-1,3,4-oxadiazole (0.050 g, 0.181 mmol) and N,N-diisopropylethylamine (0.095 mL, 0.544 mmol) in dichloromethane (10 mL) prepared at the room temperature was stirred at the same temperature for 12 hr. Water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 15%) to give 5-(5-(difluoromethyl)-1,3,4-oxadiazol-2-yl)-N-(1-(2-fluorophenyl)cyclopropyl)pyrimidin-2-amine as White solid (0.010 g, 15.9%).

¹H NMR (400 MHz, CDCl₃) δ 9.05-8.89 (m, 2H), 7.69 (td, J=7.6, 1.8 Hz, 1H), 7.26-7.22 (m, 1H), 7.11-7.01 (m, 2H), 7.00-6.78 (m, 1H), 6.74 (s, 1H), 1.50-1.30 (m, 4H); LRMS (ES) m/z 348.38 (M⁺+1).

Example 36: Compound 1711, 5-(5-(difluoromethyl)-1,3,4-oxadiazol-2-yl)-N-(1-(4-fluorophenyl)cyclopropyl)pyrimidin-2-amine

[Step 1] N'-(2,2-difluoroacetyl)-2-((1-(4-fluorophenyl)cyclopropyl)amino)pyrimidine-5-carbohydrazide

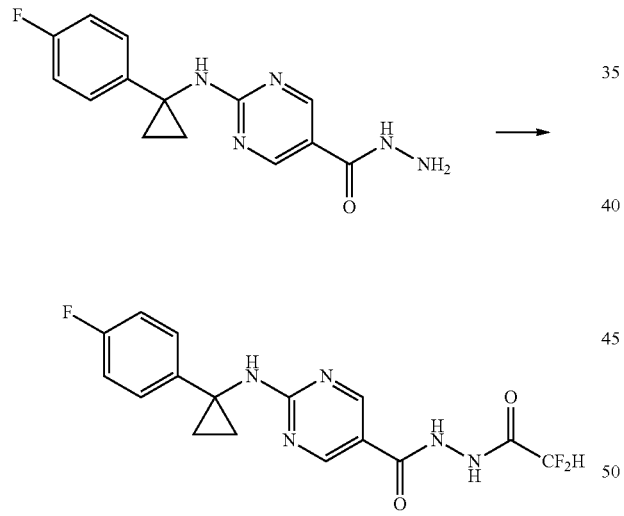

A solution of 2-((1-(4-fluorophenyl)cyclopropyl)amino)pyrimidine-5-carbohydrazide (0.150 g, 0.522 mmol) and triethylamine (0.109 mL, 0.783 mmol) in dichloromethane (10 mL) was mixed at the room temperature with 2,2-difluoroacetic anhydride (0.058 mL, 0.470 mmol), and stirred at the same temperature for 17 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. N'-(2,2-difluoroacetyl)-2-((1-(4-fluorophenyl)cyclopropyl)amino)pyrimidin(2,2-difluo)pyrimidine-5-carbohydrazide was used without further purification (0.105 g, 55.1%, white solid).

[Step 2] Compound 1711

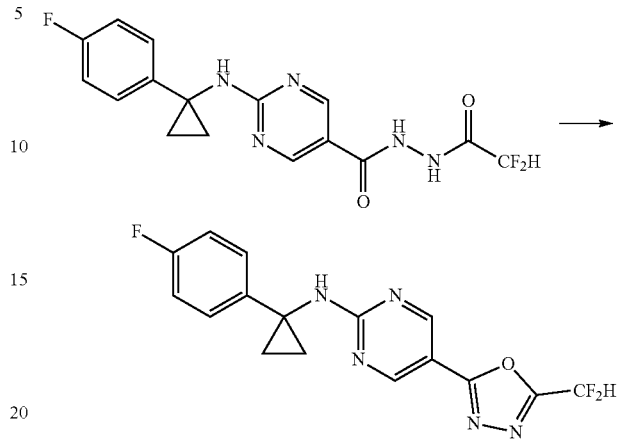

N'-(2,2-difluoroacetyl)-2-((1-(4-fluorophenyl)cyclopropyl)amino)pyrimidine-5-carbohydrazide (0.105 g, 0.287 mmol) and 1-methoxy-N-triethylammoniosulfonyl-methanimidate (Burgess reagent, 0.103 g, 0.431 mmol) were mixed at the room temperature in tetrahydrofuran (4 mL), stirred at 100° C. for 17 hr and cooled down to the room temperature. The reaction mixture was concentrated under the reduced pressure to remove the solvent. Water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; ethyl acetate/hexane=0% to 20%) to give 5-(5-(difluoromethyl)-1,3,4-oxadiazol-2-yl)-N-(1-(4-fluorophenyl)cyclopropyl)pyrimidin-2-amine as white solid (0.019 g, 19.0%).

¹H NMR (400 MHz, CDCl₃) δ 9.01 (s, 1H), 8.90 (s, 1H), 7.29-7.24 (m, 1H), 7.05-6.79 (m, 4H), 6.54 (s, 1H), 1.48-1.44 (m, 4H); LRMS (ES) m/z 348.1 (M⁺+1).

Example 37: Compound 1712, N-(1-(4-fluorophenyl)cyclopropyl)-5-(5-(trifluoromethyl)-1,3,4-oxadiazol-2-yl)pyrimidin-2-amine

[Step 1] 2-((1-(4-fluorophenyl)cyclopropyl)amino)-N'-(2,2,2-trifluoroacetyl)pyrimidine-5-carbohydrazide

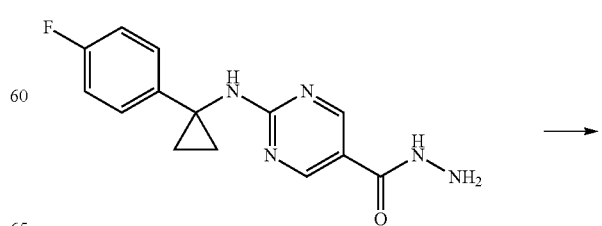

-continued

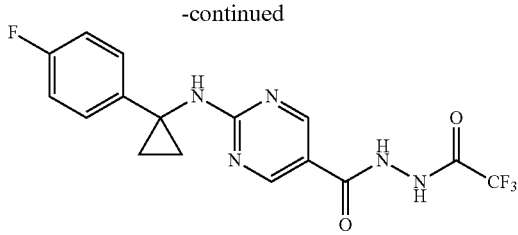

A solution of 2-((1-(4-fluorophenyl)cyclopropyl)amino)pyrimidine-5-carbohydrazide (0.150 g, 0.522 mmol) and triethylamine (0.109 mL, 0.783 mmol) in dichloromethane (10 mL) was mixed at the room temperature with trifluoroacetic anhydride (0.066 mL, 0.470 mmol), and stirred at the same temperature for 17 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. 2-((1-(4-fluorophenyl)cyclopropyl)amino)-N'-(2,2,2-trifluoroacetyl)pyrimidine-5-carbohydrazide was used without further purification (0.132 g, 89.2%, white solid).

[Step 2] Compound 1712

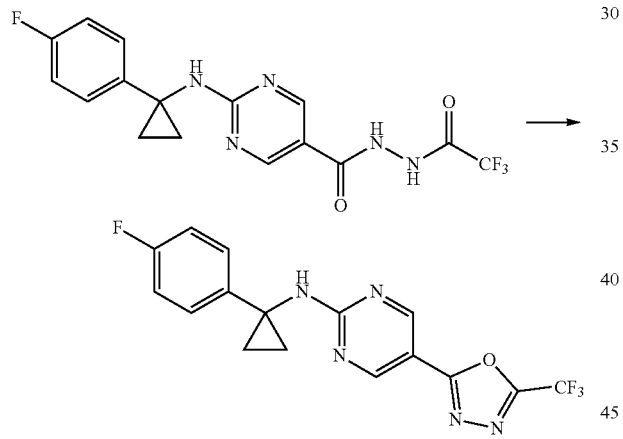

2-((1-(4-fluorophenyl)cyclopropyl)amino)-N'-(2,2,2-trifluoroacetyl)pyrimidine-5-carbohydrazide (0.132 g, 0.344 mmol) and 1-methoxy-N-triethylammoniosulfonyl-methanimidate (Burgess reagent, 0.123 g, 0.517 mmol) were mixed at the room temperature in tetrahydrofuran (4 mL), stirred at 100° C. for 17 hr, and cooled down to the room temperature to terminate the reaction. The reaction mixture was concentrated under the reduced pressure to remove the solvent. Water was added to the concentrate, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(4-fluorophenyl)cyclopropyl)-5-(5-(trifluoromethyl)-1,3,4-oxadiazol-2-yl)pyrimidin-2-amine as white solid (0.010 g, 7.9%).

$^1$H NMR (400 MHz, CDCl$_3$) δ 9.01 (s, 1H), 8.98 (s, 1H), 7.29-7.24 (m, 1H), 7.03-6.89 (m, 3H), 6.55 (s, 1H), 1.50-1.42 (m, 4H); LRMS (ES) m/z 366.4 (M$^+$+1).

Example 38: Compound 1713, 5-(5-(difluoromethyl)-1,3,4-oxadiazol-2-yl)-N-(1-(3-fluorophenyl)cyclopropyl)pyrimidin-2-amine

[Step 1] N'-(2,2-difluoroacetyl)-2-((1-(3-fluorophenyl)cyclopropyl)amino)pyrimidine-5-carbohydrazide

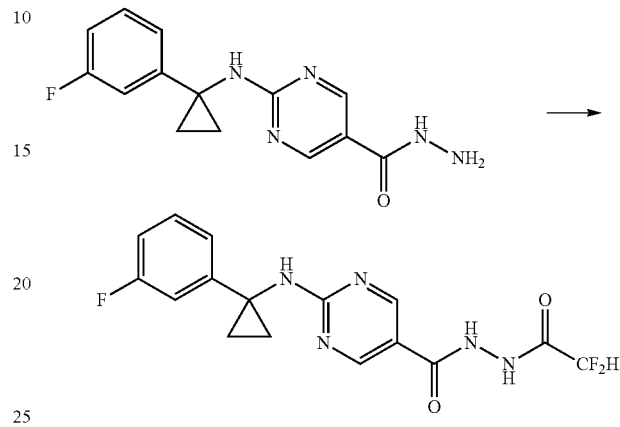

A solution of 2-((1-(3-fluorophenyl)cyclopropyl)amino)pyrimidine-5-carbohydrazide (0.327 g, 1.138 mmol) and triethylamine (0.238 mL, 1.707 mmol) in dichloromethane (10 mL) was mixed at the room temperature with 2,2-difluoroacetic anhydride (0.127 mL, 1.024 mmol), and stirred at the same temperature for 17 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. N'-(2,2-difluoroacetyl)-2-((1-(3-fluorophenyl)cyclopropyl)amino)pyrimidine-5-carbohydrazide was used without further purification (0.232 g, 55.8%, white solid).

[Step 2] Compound 1713

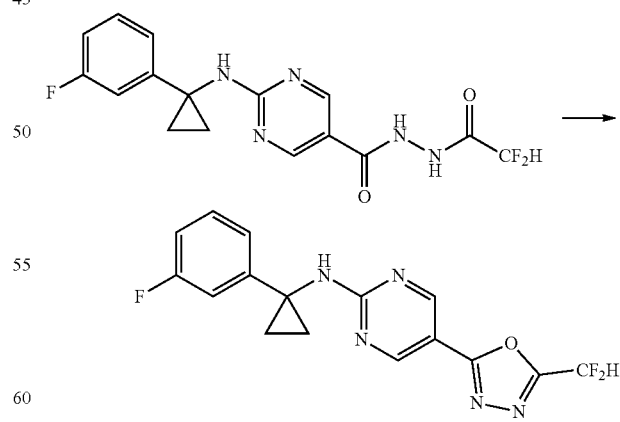

N'-(2,2-difluoroacetyl)-2-((1-(3-fluorophenyl)cyclopropyl)amino)pyrimidine-5-carbohydrazide (0.232 g, 0.635 mmol) and 1-methoxy-N-triethylammoniosulfonyl-methanimidate (Burgess reagent, 0.227 g, 0.953 mmol) were mixed at the room temperature in tetrahydrofuran (4 mL), stirred at 100° C. for 17 hr, and cooled down to the room temperature. The reaction mixture was concentrated under the reduced pressure to remove the solvent. Water was added to the concentrate, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give 5-(5-(difluoromethyl)-1,3,4-oxadiazol-2-yl)-N-(1-(3-fluorophenyl)cyclopropyl)pyrimidin-2-amine as white solid (0.066 g, 29.9%).

$^1$H NMR (400 MHz, CDCl$_3$) δ 9.02 (s, 1H), 7.32-7.28 (m, 2H), 7.04-6.79 (m, 3H), 6.55 (s, 1H), 1.42-1.39 (m, 4H); LRMS (ES) m/z 348.1 (M$^+$+1).

Example 39: Compound 1714, N-(1-(3-fluorophenyl)cyclopropyl)-5-(5-(trifluoromethyl)-1,3,4-oxadiazol-2-yl)pyrimidin-2-amine

[Step 1] 2-((1-(3-fluorophenyl)cyclopropyl)amino)-N'-(2,2,2-trifluoroacetyl)pyrimidine-5-carbohydrazide

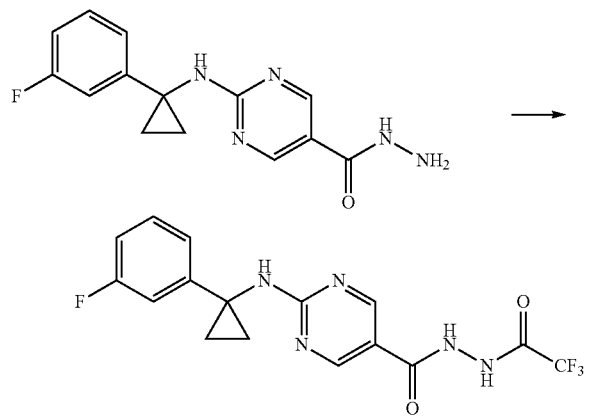

A solution of 2-((1-(3-fluorophenyl)cyclopropyl)amino) pyrimidine-5-carbohydrazide (0.300 g, 1.044 mmol) and triethylamine (0.218 mL, 1.566 mmol) in dichloromethane (10 mL) was mixed at the room temperature with trifluoroacetic anhydride (0.117 mL, 0.940 mmol), and stirred at the same temperature for 17 hr. Saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. 2-((1-(3-fluorophenyl)cyclopropyl)amino)-N'-(2,2,2-trifluoroacetyl)pyrimidine-5-carbohydrazide was used without further purification (0.084 g, 21.0%, pale yellow solid).

[Step 2] Compound 1714

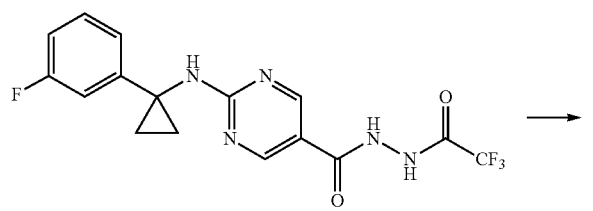

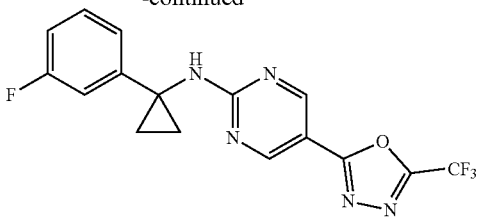

2-((1-(3-fluorophenyl)cyclopropyl)amino)-N'-(2,2,2-trifluoroacetyl)pyrimidine-5-carbohydrazide (0.084 g, 0.219 mmol) and 1-methoxy-N-triethylammoniosulfonyl-methanimidate (Burgess reagent, 0.078 g, 0.329 mmol) were mixed at the room temperature in tetrahydrofuran (4 mL), stirred at 100° C. for 17 hr, and cooled down to the room temperature to terminate the reaction. The reaction mixture was concentrated under the reduced pressure to remove the solvent. Water was added to the concentrate, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(3-fluorophenyl) cyclopropyl)-5-(5-(trifluoromethyl)-1,3,4-oxadiazol-2-yl) pyrimidin-2-amine as white solid (0.032 g, 40.0%).

$^1$H NMR (400 MHz, CDCl$_3$) δ 9.02 (s, 1H), 8.96 (s, 1H), 7.32-7.28 (m, 2H), 7.01-6.97 (m, 2H), 6.59 (s, 1H), 1.42-1.39 (m, 4H); LRMS (ES) m/z 366.4 (M$^+$+1).

Example 40: Compound 1722, N-(1-(3-chloro-4-fluorophenyl)cyclopropyl)-5-(5-(difluoromethyl)-1,3,4-oxadiazol-2-yl)pyrimidin-2-amine

[Step 1] Ethyl 4-((1-(3-chloro-4-fluorophenyl)cyclopropyl)amino)benzoate

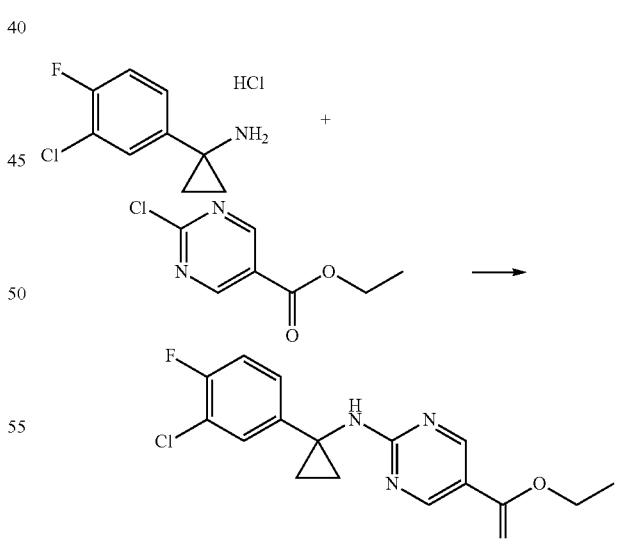

1-(3-chloro-4-fluorophenyl)cyclopropan-1-amine hydrochloride (2.000 g, 9.006 mmol), ethyl 2-chloropyrimidine-5-carboxylate (1.764 g, 9.456 mmol) and N,N-diisopropylethylamine (4.706 mL, 27.017 mmol) were mixed at the room temperature in 1,4-dioxane (20 mL), stirred at 110° C. for 17 hr, and cooled down to the room temperature. The reaction mixture was concentrated under the reduced pressure to remove the solvent. The concentrate was purified and concentrated by column chromatography (SiO$_2$, 24 g cartridge; ethyl acetate/hexane=0% to 15%) to give ethyl 4-((1-(3-chloro-4-fluorophenyl)cyclopropyl)amino)benzoate as white solid (1.530 g, 50.9%).

[Step 2] 2-((1-(3-chloro-4-fluorophenyl)cyclopropyl)amino)pyrimidine-5-carbohydrazide

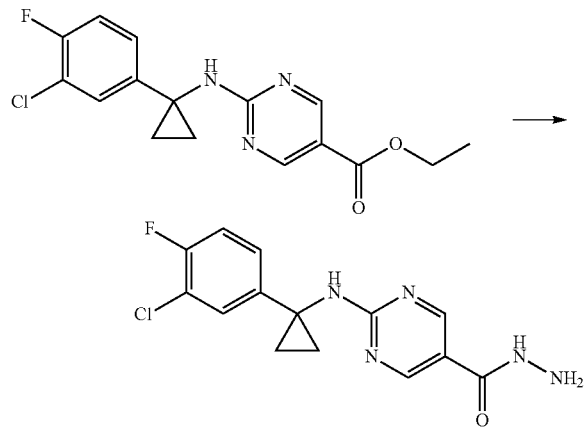

Ethyl 4-((1-(3-chloro-4-fluorophenyl)cyclopropyl)amino)benzoate (1.000 g, 2.996 mmol) and hydrazine monohydrate (2.912 mL, 59.918 mmol) were mixed at the room temperature in ethanol (15 mL), stirred at 120° C. for 17 hr, and cooled down to the room temperature to terminate reaction. The precipitates were collected by filtration, washed by ethanol, and dried to give 2-((1-(3-chloro-4-fluorophenyl)cyclopropyl)amino)pyrimidine-5-carbohydrazide as white solid (0.813 g, 84.3%).

[Step 3] 2-((1-(3-chloro-4-fluorophenyl)cyclopropyl)amino)-N'-(2,2-difluoroacetyl)pyrimidine-5-carbohydrazide

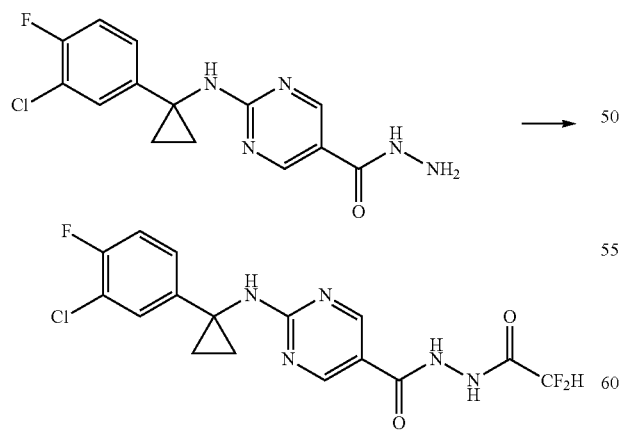

A solution of 2-((1-(3-chloro-4-fluorophenyl)cyclopropyl)amino)pyrimidine-5-carbohydrazide (0.200 g, 0.622 mmol) and triethylamine (0.130 mL, 0.932 mmol) in tetrahydrofuran (10 mL) was mixed at the room temperature with 2,2-difluoroacetic anhydride (0.070 mL, 0.559 mmol), stirred at the same temperature for 17 hr, and concentrated under the reduced pressure to remove the solvent. Then, water was added to the concentrate, followed by extraction with dichloromethane. The bi-phasic mixture was passed through a plastic frit to remove the solid residues and aqueous layer, and the organic layer collected was concentrated in vacuo. The concentrate was diluted with water (10 mL) and dichloromethane (5 mL) and stirred at the ambient temperature. The resulting precipitates were collected by filtration, washed by dichloromethane, and dried to give 2-((1-(3-chloro-4-fluorophenyl)cyclopropyl)amino)-N'-(2,2-difluoroacetyl)pyrimidine-5-carbohydrazide as white solid (0.200 g, 80.5%).

[Step 4] Compound 1722

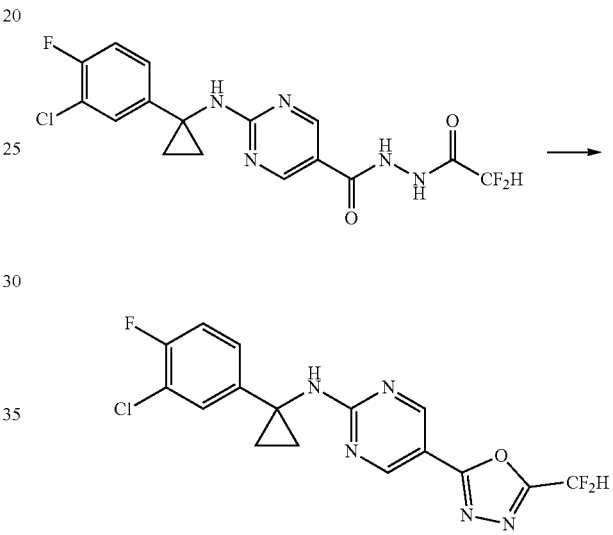

2-((1-(3-chloro-4-fluorophenyl)cyclopropyl)amino)-N'-(2,2-difluoroacetyl)pyrimidine-5-carbohydrazide (0.200 g, 0.500 mmol) and 1-methoxy-N-triethylammoniosulfonyl-methanimidate (Burgess reagent, 0.179 g, 0.750 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give N-(1-(3-chloro-4-fluorophenyl)cyclopropyl)-5-(5-(difluoromethyl)-1,3,4-oxadiazol-2-yl)pyrimidin-2-amine as pale yellow solid (0.155 g, 81.2%).

$^1$H NMR (400 MHz, CDCl$_3$) δ 9.03 (s, 1H), 8.98 (s, 1H), 7.37 (dd, J=6.9, 2.4 Hz, 1H), 7.22-7.18 (m, 1H), 7.09-6.79 (m, 2H), 6.49 (s, 1H), 1.42-1.40 (m, 4H); LRMS (ES) m/z 382.3 (M$^+$+1).

Example 41: Compound 1723, N-(1-(3-chloro-4-fluorophenyl)cyclopropyl)-5-(5-(trifluoromethyl)-1,3,4-oxadiazol-2-yl)pyrimidin-2-amine

[Step 1] 2-((1-(3-chloro-4-fluorophenyl)cyclopropyl)amino)-N'-(2,2,2-trifluoroacetyl)pyrimidine-5-carbohydrazide

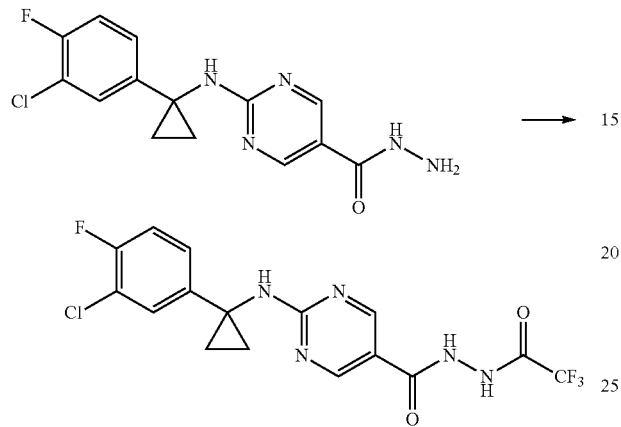

A solution of 2-((1-(3-chloro-4-fluorophenyl)cyclopropyl)amino)pyrimidine-5-carbohydrazide (0.200 g, 0.622 mmol) and triethylamine (0.130 mL, 0.932 mmol) in tetrahydrofuran (10 mL) was mixed at the room temperature with trifluoroacetic anhydride (0.079 mL, 0.559 mmol), stirred at the same temperature for 17 hr, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-(3-chloro-4-fluorophenyl)cyclopropyl)amino)-N'-(2,2,2-trifluoroacetyl)pyrimidine-5-carbohydrazide was used without further purification (0.258 g, 99.4%, pale orange solid).

[Step 2] Compound 1723

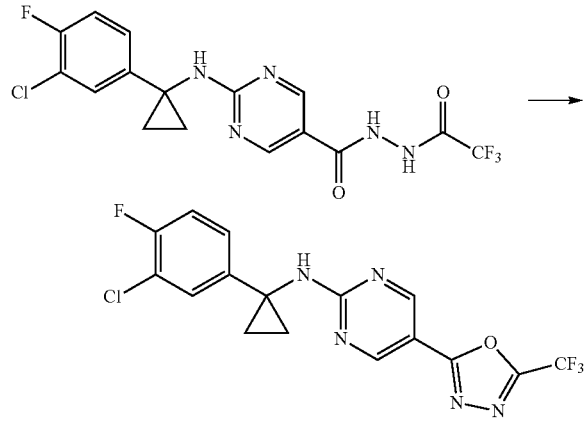

2-((1-(3-chloro-4-fluorophenyl)cyclopropyl)amino)-N'-(2,2,2-trifluoroacetyl)pyrimidine-5-carbohydrazide (0.200 g, 0.479 mmol) and 1-methoxy-N-triethylammoniosulfonyl-methanimidate (Burgess reagent, 0.171 g, 0.718 mmol) in tetrahydrofuran (3 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$, 4 g cartridge; ethyl acetate/hexane=0% to 15%) to give N-(1-(3-chloro-4-fluorophenyl)cyclopropyl)-5-(5-(trifluoromethyl)-1,3,4-oxadiazol-2-yl)pyrimidin-2-amine as white solid (0.064 g, 33.4%).
$^1$H NMR (400 MHz, $CDCl_3$) δ 9.02 (s, 1H), 8.97 (s, 1H), 7.37 (dd, J=6.9, 2.4 Hz, 1H), 7.22-7.18 (m, 1H), 7.07 (t, J=8.7 Hz, 1H), 6.51 (s, 1H), 1.45-1.40 (m, 4H); LRMS (ES) m/z 400.2 ($M^+$+1).

Example 42: Compound 1738, 5-(5-(difluoromethyl)-1,3,4-oxadiazol-2-yl)-N-(1-(4-(trifluoromethyl)phenyl)cyclopropyl)pyrimidin-2-amine

[Step 1] 1-(4-(trifluoromethyl)phenyl)cyclopropan-1-amine hydrochloride

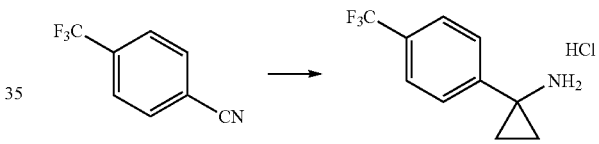

Ethylmagnesium bromide (3.00 M solution, 8.961 mL, 26.882 mmol) and titanium isopropoxide (5.190 mL, 17.532 mmol) was added to a stirred solution of 4-(trifluoromethyl)benzonitrile (2.000 g, 11.688 mmol) in 2-methoxy-2-methylpropane (MTBE, 50 mL) at 0° C. The reaction mixture was stirred at the same temperature (0° C.) for 1 hr, treated at the room temperature with Boron trifluoro etherate (3.318 g, 23.375 mmol) and stirred for additional 12 hr. Then, saturated aqueous sodium bicarbonate solution was added to the reaction mixture, followed by extraction with ethyl acetate. The organic layer was washed with aqueous saturated sodium chloride solution, dried with anhydrous $MgSO_4$, filtered, and concentrated in vacuo. Then, the residue was diluted with dichloromethane (30 ml), added hydrochloric acid (11.688 mL, 46.751 mmol) and stirred at the ambient temperature for 1 hr. The resulting precipitates were collected by filtration and dried to give the desired product as White solid (1.400 g, 50.4%).

[Step 2] ethyl 2-((1-(4-(trifluoromethyl)phenyl)cyclopropyl)amino)pyrimidine-5-carboxylate

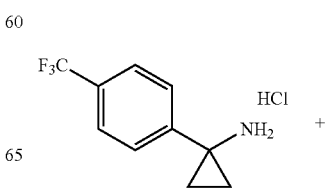

-continued

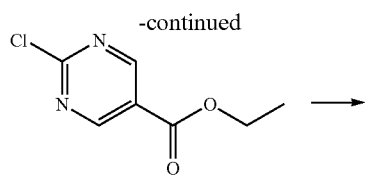

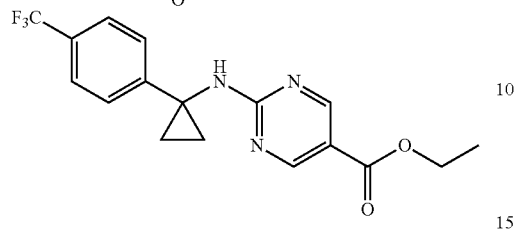

A solution of 1-(4-(trifluoromethyl)phenyl)cyclopropan-1-amine hydrochloride (0.500 g, 2.104 mmol), ethyl 2-chloropyrimidine-5-carboxylate (0.510 g, 2.735 mmol) and N,N-diisopropylethylamine (0.916 mL, 5.260 mmol) in 1,4-dioxane (10 mL) was stirred at 80° C. for 12 hr, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(4-(trifluoromethyl)phenyl)cyclopropyl)amino)pyrimidine-5-carboxylate as Colorless oil (0.350 g, 47.4%).

[Step 3] 2-((1-(4-(trifluoromethyl)phenyl)cyclopropyl)amino)pyrimidine-5-carbohydrazide

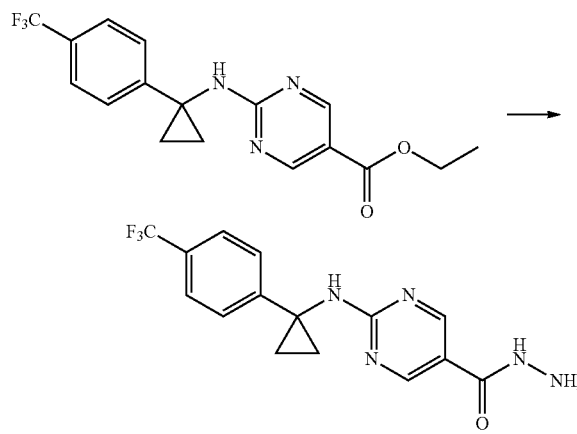

A mixture of ethyl 2-((1-(4-(trifluoromethyl)phenyl)cyclopropyl)amino)pyrimidine-5-carboxylate (0.350 g, 0.996 mmol) and hydrazine monohydrate (0.968 mL, 19.924 mmol) in ethanol (10 mL) was heated at 120° C. for 1 hr under the microwaves, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(4-(trifluoromethyl)phenyl)cyclopropyl)amino)pyrimidine-5-carbohydrazide, 0.330 g, 98.2%, White solid).

[Step 4] Compound 1738

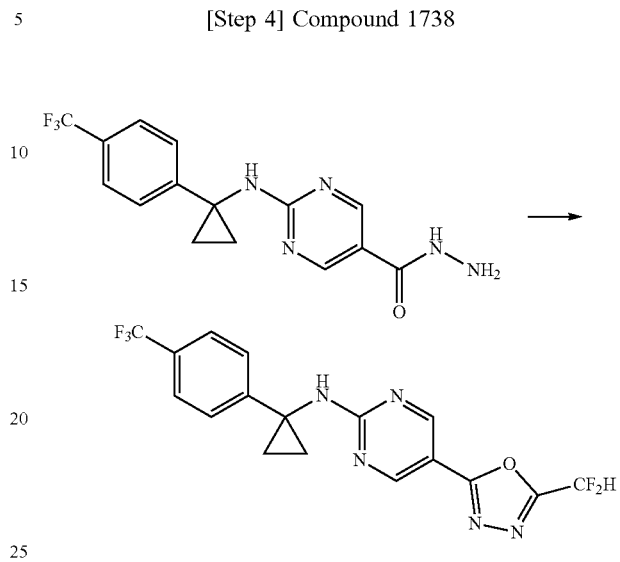

A solution of 2-((1-(4-(trifluoromethyl)phenyl)cyclopropyl)amino)pyrimidine-5-carbohydrazide (0.157 g, 0.465 mmol), 2,2-difluoroacetic anhydride (0.052 mL, 0.419 mmol) and triethylamine (0.097 mL, 0.698 mmol) in dichloromethane (5 mL) prepared at the room temperature was stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give the desired product as White solid (0.020 g, 10.8%).

$^1$H NMR (400 MHz, CDCl$_3$) δ 8.99 (s, 2H), 7.55 (d, J=8.0 Hz, 2H), 7.35 (d, J=7.8 Hz, 2H), 7.05 (s, 0.25H), 6.91 (s, 0.5H), 6.79 (s, 0.25H), 1.55-1.26 (m, 4H); LRMS (ES) m/z 398.2 (M$^+$+1).

Example 43: Compound 1740, 5-(5-(difluoromethyl)-1,3,4-oxadiazol-2-yl)-N-(1-(3-(trifluoromethyl)phenyl)cyclopropyl)pyrimidin-2-amine

[Step 1] ethyl 2-((1-(3-(trifluoromethyl)phenyl)cyclopropyl)amino)pyrimidine-5-carboxylate

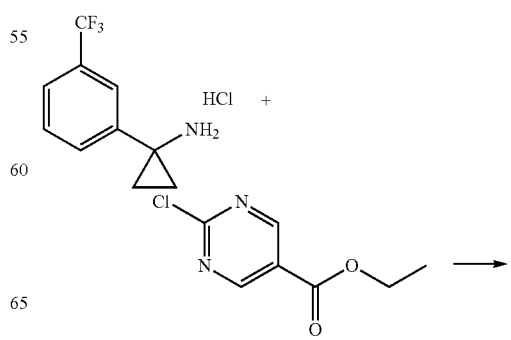

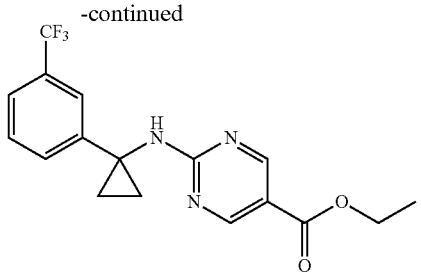

A solution of 1-(3-(trifluoromethyl)phenyl)cyclopropan-1-amine hydrochloride (0.500 g, 2.104 mmol), ethyl 2-chloropyrimidine-5-carboxylate (0.510 g, 2.735 mmol) and N,N-diisopropylethylamine (0.916 mL, 5.260 mmol) in 1,4-dioxane (10 mL) was stirred at 80° C. for 12 hr, and cooled down to the room temperature to terminate reaction. The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(3-(trifluoromethyl)phenyl)cyclopropyl)amino)pyrimidine-5-carboxylate as Colorless oil (0.567 g, 76.7%).

[Step 2] 2-((1-(3-(trifluoromethyl)phenyl)cyclopropyl)amino)pyrimidine-5-carbohydrazide

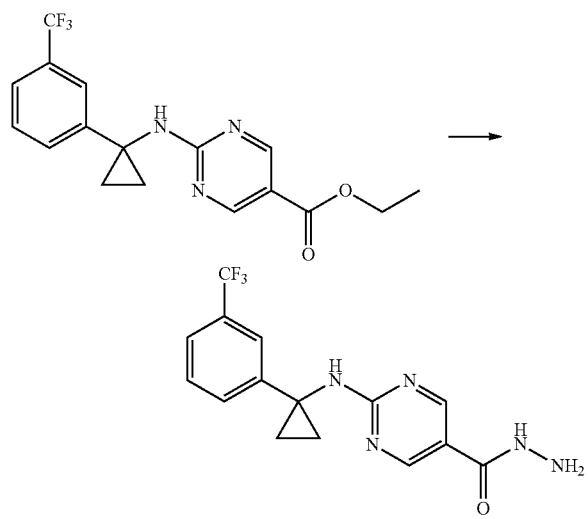

A mixture of ethyl 2-((1-(3-(trifluoromethyl)phenyl)cyclopropyl)amino)pyrimidine-5-carboxylate (0.567 g, 1.614 mmol) and hydrazine monohydrate (1.569 mL, 32.277 mmol) in ethanol (10 mL) was heated at 120° C. for 1 hr under the microwaves, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(3-(trifluoromethyl)phenyl)cyclopropyl)amino)pyrimidine-5-carbohydrazide, 0.500 g, 91.8%, White solid).

[Step 3] N'-(2,2-difluoroacetyl)-2-((1-(3-(trifluoromethyl)phenyl)cyclopropyl)amino)pyrimidine-5-carbohydrazide

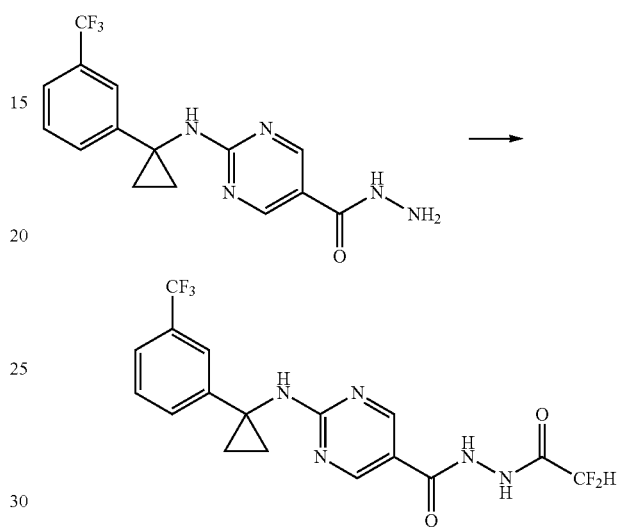

A solution of 2-((1-(3-(trifluoromethyl)phenyl)cyclopropyl)amino)pyrimidine-5-carbohydrazide (0.045 g, 0.133 mmol), 2,2-difluoroacetic anhydride (0.015 mL, 0.120 mmol) and triethylamine (0.028 mL, 0.200 mmol) in dichloromethane (5 mL) prepared at the room temperature was stirred at the same temperature for 1 hr. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was chromatographed (SiO$_2$, 12 g cartridge; methanol/dichloromethane=0% to 10%) to give N'-(2,2-difluoroacetyl)-2-((1-(3-(trifluoromethyl)phenyl)cyclopropyl)amino)pyrimidine-5-carbohydrazide as White solid (0.055 g, 99.3%).

[Step 4] Compound 1740

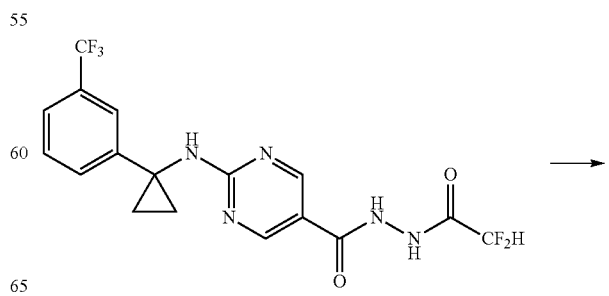

-continued

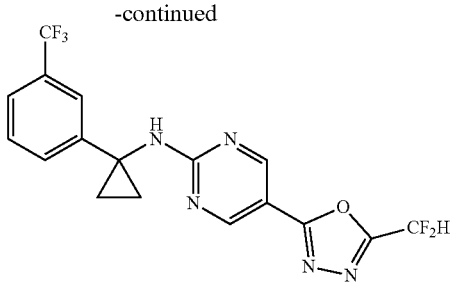

A mixture of N'-(2,2-difluoroacetyl)-2-((1-(3-(trifluoromethyl)phenyl)cyclopropyl)amino)pyrimidine-5-carbohydrazide (0.055 g, 0.132 mmol) and 1-methoxy-N-triethylammoniosulfonyl-methanimidate (Burgess reagent, 0.047 g, 0.199 mmol) in tetrahydrofuran (5 mL) was heated at 150° C. for 1 hr under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give 5-(5-(difluoromethyl)-1,3,4-oxadiazol-2-yl)-N-(1-(3-(trifluoromethyl)phenyl)cyclopropyl)pyrimidin-2-amine as white solid (0.040 g, 76.0%).

$^1$H NMR (400 MHz, CDCl$_3$) δ 9.00 (s, 2H), 7.52-7.40 (m, 4H), 7.05 (s, 0.25H), 6.92 (s, 0.5H), 6.79 (s, 0.25H), 6.68 (s, 1H), 1.53-1.45 (m, 4H); LRMS (ES) m/z 398.38 (M⁺+1).

Example 44: Compound 1741, 5-(5-(trifluoromethyl)-1,3,4-oxadiazol-2-yl)-N-(1-(3-(trifluoromethyl)phenyl)cyclopropyl)pyrimidin-2-amine

[Step 1] N'-(2,2,2-trifluoroacetyl)-2-((1-(3-(trifluoromethyl)phenyl)cyclopropyl)amino)pyrimidine-5-carbohydrazide

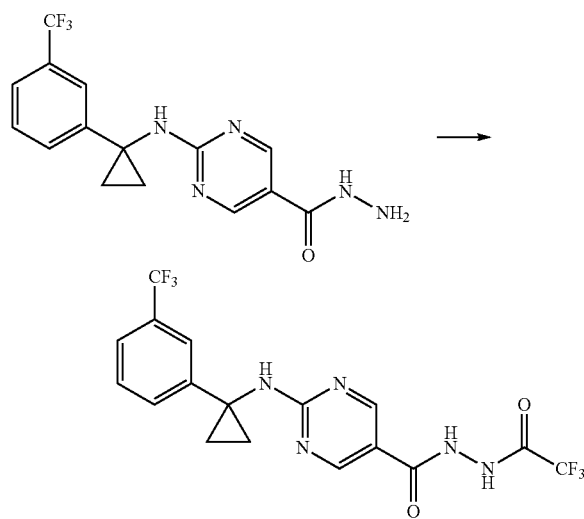

A solution of 2-((1-(3-(trifluoromethyl)phenyl)cyclopropyl)amino)pyrimidine-5-carbohydrazide (0.270 g, 0.800 mmol), trifluoroacetic anhydride (0.102 mL, 0.720 mmol) and triethylamine (0.167 mL, 1.201 mmol) in dichloromethane (5 mL) prepared at the room temperature was stirred at the same temperature for 2 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N'-(2,2,2-trifluoroacetyl)-2-((1-(3-(trifluoromethyl)phenyl)cyclopropyl)amino)pyrimidine-5-carbohydrazide as white solid (0.136 g, 39.2%).

[Step 2] Compound 1741

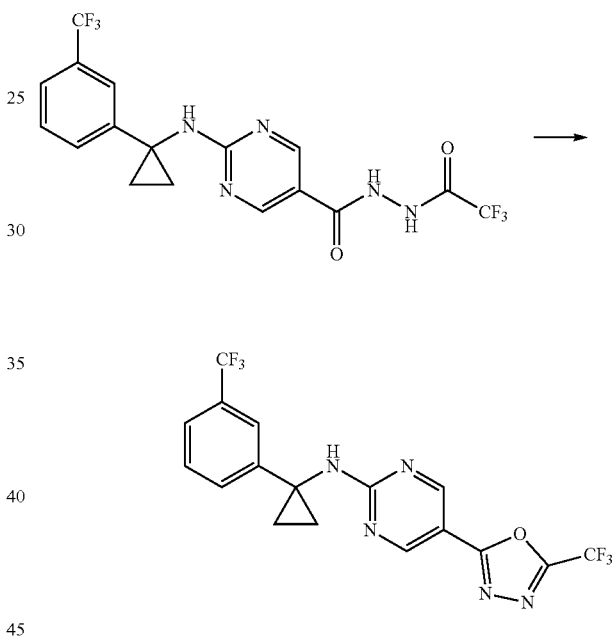

A mixture of N'-(2,2,2-trifluoroacetyl)-2-((1-(3-(trifluoromethyl)phenyl)cyclopropyl)amino)pyrimidine-5-carbohydrazide (0.136 g, 0.314 mmol) and 1-methoxy-N-triethylammoniosulfonyl-methanimidate (Burgess reagent, 0.112 g, 0.471 mmol) in tetrahydrofuran (5 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was chromatographed (SiO₂, 12 g cartridge; ethyl acetate/hexane=0% to 30%) to give 5-(5-(trifluoromethyl)-1,3,4-oxadiazol-2-yl)-N-(1-(3-(trifluoromethyl)phenyl)cyclopropyl)pyrimidin-2-amine as white solid (0.100 g, 76.7%).

$^1$H NMR (400 MHz, CDCl$_3$) δ 9.00-8.99 (m, 2H), 7.53-7.40 (m, 4H), 6.71 (s, 1H), 1.54-1.43 (m, 4H); LRMS (ES) m/z 416.17 (M⁺+1).

Example 45: Compound 1742, 5-(5-(trifluoromethyl)-1,3,4-oxadiazol-2-yl)-N-(1-(4-(trifluoromethyl)phenyl)cyclopropyl)pyrimidin-2-amine

[Step 1] N'-(2,2,2-trifluoroacetyl)-2-((1-(4-(trifluoromethyl)phenyl)cyclopropyl)amino)pyrimidine-5-carbohydrazide

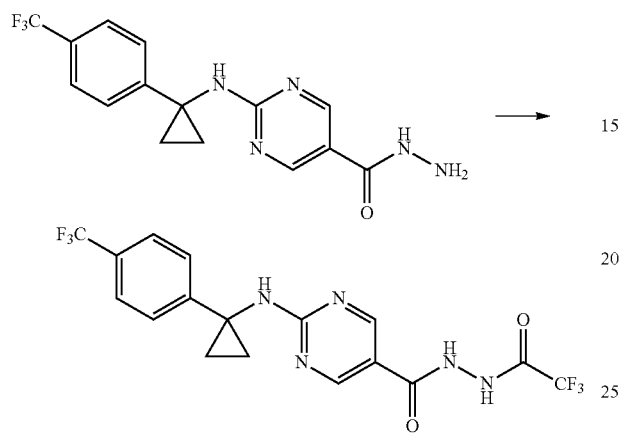

A solution of 2-((1-(4-(trifluoromethyl)phenyl)cyclopropyl)amino)pyrimidine-5-carbohydrazide (0.130 g, 0.385 mmol), trifluoroacetic anhydride (0.054 mL, 0.385 mmol) and triethylamine (0.081 mL, 0.578 mmol) in dichloromethane (5 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N'-(2,2,2-trifluoroacetyl)-2-((1-(4-(trifluoromethyl)phenyl)cyclopropyl)amino)pyrimidine-5-carbohydrazide as White solid (0.111 g, 66.5%).

[Step 2] Compound 1742

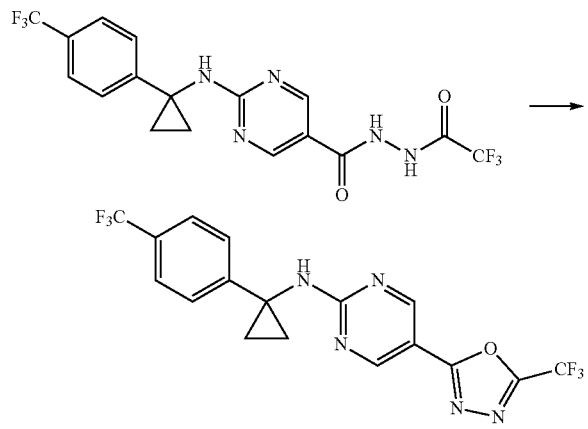

A mixture of N'-(2,2,2-trifluoroacetyl)-2-((1-(4-(trifluoromethyl)phenyl)cyclopropyl)amino)pyrimidine-5-carbohydrazide (0.110 g, 0.254 mmol) and 1-methoxy-N-triethylammoniosulfonyl-methanimidate (Burgess reagent, 0.091 g, 0.381 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(trifluoromethyl)-1,3,4-oxadiazol-2-yl)-N-(1-(4-(trifluoromethyl)phenyl)cyclopropyl)pyrimidin-2-amine as white solid (0.040 g, 37.9%).

$^1$H NMR (400 MHz, CDCl$_3$) δ 8.99 (s, 2H), 7.56 (d, J=8.3 Hz, 2H), 7.36 (d, J=8.2 Hz, 2H), 6.68 (s, 1H), 1.55-1.43 (m, 4H); LRMS (ES) m/z 416.23 (M$^+$+1).

Example 46: Compound 1761, 3-(1-((5-(5-(difluoromethyl)-1,3,4-oxadiazol-2-yl)pyrimidin-2-yl)amino)cyclobutyl)phenol

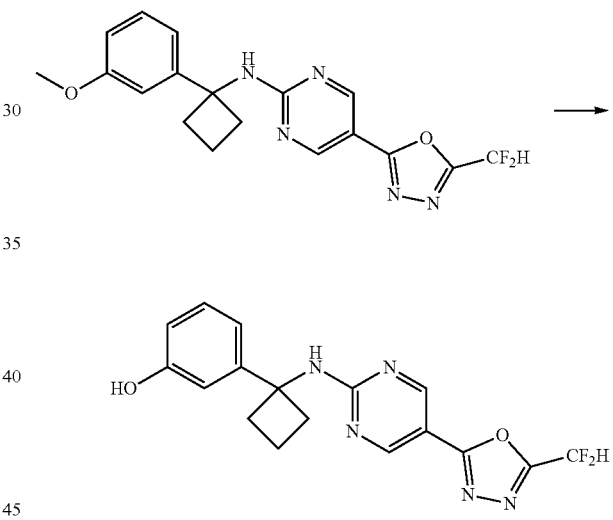

A solution of 5-(5-(difluoromethyl)-1,3,4-oxadiazol-2-yl)-N-(1-(3-methoxyphenyl)cyclobutyl)pyrimidin-2-amine (0.056 g, 0.150 mmol) and Boron tribromide (1.00 M solution in DCM, 0.375 mL, 0.375 mmol) in dichloromethane (5 mL) was stirred at −78° C. for 2 hr and then for additional 8 hr at the room temperature. The precipitates were collected by filtration, washed by hexane, and dried to give 3-(1-((5-(5-(difluoromethyl)-1,3,4-oxadiazol-2-yl)pyrimidin-2-yl)amino)cyclobutyl)phenol as brown solid (0.032 g, 59.4%).

$^1$H NMR (400 MHz, DMSO-d6) δ 9.02 (s, 1H), 8.85 (s, 1H), 8.71 (s, 1H), 7.63 (s, 0.25H), 7.51 (s, 0.5H), 7.38 (s, 0.25H), 7.09 (t, J=7.9 Hz, 1H), 6.92-6.90 (m, 1H), 6.86 (t, J=2.0 Hz, 1H), 6.58-6.57 (m, 1H), 2.56-2.50 (m, 4H), 2.05-1.91 (m, 1H), 1.89-1.86 (m, 1H); LRMS (ES) m/z 360.34 (M$^+$+1).

Example 47: Compound 1779, 5-(5-(difluoromethyl)-1,3,4-oxadiazol-2-yl)-N-(1-(3,4-difluorophenyl)cyclopropyl)pyrimidin-2-amine

[Step 1] 1-(3,4-difluorophenyl)cyclopropan-1-amine hydrochloride

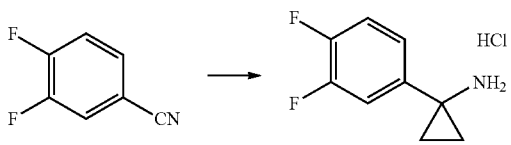 [SMILES: N#Cc1ccc(F)c(F)c1 ; NC1(c2ccc(F)c(F)c2)CC1 ; Cl]

A solution of 3,4-difluorobenzonitrile (3.000 g, 21.567 mmol), titanium isopropoxide (9.578 mL, 32.351 mmol) and EtMgBr (3.00 M solution, 16.535 mL, 49.605 mmol) in 2-methoxy-2-methylpropane (MTBE, 200 mL) was stirred at 0° C. for 1 hr, and mixed with boron trifluoride diethyl etherate (5.324 mL, 43.134 mmol). The reaction mixture was stirred at the room temperature for additional 2 hr, and quenched at 0° C. by the addition of water (10 mL, 10 min stirring). Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was diluted with ethyl acetate, added hydrochloric acid (1.00 M solution in EA, 23.724 mL, 23.724 mmol) and stirred at the ambient temperature. The resulting precipitates were collected by filtration, washed by ethyl acetate, and dried to give 1-(3,4-difluorophenyl)cyclopropan-1-amine hydrochloride as white solid (0.142 g, 3.2%).

[Step 2] Ethyl 2-((1-(3,4-difluorophenyl)cyclopropyl)amino)pyrimidine-5-carboxylate

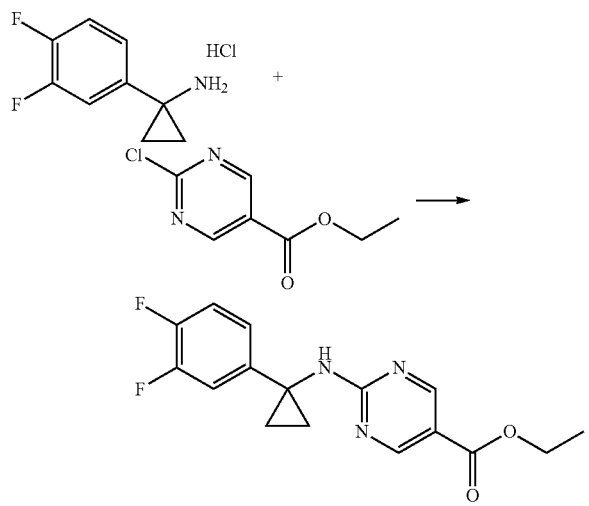

1-(3,4-difluorophenyl)cyclopropan-1-amine hydrochloride (0.142 g, 0.691 mmol), ethyl 2-chloropyrimidine-5-carboxylate (0.142 g, 0.760 mmol) and N,N-diisopropylethylamine (0.361 mL, 2.072 mmol) were mixed at the room temperature in 1,4-dioxane (4 mL), stirred at 110° C. for 17 hr, and cooled down to the room temperature to terminate reaction. The reaction mixture was concentrated under the reduced pressure to remove the solvent. The concentrate was purified and concentrated by column chromatography (SiO₂, 4 g cartridge; ethyl acetate/hexane=0% to 10%) to give ethyl 2-((1-(3,4-difluorophenyl)cyclopropyl)amino)pyrimidine-5-carboxylate as white solid (0.127 g, 57.6%).

[Step 3] 2-((1-(3,4-difluorophenyl)cyclopropyl)amino)pyrimidine-5-carbohydrazide

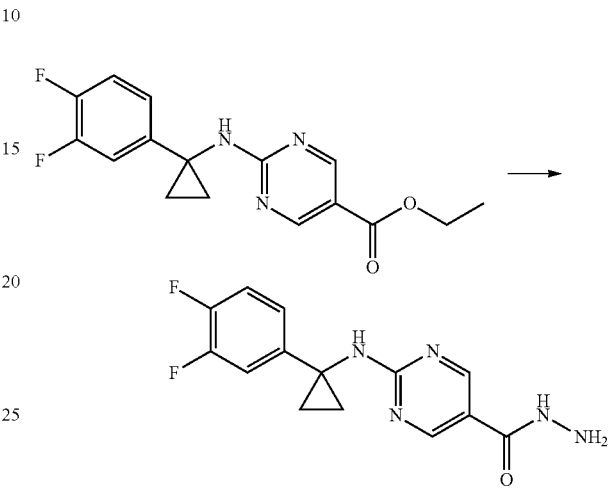

Ethyl 2-((1-(3,4-difluorophenyl)cyclopropyl)amino)pyrimidine-5-carboxylate (0.127 g, 0.398 mmol) and hydrazine monohydrate (0.387 mL, 7.955 mmol) in ethanol (4 mL) was mixed at the room temperature, heated at 110° C. under the microwaves for 1 hr, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO₄, filtered, and concentrated in vacuo. 2-((1-(3,4-difluorophenyl)cyclopropyl)amino)pyrimidine-5-carbohydrazide was used without further purification (0.115 g, 94.7%, pale yellow oil).

[Step 4] N'-(2,2-difluoroacetyl)-2-((1-(3,4-difluorophenyl)cyclopropyl)amino)pyrimidine-5-carbohydrazide

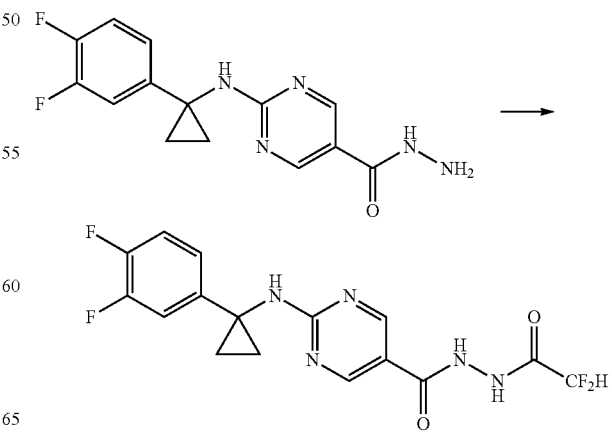

A solution of 2-((1-(3,4-difluorophenyl)cyclopropyl)amino)pyrimidine-5-carbohydrazide (0.065 g, 0.213 mmol) and triethylamine (0.045 mL, 0.319 mmol) in dichloromethane (5 mL) was mixed at the room temperature with 2,2-difluoroacetic anhydride (0.024 mL, 0.192 mmol), and stirred at the same temperature for 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. N'-(2,2-difluoroacetyl)-2-((1-(3,4-difluorophenyl)cyclopropyl)amino)pyrimidine-5-carbohydrazide was used without further purification (0.080 g, 98.0%, yellow oil).

[Step 5] Compound 1779

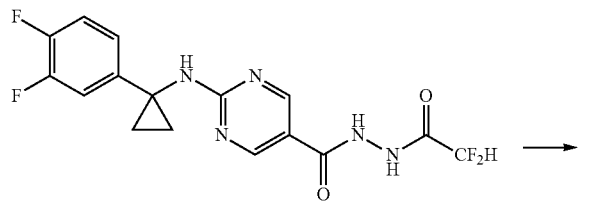

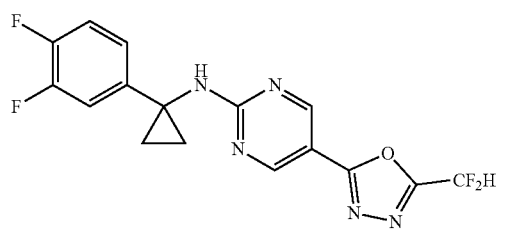

N'-(2,2-difluoroacetyl)-2-((1-(3,4-difluorophenyl)cyclopropyl)amino)pyrimidine-5-carbohydrazide (0.080 g, 0.209 mmol) and 1-methoxy-N-triethylammoniosulfonyl-methanimidate (Burgess reagent, 0.149 g, 0.626 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give 5-(5-(difluoromethyl)-1,3,4-oxadiazol-2-yl)-N-(1-(3,4-difluorophenyl)cyclopropyl)pyrimidin-2-amine as pale yellow solid (0.030 g, 39.3%).

$^1$H NMR (400 MHz, CDCl$_3$) δ 9.02 (s, 1H), 8.98 (s, 1H), 7.17-7.12 (m, 1H), 7.10-7.07 (m, 1H), 7.05-6.79 (m, 2H), 6.58 (s, 1H), 1.42 (s, 4H); LRMS (ES) m/z 366.1 (M$^+$+1).

Example 48: Compound 1780, N-(1-(3,4-difluorophenyl)cyclopropyl)-5-(5-(trifluoromethyl)-1,34-oxadiazol-2-yl)pyrimidin-2-amine

[Step 1] 2-((1-(3,4-difluorophenyl)cyclopropyl)amino)-N'-(2,2,2-trifluoroacetyl)pyrimidine-5-carbohydrazide

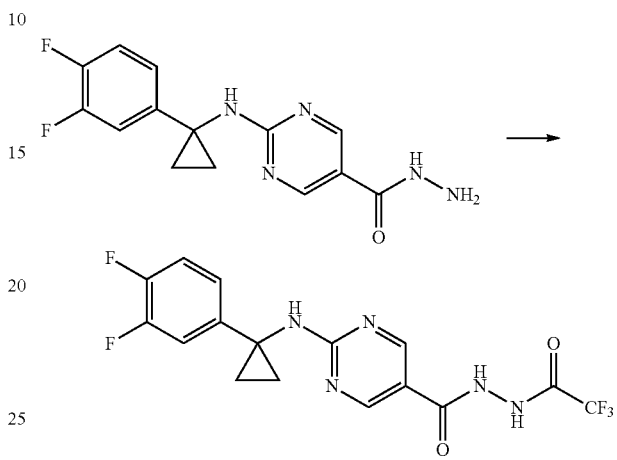

A solution of 2-((1-(3,4-difluorophenyl)cyclopropyl)amino)pyrimidine-5-carbohydrazide (0.050 g, 0.164 mmol) and triethylamine (0.034 mL, 0.246 mmol) in dichloromethane (5 mL) was mixed at the room temperature with trifluoroacetic anhydride (0.021 mL, 0.147 mmol), and stirred at the same temperature for 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-(3,4-difluorophenyl)cyclopropyl)amino)-N'-(2,2,2-trifluoroacetyl)pyrimidine-5-carbohydrazide was used without further purification (0.065 g, 98.9%, yellow oil).

[Step 2] Compound 1780

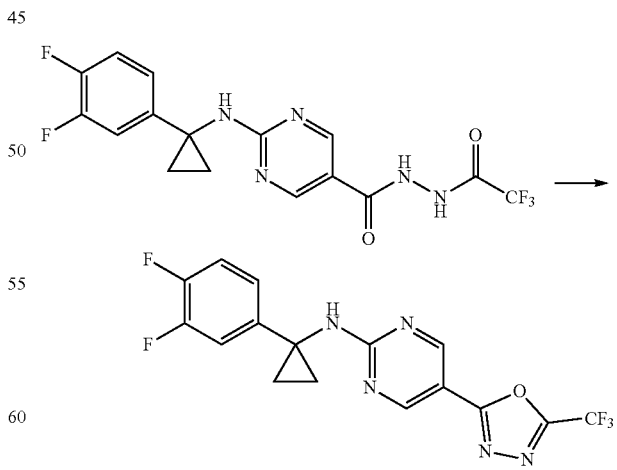

2-((1-(3,4-difluorophenyl)cyclopropyl)amino)-N'-(2,2,2-trifluoroacetyl)pyrimidine-5-carbohydrazide (0.065 g, 0.162 mmol) and 1-methoxy-N-triethylammoniosulfonyl-methanimidate (Burgess reagent, 0.116 g, 0.486 mmol) in tetrahydrofuran (4 mL) was mixed at the room temperature, heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 20%) to give N-(1-(3,4-difluorophenyl)cyclopropyl)-5-(5-(trifluoromethyl)-1,3,4-oxadiazol-2-yl)pyrimidin-2-amine as white solid (0.032 g, 51.5%).

$^1$H NMR (400 MHz, CDCl$_3$) δ 9.02 (s, 1H), 8.97 (s, 1H), 7.17-7.12 (m, 1H), 7.10-7.07 (m, 1H), 7.04-7.00 (m, 1H), 6.52 (s, 1H), 1.42-1.41 (m, 4H); LRMS (ES) m/z 384.0 (M$^+$+1).

Example 49: Compound 1817, N-(1-(3-chloro-4-fluorophenyl)cyclobutyl)-5-(5-(difluoromethyl)-1,3,4-oxadiazol-2-yl)pyrimidin-2-amine

[Step 1] 1-(3-chloro-4-fluorophenyl)cyclobutan-1-amine hydrochloride

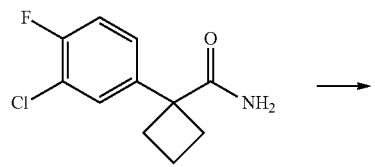

A solution of 1-(3-chloro-4-fluorophenyl)cyclobutane-1-carboxamide (4.360 g, 19.151 mmol), sodium hydroxide (3.00 M solution in H$_2$O, 19.151 mL, 57.454 mmol), Sodium hypochlorite (8.90%, 23.921 g, 28.727 mmol) and hydrochloric acid (4.00 M solution in Dioxane, 9.576 mL, 38.303 mmol) in 1-butanol (30 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The obtained compound was used without further purification (1-(3-chloro-4-fluorophenyl)cyclobutan-1-amine hydrochloride, (3.000 g, 66.3%, white solid).

[Step 2] ethyl 2-((1-(3-chloro-4-fluorophenyl)cyclobutyl)amino)pyrimidine-5-carboxylate

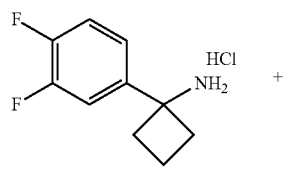

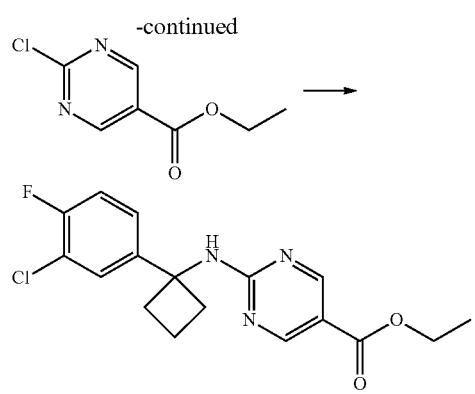

A solution of 1-(3-chloro-4-fluorophenyl)cyclobutan-1-amine hydrochloride (1.000 g, 4.235 mmol), ethyl 2-chloropyrimidine-5-carboxylate (0.869 g, 4.659 mmol) and N,N-diisopropylethylamine (1.844 mL, 10.588 mmol) in 1,4-dioxane (10 mL) was stirred at 90° C. for 10 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(3-chloro-4-fluorophenyl)cyclobutyl)amino)pyrimidine-5-carboxylate as White solid (1.020 g, 68.9%).

[Step 3] 2-((1-(3-chloro-4-fluorophenyl)cyclobutyl)amino)pyrimidine-5-carbohydrazide

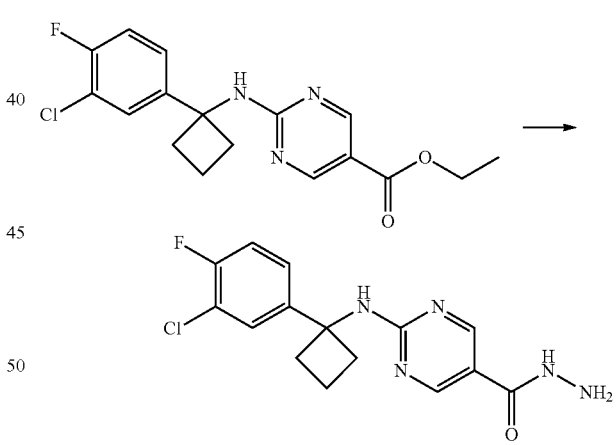

A mixture of ethyl 2-((1-(3-chloro-4-fluorophenyl)cyclobutyl)amino)pyrimidine-5-carboxylate (1.080 g, 3.088 mmol) and hydrazine monohydrate (3.001 mL, 61.751 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(3-chloro-4-fluorophenyl)cyclobutyl)amino)pyrimidine-5-carbohydrazide, 0.980 g, 94.5%, White solid).

[Step 4] 2-((1-(3-chloro-4-fluorophenyl)cyclobutyl)amino)-N'-(2,2-difluoroacetyl)pyrimidine-5-carbohydrazide

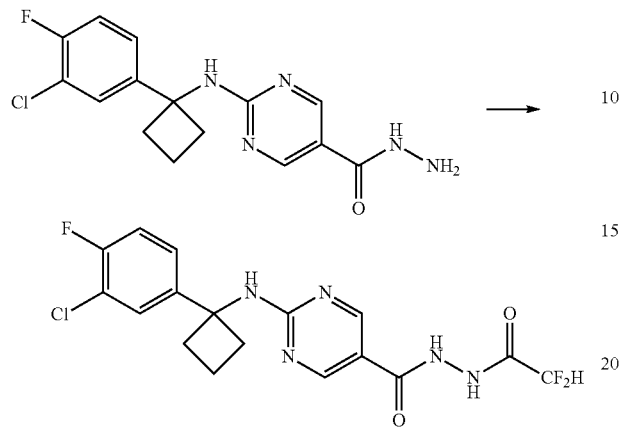

A solution of 2-((1-(3-chloro-4-fluorophenyl)cyclobutyl)amino)pyrimidine-5-carbohydrazide (0.188 g, 0.560 mmol), 2,2-difluoroacetic anhydride (0.070 mL, 0.560 mmol) and triethylamine (0.117 mL, 0.840 mmol) in dichloromethane (10 mL) prepared at the room temperature was stirred at the same temperature for 1 hr. The precipitates were collected by filtration, washed by hexane, and dried to give 2-((1-(3-chloro-4-fluorophenyl)cyclobutyl)amino)-N'-(2,2-difluoroacetyl)pyrimidine-5-carbohydrazide as White solid (0.158 g, 68.2%).

[Step 5] Compound 1817

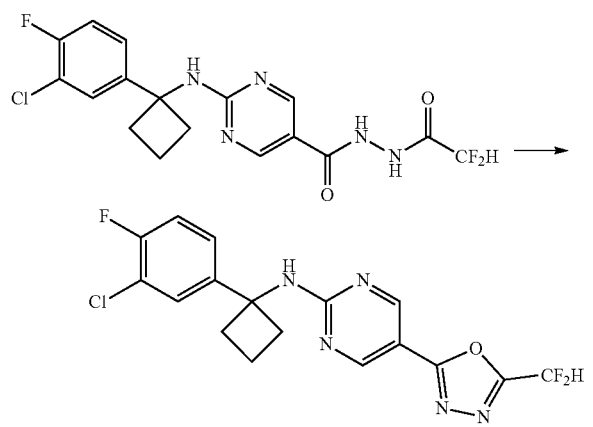

A mixture of 2-((1-(3-chloro-4-fluorophenyl)cyclobutyl)amino)-N'-(2,2-difluoroacetyl)pyrimidine-5-carbohydrazide (0.150 g, 0.363 mmol) and 1-methoxy-N-triethylammoniosulfonyl-methanimidate (Burgess reagent, 0.173 g, 0.725 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give N-(1-(3-chloro-4-fluorophenyl)cyclobutyl)-5-(5-(difluoromethyl)-1,3,4-oxadiazol-2-yl)pyrimidin-2-amine as White solid (0.078 g, 54.4%).

¹H NMR (400 MHz, CDCl₃) δ 8.90 (d, J=15.8 Hz, 2H), 7.55 (dd, J=7.0, 2.4 Hz, 1H), 7.40-7.36 (m, 1H), 7.09 (t, J=8.7 Hz, 1H), 7.04 (s, 0.25H), 6.91 (s, 0.5H), 6.78 (s, 0.25H), 6.77 (s, 1H), 2.75-2.68 (m, 2H), 2.61-2.54 (m, 2H), 2.23-2.16 (m, 1H), 2.06-1.90 (m, 1H); LRMS (ES) m/z 396.3 (M⁺+1).

Example 50: Compound 1818, N-(1-(3-chloro-4-fluorophenyl)cyclobutyl)-5-(5-(trifluoromethyl)-1,3,4-oxadiazol-2-yl)pyrimidin-2-amine

[Step 1] 2-((1-(3-chloro-4-fluorophenyl)cyclobutyl)amino)-N'-(2,2,2-trifluoroacetyl)pyrimidine-5-carbohydrazide

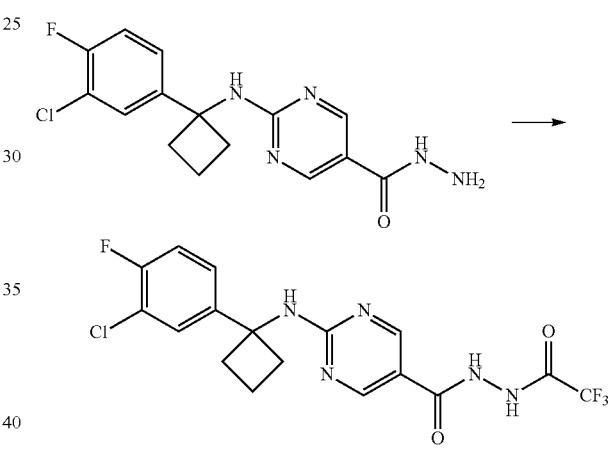

A solution of 2-((1-(3-chloro-4-fluorophenyl)cyclobutyl)amino)pyrimidine-5-carbohydrazide (0.309 g, 0.920 mmol), trifluoroacetic anhydride (0.130 mL, 0.920 mmol) and triethylamine (0.192 mL, 1.380 mmol) in dichloromethane (10 mL) prepared at the room temperature was stirred at the same temperature for 1 hr. The precipitates were collected by filtration, washed by hexane, and dried to give 2-((1-(3-chloro-4-fluorophenyl)cyclobutyl)amino)-N'-(2,2,2-trifluoroacetyl)pyrimidine-5-carbohydrazide as White solid (0.276 g, 69.5%).

[Step 2] Compound 1818

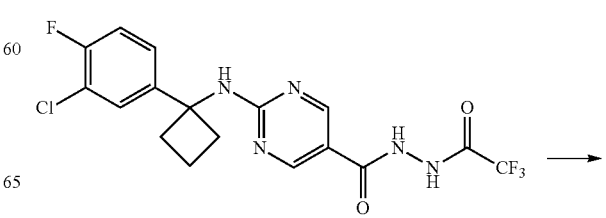

183

-continued

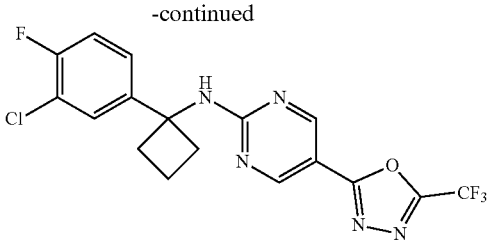

A mixture of 2-((1-(3-chloro-4-fluorophenyl)cyclobutyl)amino)-N'-(2,2,2-trifluoroacetyl)pyrimidine-5-carbohydrazide (0.276 g, 0.639 mmol) and 1-methoxy-N-triethylammoniosulfonyl-methanimidate (Burgess reagent, 0.305 g, 1.278 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give N-(1-(3-chloro-4-fluorophenyl)cyclobutyl)-5-(5-(trifluoromethyl)-1,3,4-oxadiazol-2-yl)pyrimidin-2-amine as White solid (0.200 g, 75.6%).

$^1$H NMR (400 MHz, CDCl$_3$) δ 8.90 (d, J=15.8 Hz, 2H), 7.55 (dd, J=7.0, 2.4 Hz, 1H), 7.40-7.36 (m, 1H), 7.09 (t, J=8.7 Hz, 1H), 6.76 (s, 1H), 2.76-2.68 (m, 2H), 2.62-2.25 (m, 2H), 2.24-2.14 (m, 1H), 2.07-1.95 (m, 1H); LRMS (ES) m/z 414.3 (M$^+$+1).

Example 51: Compound 1819, 5-(5-(difluoromethyl)-1,3,4-oxadiazol-2-yl)-N-(1-(3,5-difluorophenyl)cyclobutyl)pyrimidin-2-amine

[Step 1]
1-(3,5-difluorophenyl)cyclobutane-1-carbonitrile

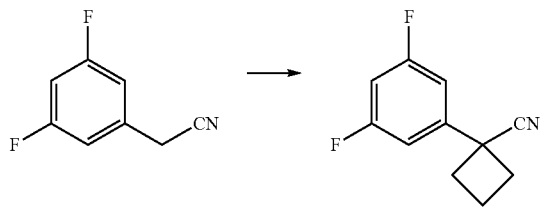 [SMILES: N#CCc1cc(F)cc(F)c1 ; N#CC1(c2cc(F)cc(F)c2)CCC1]

To a stirred solution of 2-(3,5-difluorophenyl)acetonitrile (4.620 g, 30.170 mmol) in N,N-dimethylformide (50 mL) was added at 0° C. sodium hydride (60.00%, 3.017 g, 75.426 mmol). The reaction mixture was stirred at the same temperature for 30 min, treated at the room temperature with 1,3-dibromopropane (6.091 g, 30.170 mmol), stirred for additional 6 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(3,5-difluorophenyl)cyclobutane-1-carbonitrile as White solid (3.400 g, 58.3%).

184

[Step 2]
1-(3,5-difluorophenyl)cyclobutane-1-carboxamide

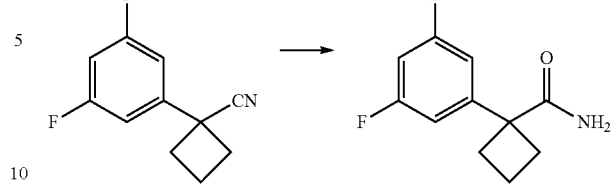

A solution of 1-(3,5-difluorophenyl)cyclobutane-1-carbonitrile (3.400 g, 17.598 mmol), tetra-n-butylammonium bromide (0.057 g, 0.176 mmol), sodium hydroxide (3.00 M solution in H$_2$O, 17.598 mL, 52.795 mmol) and hydrogen peroxide (30.00% solution, 4.128 mL, 52.795 mmol) in methanol (30 mL) prepared at the room temperature was stirred at the same temperature for 18 hr. The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(3,5-difluorophenyl)cyclobutane-1-carboxamide, 3.400 g, 91.5%, Colorless oil).

[Step 3] 1-(3,5-difluorophenyl)cyclobutan-1-amine

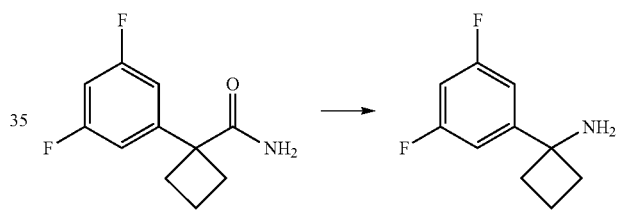

A solution of 1-(3,5-difluorophenyl)cyclobutane-1-carboxamide (3.400 g, 16.098 mmol), sodium hydroxide (3.00 M solution in H$_2$O, 16.098 mL, 48.293 mmol) and Sodium hypochlorite (8.90% solution, 18.195 mL, 24.147 mmol) in 1-butanol (30 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(3,5-difluorophenyl)cyclobutan-1-amine, 2.000 g, 67.8%, Colorless oil).

[Step 4] ethyl 2-((1-(3,5-difluorophenyl)cyclobutyl)amino)pyrimidine-5-carboxylate

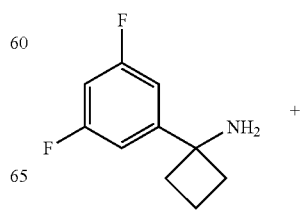

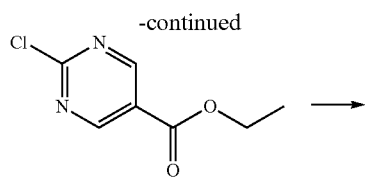

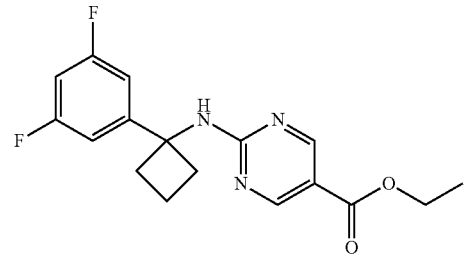

A solution of 1-(3,5-difluorophenyl)cyclobutan-1-amine (0.500 g, 2.729 mmol), ethyl 2-chloropyrimidine-5-carboxylate (0.560 g, 3.002 mmol) and N,N-diisopropylethylamine (1.188 mL, 6.823 mmol) in 1,4-dioxane (10 mL) was stirred at 90° C. for 10 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(3,5-difluorophenyl)cyclobutyl)amino)pyrimidine-5-carboxylate as Brown oil (0.240 g, 26.4%).

[Step 5] 2-((1-(3,5-difluorophenyl)cyclobutyl)amino)pyrimidine-5-carbohydrazide

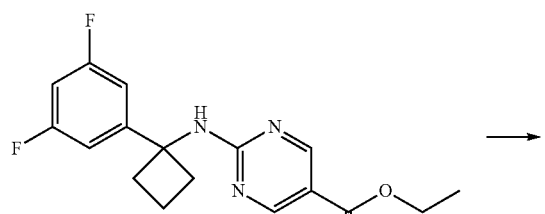

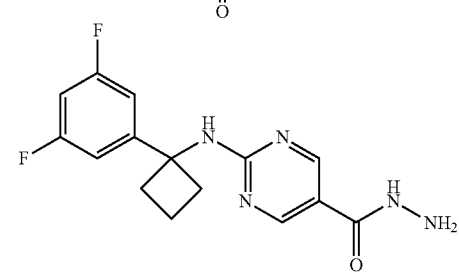

A mixture of ethyl 2-((1-(3,5-difluorophenyl)cyclobutyl)amino)pyrimidine-5-carboxylate (0.240 g, 0.720 mmol) and Hydrazine monohydrate (0.350 mL, 7.200 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 2-((1-(3,5-difluorophenyl)cyclobutyl)amino)pyrimidine-5-carbohydrazide as White solid (0.230 g, 100.0%).

[Step 6] N'-(2,2-difluoroacetyl)-2-((1-(3,5-difluorophenyl)cyclobutyl)amino)pyrimidine-5-carbohydrazide

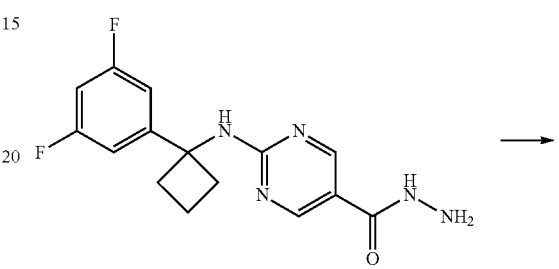

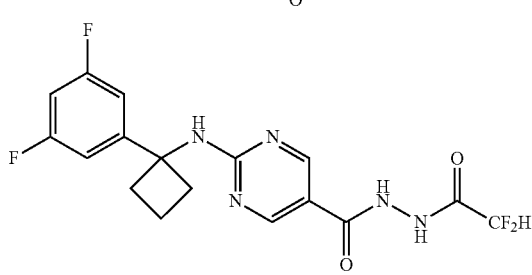

A solution of 2-((1-(3,5-difluorophenyl)cyclobutyl)amino)pyrimidine-5-carbohydrazide (0.270 g, 0.846 mmol), triethylamine (0.177 mL, 1.268 mmol) and trifluoroacetic anhydride (0.119 mL, 0.846 mmol) in dichloromethane (5 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N'-(2,2-difluoroacetyl)-2-((1-(3,5-difluorophenyl)cyclobutyl)amino)pyrimidine-5-carbohydrazide as White solid (0.078 g, 23.2%).

[Step 7] Compound 1819

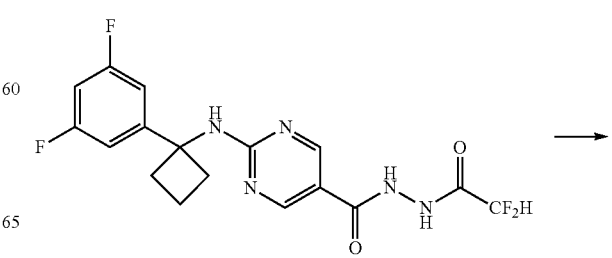

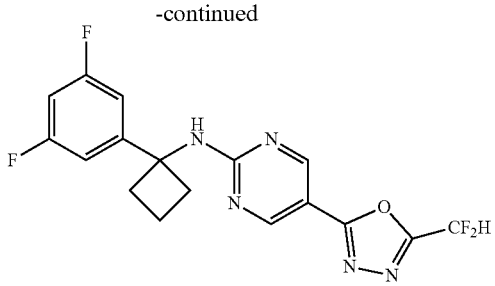

A mixture of N'-(2,2-difluoroacetyl)-2-((1-(3,5-difluorophenyl)cyclobutyl)amino)pyrimidine-5-carbohydrazide (0.156 g, 0.393 mmol) and 1-methoxy-N-triethylammoniosulfonyl-methanimidate (Burgess reagent, 0.140 g, 0.589 mmol) in tetrahydrofuran (10 mL) was heated at 150° C. for 30 min under the microwaves, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(3,5-difluorophenyl)cyclobutyl)pyrimidin-2-amine as White solid (0.078 g, 52.4%).

$^1$H NMR (400 MHz, CDCl$_3$) δ 8.91-8.87 (m, 2H), 7.06-7.00 (m, 2H), 7.03 (s, 0.25H), 7.00 (s, 0.5H), 6.78 (s, 0.25H), 6.84 (s, 1H), 6.71-6.68 (m, 1H), 2.74-2.67 (m, 2H), 2.61-2.54 (m, 2H), 2.22-2.17 (m, 1H), 2.08-2.01 (m, 1H).; LRMS (ES) m/z 380.3 (M$^+$+1).

Example 52: Compound 1820, N-(1-(benzo[d][1,3]dioxol-5-yl)cyclobutyl)-5-(5-(difluoromethyl)-1,3,4-oxadiazol-2-yl)pyrimidin-2-amine

[Step 1] 1-(benzo[d][1,3]dioxol-5-yl)cyclobutane-1-carbonitrile

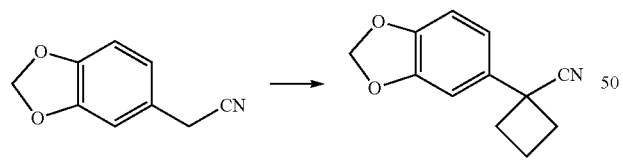

To a stirred solution of 2-(benzo[d] [1,3]dioxol-5-yl) acetonitrile (5.120 g, 31.770 mmol) in N,N-dimethylformide (50 mL) was added at 0° C. sodium hydride (60.00%, 3.177 g, 79.424 mmol). The reaction mixture was stirred at the same temperature for 30 min, treated at the room temperature with 1,3-dibromopropane (6.414 g, 31.770 mmol), stirred for additional 6 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(benzo[d][1,3]dioxol-5-yl)cyclobutane-1-carbonitrile as Colorless oil (2.840 g, 44.4%).

[Step 2] 1-(benzo[d][1,3]dioxol-5-yl)cyclobutane-1-carboxamide

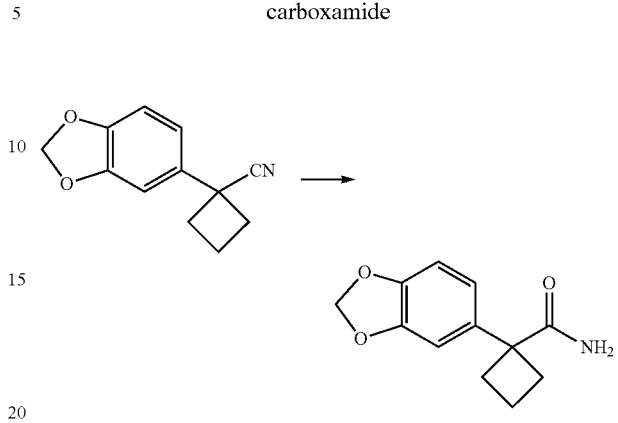

A solution of 1-(benzo[d][1,3]dioxol-5-yl)cyclobutane-1-carbonitrile (2.840 g, 14.113 mmol), tetra-n-butylammonium bromide (0.045 g, 0.141 mmol), sodium hydroxide (3.00 M solution in H$_2$O, 14.113 mL, 42.340 mmol) and hydrogen peroxide (30.00% solution, 3.311 mL, 42.340 mmol) in methanol (30 mL) prepared at the room temperature was stirred at the same temperature for 18 hr. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (1-(benzo[d][1,3]dioxol-5-yl)cyclobutane-1-carboxamide, 2.800 g, 90.5%, Colorless oil).

[Step 3] 1-(benzo[d][1,3]dioxol-5-yl)cyclobutan-1-amine hydrochloride

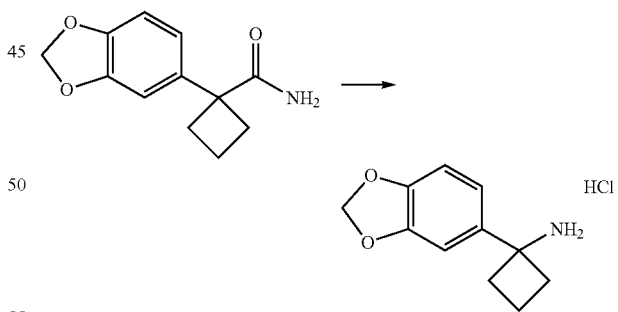

A solution of 1-(benzo[d][1,3]dioxol-5-yl)cyclobutane-1-carboxamide (3.400 g, 15.508 mmol), sodium hydroxide (3.00 M solution in H$_2$O, 15.508 mL, 46.524 mmol), Sodium hypochlorite (8.90% solution, 17.528 mL, 23.262 mmol) and hydrochloric acid (4.00 M solution in Dioxane, 7.754 mL, 31.016 mmol) in 1-butanol (30 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification 1-(benzo[d][1,3]dioxol-5-yl)cyclobutan-1-amine hydrochloride, 2.500 g, 70.8%, White solid).

[Step 4] ethyl 2-((1-(benzo[d][1,3]dioxol-5-yl)cyclobutyl)amino)pyrimidine-5-carboxylate

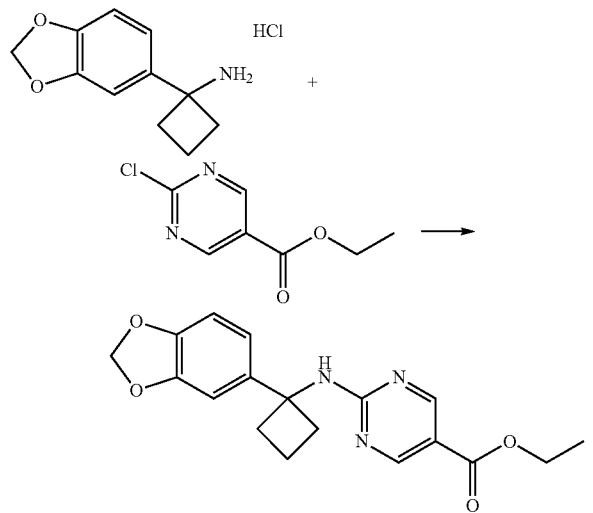

A solution of 1-(benzo[d][1,3]dioxol-5-yl)cyclobutan-1-amine hydrochloride (0.500 g, 2.196 mmol), ethyl 2-chloropyrimidine-5-carboxylate (0.451 g, 2.416 mmol) and N,N-diisopropylethylamine (0.956 mL, 5.490 mmol) in 1,4-dioxane (20 mL) was stirred at 90° C. for 10 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 20%) to give ethyl 2-((1-(benzo[d][1,3]dioxol-5-yl)cyclobutyl)amino)pyrimidine-5-carboxylate as White solid (0.490 g, 65.4%).

[Step 5] 2-((1-(benzo[d][1,3]dioxol-5-yl)cyclobutyl)amino)pyrimidine-5-carbohydrazide

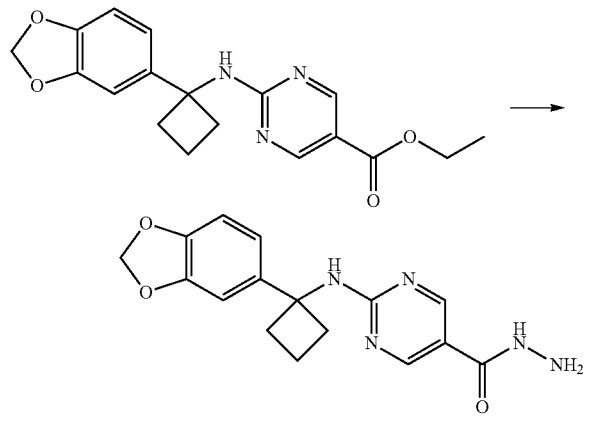

A mixture of ethyl 2-((1-(benzo[d][1,3]dioxol-5-yl)cyclobutyl)amino)pyrimidine-5-carboxylate (0.450 g, 1.318 mmol) and Hydrazine monohydrate (1.281 mL, 26.364 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The crude product was used without further purification (2-((1-(benzo[d][1,3]dioxol-5-yl)cyclobutyl)amino)pyrimidine-5-carbohydrazide, 0.430 g, 99.7%, White solid).

[Step 6] 2-((1-(benzo[d][1,3]dioxol-5-yl)cyclobutyl)amino)-N'-(2,2-difluoroacetyl)pyrimidine-5-carbohydrazide

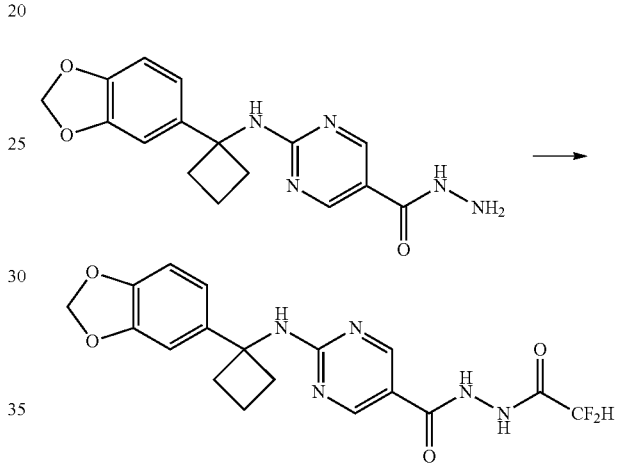

A solution of 2-((1-(benzo[d][1,3] dioxol-5-yl)cyclobutyl)amino)pyrimidine-5-carbohydrazide (0.345 g, 1.054 mmol), 2,2-difluoroacetic anhydride (0.131 mL, 1.054 mmol) and triethylamine (0.220 mL, 1.581 mmol) in dichloromethane (5 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give 2-((1-(benzo[d] [1,3]dioxol-5-yl)cyclobutyl)amino)-N'-(2,2-difluoroacetyl)pyrimidine-5-carbohydrazide as white solid (0.178 g, 41.7%).

[Step 7] Compound 1820

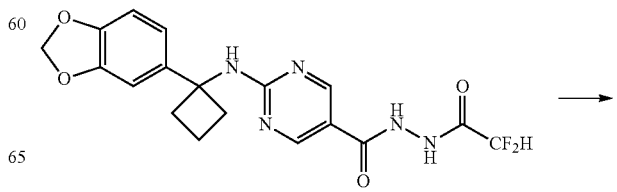

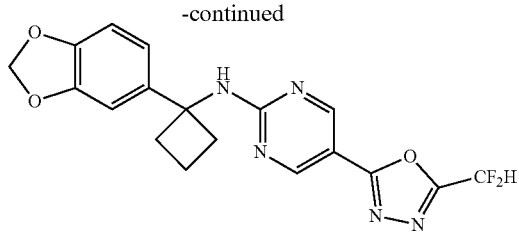

A mixture of 2-((1-(benzo[d][1,3]dioxol-5-yl)cyclobutyl)amino)-N'-(2,2-difluoroacetyl)pyrimidine-5-carbohydrazide (0.337 g, 0.831 mmol) and 1-methoxy-N-triethylammoniosulfonyl-methanimidate (Burgess reagent, 0.297 g, 1.247 mmol) in tetrahydrofuran (10 mL) was heated at 150° C. for 30 min under the microwaves, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give N-(1-(benzo[d][1,3]dioxol-5-yl)cyclobutyl)-5-(5-(difluoromethyl)-1,3,4-oxadiazol-2-yl)pyrimidin-2-amine as White solid (0.178 g, 55.3%).

$^1$H NMR (400 MHz, CDCl$_3$) δ 8.86 (s, 2H), 7.30 (s, 1H), 7.04 (s, 0.25H), 6.91 (s, 0.5H), 6.78 (s, 0.25H), 7.01-6.96 (m, 2H), 6.73 (d, J=8.1 Hz, 1H), 5.90 (s, 2H), 2.98-2.60 (m, 4H), 2.11-1.93 (m, 2H).; LRMS (ES) m/z 388.3 (M$^+$+1).

Example 53: Compound 1821, 5-(5-(difluoromethyl)-1,3,4-oxadiazol-2-yl)-N-(1-(2,5-difluorophenyl)cyclobutyl)pyrimidin-2-amine

[Step 1]
1-(2,5-difluorophenyl)cyclobutane-1-carbonitrile

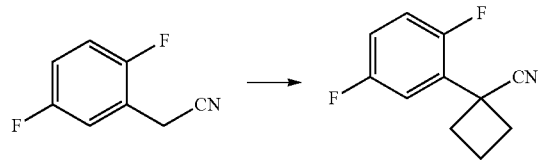 [SMILES: N#CCc1cc(F)ccc1F ; N#CC1(c2cc(F)ccc2F)CCC1]

To a stirred solution of 2-(2,5-difluorophenyl)acetonitrile (5.000 g, 32.652 mmol) in N,N-dimethylformide (50 mL) was added at 0° C. sodium hydride (60.00%, 3.265 g, 81.630 mmol). The reaction mixture was stirred at the same temperature for 30 min, treated at the room temperature with 1,3-dibromopropane (6.592 g, 32.652 mmol), stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 10%) to give 1-(2,5-difluorophenyl)cyclobutane-1-carbonitrile as colorless oil (3.160 g, 50.1%).

[Step 2]
1-(2,5-difluorophenyl)cyclobutane-1-carboxamide

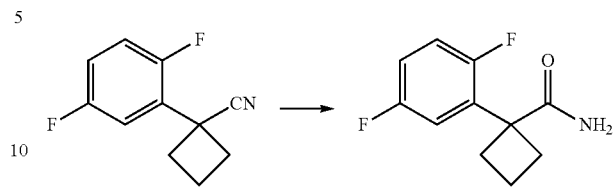

A solution of 1-(2,5-difluorophenyl)cyclobutane-1-carbonitrile (3.160 g, 16.356 mmol), tetra-n-butylammonium bromide (0.527 g, 1.636 mmol), sodium hydroxide (3.00 M solution in H$_2$O, 16.356 mL, 49.068 mmol) and hydrogen peroxide (1.669 g, 49.068 mmol) in methanol (30 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(2,5-difluorophenyl)cyclobutane-1-carboxamide, 3.150 g, 91.2%, Colorless oil).

[Step 3] 1-(2,5-difluorophenyl)cyclobutan-1-amine hydrochloride

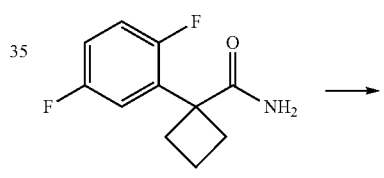

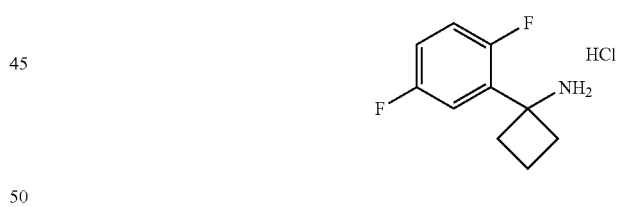

A solution of 1-(2,5-difluorophenyl)cyclobutane-1-carboxamide (3.150 g, 14.914 mmol), sodium hydroxide (3.00 M solution in H$_2$O, 14.914 mL, 44.742 mmol) and sodium hypochlorite (8.90% solution, 17.010 mL, 22.371 mmol) in 1-butanol (20 mL) prepared at the room temperature was stirred at the same temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with dichloromethane (20 mL) and then was added hydrochloric acid (4.00 M solution in dioxane, 7.457 mL, 29.828 mmol), and stirred at the ambient temperature. The resulting precipitates were collected by filtration, and dried to give 1-(2,5-difluorophenyl)cyclobutan-1-amine hydrochloride as White solid (1.500 g, 45.8%).

[Step 4] ethyl 2-((1-(2,5-difluorophenyl)cyclobutyl)amino)pyrimidine-5-carboxylate

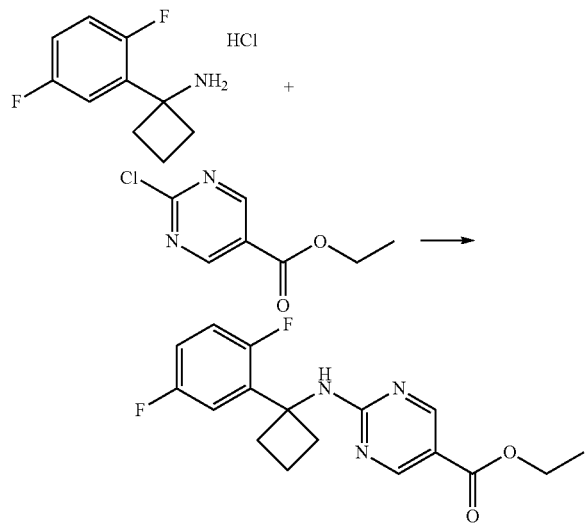

A solution of 1-(2,5-difluorophenyl)cyclobutan-1-amine hydrochloride (0.385 g, 1.753 mmol), ethyl 2-chloropyrimidine-5-carboxylate (0.360 g, 1.928 mmol) and N,N-diisopropylethylamine (0.763 mL, 4.382 mmol) in 1,4-dioxane (5 mL) was stirred at 90° C. for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give ethyl 2-((1-(2,5-difluorophenyl)cyclobutyl)amino)pyrimidine-5-carboxylate as Colorless oil (0.400 g, 68.5%).

[Step 5] 2-((1-(2,5-difluorophenyl)cyclobutyl)amino)pyrimidine-5-carbohydrazide

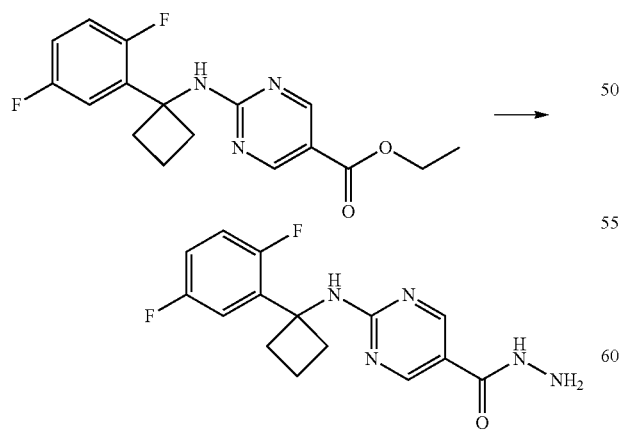

A mixture of ethyl 2-((1-(2,5-difluorophenyl)cyclobutyl)amino)pyrimidine-5-carboxylate (0.400 g, 1.200 mmol) and Hydrazine monohydrate (1.166 mL, 24.000 mmol) in ethanol (10 mL) was heated at 120° C. for 1 hr under the microwaves, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(2,5-difluorophenyl)cyclobutyl)amino)pyrimidine-5-carbohydrazide, 0.350 g, 91.3%, White solid).

[Step 6] N'-(2,2-difluoroacetyl)-2-((1-(2,5-difluorophenyl)cyclobutyl)amino)pyrimidine-5-carbohydrazide

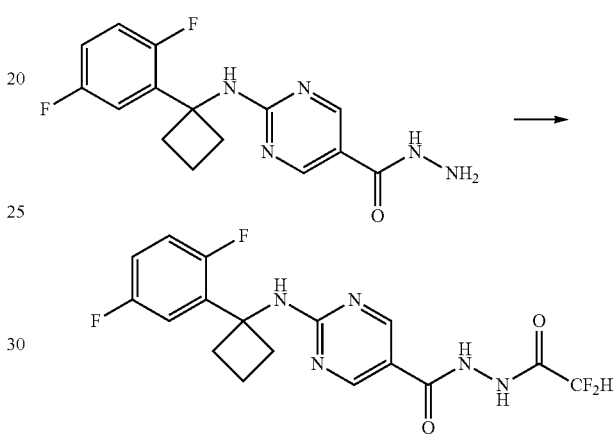

A solution of 2-((1-(2,5-difluorophenyl)cyclobutyl)amino)pyrimidine-5-carbohydrazide (0.248 g, 0.777 mmol), triethylamine (0.162 mL, 1.165 mmol) and 2,2-difluoroacetic anhydride (0.097 mL, 0.777 mmol) in dichloromethane (5 mL) prepared at the room temperature was stirred at the same temperature for 12 hr. The precipitates were collected by filtration, washed by hexane, and dried to give N'-(2,2-difluoroacetyl)-2-((1-(2,5-difluorophenyl)cyclobutyl)amino)pyrimidine-5-carbohydrazide as White solid (0.037 g, 12.0%).

[Step 7] Compound 1821

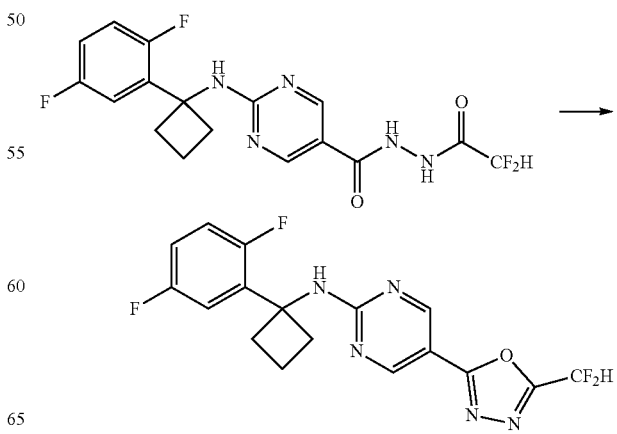

A mixture of N'-(2,2-difluoroacetyl)-2-((1-(2,5-difluorophenyl)cyclobutyl)amino)pyrimidine-5-carbohydrazide (0.037 g, 0.093 mmol) and 1-methoxy-N-triethylammoniosulfonyl-methanimidate (Burgess reagent, 0.044 g, 0.186 mmol) in tetrahydrofuran (5 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(2,5-difluorophenyl)cyclobutyl)pyrimidin-2-amine as White solid (0.025 g, 70.8%).

$^1$H NMR (400 MHz, CDCl$_3$) δ 8.90 (s, 2H), 7.38-7.33 (m, 1H), 7.02 (s, 0.25H), 6.90 (s, 0.5H), 6.77 (s, 0.25H), 6.98-6.87 (m, 2H), 6.69 (s, 1H), 2.83-2.75 (m, 2H), 2.66-2.59 (m, 2H), 2.26-2.19 (m, 1H), 2.00-1.93 (m, 1H).; LRMS (ES) m/z 380.3 (M$^+$+1).

Example 54: Compound 1822, 5-(5-(difluoromethyl)-1,3,4-oxadiazol-2-yl)-N-(1-(4-(trifluoromethoxy)phenyl)cyclobutyl)pyrimidin-2-amine

[Step 1] 1-(4-(trifluoromethoxy)phenyl)cyclobutane-1-carbonitrile

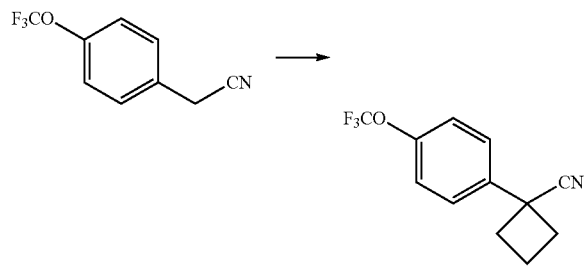

To a stirred solution of 2-(4-trifluoromethoxy)phenyl)acetonitrile (5.000 g, 24.857 mmol) in N,N-dimethylformide (50 mL) was added at 0° C. sodium hydride (60.00%, 2.485 g, 62.143 mmol). The reaction mixture was stirred at the same temperature for 30 min, treated at the room temperature with 1,3-dibromopropane (5.018 g, 24.857 mmol), stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 10%) to give 1-(4-(trifluoromethoxy)phenyl)cyclobutane-1-carbonitrile as colorless oil (3.300 g, 55.0%).

[Step 2] 1-(4-(trifluoromethoxy)phenyl)cyclobutane-1-carboxamide

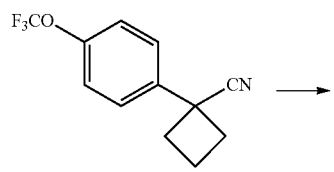

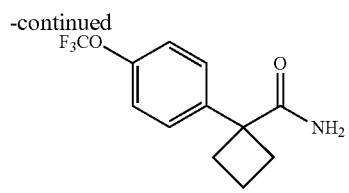

A solution of 1-(4-(trifluoromethoxy)phenyl)cyclobutane-1-carbonitrile (3.300 g, 13.681 mmol), tetra-n-butylammonium bromide (0.441 g, 1.368 mmol), sodium hydroxide (3.00 M solution in H$_2$O, 13.681 mL, 41.043 mmol) and hydrogen peroxide (1.396 g, 41.043 mmol) in methanol (30 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(4-(trifluoromethoxy)phenyl)cyclobutane-1-carboxamide, 3.300 g, 93.0%, Colorless oil).

[Step 3] 1-(4-(trifluoromethoxy)phenyl)cyclobutan-1-amine hydrochloride

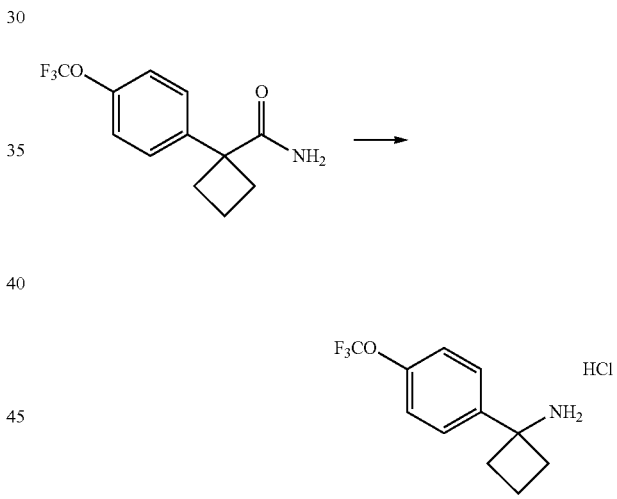

A solution of 1-(4-(trifluoromethoxy)phenyl)cyclobutane-1-carboxamide (3.300 g, 12.730 mmol), sodium hydroxide (3.00 M solution in H$_2$O, 12.730 mL, 38.190 mmol) and sodium hypochlorite (8.90% solution, 14.519 mL, 19.095 mmol) in 1-butanol (20 mL) prepared at the room temperature was stirred at the same temperature for 5 hr. Then, water was added to the reaction mixture, followed by extraction with ethyl acetate The organic layer was washed with aqueous saturated sodium chloride solution, dried with anhydrous MgSO$_4$, filtered, and concentrated in vacuo. The residue was diluted with dichloromethane (20 mL) DCM and then was added hydrochloric acid (4.00 M solution in Dioxane, 6.365 mL, 25.460 mmol) stirred at the ambient temperature. The resulting precipitates were collected by filtration, washed by hexane, and dried to give 1-(4-(trifluoromethoxy)phenyl)cyclobutan-1-amine hydrochloride as White solid (1.200 g, 35.2%).

[Step 4] ethyl 2-((1-(4-(trifluoromethoxy)phenyl)cyclobutyl)amino)pyrimidine-5-carboxylate

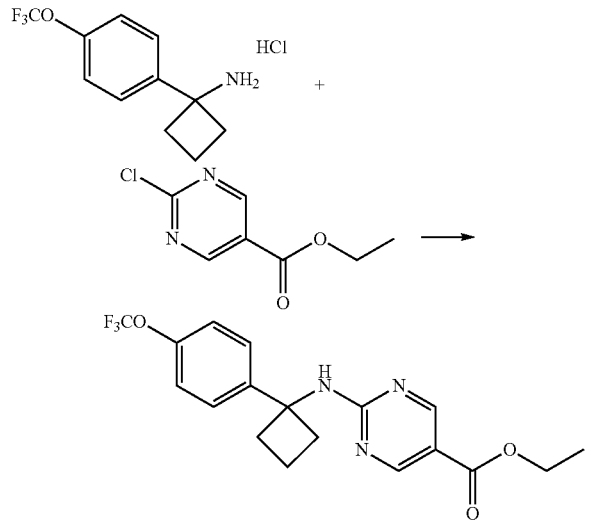

A solution of 1-(4-(trifluoromethoxy)phenyl)cyclobutan-1-amine hydrochloride (0.373 g, 1.393 mmol), ethyl 2-chloropyrimidine-5-carboxylate (0.286 g, 1.533 mmol) and N,N-diisopropylethylamine (0.607 mL, 3.484 mmol) in 1,4-dioxane (5 mL) was stirred at 90° C. for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give ethyl 2-((1-(4-(trifluoromethoxy)phenyl)cyclobutyl)amino)pyrimidine-5-carboxylate as Colorless oil (0.330 g, 62.1%).

[Step 5] 2-((1-(4-(trifluoromethoxy)phenyl)cyclobutyl)amino)pyrimidine-5-carbohydrazide

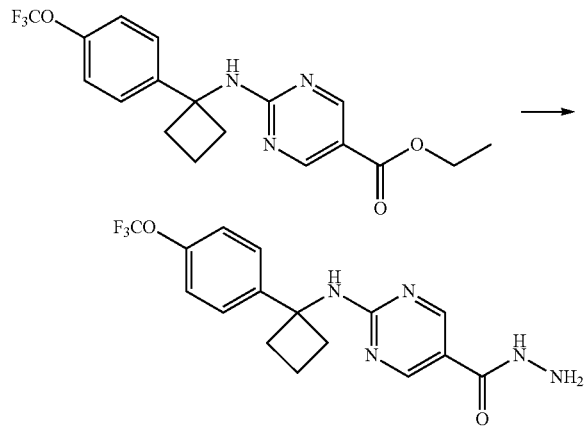

A mixture of ethyl 2-((1-(4-(trifluoromethoxy)phenyl)cyclobutyl)amino)pyrimidine-5-carboxylate (0.330 g, 0.865 mmol) and Hydrazine monohydrate (0.841 mL, 17.306 mmol) in ethanol (10 mL) was heated at 120° C. for 1 hr under the microwaves, and cooled down to the room temperature to terminate reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(4-(trifluoromethoxy)phenyl)cyclobutyl)amino)pyrimidine-5-carbohydrazide, 0.250 g, 78.7%, White solid).

[Step 6] N'-(2,2-difluoroacetyl)-2-((1-(4-(trifluoromethoxy)phenyl)cyclobutyl)amino)pyrimidine-5-carbohydrazide

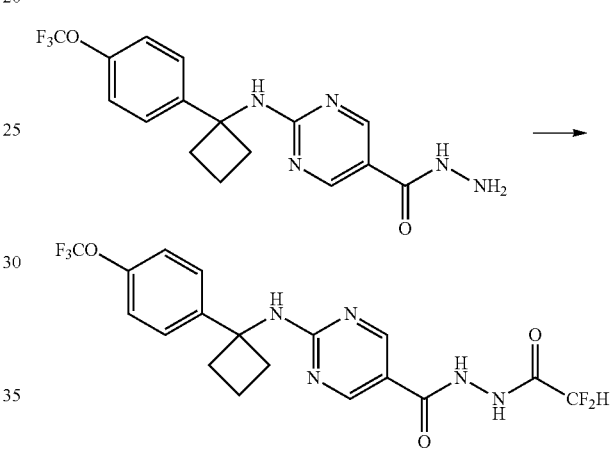

A solution of 2-((1-(4-(trifluoromethoxy)phenyl)cyclobutyl)amino)pyrimidine-5-carbohydrazide (0.250 g, 0.681 mmol), triethylamine (0.142 mL, 1.021 mmol) and 2,2-difluoroacetic anhydride (0.085 mL, 0.681 mmol) in dichloromethane (10 mL) prepared at the room temperature was stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N'-(2,2-difluoroacetyl)-2-((1-(4-(trifluoromethoxy)phenyl)cyclobutyl)amino)pyrimidine-5-carbohydrazide as White solid (0.219 g, 72.3%).

[Step 7] Compound 1822

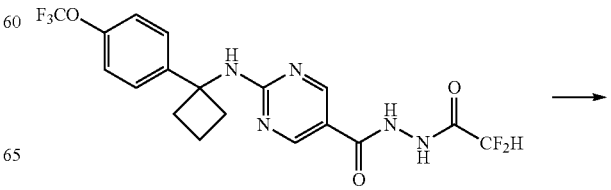

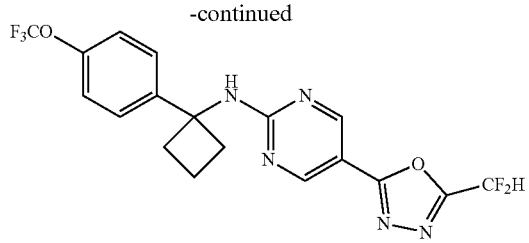

A mixture of N'-(2,2-difluoroacetyl)-2-((1-(4-(trifluoromethoxy)phenyl)cyclobutyl)amino)pyrimidine-5-carbohydrazide (0.219 g, 0.492 mmol) and 1-methoxy-N-triethylammoniosulfonyl-methanimidate (Burgess reagent, 0.234 g, 0.983 mmol) in tetrahydrofuran (5 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(4-(trifluoromethoxy)phenyl)cyclobutyl)pyrimidin-2-amine as White solid (0.180 g, 85.7%).

$^1$H NMR (400 MHz, CDCl$_3$) δ 8.90-8.88 (m, 2H), 7.56-7.52 (m, 2H), 7.19-7.15 (m, 2H), 7.03 (s, 0.25H), 6.90 (s, 0.5H), 6.77 (s, 0.25H), 6.76 (s, 1H), 2.78-2.71 (m, 2H), 2.65-2.58 (m, 2H), 2.25-2.05 (m, 2H).; LRMS (ES) m/z 428.3 (M$^+$+1).

Example 55: Compound 1826, 5-(5-(difluoromethyl)-1,3,4-oxadiazol-2-yl)-N-(1-(2,4,5-trifluorophenyl)cyclobutyl)pyrimidin-2-amine

[Step 1] 1-(2,4,5-trifluorophenyl)cyclobutane-1-carbonitrile

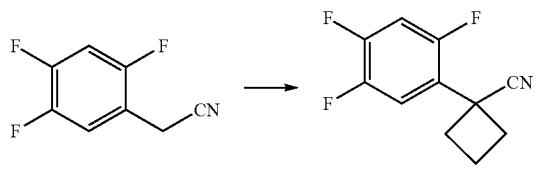 [SMILES: N#CCc1cc(F)c(F)cc1F ; N#CC1(c2cc(F)c(F)cc2F)CCC1]

To a stirred solution of 2-(2,4,5-trifluorophenyl)acetonitrile (5.000 g, 29.219 mmol) in N,N-dimethylformide (30 mL) was added at 0° C. sodium hydride (60.00%, 2.922 g, 73.048 mmol). The reaction mixture was stirred at the same temperature for 30 min, treated at the room temperature with 1,3-dibromopropane (5.899 g, 29.219 mmol), stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give 1-(2,4,5-trifluorophenyl)cyclobutane-1-carbonitrile as Colorless oil (2.660 g, 43.1%).

[Step 2]
1-(2,4,5-trifluorophenyl)cyclobutane-1-carboxamide

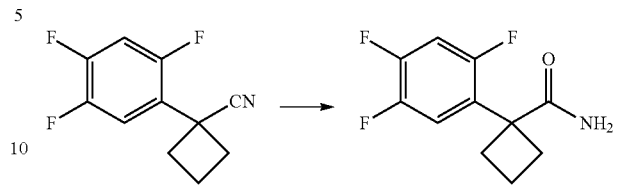

A solution of 1-(2,4,5-trifluorophenyl)cyclobutane-1-carbonitrile (2.660 g, 12.595 mmol), tetra-n-butylammonium bromide (0.406 g, 1.260 mmol), sodium hydroxide (3.00 M solution in H$_2$O, 12.595 mL, 37.786 mmol) and hydrogen peroxide (30.00% solution, 2.955 mL, 37.786 mmol) in methanol (20 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 50%) to give 1-(2,4,5-trifluorophenyl)cyclobutane-1-carboxamide as White solid (1.790 g, 62.0%).

[Step 3]
1-(2,4,5-trifluorophenyl)cyclobutan-1-amine hydrochloride

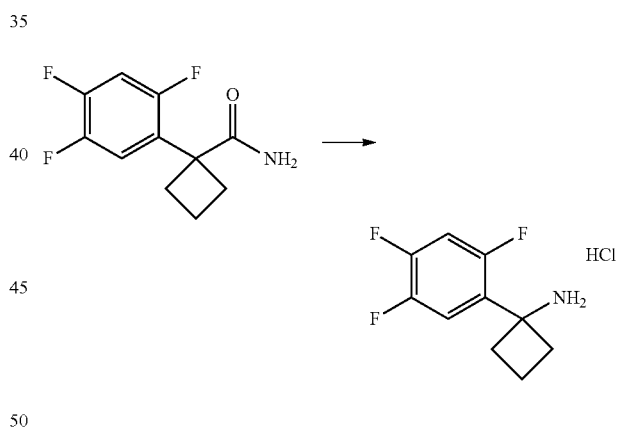

A solution of 1-(2,4,5-trifluorophenyl)cyclobutane-1-carboxamide (1.790 g, 7.810 mmol), sodium hydroxide (3.00 M solution in H$_2$O, 7.810 mL, 23.429 mmol) and sodium hypochlorite (8.90% solution, 8.827 mL, 11.715 mmol) in 1-butanol (10 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with dichloromethane (20 mL) and then was added hydrochloric acid (1.00 M solution in ethylacetate, 11.715 mL, 11.715 mmol) stirred at the ambient temperature for 2 hr. The resulting precipitates were collected by filtration, washed by hexane and dried to give 1-(2,4,5-trifluorophenyl)cyclobutan-1-amine hydrochloride as white solid (1.200 g, 64.7%).

[Step 4] ethyl 2-((1-(2,4,5-trifluorophenyl)cyclobutyl)amino)pyrimidine-5-carboxylate

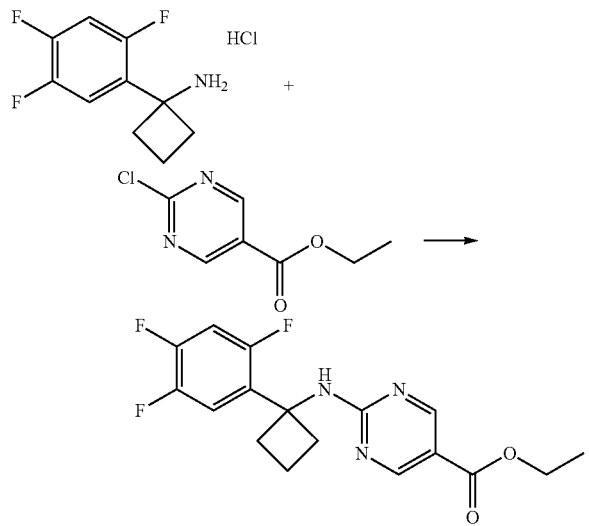

A solution of 1-(2,4,5-trifluorophenyl)cyclobutan-1-amine hydrochloride (0.400 g, 1.683 mmol), ethyl 2-chloropyrimidine-5-carboxylate (0.314 g, 1.683 mmol) and N,N-diisopropylethylamine (0.733 mL, 4.208 mmol) in 1,4-dioxane (10 mL) was stirred at 90° C. for 8 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give ethyl 2-((1-(2,4,5-trifluorophenyl)cyclobutyl)amino)pyrimidine-5-carboxylate as Colorless oil (0.447 g, 75.6%).

[Step 5] 2-((1-(2,4,5-trifluorophenyl)cyclobutyl)amino)pyrimidine-5-carbohydrazide

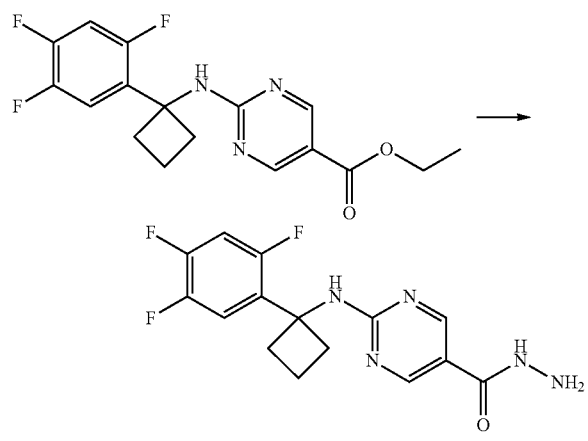

A mixture of ethyl 2-((1-(2,4,5-trifluorophenyl)cyclobutyl)amino)pyrimidine-5-carboxylate (0.477 g, 1.358 mmol) and Hydrazine monohydrate (1.320 mL, 27.154 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The crude product was used without further purification (2-((1-(2,4,5-trifluorophenyl)cyclobutyl)amino)pyrimidine-5-carbohydrazide, 0.394 g, 86.0%, White solid).

[Step 6] N'-(2,2-difluoroacetyl)-2-((1-(2,4,5-trifluorophenyl)cyclobutyl)amino)pyrimidine-5-carbohydrazide

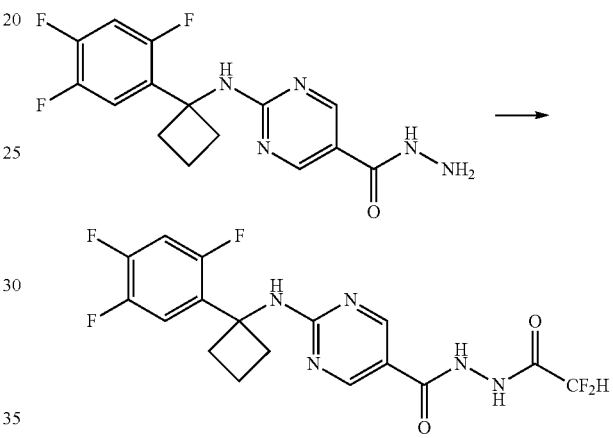

A solution of 2-((1-(2,4,5-trifluorophenyl)cyclobutyl)amino)pyrimidine-5-carbohydrazide (0.394 g, 1.168 mmol), 2,2-difluoroacetic anhydride (0.145 mL, 1.168 mmol) and triethylamine (0.244 mL, 1.752 mmol) in dichloromethane (10 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N'-(2,2-difluoroacetyl)-2-((1-(2,4,5-trifluorophenyl)cyclobutyl)amino)pyrimidine-5-carbohydrazide as White solid (0.364 g, 75.0%).

[Step 7] Compound 1826

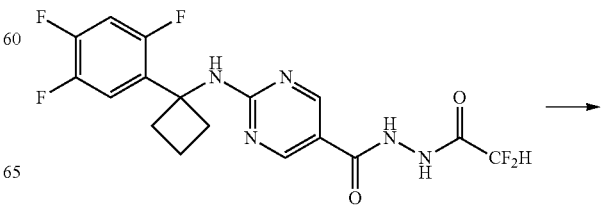

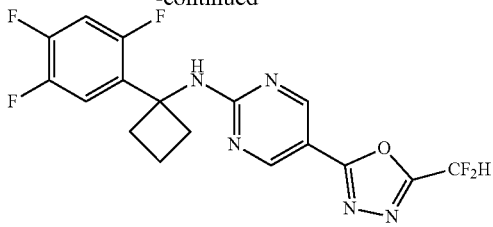

A mixture of N'-(2,2-difluoroacetyl)-2-((1-(2,4,5-trifluorophenyl)cyclobutyl)amino)pyrimidine-5-carbohydrazide (0.364 g, 0.876 mmol) and 1-methoxy-N-triethylammoniosulfonyl-methanimidate (Burgess reagent, 0.313 g, 1.315 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(2,4,5-trifluorophenyl)cyclobutyl)pyrimidin-2-amine as White formy solid (0.250 g, 71.8%).

$^1$H NMR (400 MHz, CDCl$_3$) δ 8.91 (s, 2H), 7.53-7.46 (m, 1H), 7.13 (s, 1H)., 7.04 (s, 0.25H), 6.91 (s, 0.5H), 6.78 (s, 0.25H), 6.88-6.81 (m, 1H), 2.80-2.73 (m, 2H), 2.65-2.59 (m, 2H), 2.27-2.16 (m, 1H), 1.99-1.90 (m, 1H).; LRMS (ES) m/z 398.3 (M$^+$+1).

Example 56: Compound 1827, 5-(5-(difluoromethyl)-1,3,4-oxadiazol-2-yl)-N-(1-(2,3-difluorophenyl)cyclobutyl)pyrimidin-2-amine

[Step 1]
1-(2,3-difluorophenyl)cyclobutane-1-carbonitrile

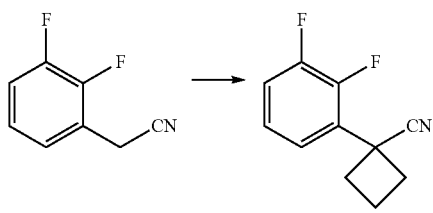 [SMILES: N#CCc1cccc(F)c1F ; N#CC1(c2cccc(F)c2F)CCC1]

To a stirred solution of 2-(2,3-difluorophenyl)acetonitrile (5.000 g, 32.652 mmol) in N,N-dimethylformamide (30 mL) was added at 0° C. sodium hydride (60.00%, 3.265 g, 81.630 mmol). The reaction mixture was stirred at the same temperature for 30 min, treated at the room temperature with 1,3-dibromopropane (6.592 g, 32.652 mmol), and stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was chromatographed (SiO$_2$, 40 g cartridge; ethyl acetate/heaxane=0% to 10%) to give 1-(2,3-difluorophenyl)cyclobutane-1-carbonitrile as Colorless oil (3.510 g, 55.6%).

[Step 2]
1-(2,3-difluorophenyl)cyclobutane-1-carboxamide

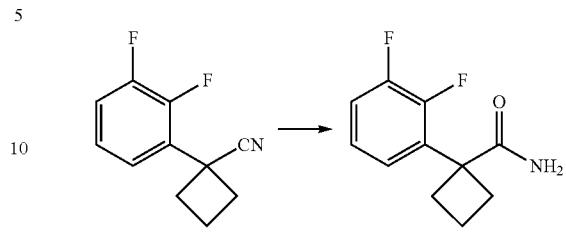

A solution of 1-(2,3-difluorophenyl)cyclobutane-1-carbonitrile (3.510 g, 18.168 mmol), tetra-n-butylammonium bromide (0.586 g, 1.817 mmol), sodium hydroxide (3.00 M solution in H$_2$O, 3.633 g, 54.503 mmol) and hydrogen peroxide (30.00%, 6.180 g, 54.503 mmol) in methanol (20 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was chromatographed (SiO$_2$, 40 g cartridge; ethyl acetate/hexane=0% to 50%) to give 1-(2,3-difluorophenyl)cyclobutane-1-carboxamide as White solid (2.290 g, 59.7%).

[Step 3] 1-(2,3-difluorophenyl)cyclobutan-1-amine hydrochloride

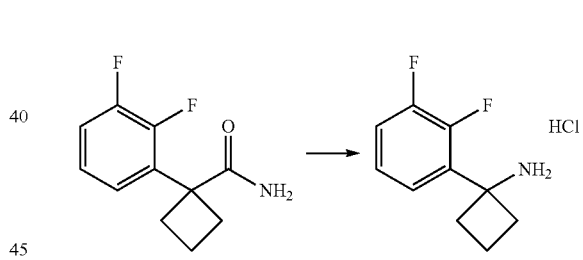

A solution of 1-(2,3-difluorophenyl)cyclobutane-1-carboxamide (2.290 g, 10.842 mmol), sodium hydroxide (3.00 M solution in H$_2$O, 10.842 mL, 32.527 mmol), sodium hypochlorite (8.90% solution, 13.602 g, 16.263 mmol) and hydrochloric acid (1.00 M solution in ethyl acetate, 16.263 mL, 16.263 mmol) in 1-butanol (10 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and then was added hydrogen chloride (1.00 M solution in ethylacetate, 16.263 mL, 16.263 mmol) stirred at the ambient temperature. The resulting precipitates were collected by filtration, washed by hexane and dried to give 1-(2,3-difluorophenyl)cyclobutan-1-amine hydrochloride as White solid (1.250 g, 52.5%).

[Step 4] ethyl 2-((1-(2,3-difluorophenyl)cyclobutyl)amino)pyrimidine-5-carboxylate

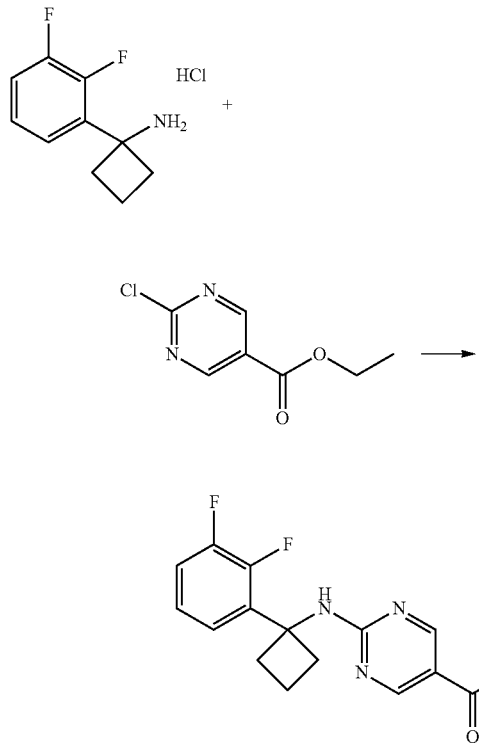

1-(2,3-difluorophenyl)cyclobutane-1-carboxamide (0.400 g, 1.821 mmol), ethyl 2-chloropyrimidine-5-carboxylate (0.340 g, 1.821 mmol) and N,N-diisopropylethylamine (0.793 mL, 4.552 mmol) in 1,4-dioxane (10 mL) was stirred at 90° C. for 8 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give ethyl 2-((1-(2,3-difluorophenyl)cyclobutyl)amino)pyrimidine-5-carboxylate as Colorless oil (0.506 g, 83.4%).

[Step 5] 2-((1-(2,3-difluorophenyl)cyclobutyl)amino)pyrimidine-5-carbohydrazide

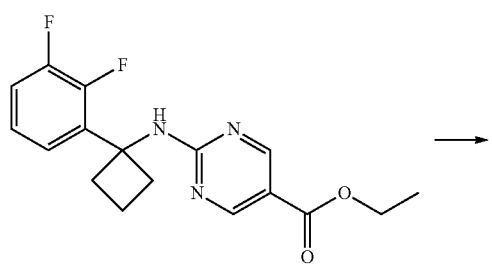

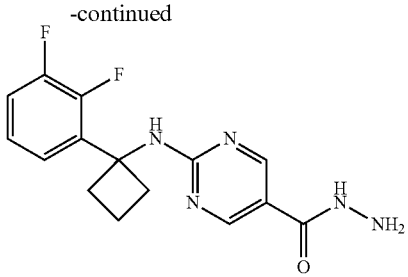

A mixture of ethyl 2-((1-(2,3-difluorophenyl)cyclobutyl)amino)pyrimidine-5-carboxylate (0.504 g, 1.512 mmol) and Hydrazine monohydrate (1.470 mL, 30.239 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(2,3-difluorophenyl)cyclobutyl)amino)pyrimidine-5-carbohydrazide, 0.412 g, 85.3%, White solid).

[Step 6] N'-(2,2-difluoroacetyl)-2-((1-(2,3-difluorophenyl)cyclobutyl)amino)pyrimidine-5-carbohydrazide

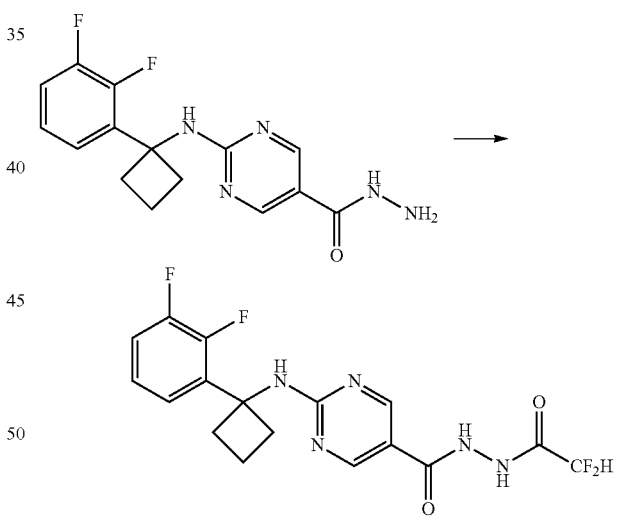

A solution of 2-((1-(2,3-difluorophenyl)cyclobutyl)amino)pyrimidine-5-carbohydrazide (0.412 g, 1.290 mmol), 2,2-difluoroacetic anhydride (0.160 mL, 1.290 mmol) and triethylamine (0.270 mL, 1.935 mmol) in dichloromethane (10 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N'-(2,2-difluoroacetyl)-2-((1-(2,3-difluorophenyl)cyclobutyl)amino)pyrimidine-5-carbohydrazide as White solid (0.350 g, 68.3%).

[Step 7] Compound 1827

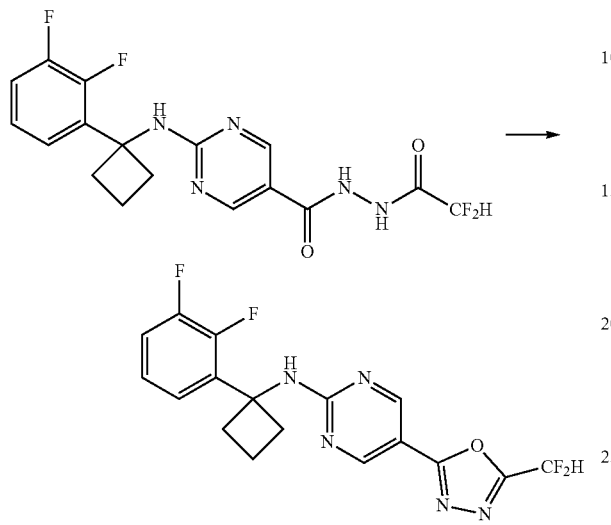

A mixture of N'-(2,2-difluoroacetyl)-2-((1-(2,3-difluorophenyl)cycyclbutyl)amino)pyrimidine-5-carbohydrazide (0.116 g, 0.292 mmol) and 1-methoxy-N-triethylammoniosulfonyl-methanimidate (Burgess reagent, 0.104 g, 0.438 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 12 g cartridge; ethyl acetate/hexane=0% to 30%) to give 5-(5-(difluoromethyl)-1,3,4-oxadiazol-2-yl)-N-(1-(2,3-difluorophenyl)cyclobutyl)pyrimidin-2-amine as White formy solid (0.067 g, 60.5%).

$^1$H NMR (400 MHz, $CDCl_3$) δ 8.88 (s, 2H), 7.42~7.37 (m, 1H), 7.08 (s, 0.25H), 6.90 (s, 0.5H), 6.77 (s, 0.25H), 7.08~7.01 (m, 2H), 6.79 (s, 1H), 2.87~2.80 (m, 2H), 2.68~2.61 (m, 2H), 2.29~2.18 (m, 1H), 2.07~1.98 (m, 1H).; LRMS (ES) m/z 380.2 ($M^++1$).

Example 57: Compound 1828, 5-(5-(difluoromethyl)-1,3,4-oxadiazol-2-yl)-N-(1-(2,6-difluorophenyl)cyclobutyl)pyrimidin-2-amine

[Step 1]
1-(2,6-difluorophenyl)cyclobutane-1-carbonitrile

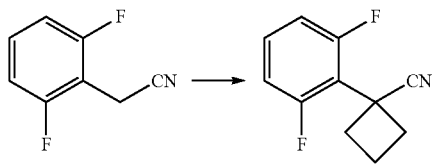 [SMILES: N#CCc1c(F)cccc1F ; N#CC1(c2c(F)cccc2F)CCC1]

To a stirred solution of 2-(2,6-difluorophenyl)acetonitrile (5.000 g, 32.652 mmol) in N,N-dimethylformamide (30 mL) was added at 0° C. sodium hydride (60.00%, 3.265 g, 81.630 mmol). The reaction mixture was stirred at the same temperature for 30 min, treated at the room temperature with 1,3-dibromopropane (6.592 g, 32.652 mmol), and stirred for additional 12 hr. Then, water was added to the reaction mixture, followed by extraction with ethyl acetate. The organic layer was dried (anhydrous $MgSO_4$), filtered, and concentrated in vacuo. The concentrate was chromatographed ($SiO_2$, 40 g cartridge; ethyl acetate/hexane=0% to 10%) to give 1-(2,6-difluorophenyl)cyclobutane-1-carbonitrile as Colorless oil (2.340 g, 37.1%).

[Step 2]
1-(2,6-difluorophenyl)cyclobutane-1-carboxamide

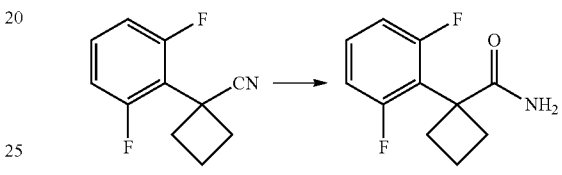

A solution of 1-(2,6-difluorophenyl)cyclobutane-1-carbonitrile (2.340 g, 12.112 mmol), tetra-n-butylammonium bromide (0.390 g, 1.211 mmol), sodium hydroxide (3.00 M solution in $H_2O$, 12.112 mL, 36.335 mmol) and hydrogen peroxide (30.00%, 4.120 g, 36.335 mmol) in methanol (20 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 40 g cartridge; ethyl acetate/hexane=0% to 50%) to give 1-(2,6-difluorophenyl)cyclobutane-1-carboxamide as White solid (1.208 g, 47.2%).

[Step 3] 1-(2,6-difluorophenyl)cyclobutan-1-amine hydrochloride

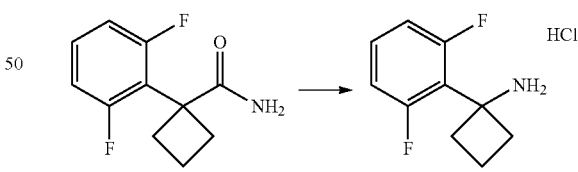

A solution of 1-(2,6-difluorophenyl)cyclobutane-1-carboxamide (1.208 g, 5.719 mmol), sodium hydroxide (3.00 M solution in $H_2O$, 5.719 mL, 17.158 mmol), sodium hypochlorite (8.90%, 6.464 mL, 8.579 mmol) and hydrochloric acid (1.00 M solution in ethyl acetate, 8.579 mL, 8.579 mmol) in 1-butanol (10 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was diluted with ethyl acetate and then was added hydrogen chloride (1.00 M solution in ethylacetate, 8.579 mL, 8.579 mmol) stirred at the ambient temperature. The resulting precipitates were collected by filtration, washed by hexane and dried to give 1-(2,6-difluorophenyl)cyclobutan-1-amine hydrochloride as White solid (0.800 g, 63.7%).

[Step 4] ethyl 2-((1-(2,6-difluorophenyl)cyclobutyl)amino)pyrimidine-5-carboxylate

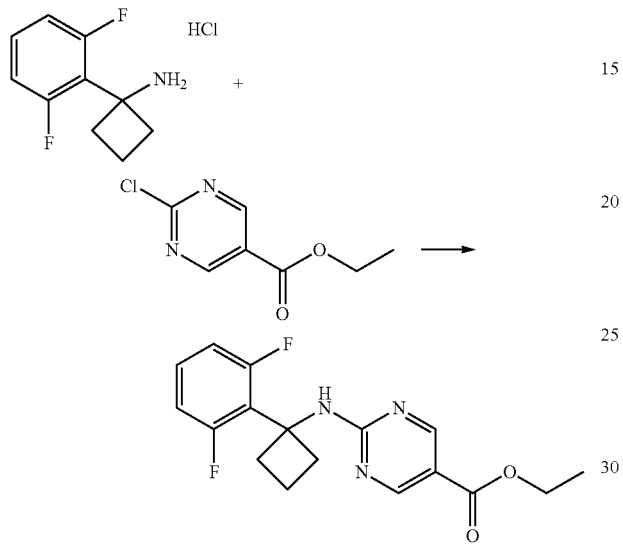

A solution of 1-(2,6-difluorophenyl)cyclobutan-1-amine hydrochloride (0.400 g, 1.821 mmol), ethyl 2-chloropyrimidine-5-carboxylate (0.340 g, 1.821 mmol) and N,N-diisopropylethylamine (0.793 mL, 4.552 mmol) in 1,4-dioxane (10 mL) was stirred at 90° C. for 8 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 15%) to give ethyl 2-((1-(2,6-difluorophenyl)cyclobutyl)amino)pyrimidine-5-carboxylate as Colorless oil (0.342 g, 56.3%).

[Step 5] 2-((1-(2,6-difluorophenyl)cyclobutyl)amino)pyrimidine-5-carbohydrazide

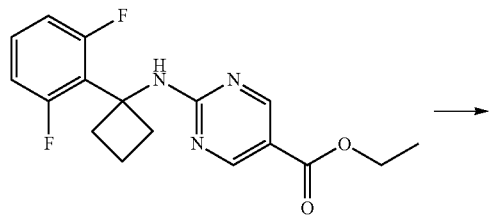

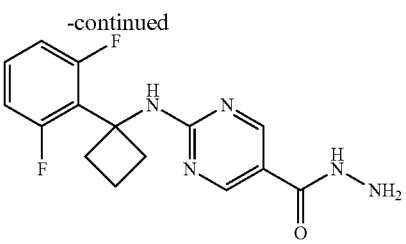

A mixture of ethyl 2-((1-(2,6-difluorophenyl)cyclobutyl)amino)pyrimidine-5-carboxylate (0.342 g, 1.026 mmol) and Hydrazine monohydrate (0.997 mL, 20.520 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The crude product was used without further purification (2-((1-(2,6-difluorophenyl)cyclobutyl)amino)pyrimidine-5-carbohydrazide, 0.290 g, 88.5%, White solid).

[Step 6] N'-(2,2-difluoroacetyl)-2-((1-(2,6-difluorophenyl)cyclobutyl)amino)pyrimidine-5-carbohydrazide

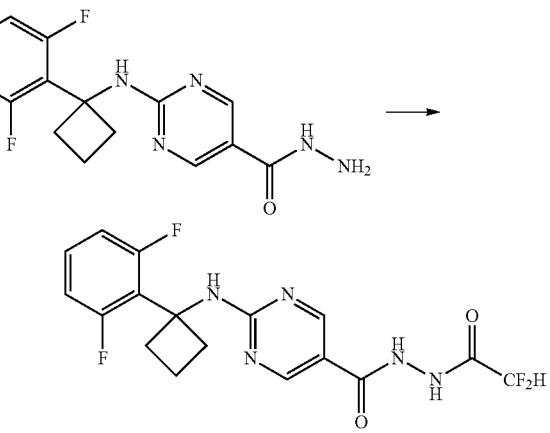

A solution of 2-((1-(2,6-difluorophenyl)cyclobutyl)amino)pyrimidine-5-carbohydrazide (0.249 g, 0.780 mmol), 2,2-difluoroacetic anhydride (0.097 mL, 0.780 mmol) and triethylamine (0.163 mL, 1.170 mmol) in dichloromethane (10 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N'-(2,2-difluoroacetyl)-2-((1-(2,6-difluorophenyl)cyclobutyl)amino)pyrimidine-5-carbohydrazide as White solid (0.127 g, 41.0%).

[Step 7] Compound 1828

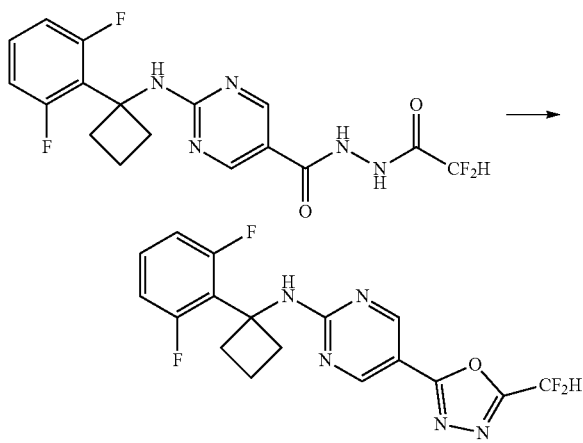

A mixture of N'-(2,2-difluoroacetyl)-2-((1-(2,6-difluorophenyl)cyclobutyl)amino)pyrimidine-5-carbohydrazide (0.127 g, 0.320 mmol) and 1-methoxy-N-triethylammoniosulfonyl-methanimidate (Burgess reagent, 0.114 g, 0.479 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(2,6-difluorophenyl)cyclobutyl)pyrimidin-2-amine as White formy solid (0.080 g, 66.0%).

$^1$H NMR (400 MHz, CDCl$_3$) δ 8.92 (s, 2H), 7.17~7.13 (m, 1H), 7.02 (s, 0.25H), 6.89 (s, 0.5H), 6.76 (s, 0.25H), 6.84~6.79 (m, 2H), 6.61 (s, 1H), 2.90~2.85 (m, 2H), 2.69~2.64 (m, 2H), 2.36~2.19 (m, 1H), 2.03~2.00 (m, 1H).; LRMS (ES) m/z 380.2 (M$^+$+1).

Example 58. Compound 1832: N-(1-(2,3-dichlorophenyl)cyclobutyl)-5-(5-(difluoromethyl)-1,3,4-oxadiazol-2-yl)pyrimidin-2-amine

[Step 1]
1-(2,3-dichlorophenyl)cyclobutane-1-carbonitrile

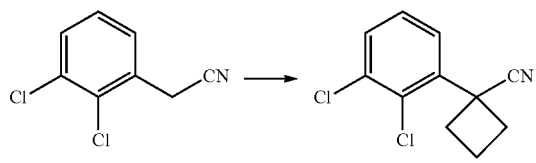 [SMILES: N#CCc1cccc(Cl)c1Cl ; N#CC1(c2cccc(Cl)c2Cl)CCC1]

To a stirred solution of 2-(2,3-dichlorophenyl)acetonitrile (5.581 g, 29.999 mmol) in N,N-dimethylformamide (50 mL) was added at 0° C. sodium hydride (60.00%, 3.000 g, 74.997 mmol). The reaction mixture was stirred at the same temperature for 30 min, treated at the room temperature with 1,3-dibromopropane (3.059 mL, 29.999 mmol), and stirred for additional 21 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 50%) to give the desired product as White solid (3.696 g, 54.5%).

[Step 2]
1-(2,3-dichlorophenyl)cyclobutane-1-carboxamide

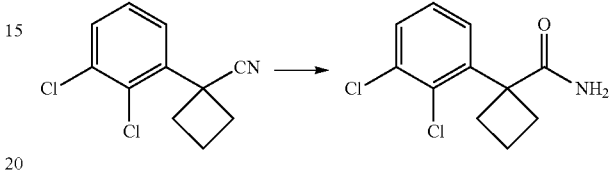

A solution of 1-(2,3-dichlorophenyl)cyclobutane-1-carbonitrile (3.696 g, 16.347 mmol), sodium hydroxide (3.00 M solution, 1.362 mL, 4.087 mmol), hydrogen peroxide (30.00%, 5.560 g, 49.042 mmol) and tetrabutylammonium bromide (0.053 g, 0.163 mmol) in methanol (100 mL) prepared at the room temperature was stirred at the same temperature for 20 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 80%) to give 1-(2,3-dichlorophenyl)cyclobutane-1-carboxamide as White solid (1.525 g, 38.2%).

[Step 3] 1-(2,3-dichlorophenyl)cyclobutan-1-amine hydrochloride

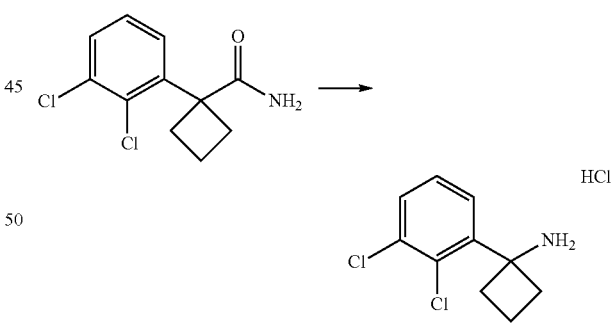

A solution of 1-(2,3-dichlorophenyl)cyclobutane-1-carboxamide (1.525 g, 6.247 mmol), Sodium hypochlorite (8.51%, 7.650 g, 8.746 mmol) and sodium hydroxide (3.00 M solution in water, 5.830 mL, 17.491 mmol) in 1-butanol (25 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was added hydrogen chloride (1.00 M solution in ethylacetate, 9.370 mL, 9.370 mmol) and stirred at the ambient temperature. The resulting precipitates were collected by filtration, washed by ethyl acetate, and dried to give 1-(2,3-dichlorophenyl)cyclobutan-1-amine hydrochloride as White solid (0.884 g, 56.0%).

[Step 4] ethyl 2-((1-(2,3-dichlorophenyl)cyclobutyl)amino)pyrimidine-5-carboxylate

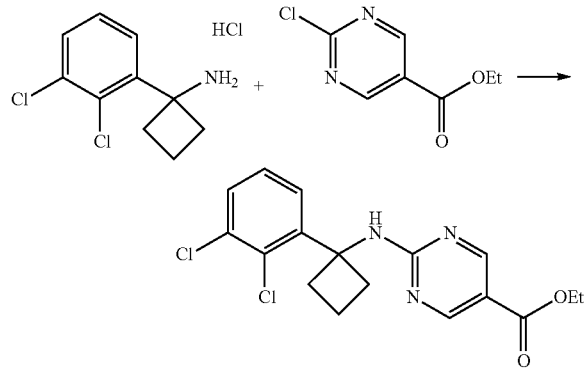

A solution of 1-(2,3-dichlorophenyl)cyclobutan-1-amine hydrochloride (0.800 g, 3.168 mmol), ethyl 2-chloropyrimidine-5-carboxylate (0.650 g, 3.484 mmol) and N-ethyl-N-isopropylpropan-2-amine (1.383 mL, 7.919 mmol) in 1,4-dioxane (5 mL) was stirred at 90° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 50%) to give ethyl 2-((1-(2,3-dichlorophenyl)cyclobutyl)amino)pyrimidine-5-carboxylate as White solid (0.990 g, 85.3%).

[Step 5] 2-((1-(2,3-dichlorophenyl)cyclobutyl)amino)pyrimidine-5-carbohydrazide

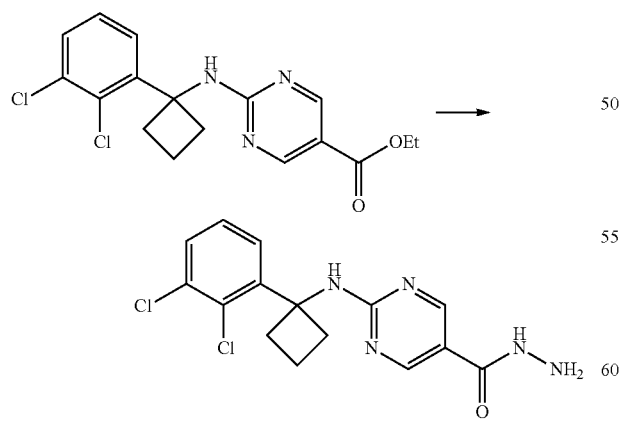

A solution of ethyl 2-((1-(2,3-dichlorophenyl)cyclobutyl)amino)pyrimidine-5-carboxylate (1.153 g, 3.148 mmol) and hydrazine (50.00% solution in water, 3.952 mL, 62.964 mmol) in ethanol (20 mL) was stirred at 120° C. for 18 hr, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(2,3-dichlorophenyl)cyclobutyl)amino)pyrimidine-5-carbohydrazide, 0.692 g, 62.4%, White solid).

[Step 6] 2-((1-(2,3-dichlorophenyl)cyclobutyl)amino)-N'-(2,2-difluoroacetyl)pyrimidine-5-carbohydrazide

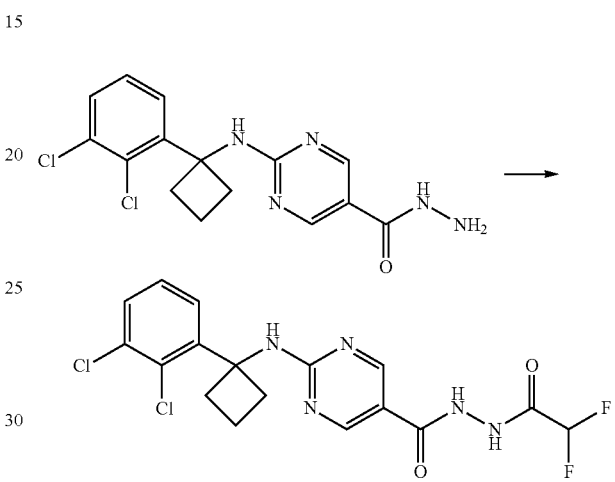

A solution of 2-((1-(2,3-dichlorophenyl)cyclobutyl)amino)pyrimidine-5-carbohydrazide (0.250 g, 0.710 mmol) in dichloromethane (8 mL) was mixed at the room temperature with triethylamine (0.148 mL, 1.065 mmol) and 2,2-difluoroacetic anhydride (0.088 mL, 0.710 mmol). The reaction mixture was stirred at the same temperature for 2 hr, and concentrated under the reduced pressure to remove the solvent. The concentrate was purified and concentrated by column chromatography (SiO$_2$, 12 g cartridge; dichloromethane/methanol=0% to 20%) to give 2-((1-(2,3-dichlorophenyl)cyclobutyl)amino)-N'-(2,2-difluoroacetyl)pyrimidine-5-carbohydrazide as White solid (0.250 g, 81.9%).

[Step 7] Compound 1832

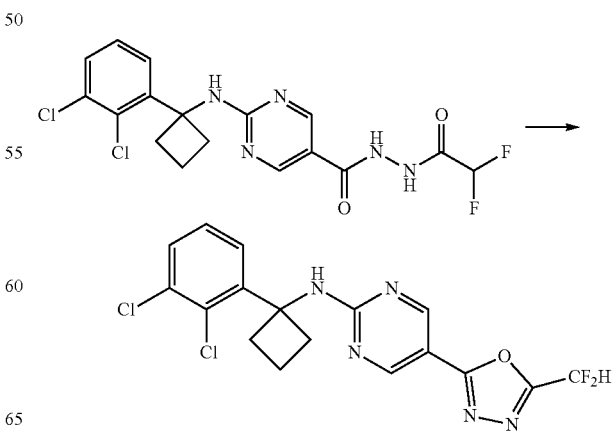

A mixture of 2-((1-(2,3-dichlorophenyl)cyclobutyl)amino)-N'-(2,2-difluoroacetyl)pyrimidine-5-carbohydrazide (0.100 g, 0.232 mmol) and 1-methoxy-N-triethylammoniosulfonyl-methanimidate (Burgess reagent, 0.111 g, 0.465 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (10 mL) and water (5 mL), and filtered throughout a plastic frit to remove the solid residues and aqueous layer. The resulting organic layer was concentrated in vacuo to give the crude product which was subsequently chromatographed (SiO$_2$, 4 g cartridge; ethyl acetate/hexane=5% to 50%) to give N-(1-(2,3-dichlorophenyl)cyclobutyl)-5-(5-(difluoromethyl)-1,3,4-oxadiazol-2-yl)pyrimidin-2-amine as white solid (0.062 g, 64.7%).

$^1$H NMR (400 MHz, CDCl$_3$) δ 8.83 (d, J=13.8 Hz, 2H), 7.65 (dd, J=7.8, 1.6 Hz, 1H), 7.33 (dd, J=8.0, 1.6 Hz, 1H), 7.18 (t, J=7.9 Hz, 1H), 6.99 (s, 0.25H), 6.86 (s, 0.5H), 6.73 (s, 0.5H), 6.64 (s, 1H), 2.90-2.62 (m, 4H), 2.32-2.16 (m, 1H), 1.89 (dtt, J=11.2, 8.9, 4.4 Hz, 1H); LRMS (ES) m/z 412.0 (M$^+$+1).

Example 59. Compound 1833: N-(1-(2,3-dichlorophenyl)cyclobutyl)-5-(5-(trifluoromethyl)-1,3,4-oxadiazol-2-yl)pyrimidin-2-amine

[Step 1] 2-((1-(2,3-dichlorophenyl)cyclobutyl)amino)-N'-(2,2,2-trifluoroacetyl)pyrimidine-5-carbohydrazide

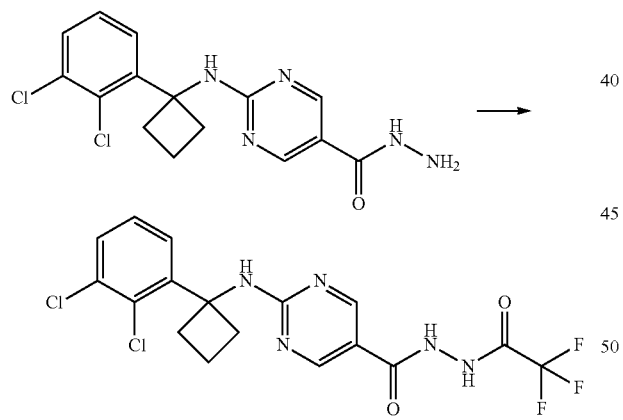

A solution of 2-((1-(2,3-dichlorophenyl)cyclobutyl)amino)pyrimidine-5-carbohydrazide (0.250 g, 0.710 mmol) in dichloromethane (8 mL) was mixed at the room temperature with triethylamine (0.148 mL, 1.065 mmol) and trifluoroacetic anhydride (0.100 mL, 0.710 mmol). The reaction mixture was stirred at the same temperature for 2 hr. The reaction mixture was concentrated under the reduced pressure to remove the solvent. The concentrate was purified and concentrated by column chromatography (SiO$_2$, 12 g cartridge; dichloromethane/methanol=0% to 20%) to give 2-((1-(2,3-dichlorophenyl)cyclobutyl)amino)-N'-(2,2,2-trifluoroacetyl)pyrimidine-5-carbohydrazide as White solid (0.302 g, 94.9%).

[Step 2] Compound 1833

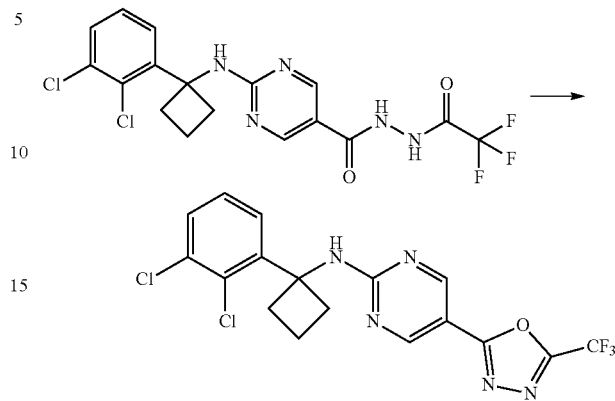

A mixture of 2-((1-(2,3-dichlorophenyl)cyclobutyl)amino)-N'-(2,2,2-trifluoroacetyl)pyrimidine-5-carbohydrazide (0.100 g, 0.223 mmol) and 1-methoxy-N-triethylammoniosulfonyl-methanimidate (Burgess reagent, 0.106 g, 0.446 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (10 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=5% to 50%) to give N-(1-(2,3-dichlorophenyl)cyclobutyl)-5-(5-(difluoromethyl)-1,3,4-oxadiazol-2-yl)pyrimidin-2-amine as white solid (0.054 g, 58.7%).

$^1$H NMR (400 MHz, CDCl$_3$) δ 8.83 (d, J=15.1 Hz, 2H), 7.64 (dd, J=7.8, 1.6 Hz, 1H), 7.33 (dt, J=8.6, 4.3 Hz, 1H), 7.19 (t, J=7.9 Hz, 1H), 6.68 (s, 1H), 2.89-2.68 (m, 4H), 2.33-2.16 (m, 1H), 1.90 (ddq, J=15.7, 9.0, 4.4 Hz, 1H); LRMS (ES) m/z 430.0 (M$^+$+1).

Example 60. Compound 1834: N-(1-(3,4-dichlorophenyl)cyclobutyl)-5-(5-(difluoromethyl)-1,3,4-oxadiazol-2-yl)pyrimidin-2-amine

[Step 1] 1-(3,4-dichlorophenyl)cyclobutane-1-carbonitrile

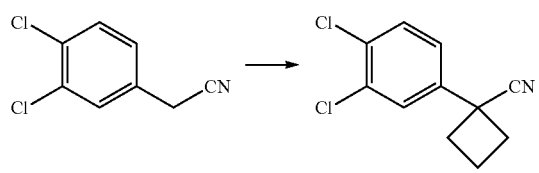 [SMILES: N#CCc1ccc(Cl)c(Cl)c1 ; N#CC1(c2ccc(Cl)c(Cl)c2)CCC1]

To a stirred solution of 2-(3,4-dichlorophenyl)acetonitrile (5.581 g, 29.999 mmol) in N,N-dimethylformide (50 mL) was added at 0° C. sodium hydride (60.00%, 3.000 g, 74.997 mmol). The reaction mixture was stirred at the same temperature for 30 min, treated at the room temperature with 1,3-dibromopropane (3.059 mL, 29.999 mmol), and stirred for additional 21 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 50%) to give 1-(3,4-dichlorophenyl)cyclobutane-1-carbonitrile as colorless liquid (3.864 g, 57.0%).

[Step 2] 1-(3,4-dichlorophenyl)cyclobutane-1-carboxamide

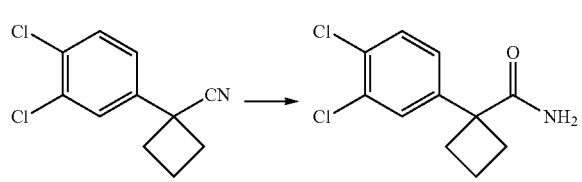 [SMILES: N#CC1(c2ccc(Cl)c(Cl)c2)CCC1 ; NC(=O)C1(c2ccc(Cl)c(Cl)c2)CCC1]

A solution of 1-(3,4-dichlorophenyl)cyclobutane-1-carbonitrile (3.864 g, 17.091 mmol), sodium hydroxide (3.00 M solution, 1.424 mL, 4.273 mmol), hydrogen peroxide (30.00%, 5.814 g, 51.273 mmol) and tetrabutylammonium bromide (0.055 g, 0.171 mmol) in methanol (100 mL) prepared at the room temperature was stirred at the same temperature for 20 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 80%) to give 1-(3,4-dichlorophenyl)cyclobutane-1-carboxamide as Colorless oil (2.332 g, 55.9%).

[Step 3] 1-(3,4-dichlorophenyl)cyclobutan-1-amine hydrochloride

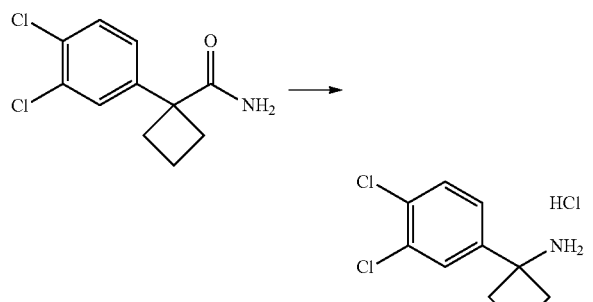

A solution of 1-(3,4-dichlorophenyl)cyclobutane-1-carboxamide (2.332 g, 9.551 mmol), Sodium hypochlorite (8.51%, 11.696 g, 13.371 mmol) and sodium hydroxide (3.00 M solution in water, 8.914 mL, 26.742 mmol) in 1-butanol (25 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was added hydrogen chloride (1.00 M in ethylacetate, 14.326 mL, 14.326 mmol) and diluted with ethyl acetate (20 mL) and stirred at the ambient temperature. The resulting precipitates were collected by filtration, washed by ethyl acetate, and dried to give 1-(3,4-dichlorophenyl)cyclobutan-1-amine hydrochloride as pale yellow solid (1.116 g, 46.3%).

[Step 4] ethyl 2-((1-(3,4-dichlorophenyl)cyclobutyl)amino)pyrimidine-5-carboxylate

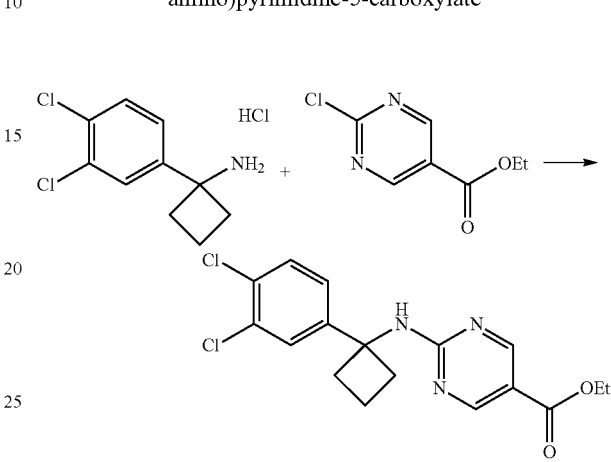

A solution of 1-(3,4-dichlorophenyl)cyclobutan-1-amine hydrochloride (1.000 g, 3.959 mmol), ethyl 2-chloropyrimidine-5-carboxylate (0.813 g, 4.355 mmol) and N-ethyl-N-isopropylpropan-2-amine (1.729 mL, 9.899 mmol) in 1,4-dioxane (5 mL) was stirred at 90° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; ethyl acetate/hexane=0% to 50%) to give ethyl 2-((1-(3,4-dichlorophenyl)cyclobutyl)amino)pyrimidine-5-carboxylate as White solid (1.153 g, 79.5%).

[Step 5] 2-((1-(3,4-dichlorophenyl)cyclobutyl)amino)pyrimidine-5-carbohydrazide

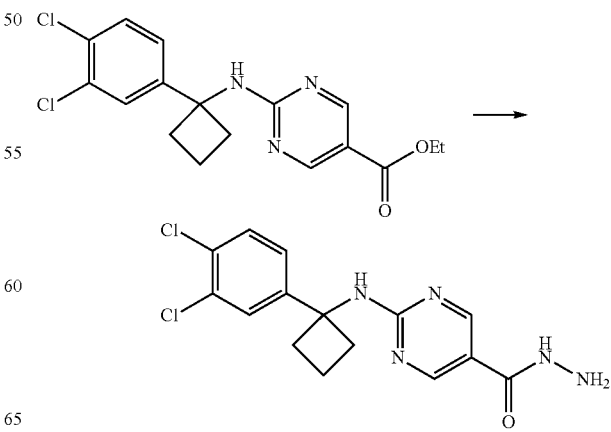

A solution of ethyl 2-((1-(3,4-dichlorophenyl)cyclobutyl)amino)pyrimidine-5-carboxylate (1.153 g, 3.148 mmol) and hydrazine (50.00% solution in water, 3.952 mL, 62.964 mmol) in ethanol (20 mL) was stirred at 120° C. for 18 hr, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(3,4-dichlorophenyl)cyclobutyl)amino)pyrimidine-5-carbohydrazide, 1.108 g, 99.9%, Pale yellow solid).

[Step 6] 2-((1-(3,4-dichlorophenyl)cyclobutyl)amino)-N'-(2,2-difluoroacetyl)pyrimidine-5-carbohydrazide

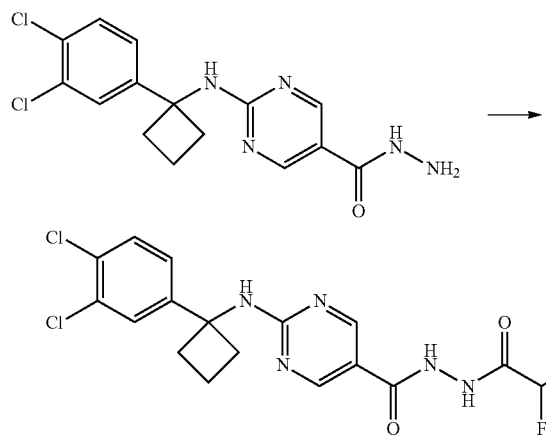

A solution of 2-((1-(3,4-dichlorophenyl)cyclobutyl)amino)pyrimidine-5-carbohydrazide (0.250 g, 0.710 mmol) in dichloromethane (8 mL) was mixed at the room temperature with triethylamine (0.148 mL, 1.065 mmol) and 2,2-difluoroacetic anhydride (0.088 mL, 0.710 mmol). The reaction mixture was stirred at the same temperature for 2 hr. The reaction mixture was concentrated under the reduced pressure to remove the solvent. The concentrate was purified and concentrated by column chromatography (SiO$_2$, 12 g cartridge; dichloromethane/methanol=0% to 20%) to give 2-((1-(3,4-dichlorophenyl)cyclobutyl)amino)-N'-(2,2-difluoroacetyl)pyrimidine-5-carbohydrazide as White solid (0.205 g, 67.1%).

[Step 7] Compound 1834

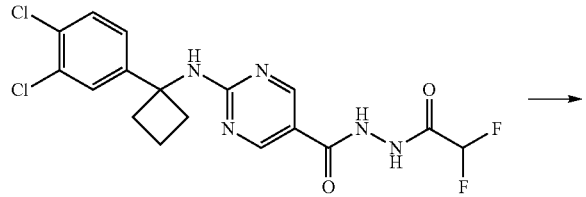

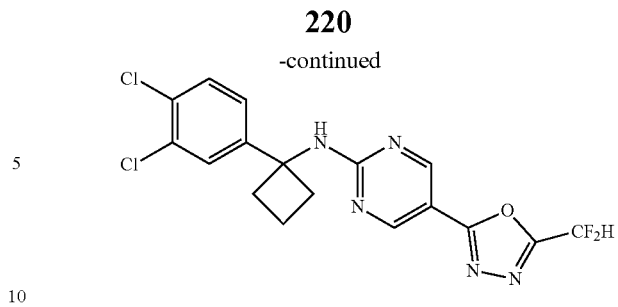

A mixture of 2-((1-(3,4-dichlorophenyl)cyclobutyl)amino)-N'-(2,2-difluoroacetyl)pyrimidine-5-carbohydrazide (0.100 g, 0.232 mmol) and 1-methoxy-N-triethylammonio-sulfonyl-methanimidate (Burgess reagent, 0.111 g, 0.465 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (10 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=5% to 50%) to give N-(1-(3,4-dichlorophenyl)cyclobutyl)-5-(5-(difluoromethyl)-1,3,4-oxadiazol-2-yl)pyrimidin-2-amine as white solid (0.078 g, 81.4%).

$^1$H NMR (400 MHz, CDCl$_3$) δ 8.92 (br, 2H), 7.60 (d, J=2.1 Hz, 1H), 7.40 (d, J=8.4 Hz, 1H), 7.34 (dd, J=8.4, 2.2 Hz, 1H), 7.02 (s, 0.25H), 6.90 (s, 0.5H), 6.77 (s, 0.25H), 6.30 (br, 1H), 2.77-2.66 (m, 2H), 2.61-2.49 (m, 2H), 2.27-2.18 (m, 1H), 2.06-1.95 (m, 1H); LRMS (ES) m/z 411.9 (M$^+$+1).

Example 61. Compound 1835: N-(1-(3,4-dichlorophenyl)cyclobutyl)-5-(5-(trifluoromethyl)-1,3,4-oxadiazol-2-yl)pyrimidin-2-amine

[Step 1] 2-((1-(3,4-dichlorophenyl)cyclobutyl)amino)-N'-(2,2,2-trifluoroacetyl)pyrimidine-5-carbohydrazide

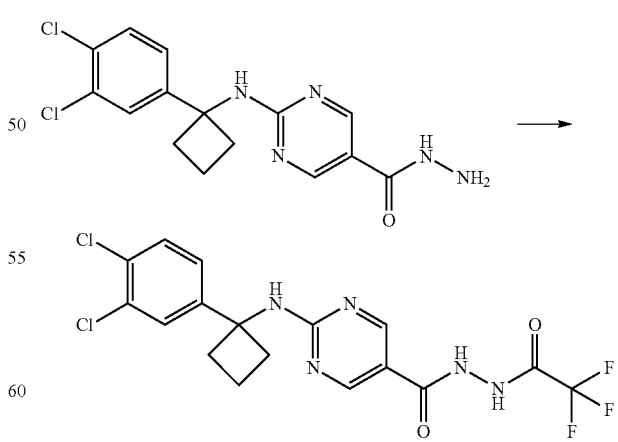

A solution of 2-((1-(3,4-dichlorophenyl)cyclobutyl)amino)pyrimidine-5-carbohydrazide (0.250 g, 0.710 mmol) in dichloromethane (8 mL) was mixed at the room temperature with triethylamine (0.148 mL, 1.065 mmol) and trifluoroacetic anhydride (0.100 mL, 0.710 mmol). The reaction mixture was stirred at the same temperature for 2 hr, and concentrated under the reduced pressure to remove the solvent. The concentrate was purified and concentrated by column chromatography (SiO$_2$, 12 g cartridge; dichloromethane/methanol=0% to 20%) to give 2-((1-(3,4-dichlorophenyl)cyclobutyl)amino)-N'-(2,2,2-trifluoroacetyl)pyrimidine-5-carbohydrazide as White solid (0.315 g, 99.0%).

[Step 2] Compound 1835

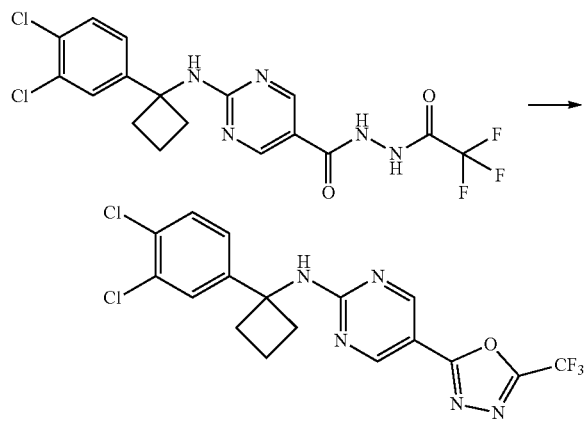

A mixture of 2-((1-(3,4-dichlorophenyl)cyclobutyl)amino)-N'-(2,2,2-trifluoroacetyl)pyrimidine-5-carbohydrazide (0.100 g, 0.223 mmol) and 1-methoxy-N-triethylammoniosulfonyl-methanimidate (Burgess reagent, 0.106 g, 0.446 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (10 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=5% to 50%) to give N-(1-(3,4-dichlorophenyl)cyclobutyl)-5-(5-(trifluoromethyl)-1,3,4-oxadiazol-2-yl)pyrimidin-2-amine as white solid (0.082 g, 85.4%).

$^1$H NMR (400 MHz, CDCl$_3$) δ 8.90 (d, J=27.7 Hz, 2H), 7.60 (d, J=2.1 Hz, 1H), 7.43-7.38 (m, 1H), 7.34 (dd, J=8.4, 2.2 Hz, 1H), 6.40 (br, 1H), 2.78-2.66 (m, 2H), 2.63-2.50 (m, 2H), 2.30-2.14 (m, 1H), 2.08-1.95 (m, 1H); LRMS (ES) m/z 429.9 (M$^+$+1).

Example 62. Compound 1836: N-(1-(2,4-dichlorophenyl)cyclobutyl)-5-(5-(difluoromethyl)-1,3,4-oxadiazol-2-yl)pyrimidin-2-amine

[Step 1]
1-(2,4-dichlorophenyl)cyclobutane-1-carbonitrile

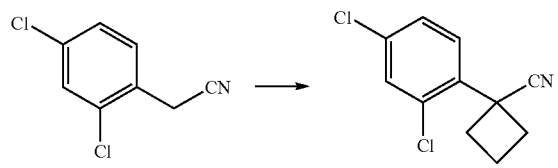 [SMILES: N#CCc1ccc(Cl)cc1Cl ; N#CC1(c2ccc(Cl)cc2Cl)CCC1]

To a stirred solution of 2-(2,4-dichlorophenyl)acetonitrile (5.581 g, 29.999 mmol) in N,N-dimethylformide (50 mL) was added at 0° C. sodium hydride (60.00%, 3.000 g, 74.997 mmol). The reaction mixture was stirred at the same temperature for 30 min, treated at the room temperature with 1,3-dibromopropane (3.059 mL, 29.999 mmol), and stirred for additional 21 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 50%) to give 1-(2,4-dichlorophenyl)cyclobutane-1-carbonitrile as White solid (1.918 g, 28.3%).

[Step 2]
1-(2,4-dichlorophenyl)cyclobutane-1-carboxamide

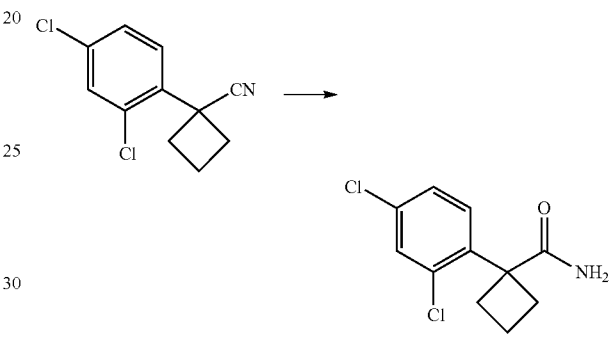

A solution of 1-(2,4-dichlorophenyl)cyclobutane-1-carbonitrile (1.918 g, 8.482 mmol), sodium hydroxide (3.00 M solution, 0.707 mL, 2.121 mmol), hydrogen peroxide (30.00%, 2.885 g, 25.446 mmol) and tetrabutylammonium bromide (0.027 g, 0.085 mmol) in methanol (50 mL) prepared at the room temperature was stirred at the same temperature for 20 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 80%) to give 1-(2,4-dichlorophenyl)cyclobutane-1-carboxamide as White solid (0.764 g, 36.9%).

[Step 3] 1-(2,4-dichlorophenyl)cyclobutan-1-amine hydrochloride

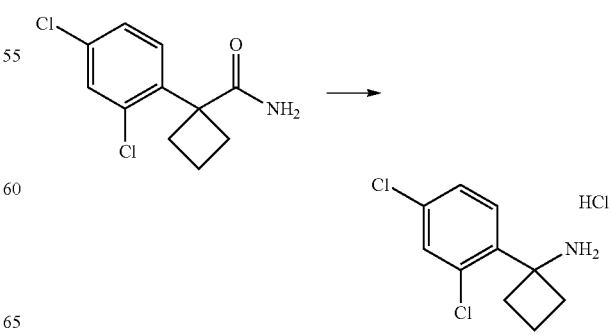

A solution of 1-(2,4-dichlorophenyl)cyclobutane-1-carboxamide (0.764 g, 3.130 mmol), Sodium hypochlorite (8.51%, 3.833 g, 4.381 mmol) and sodium hydroxide (3.00 M solution in water, 2.921 mL, 8.763 mmol) in 1-butanol (25 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was added hydrogen chloride (1.00 M in ethylacetate, 4.694 mL, 4.694 mmol) and diluted with ethyl acetate (20 mL) and stirred at the ambient temperature. The resulting precipitates were collected by filtration, washed by ethyl acetate, and dried to give 1-(2,4-dichlorophenyl)cyclobutan-1-amine hydrochloride as White solid (0.496 g, 62.8%).

[Step 4] ethyl 2-((1-(2,4-dichlorophenyl)cyclobutyl)amino)pyrimidine-5-carboxylate

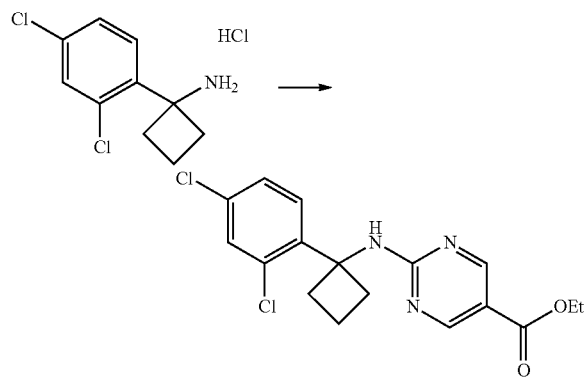

A solution of 1-(2,4-dichlorophenyl)cyclobutan-1-amine hydrochloride (0.496 g, 1.964 mmol), ethyl 2-chloropyrimidine-5-carboxylate (0.403 g, 2.160 mmol) and N-ethyl-N-isopropylpropan-2-amine (0.858 mL, 4.910 mmol) in 1,4-dioxane (5 mL) was stirred at 90° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; ethyl acetate/hexane=0% to 50%) to give ethyl 2-((1-(2,4-dichlorophenyl)cyclobutyl)amino)pyrimidine-5-carboxylate as white solid (0.663 g, 92.2%).

[Step 5] 2-((1-(2,4-dichlorophenyl)cyclobutyl)amino)pyrimidine-5-carbohydrazide

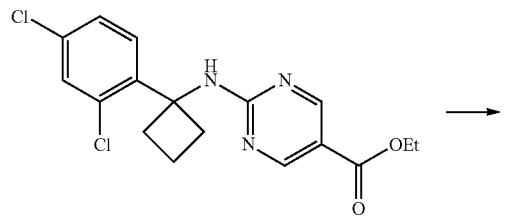

-continued

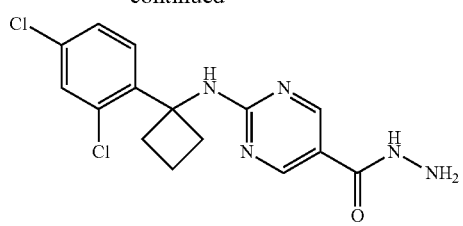

A solution of ethyl 2-((1-(2,4-dichlorophenyl)cyclobutyl)amino)pyrimidine-5-carboxylate (0.660 g, 1.802 mmol) and hydrazine (50.00% solution in water, 2.262 mL, 36.042 mmol) in ethanol (15 mL) was stirred at 120° C. for 18 hr, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The crude product was used without further purification (2-((1-(2,4-dichlorophenyl)cyclobutyl)amino)pyrimidine-5-carbohydrazide, 0.437 g, 68.8%, White solid).

[Step 6] 2-((1-(2,4-dichlorophenyl)cyclobutyl)amino)-N'-(2,2-difluoroacetyl)pyrimidine-5-carbohydrazide

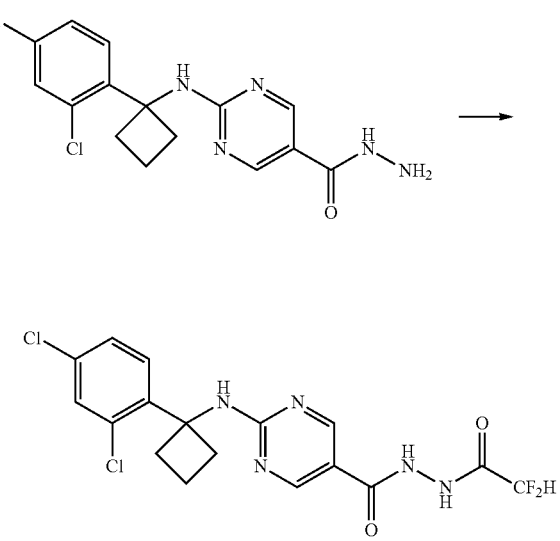

A solution of 2-((1-(2,4-dichlorophenyl)cyclobutyl)amino)pyrimidine-5-carbohydrazide (0.236 g, 0.670 mmol) in dichloromethane (8 mL) was mixed at the room temperature with triethylamine (0.140 mL, 1.005 mmol) and 2,2-difluoroacetic anhydride (0.083 mL, 0.670 mmol). The reaction mixture was stirred at the same temperature for 2 hr, and concentrated under the reduced pressure to remove the solvent. The concentrate was purified and concentrated by column chromatography (SiO₂, 12 g cartridge; dichloromethane/methanol=0% to 20%) to give 2-((1-(2,4-dichlorophenyl)cyclobutyl)amino)-N'-(2,2-difluoroacetyl)pyrimidine-5-carbohydrazide as White solid (0.175 g, 60.7%).

[Step 7] Compound 1836

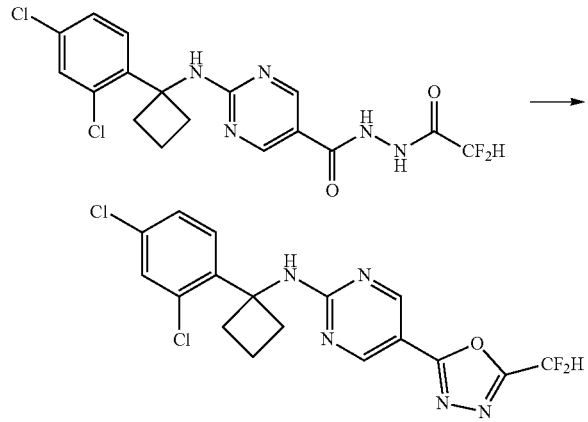

A mixture of 2-((1-(2,4-dichlorophenyl)cyclobutyl)amino)-N'-(2,2-difluoroacetyl)pyrimidine-5-carbohydrazide (0.110 g, 0.256 mmol) and 1-methoxy-N-triethylammoniosulfonyl-methanimidate (Burgess reagent, 0.122 g, 0.511 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (20 mL) and water (10 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=5% to 50%) to give N-(1-(2,4-dichlorophenyl)cyclobutyl)-5-(5-(difluoromethyl)-1,3,4-oxadiazol-2-yl)pyrimidin-2-amine as white solid (0.096 g, 91.1%).

$^1$H NMR (400 MHz, CDCl$_3$) δ 8.86 (d, J=14.6 Hz, 2H), 7.31 (d, J=2.1 Hz, z 1H), 7.24 (dd, J=8.4, 2.2 Hz, 1H), 7.02 (s, 0.25H), 6.89 (s, 0.5H), 6.76 (s, 0.25H), 6.64 (br, 1H), 2.90-2.64 (m, 4H), 2.34-2.15 (m, 1H), 1.92 (dtt, J=11.3, 9.1, 4.6 Hz, 1H); LRMS (ES) m/z 412.0 (M$^+$+1).

Example 63. Compound 1837: N-(1-(2,4-dichlorophenyl)cyclobutyl)-5-(5-(trifluoromethyl)-1,3,4-oxadiazol-2-yl)pyrimidin-2-amine

[Step 1] 2-((1-(2,4-dichlorophenyl)cyclobutyl)amino)-N'-(2,2,2-trifluoroacetyl)pyrimidine-5-carbohydrazide

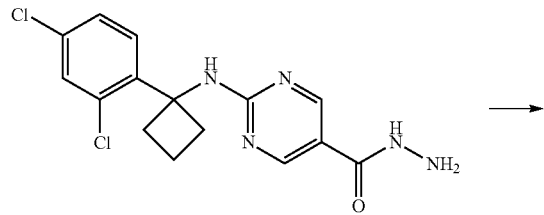

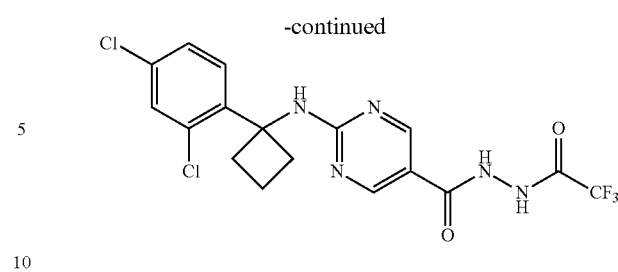

A solution of 2-((1-(2,4-dichlorophenyl)cyclobutyl)amino)pyrimidine-5-carbohydrazide (0.236 g, 0.670 mmol) in dichloromethane (8 mL) was mixed at the room temperature with triethylamine (0.140 mL, 1.005 mmol) and trifluoroacetic anhydride (0.095 mL, 0.670 mmol). The reaction mixture was stirred at the same temperature for 2 hr, and concentrated under the reduced pressure to remove the solvent. The concentrate was purified and concentrated by column chromatography (SiO$_2$, 12 g cartridge; dichloromethane/methanol=0% to 20%) to give 2-((1-(2,4-dichlorophenyl)cyclobutyl)amino)-N'-(2,2,2-trifluoroacetyl)pyrimidine-5-carbohydrazide as White solid (0.150 g, 49.9%).

[Step 2] Compound 1837

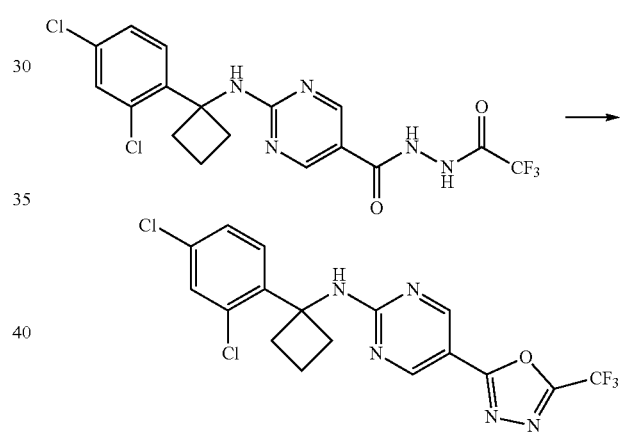

A mixture of 2-((1-(2,4-dichlorophenyl)cyclobutyl)amino)-N'-(2,2,2-trifluoroacetyl)pyrimidine-5-carbohydrazide (0.100 g, 0.223 mmol) and 1-methoxy-N-triethylammoniosulfonyl-methanimidate (Burgess reagent, 0.106 g, 0.446 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (20 mL) and water (10 mL), and filtered through a plastic frit to remove the solid residues and aqueous layer. The resulting organic layer was concentrated in vacuo to give the crude product which was purified and concentrated by column chromatography (SiO$_2$, 4 g cartridge; ethyl acetate/hexane=5% to 50%) to give N-(1-(2,4-dichlorophenyl)cyclobutyl)-5-(5-(trifluoromethyl)-1,3,4-oxadiazol-2-yl)pyrimidin-2-amine as white solid (0.075 g, 78.1%).

$^1$H NMR (400 MHz, CDCl$_3$) δ 8.86 (d, J=16.4 Hz, 2H), 7.31 (d, J=2.1 Hz, 1H), 7.24 (dd, J=8.4, 2.2 Hz, 1H), 6.70 (br, 1H), 2.82 (ddd, J=17.3, 9.8, 5.4 Hz, 2H), 2.77-2.60 (m, 2H), 2.31-2.22 (m, 1H), 1.92 (dtt, J=11.3, 9.1, 4.6 Hz, 1H); LRMS (ES) m/z 429.9 (M$^+$+1).

Example 64. Compound 1838: N-(1-(2,6-dichlorophenyl)cyclobutyl)-5-(5-(difluoromethyl)-1,3,4-oxadiazol-2-yl)pyrimidin-2-amine

[Step 1]
1-(2,6-dichlorophenyl)cyclobutane-1-carbonitrile

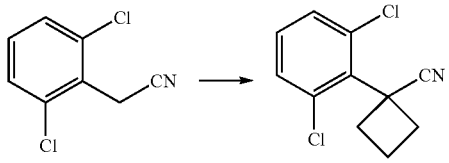 [SMILES: N#CCc1c(Cl)cccc1Cl ; N#CC1(c2c(Cl)cccc2Cl)CCC1]

To a stirred solution of 2-(2,6-dichlorophenyl)acetonitrile (5.581 g, 29.999 mmol) in N,N-dimethylformide (50 mL) was added at 0° C. sodium hydride (60.00%, 3.000 g, 74.997 mmol). The reaction mixture was stirred at the same temperature for 30 min, treated at the room temperature with 1,3-dibromopropane (3.059 mL, 29.999 mmol), and stirred for additional 21 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 50%) to give 1-(2,6-dichlorophenyl)cyclobutane-1-carbonitrile as White solid (2.174 g, 32.0%).

[Step 2]
1-(2,6-dichlorophenyl)cyclobutane-1-carboxamide

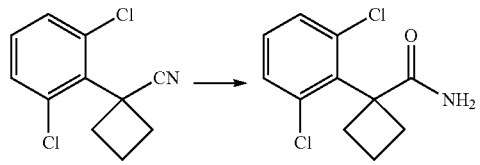 [SMILES: N#CC1(c2c(Cl)cccc2Cl)CCC1 ; NC(=O)C1(c2c(Cl)cccc2Cl)CCC1]

A solution of 1-(2,6-dichlorophenyl)cyclobutane-1-carbonitrile (2.174 g, 9.614 mmol), sodium hydroxide (3.00 M solution, 0.801 mL, 2.404 mmol), hydrogen peroxide (30.00%, 3.270 g, 28.843 mmol) and tetrabutylammonium bromide (0.031 g, 0.096 mmol) in methanol (50 mL) prepared at the room temperature was stirred at the same temperature for 20 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 80%) to give 1-(2,6-dichlorophenyl)cyclobutane-1-carboxamide as White solid (0.603 g, 25.7%).

[Step 3] 1-(2,6-dichlorophenyl)cyclobutan-1-amine hydrochloride

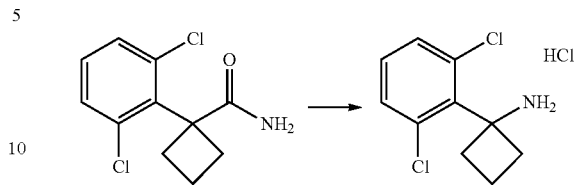

A solution of 1-(2,6-dichlorophenyl)cyclobutane-1-carboxamide (0.603 g, 2.470 mmol), Sodium hypochlorite (8.51%, 3.025 g, 3.458 mmol) and sodium hydroxide (3.00 M solution in water, 2.305 mL, 6.916 mmol) in 1-butanol (25 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was added hydrogen chloride (1.00 M in ethylacetate, 3.705 mL, 3.705 mmol) and diluted with ethyl acetate (20 mL) and stirred at the ambient temperature. The resulting precipitates were collected by filtration, washed by ethyl acetate, and dried to give 1-(2,6-dichlorophenyl)cyclobutan-1-amine hydrochloride as White solid (0.359 g, 57.5%).

[Step 4] ethyl 2-((1-(2,6-dichlorophenyl)cyclobutyl)amino)pyrimidine-5-carboxylate

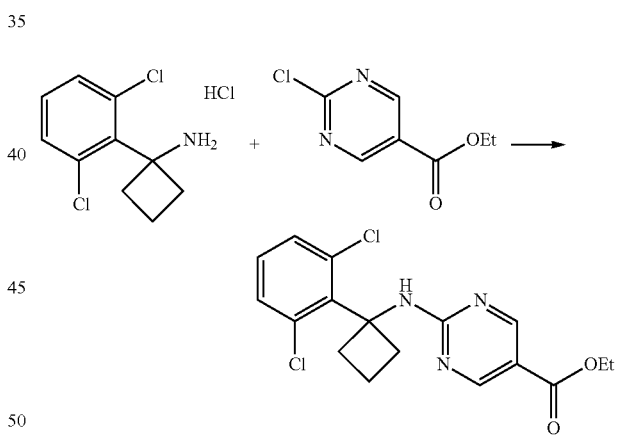

A solution of 1-(2,6-dichlorophenyl)cyclobutan-1-amine hydrochloride (0.359 g, 1.421 mmol), ethyl 2-chloropyrimidine-5-carboxylate (0.292 g, 1.564 mmol) and N-ethyl-N-isopropylpropan-2-amine (0.621 mL, 3.554 mmol) in 1,4-dioxane (5 mL) was stirred at 90° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 50%) to give ethyl 2-((1-(2,6-dichlorophenyl)cyclobutyl)amino)pyrimidine-5-carboxylate as White solid (0.506 g, 97.2%).

[Step 5] 2-((1-(2,6-dichlorophenyl)cyclobutyl)amino)pyrimidine-5-carbohydrazide

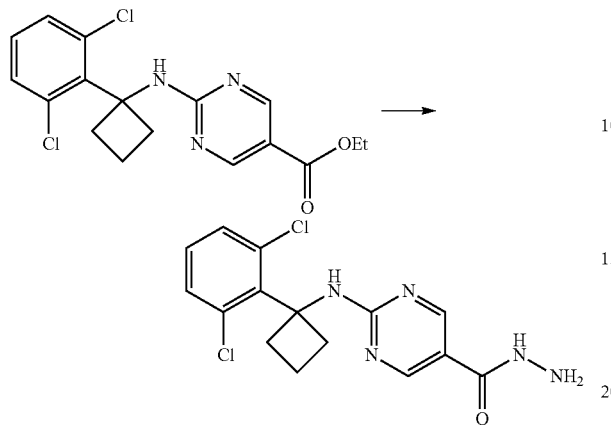

A solution of ethyl 2-((1-(2,6-dichlorophenyl)cyclobutyl)amino)pyrimidine-5-carboxylate (0.505 g, 1.379 mmol) and hydrazine (50.00% solution in water, 1.731 mL, 27.578 mmol) in ethanol (15 mL) was stirred at 120° C. for 18 hr, and cooled down to the room temperature to terminate reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The crude product was used without further purification (2-((1-(2,6-dichlorophenyl)cyclobutyl)amino)pyrimidine-5-carbohydrazide, 0.382 g, 78.7%, White solid).

[Step 6] 2-((1-(2,6-dichlorophenyl)cyclobutyl)amino)-N'-(2,2-difluoroacetyl)pyrimidine-5-carbohydrazide

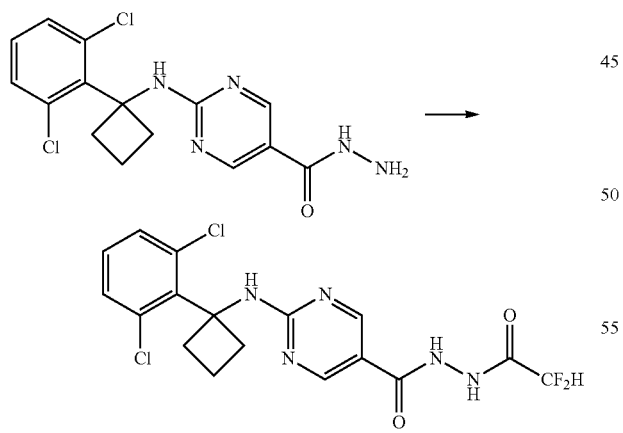

A solution of 2-((1-(2,6-dichlorophenyl)cyclobutyl)amino)pyrimidine-5-carbohydrazide (0.381 g, 1.082 mmol) in dichloromethane (8 mL) was mixed at the room temperature with triethylamine (0.226 mL, 1.623 mmol) and 2,2-difluoroacetic anhydride (0.134 mL, 1.082 mmol). The reaction mixture was stirred at the same temperature for 2 hr, and concentrated under the reduced pressure to remove the solvent. The concentrate was purified and concentrated by column chromatography (SiO$_2$, 12 g cartridge; dichloromethane/methanol=0% to 20%) to give 2-((1-(2,6-dichlorophenyl)cyclobutyl)amino)-N'-(2,2-difluoroacetyl)pyrimidine-5-carbohydrazide as White solid (0.038 g, 8.2%).

[Step 7] Compound 1838

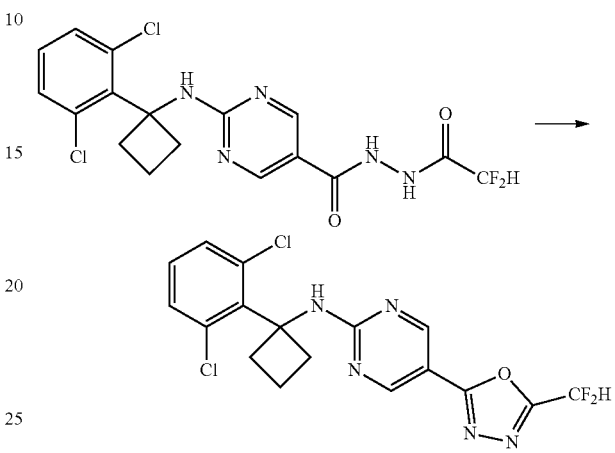

A mixture of 2-((1-(2,6-dichlorophenyl)cyclobutyl)amino)-N'-(2,2-difluoroacetyl)pyrimidine-5-carbohydrazide (0.038 g, 0.088 mmol) and Burgess reagent (0.042 g, 0.177 mmol) in tetrahydrofuran (5 mL) was heated at 150° C. for 30 min under the microwaves, and cooled down to the room temperature to terminate reaction. The reaction mixture was concentrated under the reduced pressure to remove the solvent. The obtained compound was added to dichloromethane (20 mL) and water (10 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=5% to 50%) to give N-(1-(2,6-dichlorophenyl)cyclobutyl)-5-(5-(difluoromethyl)-1,3,4-oxadiazol-2-yl)pyrimidin-2-amine as white solid (0.028 g, 76.9%).

$^1$H NMR (400 MHz, CDCl$_3$) δ 8.91 (s, 2H), 7.29-7.24 (m, 1H), 7.05 (dd, J=8.3, 7.7 Hz, 1H), 7.02 (s, 0.25H), 6.89 (s, 0.5H), 6.78 (br, 1H), 6.76 (s, 0.25H), 3.01 (qt, J=8.9, 3.2 Hz, 2H), 2.93-2.82 (m, 2H), 2.26 (ddt, J=18.7, 8.0, 5.4 Hz, 1H), 1.88 (ddd, J=17.8, 8.9, 5.3 Hz, 1H); LRMS (ES) m/z 411.9 (M$^+$+1).

Example 65: Compound 1913, 5-(5-(difluoromethyl)-1,3,4-oxadiazol-2-yl)-N-(1-(pyridin-3-yl)cyclobutyl)pyrimidin-2-amine

[Step 1] 1-(pyridin-3-yl)cyclobutane-1-carbonitrile

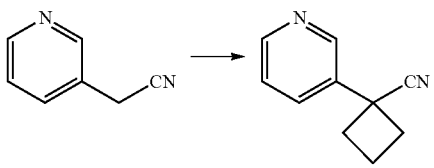 [SMILES: N#CCc1cccnc1 ; N#CC1(c2cccnc2)CCC1]

To a stirred solution of 2-(pyridin-3-yl)acetonitrile (8.000 g, 67.716 mmol) in N,N-dimethylformamide (50 mL) was added at 0° C. sodium hydride (60.00%, 6.771 g, 169.291 mmol). The reaction mixture was stirred at the same temperature for 1 hr, treated at the room temperature with 1,3-dibromopropane (13.671 g, 67.716 mmol), and stirred for additional 6 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give 1-(pyridin-3-yl)cyclobutane-1-carbonitrile as Colorless oil (6.200 g, 57.9%).

[Step 2] 1-(pyridin-3-yl)cyclobutane-1-carboxamide

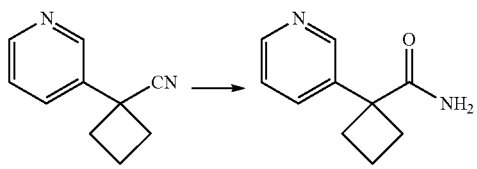 [SMILES: N#CC1(c2cccnc2)CCC1 ; NC(=O)C1(c2cccnc2)CCC1]

A solution of 1-(pyridin-3-yl)cyclobutane-1-carbonitrile (6.800 g, 42.984 mmol), tetra-n-butylammonium bromide (1.386 g, 4.298 mmol), sodium hydroxide (3.00 M solution in H₂O, 42.984 mL, 128.951 mmol) and hydrogen peroxide (30.00% solution, 10.083 mL, 128.951 mmol) in methanol (50 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The crude product was used without further purification (1-(pyridin-3-yl)cyclobutane-1-carboxamide, 5.900 g, 77.9%, Colorless oil).

[Step 3] 1-(pyridin-3-yl)cyclobutan-1-amine hydrochloride

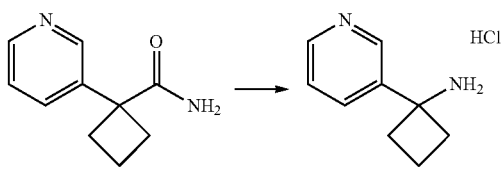 [SMILES: NC(=O)C1(c2cccnc2)CCC1 ; NC1(c2cccnc2)CCC1 ; Cl]

A solution of 1-(pyridin-3-yl)cyclobutane-1-carboxamide (5.900 g, 33.481 mmol), sodium hydroxide (4.017 g, 100.443 mmol) and sodium hypochlorite (3.738 g, 50.221 mmol) in t-butanol (30 mL) was stirred at the room temperature for 6 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was diluted with ethyl acetate (20 mL) and then hydrochloric acid (1.00 M solution in EA, 50.221 mL, 50.221 mmol) stirred at the ambient temperature. The resulting precipitates were collected by filtration, washed by hexane, and dried to give 1-(pyridin-3-yl)cyclobutan-1-amine hydrochloride as Yellow solid (3.500 g, 56.6%).

[Step 4] ethyl 2-((1-(pyridin-3-yl)cyclobutyl)amino) pyrimidine-5-carboxylate

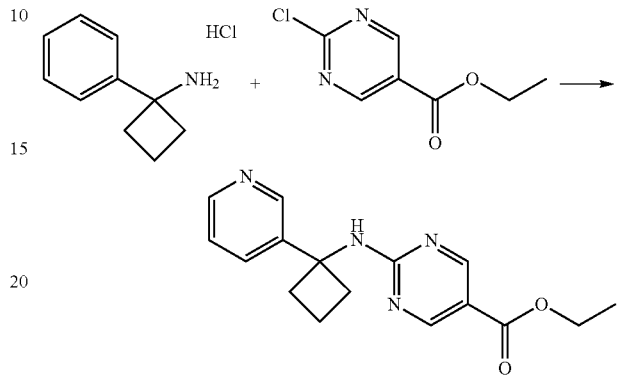

A solution of 1-(pyridin-3-yl)cyclobutan-1-amine hydrochloride (0.180 g, 0.975 mmol), ethyl 2-chloropyrimidine-5-carboxylate (0.200 g, 1.072 mmol) and N,N-diisopropylethylamine (0.424 mL, 2.437 mmol) in 1,4-dioxane (20 mL) was stirred at 90° C. for 8 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give ethyl 2-((1-(pyridin-3-yl)cyclobutyl)amino)pyrimidine-5-carboxylate as Colorless oil (0.260 g, 89.4%).

[Step 5] 2-((1-(pyridin-3-yl)cyclobutyl)amino)pyrimidine-5-carbohydrazide

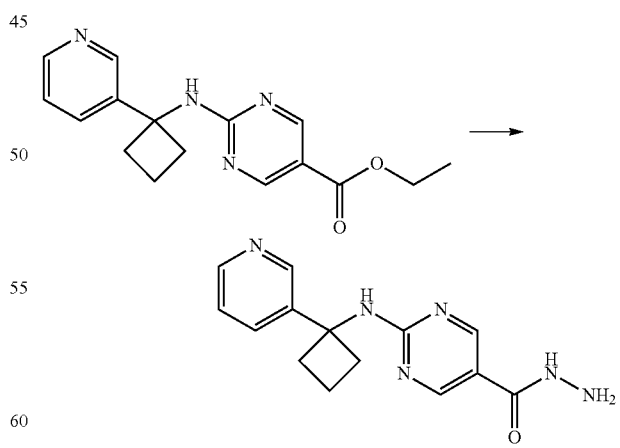

A mixture of ethyl 2-((1-(pyridin-3-yl)cyclobutyl)amino) pyrimidine-5-carboxylate (0.260 g, 0.871 mmol) and Hydrazine monohydrate (0.424 mL, 8.715 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The crude product was used without further purification (2-((1-(pyridin-3-yl)cyclobutyl)amino)pyrimidine-5-carbohydrazide, 0.250 g, 100.9%, White solid).

[Step 6] N'-(2,2-difluoroacetyl)-2-((1-(pyridin-3-yl)cyclobutyl)amino)pyrimidine-5-carbohydrazide

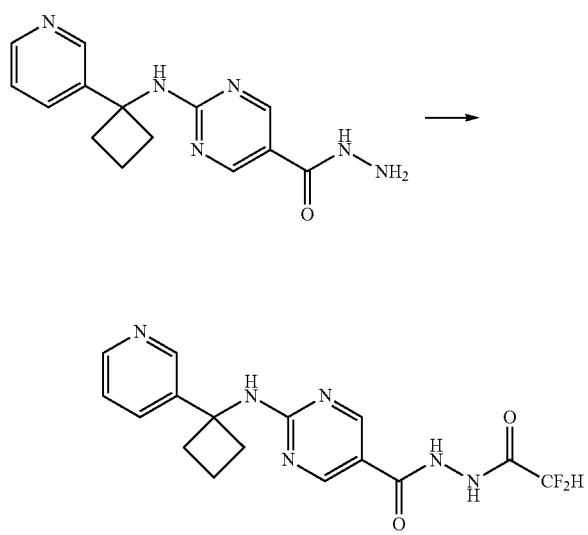 [SMILES: NNC(=O)c1cnc(NC2(c3cccnc3)CCC2)nc1 ; O=C(NNC(=O)C(F)F)c1cnc(NC2(c3cccnc3)CCC2)nc1]

A solution of 2-((1-(pyridin-3-yl)cyclobutyl)amino)pyrimidine-5-carbohydrazide (0.320 g, 1.125 mmol), 2,2-difluoroacetic anhydride (0.140 mL, 1.125 mmol) and triethylamine (0.235 mL, 1.688 mmol) in dichloromethane (10 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N'-(2,2-difluoroacetyl)-2-((1-(pyridin-3-yl)cyclobutyl)amino)pyrimidine-5-carbohydrazide as White solid (0.265 g, 65.0%).

[Step 7] Compound 1913

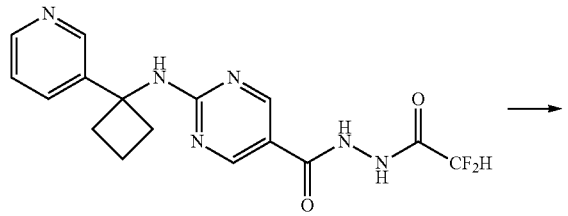

-continued

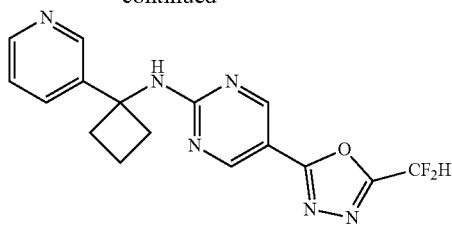

A mixture of N'-(2,2-difluoroacetyl)-2-((1-(pyridin-3-yl)cyclobutyl)amino)pyrimidine-5-carbohydrazide (0.256 g, 0.707 mmol) and 1-methoxy-N-triethylammoniosulfonyl-methanimidate (Burgess reagent, 0.337 g, 1.413 mmol) in tetrahydrofuran (5 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give 5-(5-(difluoromethyl)-1,3,4-oxadiazol-2-yl)-N-(1-(pyridin-3-yl)cyclobutyl)pyrimidin-2-amine as Colorless oil (0.140 g, 57.5%).

¹H NMR (400 MHz, CDCl₃) 8.90-8.82 (m, 2H), 8.82 (dd, J=2.4, 0.8 Hz, 1H), 8.49 (dd, J=4.8, 1.6 Hz, 1H), 7.89-7.86 (m, 1H), 7.31-7.28 (m, 1H), 7.03 (s, 0.25H), 6.90 (s, 0.5H), 6.77 (s, 0.25H), 6.95 (s, 1H), 2.82-2.75 (m, 2H), 2.66-2.58 (m, 2H), 2.27-2.19 (m, 1H), 2.07-2.01 (m, 1H).; LRMS (ES) m/z 345.3 (M⁺+1).

Example 66. Compound 1959: N-(1-(2-chloro-4-fluorophenyl)cyclobutyl)-5-(5-(difluoromethyl)-1,3,4-oxadiazol-2-yl)pyrimidin-2-amine

[Step 1] 2-(2-chloro-4-fluorophenyl)acetonitrile

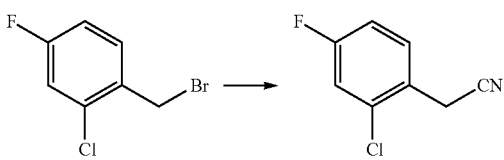 [SMILES: Fc1ccc(CBr)c(Cl)c1 ; N#CCc1ccc(F)cc1Cl]

A solution of 1-(bromomethyl)-2-chloro-4-fluorobenzene (10.000 g, 44.749 mmol), potassiumcyanide (8.739 g, 134.246 mmol) and tetrabutylammonium bromide (1.443 g, 4.475 mmol) in dichloromethane (60 mL)/water (60 mL) prepared at the room temperature was stirred at the same temperature for 4 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The concentrate was purified and concentrated by column chromatography (SiO₂, 120 g cartridge; ethyl acetate/hexane=0% to 30%) to give 2-(2-chloro-4-fluorophenyl)acetonitrile as white solid (6.830 g, 90.0%).

[Step 2] 1-(2-chloro-4-fluorophenyl)cyclobutane-1-carbonitrile

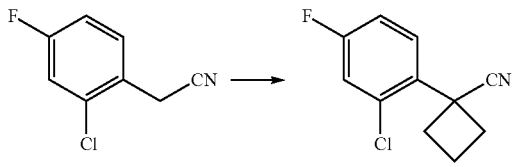 [SMILES: N#CCc1ccc(F)cc1Cl ; N#CC1(c2ccc(F)cc2Cl)CCC1]

A solution of 2-(2-chloro-4-fluorophenyl)acetonitrile (5.000 g, 29.485 mmol) and sodium hydride (60.00%, 2.948 g, 73.712 mmol) in N,N-dimethylformide (40 mL) was stirred at 0° C. for 30 min, and mixed with 1,3-dibromopropane (3.006 mL, 29.485 mmol). The reaction mixture was stirred at the room temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 30%) to give 1-(2-chloro-4-fluorophenyl)cyclobutane-1-carbonitrile as white solid (1.629 g, 26.4%).

[Step 3] 1-(2-chloro-4-fluorophenyl)cyclobutane-1-carboxamide

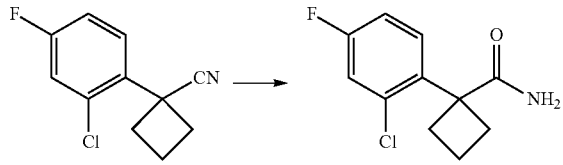 [SMILES: N#CC1(c2ccc(F)cc2Cl)CCC1 ; NC(=O)C1(c2ccc(F)cc2Cl)CCC1]

A solution of 1-(2-chloro-4-fluorophenyl)cyclobutane-1-carbonitrile (1.629 g, 7.770 mmol), sodium hydroxide (3.00 M solution in water, 1.295 mL, 3.885 mmol), hydrogen peroxide (30.00%, 2.643 g, 23.310 mmol) and tetrabutylammonium bromide (0.050 g, 0.155 mmol) in methanol (50 mL) was stirred at the room temperature for 20 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 80%) to give 1-(2-chloro-4-fluorophenyl)cyclobutane-1-carboxamide as white solid (0.982 g, 55.5%).

[Step 4] 1-(2-chloro-4-fluorophenyl)cyclobutan-1-amine hydrochloride

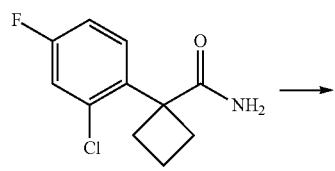

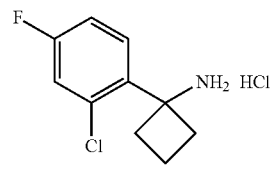

A solution of 1-(2-chloro-4-fluorophenyl)cyclobutane-1-carboxamide (0.982 g, 4.313 mmol), sodium hypochlorite (8.51%, 5.282 g, 6.039 mmol) and sodium hydroxide (3.00 M solution in water, 4.026 mL, 12.078 mmol) in 1-butanol (15 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with hydrochloric acid (1.0 M solution in ethyl acetate, 6.47 mL) and stirred at the ambient temperature for 30 min. The resulting precipitates were collected by filtration, washed by ethyl acetate, and dried to give 1-(2-chloro-4-fluorophenyl)cyclobutan-1-amine hydrochloride as white solid (0.620 g, 60.9%).

[Step 5] ethyl 2-((1-(2-chloro-4-fluorophenyl)cyclobutyl)amino)pyrimidine-5-carboxylate

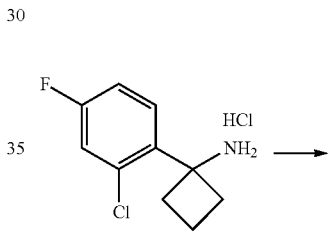

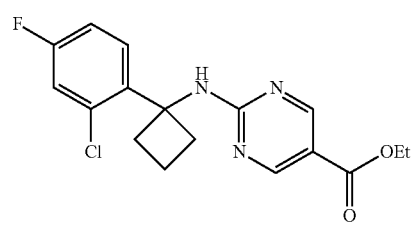

A solution of 1-(2-chloro-4-fluorophenyl)cyclobutan-1-amine hydrochloride (0.600 g, 2.541 mmol), ethyl 2-chloropyrimidine-5-carboxylate (0.522 g, 2.795 mmol) and N,N-diisopropylethylamine (1.107 mL, 6.353 mmol) in 1,4-dioxane (4 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 25 g cartridge; ethyl acetate/hexane=0% to 50%) to give ethyl 2-((1-(2-chloro-4-fluorophenyl)cyclobutyl)amino)pyrimidine-5-carboxylate as pale yellow solid (0.832 g, 93.6%).

[Step 6] 2-((1-(2-chloro-4-fluorophenyl)cyclobutyl)amino)pyrimidine-5-carbohydrazide

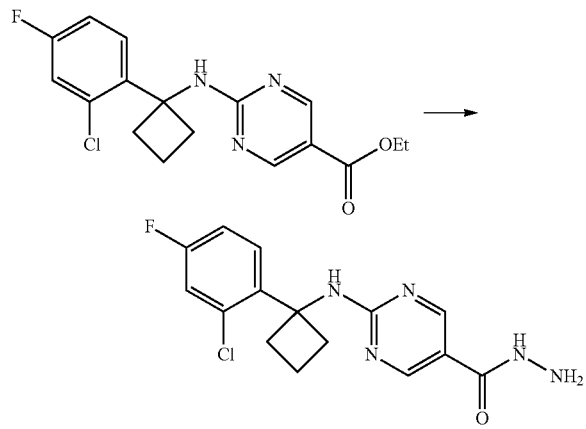

A solution of ethyl 2-((1-(2-chloro-4-fluorophenyl)cyclobutyl)amino)pyrimidine-5-carboxylate (0.600 g, 1.715 mmol) and hydrazine (50.00% solution in water, 2.153 mL, 34.306 mmol) in ethanol (5 mL) was stirred at 120° C. for 18 hr, and cooled down to the room temperature to terminate reaction. The reaction mixture was concentrated under the reduced pressure to remove the solvent. The crude product was used without further purification (2-((1-(2-chloro-4-fluorophenyl)cyclobutyl)amino)pyrimidine-5-carbohydrazide, 0.504 g, 87.5%, white solid).

[Step 7] 2-((1-(2-chloro-4-fluorophenyl)cyclobutyl)amino)pyrimidine-5-carbohydrazide

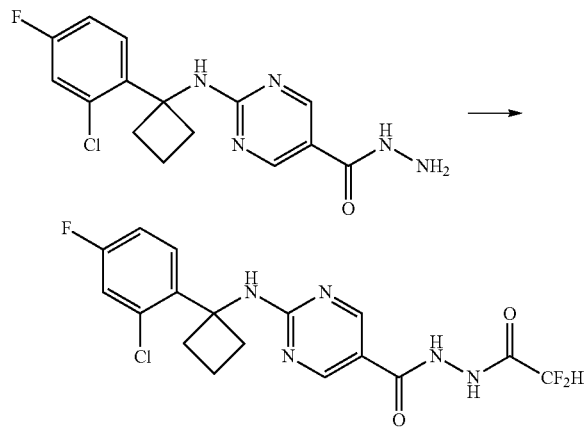

A solution of 2-((1-(2-chloro-4-fluorophenyl)cyclobutyl)amino)pyrimidine-5-carbohydrazide (0.250 g, 0.745 mmol), triethylamine (0.208 mL, 1.489 mmol) and 2,2-difluoroacetic anhydride (0.102 mL, 0.819 mmol) in dichloromethane (4 mL) was stirred at the room temperature for 1 hr, and concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 12 g cartridge; dichloromethane/methanol=0% to 20%) to give 2-((1-(2-chloro-4-fluorophenyl)cyclobutyl)amino)pyrimidine-5-carbohydrazide as white solid (0.210 g, 84.0%).

[Step 8] Compound 1959

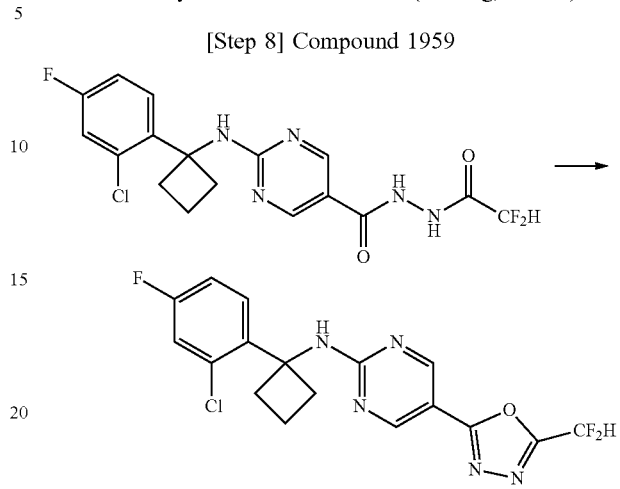

A mixture of 2-((1-(2-chloro-4-fluorophenyl)cyclobutyl)amino)-N'-(2,2-difluoroacetyl)pyrimidine-5-carbohydrazide (0.150 g, 0.363 mmol) and 1-methoxy-N-triethylammoniosulfonyl-methanimidate (Burgess reagent, 0.173 g, 0.725 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=0% to 50%) to give N-(1-(2-chloro-4-fluorophenyl)cyclobutyl)-5-(5-(difluoromethyl)-1,3,4-oxadiazol-2-yl)pyrimidin-2-amine as white solid (0.032 g, 22.3%).

$^1$H NMR (400 MHz, CDCl$_3$) δ 8.88 (d, J=6.1 Hz, 2H), 7.47 (dd, J=9.8, 3.0 Hz, 1H), 7.24 (dd, J=8.7, 5.2 Hz, 1H), 7.02 (s, 0.25H), 6.93-6.86 (m, 1H), 6.89 (s, 0.5H), 6.76 (s, 0.25H), 6.64 (br, 1H), 2.82 (dt, J=19.5, 8.7 Hz, 3H), 2.76-2.68 (m, 3H), 2.34-2.17 (m, 2H), 1.99-1.86 (m, 2H).; LRMS (ES) m/z 396.0 (M$^+$+1).

Example 67. Compound 1960: N-(1-(2-chloro-4-fluorophenyl)cyclobutyl)-5-(5-(trifluoromethyl)-1,3,4-oxadiazol-2-yl)pyrimidin-2-amine

[Step 1] 2-((1-(2-chloro-4-fluorophenyl)cyclobutyl)amino)-N'-(2,2,2-trifluoroacetyl)pyrimidine-5-carbohydrazide

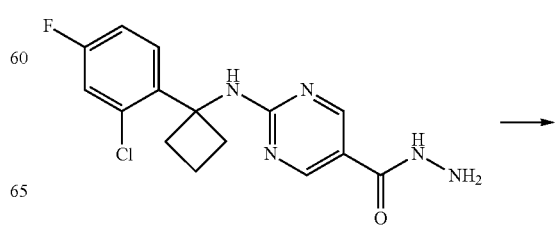

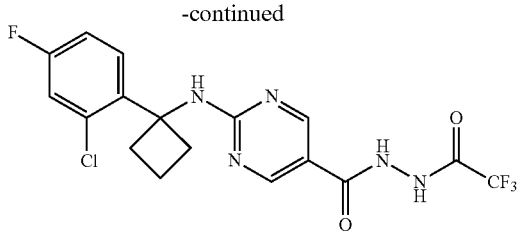

A solution of 2-((1-(2-chloro-4-fluorophenyl)cyclobutyl)amino)pyrimidine-5-carbohydrazide (0.250 g, 0.745 mmol), triethylamine (0.208 mL, 1.489 mmol) and trifluoroacetic anhydride (0.116 mL, 0.819 mmol) in dichloromethane (4 mL) was stirred at the room temperature for 1 hr, and concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 12 g cartridge; dichloromethane/methanol=0% to 15%) to give 2-((1-(2-chloro-4-fluorophenyl)cyclobutyl)amino)-N'-(2,2,2-trifluoroacetyl)pyrimidine-5-carbohydrazide as white solid (0.208 g, 64.7%).

[Step 2] Compound 1960

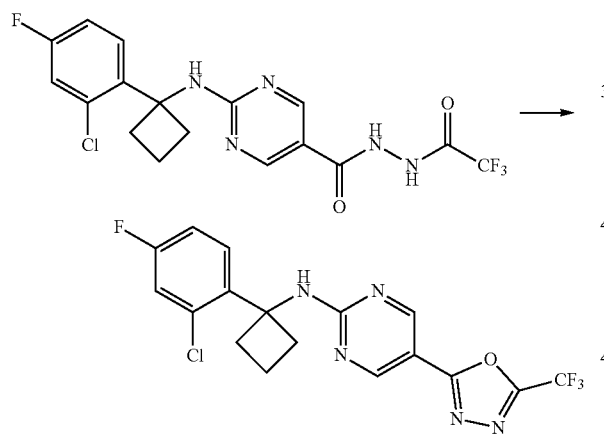

A mixture of 2-((1-(2-chloro-4-fluorophenyl)cyclobutyl)amino)-N'-(2,2,2-trifluoroacetyl)pyrimidine-5-carbohydrazide (0.150 g, 0.347 mmol) and 1-methoxy-N-triethylammoniosulfonyl-methanimidate (Burgess reagent, 0.166 g, 0.695 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The residue was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=0% to 50%) to give N-(1-(2-chloro-4-fluorophenyl)cyclobutyl)-5-(5-(trifluoromethyl)-1,3,4-oxadiazol-2-yl)pyrimidin-2-amine as white solid (0.094 g, 65.4%).

$^1$H NMR (400 MHz, CDCl$_3$) δ 8.88 (d, J=10.2 Hz, 2H), 7.46 (dt, J=10.4, 5.2 Hz, 1H), 7.24 (dd, J=8.7, 5.2 Hz, 1H), 6.90 (ddd, J=8.7, 7.6, 3.1 Hz, 1H), 6.68 (br, 1H), 2.83 (ddd, J=17.1, 9.7, 5.3 Hz, 2H), 2.76-2.67 (m, 2H), 2.31-2.17 (m, 1H), 1.99-1.87 (m, 1H).; LRMS (ES) m/z 413.8 (M$^+$+1).

Example 68. Compound 1961: N-(1-(2-chloro-5-fluorophenyl)cyclobutyl)-5-(5-(difluoromethyl)-1,3,4-oxadiazol-2-yl)pyrimidin-2-amine

[Step 1] 2-(2-chloro-5-fluorophenyl)acetonitrile

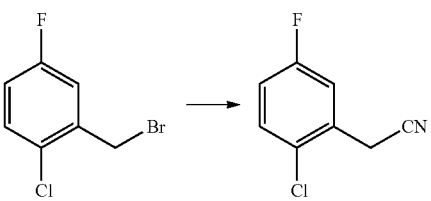 [SMILES: Fc1ccc(Cl)c(CBr)c1 ; N#CCc1cc(F)ccc1Cl]

A solution of 2-(bromomethyl)-1-chloro-4-fluorobenzene (10.000 g, 44.749 mmol), potassiumcyanide (8.739 g, 134.246 mmol) and tetrabutylammonium bromide (1.443 g, 4.475 mmol) in dichloromethane (60 mL)/water (60 mL) prepared at the room temperature was stirred at the same temperature for 4 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The concentrate was purified and concentrated by column chromatography d (SiO$_2$, 120 g cartridge; ethyl acetate/hexane=0% to 20%) to give 2-(2-chloro-5-fluorophenyl)acetonitrile as white solid (7.120 g, 93.8%).

[Step 2] 1-(2-chloro-5-fluorophenyl)cyclobutane-1-carbonitrile

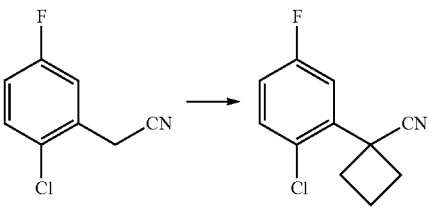 [SMILES: N#CCc1cc(F)ccc1Cl ; N#CC1(c2cc(F)ccc2Cl)CCC1]

A solution of 2-(2-chloro-5-fluorophenyl)acetonitrile (5.000 g, 29.485 mmol) and sodium hydride (60.00%, 2.948 g, 73.712 mmol) in N,N-dimethylformide (40 mL) was stirred at 0° C. for 30 min, and mixed with 1,3-dibromopropane (3.006 mL, 29.485 mmol). The reaction mixture was stirred at the room temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 30%) to give 1-(2-chloro-5-fluorophenyl)cyclobutane-1-carbonitrile as white solid (2.271 g, 36.7%).

[Step 3] 1-(2-chloro-5-fluorophenyl)cyclobutane-1-carboxamide

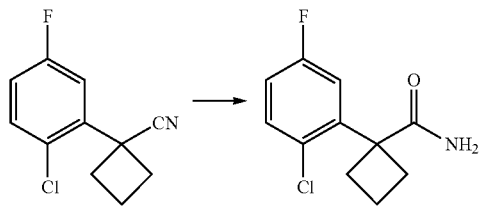 [SMILES: N#CC1(c2cc(F)ccc2Cl)CCC1 ; NC(=O)C1(c2cc(F)ccc2Cl)CCC1]

A solution of 1-(2-chloro-5-fluorophenyl)cyclobutane-1-carbonitrile (2.271 g, 10.832 mmol), sodium hydroxide (3.00 M solution in water, 1.805 mL, 5.416 mmol), hydrogen peroxide (30.00%, 3.685 g, 32.497 mmol) and tetrabutylammonium bromide (0.070 g, 0.217 mmol) in methanol (50 mL) was stirred at the room temperature for 20 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 80%) to give 1-(2-chloro-5-fluorophenyl)cyclobutane-1-carboxamide as white solid (1.444 g, 58.6%).

[Step 4] 1-(2-chloro-5-fluorophenyl)cyclobutan-1-amine hydrochloride

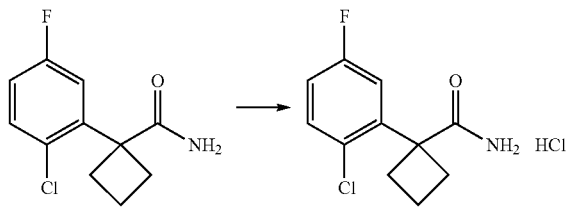 [SMILES: NC(=O)C1(c2cc(F)ccc2Cl)CCC1 ; NC(=O)C1(c2cc(F)ccc2Cl)CCC1 ; Cl]

A solution of 1-(2-chloro-5-fluorophenyl)cyclobutane-1-carboxamide (1.444 g, 6.343 mmol), sodium hypochlorite (8.51%, 7.768 g, 8.880 mmol) and sodium hydroxide (3.00 M solution in water, 5.920 mL, 17.760 mmol) in 1-butanol (15 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was diluted with hydrochloric acid (1.0 M solution in ethyl acetate, 9.514 mL) and stirred at the ambient temperature. The resulting precipitates were collected by filtration, washed by ethyl acetate, and dried to give 1-(2-chloro-5-fluorophenyl)cyclobutan-1-amine hydrochloride as white solid (0.573 g, 38.3%).

[Step 5] ethyl 2-((1-(2-chloro-5-fluorophenyl)cyclobutyl)amino)pyrimidine-5-carboxylate

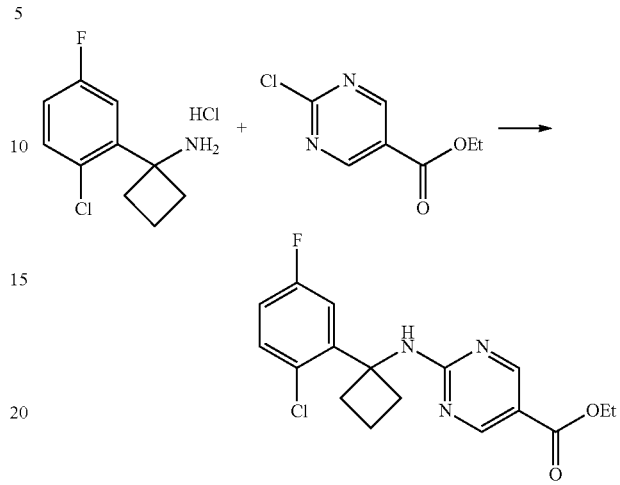

A solution of 1-(2-chloro-5-fluorophenyl)cyclobutan-1-amine hydrochloride (0.600 g, 2.541 mmol), ethyl 2-chloropyrimidine-5-carboxylate (0.522 g, 2.795 mmol) and N,N-diisopropylethylamine (1.107 mL, 6.353 mmol) in 1,4-dioxane (4 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 25 g cartridge; ethyl acetate/hexane=0% to 50%) to give ethyl 2-((1-(2-chloro-5-fluorophenyl)cyclobutyl)amino)pyrimidine-5-carboxylate as (0.747 g, 84.0%).

[Step 6] 2-((1-(2-chloro-5-fluorophenyl)cyclobutyl)amino)pyrimidine-5-carbohydrazide

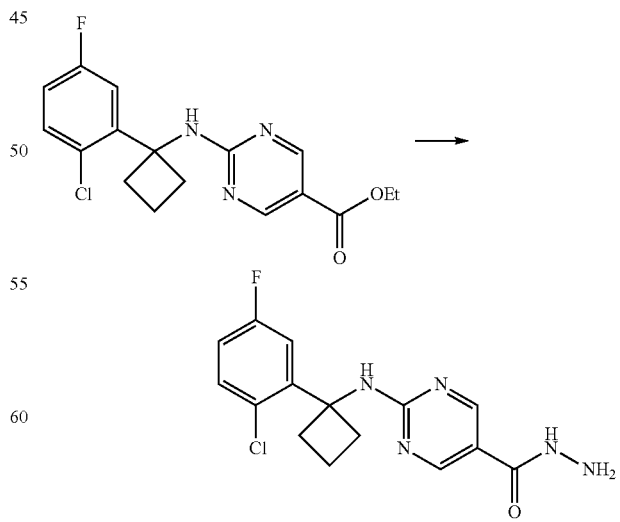

A solution of ethyl 2-((1-(2-chloro-5-fluorophenyl)cyclobutyl)amino)pyrimidine-5-carboxylate (0.600 g, 1.715 mmol) and hydrazine (50.00% solution in water, 2.153 mL, 34.306 mmol) in ethanol (5 mL) was stirred at 120° C. for 18 hr, and cooled down to the room temperature to terminate reaction. The reaction mixture was concentrated under the reduced pressure to remove the solvent. The crude product was used without further purification (2-((1-(2-chloro-5-fluorophenyl)cyclobutyl)amino)pyrimidine-5-carbohydrazide, 0.530 g, 92.0%, white solid).

[Step 7] 2-((1-(2-chloro-5-fluorophenyl)cyclobutyl)amino)-N'-(2,2-difluoroacetyl)pyrimidine-5-carbohydrazide

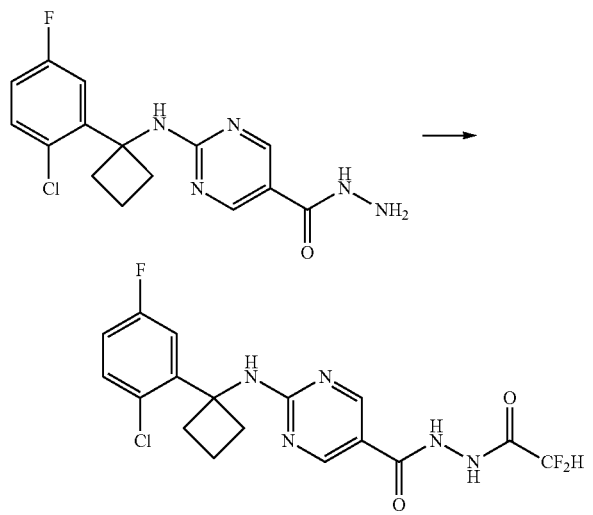

A solution of 2-((1-(2-chloro-5-fluorophenyl)cyclobutyl)amino)pyrimidine-5-carbohydrazide (0.250 g, 0.745 mmol), triethylamine (0.208 mL, 1.489 mmol) and 2,2-difluoroacetic anhydride (0.102 mL, 0.819 mmol) in dichloromethane (4 mL) prepared at the room temperature was stirred at the same temperature for 1 hr. The reaction mixture was concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 12 g cartridge; dichloromethane/methanol=0% to 20%) to give 2-((1-(2-chloro-5-fluorophenyl)cyclobutyl)amino)-N'-(2,2-difluoroacetyl)pyrimidine-5-carbohydrazide as white solid (0.195 g, 63.3%).

[Step 8] Compound 1961

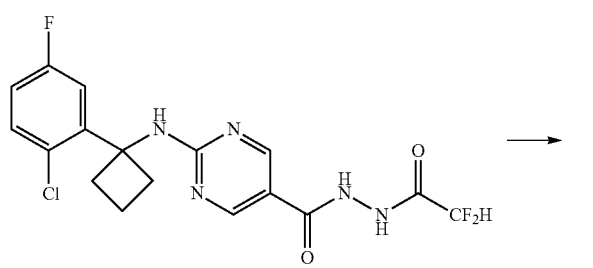

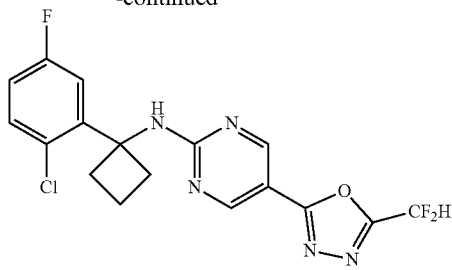

A mixture of 2-((1-(2-chloro-5-fluorophenyl)cyclobutyl)amino)-N'-(2,2-difluoroacetyl)pyrimidine-5-carbohydrazide (0.150 g, 0.363 mmol) and 1-methoxy-N-triethylammoniosulfonyl-methanimidate (Burgess reagent, 0.173 g, 0.725 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=0% to 50%) to give N-(1-(2-chloro-5-fluorophenyl)cyclobutyl)-5-(5-(difluoromethyl)-1,3,4-oxadiazol-2-yl)pyrimidin-2-amine as white solid (0.064 g, 44.6%).

$^1$H NMR (400 MHz, CDCl$_3$) δ 8.86 (d, J=14.4 Hz, 2H), 7.72 (dd, J=8.7, 6.2 Hz, 1H), 7.04 (dd, J=8.4, 2.6 Hz, 1H), 7.02 (s, 0.25H), 6.98 (ddd, J=8.7, 7.9, 2.7 Hz, 1H), 6.89 (s, 0.5H), 6.76 (s, 0.25H), 6.63 (br, 1H), 2.82 (ddd, J=16.4, 9.3, 5.1 Hz, 2H), 2.77-2.66 (m, 2H), 2.26 (dp, J=11.1, 8.5 Hz, 1H), 1.97-1.87 (m, 1H); LRMS (ES) m/z 396.0 (M$^+$+1).

Example 69. Compound 1962: N-(1-(2-chloro-5-fluorophenyl)cyclobutyl)-5-(5-(trifluoromethyl)-1,3,4-oxadiazol-2-yl)pyrimidin-2-amine

[Step 1] 2-((1-(2-chloro-5-fluorophenyl)cyclobutyl)amino)-N'-(2,2,2-trifluoroacetyl)pyrimidine-5-carbohydrazide

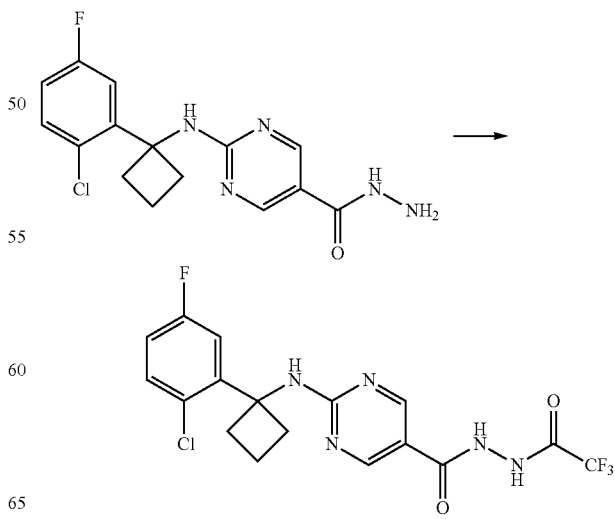

A solution of 2-((1-(2-chloro-5-fluorophenyl)cyclobutyl)amino)pyrimidine-5-carbohydrazide (0.250 g, 0.745 mmol), triethylamine (0.208 mL, 1.489 mmol) and trifluoroacetic anhydride (0.116 mL, 0.819 mmol) in dichloromethane (4 mL) prepared at the room temperature was stirred at the same temperature for 1 hr, and concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 12 g cartridge; dichloromethane/methanol=0% to 20%) to give 2-((1-(2-chloro-5-fluorophenyl)cyclobutyl)amino)-N'-(2,2,2-trifluoroacetyl)pyrimidine-5-carbohydrazide as white solid (0.258 g, 80.3%).

[Step 2] Compound 1962

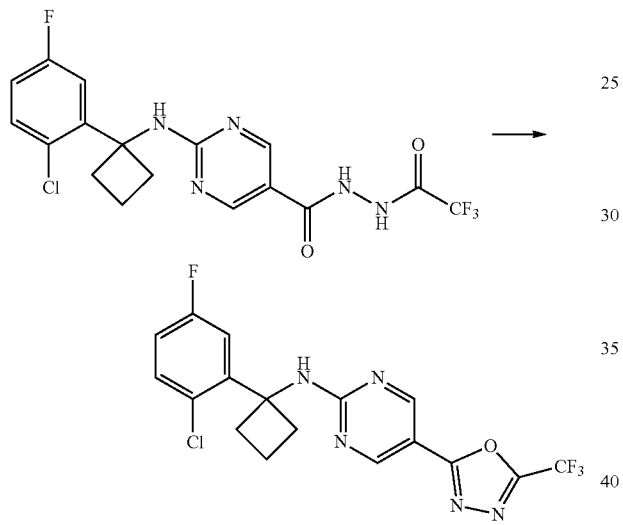

A mixture of 2-((1-(2-chloro-5-fluorophenyl)cyclobutyl)amino)-N'-(2,2,2-trifluoroacetyl)pyrimidine-5-carbohydrazide (0.250 g, 0.579 mmol) and 1-methoxy-N-triethylammoniosulfonyl-methanimidate (Burgess reagent, 0.276 g, 1.158 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The obtained compound was added to dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=0% to 50%) to give 2-((1-(2-chloro-5-fluorophenyl)cyclobutyl)amino)-N'-(2,2,2-trifluoroacetyl)pyrimidine-5-carbohydrazide as white solid (0.196 g, 78.4%).

$^1$H NMR (400 MHz, CDCl$_3$) δ 8.86 (d, J=14.9 Hz, 2H), 7.72 (dd, J=8.7, 6.1 Hz, 1H), 7.05 (dd, J=8.4, 2.6 Hz, 1H), 6.98 (ddd, J=8.7, 7.9, 2.7 Hz, 1H), 6.66 (br, 1H), 2.83 (ddd, J=17.3, 9.8, 5.5 Hz, 2H), 2.76-2.67 (m, 2H), 2.26 (dp, J=11.6, 8.7 Hz, 1H), 1.93 (dtt, J=11.2, 9.0, 4.5 Hz, 1H).; LRMS (ES) m/z 413.8 (M$^+$+1).

Example 70. Compound 1963: N-(1-(5-chloro-2-fluorophenyl)cyclobutyl)-5-(5-(difluoromethyl)-1,3,4-oxadiazol-2-yl)pyrimidin-2-amine

[Step 1] 2-(5-chloro-2-fluorophenyl)acetonitrile

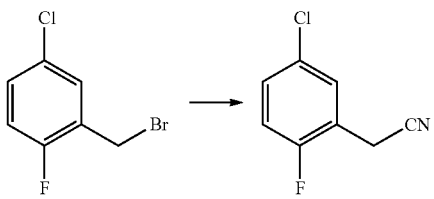 [SMILES: Fc1ccc(Cl)cc1CBr ; N#CCc1cc(Cl)ccc1F]

A solution of 2-(bromomethyl)-4-chloro-1-fluorobenzene (5.000 g, 22.371 mmol), potassiumcyanide (4.369 g, 67.114 mmol) and tetrabutylammonium bromide (0.721 g, 2.237 mmol) in dichloromethane (30 mL)/water (30 mL) prepared at the room temperature was stirred at the same temperature for 4 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The concentrate was purified and concentrated by column chromatography (SiO$_2$, 80 g cartridge; ethyl acetate/hexane=0% to 20%) to give 2-(5-chloro-2-fluorophenyl)acetonitrile as colorless liquid (3.440 g, 90.7%).

[Step 2] 1-(5-chloro-2-fluorophenyl)cyclobutane-1-carbonitrile

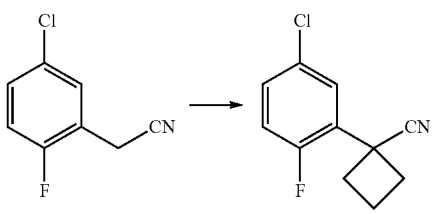 [SMILES: N#CCc1cc(Cl)ccc1F ; N#CC1(c2cc(Cl)ccc2F)CCC1]

A solution of 2-(5-chloro-2-fluorophenyl)acetonitrile (5.000 g, 29.485 mmol) and sodium hydride (60.00%, 2.948 g, 73.712 mmol) in N,N-dimethylformide (40 mL) was stirred at 0° C. for 30 min, and mixed with 1,3-dibromopropane (3.006 mL, 29.485 mmol). The reaction mixture was stirred at the room temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 30%) to give 1-(5-chloro-2-fluorophenyl)cyclobutane-1-carbonitrile as white solid (3.543 g, 57.3%).

[Step 3] 1-(5-chloro-2-fluorophenyl)cyclobutane-1-carboxamide

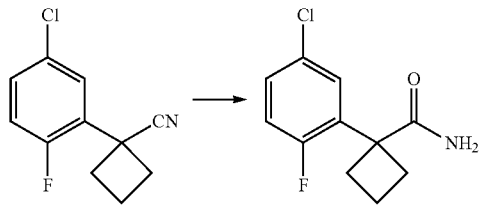 [SMILES: N#CC1(c2cc(Cl)ccc2F)CCC1 ; NC(=O)C1(c2cc(Cl)ccc2F)CCC1]

A solution of 1-(5-chloro-2-fluorophenyl)cyclobutane-1-carbonitrile (3.543 g, 16.900 mmol), sodium hydroxide (3.00 M solution in water, 2.817 mL, 8.450 mmol), hydrogen peroxide (30.00%, 5.748 g, 50.699 mmol) and tetrabutylammonium bromide (0.109 g, 0.338 mmol) in methanol (50 mL) prepared at the room temperature was stirred at the same temperature for 20 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 80%) to give 1-(5-chloro-2-fluorophenyl)cyclobutane-1-carboxamide as white solid (2.480 g, 64.5%).

[Step 4] 1-(5-chloro-2-fluorophenyl)cyclobutan-1-amine hydrochloride

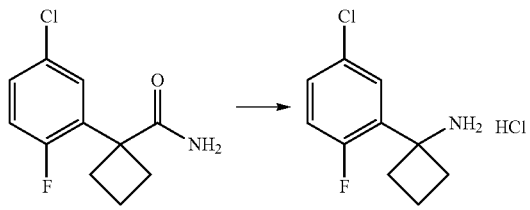 [SMILES: NC(=O)C1(c2cc(Cl)ccc2F)CCC1 ; NC1(c2cc(Cl)ccc2F)CCC1 ; Cl]

A solution of 1-(5-chloro-2-fluorophenyl)cyclobutane-1-carboxamide (2.480 g, 10.893 mmol), sodium hypochlorite (8.51%, 13.340 g, 15.251 mmol) and sodium hydroxide (3.00 M solution in water, 10.167 mL, 30.502 mmol) in 1-butanol (20 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was diluted with hydrochloric acid (1.0 M solution in ethyl acetate, 16.34 mL) and stirred at the ambient temperature for 30 min. The resulting precipitates were collected by filtration, washed by ethyl acetate, and dried to give 1-(5-chloro-2-fluorophenyl)cyclobutan-1-amine hydrochloride as white solid (1.336 g, 51.9%).

[Step 5] ethyl 2-((1-(5-chloro-2-fluorophenyl)cyclobutyl)amino)pyrimidine-5-carboxylate

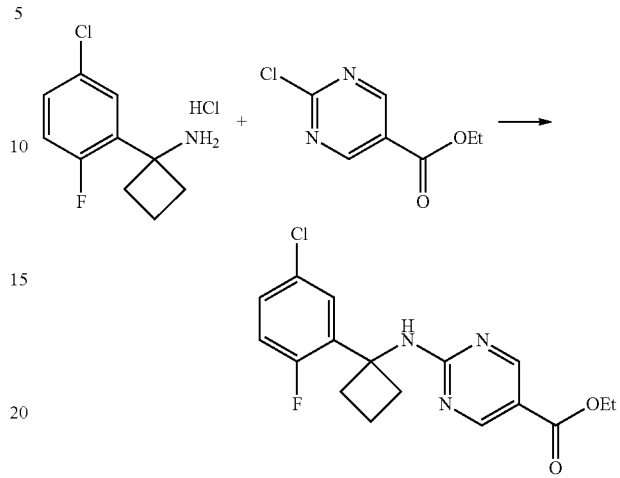

A solution of 1-(5-chloro-2-fluorophenyl)cyclobutan-1-amine hydrochloride (0.600 g, 2.541 mmol), ethyl 2-chloropyrimidine-5-carboxylate (0.522 g, 2.795 mmol) and N,N-diisopropylethylamine (1.107 mL, 6.353 mmol) in 1,4-dioxane (4 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 25 g cartridge; ethyl acetate/hexane=0% to 60%) to give ethyl 2-((1-(5-chloro-2-fluorophenyl)cyclobutyl)amino)pyrimidine-5-carboxylate as white solid (0.742 g, 83.5%).

[Step 6] 2-((1-(5-chloro-2-fluorophenyl)cyclobutyl)amino)pyrimidine-5-carbohydrazide

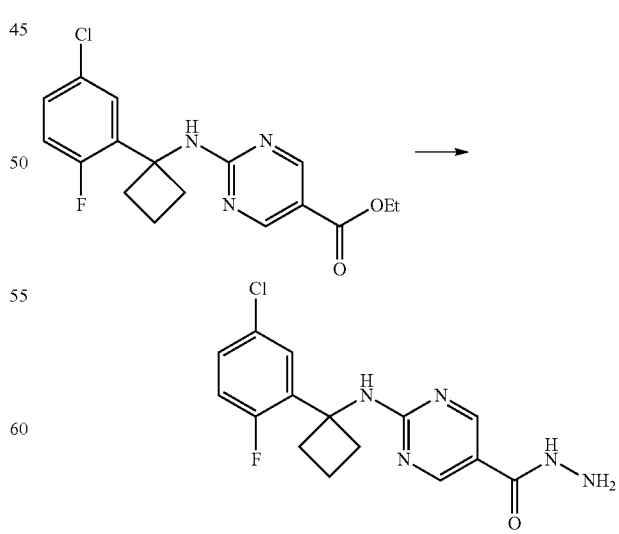

A solution of ethyl 2-((1-(5-chloro-2-fluorophenyl)cyclobutyl)amino)pyrimidine-5-carboxylate (0.600 g, 1.715 mmol) and hydrazine (50.00% solution in water, 2.153 mL, 34.306 mmol) in ethanol (5 mL) was stirred at 120° C. for 18 hr, and cooled down to the room temperature to terminate reaction. The reaction mixture was concentrated under the reduced pressure to remove the solvent. The crude product was used without further purification (2-((1-(5-chloro-2-fluorophenyl)cyclobutyl)amino)pyrimidine-5-carbohydrazide, 0.521 g, 90.5%, white solid).

[Step 7] 2-((1-(5-chloro-2-fluorophenyl)cyclobutyl) amino)-N'-(2,2-difluoroacetyl)pyrimidine-5-carbohydrazide

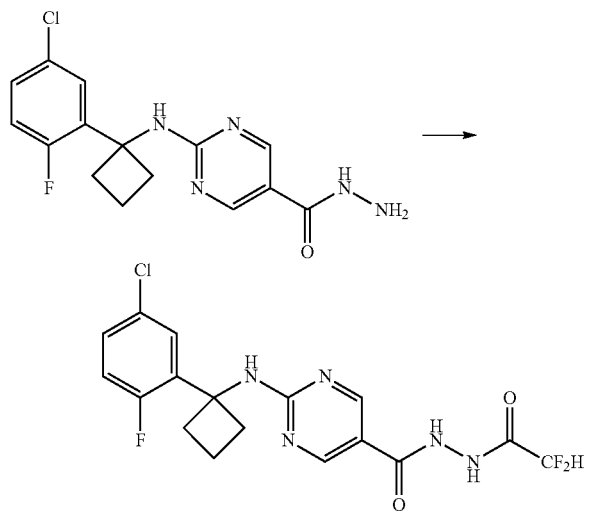

A solution of 2-((1-(5-chloro-2-fluorophenyl)cyclobutyl) amino)pyrimidine-5-carbohydrazide (0.250 g, 0.745 mmol), triethylamine (0.208 mL, 1.489 mmol) and 2,2-difluoroacetic anhydride (0.102 mL, 0.819 mmol) in dichloromethane (4 mL) prepared at the room temperature was stirred at the same temperature for 1 hr. The reaction mixture was concentrated under the reduced pressure to remove the solvent. The obtained compound was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 12 g cartridge; dichloromethane/methanol=0% to 20%) to give 2-((1-(5-chloro-2-fluorophenyl)cyclobutyl)amino)-N'-(2,2-difluoroacetyl)pyrimidine-5-carbohydrazide as white solid (0.225 g, 73.0%).

[Step 8] Compound 1963

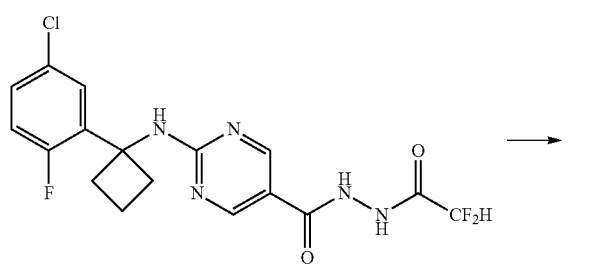

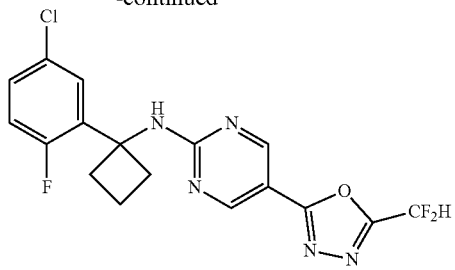

A mixture of 2-((1-(5-chloro-2-fluorophenyl)cyclobutyl) amino)-N'-(2,2-difluoroacetyl)pyrimidine-5-carbohydrazide (0.150 g, 0.363 mmol) and 1-methoxy-N-triethylammoniosulfonyl-methanimidate (Burgess reagent, 0.173 g, 0.725 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The residue was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=0% to 50%) to give N-(1-(5-chloro-2-fluorophenyl)cyclobutyl)-5-(5-(difluoromethyl)-1,3,4-oxadiazol-2-yl)pyrimidin-2-amine as white solid (0.093 g, 64.8%).

$^1$H NMR (400 MHz, CDCl$_3$) δ 8.90 (s, 2H), 7.62 (dd, J=6.9, 2.7 Hz, 1H), 7.18 (ddd, J=8.7, 4.3, 2.7 Hz, 1H), 7.03 (s, 0.25H), 6.94 (dd, J=10.6, 8.7 Hz, 1H), 6.90 (s, 0.5H), 6.77 (s, 0.25H), 6.44 (br, 1H), 2.86-2.70 (m, 2H), 2.71-2.53 (m, 2H), 2.22 (tt, J=8.8, 6.2 Hz, 1H), 2.07-1.80 (m, 1H); LRMS (ES) m/z 396.0 (M$^+$+1).

Example 71. Compound 1964: N-(1-(5-chloro-2-fluorophenyl)cyclobutyl)-5-(5-(trifluoromethyl)-1,3,4-oxadiazol-2-yl)pyrimidin-2-amine

[Step 1] 2-((1-(5-chloro-2-fluorophenyl)cyclobutyl) amino)-N'-(2,2,2-trifluoroacetyl)pyrimidine-5-carbohydrazide

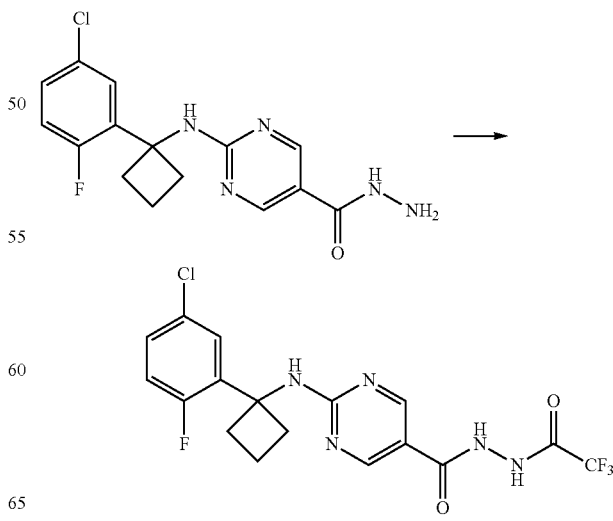

A solution of 2-((1-(5-chloro-2-fluorophenyl)cyclobutyl)amino)pyrimidine-5-carbohydrazide (0.250 g, 0.745 mmol), triethylamine (0.208 mL, 1.489 mmol) and trifluoroacetic anhydride (0.116 mL, 0.819 mmol) in dichloromethane (4 mL) was stirred at the room temperature for 1 hr, and concentrated under the reduced pressure. The concentrate was partitioned between dichloromethane (5 mL) and water (5 mL), and filtered through a plastic frit. The resulting organic layer was concentrated in vacuo to give the crude product which was subsequently purified and concentrated by column chromatography (SiO₂, 12 g cartridge; dichloromethane/methanol=0% to 20%) to give 2-((1-(5-chloro-2-fluorophenyl)cyclobutyl)amino)-N'-(2,2,2-trifluoroacetyl)pyrimidine-5-carbohydrazide as white solid (0.265 g, 82.4%).

[Step 2] Compound 1964

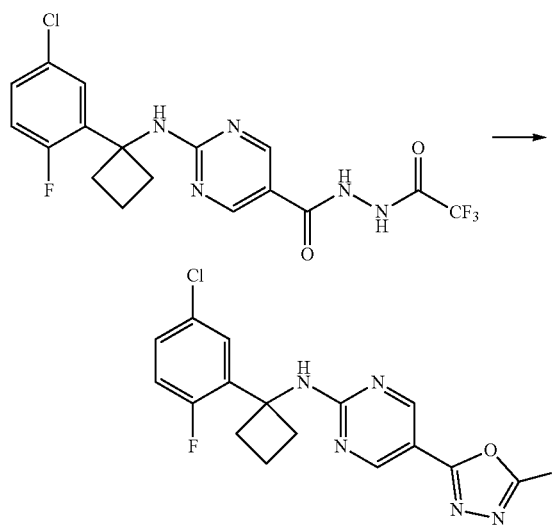

A mixture of 2-((1-(5-chloro-2-fluorophenyl)cyclobutyl)amino)-N'-(2,2,2-trifluoroacetyl)pyrimidine-5-carbohydrazide (0.150 g, 0.347 mmol) and 1-methoxy-N-triethylammoniosulfonyl-methanimidate (Burgess reagent, 0.166 g, 0.695 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The concentrate was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO₂, 4 g cartridge; ethyl acetate/hexane=0% to 50%) to give N-(1-(5-chloro-2-fluorophenyl)cyclobutyl)-5-(5-(trifluoromethyl)-1,3,4-oxadiazol-2-yl)pyrimidin-2-amine as white solid (0.063 g, 43.8%).

¹H NMR (400 MHz, CDCl₃) δ 8.90 (s, 2H), 7.61 (dd, J=6.9, 2.7 Hz, 1H), 7.19 (ddd, J=8.7, 4.3, 2.7 Hz, 1H), 6.94 (dd, J=10.6, 8.7 Hz, 1H), 6.48 (br, 1H), 2.85-2.72 (m, 2H), 2.68-2.57 (m, 2H), 2.30-2.14 (m, 1H), 2.04-1.91 (m, 1H); LRMS (ES) m/z 413.8 (M⁺+1).

Example 72. Compound 1965: N-(1-(3-chloro-2-fluorophenyl)cyclobutyl)-5-(5-(difluoromethyl)-1,3,4-oxadiazol-2-yl)pyrimidin-2-amine

[Step 1] 2-(3-chloro-2-fluorophenyl)acetonitrile

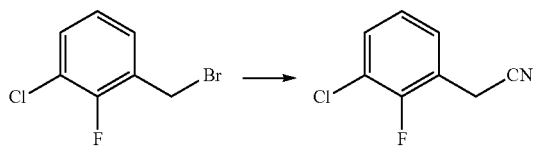 [SMILES: Fc1c(Cl)cccc1CBr ; N#CCc1cccc(Cl)c1F]

A solution of 1-(bromomethyl)-3-chloro-2-fluorobenzene (5.000 g, 22.371 mmol), potassiumcyanide (4.369 g, 67.114 mmol) and tetrabutylammonium bromide (0.721 g, 2.237 mmol) in dichloromethane (30 mL)/water (30 mL) prepared at the room temperature was stirred at the same temperature for 4 hr, and partitioned between dichloromethane and water. The organic layer was washed with aqueous saturated sodium bicarbonate solution, dried with anhydrous MgSO₄, filtered, and concentrated in vacuo. The concentrate was purified and concentrated by column chromatography (SiO₂, 80 g cartridge; ethyl acetate/hexane=0% to 20%) to give 2-(3-chloro-2-fluorophenyl)acetonitrile as pale yellow liquid (3.047 g, 80.3%).

[Step 2] 1-(3-chloro-2-fluorophenyl)cyclobutane-1-carbonitrile

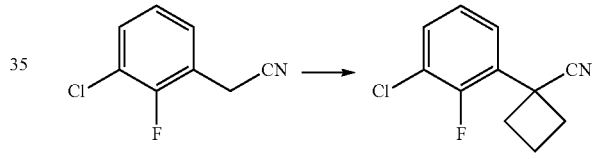

A solution of 2-(3-chloro-2-fluorophenyl)acetonitrile (5.000 g, 29.485 mmol) and sodium hydride (60.00%, 2.948 g, 73.712 mmol) in N,N-dimethylformide (40 mL) was stirred at 0° C. for 30 min, and mixed with 1,3-dibromopropane (3.006 mL, 29.485 mmol). The reaction mixture was stirred at the room temperature for additional 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 80 g cartridge; ethyl acetate/hexane=0% to 30%) to give 1-(3-chloro-2-fluorophenyl)cyclobutane-1-carbonitrile as colorless liquid (3.736 g, 60.4%).

[Step 3] 1-(3-chloro-2-fluorophenyl)cyclobutane-1-carboxamide

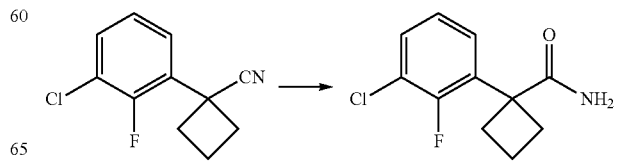

A solution of 1-(3-chloro-2-fluorophenyl)cyclobutane-1-carbonitrile (3.736 g, 17.820 mmol), sodium hydroxide (3.00 M solution in water, 2.970 mL, 8.910 mmol), hydrogen peroxide (30.00%, 6.062 g, 53.461 mmol) and tetrabutylammonium bromide (0.115 g, 0.356 mmol) in methanol (50 mL) prepared at the room temperature was stirred at the same temperature for 20 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 80%) to give 1-(3-chloro-2-fluorophenyl)cyclobutane-1-carboxamide as white solid (2.330 g, 57.4%).

[Step 4] 1-(3-chloro-2-fluorophenyl)cyclobutan-1-amine hydrochloride

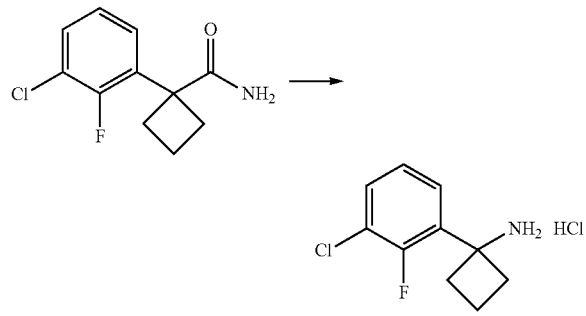

A solution of 1-(3-chloro-2-fluorophenyl)cyclobutane-1-carboxamide (2.330 g, 10.235 mmol), sodium hypochlorite (8.51%, 12.534 g, 14.328 mmol) and sodium hydroxide (3.00 M solution in water, 9.552 mL, 28.657 mmol) in 1-butanol (20 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with hydrochloric acid (1.0 M solution in ethyl acetate, 15.352 mL) and stirred at the ambient temperature for 30 min. The resulting precipitates were collected by filtration, washed by ethyl acetate, and dried to give 1-(3-chloro-2-fluorophenyl)cyclobutan-1-amine hydrochloride as white solid (1.510 g, 62.5%).

[Step 5] ethyl 2-((1-(3-chloro-2-fluorophenyl)cyclobutyl)amino)pyrimidine-5-carboxylate

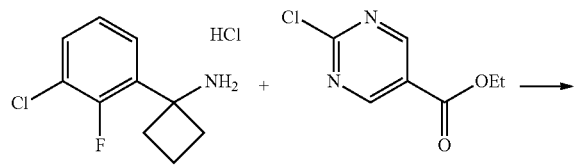

-continued

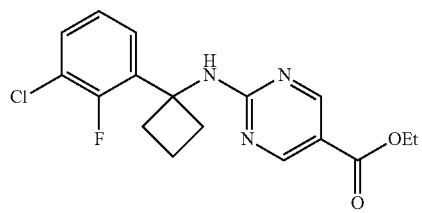

A solution of 1-(3-chloro-2-fluorophenyl)cyclobutan-1-amine hydrochloride (0.600 g, 2.541 mmol), ethyl 2-chloropyrimidine-5-carboxylate (0.522 g, 2.795 mmol) and N,N-diisopropylethylamine (1.107 mL, 6.353 mmol) in 1,4-dioxane (4 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 25 g cartridge; ethyl acetate/hexane=0% to 50%) to give ethyl 2-((1-(3-chloro-2-fluorophenyl)cyclobutyl)amino)pyrimidine-5-carboxylate as pale yellow solid (0.811 g, 91.2%).

[Step 6] 2-((1-(3-chloro-2-fluorophenyl)cyclobutyl)amino)pyrimidine-5-carbohydrazide

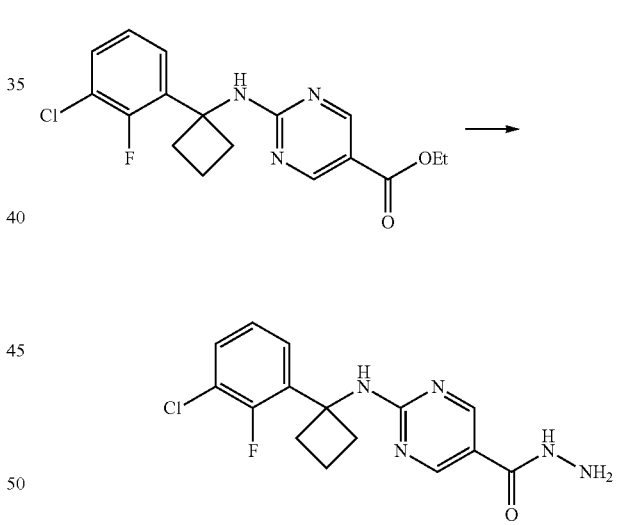

A solution of ethyl 2-((1-(3-chloro-2-fluorophenyl)cyclobutyl)amino)pyrimidine-5-carboxylate (0.600 g, 1.715 mmol) and hydrazine (50.00% solution in water, 2.153 mL, 34.306 mmol) in ethanol (5 mL) was stirred at 120° C. for 18 hr, and cooled down to the room temperature to terminate reaction. The reaction mixture was concentrated under the reduced pressure to remove the solvent. The concentrate was purified and concentrated by column chromatography (SiO$_2$, 12 g cartridge; ethyl acetate/hexane=0% to 30%) to give 2-((1-(3-chloro-2-fluorophenyl)cyclobutyl)amino)pyrimidine-5-carbohydrazide as white solid (0.522 g, 90.6%).

[Step 7] 2-((1-(3-chloro-2-fluorophenyl)cyclobutyl)amino)-N'-(2,2-difluoroacetyl)pyrimidine-5-carbohydrazide

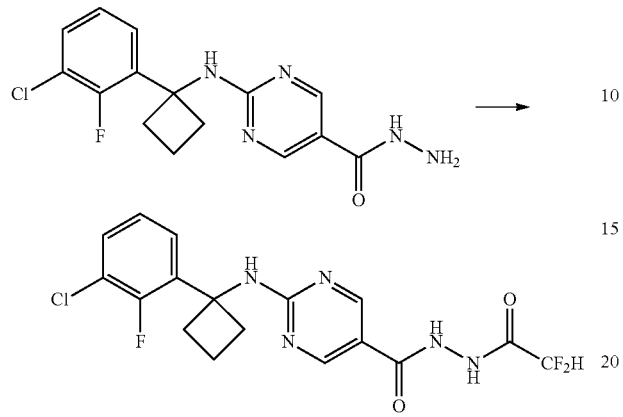

A solution of 2-((1-(3-chloro-2-fluorophenyl)cyclobutyl)amino)pyrimidine-5-carbohydrazide (0.250 g, 0.745 mmol), triethylamine (0.208 mL, 1.489 mmol) and 2,2-difluoroacetic anhydride (0.102 mL, 0.819 mmol) in dichloromethane (4 mL) was stirred at the room temperature for 1 hr, and concentrated under the reduced pressure to remove the solvent. The concentrate was partitioned between dichloromethane (5 mL) and water (5 mL), and filtered through a plastic frit to remove the solid residues and aqueous layer. The resulting organic layer was concentrated in vacuo to give the crude product which was subsequently concentrate was purified and concentrated by column chromatography (SiO₂, 12 g cartridge; dichloromethane/methanol=0% to 15%) to give 2-((1-(3-chloro-2-fluorophenyl)cyclobutyl)amino)-N'-(2,2-difluoroacetyl)pyrimidine-5-carbohydrazide as white solid (0.268 g, 87.0%).

[Step 8] Compound 1965

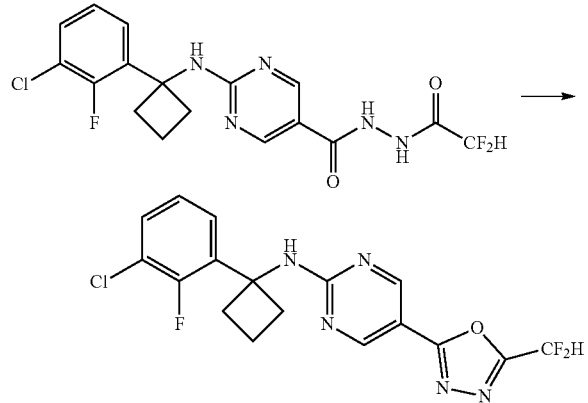

A mixture of 2-((1-(3-chloro-2-fluorophenyl)cyclobutyl)amino)-N'-(2,2-difluoroacetyl)pyrimidine-5-carbohydrazide (0.180 g, 0.435 mmol) and 1-methoxy-N-triethylammoniosulfonyl-methanimidate (Burgess reagent, 0.207 g, 0.870 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The concentrate was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO₂, 4 g cartridge; ethyl acetate/hexane=0% to 50%) to give N-(1-(3-chloro-2-fluorophenyl)cyclobutyl)-5-(5-(difluoromethyl)-1,3,4-oxadiazol-2-yl)pyrimidin-2-amine as white solid (0.139 g, 80.7%).

¹H NMR (400 MHz, CDCl₃) δ 8.88 (d, J=7.5 Hz, 2H), 7.55 (td, J=7.7, 1.6 Hz, 1H), 7.31-7.25 (m, 2H), 7.06 (td, J=7.9, 1.0 Hz, 1H), 7.02 (s, 1H), 6.89 (s, 1H), 6.76 (s, 1H), 6.58 (s, 1H), 2.82 (ddd, J=12.1, 9.1, 7.9 Hz, 2H), 2.64 (tdd, J=8.8, 6.5, 3.5 Hz, 2H), 2.29-2.18 (m, 1H), 1.97 (dtt, J=11.1, 9.0, 5.4 Hz, 1H); LRMS (ES) m/z 396.0 (M⁺+1).

Example 73. Compound 1966: N-(1-(3-chloro-2-fluorophenyl)cyclobutyl)-5-(5-(trifluoromethyl)-1,3,4-oxadiazol-2-yl)pyrimidin-2-amine

[Step 1] 2-((1-(3-chloro-2-fluorophenyl)cyclobutyl)amino)-N'-(2,2,2-trifluoroacetyl)pyrimidine-5-carbohydrazide

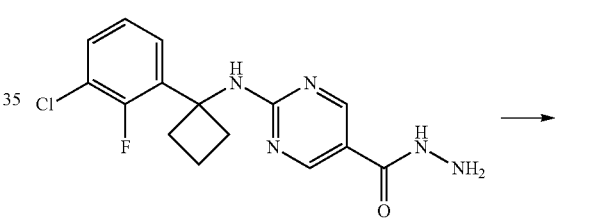

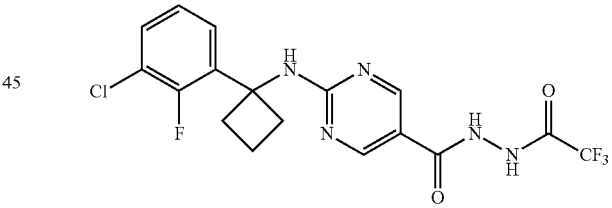

A solution of 2-((1-(3-chloro-2-fluorophenyl)cyclobutyl)amino)pyrimidine-5-carbohydrazide (0.250 g, 0.745 mmol), triethylamine (0.208 mL, 1.489 mmol) and trifluoroacetic anhydride (0.116 mL, 0.819 mmol) in dichloromethane (4 mL) was stirred at the room temperature for 1 hr, and concentrated under the reduced pressure to remove the solvent. The residue was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO₂, 12 g cartridge; dichloromethane/methanol=0% to 15%) to give 2-((1-(3-chloro-2-fluorophenyl)cyclobutyl)amino)-N'-(2,2,2-trifluoroacetyl)pyrimidine-5-carbohydrazide as white solid (0.281 g, 87.4%).

[Step 2] Compound 1966

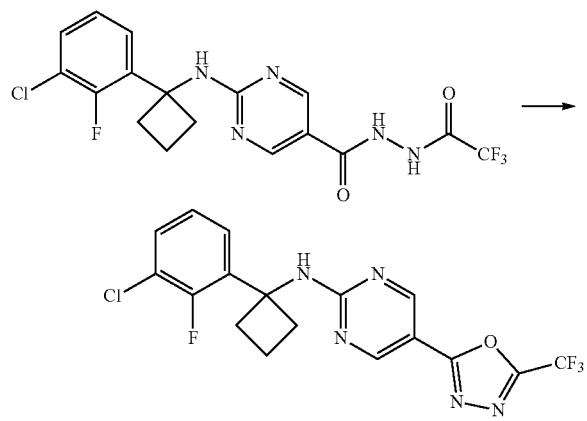

A mixture of 2-((1-(3-chloro-2-fluorophenyl)cyclobutyl)amino)-N'-(2,2,2-trifluoroacetyl)pyrimidine-5-carbohydrazide (0.150 g, 0.347 mmol) and 1-methoxy-N-triethylammoniosulfonyl-methanimidate (Burgess reagent, 0.166 g, 0.695 mmol) in tetrahydrofuran (3 mL) was heated at 150° C. for 30 min under the microwaves, and cooled down to the room temperature to terminate reaction. The reaction mixture was concentrated under the reduced pressure to remove the solvent. The concentrate was partitioned between dichloromethane (5 mL) and water (5 mL), and filtered through a plastic frit to remove the solid residues and aqueous layer. The resulting organic layer was concentrated in vacuo to give the crude product which was subsequently purified and concentrated by column chromatography (SiO$_2$, 4 g cartridge; ethyl acetate/hexane=0% to 50%) to give N-(1-(3-chloro-2-fluorophenyl)cyclobutyl)-5-(5-(trifluoromethyl)-1,3,4-oxadiazol-2-yl)pyrimidin-2-amine as white solid (0.080 g, 55.7%).
$^1$H NMR (400 MHz, CDCl$_3$) δ 8.88 (d, J=9.1 Hz, 2H), 7.54 (td, J=7.8, 1.6 Hz, 1H), 7.32-7.25 (m, 1H), 7.07 (td, J=7.9, 1.1 Hz, 1H), 6.51 (br, 1H), 2.82 (ddd, J=12.1, 9.1, 7.8 Hz, 2H), 2.68-2.59 (m, 2H), 2.32-2.17 (m, 1H), 2.04-1.90 (m, 1H); LRMS (ES) m/z 413.8 (M$^+$+1).

Example 74: Compound 2023, 5-(5-(difluoromethyl)-1,3,4-oxadiazol-2-yl)-N-(1-(4-(1-(oxetan-3-yl)piperidin-4-yl)phenyl)cyclobutyl)pyrimidin-2-amine

[Step 1]
1-(4-bromophenyl)cyclobutane-1-carbonitrile

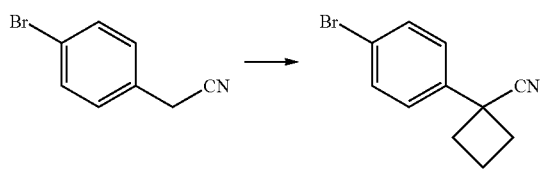 [SMILES: N#CCc1ccc(Br)cc1 ; N#CC1(c2ccc(Br)cc2)CCC1]

A solution of 2-(4-bromophenyl)acetonitrile (10.000 g, 51.007 mmol) and sodium hydride (60.00%, 4.488 g, 112.216 mmol) in N,N-dimethylformamide (150 mL) was stirred at 0° C. for 30 min, and mixed with 1,3-dibromopropane (5.175 mL, 51.007 mmol). The reaction mixture was stirred at the same temperature for additional 1 hr, quenched at 0° C. by the addition of water (50 mL, 30 min stirring), and partitioned between hexane and water. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 5%) to give 1-(4-bromophenyl)cyclobutane-1-carbonitrile as colorless oil (7.220 g, 60.0%).

[Step 2]
1-(4-bromophenyl)cyclobutane-1-carboxamide

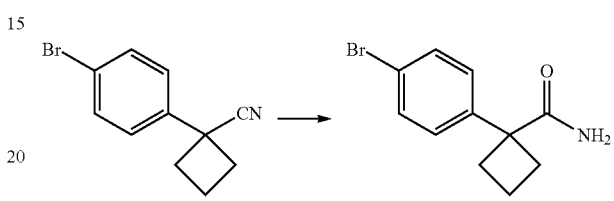

A solution of 1-(4-bromophenyl)cyclobutane-1-carbonitrile (7.500 g, 31.765 mmol), sodium hydroxide (25.00%, 1.270 g, 7.941 mmol), hydrogen peroxide (30.00%, 10.805 g, 95.295 mmol) and tetra-n-butylammonium bromide (0.102 g, 0.318 mmol) in methanol (150 mL) was stirred at the room temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-(4-bromophenyl)cyclobutane-1-carboxamide was used without further purification (8.120 g, 100.6%, white solid).

[Step 3] 1-(4-bromophenyl)cyclobutan-1-amine hydrochloride

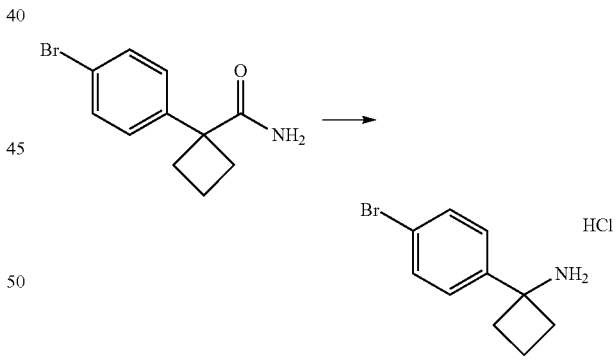

A solution of 1-(4-bromophenyl)cyclobutane-1-carboxamide (8.120 g, 31.952 mmol), sodium hypochlorite (11.00% solution, 25.101 mL, 44.733 mmol) and sodium hydroxide (3.00 M solution in water, 29.822 mL, 89.466 mmol) in 1-butanol (50 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate (20 mL) and then treated with hydrochloric acid (4.00 M solution in 1,4-dioxane, 11.982 mL, 47.928 mmol) and stirred at the ambient temperature. The resulting precipitates were collected by filtration, washed by ethyl acetate, and dried to give 1-(4-bromophenyl)cyclobutan-1-amine hydrochloride as white solid (3.320 g, 39.6%).

[Step 4] Ethyl 2-((1-(4-bromophenyl)cyclobutyl)amino)pyrimidine-5-carboxylate

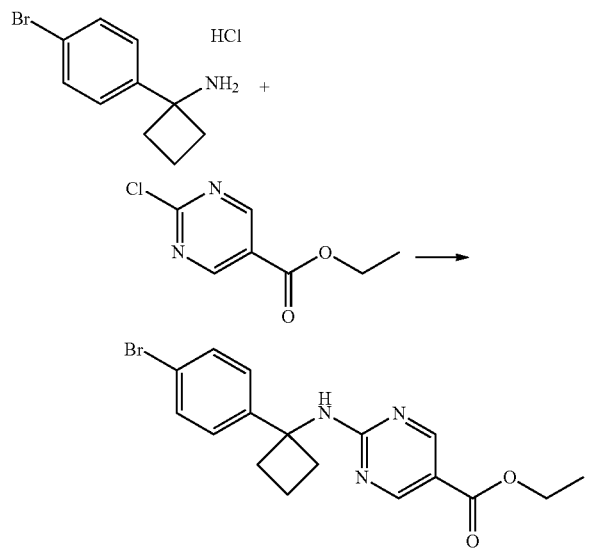

1-(4-bromophenyl)cyclobutan-1-amine hydrochloride (3.300 g, 12.568 mmol), ethyl 2-chloropyrimidine-5-carboxylate (2.462 g, 13.196 mmol) and N,N-diisopropylethylamine (6.567 mL, 37.703 mmol) were mixed at the room temperature in 1,4-dioxane (100 mL) and then stirred at 110° C. for 17 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 20%) to give ethyl 2-((1-(4-bromophenyl)cyclobutyl)amino)pyrimidine-5-carboxylate as pale yellow solid (2.320 g, 49.1%).

[Step 5] Ethyl 2-((1-(4-(1-((benzyloxy)carbonyl)-1,2,3,6-tetrahydropyridin-4-yl)phenyl)cyclobutyl)amino)pyrimidine-5-carboxylate

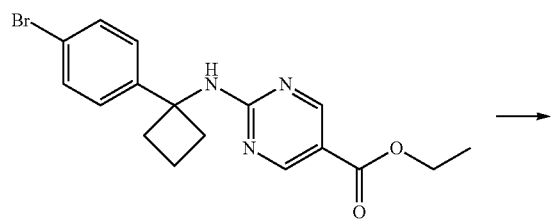

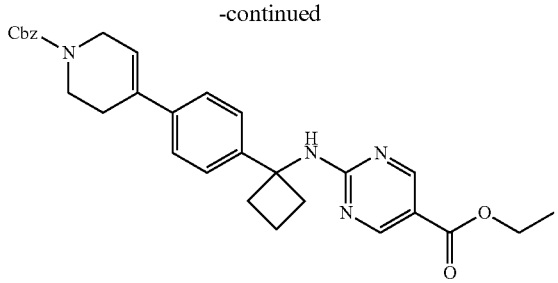

Ethyl 2-((1-(4-bromophenyl)cyclobutyl)amino)pyrimidine-5-carboxylate (1.500 g, 3.987 mmol), benzyl 4-(4,4,5,5-tetramethyl-1,3,2-dioxaborolan-2-yl)-3,6-dihydropyridine-1(2H)-carboxylat e (1.642 g, 4.784 mmol), [1,1'-bis(di-tert-butylphosphino)ferrocene]palladium(II) dichloride (Pd(dtbpf)Cl$_2$, 0.130 g, 0.199 mmol) and cesium carbonate (3.897 g, 11.960 mmol) in 1,4-dioxane (6 mL)/water (2 mL) was mixed at the room temperature and then heated at 100° C. under the microwaves for 20 min, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=5% to 40%) to give ethyl 2-((1-(4-(1-((benzyloxy)carbonyl)-1,2,3,6-tetrahydropyridin-4-yl)phenyl)cyclobutyl)amino)pyrimidine-5-carboxylate as brown solid (1.640 g, 80.2%).

[Step 6] Ethyl 2-((1-(4-(piperidin-4-yl)phenyl)cyclobutyl)amino)pyrimidine-5-carboxylate

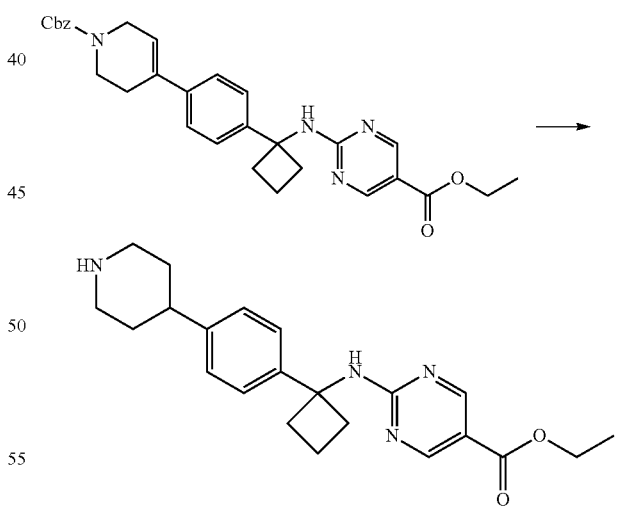

Ethyl 2-((1-(4-(1-((benzyloxy)carbonyl)-1,2,3,6-tetrahydropyridin-4-yl)phenyl)cyclobutyl)amino)pyrimidine-5-carboxylate (1.640 g, 3.199 mmol) was dissolved in methanol (20 mL)/tetrahydrofuran (10 mL) at room temperature. 10%-Pd/C (200 mg) was slowly added to the solution, stirred at the same temperature under the hydrogen atmosphere (H$_2$ balloon) for 17 hr, and concentrated under the reduced pressure. The concentrate was purified and concentrated by column chromatography (SiO$_2$, 24 g cartridge;

methanol/dichloromethane=0% to 40%) to give ethyl 2-((1-(4-(piperidin-4-yl)phenyl)cyclobutyl)amino)pyrimidine-5-carboxylate as white solid (0.710 g, 58.3%).

[Step 7] Ethyl 2-((1-(4-(1-(oxetan-3-yl)piperidin-4-yl)phenyl)cyclobutyl)amino)pyrimidine-5-carboxylate

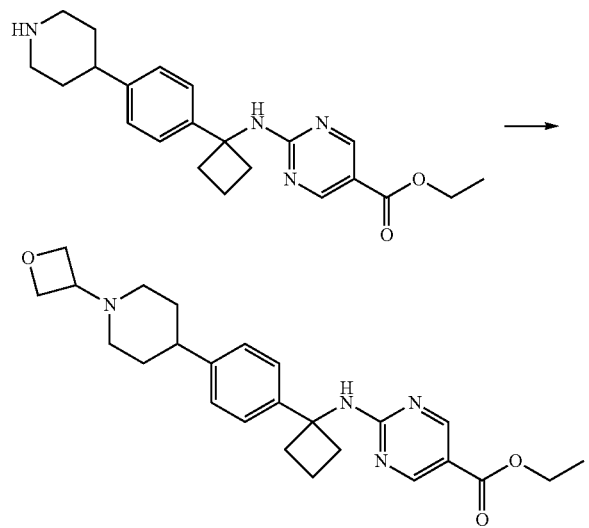

A solution of ethyl 2-((1-(4-(piperidin-4-yl)phenyl)cyclobutyl)amino)pyrimidine-5-carboxylate (0.300 g, 0.788 mmol), oxetan-3-one (0.085 g, 1.183 mmol) and sodium triacetoxyborohydride (0.334 g, 1.577 mmol) in dichloromethane (5 mL) was stirred at the room temperature for 10 min and then for additional 17 hr at the same temperature. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was diluted with ethanol (5 mL) and stirred at the ambient temperature. The resulting precipitates were collected by filtration, washed by ethanol, and dried to give ethyl 2-((1-(4-(1-(oxetan-3-yl)piperidin-4-yl)phenyl)cyclobutyl)amino)pyrimidine-5-carboxylate as white solid (0.274 g, 79.6%).

[Step 8] 2-((1-(4-(1-(oxetan-3-yl)piperidin-4-yl)phenyl)cyclobutyl)amino)pyrimidine-5-carbohydrazide

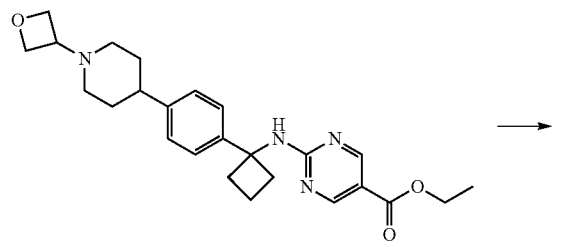

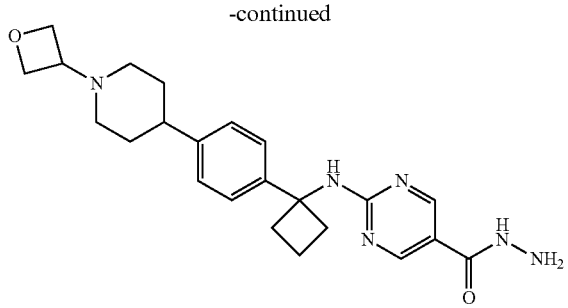

Ethyl 2-((1-(4-(1-(oxetan-3-yl)piperidin-4-yl)phenyl)cyclobutyl)amino)pyrimidine-5-carboxylate (0.276 g, 0.632 mmol) and hydrazine monohydrate (0.615 mL, 12.644 mmol) were mixed at the room temperature in ethanol (4 mL) and then stirred at 110° C. for 17 hr, and cooled down to the room temperature to terminate reaction. The precipitates were collected by filtration, washed by ethanol, and dried to give 2-((1-(4-(1-(oxetan-3-yl)piperidin-4-yl)phenyl)cyclobutyl)amino)pyrimidine-5-carbohydrazide as white solid (0.200 g, 74.9%).

[Step 9] N'-(2,2-difluoroacetyl)-2-((1-(4-(1-(oxetan-3-yl)piperidin-4-yl)phenyl)cyclobutyl)amino)pyrimidine-5-carbohydrazide

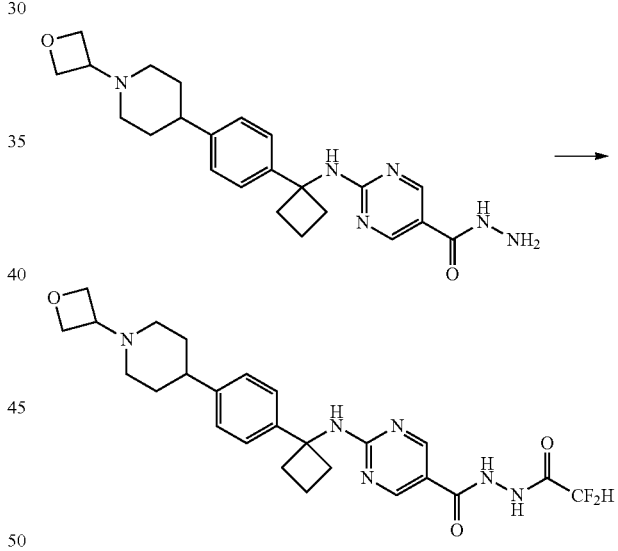

2-((1-(4-(1-(oxetan-3-yl)piperidin-4-yl)phenyl)cyclobutyl)amino)pyrimidine-5-carbohydrazide (0.200 g, 0.473 mmol), 2,2-difluoroacetic anhydride (0.088 mL, 0.710 mmol) and triethylamine (0.132 mL, 0.947 mmol) were mixed at the room temperature in tetrahydrofuran (10 mL) and then stirred at the same temperature for 17 hr. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo.

N'-(2,2-difluoroacetyl)-2-((1-(4-(1-(oxetan-3-yl)piperidin-4-yl)phenyl)cyclobutyl)amino)pyrimidine-5-carbohydrazide was used without further purification (0.100 g, 42.2%, white solid).

[Step 10] Compound 2023

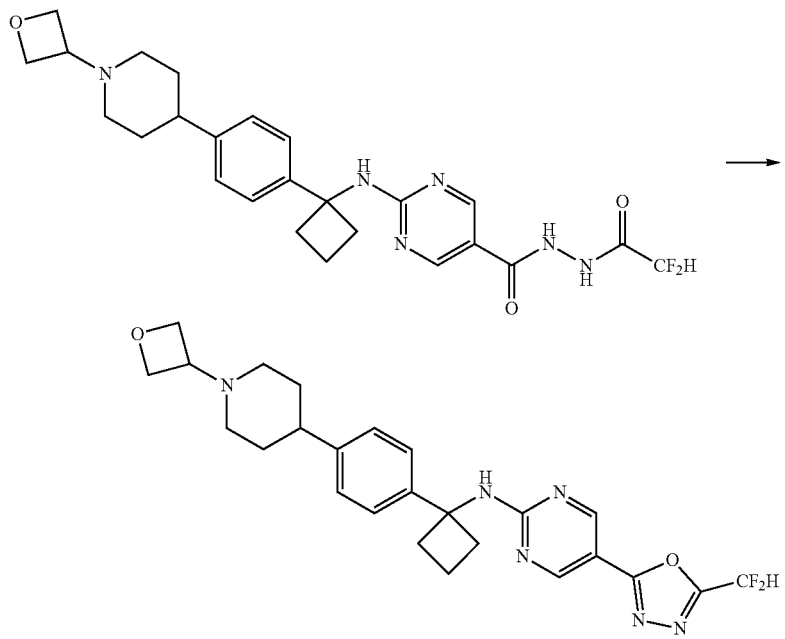

N'-(2,2-difluoroacetyl)-2-((1-(4-(1-(oxetan-3-yl)piperidin-4-yl)phenyl)cyclobutyl)amino)pyrimidine-5-carbohydrazide (0.100 g, 0.200 mmol) and 1-methoxy-N-triethylammoniosulfonyl-methanimidate (Burgess reagent, 0.143 g, 0.599 mmol) in tetrahydrofuran (3 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=60% to 100%) to give 5-(5-(difluoromethyl)-1,3,4-oxadiazol-2-yl)-N-(1-(4-(1-(oxetan-3-yl)piperidin-4-yl)phenyl)cyclobutyl)pyrimidin-2-amine as white solid (0.031 g, 32.2%).

$^1$H NMR (400 MHz, CDCl$_3$) δ 8.89 (brs, 2H), 7.45 (d, J=8.3 Hz, 2H), 7.21 (d, J=8.3 Hz, 2H), 7.02-6.76 (m, 1H), 6.34 (s, 1H), 4.81-4.70 (m, 4H), 3.64 (brs, 1H), 3.01 (brs, 2H), 2.78-2.73 (m, 2H), 2.65-2.58 (m, 3H), 2.23-1.92 (m, 8H); LRMS (ES) m/z 483.3 (M$^+$+1).

Example 75. Compound 2026: 5-(5-(difluoromethyl)-1,3,4-oxadiazol-2-yl)-N-(1-(tosylmethyl)cyclobutyl)pyrimidin-2-amine

[Step 1] N-cyclobutylidene-2-methylpropane-2-sulfinamide

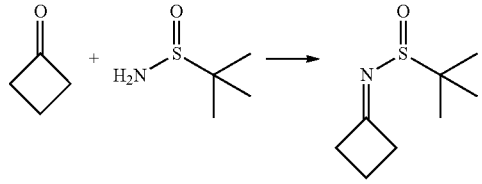

A solution of cyclobutanone (1.613 mL, 21.401 mmol), 2-methylpropane-2-sulfinamide (2.723 g, 22.471 mmol) and titanium ethoxide (8.974 mL, 42.802 mmol) in tetrahydrofuran (10 mL) prepared at the room temperature was stirred at the same temperature for 3 hr. The reaction mixture was quenched at the room temperature by the addition of ammonium chloride (5.00 M solution in water, 17.121 mL, 85.604 mmol, 5 min stirring), filtered through a celite pad to remove solids. Then, saturated aqueous ammonium chloride solution was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 30%) to give N-cyclobutylidene-2-methylpropane-2-sulfinamide as colorless liquid (2.648 g, 71.4%).

[Step 2] 1-(tosylmethyl)cyclobutan-1-amine hydrochloride

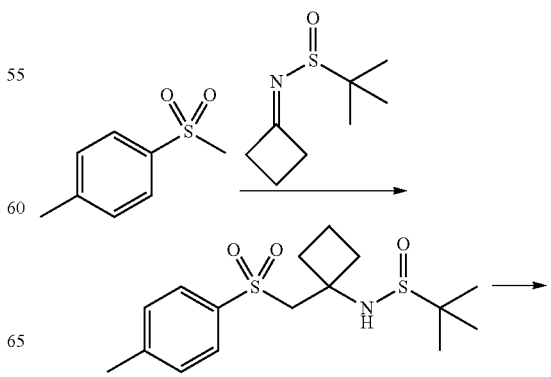

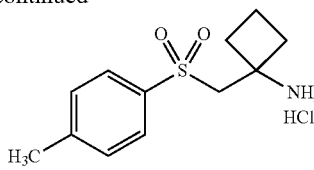

To a stirred solution of 1-methyl-4-(methylsulfonyl)benzene (0.400 g, 2.350 mmol) and butyllithium (1.60 M solution in hexane, 1.615 mL, 2.585 mmol) in tetrahydrofuran (5 mL) were added at −78° C. The reaction mixture was stirred at the same temperature for 30 min, treated at the same temperature with N-cyclobutylidene-2-methylpropane-2-sulfinamide (0.407 g, 2.350 mmol) and titanium ethoxide (0.493 mL, 2.350 mmol), stirred for additional 1 hr. Then, saturated aqueous ammonium chloride solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=50% to 90%) to give the crude product which was dissolved in ethyl acetate (10 mL) and aqueous 1M-hydrochloric acid solution (15 mL) and stirred at the ambient temperature. The resulting precipitates were collected by filtration, washed by ethyl acetate, and dried to give 1-(tosylmethyl)cyclobutan-1-amine hydrochloride as white solid (0.238 g, 36.7%).

[Step 3] ethyl 2-((1-(tosylmethyl)cyclobutyl)amino)pyrimidine-5-carboxylate

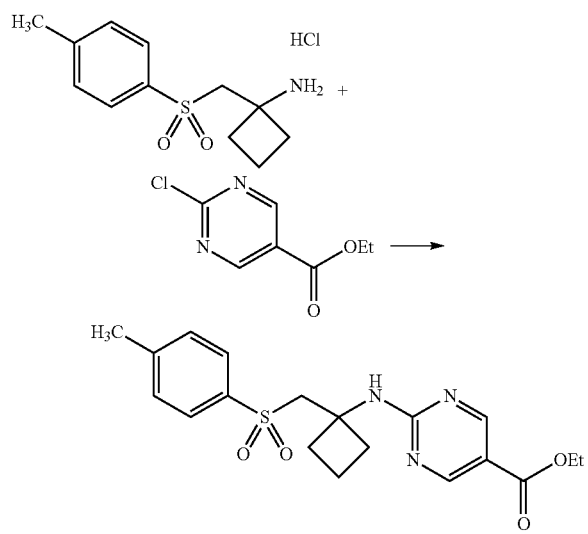

A solution of 1-(tosylmethyl)cyclobutan-1-amine hydrochloride (0.238 g, 0.863 mmol), ethyl 2-chloropyrimidine-5-carboxylate (0.161 g, 0.863 mmol) and N,N-diisopropylethylamine (0.376 mL, 2.157 mmol) in 1,4-dioxane (5 mL) prepared at the room temperature was stirred at the same temperature for 18 hr. The reaction mixture was concentrated under the reduced pressure to remove the solvent. The concentrate was purified and concentrated by column chromatography (SiO$_2$, 12 g cartridge; ethyl acetate/hexane=0% to 50%) to give ethyl 2-((1-(tosylmethyl)cyclobutyl)amino)pyrimidine-5-carboxylate as white solid (0.167 g, 49.7%).

[Step 4] 2-((1-(tosylmethyl)cyclobutyl)amino)pyrimidine-5-carbohydrazide

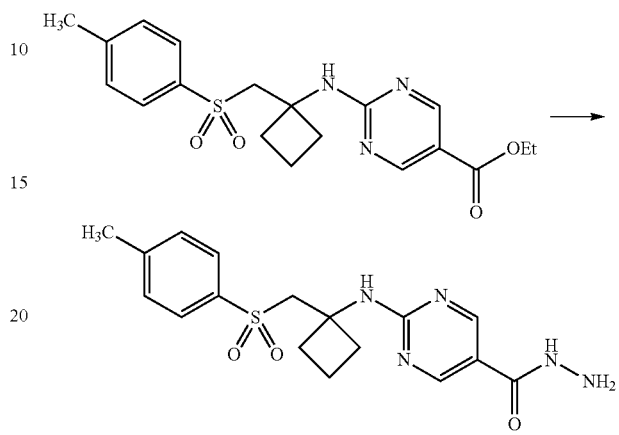

A solution of ethyl 2-((1-(tosylmethyl)cyclobutyl)amino)pyrimidine-5-carboxylate (0.167 g, 0.429 mmol) and hydrazine (50.00% solution in water, 0.538 mL, 8.576 mmol) in ethanol (4 mL) prepared at the room temperature was stirred at the same temperature for 18 hr. The reaction mixture was concentrated under the reduced pressure to remove the solvent. The crude product was used without further purification (2-((1-(tosylmethyl)cyclobutyl)amino)pyrimidine-5-carbohydrazide, 0.155 g, 96.3%, white solid).

[Step 5] N'-(2,2-difluoroacetyl)-2-((1-(tosylmethyl)cyclobutyl)amino)pyrimidine-5-carbohydrazide

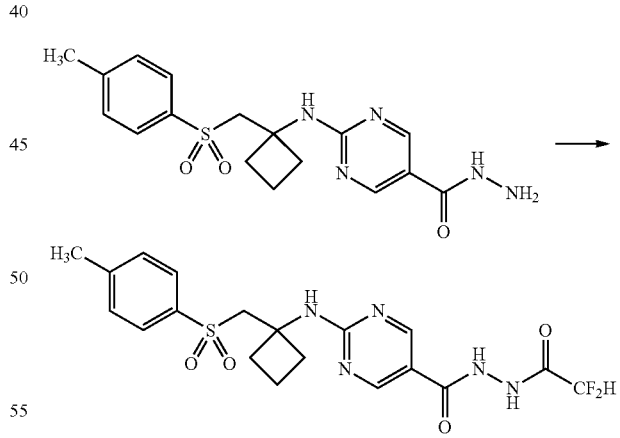

A solution of 2-((1-(tosylmethyl)cyclobutyl)amino)pyrimidine-5-carbohydrazide (0.155 g, 0.413 mmol), 2,2-difluoroacetic anhydride (0.051 mL, 0.413 mmol) and triethylamine (0.144 mL, 1.032 mmol) in dichloromethane (5 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=5% to 20%) to give N'-(2,2-difluoroacetyl)-2-((1-(tosylmethyl)cyclobutyl)amino)pyrimidine-5-carbohydrazide as white solid (0.162 g, 86.5%).

[Step 6] Compound 2026

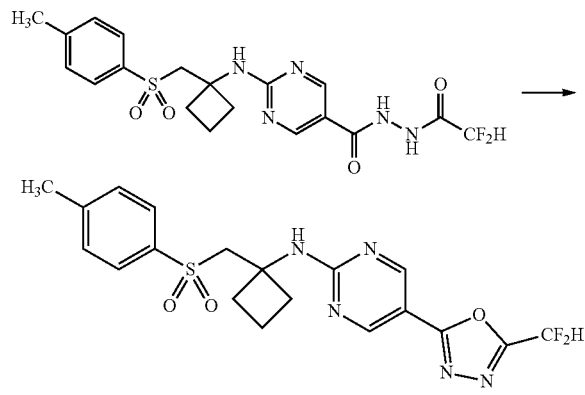

A mixture of N'-(2,2-difluoroacetyl)-2-((1-(tosylmethyl)cyclobutyl)amino)pyrimidine-5-carbohydrazide (0.160 g, 0.353 mmol) and 1-methoxy-N-triethylammoniosulfonyl-methanimidate (Burgess reagent, 0.168 g, 0.706 mmol) in tetrahydrofuran (4 mL) was heated at the room temperature for 30 min under the microwaves, and cooled down to the room temperature to terminate the reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 12 g cartridge; ethyl acetate/hexane=0% to 50%) to give 5-(5-(difluoromethyl)-1,3,4-oxadiazol-2-yl)-N-(1-(tosylmethyl)cyclobutyl)pyrimidin-2-amine as white solid (0.110 g, 71.6%).

$^1$H NMR (400 MHz, CDCl$_3$) δ 8.78 (s, 2H), 7.69-7.62 (m, 2H), 7.21-7.15 (m, 2H), 7.06 (s, 0.25H), 6.93 (s, 0.5H), 6.80 (s, 0.25H), 6.08 (br, 1H), 4.05 (s, 2H), 2.63-2.54 (m, 2H), 2.35 (ddd, J=11.0, 10.0, 5.3 Hz, 2H), 2.30 (s, 3H), 2.13-1.97 (m, 2H); LRMS (ES) m/z 436.1 (M$^+$+1).

Example 76: Compound 2027, 5-(5-(difluoromethyl)-1,3,4-oxadiazol-2-yl)-N-(1-(2,4-difluorophenyl)cyclobutyl)pyrimidin-2-amine

[Step 1]
1-(2-difluorophenyl)cyclobutane-1-carbonitrile

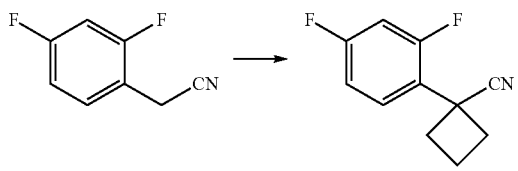 [SMILES: N#CCc1ccc(F)cc1F ; N#CC1(c2ccc(F)cc2F)CCC1]

2-(2,4-difluorophenyl)acetonitrile (5.000 g, 32.652 mmol) was dissolved at 0° C. to N,N-dimethylformide (50 mL). Sodium hydride (60.00%, 3.265 g, 81.630 mmol) was added to the reaction mixture, and stirred at the same temperature for 30 min. 1,3-dibromopropane (6.592 g, 32.652 mmol) was added to the reaction mixture, and stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 120 g cartridge; ethyl acetate/hexane=0% to 10%) to give 1-(2,4-difluorophenyl)cyclobutane-1-carbonitrile as Colorless oil (2.860 g, 45.3%).

[Step 2]
1-(2,4-difluorophenyl)cyclobutane-1-carboxamide

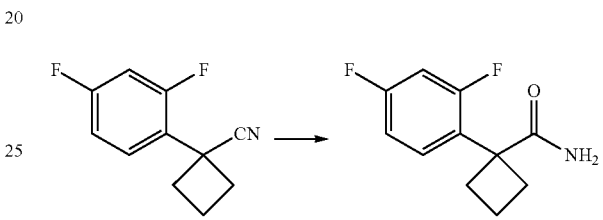

A solution of 1-(2,4-difluorophenyl)cyclobutane-1-carbonitrile (2.860 g, 14.803 mmol), sodium hydroxide (1.776 g, 44.410 mmol), hydrogen peroxide (1.511 g, 44.410 mmol) and tetra-n-butylammonium bromide (0.477 g, 1.480 mmol) in methanol (30 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 50%) to give 1-(2,4-difluorophenyl)cyclobutane-1-carboxamide as White solid (3.240 g, 103.6%).

[Step 3] 1-(2,4-difluorophenyl)cyclobutan-1-amine hydrochloride

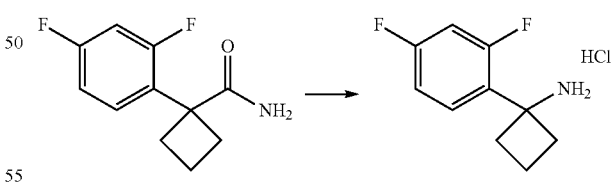

1-(2,4-difluorophenyl)cyclobutane-1-carboxamide (3.240 g, 15.340 mmol), sodium hydroxide (1.841 g, 46.021 mmol) and sodium hypochlorite (3.426 g, 46.021 mmol) was dissolved at 0° C. to 1-butanol (30 mL), and stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and then was added hydrochloric acid (1.00 M solution in EA, 23.010 mL, 23.010 mmol). The resulting precipitates were collected by filtration, washed by hexane and dried to give 1-(2,4-difluorophenyl)cyclobutan-1-amine hydrochloride as White solid (0.800 g, 23.7%).

[Step 4] ethyl 2-((1-(2,4-difluorophenyl)cyclobutyl)amino)pyrimidine-5-carboxylate

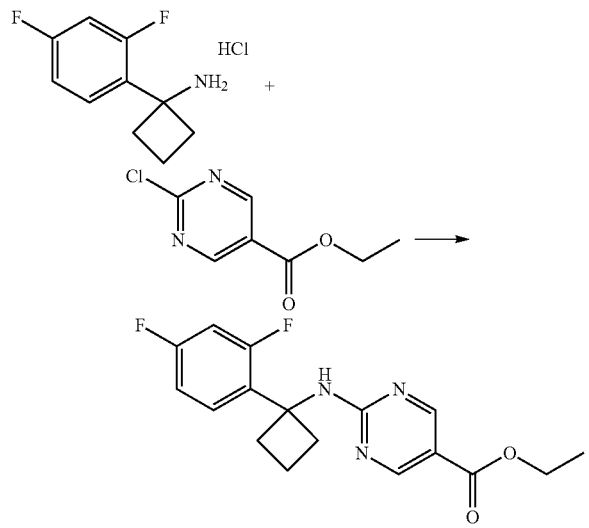

A solution of 1-(2,4-difluorophenyl)cyclobutan-1-amine hydrochloride (0.350 g, 1.593 mmol), ethyl 2-chloropyrimidine-5-carboxylate (0.297 g, 1.593 mmol) and N,N-diisopropylethylamine (0.694 mL, 3.983 mmol) in 1,4-dioxane (10 mL) was stirred at 90° C. for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give ethyl 2-((1-(2,4-difluorophenyl)cyclobutyl)amino)pyrimidine-5-carboxylate as White solid (0.460 g, 86.6%).

[Step 5] 2-((1-(2,4-difluorophenyl)cyclobutyl)amino)pyrimidine-5-carbohydrazide

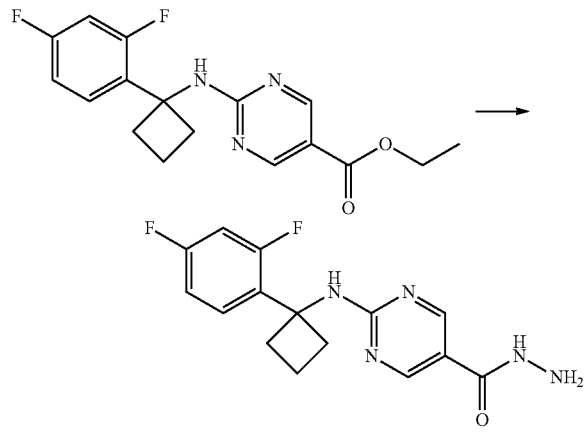

A mixture of ethyl 2-((1-(2,4-difluorophenyl)cyclobutyl)amino)pyrimidine-5-carboxylate (0.460 g, 1.380 mmol) and hydrazine monohydrate (1.341 mL, 27.599 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The precipitates were collected by filtration, washed by hexane, and dried to give 2-((1-(2,4-difluorophenyl)cyclobutyl)amino)pyrimidine-5-carbohydrazide as White solid (0.400 g, 90.8%).

[Step 6] N'-(2,2-difluoroacetyl)-2-((1-(2,4-difluorophenyl)cyclobutyl)amino)pyrimidine-5-carbohydrazide

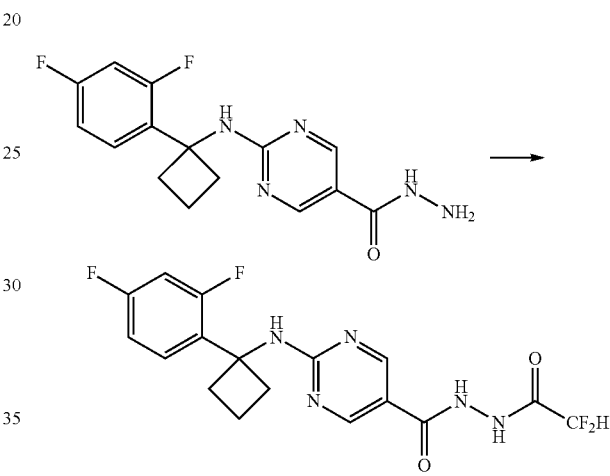

A solution of 2-((1-(2,4-difluorophenyl)cyclobutyl)amino)pyrimidine-5-carbohydrazide (0.200 g, 0.626 mmol), 2,2-difluoroacetic anhydride (0.078 mL, 0.626 mmol) and triethylamine (0.131 mL, 0.939 mmol) in dichloromethane (10 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO₄ filtered, and concentrated in vacuo. The concentrate was purified and concentrated by column chromatography (SiO₂, 12 g cartridge; methanol/dichloromethane=0% to 10%) to give N'-(2,2-difluoroacetyl)-2-((1-(2,4-difluorophenyl)cyclobutyl)amino)pyrimidine-5-carbohydrazide as White solid (0.125 g, 50.2%).

[Step 7] Compound 2027

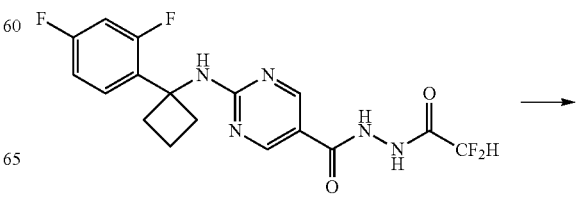

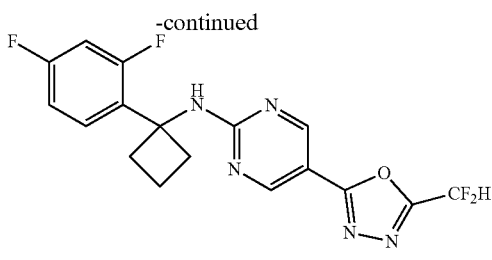

A mixture of N'-(2,2-difluoroacetyl)-2-((1-(2,4-difluorophenyl)cyclobutyl)amino)pyrimidine-5-carbohydrazide (0.162 g, 0.408 mmol) and 1-methoxy-N-triethylammoniosulfonyl-methanimidate (Burgess reagent, 0.146 g, 0.612 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give 5-(5-(difluoromethyl)-1,3,4-oxadiazol-2-yl)-N-(1-(2,4-difluorophenyl)cyclobutyl)pyrimidin-2-amine as White solid (0.110 g, 71.1%).

$^1$H NMR (400 MHz, CDCl$_3$) δ 8.88 (s, 2H), 7.65-7.59 (m, 1H), 7.02 (s, 0.25H), 6.89 (s, 0.5H), 6.76 (s, 0.5H), 6.86-6.82 (m, 1H), 6.79-6.74 (m, 1H), 6.46 (s, 1H), 2.83-2.76 (m, 2H), 2.66-2.59 (m, 2H), 2.27-2.20 (m, 1H), 1.99-1.93 (m, 1H).; LRMS (ES) m/z 380.0 (M⁺+1).

Example 77: Compound 2028, 5-(5-(difluoromethyl)-1,3,4-oxadiazol-2-yl)-N-(1-(2-(trifluoromethoxy)phenyl)cyclobutyl)pyrimidin-2-amine

[Step 1] 1-(2-(trifluoromethoxy)phenyl)cyclobutane-1-carbonitrile

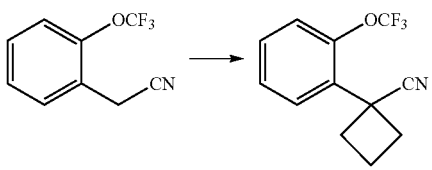 [SMILES: N#CCc1ccccc1OC(F)(F)F ; N#CC1(c2ccccc2OC(F)(F)F)CCC1]

2-(2-(trifluoromethoxy)phenyl)acetonitrile (5.000 g, 24.857 mmol) was dissolved at 0° C. to N,N-dimethylformide (50 mL). Sodium hydride (60.00%, 2.485 g, 62.143 mmol) was added to the reaction mixture, and stirred at the same temperature for 30 min, treated at the room temperature with 1,3-dibromopropane (5.018 g, 24.857 mmol), and stirred for additional 12 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 120 g cartridge; ethyl acetate/hexane=0% to 10%) to give 1-(2-(trifluoromethoxy)phenyl)cyclobutane-1-carbonitrile as Colorless oil (3.170 g, 52.9%).

[Step 2] 1-(2-(trifluoromethoxy)phenyl)cyclobutane-1-carboxamide

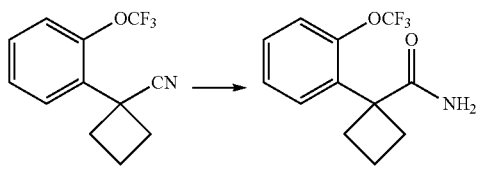 [SMILES: N#CC1(c2ccccc2OC(F)(F)F)CCC1 ; NC(=O)C1(c2ccccc2OC(F)(F)F)CCC1]

A solution of 1-(2-(trifluoromethoxy)phenyl)cyclobutane-1-carbonitrile (3.420 g, 14.179 mmol), sodium hydroxide (1.701 g, 42.536 mmol), hydrogen peroxide (1.447 g, 42.536 mmol) and tetra-n-butylammonium bromide (0.457 g, 1.418 mmol) in methanol (30 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 50%) to give 1-(2-(trifluoromethoxy)phenyl)cyclobutane-1-carboxamide as White solid (3.980 g, 108.3%).

[Step 3] 1-(2-(trifluoromethoxy)phenyl)cyclobutan-1-amine hydrochloride

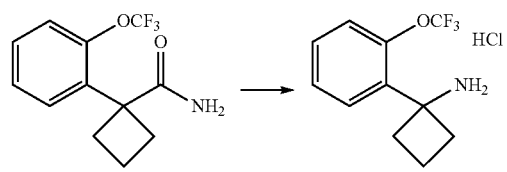 [SMILES: NC(=O)C1(c2ccccc2OC(F)(F)F)CCC1 ; NC1(c2ccccc2OC(F)(F)F)CCC1 ; Cl]

A solution of 1-(2-(trifluoromethoxy)phenyl)cyclobutane-1-carboxamide (3.930 g, 15.160 mmol), sodium hydroxide (1.819 g, 45.481 mmol), and sodium hypochlorite (3.386 g, 45.481 mmol) in 1-butanol (30 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate (20 mL) and then was added hydrochloric acid (1.00 M solution in EA, 22.740 mL, 22.740 mmol). The resulting precipitates were collected by filtration, washed by hexane and dried to give 1-(2-(trifluoromethoxy)phenyl)cyclobutan-1-amine hydrochloride as White solid (0.900 g, 22.2%).

[Step 4] ethyl 2-((1-(2-(trifluoromethoxy)phenyl)cyclobutyl)amino)pyrimidine-5-carboxylate

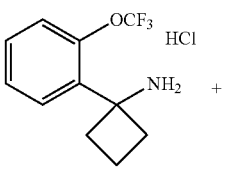 +

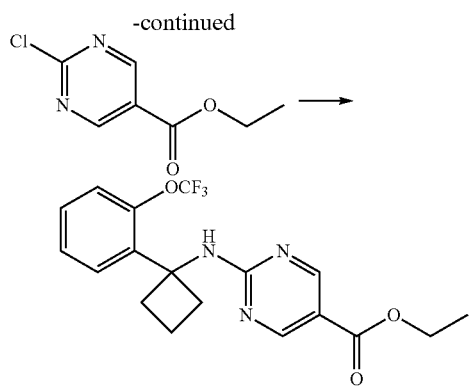

A solution of 1-(2-(trifluoromethoxy)phenyl)cyclobutan-1-amine hydrochloride (0.350 g, 1.308 mmol), ethyl 2-chloropyrimidine-5-carboxylate (0.244 g, 1.308 mmol) and N,N-diisopropylethylamine (0.569 mL, 3.269 mmol) in 1,4-dioxane (10 mL) was stirred at 90° C. for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give ethyl 2-((1-(2-(trifluoromethoxy)phenyl)cyclobutyl)amino)pyrimidine-5-carboxylate as White solid (0.480 g, 96.3%).

[Step 5] 2-((1-(2-(trifluoromethoxy)phenyl)cyclobutyl)amino)pyrimidine-5-carbohydrazide

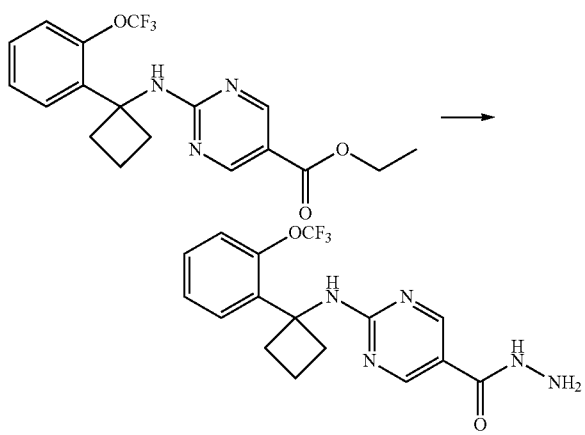

A mixture of ethyl 2-((1-(2-(trifluoromethoxy)phenyl)cyclobutyl)amino)pyrimidine-5-carboxylate (0.200 g, 0.524 mmol) and hydrazine monohydrate (0.510 mL, 10.489 mmol) in ethanol (10 mL) was heated at 120° C. for 1 hr under the microwaves, and cooled down to the room temperature to terminate reaction. Then, water was added to the reaction mixture, followed by extraction with dichloromethane. The organic layer was washed with aqueous saturated sodium chloride solution, dried with anhydrous MgSO₄, filtered, and concentrated in vacuo. The precipitates were collected by filtration, washed by hexane, and dried to give 2-((1-(2-(trifluoromethoxy)phenyl)cyclobutyl)amino)pyrimidine-5-carbohydrazide as white solid (0.112 g, 58.1%).

[Step 6] N'-(2,2-difluoroacetyl)-2-((1-(2-(trifluoromethoxy)phenyl)cyclobutyl)amino)pyrimidine-5-carbohydrazide

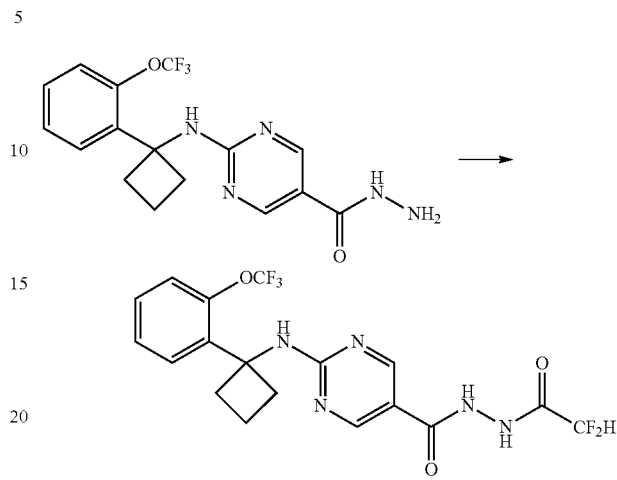

A solution of 2-((1-(2-(trifluoromethoxy)phenyl)cyclobutyl)amino)pyrimidine-5-carbohydrazide (0.200 g, 0.544 mmol), 2,2-difluoroacetic anhydride (0.068 mL, 0.544 mmol) and triethylamine (0.114 mL, 0.817 mmol) in dichloromethane (10 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N'-(2,2-difluoroacetyl)-2-((1-(2-(trifluoromethoxy)phenyl)cyclobutyl)amino)pyrimidine-5-carbohydrazide as White solid (0.112 g, 46.2%).

[Step 7] Compound 2028

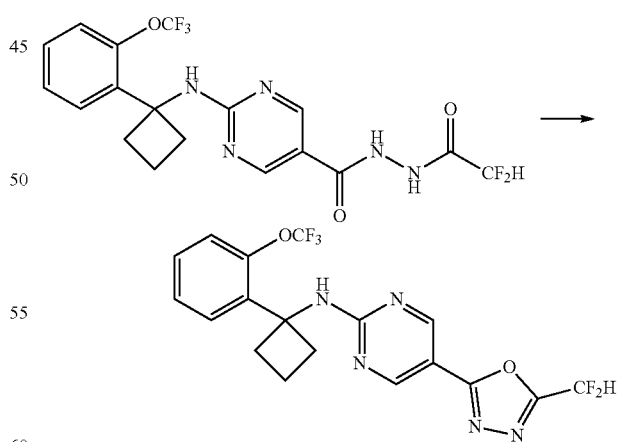

A mixture of N'-(2,2-difluoroacetyl)-2-((1-(2-(trifluoromethoxy)phenyl)cyclobutyl)amino)pyrimidine-5-carbohydrazide (0.137 g, 0.308 mmol) and 1-methoxy-N-triethylammoniosulfonyl-methanimidate (Burgess reagent, 0.110 g, 0.461 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(2-(trifluoromethoxy)phenyl)cyclobutyl)pyrimidin-2-amine as White solid (0.060 g, 45.6%).

$^1$H NMR (400 MHz, CDCl$_3$) δ 8.86 (d, J=3.9 Hz, 2H), 7.74 (dd, J=7.3, 2.1 Hz, 1H), 7.29~7.19 (m, 3H), 7.01 (s, 0.25H), 6.89 (s, 0.5H), 6.76 (s, 0.25H), 6.42 (s, 1H), 2.84~2.76 (m, 2H), 2.69~2.63 (m, 2H), 2.33~2.25 (m, 1H), 1.98~1.94 (m, 1H).; LRMS (ES) m/z 428.1 (M$^+$+1).

Example 78. Compound 2030: N-(1-benzylcyclobutyl)-5-(5-(difluoromethyl)-1,3,4-oxadiazol-2-yl)pyrimidin-2-amine

[Step 1] 1-benzylcyclobutan-1-amine hydrochloride

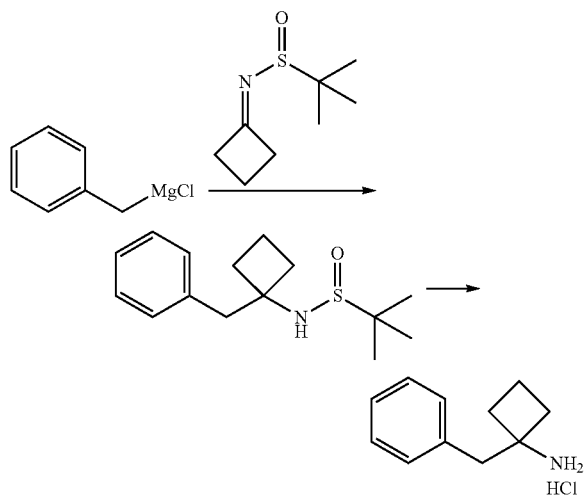

A solution of N-cyclobutylidene-2-methylpropane-2-sulfinamide (0.600 g, 3.463 mmol) and boron trifluoro diethyl etherate (0.855 mL, 6.926 mmol) in tetrahydrofuran (3 mL) was mixed at the room temperature with benzylmagnesium chloride (2.00 M solution in THF, 3.463 mL, 6.926 mmol), and stirred at the same temperature for 30 min. The reaction mixture was stirred at 25° C. for additional 2 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=30% to 100%) to give the crude product which was dissolved in hydrochloric acid (1.0 M solution in ethyl acetate, 3 mmol, 3 mL) and stirred at the ambient temperature. The resulting precipitates were collected by filtration, washed by hexane, and dried to give 1-benzylcyclobutan-1-amine hydrochloride as white solid (0.212 g, 31.0%).

[Step 2] ethyl 2-((1-benzylcyclobutyl)amino)pyrimidine-5-carboxylate

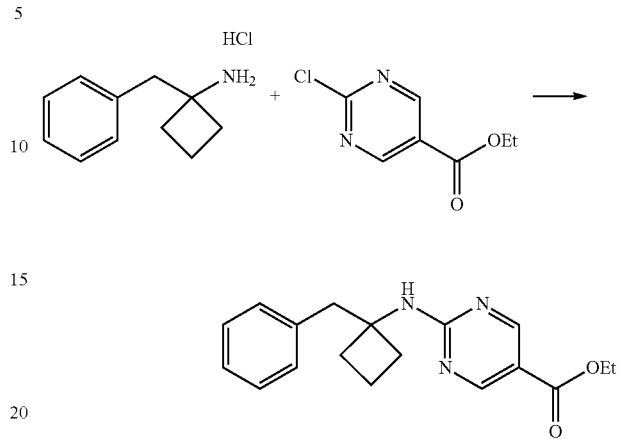

A solution of 1-benzylcyclobutan-1-amine hydrochloride (0.200 g, 1.012 mmol), ethyl 2-chloropyrimidine-5-carboxylate (0.189 g, 1.012 mmol) and N,N-diisopropylethylamine (0.440 mL, 2.529 mmol) in 1,4-dioxane (5 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO$_2$, 24 g cartridge; ethyl acetate/hexane=0% to 50%) to give ethyl 2-((1-benzylcyclobutyl)amino)pyrimidine-5-carboxylate as white solid (0.158 g, 50.2%).

[Step 3] 2-((1-benzylcyclobutyl)amino)pyrimidine-5-carbohydrazide

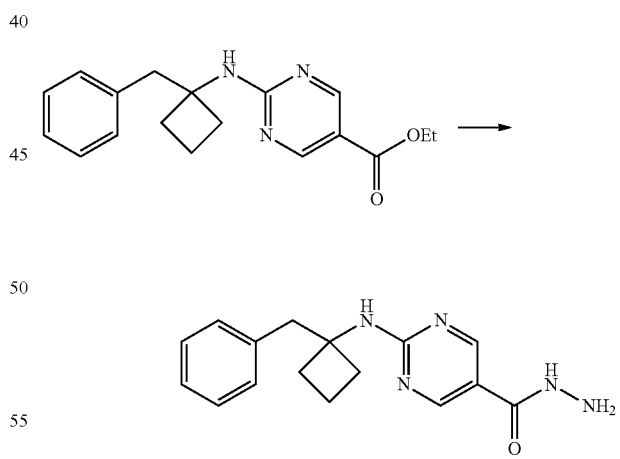

A solution of ethyl 2-((1-benzylcyclobutyl)amino)pyrimidine-5-carboxylate (0.150 g, 0.482 mmol) and hydrazine (50.00% solution in water, 0.605 mL, 9.634 mmol) in ethanol (4 mL) was stirred at 120° C. for 5 hr, and cooled down to the room temperature to terminate reaction. The reaction mixture was concentrated under the reduced pressure to remove the solvent. The crude product was used without further purification (2-((1-benzylcyclobutyl)amino) pyrimidine-5-carbohydrazide, 0.140 g, 97.7%, white solid).

277

[Step 4] 2-((1-benzylcyclobutyl)amino)-N'-(2,2-difluoroacetyl)pyrimidine-5-carbohydrazide

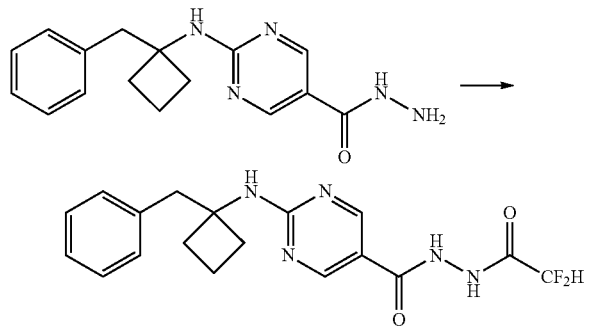

A solution of 2-((1-benzylcyclobutyl)amino)pyrimidine-5-carbohydrazide (0.150 g, 0.504 mmol), 2,2-difluoroacetic anhydride (0.063 mL, 0.504 mmol) and triethylamine (0.141 mL, 1.009 mmol) in dichloromethane (5 mL) prepared at the room temperature was stirred at the same temperature for 30 min, and concentrated under the reduced pressure to remove the solvent. The concentrate was purified and concentrated by column chromatography (SiO$_2$, 12 g cartridge; methanol/dichloromethane=5% to 30%) to give 2-((1-benzylcyclobutyl)amino)-N'-(2,2-difluoroacetyl)pyrimidine-5-carbohydrazide as white solid (0.115 g, 60.7%).

[Step 5] Compound 2030

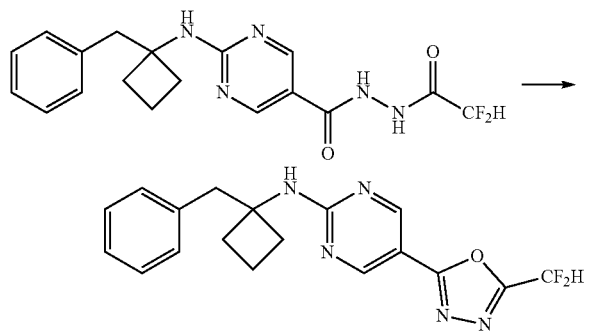

A mixture of 2-((1-benzylcyclobutyl)amino)-N'-(2,2-difluoroacetyl)pyrimidine-5-carbohydrazide (0.110 g, 0.293 mmol) and 1-methoxy-N-triethylammoniosulfonyl-methanimidate (Burgess reagent, 0.140 g, 0.586 mmol) in tetrahydrofuran (3 mL) was heated at 150° C. for 30 min under the microwaves and cooled down to the room temperature to terminate reaction. The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 12 g cartridge; ethyl acetate/hexane=0% to 30%) to give N-(1-benzylcyclobutyl)-5-(5-(difluoromethyl)-1,3,4-oxadiazol-2-yl)pyrimidin-2-amine as white solid (0.054 g, 51.6%).

$^1$H NMR (400 MHz, CDCl$_3$) δ 9.04 (s, 1H), 8.88 (s, 1H), 7.28-7.19 (m, 3H), 7.07 (dd, J=6.2, 1.8 Hz, 2H), 7.05 (s, 0.25H), 6.93 (s, 0.5H), 6.80 (s, 0.25H), 5.79 (br, 1H), 3.31 (s, 2H), 2.45-2.30 (m, 2H), 2.28-2.18 (m, 2H), 1.99 (qdd, J=16.9, 7.5, 3.9 Hz, 2H); LRMS (ES) m/z 358.0 (M$^+$+1).

Example 79: Compound 2033, N-(1-(2-(trifluoromethoxy)phenyl)cyclobutyl)-5-(5-(trifluoromethyl)1,3,4-oxadiazol-2-yl)pyrimidin-2-amine

[Step 1] N'-(2,2,2-trifluoroacetyl)-2-((1-(2-(trifluoromethoxy)phenyl)cyclobutyl)amino)pyrimidine-5-carbohydrazide

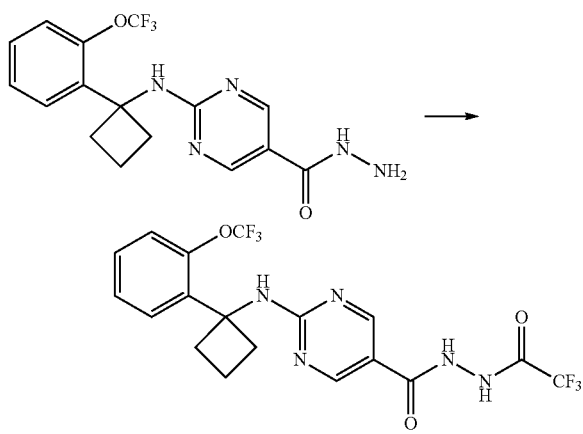

A solution of 2-((1-(2-(trifluoromethoxy)phenyl)cyclobutyl)amino)pyrimidine-5-carbohydrazide (0.112 g, 0.305 mmol), trifluoroacetic anhydride (0.043 mL, 0.305 mmol) and triethylamine (0.064 mL, 0.457 mmol) in dichloromethane (5 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N'-(2,2,2-trifluoroacetyl)-2-((1-(2-(trifluoromethoxy)phenyl)cyclobutyl)amino)pyrimidine-5-carbohydrazide as White solid (0.100 g, 70.8%).

[Step 2] Compound 2033

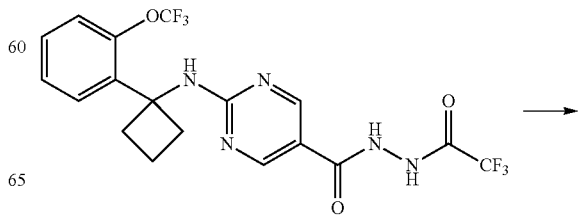

-continued

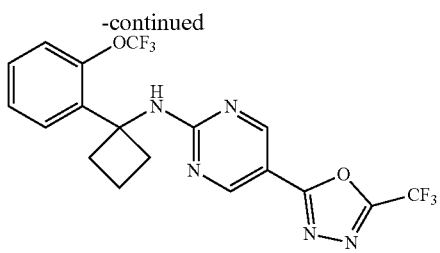

A mixture of N'-(2,2,2-trifluoroacetyl)-2-((1-(2-(trifluoromethoxy)phenyl)cyclobutyl)amino)pyrimidine-5-carbohydrazide (0.100 g, 0.216 mmol) and 1-methoxy-N-triethylammoniosulfonyl-methanimidate (Burgess reagent, 0.077 g, 0.324 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give N-(1-(2-(trifluoromethoxy)phenyl)cyclobutyl)-5-(5-(trifluoromethyl) 1,3,4-oxadiazol-2-yl)pyrimidin-2-amine as White solid (0.050 g, 52.0%).

$^1$H NMR (400 MHz, CDCl$_3$) δ 8.86 (d, J=6.8 Hz, 2H), 7.75~7.72 (m, 1H), 7.30~7.18 (m, 3H), 6.54 (s, 1H), 2.84~2.77 (m, 2H), 2.69~2.63 (m, 2H), 2.32~2.25 (m, 1H), 1.99~1.92 (m, 1H).; LRMS (ES) m/z 447.0 (M$^+$+1).

Example 80: Compound 2034, N-(1-(2,4-difluorophenyl)cyclobutyl)-5-(5-(trifluoromethyl)-1,3,4-oxadiazol-2-yl)pyrimidin-2-amine

[Step 1] 2-((1-(2,4-difluorophenyl)cyclobutyl)amino)-N'-(2,2,2-trifluoroacetyl)pyrimidine-5-carbohydrazide

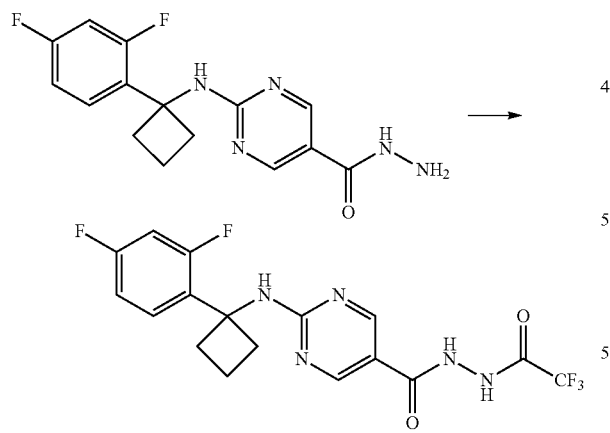

A solution of 2-((1-(2,4-difluorophenyl)cyclobutyl)amino)pyrimidine-5-carbohydrazide (0.125 g, 0.391 mmol), trifluoroacetic anhydride (0.055 mL, 0.391 mmol) and triethylamine (0.082 mL, 0.587 mmol) in dichloromethane (5 mL) prepared at the room temperature was stirred at the same temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give 2-((1-(2,4-difluorophenyl)cyclobutyl)amino)-N'-(2,2,2-trifluoroacetyl)pyrimidine-5-carbohydrazide as White solid (0.030 g, 18.5%).

[Step 2] Compound 2034

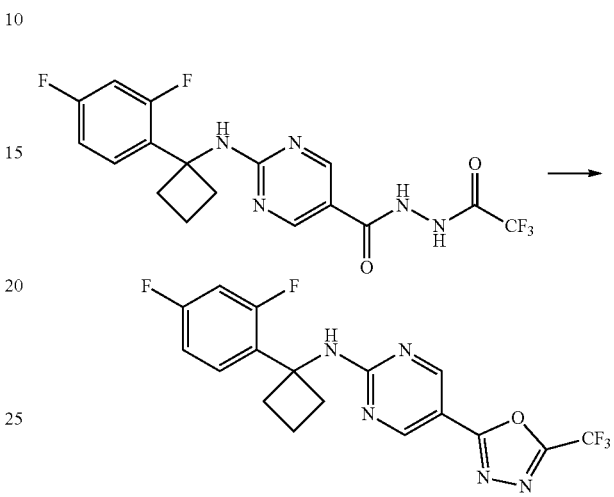

A mixture of 2-((1-(2,4-difluorophenyl)cyclobutyl)amino)-N'-(2,2,2-trifluoroacetyl)pyrimidine-5-carbohydrazide (0.030 g, 0.072 mmol) and 1-methoxy-N-triethylammoniosulfonyl-methanimidate (Burgess reagent, 0.026 g, 0.108 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 15%) to give N-(1-(2,4-difluorophenyl)cyclobutyl)-5-(5-(trifluoromethyl)-1,3,4-oxadiazol-2-yl)pyrimidin-2-amine as White solid (0.018 g, 62.7%).

$^1$H NMR (400 MHz, CDCl$_3$) δ 8.87 (s, 2H), 7.65~7.54 (m, 1H), 7.02~6.82 (m, 1H), 6.79~6.73 (m, 1H), 6.57 (s, 1H), 2.83~2.76 (m, 2H), 2.66~2.59 (m, 2H), 2.27~2.19 (m, 1H), 2.00~1.92 (m, 1H).; LRMS (ES) m/z 398.1 (M$^+$+1).

Example 81: Compound 2035, 5-(5-(difluoromethyl)-1,3,4-oxadiazol-2-yl)-N-(1-(4-(1-methylpiperidin-4-yl)phenyl)cyclobutyl)pyrimidin-2-amine

[Step 1] 2-((1-(4-bromophenyl)cyclobutyl)amino)pyrimidine-5-carbohydrazide

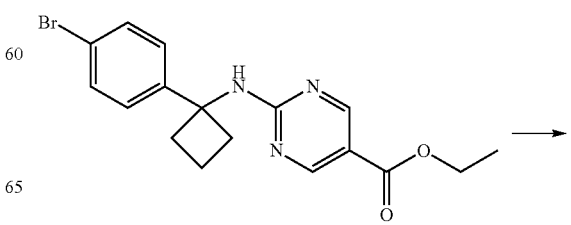

-continued

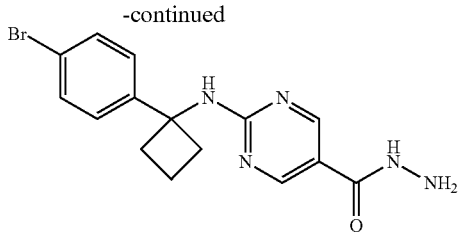

Ethyl 2-((1-(4-bromophenyl)cyclobutyl)amino)pyrimidine-5-carboxylate (0.700 g, 1.860 mmol) and hydrazine monohydrate (1.808 mL, 37.209 mmol) were mixed at the room temperature in ethanol (10 mL) and then stirred at 110° C. for 17 hr, cooled down to the room temperature to terminate reaction. The precipitates were collected by filtration, washed by hexane, and dried to give 2-((1-(4-bromophenyl)cyclobutyl)amino)pyrimidine-5-carbohydrazide as white solid (0.700 g, 103.9%).

[Step 2] 2-((1-(4-bromophenyl)cyclobutyl)amino)-N'-(2,2-difluoroacetyl)pyrimidine-5-carbohydrazide

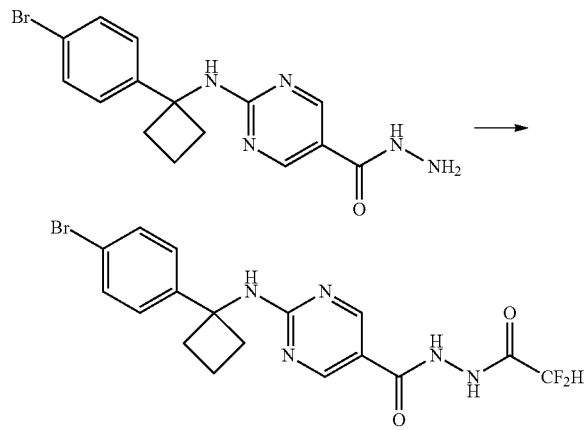

A solution of 2-((1-(4-bromophenyl)cyclobutyl)amino)pyrimidine-5-carbohydrazide (0.700 g, 1.932 mmol) and triethylamine (0.808 mL, 5.797 mmol) in tetrahydrofuran (10 mL) was mixed at the room temperature with 2,2-difluoroacetic anhydride (0.360 mL, 2.899 mmol), stirred at the same temperature for 17 hr, and concentrated under the reduced pressure to remove the solvent. The reaction mixture was diluted with water (10 mL) and dichloromethane (10 mL) and stirred at the ambient temperature. The resulting precipitates were collected by filtration, washed by dichloromethane, and dried to give 2-((1-(4-bromophenyl)cyclobutyl)amino)-N'-(2,2-difluoroacetyl)pyrimidine-5-carbohydrazide as white solid (0.736 g, 86.5%).

[Step 3] N-(1-(4-bromophenyl)cyclobutyl)-5-(5-(difluoromethyl)-1,3,4-oxadiazol-2-yl)pyrimidin-2-amine

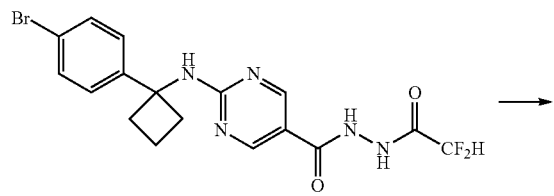

-continued

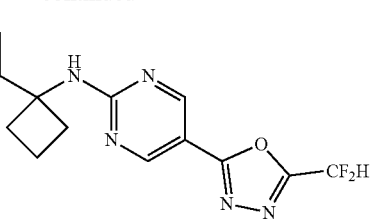

2-((1-(4-bromophenyl)cyclobutyl)amino)-N'-(2,2-difluoroacetyl)pyrimidine-5-carbohydrazide (0.736 g, 1.672 mmol) and 1-methoxy-N-triethylammoniosulfonyl-methanimidate (Burgess reagent, 1.195 g, 5.015 mmol) in tetrahydrofuran (10 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; ethyl acetate/hexane=0% to 20%) to give N-(1-(4-bromophenyl)cyclobutyl)-5-(5-(difluoromethyl)-1,3,4-oxadiazol-2-yl)pyrimidin-2-amine as white solid (0.523 g, 74.1%).

[Step 4] 5-(5-(difluoromethyl)-1,3,4-oxadiazol-2-yl)-N-(1-(4-(1-methyl-1,2,3,6-tetrahydropyridin-4-yl)phenyl)cyclobutyl)pyrimidin-2-amine

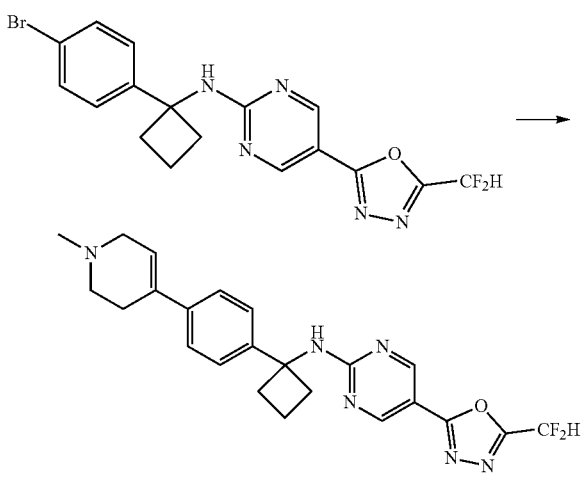

N-(1-(4-bromophenyl)cyclobutyl)-5-(5-(difluoromethyl)-1,3,4-oxadiazol-2-yl)pyrimidin-2-amine (0.100 g, 0.237 mmol), 1-methyl-4-(4,4,5,5-tetramethyl-1,3,2-dioxaborolan-2-yl)-1,2,3,6-tetrahydropyridine (0.063 g, 0.284 mmol), [1,1'-bis(di-tert-butylphosphino)ferrocene]palladium(II) dichloride (Pd(dtbpf)Cl$_2$, 0.008 g, 0.012 mmol) and cesium carbonate (0.231 g, 0.711 mmol) in 1,4-dioxane (3 mL)/water (1 mL) was mixed at the room temperature and then heated at 100° C. under the microwaves for 20 min, and cooled down to the room temperature to terminate reaction. Then, saturated aqueous sodium bicarbonate solution was added to the reaction mixture, followed by extraction with ethyl acetate. The organic layer was concentrated in vacuo. The concentrate was purified and concentrated by column chromatography (SiO$_2$, 4 g cartridge; methanol/dichloromethane=0% to 15%) to give 5-(5-(difluoromethyl)-1,3,4-oxadiazol-2-yl)-N-(1-(4-(1-methyl-1,2,3,6-tetrahydropyrid in-4-yl)phenyl)cyclobutyl)pyrimidin-2-amine as brown solid (0.068 g, 65.5%).

[Step 5] Compound 2035

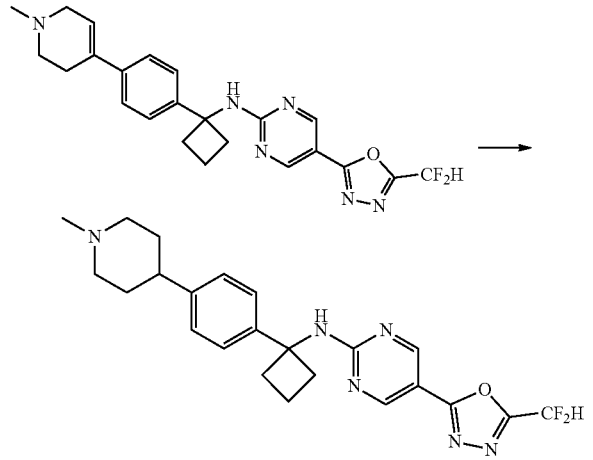

5-(5-(difluoromethyl)-1,3,4-oxadiazol-2-yl)-N-(1-(4-(1-methyl-1,2,3,6-tetrahydropyridin-4-yl)phenyl)cyclobutyl) pyrimidin-2-amine (0.068 g, 0.155 mmol) was dissolved in methanol (4 mL)/tetrahydrofuran (1 mL), and stirred at the room temperature for 17 hr. 10%-Pd/C (10 mg) was slowly added to the solution at the same temperature, stirred at 40° C. under the hydrogen atmosphere (H$_2$ balloon) for additional 48 hr, and cooled down to the room temperature to terminate reaction. The reaction mixture was filtered through a celite pad to remove solids, and concentrated under the reduced pressure to remove the solvent. The concentrate was purified and concentrated by column chromatography (SiO$_2$, 4 g cartridge; methanol/dichloromethane=0% to 10%) to give 5-(5-(difluoromethyl)-1,3,4-oxadiazol-2-yl)-N-(1-(4-(1-methylpiperidin-4-yl)phenyl) cyclobutyl)pyrimidin-2-amine as pale orange solid (0.009 g, 13.2%).

$^1$H NMR (400 MHz, CDCl$_3$) δ 8.88 (brs, 2H), 7.45 (d, J=8.3 Hz, 2H), 7.21 (d, J=8.2 Hz, 2H), 7.02-6.76 (m, 1H), 6.39 (s, 1H), 3.30 (d, J=11.4 Hz, 2H), 2.77-2.72 (m, 2H), 2.64-2.59 (m, 6H), 2.50-2.41 (m, 2H), 2.23-2.14 (m, 3H), 2.04-1.92 (m, 3H); LRMS (ES) m/z 441.2 (M$^+$+1).

Example 82: Compound 2036, 5-(5-(difluoromethyl)-1,3,4-oxadiazol-2-yl)-N-(1-(4-(1-ethylpiperidin-4-yl)phenyl)cyclobutyl)pyrimidin-2-amine

[Step 1] Ethyl 2-((1-(4-(1-ethylpiperidin-4-yl)phenyl)cyclobutyl)amino)pyrimidine-5-carboxylat

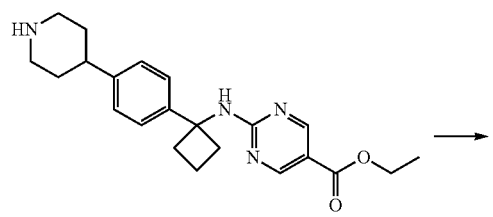

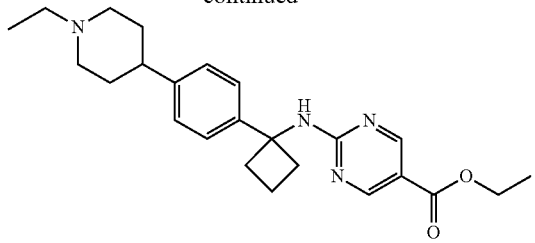

A solution of ethyl 2-((1-(4-(piperidin-4-yl)phenyl)cyclobutyl)amino)pyrimidine-5-carboxylate (0.300 g, 0.788 mmol) and acetaldehyde (0.066 mL, 1.183 mmol) in dichloromethane (5 mL) was stirred at the room temperature for 10 min, and mixed with sodium triacetoxyborohydride (0.334 g, 1.577 mmol). The reaction mixture was stirred at the same temperature for additional 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 20%) to give ethyl 2-((1-(4-(1-ethylpiperidin-4-yl)phenyl)cyclobutyl)amino)pyrimidine-5-carboxylat as white solid (0.190 g, 59.0%).

[Step 2] 2-((1-(4-(1-ethylpiperidin-4-yl)phenyl)cyclobutyl)amino)pyrimidine-5-carbohydrazide

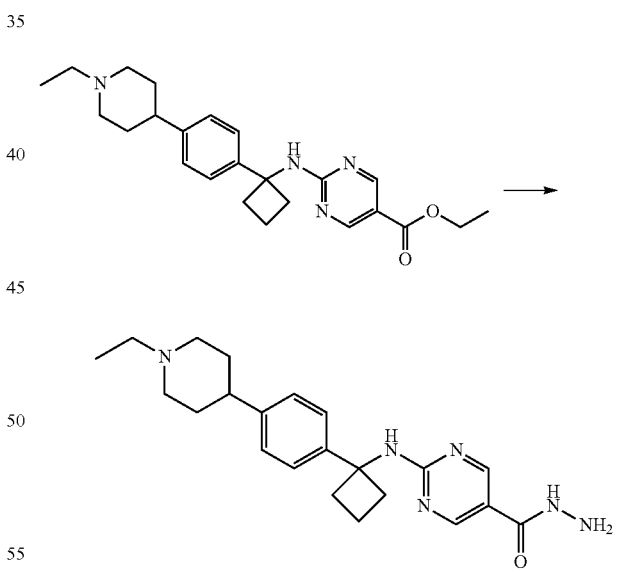

Ethyl 2-((1-(4-(1-ethylpiperidin-4-yl)phenyl)cyclobutyl) amino)pyrimidine-5-carboxylate (0.190 g, 0.465 mmol) and hydrazine monohydrate (0.452 mL, 9.301 mmol) were mixed at the room temperature in ethanol (4 mL) and then stirred at 100° C. for 17 hr, cooled down to the room temperature to terminate reaction. The precipitates were collected by filtration, washed by ethanol, and dried to give 2-((1-(4-(1-ethylpiperidin-4-yl)phenyl)cyclobutyl)amino) pyrimidine-5-carbohydrazide as white solid (0.110 g, 60.0%).

[Step 3] N'-(2,2-difluoroacetyl)-2-((1-(4-(1-ethylpiperidin-4-yl)phenyl)cyclobutyl)amino)pyrimidine-5-carbohydrazide

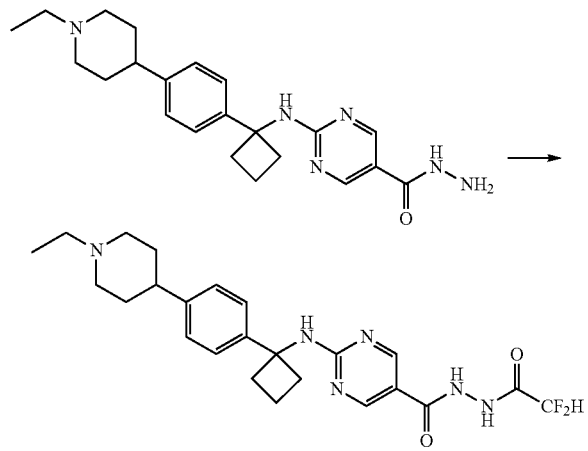

A solution of 2-((1-(4-(1-ethylpiperidin-4-yl)phenyl)cyclobutyl)amino)pyrimidine-5-carbohydrazide (0.110 g, 0.279 mmol) and triethylamine (0.078 mL, 0.558 mmol) in dichloromethane (5 mL) was mixed at the room temperature with 2,2-difluoroacetic anhydride (0.035 mL, 0.279 mmol), stirred at the same temperature for 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethanol/dichloromethane=0% to 20%) to give N'-(2,2-difluoroacetyl)-2-((1-(4-(1-ethylpiperidin-4-yl)phenyl)cyclobutyl)amino)pyrimidine-5-carbohydrazide as white solid (0.130 g, 98.7%).

[Step 4] Compound 2036

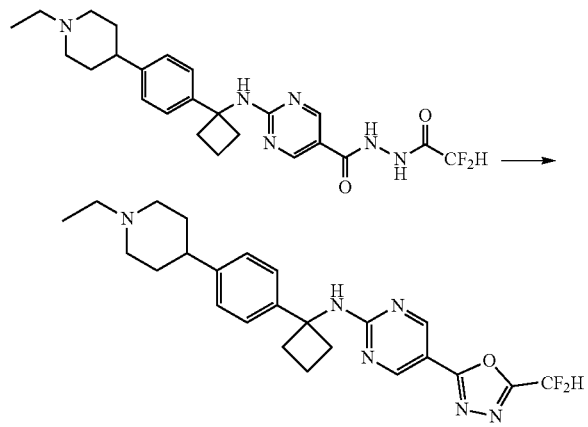

N'-(2,2-difluoroacetyl)-2-((1-(4-(1-ethylpiperidin-4-yl)phenyl)cyclobutyl)amino)pyrimidine-5-carbohydrazide (10.000 g, 21.162 mmol) and 1-methoxy-N-triethylammoniosulfonyl-methanimidate (Burgess reagent, 15.129 g, 63.487 mmol) in tetrahydrofuran (3 mL) was mixed at the room temperature and then heated at 150° C. under the microwaves for 30 min, and cooled down to the room temperature to terminate reaction. The reaction mixture was concentrated under the reduced pressure to remove the solvent. The concentrate was purified and concentrated by column chromatography (SiO$_2$, 4 g cartridge; methanol/dichloromethane=0% to 10%) to give 5-(5-(difluoromethyl)-1,3,4-oxadiazol-2-yl)-N-(1-(4-(1-ethylpiperidin-4-yl)phenyl)cyclobutyl)pyrimidin-2-amine as pale orange solid (0.007 g, 0.1%).

$^1$H NMR (400 MHz, CDCl$_3$) δ 8.89 (s, 2H), 7.47 (d, J=8.3 Hz, 2H), 7.24 (d, J=8.3 Hz, 2H), 7.02-6.76 (m, 1H), 6.61 (brs, 1H), 3.74 (d, J=11.3 Hz, 2H), 3.19-3.16 (m, 2H), 2.80-2.72 (m, 5H), 2.64-2.57 (m, 2H), 2.46-2.43 (m, 2H), 2.21-2.18 (m, 1H), 2.08-2.00 (m, 3H), 1.50 (t, J=7.3 Hz, 3H); LRMS (ES) m/z 455.5 (M$^+$+1).

Example 83: Compound 2037, 5-(5-(difluoromethyl)-1,3,4-oxadiazol-2-yl)-N-(1-(4-(1-isopropylpiperidin-4-yl)phenyl)cyclobutyl)pyrimidin-2-amine

[Step 1] Ethyl 2-((1-(4-(1-isopropylpiperidin-4-yl)phenyl)cyclobutyl)amino)pyrimidine-5-carboxylate

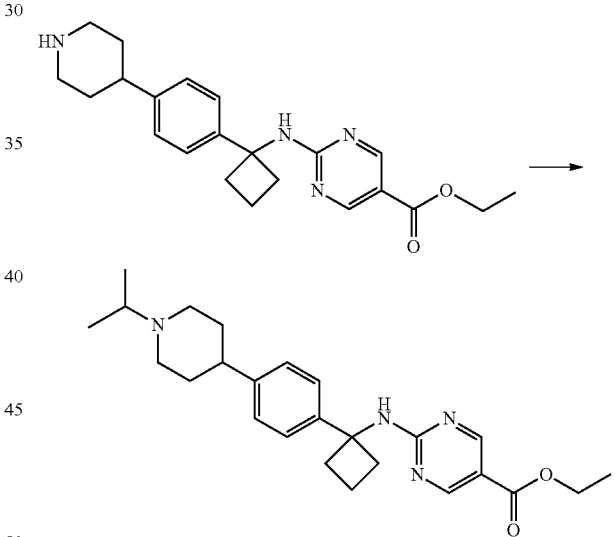

A solution of ethyl 2-((1-(4-(piperidin-4-yl)phenyl)cyclobutyl)amino)pyrimidine-5-carboxylate (0.300 g, 0.788 mmol), 2-iodopropane (0.087 mL, 0.867 mmol) and potassium carbonate (0.163 g, 1.183 mmol) in acetonitrile (10 mL) was heated at reflux for 17 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 20%) to give ethyl 2-((1-(4-(1-isopropylpiperidin-4-yl)phenyl)cyclobutyl)amino)pyrimidine-5-carboxylate as white solid (0.185 g, 55.5%).

[Step 2] 2-((1-(4-(1-isopropylpiperidin-4-yl)phenyl)cyclobutyl)amino)pyrimidine-5-carbohydrazide

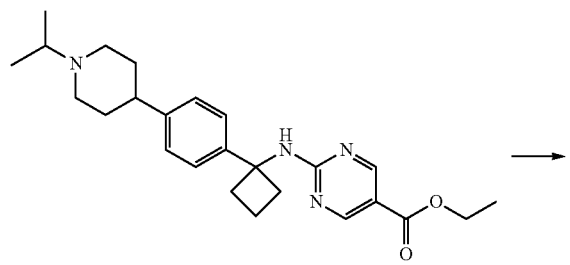

ethyl 2-((1-(4-(1-isopropylpiperidin-4-yl)phenyl)cyclobutyl)amino)pyrimidine-5-carboxylate (0.185 g, 0.438 mmol) and hydrazine monohydrate (0.426 mL, 8.756 mmol) were mixed at the room temperature in ethanol (4 mL) and then stirred at 100° C. for 17 hr, cooled down to the room temperature to terminate reaction. The concentrate was purified and concentrated by column chromatography (SiO$_2$, 12 g cartridge; ethyl acetate/hexane=0% to 30%) to give 2-((1-(4-(1-isopropylpiperidin-4-yl)phenyl)cyclobutyl)amino)pyrimidine-5-carbohydrazide as white solid (0.096 g, 53.7%).

[Step 3] N'-(2,2-difluoroacetyl)-2-((1-(4-(1-isopropylpiperidin-4-yl)phenyl)cyclobutyl)amino)pyrimidine-5-carbohydrazide

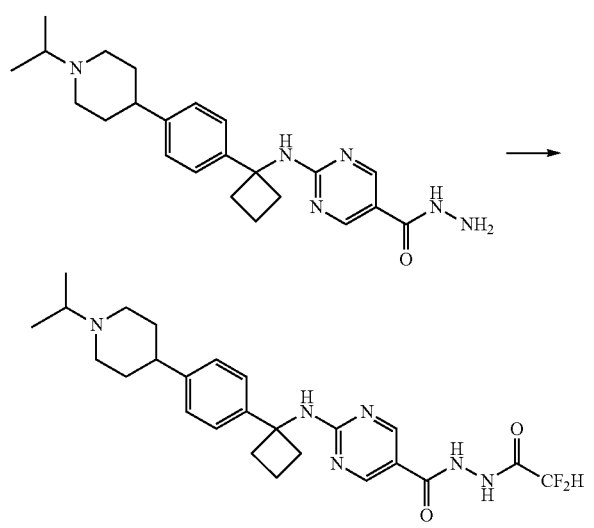

A solution of 2-((1-(4-(1-isopropylpiperidin-4-yl)phenyl)cyclobutyl)amino)pyrimidine-5-carbohydrazide (0.096 g, 0.235 mmol) and triethylamine (0.066 mL, 0.470 mmol) in dichloromethane (5 mL) was mixed at the room temperature with 2,2-difluoroacetic anhydride (0.029 mL, 0.235 mmol), stirred at the same temperature for 17 hr Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethanol/dichloromethane=0% to 20%) to give N'-(2,2-difluoroacetyl)-2-((1-(4-(1-isopropylpiperidin-4-yl)phenyl)cyclobutyl)amino)pyrimidine-5-carbohydrazide as white solid (0.110 g, 96.2%).

[Step 4] Compound 2037

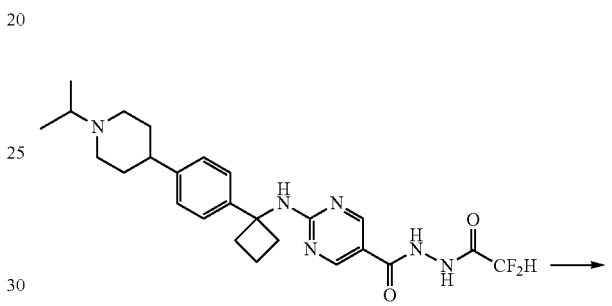

N'-(2,2-difluoroacetyl)-2-((1-(4-(1-isopropylpiperidin-4-yl)phenyl)cyclobutyl)amino)pyrimidine-5-carbohydrazide (0.500 g, 1.028 mmol) and 1-methoxy-N-triethylammoniosulfonyl-methanimidate (Burgess reagent, 0.735 g, 3.083 mmol) in tetrahydrofuran (3 mL) was mixed at the room temperature and then heated at 150° C. under the microwaves for 30 min, and cooled down to the room temperature to terminate reaction. The reaction mixture was concentrated under the reduced pressure to remove the solvent. The concentrate was purified and concentrated by column chromatography (SiO$_2$, 4 g cartridge; methanol/dichloromethane=0% to 10%) to give 5-(5-(difluoromethyl)-1,3,4-oxadiazol-2-yl)-N-(1-(4-(1-isopropylpiperidin-4-yl)phenyl)cyclobutyl)pyrimidin-2-amine as white solid (0.016 g, 3.3%).

$^1$H NMR (400 MHz, CDCl$_3$) δ 8.89 (s, 1H), 7.47 (d, J=8.3 Hz, 2H), 7.26 (d, J=8.3 Hz, 2H), 7.02-6.76 (m, 1H), 6.61 (s, 1H), 3.59-3.55 (m, 2H), 2.89-2.86 (m, 2H), 2.75-2.72 (m, 3H), 2.63-2.53 (m, 4H), 2.20-2.19 (m, 1H), 2.08-2.04 (m, 3H), 1.46 (d, J=6.7 Hz, 6H); LRMS (ES) m/z 469.5 (M$^+$+1).

Example 84. Compound 2038: 5-(5-(difluoromethyl)-1,3,4-oxadiazol-2-yl)-N-(1-(thiophen-3-yl)cyclobutyl)pyrimidin-2-amine

[Step 1] 2-methyl-N-(1-(thiophen-3-yl)cyclobutyl)propane-2-sulfinamide

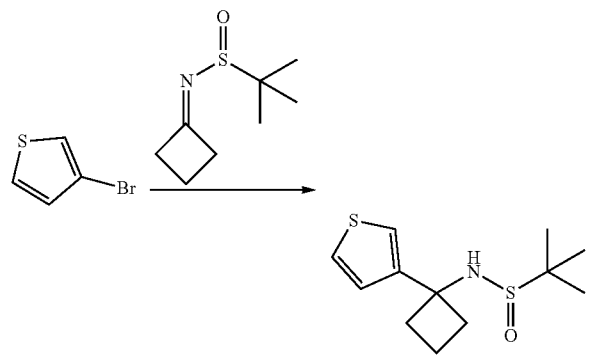

3-bromothiophene (0.460 mL, 4.907 mmol) and butyllithium (1.60 M solution in hexane, 3.067 mL, 4.907 mmol) were added to tetrahydrofuran (5 mL) at −78° C., and stirred at the same temperature for 30 min. N-cyclobutylidene-2-methylpropane-2-sulfinamide (0.425 g, 2.454 mmol) and boron trifluoro diethyl etherate (0.303 mL, 2.454 mmol) were added to the reaction mixture, and stirred for additional 1 hr. Then, saturated aqueous ammonium chloride solution was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; ethyl acetate/hexane=0% to 80%) to give 2-methyl-N-(1-(thiophen-3-yl)cyclobutyl)propane-2-sulfinamide as pale brown liquid (0.256 g, 20.3%).

[Step 2] 1-(thiophen-3-yl)cyclobutan-1-amine hydrochloride

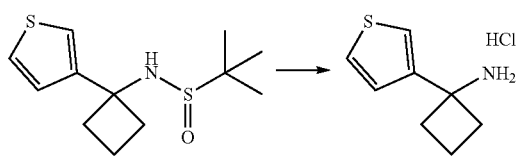 [SMILES: CC(C)(C)S(=O)NC1(c2ccsc2)CCC1 ; NC1(c2ccsc2)CCC1 ; Cl]

A solution of 2-methyl-N-(1-(thiophen-3-yl)cyclobutyl)propane-2-sulfinamide (0.263 g, 1.022 mmol) and hydrochloric acid (1.00 M solution in ethyl acetate, 2.043 mL, 2.043 mmol) in ethyl acetate (5 mL) prepared at the room temperature was stirred at the same temperature for 1 hr. The reaction mixture was concentrated under the reduced pressure to remove the solvent. The concentrate was diluted with ethyl acetate (5 mL) and hexane (5 mL) and stirred at the ambient temperature. The resulting precipitates were collected by filtration and dried to give 1-(thiophen-3-yl)cyclobutan-1-amine hydrochloride as yellow solid (0.122 g, 62.9%).

[Step 3] ethyl 2-((1-(thiophen-3-yl)cyclobutyl)amino)pyrimidine-5-carboxylate

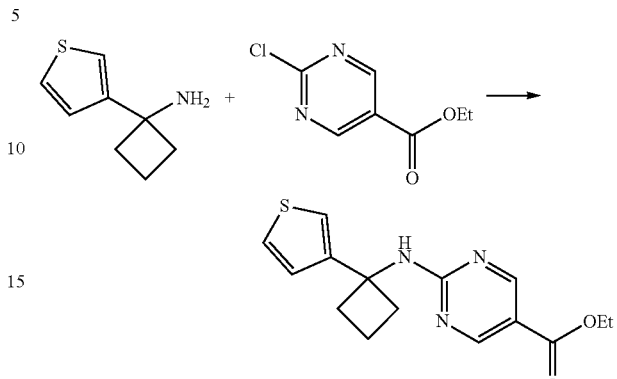

A solution of 1-(thiophen-3-yl)cyclobutan-1-amine hydrochloride (0.100 g, 0.653 mmol), ethyl 2-chloropyrimidine-5-carboxylate (0.122 g, 0.653 mmol) and N,N-diisopropylethylamine (0.227 mL, 1.305 mmol) in 1,4-dioxane (5 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO₂, 12 g cartridge; ethyl acetate/hexane=0% to 40%) to give ethyl 2-((1-(thiophen-3-yl)cyclobutyl)amino)pyrimidine-5-carboxylate as pale brown solid (0.044 g, 22.2%).

[Step 4] 2-((1-(thiophen-3-yl)cyclobutyl)amino)pyrimidine-5-carbohydrazide

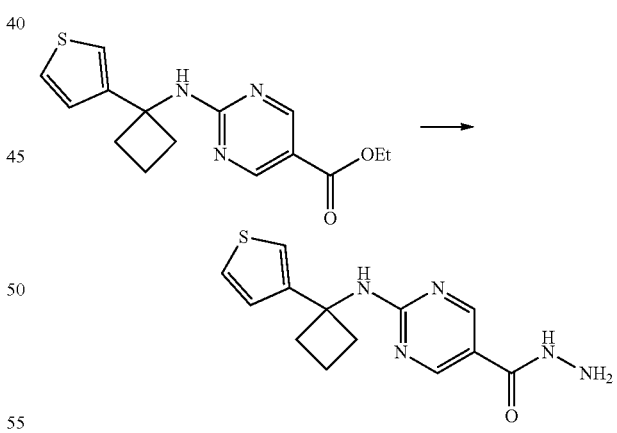

A solution of ethyl 2-((1-(thiophen-3-yl)cyclobutyl)amino)pyrimidine-5-carboxylate (0.050 g, 0.165 mmol) and hydrazine (50.00% solution in water, 0.207 mL, 3.296 mmol) in ethanol (3 mL) was stirred at 120° C. for 4 hr, and cooled down to the room temperature to terminate reaction. The reaction mixture was concentrated under the reduced pressure to remove the solvent. The crude product was used without further purification (2-((1-(thiophen-3-yl)cyclobutyl)amino)pyrimidine-5-carbohydrazide, 0.042 g, 88.1%, pale yellow solid).

291

[Step 5] N'-(2,2-difluoroacetyl)-2-((1-(thiophen-3-yl)cyclobutyl)amino)pyrimidine-5-carbohydrazide

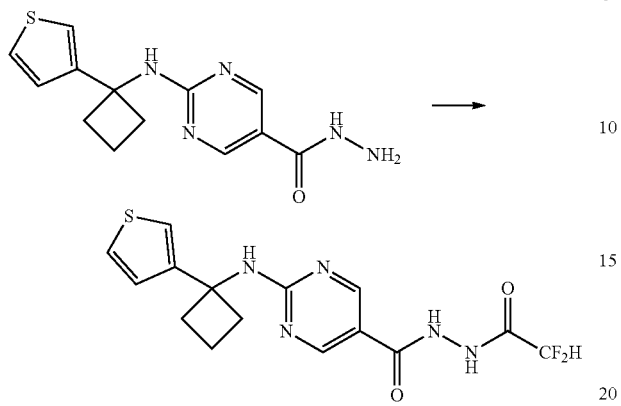

A solution of 2-((1-(thiophen-3-yl)cyclobutyl)amino)pyrimidine-5-carbohydrazide (0.042 g, 0.145 mmol), 2,2-difluoroacetic anhydride (0.018 mL, 0.145 mmol) and triethylamine (0.051 mL, 0.363 mmol) in dichloromethane (5 mL) prepared at the room temperature was stirred at the same temperature for 1 hr. The reaction mixture was concentrated under the reduced pressure to remove the solvent. The concentrate was purified and concentrated by column chromatography (SiO$_2$, 12 g cartridge; methanol/dichloromethane=0% to 20%) to give N'-(2,2-difluoroacetyl)-2-((1-(thiophen-3-yl)cyclobutyl)amino)pyrimidine-5-carbohydrazide as pale yellow solid (0.051 g, 95.6%).

[Step 6] Compound 2038

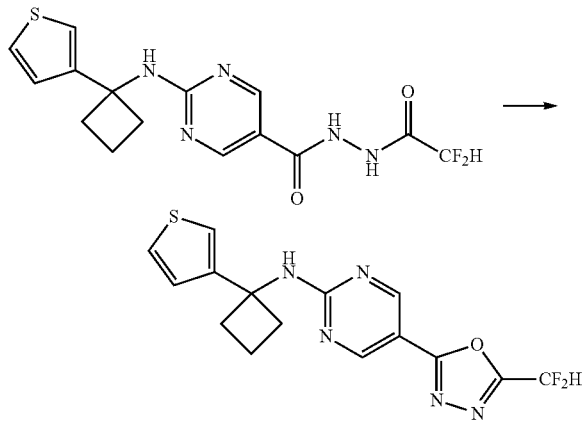

A mixture of N'-(2,2-difluoroacetyl)-2-((1-(thiophen-3-yl)cyclobutyl)amino)pyrimidine-5-carbohydrazide (0.051 g, 0.139 mmol) and 1-methoxy-N-triethylammoniosulfonylmethanimidate (Burgess reagent, 0.066 g, 0.278 mmol) in tetrahydrofuran (4 mL) was heated at 150° C. for 30 min under the microwaves, and cooled down to the room temperature to terminate reaction. The reaction mixture was concentrated under the reduced pressure to remove the solvent. Then, water (4 mL) was added to the reaction mixture, followed by extraction with dichloromethane (4 mL), and filtered through a plastic frit. The resulting organic layer was concentrated in vacuo. The concentrate was purified and concentrated by column chromatography (SiO$_2$, 4 g cartridge; ethyl acetate/hexane=0% to 40%) to give 5-(5-(difluoromethyl)-1,3,4-oxadiazol-2-yl)-N-(1-(thiophen-3-yl)cyclobutyl)pyrimidin-2-amine as pale yellow solid (0.032 g, 66.0%).

292

$^1$H NMR (400 MHz, CDCl$_3$) δ 8.94 (d, J=4.7 Hz, 2H), 7.20-7.17 (m, 1H), 7.10 (dd, J=3.6, 1.2 Hz, 1H), 7.03 (s, 0.25H), 6.96 (dd, J=5.1, 3.6 Hz, 1H), 6.90 (s, 0.5H), 6.77 (s, 0.25H), 6.35 (br, 1H), 2.81-2.64 (m, 4H), 2.20-2.02 (m, 2H); LRMS (ES) m/z 350.3 (M$^+$+1).

Example 85. Compound 2040: 5-(5-(difluoromethyl)-1,3,4-oxadiazol-2-yl)-N-(1-(thiophen-2-yl)cyclopropyl)pyrimidin-2-amine

[Step 1] 1-(thiophen-2-yl)cyclopropan-1-amine

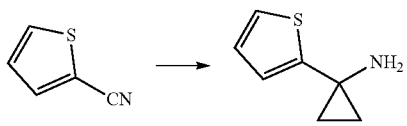 [SMILES: N#Cc1cccs1 ; NC1(c2cccs2)CC1]

To a stirred solution of thiophene-2-carbonitrile (1.709 mL, 18.323 mmol), titanium ethoxide (4.994 mL, 23.820 mmol) and ethylmagnesium bromide (1.00 M solution, 42.144 mL, 42.144 mmol) in 2-methoxy-2-methylpropane (MTBE, 100 mL) were added at −10° C., and the reaction mixture was stirred at the same temperature for 1 hr. Boron trifluoro diethyl etherate (4.523 mL, 36.647 mmol) were added to the reaction mixture, and stirred at the room temperature for additional 2 hr. The reaction was quenched at the room temperature by the addition of hydrochloric acid (1.00 M solution in water, 54.970 mL, 54.970 mmol) by stirring for 5 minutes. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give 1-(thiophen-2-yl)cyclopropan-1-amine as pale yellow solid (0.240 g, 9.4%).

[Step 2] ethyl 2-((1-(thiophen-2-yl)cyclopropyl)amino)pyrimidine-5-carboxylate

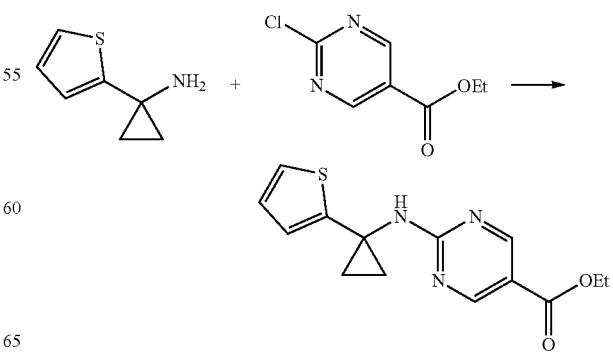

A solution of 1-(thiophen-2-yl)cyclopropan-1-amine (0.100 g, 0.718 mmol), ethyl 2-chloropyrimidine-5-carboxylate (0.134 g, 0.718 mmol) and N,N-diisopropylethylamine (0.250 mL, 1.437 mmol) in 1,4-dioxane (3 mL) was stirred at 90° C. for 5 hr, and cooled down to the room temperature to terminate reaction. The reaction mixture was concentrated under the reduced pressure to remove the solvent. The concentrate was purified and concentrated by column chromatography (SiO$_2$, 12 g cartridge; ethyl acetate/hexane=0% to 50%) to give ethyl 2-((1-(thiophen-2-yl)cyclopropyl)amino)pyrimidine-5-carboxylate as pale yellow solid (0.052 g, 19.8%).

[Step 3] 2-((1-(thiophen-2-yl)cyclopropyl)amino)pyrimidine-5-carbohydrazide

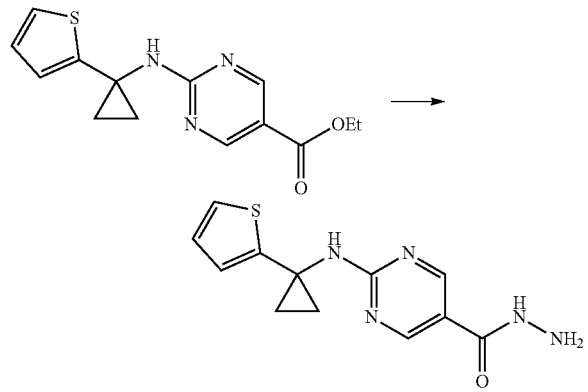

A solution of ethyl 2-((1-(thiophen-2-yl)cyclopropyl)amino)pyrimidine-5-carboxylate (0.050 g, 0.173 mmol) and hydrazine (50.00% solution in water, 0.217 mL, 3.456 mmol) in ethanol (3 mL) prepared at the room temperature was stirred at the same temperature for 18 hr, and concentrated under the reduced pressure to remove the solvent. The crude product was used without further purification (2-((1-(thiophen-2-yl)cyclopropyl)amino)pyrimidine-5-carbohydrazide, 0.044 g, 91.6%, pale yellow solid).

[Step 4] N'-(2,2-difluoroacetyl)-2-((1-(thiophen-2-yl)cyclopropyl)amino)pyrimidine-5-carbohydrazide

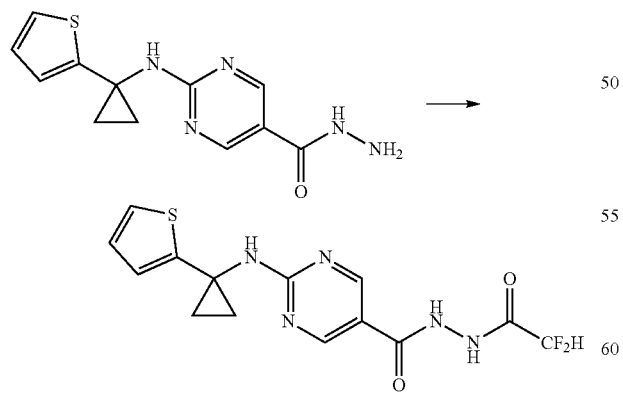

A solution of 2-((1-(thiophen-2-yl)cyclopropyl)amino)pyrimidine-5-carbohydrazide (0.044 g, 0.160 mmol), triethylamine (0.045 mL, 0.320 mmol) and 2,2-difluoroacetic anhydride (0.020 mL, 0.160 mmol) in dichloromethane (3 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; methanol/dichloromethane=5% to 20%) to give N'-(2,2-difluoroacetyl)-2-((1-(thiophen-2-yl)cyclopropyl)amino)pyrimidine-5-carbohydrazide as pale yellow solid (0.055 g, 97.4%).

[Step 5] Compound 2040

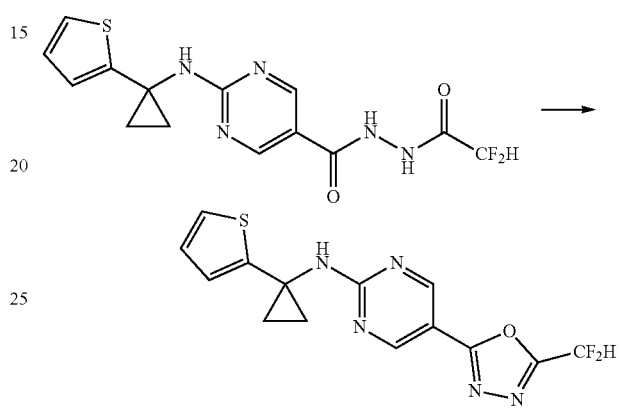

A mixture of N'-(2,2-difluoroacetyl)-2-((1-(thiophen-2-yl)cyclopropyl)amino)pyrimidine-5-carbohydrazide (0.055 g, 0.156 mmol) and 1-methoxy-N-triethylammoniosulfonylmethanimidate (Burgess reagent, 0.074 g, 0.311 mmol) in tetrahydrofuran (4 mL) was heated at 150° C. for 30 min under the microwaves, and cooled down to the room temperature to terminate reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 4 g cartridge; ethyl acetate/hexane=5% to 40%) to give 5-(5-(difluoromethyl)-1,3,4-oxadiazol-2-yl)-N-(1-(thiophen-2-yl)cyclopropyl)pyrimidin-2-amine as pale yellow solid (0.027 g, 51.7%).

$^1$H NMR (400 MHz, CDCl$_3$) δ 9.08 (s, 1H), 8.97 (s, 1H), 7.12 (dd, J=5.0, 1.4 Hz, 1H), 7.05 (s, 0.25H), 6.92 (tt, J=8.5, 2.5 Hz, 2H), 6.91 (s, 0.5H), 6.79 (s, 0.25H), 6.47 (br, 1H), 1.51-1.41 (m, 4H); LRMS (ES) m/z 336.0 (M$^+$+1).

Example 86: Compound 2041, 5-(5-(difluoromethyl)-1,3,4-oxadiazol-2-yl)-N-(1-(4-(piperidin-1-yl)phenyl)cyclobutyl)pyrimidin-2-amine

[Step 1] 1-(4-(piperidin-1-yl)phenyl)cyclobutane-1-carbonitrile

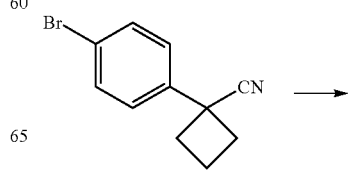

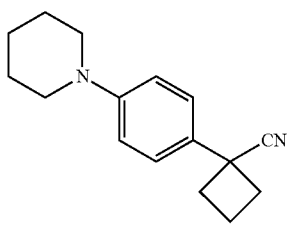

1-(4-bromophenyl)cyclobutane-1-carbonitrile (0.500 g, 2.118 mmol), piperadine (0.251 mL, 2.541 mmol), tris(dibenzylideneacetone)dipalladium (Pd$_2$(dba)$_3$, 0.097 g, 0.106 mmol), 2-dicyclohexylphosphino-2',4",6'-triisopropylbiphenyl (XPhos, 0.101 g, 0.212 mmol) and sodium tert-butoxide (0.407 g, 4.235 mmol) were mixed at the room temperature in toluene (4 mL), stirred at 100° C. for 17 hr, and cooled down to the room temperature to terminate reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 10%) to give 1-(4-(piperidin-1-yl)phenyl)cyclobutane-1-carbonitrile as brown oil (0.445 g, 87.4%).

[Step 2] 1-(4-(piperidin-1-yl)phenyl)cyclobutane-1-carboxamide

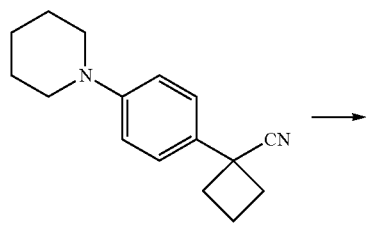

A solution of 1-(4-(piperidin-1-yl)phenyl)cyclobutane-1-carbonitrile (0.445 g, 1.851 mmol), sodium hydroxide (3.00 M solution, 0.617 mL, 1.851 mmol), hydrogen peroxide (30.00% solution, 0.567 mL, 5.554 mmol) and tetra-n-butylammonium bromide (0.006 g, 0.019 mmol) in methanol (10 mL) prepared at the room temperature was stirred at the same temperature for 18 hr, and concentrated under the reduced pressure to remove the solvent. The concentrate was purified and concentrated by column chromatography (SiO$_2$, 12 g cartridge; methanol/dichloromethane=0% to 5%) to give 1-(4-(piperidin-1-yl)phenyl)cyclobutane-1-carboxamide as pale yellow oil (0.168 g, 35.1%).

[Step 3] 1-(4-(piperidin-1-yl)phenyl)cyclobutan-1-amine hydrochloride

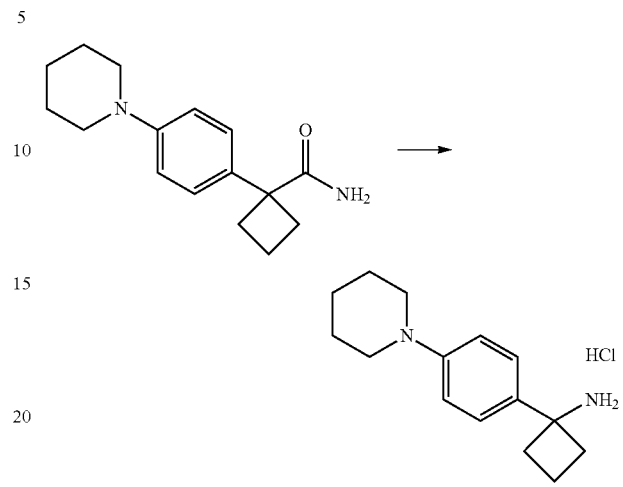

A solution of 1-(4-(piperidin-1-yl)phenyl)cyclobutane-1-carboxamide (0.168 g, 0.650 mmol), sodium hypochlorite (11.00% solution, 0.511 mL, 0.910 mmol) and sodium hydroxide (3.00 M solution in water, 0.607 mL, 1.821 mmol) in 1-butanol (5 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and was added hydrochloric acid (4.00 M solution in 1,4-dioxane, 0.163 mL, 0.650 mmol), and stirred at the ambient temperature. The resulting precipitates were collected by filtration, washed by ethyl acetate, and dried to give 1-(4-(piperidin-1-yl)phenyl)cyclobutan-1-amine hydrochloride as yellow solid as yellow solid (0.102 g, 58.8%).

[Step 4] Ethyl 2-((1-(4-(piperidin-1-yl)phenyl)cyclobutyl)amino)pyrimidine-5-carboxylate

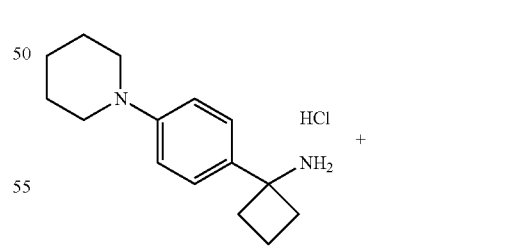

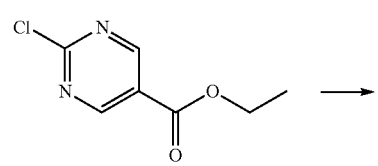

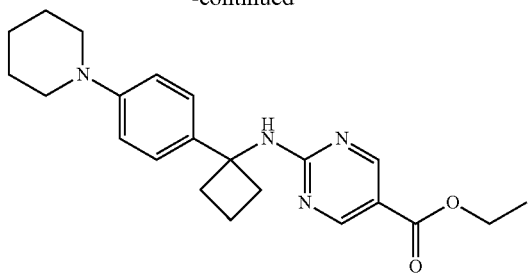

1-(4-(piperidin-1-yl)phenyl)cyclobutan-1-amine hydrochloride (0.102 g, 0.382 mmol), ethyl 2-chloropyrimidine-5-carboxylate (0.086 g, 0.459 mmol) and N,N-diisopropylethylamine (0.200 mL, 1.147 mmol) were mixed at the room temperature in 1,4-dioxane (4 mL) and then stirred at 110° C. for 17 hr, and cooled down to the room temperature to terminate reaction. The reaction mixture was concentrated under the reduced pressure to remove the solvent. The concentrate was purified and concentrated by column chromatography (SiO₂, 4 g cartridge; ethyl acetate/hexane=0% to 15%) to give ethyl 2-((1-(4-(piperidin-1-yl)phenyl)cyclobutyl)amino)pyrimidine-5-carboxylate as yellow solid (0.041 g, 28.2%).

[Step 5] 2-((1-(4-(piperidin-1-yl)phenyl)cyclobutyl)amino)pyrimidine-5-carbohydrazide

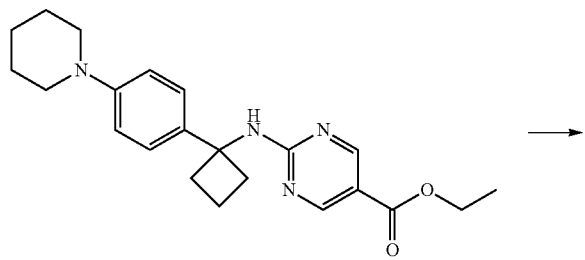

Ethyl 2-((1-(4-(piperidin-1-yl)phenyl)cyclobutyl)amino)pyrimidine-5-carboxylate (0.039 g, 0.102 mmol) and hydrazine monohydrate (0.100 mL, 2.050 mmol) were mixed at the room temperature in ethanol (2 mL) and then stirred at 110° C. for 17 hr, and cooled down to the room temperature to terminate reaction. The reaction mixture was concentrated under the reduced pressure to remove the solvent. The concentrate was diluted with ethanol (1 mL) and stirred at the ambient temperature. The resulting precipitates were collected by filtration, washed by ethanol, and dried to give 2-((1-(4-(piperidin-1-yl)phenyl)cyclobutyl)amino)pyrimidine-5-carbohydrazide as pale yellow solid (0.039 g, 103.8%).

[Step 6] N'-(2,2-difluoroacetyl)-2-((1-(4-(piperidin-1-yl)phenyl)cyclobutyl)amino)pyrimidine-5-carbohydrazide

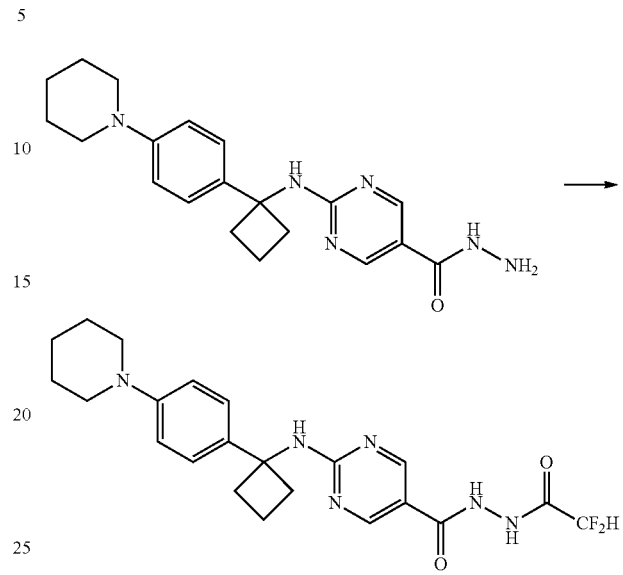

A solution of 2-((1-(4-(piperidin-1-yl)phenyl)cyclobutyl)amino)pyrimidine-5-carbohydrazide (0.039 g, 0.106 mmol) and triethylamine (0.044 mL, 0.319 mmol) in tetrahydrofuran (5 mL) was mixed at the room temperature with 2,2-difluoroacetic anhydride (0.019 g, 0.106 mmol), stirred at the same temperature for 17 hr, concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. N'-(2,2-difluoroacetyl)-2-((1-(4-(piperidin-1-yl)phenyl)cyclobutyl)amino)pyrimidine-5-carbohydrazide was used without further purification (0.045 g, 95.1%, yellow oil).

[Step 7] Compound 2041

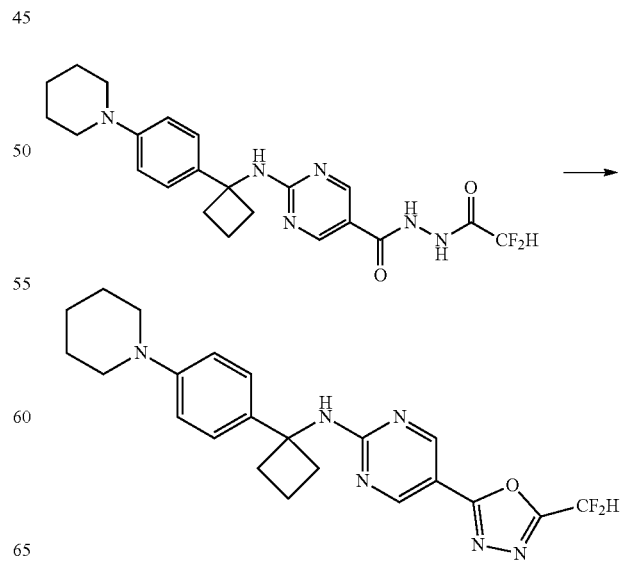

N'-(2,2-difluoroacetyl)-2-((1-(4-(piperidin-1-yl)phenyl) cyclobutyl)amino)pyrimidine-5-carbohydrazide (0.039 g, 0.088 mmol) and 1-methoxy-N-triethylammoniosulfonyl-methanimidate (Burgess reagent, 0.063 g, 0.263 mmol) in tetrahydrofuran (2 mL) was mixed at the room temperature and then heated at 150° C. under the microwaves for 30 min, and cooled down to the room temperature to terminate reaction. The reaction mixture was concentrated under the reduced pressure to remove the solvent. The concentrate was purified and concentrated by column chromatography (SiO₂, 4 g cartridge; ethyl acetate/hexane=10% to 30%) to give 5-(5-(difluoromethyl)-1,3,4-oxadiazol-2-yl)-N-(1-(4-(piperidin-1-yl)phenyl)cyclobutyl)pyrimidin-2-amine as pale brown solid (0.004 g, 9.6%).

$^1$H NMR (400 MHz, CDCl₃) δ 8.88 (s, 2H), 7.42 (d, J=7.4 Hz, 2H), 7.02-6.76 (m, 3H), 6.34 (s, 1H), 3.18 (brs, 4H), 2.75-2.68 (m, 2H), 2.63-2.58 (m, 2H), 2.17-2.14 (m, 1H), 2.00-1.94 (m, 1H), 1.74-1.60 (m, 6H); LRMS (ES) m/z 427.4 (M$^+$+1).

Example 87: Compound 2042, 5-(5-(difluoromethyl)-1,3,4-oxadiazol-2-yl)-N-(1-(2-(trifluoromethyl)phenyl)cyclobutyl)pyrimidin-2-amine

[Step 1] 1-(2-(Trifluoromethyl)phenyl)cyclobutane-1-carbonitrile

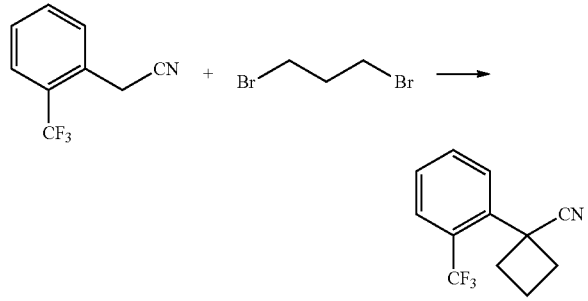

A solution of 2-(2-(trifluoromethyl)phenyl)acetonitrile (1.852 g, 10.000 mmol) and sodium hydride (60.00%, 0.880 g, 22.000 mmol) in N,N-dimethylformide (100 mL) was stirred at 0° C. for 10 min, and mixed with 1,3-dibromopropane (2.019 g, 10.000 mmol). The reaction mixture was stirred at the room temperature for additional 18 hr. Then, water was added to the reaction mixture, followed by extraction with ethyl acetate The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 5%) to give 1-(2-(trifluoromethyl)phenyl)cyclobutane-1-carbonitrile as colorless oil (0.542 g, 24.1%).

[Step 2] 1-(2-(Trifluoromethyl)phenyl)cyclobutane-1-carboxamide

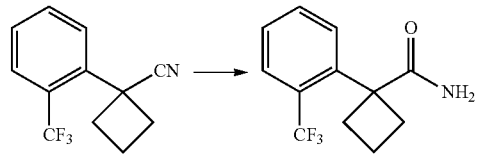 [SMILES: N#CC1(c2ccccc2C(F)(F)F)CCC1 ; NC(=O)C1(c2ccccc2C(F)(F)F)CCC1]

A solution of 1-(2-(trifluoromethyl)phenyl)cyclobutane-1-carbonitrile (0.542 g, 2.407 mmol), sodium hydroxide (3.00 M solution in water, 0.802 mL, 2.407 mmol), hydrogen peroxide (30.00% solution in water, 0.738 mL, 7.221 mmol) and tetra-n-butylammonium bromide (0.008 g, 0.024 mmol) in methanol (10 mL) prepared at the room temperature was stirred at the same temperature for 18 hr, concentrated under the reduced pressure to remove the solvent. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give 1-(2-(trifluoromethyl)phenyl)cyclobutane-1-carboxamide as white solid (0.288 g, 49.1%).

[Step 3] 1-(2-(Trifluoromethyl)phenyl)cyclobutan-1-amine hydrochloride

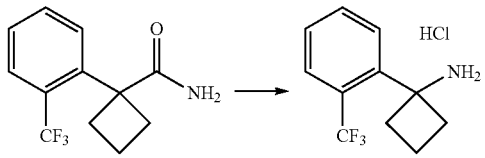 [SMILES: NC(=O)C1(c2ccccc2C(F)(F)F)CCC1 ; NC1(c2ccccc2C(F)(F)F)CCC1 ; Cl]

A solution of 1-(2-(trifluoromethyl)phenyl)cyclobutane-1-carboxamide (0.288 g, 1.182 mmol), sodium hypochlorite (10.00% solution in water, 1.018 mL, 1.655 mmol) and sodium hydroxide (3.00 M solution in water, 1.103 mL, 3.310 mmol) in 1-butanol (30 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate and hydrochloric acid (4.00 M solution in 1,4-dioxane, 0.443 mL, 1.773 mmol) and stirred at the ambient temperature. The resulting precipitates were collected by filtration and dried to give 1-(2-(trifluoromethyl)phenyl)cyclobutan-1-amine hydrochloride as white solid (0.100 g, 33.6%).

[Step 4] Ethyl 2-((1-(2-(trifluoromethyl)phenyl) cyclobutyl)amino)pyrimidine-5-carboxylate

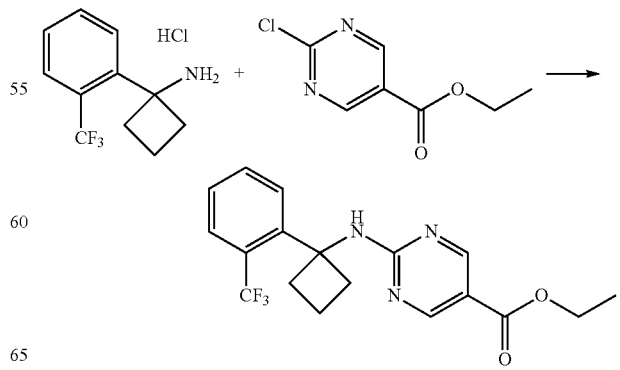

1-(2-(Trifluoromethyl)phenyl)cyclobutan-1-amine hydrochloride (0.100 g, 0.397 mmol), ethyl 2-chloropyrimidine-5-carboxylate (0.082 g, 0.437 mmol) and N,N-diisopropylethylamine (0.208 mL, 1.192 mmol) were mixed at the room temperature in 1,4-dioxane (3 mL) and then stirred at 100° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, washed by ethyl acetate and concentrated in vacuo. The concentrate was purified and concentrated by column chromatography (SiO$_2$, 4 g cartridge; ethyl acetate/hexane=0% to 5%) to give ethyl 2-((1-(2-(trifluoromethyl)phenyl)cyclobutyl)amino)pyrimidine-5-carboxylate as white solid (0.107 g, 73.4%).

[Step 5] 2-((1-(2-(Trifluoromethyl)phenyl)cyclobutyl)amino)pyrimidine-5-carbohydrazide

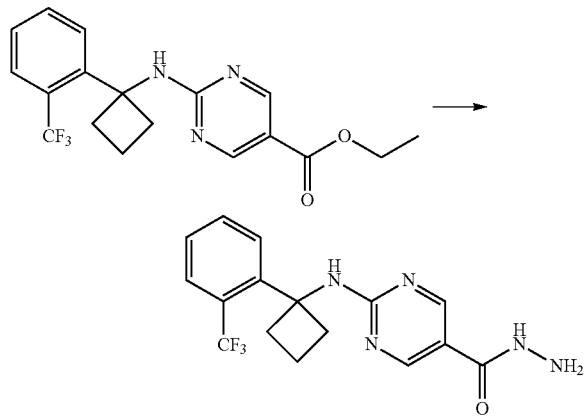

Ethyl 2-((1-(2-(trifluoromethyl)phenyl)cyclobutyl)amino)pyrimidine-5-carboxylate (0.107 g, 0.291 mmol) and hydrazine monohydrate (0.283 mL, 5.830 mmol) were mixed at the room temperature in ethanol (2 mL) and then stirred at 80° C. for 18 hr, and cooled down to the room temperature to terminate reaction. The reaction mixture was concentrated under the reduced pressure to remove the solvent. The crude product was used without further purification (2-((1-(2-(trifluoromethyl)phenyl)cyclobutyl)amino)pyrimidine-5-carbohydrazide, 0.102 g, 99.6%, white solid).

[Step 6] N'-(2,2-Difluoroacetyl)-2-((1-(2-(trifluoromethyl)phenyl)cyclobutyl)amino)pyrimidine-5-carbohydrazide

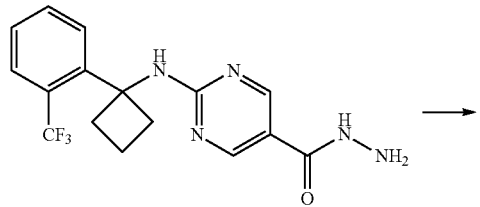

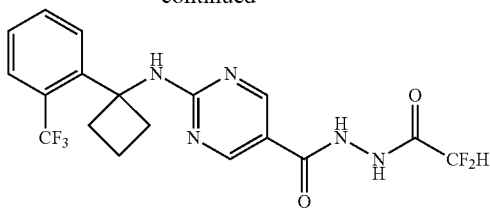

A solution of 2-((1-(2-(trifluoromethyl)phenyl)cyclobutyl)amino)pyrimidine-5-carbohydrazide (0.102 g, 0.290 mmol), triethylamine (0.081 mL, 0.581 mmol) and 2,2-difluoroacetic anhydride (0.036 mL, 0.290 mmol) in tetrahydrofuran (2 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$ filtered, and concentrated in vacuo. The concentrate was purified and concentrated by column chromatography (SiO$_2$, 4 g cartridge; ethyl acetate/hexane=0% to 50%) to give N'-(2,2-difluoroacetyl)-2-((1-(2-(trifluoromethyl)phenyl)cyclobutyl)amino)pyrimidine-5-carbohydrazide as white solid (0.029 g, 23.4%).

[Step 7] Compound 2042

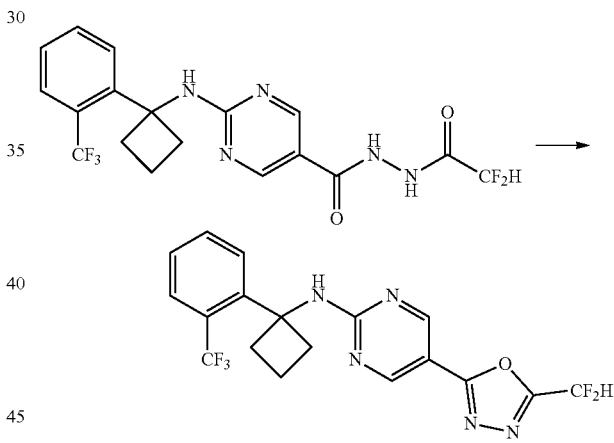

N'-(2,2-Difluoroacetyl)-2-((1-(2-(trifluoromethyl)phenyl)cyclobutyl)amino)pyrimidine-5-carbohydrazide (0.029 g, 0.068 mmol) and 1-methoxy-N-triethylammoniosulfonylmethanimidate (Burgess reagent, 0.024 g, 0.102 mmol) were mixed at the room temperature in tetrahydrofuran (1 mL) and then stirred at 80° C. for 18 hr, and cooled down to the room temperature to terminate reaction. The reaction mixture was concentrated under the reduced pressure to remove the solvent. The concentrate was purified and concentrated by column chromatography (SiO$_2$, 4 g cartridge; ethyl acetate/hexane=0% to 10%) to give 5-(5-(difluoromethyl)-1,3,4-oxadiazol-2-yl)-N-(1-(2-(trifluoromethyl)phenyl)cyclobutyl)pyrimidin-2-amine as colorless oil (0.008 g, 28.6%).

$^1$H NMR (400 MHz, CDCl$_3$) δ 8.85 (d, 2H, J=12.0 Hz), 7.94 (d, 1H, J=7.9 Hz), 7.64 (d, 1H, J=8.1 Hz), 7.55 (td, 1H, J=7.7, 0.7 Hz), 7.36 (t, 1H, J=7.6 Hz), 6.88 (t, 1H, J=51.7 Hz), 6.51 (s, 1H), 2.89-2.82 (m, 2H), 2.78-2.73 (m, 2H), 2.33-2.21 (m, 1H), 1.98-1.89 (m, 1H); LRMS (ES) m/z 412.3 (M$^+$+1).

Example 88: Compound 2043, 5-(5-(difluoromethyl)-1,3,4-oxadiazol-2-yl)-N-(1-(4-(trifluoromethyl)phenyl)cyclobutyl)pyrimidin-2-amine

[Step 1] 1-(4-(trifluoromethyl)phenyl)cyclobutane-1-carbonitrile

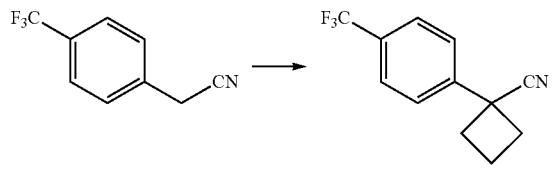 [SMILES: N#CCc1ccc(C(F)(F)F)cc1 ; N#CC1(c2ccc(C(F)(F)F)cc2)CCC1]

A solution of 2-(4-(trifluoromethyl)phenyl)acetonitrile (3.000 g, 16.203 mmol) and sodium hydride (60.00%, 1.426 g, 35.647 mmol) in N,N-dimethylformamide (20 mL) was stirred at 0° C. for 5 min, and mixed with 1,3-dibromopropane (1.645 mL, 16.203 mmol). The reaction mixture was stirred at the same temperature for additional 1 hr, quenched at 0° C. by the addition of water (10 mL, 10 min stirring), concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO2, 24 g cartridge; ethyl acetate/hexane=0% to 10%) to give 1-(4-(trifluoromethyl)phenyl)cyclobutane-1-carbonitrile as colorless oil (2.430 g, 66.6%).

[Step 2] 1-(4-(trifluoromethyl)phenyl)cyclobutane-1-carboxamide

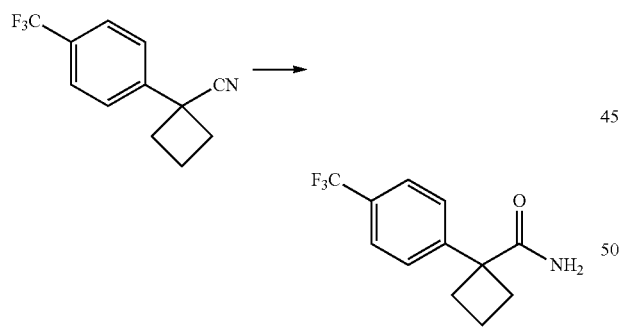

A solution of 1-(4-(trifluoromethyl)phenyl)cyclobutane-1-carbonitrile (2.430 g, 10.790 mmol), sodium hydroxide (3.00 M solution, 3.597 mL, 10.790 mmol), hydrogen peroxide (30.00% solution, 3.306 mL, 32.370 mmol) and tetra-n-butylammonium bromide (0.035 g, 0.108 mmol) in methanol (100 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (2.680 g, 102.1%, colorless oil).

[Step 3] 1-(4-(trifluoromethyl)phenyl)cyclobutan-1-amine hydrochloride

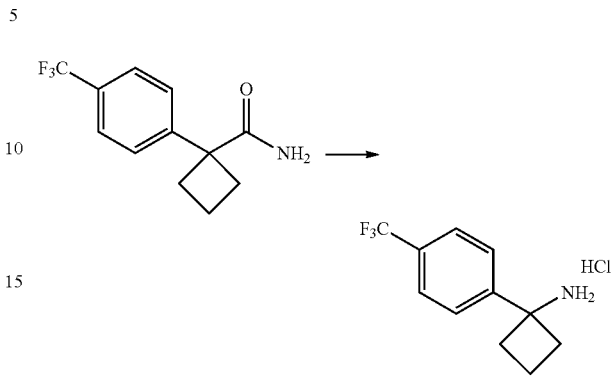

A solution of 1-(4-(trifluoromethyl)phenyl)cyclobutane-1-carboxamide (2.680 g, 11.018 mmol), sodium hypochlorite (11.00%, 10.439 g, 15.426 mmol) and sodium hydroxide (3.00 M solution in water, 10.284 mL, 30.851 mmol) and in 1-butanol (50 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and was added hydrochloric acid (4.00 M solution in 1,4-dioxane, 2.755 mL, 11.018 mmol) and stirred at the ambient temperature. The resulting precipitates were collected by filtration, washed by ethyl acetate, and dried to give 1-(4-(trifluoromethyl)phenyl)cyclobutan-1-amine hydrochloride as white solid (1.260 g, 45.4%).

[Step 4] Ethyl 2-((1-(4-(trifluoromethyl)phenyl)cyclobutyl)amino)pyrimidine-5-carboxylate

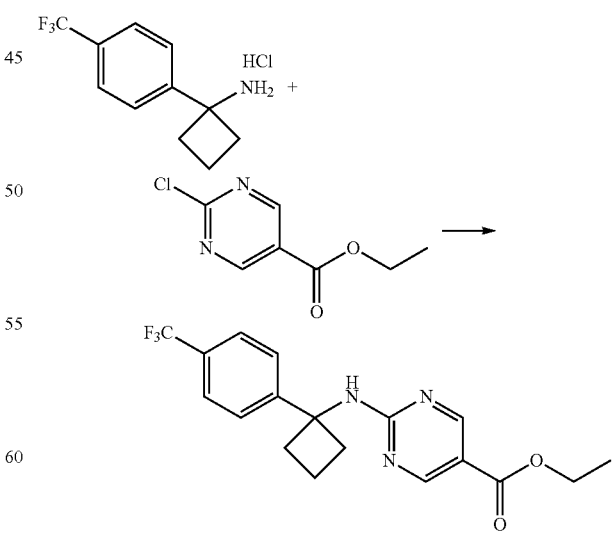

1-(4-(trifluoromethyl)phenyl)cyclobutan-1-amine hydrochloride (0.700 g, 2.781 mmol), ethyl 2-chloropyrimidine-5-carboxylate (0.571 g, 3.059 mmol) and N,N-diisopropylethylamine (1.453 mL, 8.344 mmol) were mixed at the room temperature in 1,4-dioxane (10 mL) and then stirred at 110° C. for 17 hr, and cooled down to the room temperature to terminate reaction. The reaction mixture was concentrated under the reduced pressure to remove the solvent. The residue was diluted with ethanol (5 mL) and stirred at the ambient temperature. The resulting precipitates were collected by filtration, washed by ethanol, and dried to give ethyl 2-((1-(4-(trifluoromethyl)phenyl)cyclobutyl)amino) pyrimidine-5-carboxylate as pale orange solid (0.557 g, 54.8%).

[Step 5] 2-((1-(4-(trifluoromethyl)phenyl)cyclobutyl)amino)pyrimidine-5-carbohydrazide

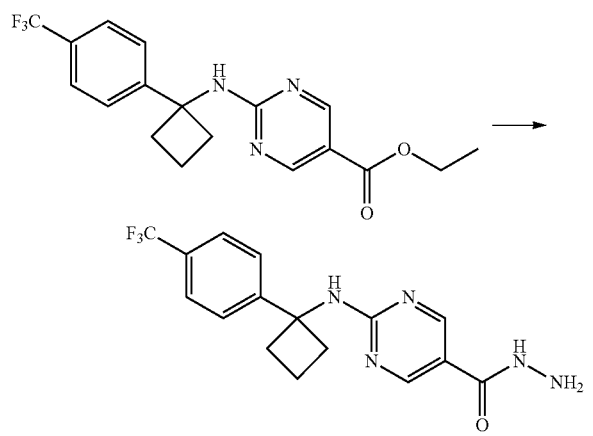

ethyl 2-((1-(4-(trifluoromethyl)phenyl)cyclobutyl)amino) pyrimidine-5-carboxylate (0.557 g, 1.525 mmol) and hydrazine monohydrate (1.482 mL, 30.490 mmol) were mixed at the room temperature in ethanol (8 mL) and then stirred at 110° C. for 17 hr, cooled down to the room temperature to terminate reaction. The precipitates were collected by filtration, washed by ethanol, and dried to give 2-((1-(4-(trifluoromethyl)phenyl)cyclobutyl)amino)pyrimidine-5-carbohydrazide as white solid (0.456 g, 85.1%).

[Step 6] N'-(2,2-difluoroacetyl)-2-((1-(4-(trifluoromethyl)phenyl)cyclobutyl)amino)pyrimidine-5-carbohydrazide

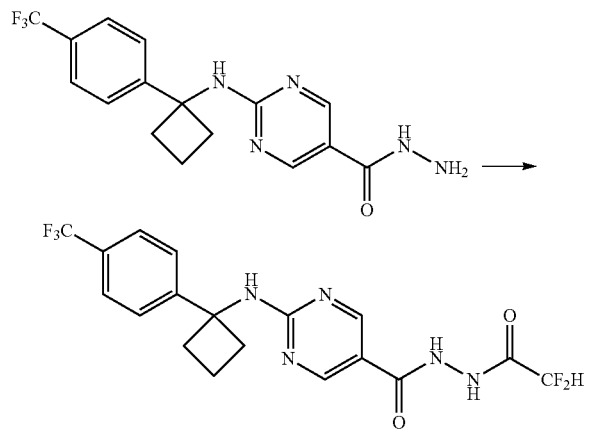

A solution of 2-((1-(4-(trifluoromethyl)phenyl)cyclobutyl)amino)pyrimidine-5-carbohydrazide (0.200 g, 0.569 mmol) and triethylamine (0.159 mL, 1.139 mmol) in tetrahydrofuran (8 mL) was mixed at the room temperature with 2,2-difluoroacetic anhydride (0.071 mL, 0.569 mmol), stirred at the same temperature for 18 hr, and concentrated under the reduced pressure to remove the solvent. The residue was diluted with dichloromethane (5 mL) and stirred at the ambient temperature. The resulting precipitates were collected by filtration, washed by dichloromethane, and dried to give N'-(2,2-difluoroacetyl)-2-((1-(4-(trifluoromethyl)phenyl)cyclobutyl)amino)pyrimidine-5-carbohydrazide as white solid (0.240 g, 98.2%).

[Step 7] Compound 2043

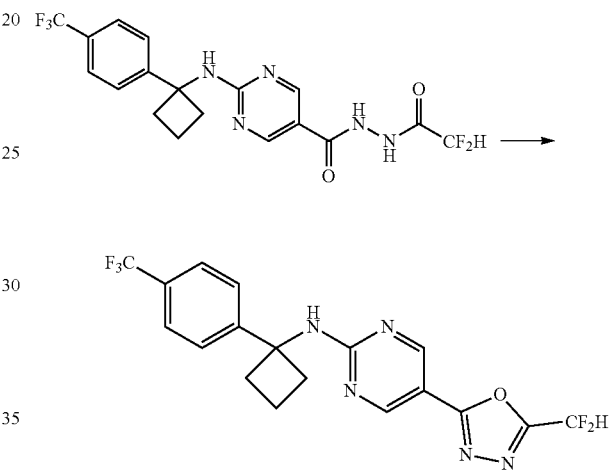

N'-(2,2-difluoroacetyl)-2-((1-(4-(trifluoromethyl)phenyl)cyclobutyl)amino)pyrimidine-5-carbohydrazide (0.240 g, 0.559 mmol) and 1-methoxy-N-triethylammoniosulfonyl-methanimidate (Burgess reagent, 0.400 g, 1.677 mmol) in tetrahydrofuran (4 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 15%) to give 5-(5-(difluoromethyl)-1,3,4-oxadiazol-2-yl)-N-(1-(4-(trifluoromethyl)phenyl)cyclobutyl)pyrimidin-2-amine as white solid (0.038 g, 16.5%).

$^1$H NMR (400 MHz, CDCl$_3$) δ 8.92 (s, 1H), 8.85 (s, 1H), 7.64 (d, J=8.5 Hz, 2H), 7.60 (d, J=8.5 Hz, 2H), 7.02-6.76 (m, 1H), 6.54 (s, 1H), 2.80-2.73 (m, 2H), 2.64-2.57 (m, 2H), 2.30-2.21 (m, 1H), 2.08-2.04 (m, 1H); LRMS (ES) m/z 412.1 (M$^+$+1).

Example 89: Compound 2044, 5-(5-(trifluoromethyl)-1,3,4-oxadiazol-2-yl)-N-(1-(4-(trifluoromethyl)phenyl)cyclobut yl)pyrimidin-2-amine

[Step 1] N'-(2,2,2-trifluoroacetyl)-2-((1-(4-(trifluoromethyl)phenyl)cyclobutyl)amino)pyrimidine-5-carbohydrazide

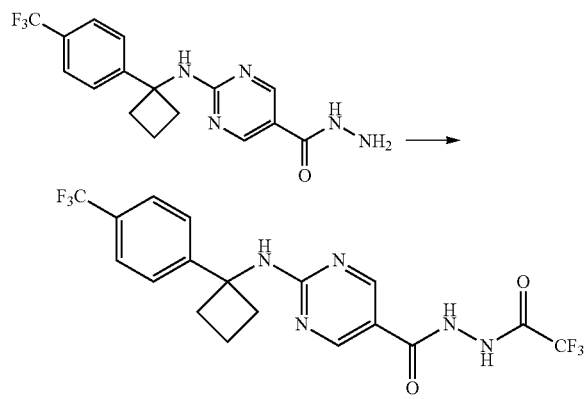

A solution of 2-((1-(4-(trifluoromethyl)phenyl)cyclobutyl)amino)pyrimidine-5-carbohydrazide (0.200 g, 0.569 mmol) and triethylamine (0.159 mL, 1.139 mmol) in tetrahydrofuran (8 mL) was mixed at the room temperature with trifluoroacetic anhydride (0.080 mL, 0.569 mmol), stirred at the same temperature for 18 hr, and concentrated under the reduced pressure to remove the solvent. The residue was diluted with dichloromethane (5 mL) and stirred at the ambient temperature. The resulting precipitates were collected by filtration, washed by dichloromethane, and dried to give N'-(2,2,2-trifluoroacetyl)-2-((1-(4-(trifluoromethyl)phenyl)cyclobutyl)amino)pyrimidine-5-carbohydrazide as white solid (0.097 g, 38.1%).

[Step 2] Compound 2044

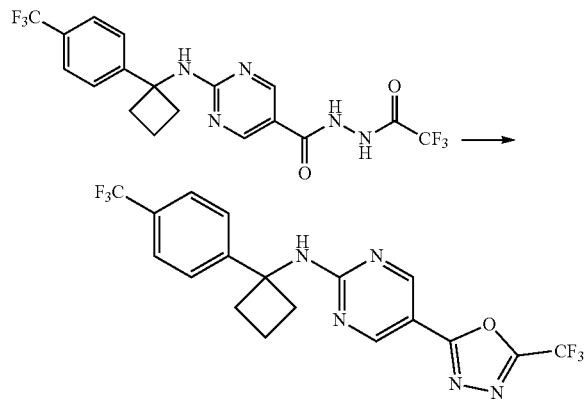

N'-(2,2,2-trifluoroacetyl)-2-((1-(4-(trifluoromethyl)phenyl)cyclobutyl)amino)pyrimidine-5-carbohydrazide (0.097 g, 0.217 mmol) and 1-methoxy-N-triethylammoniosulfonylmethanimidate (Burgess reagent, 0.155 g, 0.651 mmol) in tetrahydrofuran (4 mL) was mixed at the room temperature and then heated at the same temperature under the microwaves for 30 min, concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 15%) to give 5-(5-(trifluoromethyl)-1,3,4-oxadiazol-2-yl)-N-(1-(4-(trifluoromethyl)phenyl)cyclobut yl)pyrimidin-2-amine as pale orange solid (0.009 g, 9.7%).
$^1$H NMR (400 MHz, CDCl$_3$) δ 8.47 (s, 1H), 8.40 (s, 1H), 7.62-7.58 (m, 4H), 6.47 (s, 1H), 2.77-2.70 (m, 2H), 2.60-2.53 (m, 2H), 2.23-2.20 (m, 1H), 2.05-2.02 (m, 1H); LRMS (ES) m/z 430.3 (M$^+$+1).

Example 90: Compound 2045, 5-(5-(difluoromethyl)-1,3,4-oxadiazol-2-yl)-N-(1-(3,4-difluorophenyl)cyclobutyl)pyrimidin-2-amine

[Step 1]
1-(3,4-difluorophenyl)cyclobutane-1-carbonitrile

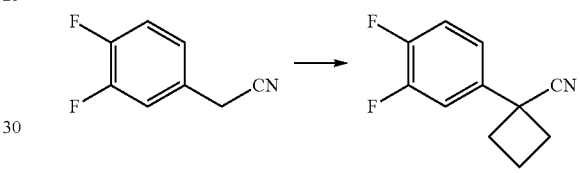

To a stirred solution of 2-(3,4-difluorophenyl)acetonitrile (7.730 g, 50.480 mmol) in N,N-dimethylformide (50 mL) was added at 0° C. sodium hydride (60.00%, 5.047 g, 126.200 mmol). The reaction mixture was stirred at the same temperature for 30 min, treated at the room temperature with 1,3-dibromopropane (10.191 g, 50.480 mmol), stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 20%) to give 1-(3,4-difluorophenyl)cyclobutane-1-carbonitrile as Colorless oil (5.100 g, 52.3%).

[Step 2]
1-(3,4-difluorophenyl)cyclobutane-1-carboxamide

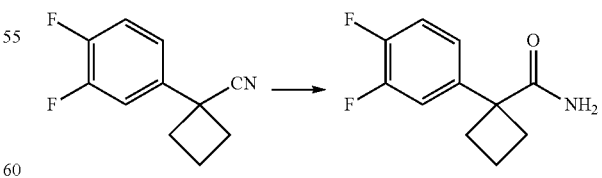

A solution of 1-(3,4-difluorophenyl)cyclobutane-1-carbonitrile (5.100 g, 26.398 mmol), sodium hydroxide (3.00 M solution in H$_2$O, 26.398 mL, 79.193 mmol), hydrogen peroxide (30.00% solution, 8.089 mL, 79.193 mmol) and tetra-n-butylammonium bromide (0.851 g, 2.640 mmol) in methanol (30 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 40%) to give 1-(3,4-difluorophenyl)cyclobutane-1-carboxamide as White solid (3.200 g, 57.4%).

[Step 3] 1-(3,4-difluorophenyl)cyclobutan-1-amine hydrochloride

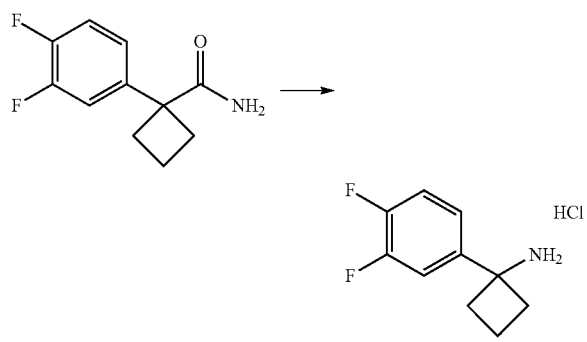

A solution of 1-(3,4-difluorophenyl)cyclobutane-1-carboxamide (3.200 g, 15.151 mmol), sodium hydroxide (3.00 M solution in H₂O, 15.151 mL, 45.452 mmol), sodium hypochlorite (1.692 g, 22.726 mmol) in 1-butanol (20 mL) prepared at the room temperature was stirred at the same temperature for 12 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate and then was added hydrochloric acid (1.00 M solution in EA, 15.151 mL, 15.151 mmol) stirred at the ambient temperature. The resulting precipitates were collected by filtration, washed by hexane and dried to give give 1-(3,4-difluorophenyl)cyclobutan-1-amine hydrochloride as White solid (1.000 g, 30.0%).

[Step 4] ethyl 2-((1-(3,4-difluorophenyl)cyclobutyl)amino)pyrimidine-5-carboxylate

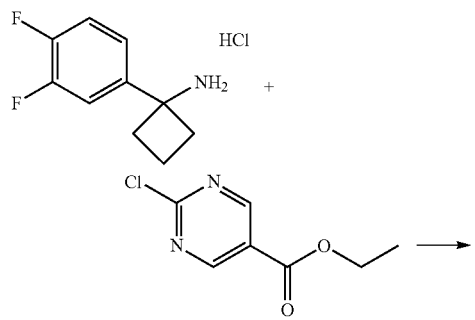

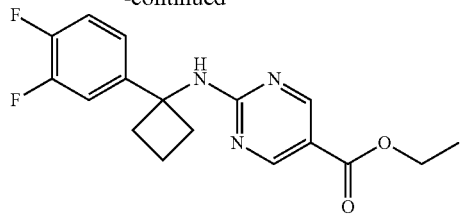

1-(3,4-difluorophenyl)cyclobutane-1-amine hydrochloride (1.000 g, 4.552 mmol), ethyl 2-chloropyrimidine-5-carboxylate (0.849 g, 4.552 mmol) and N,N-diisopropylethylamine (1.982 mL, 11.381 mmol) were mixed at 80° C. 1,4-dioxane (10 mL) and then stirred at the same temperature for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give ethyl 2-((1-(3,4-difluorophenyl)cyclobutyl)amino)pyrimidine-5-carboxylate as white solid (1.200 g, 79.1%).

[Step 5] 2-((1-(3,4-difluorophenyl)cyclobutyl)amino)pyrimidine-5-carbohydrazide

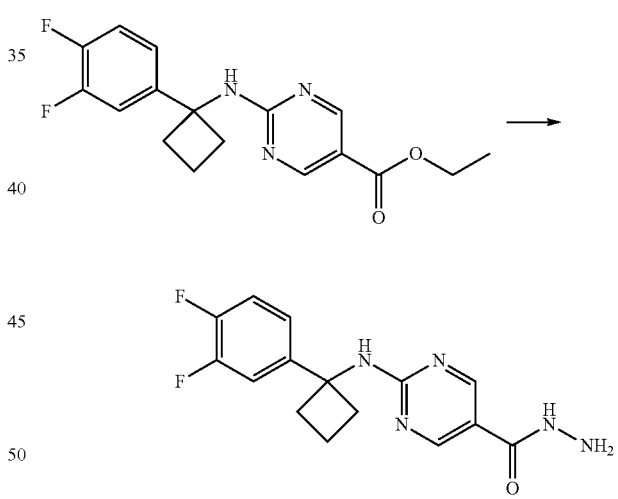

A mixture of ethyl 2-((1-(3,4-difluorophenyl)cyclobutyl)amino)pyrimidine-5-carboxylate (1.200 g, 3.600 mmol) and Hydrazine monohydrate (3.499 mL, 71.999 mmol) in ethanol (10 mL) was heated at 120° C. for 1 hr under the microwaves, and cooled down to the room temperature to terminate reaction. Then, water was added to the reaction mixture, followed by extraction with ethyl acetate The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give 2-((1-(3,4-difluorophenyl)cyclobutyl)amino)pyrimidine-5-carbohydrazide as White solid (0.740 g, 64.4%).

[Step 6] N'-(2,2-difluoroacetyl)-2-((1-(3,4-difluorophenyl)cyclobutyl)amino)pyrimidine-5-carbohydrazide

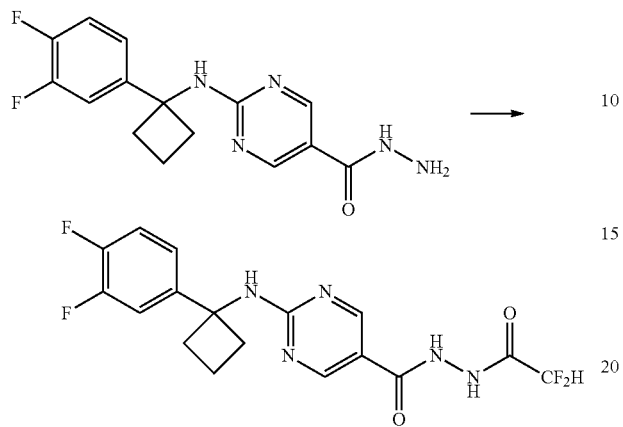

A solution of 2-((1-(3,4-difluorophenyl)cyclobutyl)amino)pyrimidine-5-carbohydrazide (0.720 g, 2.255 mmol), 2,2-difluoroacetic anhydride (0.280 mL, 2.255 mmol) and triethylamine (0.471 mL, 3.382 mmol) in dichloromethane (10 mL) prepared at the room temperature was stirred at the same temperature for 1 hr. The precipitates were collected by filtration, washed by hexane, and dried to give N'-(2,2-difluoroacetyl)-2-((1-(3,4-difluorophenyl)cyclobutyl)amino)pyrimidine-5-carbohydrazide as White solid (0.660 g, 73.7%).

[Step 7] Compound 2045

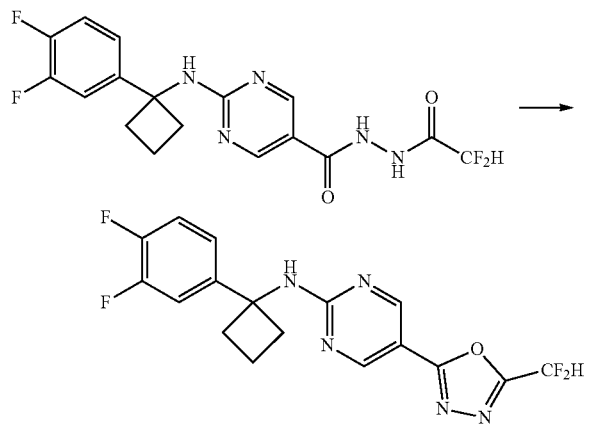

A mixture of N'-(2,2-difluoroacetyl)-2-((1-(3,4-difluorophenyl)cyclobutyl)amino)pyrimidine-5-carbohydrazide (0.700 g, 1.762 mmol) and 1-methoxy-N-triethylammoniosulfonyl-methanimidate (Burgess reagent, 0.630 g, 2.643 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(3,4-difluorophenyl)cyclobutyl)pyrimidin-2-amine as White solid (0.520 g, 77.8%).

$^1$H NMR (400 MHz, CDCl$_3$) δ 8.90 (s, 2H), 7.75-7.31 (m, 1H), 7.25-7.21 (m, 1H), 7.15-7.08 (m, 1H), 7.03 (s, 0.25H), 6.90 (s, 0.5H), 6.77 (s, 0.25H), 6.35 (s, 1H), 2.74-2.67 (m, 2H), 2.61-2.54 (m, 2H), 2.22-2.17 (m, 1H), 2.05-2.00 (m, 1H).; LRMS (ES) m/z 380.1 (M$^+$+1).

Example 91. Compound 2046: 5-(5-(difluoromethyl)-1,3,4-oxadiazol-2-yl)-N-(1-(4-fluoro-3-morpholinophenyl)cyclobutyl)pyrimidin-2-amine

[Step 1] 2-(3-bromo-4-fluorophenyl)acetonitrile

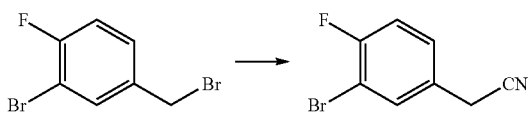 [SMILES: Fc1ccc(CBr)cc1Br ; N#CCc1ccc(F)c(Br)c1]

A solution of 2-bromo-4-(bromomethyl)-1-fluorobenzene (20.000 g, 74.649 mmol), potassium cyanide (14.583 g, 223.947 mmol) and tetra-n-butylammonium bromide (2.406 g, 7.465 mmol) in dichloromethane (80 mL)/water (80 mL) prepared at the room temperature was stirred at the same temperature for 4 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The concentrate was purified and concentrated by column chromatography (SiO$_2$, 120 g cartridge; ethyl acetate/hexane=0% to 20%) to give 2-(3-bromo-4-fluorophenyl)acetonitrile as colorless liquid (14.200 g, 88.9%).

[Step 2] 1-(3-bromo-4-fluorophenyl)cyclobutane-1-carbonitrile

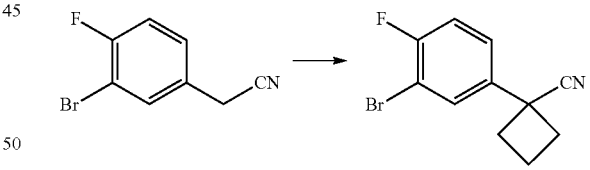

To a stirred solution of 2-(3-bromo-4-fluorophenyl)acetonitrile (10.000 g, 46.720 mmol) in N,N-dimethylformide (50 mL) was added at 0° C. sodium hydride (60.00%, 4.671 g, 116.801 mmol). The reaction mixture was stirred at the same temperature for 30 min, treated at the room temperature with 1,3-dibromopropane (4.764 mL, 46.720 mmol), stirred for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 30%) to give 1-(3-bromo-4-fluorophenyl)cyclobutane-1-carbonitrile as colorless liquid (6.958 g, 58.6%).

313

[Step 3] 1-(3-bromo-4-fluorophenyl)cyclobutane-1-carboxamide

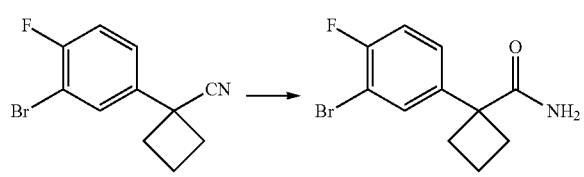 [SMILES: N#CC1(c2ccc(F)c(Br)c2)CCC1 ; NC(=O)C1(c2ccc(F)c(Br)c2)CCC1]

A solution of 1-(3-bromo-4-fluorophenyl)cyclobutane-1-carbonitrile (6.200 g, 24.400 mmol), sodium hydroxide (3.00 M solution in water, 2.033 mL, 6.100 mmol), hydrogen peroxide (30.00%, 8.300 g, 73.200 mmol) and tetra-n-butylammonium bromide (0.393 g, 1.220 mmol) in methanol (100 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 40 g cartridge; ethyl acetate/hexane=30% to 80%) to give 1-(3-bromo-4-fluorophenyl)cyclobutane-1-carboxamide as white solid (6.421 g, 96.7%).

[Step 4]
1-(3-bromo-4-fluorophenyl)cyclobutan-1-amine hydrochloride

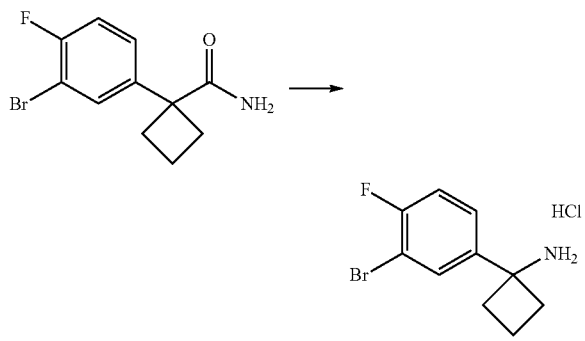

A solution of 1-(3-bromo-4-fluorophenyl)cyclobutane-1-carboxamide (7.420 g, 27.267 mmol), sodium hypochlorite (9.78%, 29.055 g, 38.174 mmol) and sodium hydroxide (3.00 M solution in water, 25.450 mL, 76.349 mmol) in 1-butanol (60 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was diluted with hydrochloric acid (7.531 mL) and stirred at the ambient temperature. The resulting precipitates were collected by filtration, washed by ethyl acetate, and dried to give 1-(3-bromo-4-fluorophenyl)cyclobutan-1-amine hydrochloride as white solid (5.284 g, 69.1%).

314

[Step 5] tert-butyl (1-(3-bromo-4-fluorophenyl)cyclobutyl)carbamate

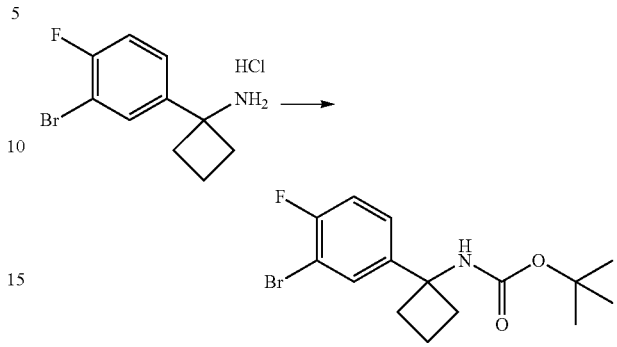

A solution of 1-(3-bromo-4-fluorophenyl)cyclobutan-1-amine hydrochloride (2.500 g, 8.910 mmol) and N,N-diisopropylethylamine (3.104 mL, 17.821 mmol) in tetrahydrofuran (50 mL) was mixed at the room temperature with di-tert-butyl dicarbonate (2.139 g, 9.801 mmol). The reaction mixture was stirred at the same temperature for 24 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 80 g cartridge; ethyl acetate/hexane=10% to 50%) to give tert-butyl (1-(3-bromo-4-fluorophenyl)cyclobutyl)carbamate as white solid (1.355 g, 44.2%).

[Step 6] tert-butyl (1-(4-fluoro-3-morpholinophenyl)cyclobutyl)carbamate

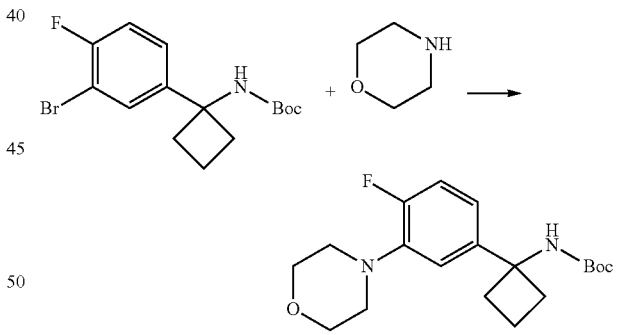

A mixture of tert-butyl (1-(3-bromo-4-fluorophenyl)cyclobutyl)carbamate (0.300 g, 0.872 mmol), morpholine (0.226 mL, 2.615 mmol), cesium carbonate (0.852 g, 2.615 mmol), tris(dibenzylideneacetone)dipalladium ($Pd_2(dba)_3$, 0.040 g, 0.044 mmol) and 2-dicyclohexylphosphino-2',4'',6'-triisopropylbiphenyl (XPhos, 0.042 g, 0.087 mmol) in toluene (5 mL) was heated at reflux for 12 hr, and cooled down to the ambient temperature to terminate reaction, filtered through a celite pad to remove solids. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography (SiO$_2$, 12 g cartridge; ethyl acetate/hexane=0% to 30%) to give tert-butyl (1-(4-fluoro-3-morpholinophenyl)cyclobutyl)carbamate as brown solid (0.220 g, 72.0%).

[Step 7] 1-(4-fluoro-3-morpholinophenyl)cyclobutan-1-amine hydrochloride

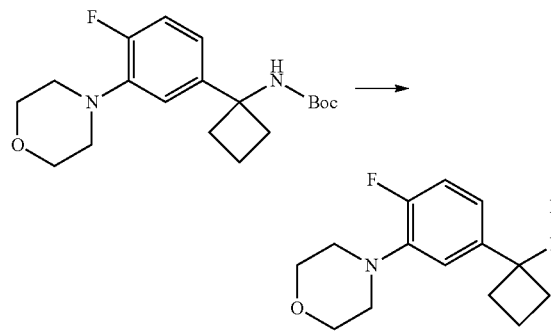

A solution of tert-butyl (1-(4-fluoro-3-morpholinophenyl)cyclobutyl)carbamate (0.220 g, 0.628 mmol) and hydrochloric acid (1.00 M solution in ethyl acetate, 1.883 mL, 1.883 mmol) in methanol (3 mL) prepared at the room temperature was stirred at the same temperature for 2 hr, and concentrated under the reduced pressure to remove the solvent. The residue was diluted with ethyl acetate (5 mL) and hexane (1 mL) and stirred at the ambient temperature. The resulting precipitates were collected by filtration, washed by hexane, and dried to give 1-(4-fluoro-3-morpholinophenyl)cyclobutan-1-amine hydrochloride as brown solid (0.180 g, 100.0%).

[Step 8] ethyl 2-((1-(4-fluoro-3-morpholinophenyl)cyclobutyl)amino)pyrimidine-5-carboxylate

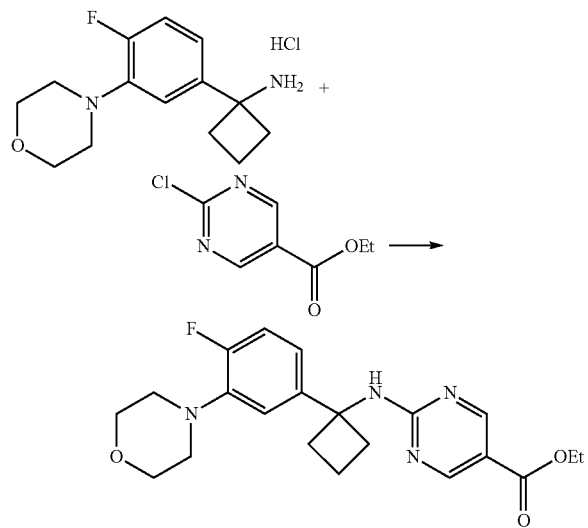

A solution of 1-(4-fluoro-3-morpholinophenyl)cyclobutan-1-amine hydrochloride (0.190 g, 0.663 mmol), ethyl 2-chloropyrimidine-5-carboxylate (0.124 g, 0.663 mmol) and N,N-diisopropylethylamine (0.288 mL, 1.656 mmol) in 1,4-dioxane (5 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO$_2$, 24 g cartridge; ethyl acetate/hexane=10% to 60%) to give ethyl 2-((1-(4-fluoro-3-morpholinophenyl)cyclobutyl)amino)pyrimidine-5-carboxylate as pale yellow solid (0.123 g, 46.4%).

[Step 9] 2-((1-(4-fluoro-3-morpholinophenyl)cyclobutyl)amino)pyrimidine-5-carbohydrazide

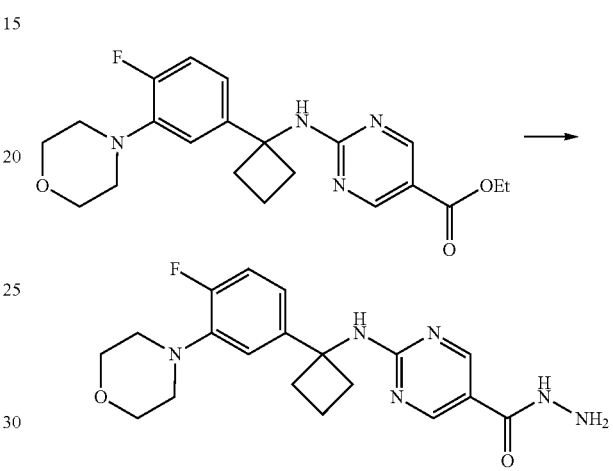

A solution of ethyl 2-((1-(4-fluoro-3-morpholinophenyl)cyclobutyl)amino)pyrimidine-5-carboxylate (0.123 g, 0.307 mmol) and hydrazine (50.00% solution in water, 0.386 mL, 6.143 mmol) in ethanol (4 mL) was stirred at 120° C. for 12 hr, and cooled down to the room temperature to terminate reaction. The reaction mixture was concentrated under the reduced pressure to remove the solvent. The crude product was used without further purification (2-((1-(4-fluoro-3-morpholinophenyl)cyclobutyl)amino)pyrimidine-5-carbohydrazide, 0.108 g, 91.0%, white solid).

[Step 10] N'-(2,2-difluoroacetyl)-2-((1-(4-fluoro-3-morpholinophenyl)cyclobutyl)amino)pyrimidine-5-carbohydrazide

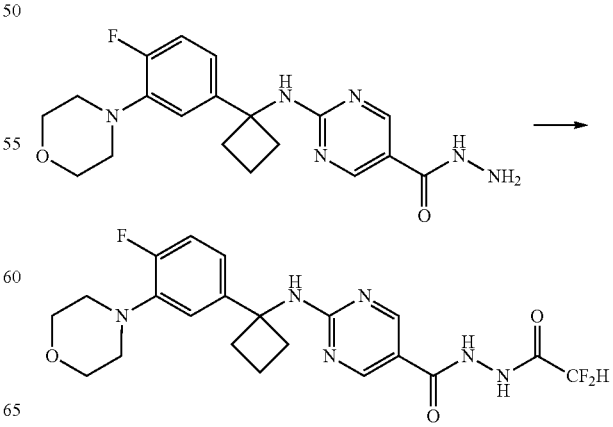

A solution of 2-((1-(4-fluoro-3-morpholinophenyl)cyclobutyl)amino)pyrimidine-5-carbohydrazide (0.108 g, 0.279 mmol), 2,2-difluoroacetic anhydride (0.035 mL, 0.279 mmol) and triethylamine (0.097 mL, 0.699 mmol) in dichloromethane (5 mL) prepared at the room temperature was stirred at the same temperature for 1 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; methanol/dichloromethane=0% to 30%) to give N'-(2,2-difluoroacetyl)-2-((1-(4-fluoro-3-morpholinophenyl)cyclobutyl)amino)pyrimidine-5-carbohydrazide as yellow liquid (0.107 g, 82.7%).

[Step 11] Compound 2046

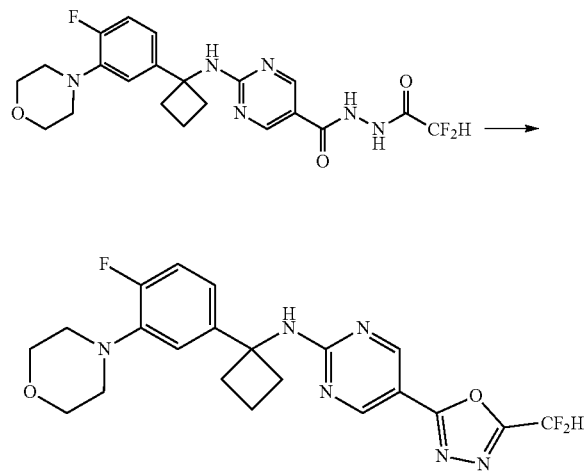

A mixture of N'-(2,2-difluoroacetyl)-2-((1-(4-fluoro-3-morpholinophenyl)cyclobutyl)amino)pyrimidine-5-carbohydrazide (0.100 g, 0.215 mmol) and 1-methoxy-N-triethylammoniosulfonyl-methanimidate (Burgess reagent, 0.054 g, 0.226 mmol) in tetrahydrofuran (3.5 mL) was heated at 150° C. for 30 min under the microwaves, and cooled down to the room temperature to terminate reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 4 g cartridge; ethyl acetate/hexane=10% to 60%) to give 5-(5-(difluoromethyl)-1,3,4-oxadiazol-2-yl)-N-(1-(4-fluoro-3-morpholinophenyl)cyclo butyl)pyrimidin-2-amine as white form (0.066 g, 68.7%).

$^1$H NMR (400 MHz, CDCl$_3$) δ 8.89 (s, 2H), 7.11-7.06 (m, 2H), 7.05-6.95 (m, 1H), 7.03 (s, 0.25H), 6.90 (s, 0.5H), 6.77 (s, 0.25H), 6.43 (br, 1H), 3.91-3.85 (m, 2H), 3.12-3.07 (m, 2H), 2.71 (tdd, J=8.0, 6.3, 4.2 Hz, 2H), 2.66-2.57 (m, 2H), 2.24-2.13 (m, 1H), 1.98 (tdd, J=10.0, 6.9, 3.8 Hz, 1H); LRMS (ES) m/z 445.3 (M$^+$+1).

Example 92: Compound 2047, 5-(5-(difluoromethyl)-1,3,4-oxadiazol-2-yl)-N-(1-(2-methoxyphenyl)cyclopropyl)pyrimidin-2-amine

[Step 1] 1-(2-methoxyphenyl)cyclopropan-1-amine hydrochloride

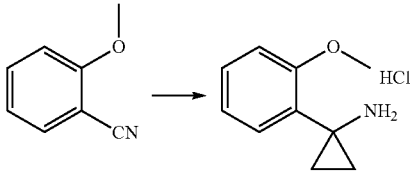

A solution of 2-methoxybenzonitrile (5.000 g, 37.552 mmol), Ethyl magnesiumbromide (1.00 M solution, 93.879 mL, 93.879 mmol) and titanium ethoxide (11.810 mL, 56.327 mmol) in 2-methoxy-2-methylpropane (MTBE, 30 mL) was stirred at 0° C. for 1 hr, and mixed with boron trifluoride diethyl etherate (9.269 mL, 75.103 mmol). The reaction mixture was stirred at the room temperature for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and then was added hydrochloric acid (1.00 M solution in EA, 37.552 mL, 37.552 mmol) stirred at the ambient temperature. The resulting precipitates were collected by filtration, washed by hexane and dried to give 1-(2-methoxyphenyl)cyclopropan-1-amine hydrochloride as White solid (1.000 g, 13.3%).

[Step 2] ethyl 2-((1-(2-methoxyphenyl)cyclopropyl)amino)pyrimidine-5-carboxylate

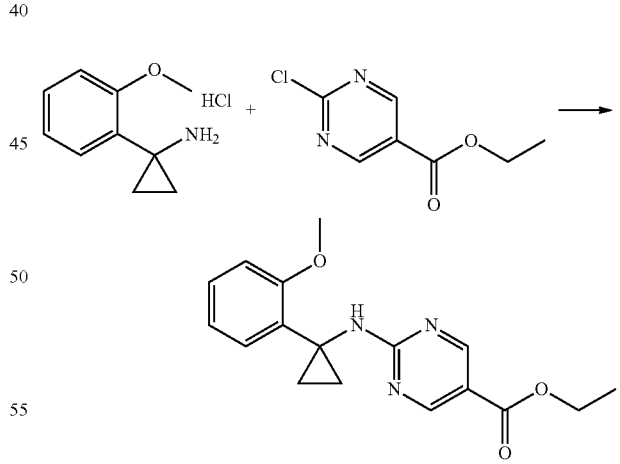

A solution of 1-(2-methoxyphenyl)cyclopropan-1-amine hydrochloride (0.500 g, 2.504 mmol), ethyl 2-chloropyrimidine-5-carboxylate (0.467 g, 2.504 mmol) and N,N-diisopropylethylamine (1.090 mL, 6.260 mmol) in 1,4-dioxane (20 mL) was stirred at 80° C. for 12 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give ethyl 2-((1-(2-methoxyphenyl)cyclopropyl)amino)pyrimidine-5-carboxylate as White solid (0.650 g, 82.8%).

[Step 3] 2-((1-(2-methoxyphenyl)cyclopropyl)amino)pyrimidine-5-carbohydrazide

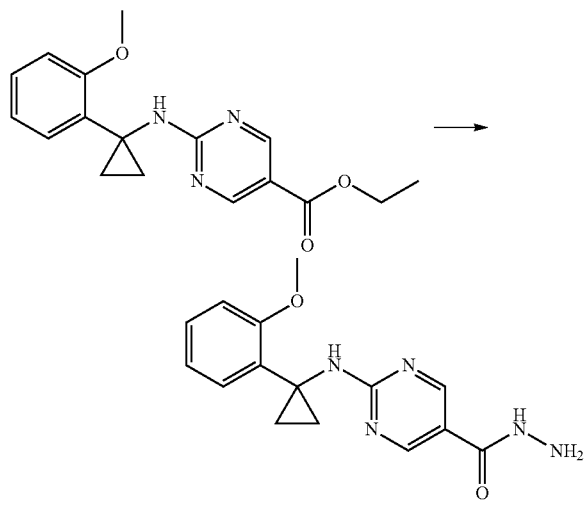

A mixture of ethyl 2-((1-(2-methoxyphenyl)cyclopropyl)amino)pyrimidine-5-carboxylate (0.500 g, 1.596 mmol) and hydrazine monohydrate (1.551 mL, 31.912 mmol) in ethanol (10 mL) was heated at 120° C. for 1 hr under the microwaves, cooled down to the room temperature to terminate reaction. The precipitates were collected by filtration, washed by hexane, and dried to give 2-((1-(2-methoxyphenyl)cyclopropyl)amino)pyrimidine-5-carbohydrazide as white solid (0.255 g, 53.4%).

[Step 4] N'-(2,2-difluoroacetyl)-2-((1-(2-methoxyphenyl)cyclopropyl)amino)pyrimidine-5-carbohydrazide

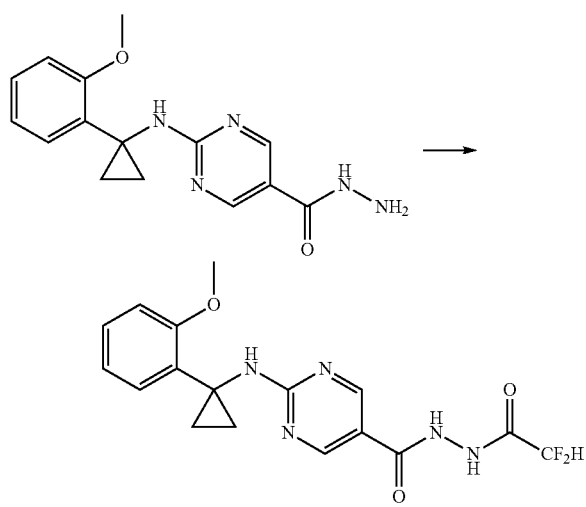

A solution of 2-((1-(2-methoxyphenyl)cyclopropyl)amino)pyrimidine-5-carbohydrazide (0.255 g, 0.852 mmol), 2,2-difluoroacetic anhydride (0.106 mL, 0.852 mmol) and triethylamine (0.178 mL, 1.278 mmol) in dichloromethane (10 mL) prepared at the room temperature was stirred at the same temperature for 1 hr. The precipitates were collected by filtration, washed by hexane, and dried to give N'-(2,2-difluoroacetyl)-2-((1-(2-methoxyphenyl)cyclopropyl)amino)pyrimidine-5-carbohydrazide as White solid (0.300 g, 93.3%).

[Step 5] Compound 2047

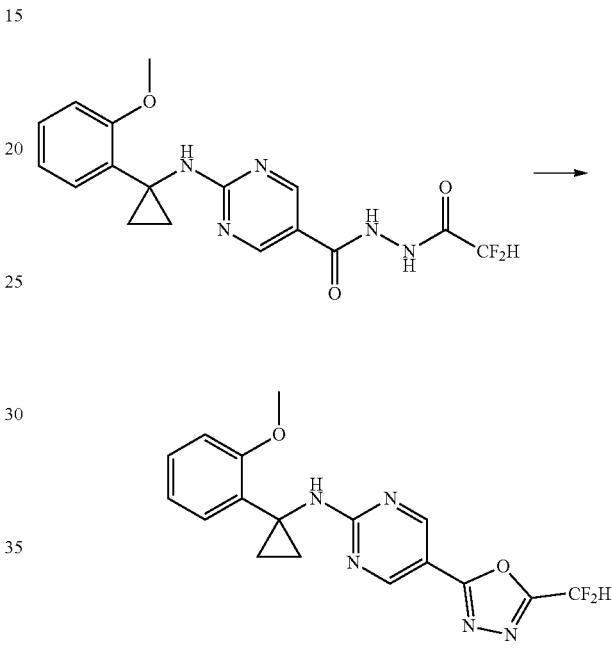

A mixture of N'-(2,2-difluoroacetyl)-2-((1-(2-methoxyphenyl)cyclopropyl)amino)pyrimidine-5-carbohydrazide (0.300 g, 0.795 mmol) and 1-methoxy-N-triethylammoniosulfonyl-methanimidate (Burgess reagent, 0.284 g, 1.193 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give 5-(5-(difluoromethyl)-1,3,4-oxadiazol-2-yl)-N-(1-(2-methoxyphenyl)cyclopropyl)pyrimidin-2-amine as White solid (0.200 g, 70.0%).

¹H NMR (400 MHz, CDCl₃) δ 9.01-8.87 (m, 2H), 7.61 (dd, J=7.5, 1.7 Hz, 1H), 7.27-7.23 (m, 1H), 7.03 (s, 0.25H), 6.90 (s, 0.5H), 6.77 (s, 0.25H), 6.98 (s, 1H), 6.93-6.85 (m, 2H), 3.89 (s, 3H), 1.28-1.23 (m, 4H).; LRMS (ES) m/z 360.3 (M⁺+1).

Example 93: Compound 2048, 5-(5-(difluoromethyl)-1,3,4-oxadiazol-2-yl)-N-(1-(3-methoxyphenyl)cyclopropyl)pyrimidin-2-amine

[Step 1] 1-(3-methoxyphenyl)cyclopropran-1-1-amine hydrochloride

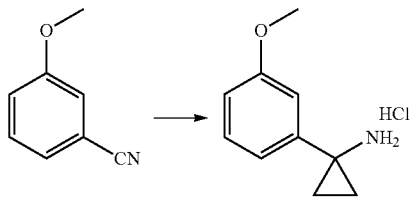

A solution of 3-methoxybenzonitrile (5.000 g, 37.552 mmol), Ethyl magnesiumbromide (1.00 M solution, 93.879 mL, 93.879 mmol) and titanium ethoxide (11.810 mL, 56.327 mmol) in 2-methoxy-2-methylpropane (MTBE, 30 mL) was stirred at 0° C. for 1 hr, and mixed with boron trifluoride diethyl etherate (9.269 mL, 75.103 mmol). The reaction mixture was stirred at the room temperature for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate (20 mL) and then was added hydrogen chloride (1.00 M solution in EA, 37.552 mL, 37.552 mmol) stirred at the ambient temperature. The resulting precipitates were collected by filtration, washed by hexane and dried to give 1-(3-methoxyphenyl)cyclopropan-1-amine hydrochloride as White solid (0.850 g, 11.3%).

[Step 2] ethyl 2-((1-(3-methoxyphenyl)cyclopropyl)amino)pyrimidine-5-carboxylate

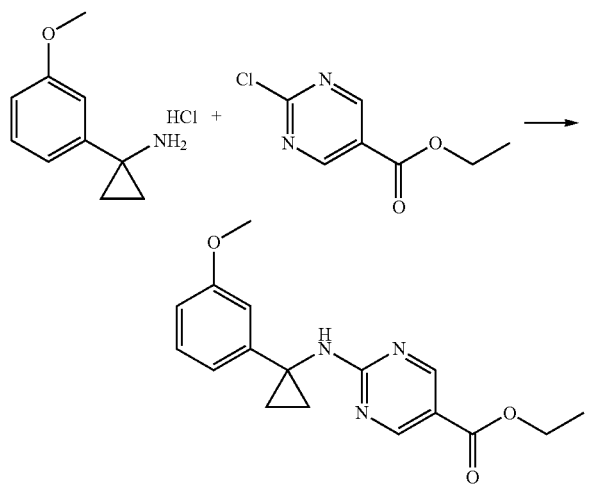

A solution of 1-(3-methoxyphenyl)cyclopropan-1-amine hydrochloride (0.750 g, 3.756 mmol), ethyl 2-chloropyrimidine-5-carboxylate (0.771 g, 4.132 mmol) and N,N-diisopropylethylamine (1.636 mL, 9.390 mmol) in 1,4-dioxane (20 mL) was stirred at 80° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(3-methoxyphenyl)cyclopropyl)amino)pyrimidine-5-carboxylate as White solid (0.850 g, 72.2%).

[Step 3] 2-((1-(3-methoxyphenyl)cyclopropyl)amino)pyrimidine-5-carbohydrazide

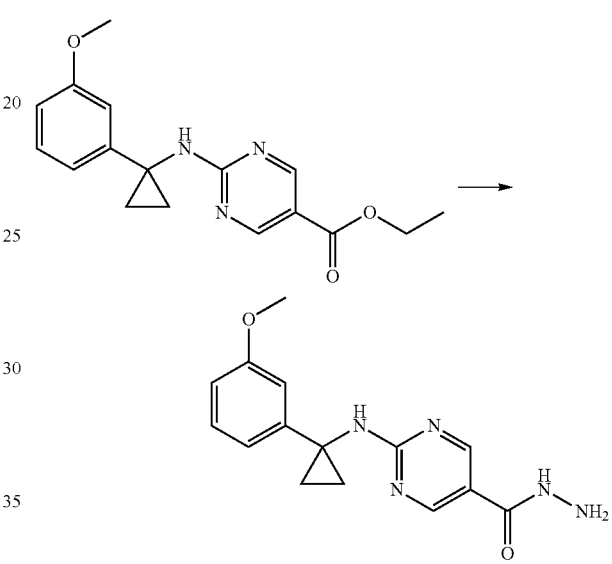

A mixture of ethyl 2-((1-(3-methoxyphenyl)cyclopropyl)amino)pyrimidine-5-carboxylate (0.500 g, 1.596 mmol) and Hydrazine monohydrate (1.551 mL, 31.912 mmol) in ethanol (10 mL) was heated at 120° C. for 1 hr under the microwaves, cooled down to the room temperature to terminate reaction. The precipitates were collected by filtration, washed by hexane, and dried to give 2-((1-(3-methoxyphenyl)cyclopropyl)amino)pyrimidine-5-carbohydrazide as White solid (0.350 g, 73.3%).

[Step 4] N'-(2,2-difluoroacetyl)-2-((1-(3-methoxyphenyl)cyclopropyl)amino)pyrimidine-5-carbohydrazide

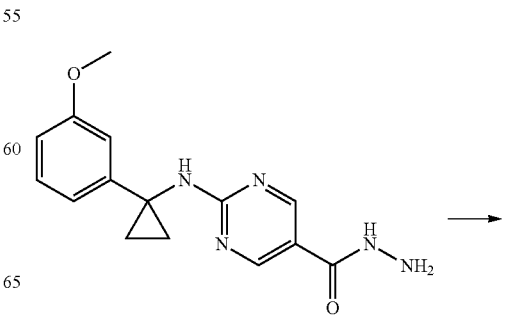

-continued

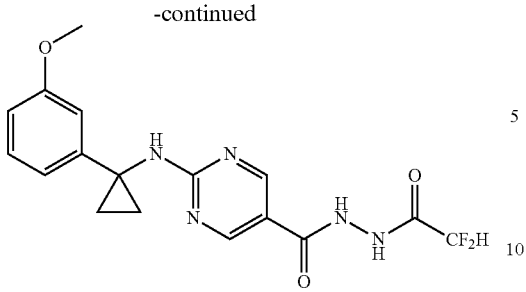

A solution of 2-((1-(3-methoxyphenyl)cyclopropyl)amino)pyrimidine-5-carbohydrazide (0.124 g, 0.414 mmol), 2,2-difluoroacetic anhydride (0.052 mL, 0.414 mmol) and triethylamine (0.087 mL, 0.621 mmol) in dichloromethane (10 mL) prepared at the room temperature was stirred at the same temperature for 1 hr. The precipitates were collected by filtration, washed by hexane, and dried to give N'-(2,2-difluoroacetyl)-2-((1-(3-methoxyphenyl)cyclopropyl)amino)pyrimidine-5-carbohydrazide as White solid (0.110 g, 70.4%).

[Step 5] Compound 204

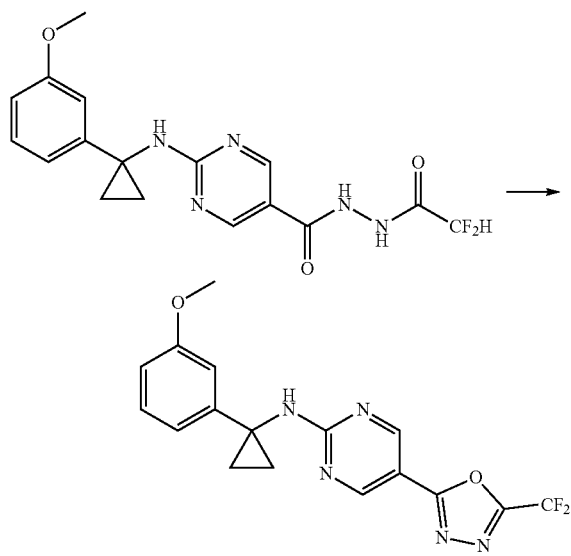

A mixture of N'-(2,2-difluoroacetyl)-2-((1-(3-methoxyphenyl)cyclopropyl)amino)pyrimidine-5-carbohydrazide (0.110 g, 0.292 mmol) and 1-methoxy-N-triethylammoniosulfonyl-methanimidate (Burgess reagent, 0.104 g, 0.437 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(3-methoxyphenyl)cyclopropyl)pyrimidin-2-amine as white solid (0.060 g, 57.3%).

$^1$H NMR (400 MHz, CDCl$_3$) δ 9.00-8.96 (m, 2H), 7.24-7.20 (m, 1H), 7.04 (s, 0.25H), 6.91 (s, 0.5H), 6.78 (s, 0.25H), 6.86-6.83 (m, 2H), 6.77-6.75 (m, 2H), 3.78 (s, 3H), 1.49-1.45 (m, 2H), 1.42-1.39 (m, 2H).; LRMS (ES) m/z 360.3 (M$^+$+1).

Example 94: Compound 2049, 5-(5-(difluoromethyl)-1,3,4-oxadiazol-2-yl)-N-(1-(4-methoxyphenyl)cyclopropyl)pyrimidin-2-amine

[Step 1] 1-(4-methoxyphenyl)cyclopropan-1-amine hydrochloride

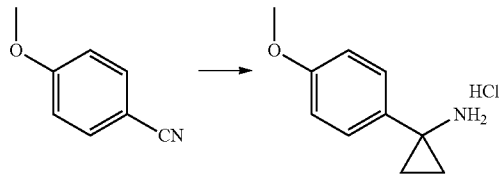

A solution of 4-methoxybenzonitrile (5.000 g, 37.552 mmol), Ethyl magnesiumbromide (1.00 M solution, 93.879 mL, 93.879 mmol) and titanium ethoxide (11.810 mL, 56.327 mmol) in 2-methoxy-2-methylpropane (MTBE, 30 mL) was stirred at 0° C. for 1 hr, and mixed with boron trifluoride diethyl etherate (9.269 mL, 75.103 mmol) and hydrogen chloride (1.00 M solution in EA, 37.552 mL, 37.552 mmol). The reaction mixture was stirred at the room temperature for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and then was added hydrogen chloride (1.00 M solution in EA, 37.552 mL, 37.552 mmol) stirred at the ambient temperature. The resulting precipitates were collected by filtration, washed by hexane and dried to give 1-(4-methoxyphenyl)cyclopropan-1-amine hydrochloride as White solid (0.990 g, 13.2%).

[Step 2] ethyl 2-((1-(4-methoxyphenyl)cyclopropyl)amino)pyrimidine-5-carboxylate

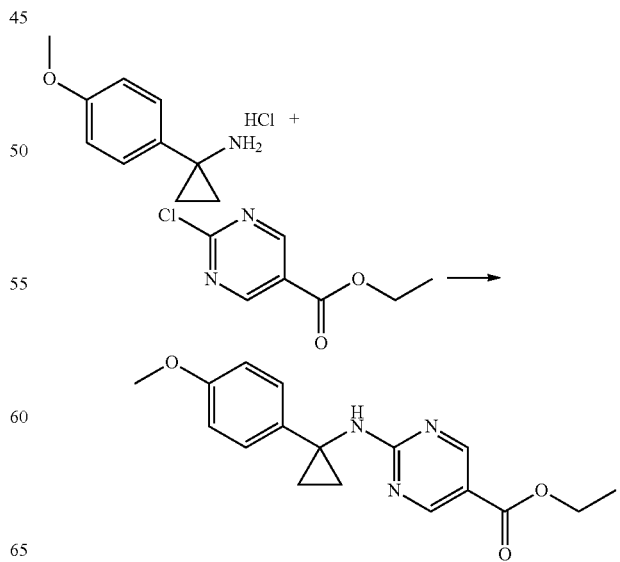

325

A solution of 1-(4-methoxyphenyl)cyclopropan-1-amine hydrochloride (0.500 g, 2.504 mmol), ethyl 2-chloropyrimidine-5-carboxylate (0.514 g, 2.754 mmol) and N,N-diisopropylethylamine (1.090 mL, 6.260 mmol) in 1,4-dioxane (20 mL) was stirred at 80° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(4-methoxyphenyl)cyclopropyl)amino)pyrimidine-5-carboxylate as White solid (0.660 g, 84.1%).

[Step 3] 2-((1-(4-methoxyphenyl)cyclopropyl)amino)pyrimidine-5-carbohydrazide

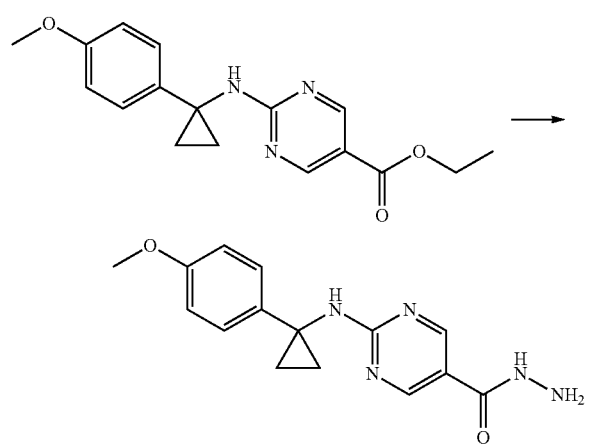

A mixture of ethyl 2-((1-(4-methoxyphenyl)cyclopropyl)amino)pyrimidine-5-carboxylate (0.500 g, 1.596 mmol) and Hydrazine monohydrate (1.551 mL, 31.912 mmol) in ethanol (10 mL) was heated at 120° C. for 1 hr under the microwaves, cooled down to the room temperature to terminate reaction. The precipitates were collected by filtration, washed by hexane, and dried to give 2-((1-(4-methoxyphenyl)cyclopropyl)amino)pyrimidine-5-carbohydrazide as White solid (0.360 g, 75.4%).

[Step 4] N'-(2,2-difluoroacetyl)-2-((1-(4-methoxyphenyl)cyclopropyl)amino)pyrimidine-5-carbohydrazide

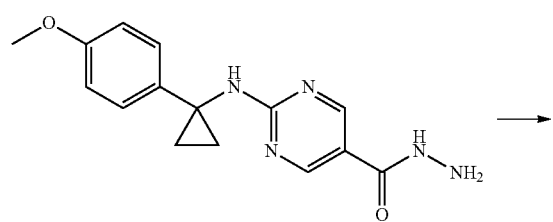

326

-continued

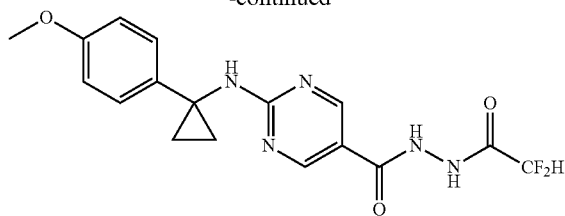

A solution of 2-((1-(4-methoxyphenyl)cyclopropyl)amino)pyrimidine-5-carbohydrazide (0.362 g, 1.209 mmol), 2,2-difluoroacetic anhydride (0.150 mL, 1.209 mmol) and triethylamine (0.253 mL, 1.814 mmol) in dichloromethane (10 mL) prepared at the room temperature was stirred at the same temperature for 1 hr. The precipitates were collected by filtration, washed by hexane, and dried to give N'-(2,2-difluoroacetyl)-2-((1-(4-methoxyphenyl)cyclopropyl)amino)pyrimidine-5-carbohydrazide as White solid (0.300 g, 65.7%).

[Step 5] Compound 2049

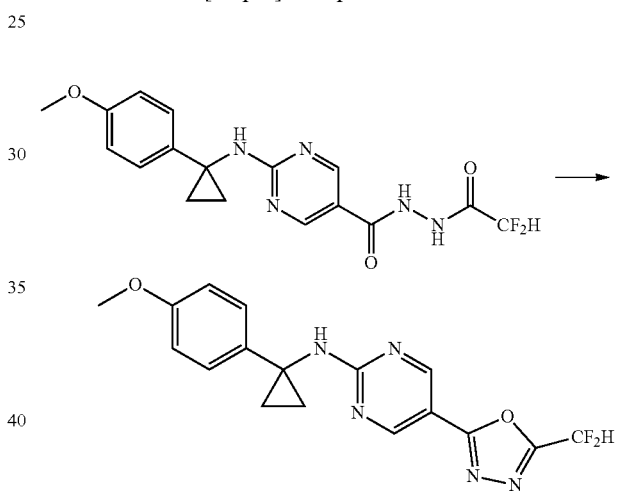

A mixture of N'-(2,2-difluoroacetyl)-2-((1-(4-methoxyphenyl)cyclopropyl)amino)pyrimidine-5-carbohydrazide (0.160 g, 0.424 mmol) and 1-methoxy-N-triethylammoniosulfonyl-methanimidate (Burgess reagent, 0.152 g, 0.636 mmol) in tetrahydrofuran (10 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(4-methoxyphenyl)cyclopropyl)pyrimidin-2-amine as White solid (0.100 g, 65.6%).

$^1$H NMR (400 MHz, CDCl$_3$) δ 9.01-8.94 (m, 2H), 7.28-7.25 (m, 2H), 7.04 (s, 0.25H), 6.91 (s, 0.5H), 6.78 (s, 0.25H), 6.85-6.83 (m, 2H), 6.74 (s, 1H), 3.79 (s, 3H), 1.39-1.34 (m, 4H).; LRMS (ES) m/z 360.3 (M$^+$+1).

Example 95: Compound 2050, N-(1-(3-chlorophenyl)cyclopropyl)-5-(5-(difluoromethyl)-1,3,4-oxadiazol-2-yl)pyrimidin-2-amine

[Step 1] 1-(3-chlorophenyl)cyclopropan-1-amine hydrochlorid

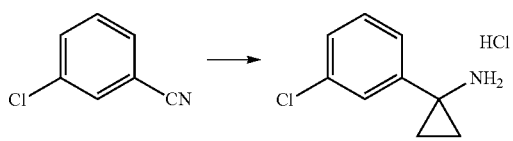 [SMILES: N#Cc1cccc(Cl)c1 ; NC1(c2cccc(Cl)c2)CC1 ; Cl]

A solution of 3-chlorobenzonitrile (1.400 g, 13.576 mmol), titanium isopropoxide (6.029 mL, 20.365 mmol) and EtMgBr (1.00 M solution, 31.226 mL, 31.226 mmol) in 2-methoxy-2-methylpropane (MTBE, 150 mL) was mixed at 0° C., and was stirred at the room temperature for 1 hr. The reaction mixture was treated with Boron trifluoride diethyl etherate (3.854 g, 27.153 mmol) at 0° C., stirred at the room temperature for additional 17 hr, quenched at the room temperature by the addition of water (10 mL, 10 min stirring). Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and was added hydrochloric acid (1.00 M solution in EtOAc, 14.934 mL, 14.934 mmol) and stirred at the ambient temperature. The resulting precipitates were collected by filtration, washed by ethyl acetate, and dried to give 1-(3-chlorophenyl)cyclopropan-1-amine hydrochloride as white solid (1.010 g, 36.5%).

[Step 2] Ethyl 2-((1-(3-chlorophenyl)cyclopropyl)amino)pyrimidine-5-carboxylate

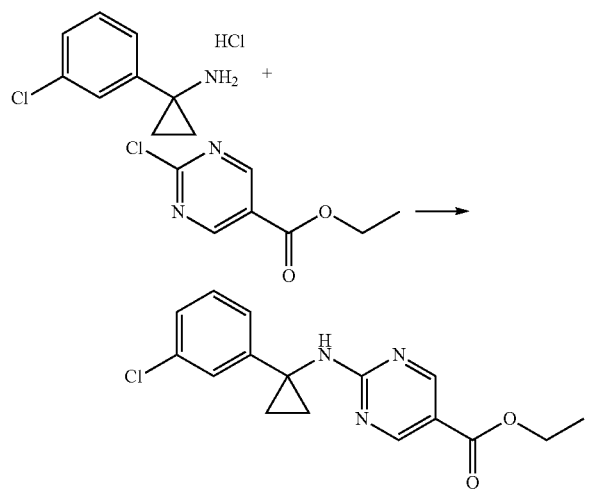

1-(3-chlorophenyl)cyclopropan-1-amine hydrochloride (0.500 g, 2.450 mmol), ethyl 2-chloropyrimidine-5-carboxylate (0.503 g, 2.695 mmol) and N,N-diisopropylethylamine (1.280 mL, 7.350 mmol) were mixed at the room temperature in 1,4-dioxane (10 mL) and then stirred at 110° C. for 18 hr, and cooled down to the room temperature to terminate reaction. The reaction mixture was concentrated under the reduced pressure to remove the solvent. The crude product was crystallized at the room temperature using ethanol (5 mL). The resulting precipitates were filtered, washed by ethanol, and dried to give ethyl 2-((1-(3-chlorophenyl)cyclopropyl)amino)pyrimidine-5-carboxylate as white solid (0.450 g, 57.8%).

[Step 3] 2-((1-(3-chlorophenyl)cyclopropyl)amino)pyrimidine-5-carbohydrazide

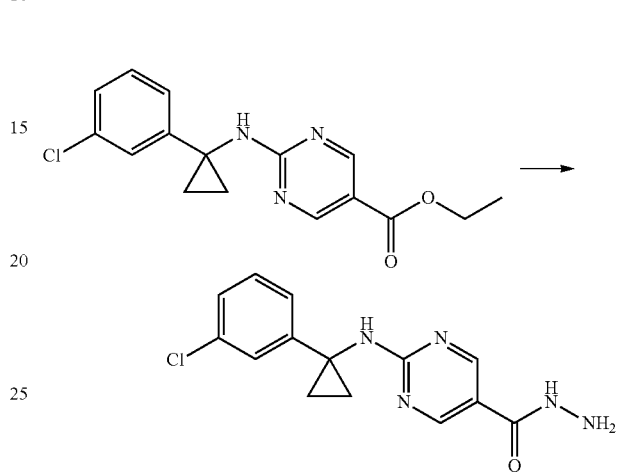

Ethyl 2-((1-(3-chlorophenyl)cyclopropyl)amino)pyrimidine-5-carboxylate (0.450 g, 1.416 mmol) and hydrazine monohydrate (1.377 mL, 28.322 mmol) were mixed at the room temperature in ethanol (5 mL) and then stirred at 110° C. for 18 hr, and cooled down to the room temperature to terminate reaction. The reaction mixture was concentrated under the reduced pressure to remove the solvent. The concentrate was diluted with ethanol (2 mL) and stirred at the ambient temperature. The resulting precipitates were collected by filtration, washed by ethanol, and dried to give 2-((1-(3-chlorophenyl)cyclopropyl)amino)pyrimidine-5-carbohydrazide as white solid (0.411 g, 95.5%).

[Step 4] 2-((1-(3-chlorophenyl)cyclopropyl)amino)-N'-(2,2-difluoroacetyl)pyrimidine-5-carbohydrazide

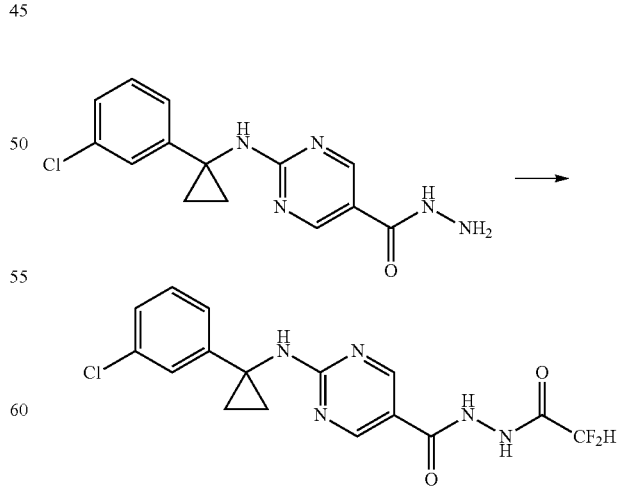

A solution of 2-((1-(3-chlorophenyl)cyclopropyl)amino)pyrimidine-5-carbohydrazide (0.200 g, 0.658 mmol) and triethylamine (0.184 mL, 1.317 mmol) in tetrahydrofuran (8 mL) was mixed at the room temperature with 2,2-difluoroacetic anhydride (0.082 mL, 0.658 mmol), stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-(3-chlorophenyl)cyclopropyl)amino)-N'-(2,2-difluoroacetyl)pyrimidine-5-carbohydrazide was used without further purification (0.200 g, 79.6%, yellow oil).

[Step 5] Compound 2050

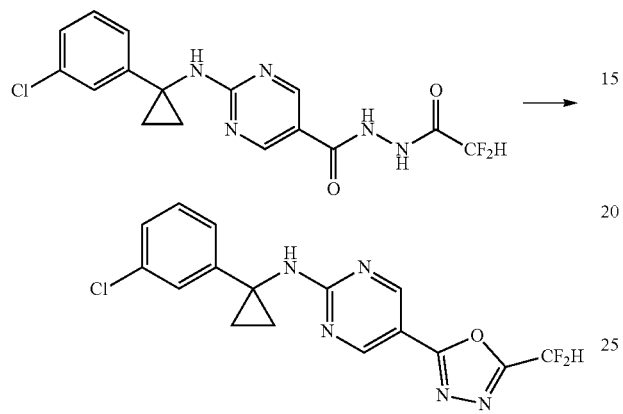

2-((1-(3-chlorophenyl)cyclopropyl)amino)-N'-(2,2-difluoroacetyl)pyrimidine-5-carbohydrazide (0.200 g, 0.524 mmol) and 1-methoxy-N-triethylammoniosulfonyl-methanimidate (Burgess reagent, 0.375 g, 1.572 mmol) in tetrahydrofuran (5 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(3-chlorophenyl)cyclopropyl)-5-(5-(difluoromethyl)-1,3,4-oxadiazol-2-yl)pyrimidin-2-amine as yellow solid (0.039 g, 20.5%).
$^1$H NMR (400 MHz, CDCl$_3$) δ 9.02 (s, 1H), 8.98 (s, 1H), 7.26-7.24 (m, 2H), 7.22-7.14 (m, 2H), 7.05-6.79 (m, 1H), 7.05-6.79 (m, 1H), 1.49-1.41 (m, 4H); LRMS (ES) m/z 364.1 (M$^+$+1).

Example 96: Compound 2051, N-(1-(3-chlorophenyl)cyclopropyl)-5-(5-(trifluoromethyl)-1,3,4-oxadiazol-2-yl)pyrimidin-2-amine

[Step 1] 2-((1-(3-chlorophenyl)cyclopropyl)amino)-N'-(2,2,2-trifluoroacetyl)pyrimidine-5-carbohydrazide

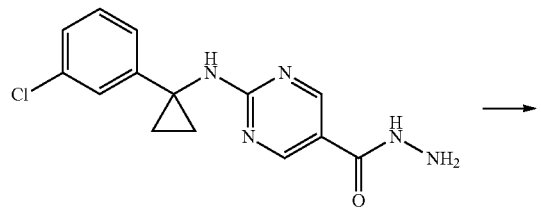

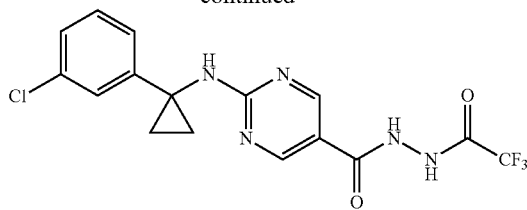

A solution of 2-((1-(3-chlorophenyl)cyclopropyl)amino)pyrimidine-5-carbohydrazide (0.200 g, 0.658 mmol) and triethylamine (0.184 mL, 1.317 mmol) in tetrahydrofuran (8 mL) was mixed at the room temperature with trifluoroacetic anhydride (0.093 mL, 0.658 mmol), stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-(3-chlorophenyl)cyclopropyl)amino)-N'-(2,2,2-trifluoroacetyl)pyrimidine-5-carbohydrazide was used without further purification (0.200 g, 76.0%, yellow oil).

[Step 2] Compound 2051

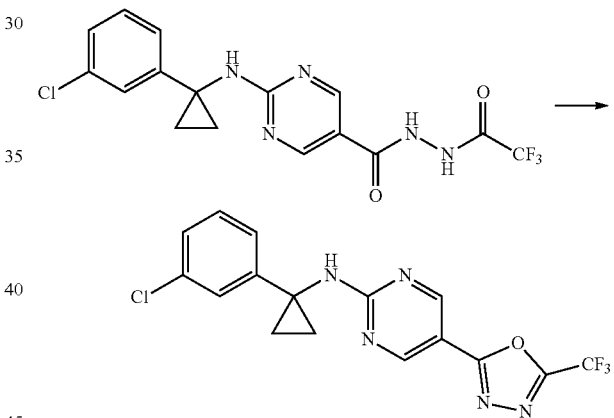

2-((1-(3-chlorophenyl)cyclopropyl)amino)-N'-(2,2,2-trifluoroacetyl)pyrimidine-5-carbohydrazide (0.200 g, 0.500 mmol) and 1-methoxy-N-triethylammoniosulfonyl-methanimidate (Burgess reagent, 0.358 g, 1.501 mmol) in tetrahydrofuran (5 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; ethyl acetate/hexane=0% to 10%) to give N-(1-(3-chlorophenyl)cyclopropyl)-5-(5-(trifluoromethyl)-1,3,4-oxadiazol-2-yl)pyrimidin-2-amine as yellow solid (0.043 g, 22.5%).
$^1$H NMR (400 MHz, CDCl$_3$) δ 9.01 (s, 1H), 8.98 (s, 1H), 7.26-7.22 (m, 2H), 7.21-7.14 (m, 2H), 6.52 (s, 1H), 1.49-1.14 (m, 4H); LRMS (ES) m/z 382.3 (M$^+$+1).

Example 97: Compound 2052, N-(1-(4-chlorophenyl)cyclopropyl)-5-(5-(difluoromethyl)-1,3,4-oxadiazol-2-yl)pyrimidin-2-amine

[Step 1] 1-(4-chlorophenyl)cyclopropan-1-amine hydrochloride

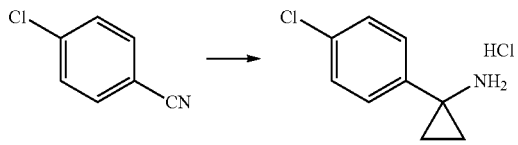 [SMILES: N#Cc1ccc(Cl)cc1 ; NC1(c2ccc(Cl)cc2)CC1 ; Cl]

A solution of 4-chlorobenzonitrile (1.500 g, 10.904 mmol), titanium isopropoxide (4.842 mL, 16.355 mmol) and EtMgBr (1.00 M solution, 25.078 mL, 25.078 mmol) in 2-methoxy-2-methylpropane (MTBE, 150 mL) was mixed at 0° C., and was stirred at the room temperature for 1 hr. The reaction mixture was treated with BF3-etherate (2.691 mL, 21.807 mmol) at 0° C., stirred at the room temperature for additional 17 hr, quenched at the room temperature by the addition of water (10 mL, 10 min stirring). Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The concentrate was diluted with ethyl acetate and was added hydrochloric acid (1.00 M solution in EtOAc, 11.994 mL, 11.994 mmol) and stirred at the ambient temperature. The resulting precipitates were collected by filtration, washed by ethyl acetate, and dried to give 1-(4-chlorophenyl)cyclopropan-1-amine hydrochloride as white solid (1.120 g, 50.3%).

[Step 2] Ethyl 2-((1-(4-chlorophenyl)cyclopropyl)amino)pyrimidine-5-carboxylate

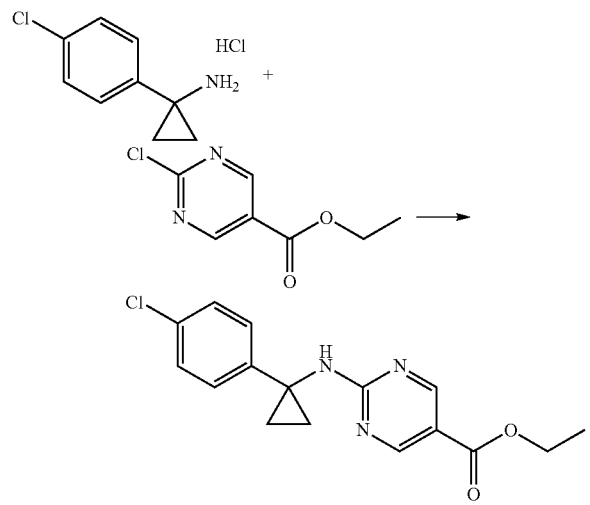

1-(4-chlorophenyl)cyclopropan-1-amine hydrochloride (0.500 g, 2.450 mmol), ethyl 2-chloropyrimidine-5-carboxylate (0.503 g, 2.695 mmol) and N,N-diisopropylethylamine (1.280 mL, 7.350 mmol) were mixed at the room temperature in 1,4-dioxane (10 mL) and then stirred at 110° C. for 18 hr, and cooled down to the room temperature to terminate reaction. The reaction mixture was concentrated under the reduced pressure to remove the solvent. The crude product was crystallized at the room temperature using ethanol (5 mL). The resulting precipitates were filtered, washed by ethanol, and dried to give ethyl 2-((1-(4-chlorophenyl)cyclopropyl)amino)pyrimidine-5-carboxylate as white solid (0.520 g, 66.8%).

[Step 3] 2-((1-(4-chlorophenyl)cyclopropyl)amino)pyrimidine-5-carbohydrazide

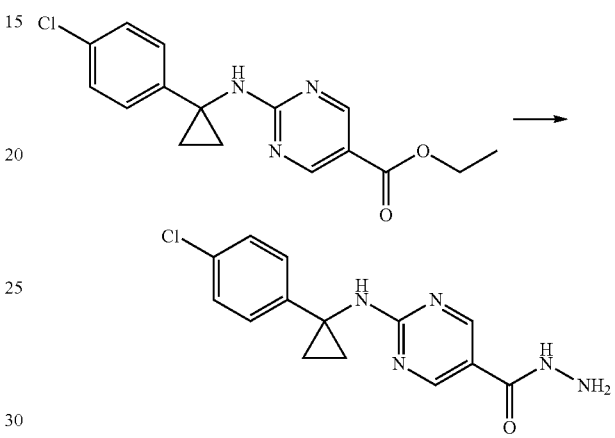

ethyl 2-((1-(4-chlorophenyl)cyclopropyl)amino)pyrimidine-5-carboxylate (0.520 g, 1.636 mmol) and hydrazine monohydrate (1.591 mL, 32.728 mmol) were mixed at the room temperature in ethanol (5 mL) and then stirred at 110° C. for 18 hr, cooled down to the room temperature to terminate reaction. The precipitates were collected by filtration, washed by ethanol, and dried to give 2-((1-(4-chlorophenyl)cyclopropyl)amino)pyrimidine-5-carbohydrazide as white solid (0.489 g, 98.4%).

[Step 4] 2-((1-(4-chlorophenyl)cyclopropyl)amino)-N'-(2,2-difluoroacetyl)pyrimidine-5-carbohydrazide

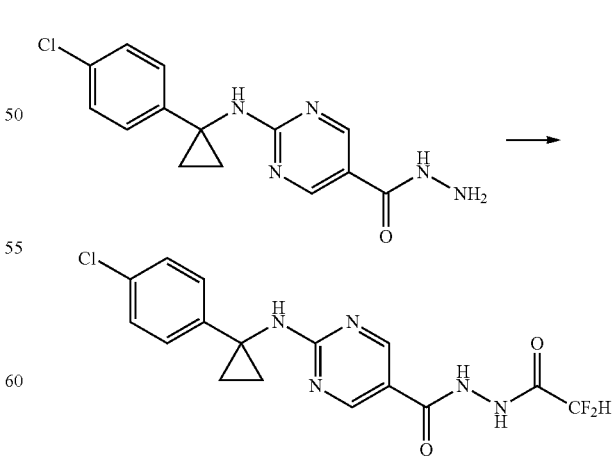

A solution of 2-((1-(4-chlorophenyl)cyclopropyl)amino)pyrimidine-5-carbohydrazide (0.150 g, 0.494 mmol) and triethylamine (0.138 mL, 0.988 mmol) in tetrahydrofuran (8 mL) was mixed at the room temperature with 2,2-difluoroacetic anhydride (0.061 mL, 0.494 mmol), stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-(4-chlorophenyl)cyclopropyl)amino)-N'-(2,2-difluoroacetyl)pyrimidine-5-carbohydrazide was used without further purification (0.150 g, 79.6%, yellow oil).

[Step 5] Compound 2052

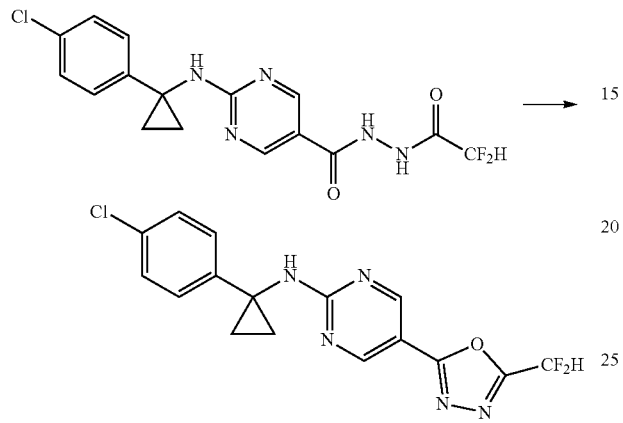

2-((1-(4-chlorophenyl)cyclopropyl)amino)-N'-(2,2-difluoroacetyl)pyrimidine-5-carbohydrazide (0.150 g, 0.393 mmol) and 1-methoxy-N-triethylammoniosulfonyl-methanimidate (Burgess reagent, 0.281 g, 1.179 mmol) in tetrahydrofuran (5 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; ethyl acetate/hexane=0% to 10%) to give N-(1-(4-chlorophenyl)cyclopropyl)-5-(5-(difluoromethyl)-1,3,4-oxadiazol-2-yl)pyrimidin-2-amine as yellow solid (0.003 g, 2.1%).

$^1$H NMR (400 MHz, CDCl$_3$) δ 9.00 (s, 1H), 8.97 (s, 1H), 7.27 (d, J=8.9 Hz, 2H), 7.22 (d, J=8.8 Hz, 2H), 7.04-6.79 (m, 1H), 6.46 (s, 1H), 1.45-1.41 (m, 4H); LRMS (ES) m/z 364.1 (M$^+$+1).

Example 98: Compound 2053, N-(1-(4-chlorophenyl)cyclopropyl)-5-(5-(trifluoromethyl)-1,3,4-oxadiazol-2-yl)pyrimidin-2-amine

[Step 1] 2-((1-(4-chlorophenyl)cyclopropyl)amino)-N'-(2,2,2-trifluoroacetyl)pyrimidine-5-carbohydrazide

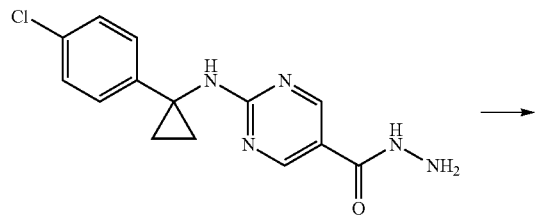

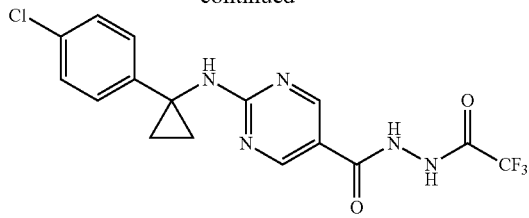

A solution of 2-((1-(4-chlorophenyl)cyclopropyl)amino)pyrimidine-5-carbohydrazide (0.150 g, 0.494 mmol) and triethylamine (0.138 mL, 0.988 mmol) in tetrahydrofuran (8 mL) was mixed at the room temperature with trifluoroacetic anhydride (0.070 mL, 0.494 mmol), stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. 2-((1-(4-chlorophenyl)cyclopropyl)amino)-N'-(2,2,2-trifluoroacetyl)pyrimidine-5-carbohydrazide was used without further purification (0.150 g, 76.0%, yellow oil).

[Step 2] Compound 2053

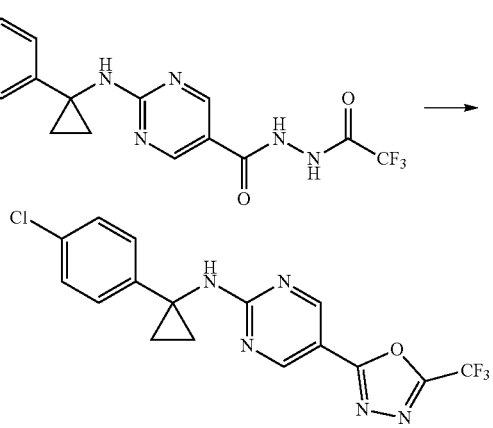

2-((1-(4-chlorophenyl)cyclopropyl)amino)-N'-(2,2,2-trifluoroacetyl)pyrimidine-5-carbohydrazide (0.150 g, 0.375 mmol) and 1-methoxy-N-triethylammoniosulfonyl-methanimidate (Burgess reagent, 0.268 g, 1.126 mmol) in tetrahydrofuran (5 mL) was mixed at the room temperature and then heated at 150° C. under the microwaves for 30 min, and cooled down to the room temperature to terminate reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 10%) to give N-(1-(4-chlorophenyl)cyclopropyl)-5-(5-(trifluoromethyl)-1,3,4-oxadiazol-2-yl)pyrimidin-2-amine as yellow solid (0.012 g, 8.4%).

$^1$H NMR (400 MHz, CDCl$_3$) δ 9.00 (s, 1H), 8.97 (s, 1H), 7.27 (d, J=8.9 Hz, 2H), 7.22 (d, J=8.8 Hz, 2H), 6.54 (s, 1H), 1.46-1.41 (m, 4H); LRMS (ES) m/z 382.1 (M$^+$+1).

Example 99. Compound 2054: N-(1-(4-chloro-3-fluorophenyl)cyclopropyl)-5-(5-(difluoromethyl)-1,3,4-oxadiazol-2-yl)pyrimidin-2-amine

[Step 1] 1-(4-chloro-3-fluorophenyl)cyclopropan-1-amine

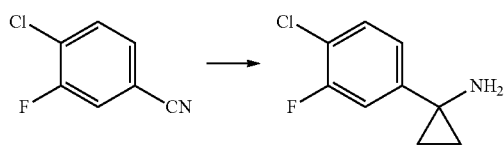 [SMILES: N#Cc1ccc(Cl)c(F)c1 ; NC1(c2ccc(Cl)c(F)c2)CC1]

To a stirred solution of 4-chloro-3-fluorobenzonitrile (2.500 g, 16.071 mmol), titanium isopropoxide (6.185 mL, 20.892 mmol) and ethylmagnesium bromide (1.00 M solution in THF, 36.963 mL, 36.963 mmol) in 2-methoxy-2-methylpropane (MTBE, 30 mL) were added at −20° C. The reaction mixture was stirred at the same temperature for 30 min, treated at the room temperature with boron trifluoride diethyl etherate (3.967 mL, 32.142 mmol), stirred for additional 3 hr, quenched at the room temperature by the addition of sodium hydroxide (3.00 M solution in water, 16.071 mL, 48.213 mmol, 30 min stirring), filtered through a celite pad to remove solids. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; methanol/dichloromethane=5% to 30%) to give 1-(4-chloro-3-fluorophenyl)cyclopropan-1-amine as pale yellow liquid (0.554 g, 18.6%).

[Step 2] ethyl 2-((1-(4-chloro-3-fluorophenyl)cyclopropyl)amino)pyrimidine-5-carboxylate

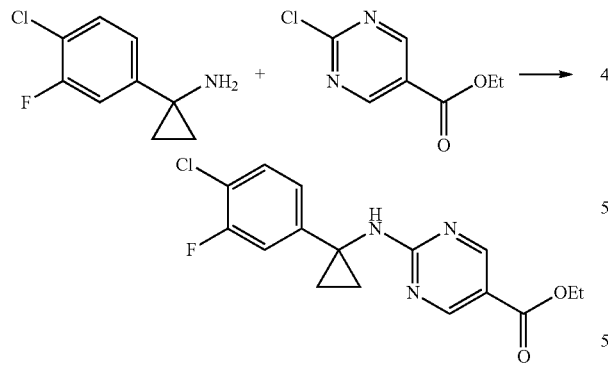

A solution of 1-(4-chloro-3-fluorophenyl)cyclopropan-1-amine hydrochloride (0.210 g, 1.131 mmol), ethyl 2-chloropyrimidine-5-carboxylate (0.222 g, 1.188 mmol) and N,N-diisopropylethylamine (0.493 mL, 2.828 mmol) in 1,4-dioxane (3 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO$_2$, 24 g cartridge; ethyl acetate/hexane=0% to 60%) to give ethyl 2-((1-(4-chloro-3-fluorophenyl)cyclopropyl)amino)pyrimidine-5-carboxylate as white solid (0.346 g, 91.1%).

[Step 3] 2-((1-(4-chloro-3-fluorophenyl)cyclopropyl)amino)pyrimidine-5-carbohydrazide

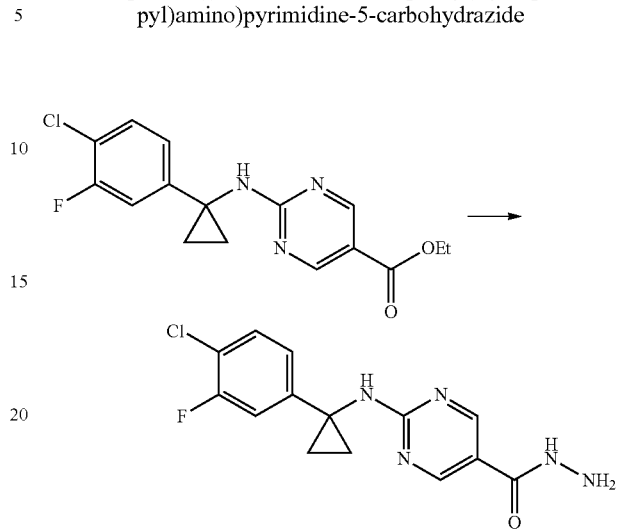

A solution of ethyl 2-((1-(4-chloro-3-fluorophenyl)cyclopropyl)amino)pyrimidine-5-carboxylate (0.150 g, 0.447 mmol) and hydrazine (50.00% solution in water, 0.561 mL, 8.935 mmol) in ethanol (4 mL) was stirred at 120° C. for 12 hr, and cooled down to the room temperature to terminate reaction. The reaction mixture was concentrated under the reduced pressure to remove the solvent. The crude product was used without further purification (2-((1-(4-chloro-3-fluorophenyl)cyclopropyl)amino)pyrimidine-5-carbohydrazide, 0.125 g, 87.0%, pale yellow solid).

[Step 4] 2-((1-(4-chloro-3-fluorophenyl)cyclopropyl)amino)-N'-(2,2-difluoroacetyl)pyrimidine-5-carbohydrazide

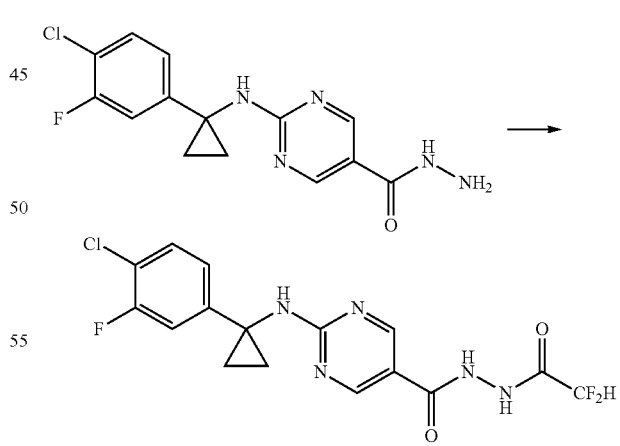

A solution of 2-((1-(4-chloro-3-fluorophenyl)cyclopropyl)amino)pyrimidine-5-carbohydrazide (0.100 g, 0.311 mmol), 2,2-difluoroacetic anhydride (0.039 mL, 0.311 mmol) and triethylamine (0.087 mL, 0.622 mmol) in dichloromethane (5 mL) prepared at the room temperature was stirred at the same temperature for 1 hr, and concentrated under the reduced pressure to remove the solvent. The concentrate was purified and concentrated by column chromatography (SiO$_2$, 12 g cartridge; methanol/dichloromethane=10% to 30%) to give 2-((1-(4-chloro-3-fluorophenyl)cyclopropyl)amino)-N'-(2,2-difluoroacetyl)pyrimidine-5-carbohydrazide as pale yellow solid (0.102 g, 82.1%).

[Step 5] Compound 2054

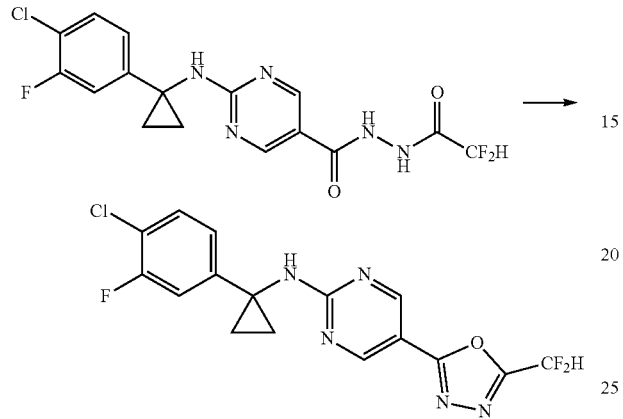

A mixture of 2-((1-(4-chloro-3-fluorophenyl)cyclopropyl)amino)-N'-(2,2-difluoroacetyl)pyrimidine-5-carbohydrazide (0.080 g, 0.200 mmol) and 1-methoxy-N-triethylammoniosulfonyl-methanimidate (Burgess reagent, 0.095 g, 0.400 mmol) in tetrahydrofuran (3 mL) was heated at 150° C. for 30 min under the microwaves and cooled down to the room temperature to terminate reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 4 g cartridge; ethyl acetate/aqueous 1%-hexane solution=5% to 50%) to give N-(1-(4-chloro-3-fluorophenyl)cyclopropyl)-5-(5-(difluoromethyl)-1,3,4-oxadiazol-2-yl)pyrimidin-2-amine as white solid (0.033 g, 43.2%).

$^1$H NMR (400 MHz, CDCl$_3$) δ 9.01 (s, 2H), 7.31 (dd, J=8.3, 7.7 Hz, 1H), 7.07 (dd, J=10.5, 2.2 Hz, 1H), 7.05 (s, 0.25H), 6.98 (ddd, J=8.4, 2.2, 0.8 Hz, 1H), 6.92 (s, 0.5H), 6.79 (s, 0.25H), 6.40 (br, 1H), 1.45 (s, 4H); LRMS (ES) m/z 382.0 (M$^+$+1).

Example 100: Compound 2055, 5-(5-(difluoromethyl)-1,3,4-oxadiazol-2-yl)-N-(1-(o-tolyl)cyclopropyl)pyrimidin-2-amine

[Step 1] 1-(o-tolyl)cyclopropan-1-amine hydrochloride

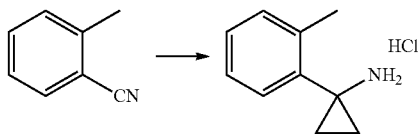

A solution of 2-methylbenzonitrile (5.000 g, 42.680 mmol), titanium isopropoxide (18.954 mL, 64.020 mmol) and ethylmagnesiumbromide (3.00 M solution, 35.567 mL, 106.701 mmol) in 2-methoxy-2-methylpropane (MTBE, 50 mL) was stirred at 0° C. for 1 hr, and mixed with boron trifluoride diethyl etherate (7.901 mL, 64.020 mmol). The reaction mixture was stirred at the room temperature for additional 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate and then was added hydrochloric acid (1.00 M solution in EA, 42.680 mL, 42.680 mmol) stirred at the ambient temperature. The resulting precipitates were collected by filtration, washed by hexane and dried to give 1-(o-tolyl)cyclopropan-1-amine hydrochloride as white solid (1.800 g, 23.0%).

[Step 2] ethyl 2-((1-(o-tolyl)cyclopropyl)amino)pyrimidine-5-carboxylate

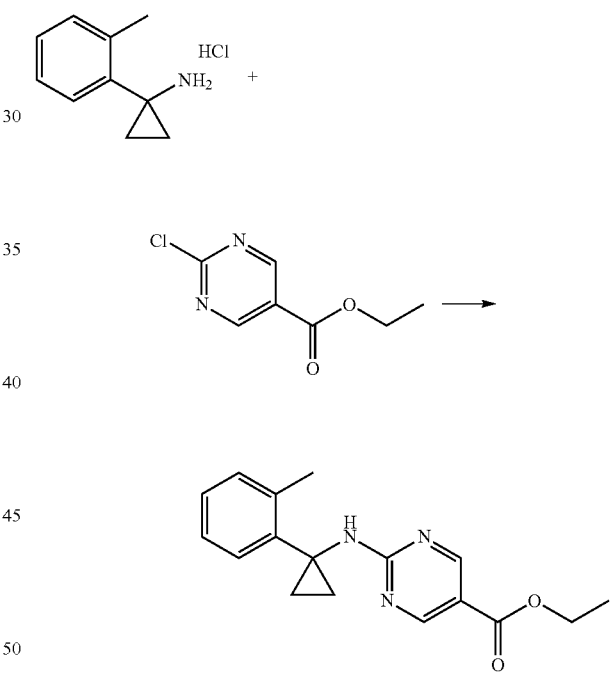

A solution of 1-(o-tolyl)cyclopropan-1-amine hydrochloride (0.500 g, 2.722 mmol), ethyl 2-chloropyrimidine-5-carboxylate (0.559 g, 2.994 mmol) and N,N-diisopropylethylamine (1.185 mL, 6.805 mmol) in 1,4-dioxane (20 mL) was stirred at 80° C. for 18 hr, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give ethyl 2-((1-(o-tolyl)cyclopropyl)amino)pyrimidine-5-carboxylate as White solid (0.670 g, 82.8%).

[Step 3] 2-((1-(o-tolyl)cyclopropyl)amino)pyrimidine-5-carbohydrazide

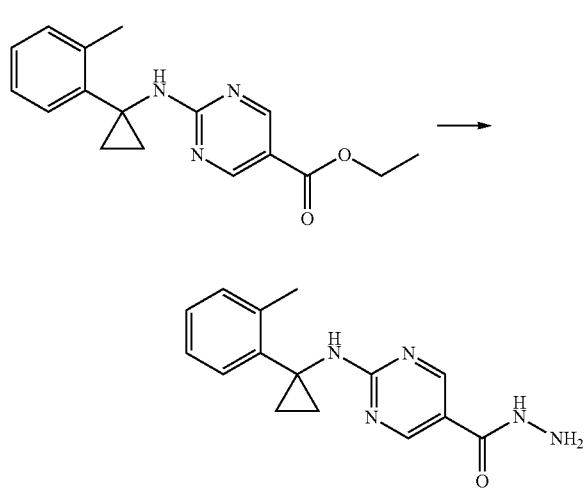

A mixture of ethyl 2-((1-(o-tolyl)cyclopropyl)amino)pyrimidine-5-carboxylate (0.670 g, 2.253 mmol) and Hydrazine monohydrate (2.190 mL, 45.063 mmol) in ethanol (10 mL) was heated at 120° C. for 1 hr under the microwaves, cooled down to the room temperature to terminate reaction. The precipitates were collected by filtration, washed by hexane, and dried to give 2-((1-(o-tolyl)cyclopropyl)amino)pyrimidine-5-carbohydrazide as White solid (0.500 g, 78.3%).

[Step 4] N'-(2,2-difluoroacetyl)-2-((1-(o-tolyl)cyclopropyl)amino)pyrimidine-5-carbohydrazide

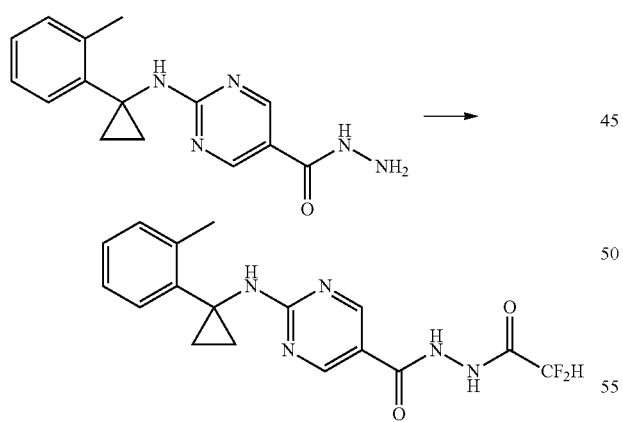

A solution of 2-((1-(o-tolyl)cyclopropyl)amino)pyrimidine-5-carbohydrazide (0.600 g, 2.118 mmol), 2,2-difluoroacetic anhydride (0.263 mL, 2.118 mmol) and triethylamine (0.443 mL, 3.176 mmol) in dichloromethane (10 mL) prepared at the room temperature was stirred at the same temperature for 1 hr. The precipitates were collected by filtration, washed by hexane, and dried to give N'-(2,2-difluoroacetyl)-2-((1-(o-tolyl)cyclopropyl)amino)pyrimidine-5-carbohydrazide as White solid (0.640 g, 83.6%).

[Step 5] Compound 2055

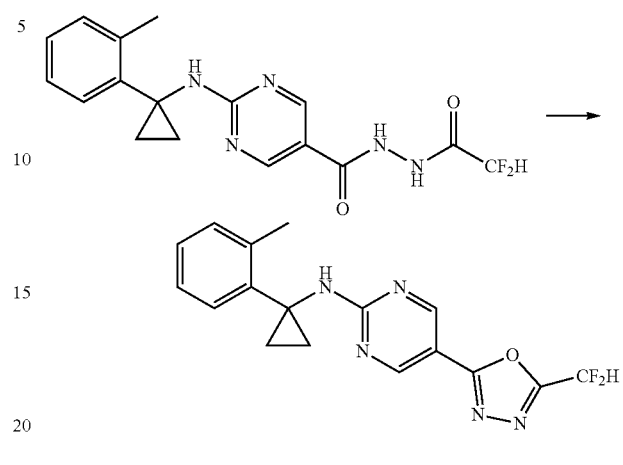

A mixture of N'-(2,2-difluoroacetyl)-2-((1-(o-tolyl)cyclobutyl)amino)pyrimidine-5-carbohydrazide (0.640 g, 1.705 mmol) and 1-methoxy-N-triethylammoniosulfonylmethanimidate (Burgess reagent, 0.609 g, 2.557 mmol) in tetrahydrofuran (15 mL) was heated at 150° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give 5-(5-(difluoromethyl)-1,3,4-oxadiazol-2-yl)-N-(1-(o-tolyl)cyclobutyl)pyrimidin-2-amine as White solid (0.400 g, 65.7%).

$^1$H NMR (400 MHz, CDCl$_3$) δ 9.03-8.86 (m, 2H), 7.80-7.78 (m, 1H), 7.19-7.14 (m, 3H), 7.04 (s, 0.25H), 6.91 (s, 0.5H), 6.78 (s, 0.25H), 6.67 (s, 1H), 2.56 (s, 3H), 1.33-1.29 (m, 4H).; LRMS (ES) m/z 344.3 (M$^+$+1).

Example 101. Compound 2056: N-(1-(4-chloro-2-fluorophenyl)cyclopropyl)-5-(5-(difluoromethyl)-1,3,4-oxadiazol-2-yl)pyrimidin-2-amine

[Step 1] 1-(4-chloro-2-fluorophenyl)cyclopropan-1-amine

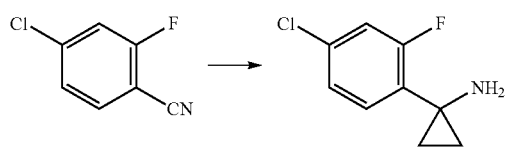 [SMILES: N#Cc1ccc(Cl)cc1F ; NC1(c2ccc(Cl)cc2F)CC1]

To a stirred solution of 4-chloro-2-fluorobenzonitrile (2.500 g, 16.071 mmol), titanium isopropoxide (6.185 mL, 20.892 mmol) and ethylmagnesium bromide (1.00 M solution in THF, 36.963 mL, 36.963 mmol) in 2-methoxy-2-methylpropane (MTBE, 30 mL) were added at −20° C. The reaction mixture was stirred at the same temperature for 30 min, treated at the room temperature with boron trifluoride diethyl etherate (3.967 mL, 32.142 mmol), stirred for additional 3 hr, quenched at the room temperature by the addition of sodium hydroxide (3.00 M solution in water, 16.071 mL, 48.213 mmol, 30 min stirring), filtered through a celite pad to remove solids. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 40 g cartridge; methanol/dichloromethane=5% to 30%) to give 1-(4-chloro-2-fluorophenyl)cyclopropan-1-amine as pale yellow liquid (0.753 g, 25.2%).

[Step 2] ethyl 2-((1-(4-chloro-2-fluorophenyl)cyclopropyl)amino)pyrimidine-5-carboxylate

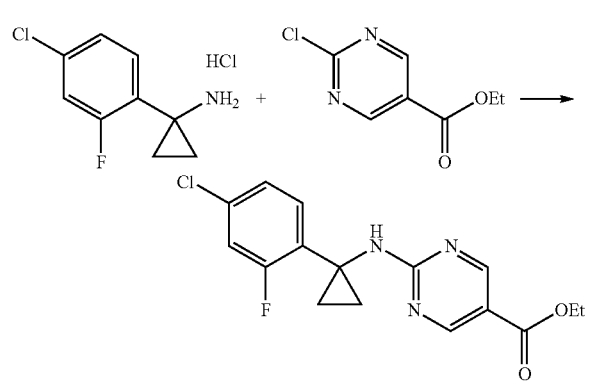

A solution of 1-(4-chloro-2-fluorophenyl)cyclopropan-1-amine hydrochloride (0.250 g, 1.126 mmol), ethyl 2-chloropyrimidine-5-carboxylate (0.221 g, 1.182 mmol) and N,N-diisopropylethylamine (0.490 mL, 2.814 mmol) in 1,4-dioxane (3 mL) was stirred at 90° C. for 12 hr, and cooled down to the room temperature to terminate reaction. The reaction mixture was concentrated under the reduced pressure to remove the solvent. The concentrate was purified and concentrated by column chromatography ($SiO_2$, 24 g cartridge; ethyl acetate/hexane=0% to 50%) to give ethyl 2-((1-(4-chloro-2-fluorophenyl)cyclopropyl)amino)pyrimidine-5-carboxylate as white solid (0.352 g, 93.1%).

[Step 3] 2-((1-(4-chloro-2-fluorophenyl)cyclopropyl)amino)pyrimidine-5-carbohydrazide

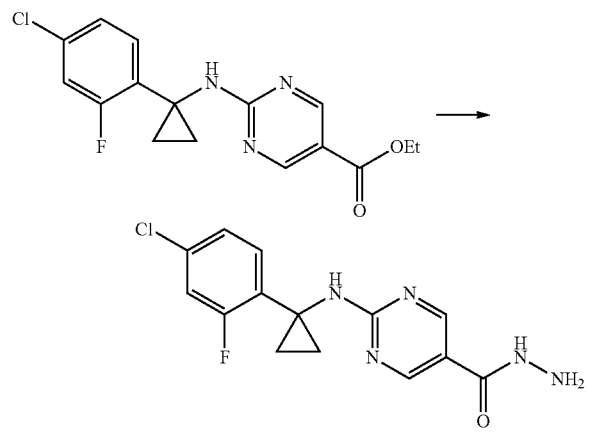

A solution of ethyl 2-((1-(4-chloro-2-fluorophenyl)cyclopropyl)amino)pyrimidine-5-carboxylate (0.150 g, 0.447 mmol) and hydrazine (50.00% solution in water, 0.561 mL, 8.935 mmol) in ethanol (4 mL) was stirred at 120° C. for 12 hr, and cooled down to the room temperature to terminate reaction. The reaction mixture was concentrated under the reduced pressure to remove the solvent. The crude product was used without further purification (2-((1-(4-chloro-2-fluorophenyl)cyclopropyl)amino)pyrimidine-5-carbohydrazide, 0.138 g, 96.0%, pale yellow solid).

[Step 4] 2-((1-(4-chloro-2-fluorophenyl)cyclopropyl)amino)-N'-(2,2-difluoroacetyl)pyrimidine-5-carbohydrazide

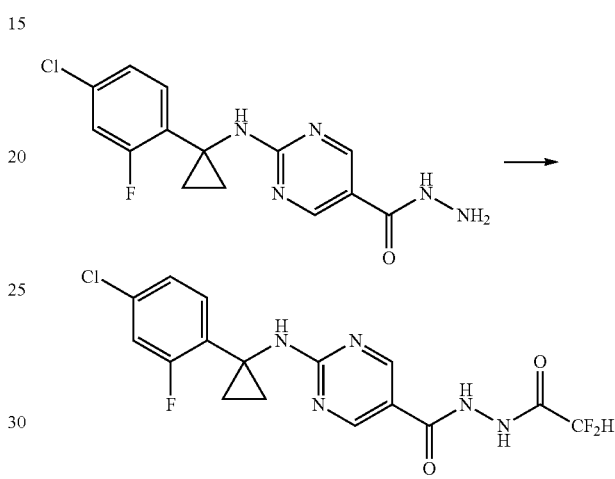

A solution of 2-((1-(4-chloro-2-fluorophenyl)cyclopropyl)amino)pyrimidine-5-carbohydrazide (0.133 g, 0.413 mmol), 2,2-difluoroacetic anhydride (0.051 mL, 0.413 mmol) and triethylamine (0.115 mL, 0.827 mmol) in dichloromethane (5 mL) prepared at the room temperature was stirred at the same temperature for 1 hr, and concentrated under the reduced pressure to remove the solvent. The concentrate was purified and concentrated by column chromatography ($SiO_2$, 12 g cartridge; methanol/dichloromethane=10% to 30%) to give 2-((1-(4-chloro-2-fluorophenyl)cyclopropyl)amino)-N'-(2,2-difluoroacetyl)pyrimidine-5-carbohydrazide as white solid (0.120 g, 72.6%).

[Step 5] Compound 2056

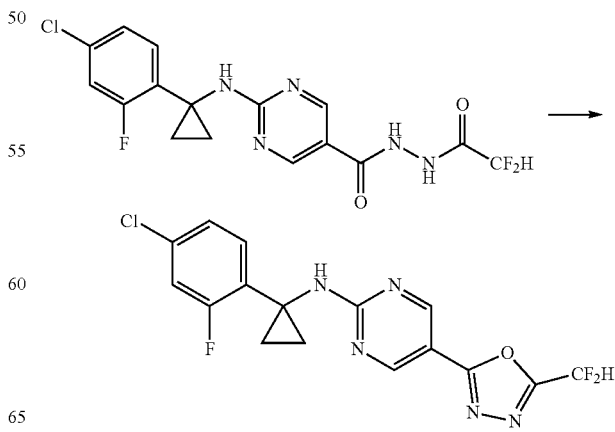

A mixture of 2-((1-(4-chloro-2-fluorophenyl)cyclopropyl)amino)-N'-(2,2-difluoroacetyl)pyrimidine-5-carbohydrazide (0.120 g, 0.300 mmol) and 1-methoxy-N-triethylammoniosulfonyl-methanimidate (Burgess reagent, 0.143 g, 0.600 mmol) in tetrahydrofuran (3 mL) was heated at 150° C. for 30 min under the microwaves, and cooled down to the room temperature to terminate reaction. The reaction mixture was concentrated under the reduced pressure to remove the solvent Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO₂, 4 g cartridge; ethyl acetate/hexane=5% to 50%) to give N-(1-(4-chloro-2-fluorophenyl)cyclopropyl)-5-(5-(difluoromethyl)-1,3,4-oxadiazol-2-yl)pyrimidin-2-amine as pale yellow solid (0.069 g, 60.2%).

$^1$H NMR (400 MHz, CDCl₃) δ 9.01 (s, 1H), 8.91 (s, 1H), 7.68-7.60 (m, 1H), 7.11-7.05 (m, 2H), 7.04 (s, 0.25H), 6.91 (s, 0.5H), 6.78 (s, 0.25H), 6.57 (br, 1H), 1.41-1.25 (m, 4H); LRMS (ES) m/z 382.2 (M⁺+1).

Example 102. Compound 2057: 5-(5-(difluoromethyl)-1,3,4-oxadiazol-2-yl)-N-(1-(3,5-difluorophenyl)cyclopropyl)pyrimidin-2-amine

[Step 1] 1-(3,5-difluorophenyl)cyclopropan-1-amine

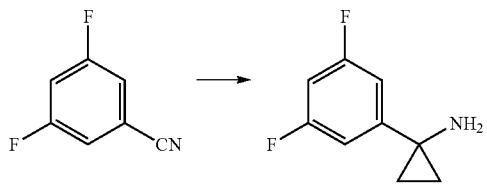 [SMILES: N#Cc1cc(F)cc(F)c1 ; NC1(c2cc(F)cc(F)c2)CC1]

To a stirred solution of 3,5-difluorobenzonitrile (2.500 g, 17.973 mmol), titanium isopropoxide (6.917 mL, 23.364 mmol) and ethylmagnesium bromide (1.00 M solution in THF, 41.337 mL, 41.337 mmol) in 2-methoxy-2-methylpropane (MTBE, 30 mL) were added at −20° C. The reaction mixture was stirred at the same temperature for 30 min, treated at the room temperature with boron trifluoride diethyl etherate (4.436 mL, 35.945 mmol), stirred for additional 3 hr, quenched at the room temperature by the addition of sodium hydroxide (3.00 M solution in water, 17.973 mL, 53.918 mmol, 30 min stirring), filtered through a celite pad to remove solids. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; methanol/dichloromethane=5% to 30%) to give 1-(3,5-difluorophenyl)cyclopropan-1-amine as pale yellow liquid (0.428 g, 14.1%).

[Step 2] ethyl 2-((1-(3,5-difluorophenyl)cyclopropyl)amino)pyrimidine-5-carboxylate

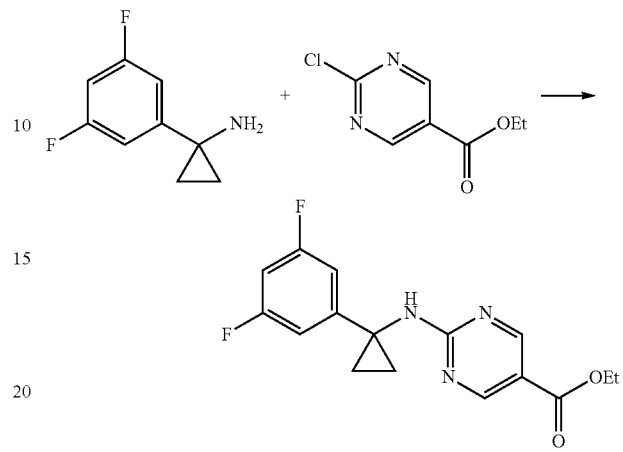

A solution of 1-(3,5-difluorophenyl)cyclopropan-1-amine (0.210 g, 1.241 mmol), ethyl 2-chloropyrimidine-5-carboxylate (0.243 g, 1.303 mmol) and N,N-diisopropylethylamine (0.529 mL, 3.039 mmol) in 1,4-dioxane (3 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO₂, 24 g cartridge; ethyl acetate/hexane=0% to 50%) to give ethyl 2-((1-(3,5-difluorophenyl)cyclopropyl)amino)pyrimidine-5-carboxylate as white solid (0.359 g, 92.5%).

[Step 3] 2-((1-(3,5-difluorophenyl)cyclopropyl)amino)pyrimidine-5-carbohydrazide

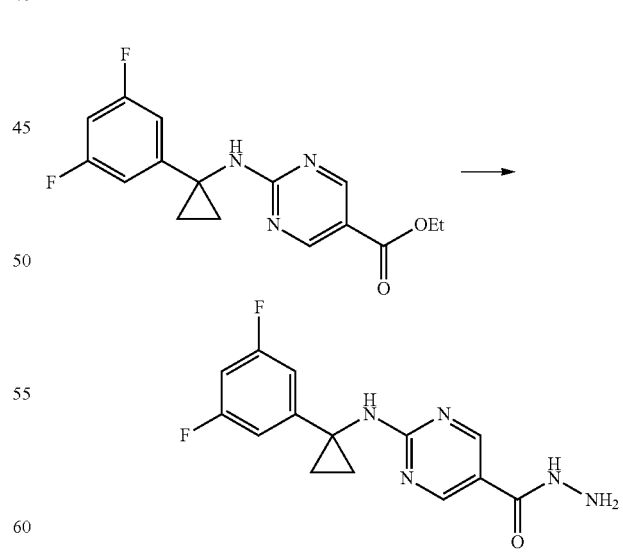

A solution of ethyl 2-((1-(3,5-difluorophenyl)cyclopropyl)amino)pyrimidine-5-carboxylate (0.150 g, 0.470 mmol) and hydrazine (50.00% solution in water, 0.590 mL, 9.395 mmol) in ethanol (4 mL) was stirred at 120° C. for 12 hr, and cooled down to the room temperature to terminate reaction.

[Step 4] N'-(2,2-difluoroacetyl)-2-((1-(3,5-difluorophenyl)cyclopropyl)amino)pyrimidine-5-carbohydrazide

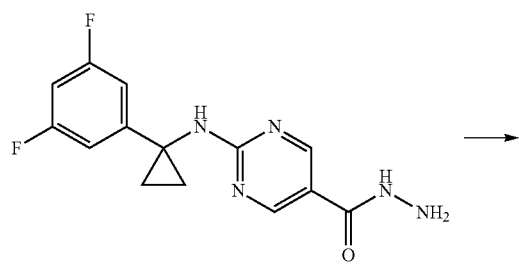

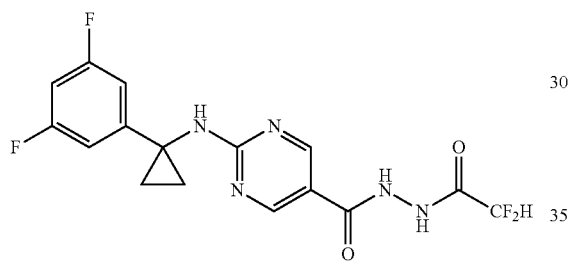

A solution of 2-((1-(3,5-difluorophenyl)cyclopropyl)amino)pyrimidine-5-carbohydrazide (0.150 g, 0.491 mmol), 2,2-difluoroacetic anhydride (0.061 mL, 0.491 mmol) and triethylamine (0.137 mL, 0.983 mmol) in dichloromethane (5 mL) prepared at the room temperature was stirred at the same temperature for 1 hr, and concentrated under the reduced pressure to remove the solvent. The concentrate was purified and concentrated by column chromatography (SiO$_2$, 12 g cartridge; methanol/dichloromethane=10% to 30%) to give N'-(2,2-difluoroacetyl)-2-((1-(3,5-difluorophenyl)cyclopropyl)amino)pyrimidine-5-carbohydrazide as white solid (0.132 g, 70.1%).

[Step 5] Compound 2057

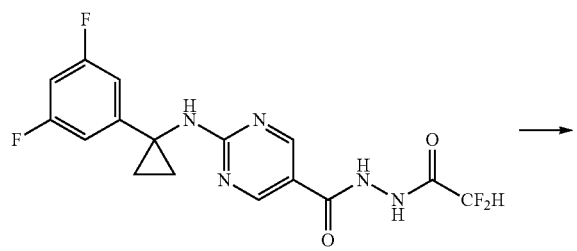

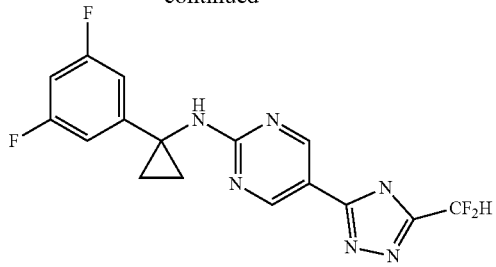

A mixture of N'-(2,2-difluoroacetyl)-2-((1-(3,5-difluorophenyl)cyclopropyl)amino)pyrimidine-5-carbohydrazide (0.100 g, 0.261 mmol) and 1-methoxy-N-triethylammoniosulfonyl-methanimidate (Burgess reagent, 0.124 g, 0.522 mmol) in tetrahydrofuran (3 mL) was heated at 150° C. for 30 min under the microwaves, and cooled down to the room temperature to terminate reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 4 g cartridge; ethyl acetate/hexane=5% to 50%) to give 5-(5-(difluoromethyl)-1,3,4-oxadiazol-2-yl)-N-(1-(3,5-difluorophenyl)cyclopropyl)pyrimidin-2-amine as white solid (0.058 g, 60.9%).
$^1$H NMR (400 MHz, CDCl$_3$) δ 9.01 (s, 2H), 7.05 (s, 0.25H), 6.92 (s, 0.5H), 6.79 (s, 0.25H), 6.79-6.72 (m, 2H), 6.66 (tt, J=8.8, 2.3 Hz, 1H), 6.38 (br, 1H), 1.47 (s, 4H); LRMS (ES) m/z 366.1 (M$^+$+1).

Example 103. Compound 2058: 5-(5-(difluoromethyl)-1,3,4-oxadiazol-2-yl)-N-(1-(3,4-difluorophenyl)cyclopropyl)pyrimidin-2-amine

[Step 1] 1-(3,4-difluorophenyl)cyclopropan-1-amine

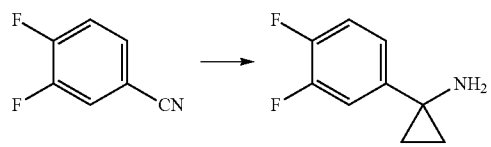 [SMILES: N#Cc1ccc(F)c(F)c1 ; NC1(c2ccc(F)c(F)c2)CC1]

To a stirred solution of 3,4-difluorobenzonitrile (2.500 g, 17.973 mmol), titanium isopropoxide (6.917 mL, 23.364 mmol) and ethylmagnesium bromide (1.00 M solution in THF, 41.337 mL, 41.337 mmol) in 2-methoxy-2-methylpropane (MTBE, 30 mL) were added at −20° C. The reaction mixture was stirred at the same temperature for 30 min, treated at the room temperature with boron trifluoride diethyl etherate (4.436 mL, 35.945 mmol), stirred for additional 3 hr, quenched at the room temperature by the addition of sodium hydroxide (3.00 M solution in water, 17.973 mL, 53.918 mmol, 30 min stirring), filtered through a celite pad to remove solids. Then, water was added to the reaction mixture, followed by extraction with ethyl acetate. The organic layer was washed with aqueous saturated sodium chloride solution, dried with anhydrous MgSO$_4$ filtered, and concentrated in vacuo. The concentrate was purified and concentrated by column chromatography (SiO$_2$, 40 g cartridge; methanol/dichloromethane=5% to 30%) to give 1-(3,4-difluorophenyl)cyclopropan-1-amine as pale yellow liquid (0.822 g, 27.0%).

[Step 2] ethyl 2-((1-(3,4-difluorophenyl)cyclopropyl)amino)pyrimidine-5-carboxylate

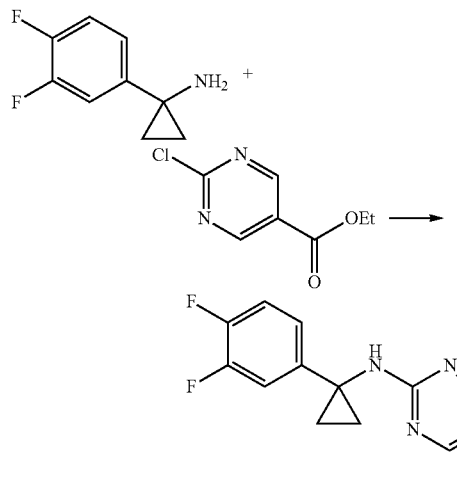

A solution of 1-(3,4-difluorophenyl)cyclopropan-1-amine hydrochloride (0.250 g, 1.241 mmol), ethyl 2-chloropyrimidine-5-carboxylate (0.238 g, 1.277 mmol) and N,N-diisopropylethylamine (0.529 mL, 3.039 mmol) in 1,4-dioxane (3 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO₂, 24 g cartridge; ethyl acetate/hexane=0% to 50%) to give ethyl 2-((1-(3,4-difluorophenyl)cyclopropyl)amino)pyrimidine-5-carboxylate as white solid (0.328 g, 84.5%).

[Step 3] 2-((1-(3,4-difluorophenyl)cyclopropyl)amino)pyrimidine-5-carbohydrazide

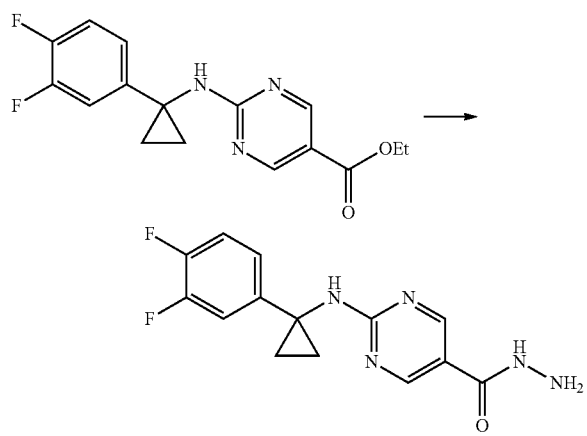

A solution of ethyl 2-((1-(3,4-difluorophenyl)cyclopropyl)amino)pyrimidine-5-carboxylate (0.150 g, 0.470 mmol) and hydrazine (50.00% solution in water, 0.590 mL, 9.395 mmol) in ethanol (4 mL) was stirred at 120° C. for 12 hr, and cooled down to the room temperature to terminate reaction. The reaction mixture was concentrated under the reduced pressure to remove the solvent. The crude product was used without further purification (2-((1-(3,4-difluorophenyl)cyclopropyl)amino)pyrimidine-5-carbohydrazide, 0.140 g, 97.6%, pale yellow liquid).

[Step 4] N'-(2,2-difluoroacetyl)-2-((1-(3,4-difluorophenyl)cyclopropyl)amino)pyrimidine-5-carbohydrazide

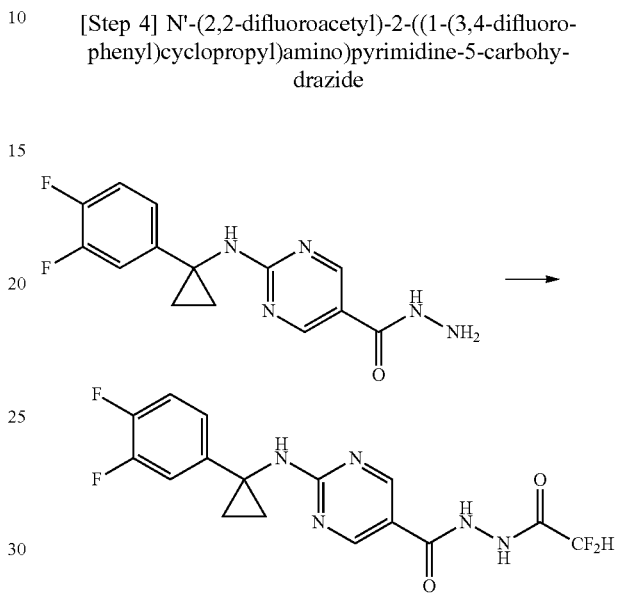

A solution of 2-((1-(3,4-difluorophenyl)cyclopropyl)amino)pyrimidine-5-carbohydrazide (0.153 g, 0.501 mmol), 2,2-difluoroacetic anhydride (0.062 mL, 0.501 mmol) and triethylamine (0.140 mL, 1.002 mmol) in dichloromethane (5 mL) prepared at the room temperature was stirred at the same temperature for 1 hr, and concentrated under the reduced pressure to remove the solvent. The concentrate was purified and concentrated by column chromatography (SiO₂, 12 g cartridge; methanol/dichloromethane=10% to 30%) to give N'-(2,2-difluoroacetyl)-2-((1-(3,4-difluorophenyl)cyclopropyl)amino)pyrimidine-5-carbohydrazide as white solid (0.135 g, 70.3%).

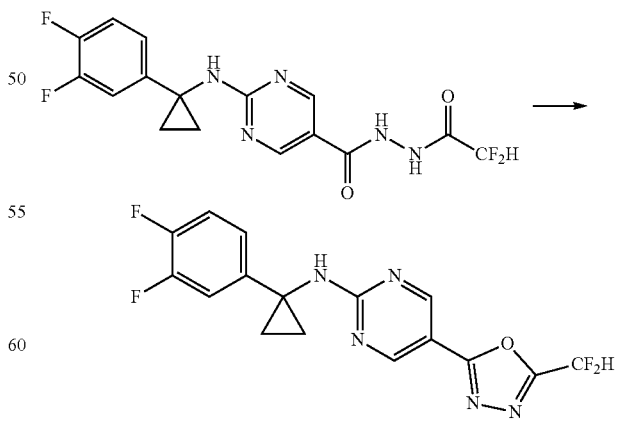

A mixture of N'-(2,2-difluoroacetyl)-2-((1-(3,4-difluorophenyl)cyclopropyl)amino)pyrimidine-5-carbohydrazide (0.100 g, 0.261 mmol) and 1-methoxy-N-triethylammoniosulfonyl-methanimidate (Burgess reagent, 0.124 g, 0.522 mmol) in tetrahydrofuran (3 mL) was heated at 150° C. for 30 min under the microwaves, and cooled down to the room temperature to terminate reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography (SiO$_2$, 4 g cartridge; ethyl acetate/hexane=10% to 50%) to give 5-(5-(difluoromethyl)-1,3,4-oxadiazol-2-yl)-N-(1-(3,4-difluorophenyl)cyclopropyl)pyrimidin-2-amine as white solid (0.059 g, 61.9%).

$^1$H NMR (400 MHz, CDCl$_3$) δ 9.02 (s, 1H), 8.91 (s, 1H), 7.77-7.60 (m, 1H), 7.04 (s, 0.25H), 6.91 (s, 0.5H), 6.81 (s, 0.25H), 6.85-6.75 (m, 2H), 6.62 (br, 1H), 1.37-1.21 (m, 4H); LRMS (ES) m/z 366.1 (M$^+$+1).

Example 104: Compound 2060, 5-(5-(difluoromethyl)-1,3,4-oxadiazol-2-yl)-N-(1-(3-(1-(oxetan-3-yl)piperidin-4-yl)phenyl)cyclobutyl)pyrimidin-2-amine

[Step 1]
1-(3-Bromophenyl)cyclobutane-1-carboxamide

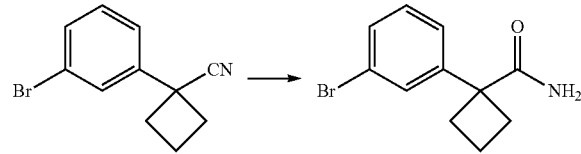 [SMILES: N#CC1(c2cccc(Br)c2)CCC1 ; NC(=O)C1(c2cccc(Br)c2)CCC1]

A solution of 1-(3-bromophenyl)cyclobutane-1-carbonitrile (21.000 g, 88.942 mmol), sodium hydroxide (3.00 M solution, 29.647 mL, 88.942 mmol), hydrogen peroxide (30.00% solution, 27.255 mL, 266.825 mmol) and tetra-n-butylammonium bromide (0.287 g, 0.889 mmol) in methanol (150 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (1-(3-bromophenyl)cyclobutane-1-carboxamide, 26.300 g, 116.4%, pale yellow oil).

[Step 2] 1-(3-Bromophenyl)cyclobutan-1-amine hydrochloride

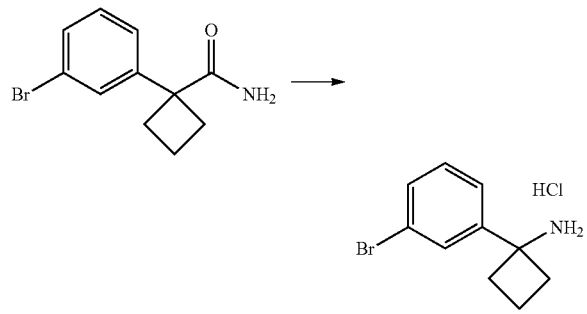

A solution of 1-(3-bromophenyl)cyclobutane-1-carboxamide (26.000 g, 102.310 mmol), sodium hypochlorite (10.00% solution in water, 88.116 mL, 143.234 mmol) and sodium hydroxide (3.00 M solution in water, 95.489 mL, 286.468 mmol) in 1-butanol (100 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate and hydrochloric acid (4.00 M solution in 1,4-dioxane, 38.366 mL, 153.465 mmol) and stirred at the ambient temperature. The resulting precipitates were collected by filtration, washed by ethyl acetate and dried to give 1-(3-bromophenyl)cyclobutan-1-amine hydrochloride as brown solid (11.243 g, 41.9%).

[Step 3] Ethyl 2-((1-(3-bromophenyl)cyclobutyl)amino)pyrimidine-5-carboxylate

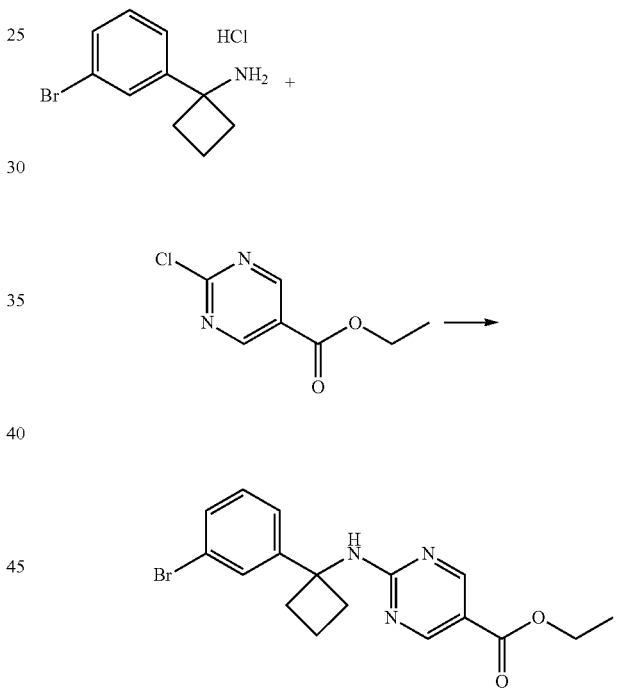

A solution of 1-(3-bromophenyl)cyclobutan-1-amine hydrochloride (7.257 g, 27.637 mmol), ethyl 2-chloropyrimidine-5-carboxylate (5.673 g, 30.400 mmol) and N,N-diisopropylethylamine (14.441 mL, 82.910 mmol) in 1,4-dioxane (110 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 10%) to give ethyl 2-((1-(3-bromophenyl)cyclobutyl)amino)pyrimidine-5-carboxylate as yellow solid (5.007 g, 48.1%).

351

[Step 4] Ethyl 2-((1-(3-(1-((benzyloxy)carbonyl)-1,2,3,6-tetrahydropyridin-4-yl)phenyl)cyclobutyl)amino)pyrimidine-5-carboxylate

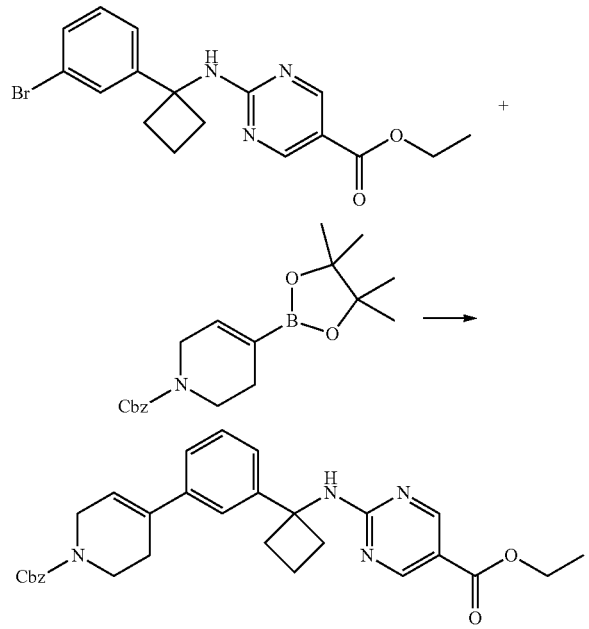

A mixture of ethyl 2-((1-(3-bromophenyl)cyclobutyl)amino)pyrimidine-5-carboxylate (2.000 g, 5.316 mmol), benzyl 4-(4,4,5,5-tetramethyl-1,3,2-dioxaborolan-2-yl)-3,6-dihydropyridine-1(2H)-carboxylate (2.189 g, 6.379 mmol), [1,1'-bis(di-tert-butylphosphino)ferrocene]palladium(II) dichloride (Pd(dtbpf)Cl$_2$, 0.173 g, 0.266 mmol) and cesium carbonate (5.196 g, 15.947 mmol) in 1,4-dioxane (6 mL)/water (2 mL) was heated at 100° C. for 30 min under the microwaves, and cooled down to the room temperature to terminate reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 30%) to give ethyl 2-((1-(3-(1-((benzyloxy)carbonyl)-1,2,3,6-tetrahydropyridin-4-yl)phenyl)cyclobutyl)amino)pyrimidine-5-carboxylate as brown oil (1.215 g, 44.6%).

[Step 5] Ethyl 2-((1-(3-(piperidin-4-yl)phenyl)cyclobutyl)amino)pyrimidine-5-carboxylate

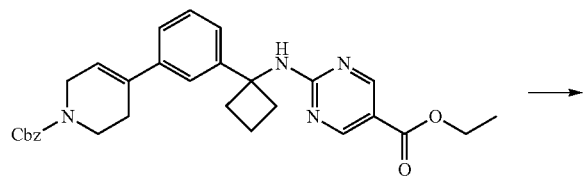

352

-continued

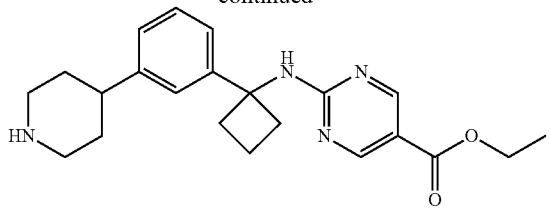

Ethyl 2-((1-(3-(1-((benzyloxy)carbonyl)-1,2,3,6-tetrahydropyridin-4-yl)phenyl)cyclobutyl)amino)pyrimidine-5-carboxylate (1.215 g, 2.371 mmol) was dissolved in ethanol (24 mL) at the room temperature. 10%-Pd/C (240 mg) was slowly added to the solution at the same temperature, the reaction mixture was stirred at 60° C. under the hydrogen atmosphere (H$_2$ balloon) for additional 20 hr, and cooled down to the room temperature to terminate reaction. The reaction mixture was concentrated under the reduced pressure to remove the solvent. The crude product was used without further purification (ethyl 2-((1-(3-(piperidin-4-yl)phenyl)cyclobutyl)amino)pyrimidine-5-carboxylate, 0.851 g, 94.3%, pale yellow oil).

[Step 6] Ethyl 2-((1-(3-(1-(oxetan-3-yl)piperidin-4-yl)phenyl)cyclobutyl)amino)pyrimidine-5-carboxylate

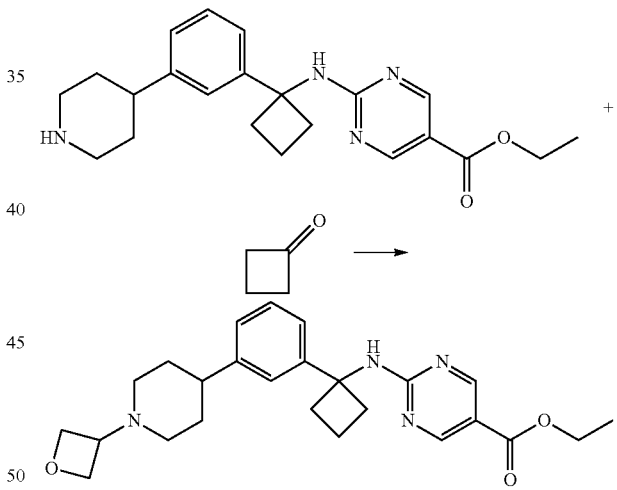

A solution of ethyl 2-((1-(3-(piperidin-4-yl)phenyl)cyclobutyl)amino)pyrimidine-5-carboxylate (0.213 g, 0.558 mmol), cyclobutanone (0.048 mL, 0.838 mmol) and sodium triacetoxyborohydride (0.178 g, 0.838 mmol) in dichloromethane (3 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give ethyl 2-((1-(3-(1-(oxetan-3-yl)piperidin-4-yl)phenyl)cyclobutyl)amino)pyrimidine-5-carboxylate as colorless oil (0.134 g, 55.0%).

[Step 7] 2-((1-(3-(1-(Oxetan-3-yl)piperidin-4-yl)phenyl)cyclobutyl)amino)pyrimidine-5-carbohydrazide

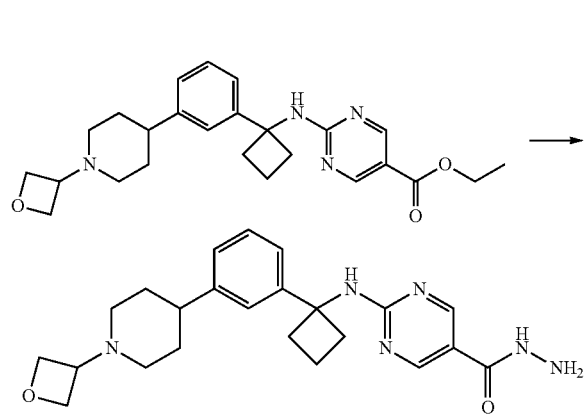

Ethyl 2-((1-(3-(1-(oxetan-3-yl)piperidin-4-yl)phenyl)cyclobutyl)amino)pyrimidine-5-carboxylate (0.134 g, 0.307 mmol) and hydrazine monohydrate (0.299 mL, 6.143 mmol) were mixed at the room temperature in ethanol (2 mL) and then stirred at 75° C. for 18 hr, and cooled down to the room temperature to terminate reaction. The reaction mixture was concentrated under the reduced pressure to remove the solvent. The concentrate was purified and concentrated by column chromatography (SiO$_2$, 4 g cartridge; methanol/dichloromethane=0% to 15%) to give 2-((1-(3-(1-(oxetan-3-yl)piperidin-4-yl)phenyl)cyclobutyl)amino)pyrimidine-5-carbohydrazide as white solid (0.115 g, 88.2%).

[Step 8] N'-(2,2-Difluoroacetyl)-2-((1-(3-(1-(oxetan-3-yl)piperidin-4-yl)phenyl)cyclobutyl)amino)pyrimidine-5-carbohydrazide

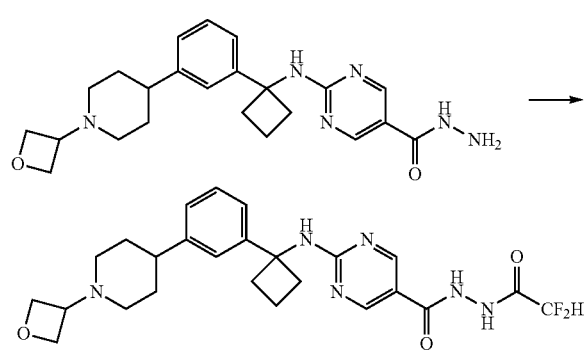

A solution of 2-((1-(3-(1-(oxetan-3-yl)piperidin-4-yl)phenyl)cyclobutyl)amino)pyrimidine-5-carbohydrazide (0.115 g, 0.271 mmol), triethylamine (0.038 mL, 0.271 mmol) and 2,2-difluoroacetic anhydride (0.034 mL, 0.271 mmol) in dichloromethane (1 mL) prepared at the room temperature was stirred at the same temperature for 18 hr, and concentrated under the reduced pressure to remove the solvent. The crude product was used without further purification (N'-(2,2-difluoroacetyl)-2-((1-(3-(1-(oxetan-3-yl)piperidin-4-yl)phenyl)cyclobutyl)amino)pyrimidine-5-carbohydrazide, 0.135 g, 99.5%, pale yellow oil).

[Step 9] Compound 2060

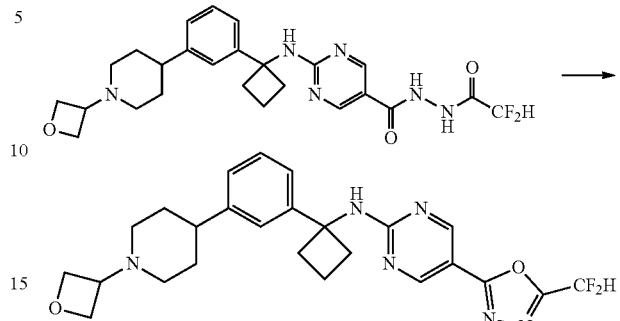

N'-(2,2-difluoroacetyl)-2-((1-(3-(1-(oxetan-3-yl)piperidin-4-yl)phenyl)cyclobutyl)amino)pyrimidine-5-carbohydrazide (0.135 g, 0.270 mmol) and 1-methoxy-N-triethylammoniosulfonyl-methanimidate (Burgess reagent, 0.096 g, 0.405 mmol) were mixed at the room temperature in tetrahydrofuran (1 mL) and then stirred at 70° C. for 18 hr, and cooled down to the room temperature to terminate reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 5-(5-(difluoromethyl)-1,3,4-oxadiazol-2-yl)-N-(1-(3-(1-(oxetan-3-yl)piperidin-4-yl)phenyl)cyclobutyl)pyrimidin-2-amine as pale yellow solid (0.028 g, 21.5%).

$^1$H NMR (400 MHz, CDCl$_3$) δ 8.88 (s, 2H), 7.40-7.38 (m, 2H), 7.31-7.28 (m, 1H), 7.14 (d, 1H, J=7.6 Hz), 6.89 (t, 1H, J=51.7 Hz), 6.53 (s, 1H), 5.00 (s, 2H), 4.75 (t, 1H, J=7.1 Hz), 3.87 (brs, 1H), 3.21 (brs, 2H), 2.78-2.70 (m, 2H), 2.68-2.59 (m, 3H), 2.37-2.36 (m, 2H), 2.25-2.14 (m, 3H), 2.03-1.96 (m, 3H); LRMS (ES) m/z 483.5 (M$^+$+1).

Example 105. Compound 2061: 5-(5-(difluoromethyl)-1,3,4-oxadiazol-2-yl)-N-(1-(2,4-difluorophenyl)cyclopropyl)pyrimidin-2-amine

[Step 1] 1-(2,4-difluorophenyl)cyclopropan-1-amine hydrochloride

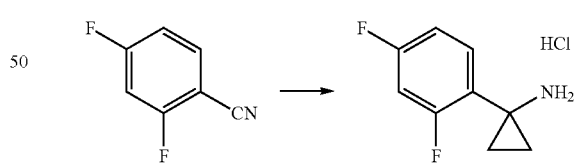

To a stirred solution of 2,4-difluorobenzonitrile (5.000 g, 35.945 mmol) and titanium isopropoxide (13.835 mL, 46.729 mmol) in 2-methoxy-2-methylpropane (MTBE, 60 mL) was added at −20° C. ethylmagnesium bromide (1.00 M solution in THF, 82.674 mL, 82.674 mmol). The reaction mixture was stirred at the same temperature for 1 hr, treated at the room temperature with boron trifluoride diethyl etherate (8.873 mL, 71.891 mmol), stirred for additional 12 hr, quenched at the room temperature by the addition of sodium hydroxide (3.00 M solution in water, 35.945 mL, 107.836 mmol, 30 min stirring), filtered through a celite pad to remove solids. Then, saturated aqueous sodium chloride solution was added to the reaction mixture, followed by extraction with ethyl acetate. The organic layer was washed with aqueous saturated sodium chloride solution, dried with anhydrous MgSO₄, filtered, and concentrated in vacuo. The residue was diluted with hydrochloric acid (20 mL) and hexane (10 mL) and stirred at the ambient temperature. The resulting precipitates were collected by filtration, washed by ethyl acetate, and dried to give 1-(2,4-difluorophenyl)cyclopropan-1-amine hydrochloride as white solid (1.559 g, 21.1%).

[Step 2] ethyl 2-((1-(2,4-difluorophenyl)cyclopropyl)amino)pyrimidine-5-carboxylate

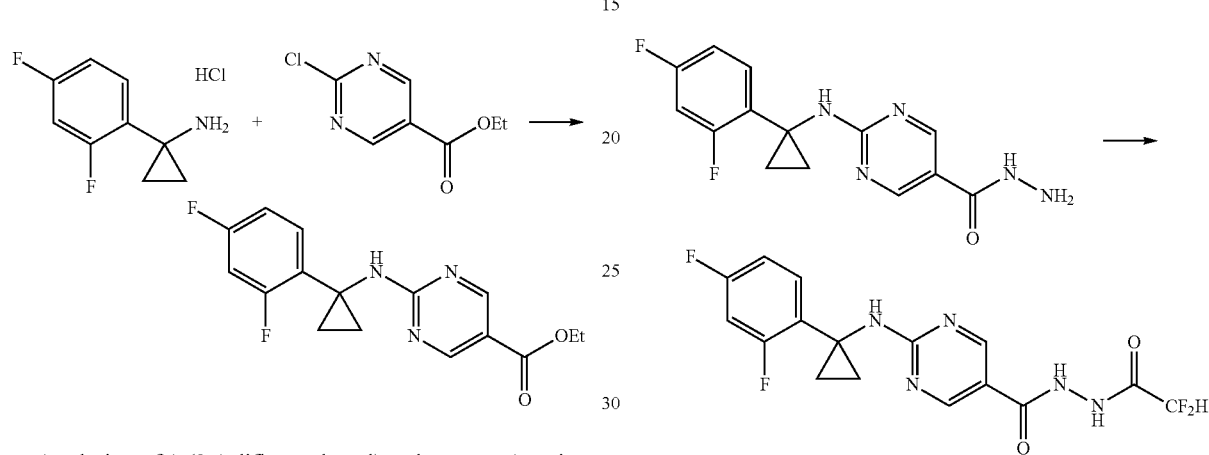

A solution of 1-(2,4-difluorophenyl)cyclopropan-1-amine hydrochloride (0.200 g, 0.973 mmol), ethyl 2-chloropyrimidine-5-carboxylate (0.191 g, 1.021 mmol) and N,N-diisopropylethylamine (0.424 mL, 2.432 mmol) in 1,4-dioxane (5 mL) was stirred at 90° C. for 12 hr, and cooled down to the room temperature to terminate reaction. The reaction mixture was concentrated under the reduced pressure to remove the solvent. The concentrate was purified and concentrated by column chromatography (SiO₂, 24 g cartridge; ethyl acetate/hexane=10% to 50%) to give ethyl 2-((1-(2,4-difluorophenyl)cyclopropyl)amino)pyrimidine-5-carboxylate as white solid (0.217 g, 69.9%).

[Step 3] 2-((1-(2,4-difluorophenyl)cyclopropyl)amino)pyrimidine-5-carbohydrazide A solution of ethyl 2-((1-(2,4-difluorophenyl)cyclopropyl)amino)pyrimidine-5-carboxylate (0.220 g, 0.689 mmol) and hydrazine (50.00% solution in water, 0.865 mL, 13.780 mmol) in ethanol (3 mL) was stirred at 120° C. for 8 hr, and cooled down to the room temperature to terminate reaction. The reaction mixture was concentrated under the reduced pressure to remove the solvent. The crude product was used without further purification (2-((1-(2,4-difluorophenyl)cyclopropyl)amino)pyrimidine-5-carbohydrazide, 0.200 g, 95.1%, white solid).

[Step 4] N'-(2,2-difluoroacetyl)-2-((1-(2,4-difluorophenyl)cyclopropyl)amino)pyrimidine-5-carbohydrazide

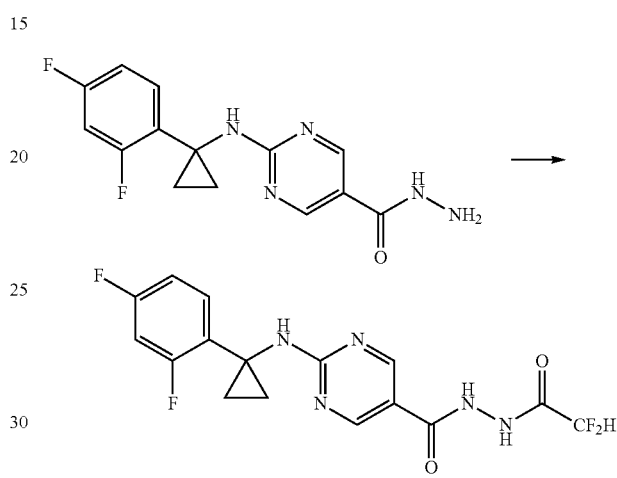

A solution of 2-((1-(2,4-difluorophenyl)cyclopropyl)amino)pyrimidine-5-carbohydrazide (0.200 g, 0.655 mmol), 2,2-difluoroacetic anhydride (0.090 mL, 0.721 mmol) and triethylamine (0.183 mL, 1.310 mmol) in tetrahydrofuran (4 mL) prepared at the room temperature was stirred at the same temperature for 1 hr, and concentrated under the reduced pressure to remove the solvent. The concentrate was purified and concentrated by column chromatography (SiO₂, 12 g cartridge; methanol/dichloromethane=5% to 20%) to give N'-(2,2-difluoroacetyl)-2-((1-(2,4-difluorophenyl)cyclopropyl)amino)pyrimidine-5-carbohydrazide as white solid (0.132 g, 52.6%).

[Step 5] Compound 2061

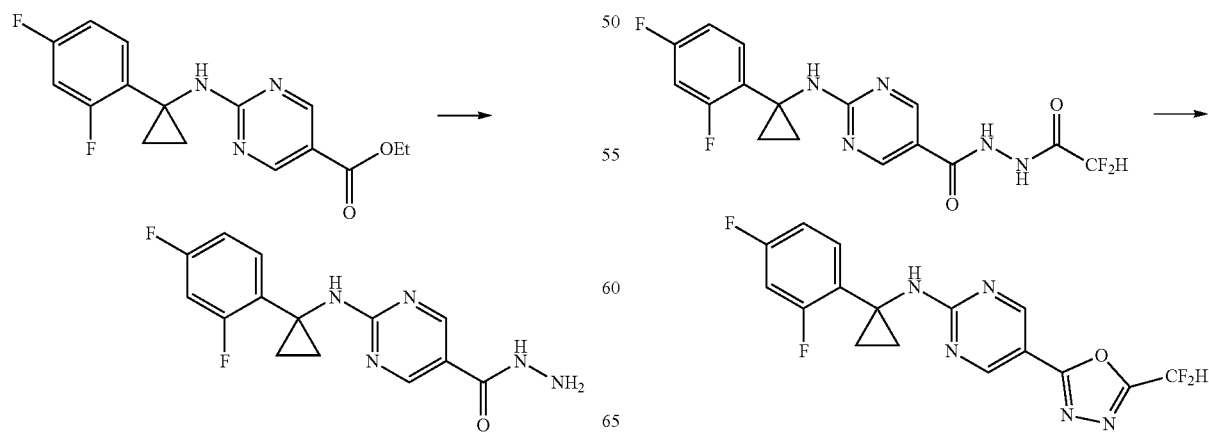

A mixture of N'-(2,2-difluoroacetyl)-2-((1-(2,4-difluorophenyl)cyclopropyl)amino)pyrimidine-5-carbohydrazide (0.100 g, 0.261 mmol) and 1-methoxy-N-triethylammoniosulfonyl-methanimidate (Burgess reagent, 0.124 g, 0.522 mmol) in tetrahydrofuran (5 mL) was heated at 150° C. for 30 min under the microwaves, and cooled down to the room temperature to terminate reaction. The reaction mixture was concentrated under the reduced pressure to remove the solvent. Then, water (5 mL) was added to the reaction mixture, followed by extraction with dichloromethane (5 mL), and filtered through a plastic frit. The resulting organic layer was concentrated in vacuo. The concentrate was purified and concentrated by column chromatography ($SiO_2$, 4 g cartridge; ethyl acetate/hexane=5% to 50%) to give 5-(5-(difluoromethyl)-1,3,4-oxadiazol-2-yl)-N-(1-(2,4-difluorophenyl)cyclopropyl)pyrimidin-2-amine as white solid (0.028 g, 29.4%).

$^1$H NMR (400 MHz, $CDCl_3$) δ 8.99 (d, J=13.6 Hz, 2H), 7.17-7.11 (m, 1H), 7.11-7.06 (m, 1H), 7.04 (s, 0.25H), 7.01 (dddd, J=8.6, 4.2, 2.3, 1.1 Hz, 1H), 6.92 (s, 0.5H), 6.79 (s, 0.25H), 6.65 (br, 1H), 1.41 (s, 4H); LRMS (ES) m/z 366.1 ($M^+$+1).

Example 106: Compound 2062, 5-(5-(difluoromethyl)-1,3,4-oxadiazol-2-yl)-N-(1-(4-morpholinophenyl)cyclobutyl)pyrimidin-2-amin

[Step 1] tert-butyl (1-(4-morpholinophenyl)cyclobutyl)carbamate

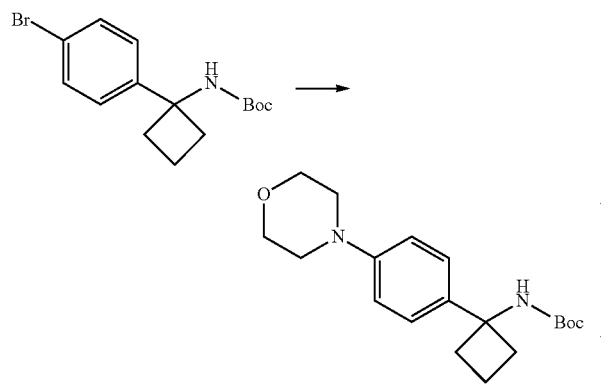

tert-butyl (1-(4-bromophenyl)cyclobutyl)carbamate (0.500 g, 1.533 mmol), morpholine (0.159 mL, 1.839 mmol), tris(dibenzylideneacetone)dipalladium (Pd2(dba)3, 0.140 g, 0.153 mmol), 2-dicyclohexylphosphino-2',4'',6'-triisopropylbiphenyl (XPhos, 0.073 g, 0.153 mmol) and sodium tert-butoxide (0.295 g, 3.065 mmol) in toluene (10 mL) was mixed at the room temperature and then heated at 100° C. under the microwaves for 30 min, cooled down to the room temperature to terminate reaction. Then, saturated aqueous sodium bicarbonate solution was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 24 g cartridge; ethyl acetate/hexane=0% to 20%) to give the crude product which was dissolved in hexane (10 mL) and stirred at the ambient temperature. The resulting precipitates were collected by filtration, washed by hexane, and dried to give tert-butyl (1-(4-morpholinophenyl)cyclobutyl)carbamate as pale brown solid (0.347 g, 68.1%).

[Step 2] 1-(4-morpholinophenyl)cyclobutan-1-amine

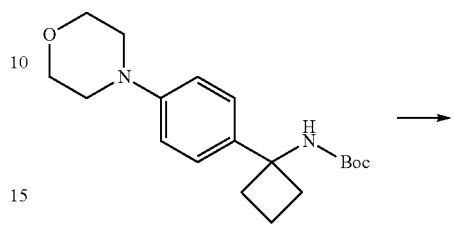

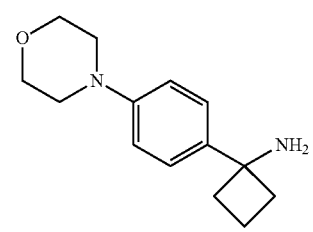

A solution of tert-butyl (1-(4-morpholinophenyl)cyclobutyl)carbamate (0.347 g, 1.044 mmol) and hydrochloric acid (4.00 M solution, 1.305 mL, 5.219 mmol) in dichloromethane (10 mL) prepared at the room temperature was stirred at the same temperature for 18 hr. Then, saturated aqueous sodium bicarbonate solution was added to the reaction mixture, followed by extraction with dichloromethane. The aqueous layer was concentrated in vacuo and diluted with tetrahydrofuran (30 mL)/dichloromethane (10 mL) and stirred at the ambient temperature. The precipitates were collected by filtration, 1-(4-morpholinophenyl)cyclobutan-1-amine was used without further purification (0.240 g, 99.0%, colorless oil).

[Step 3] Ethyl 2-((1-(4-morpholinophenyl)cyclobutyl)amino)pyrimidine-5-carboxylate

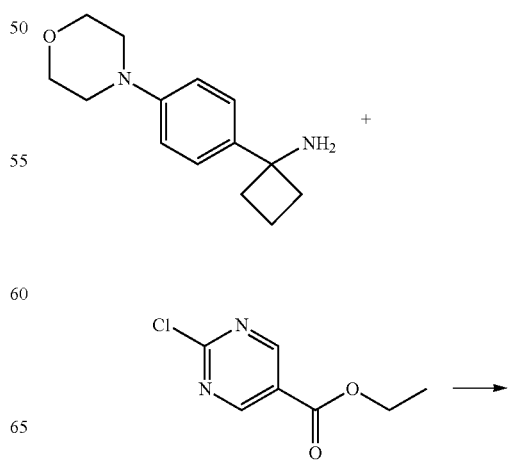

-continued

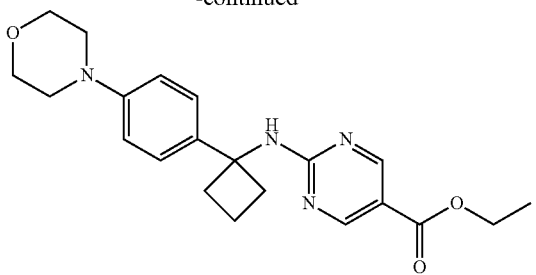

1-(4-morpholinophenyl)cyclobutan-1-amine (0.240 g, 1.033 mmol), ethyl 2-chloropyrimidine-5-carboxylate (0.212 g, 1.136 mmol) and N,N-diisopropylethylamine (0.540 mL, 3.099 mmol) were mixed at the room temperature in 1,4-dioxane (5 mL) and then stirred at 110° C. for 18 hr, and cooled down to the room temperature to terminate reaction. The reaction mixture was concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=10% to 40%) to give the crude product which was dissolved in ethanol (5 mL) and stirred at the ambient temperature. The resulting precipitates were collected by filtration, washed by ethanol, and dried to give ethyl 2-((1-(4-morpholinophenyl)cyclobutyl)amino)pyrimidine-5-carboxylate as white solid (0.280 g, 70.9%).

[Step 4] 2-((1-(4-morpholinophenyl)cyclobutyl)amino)pyrimidine-5-carbohydrazide

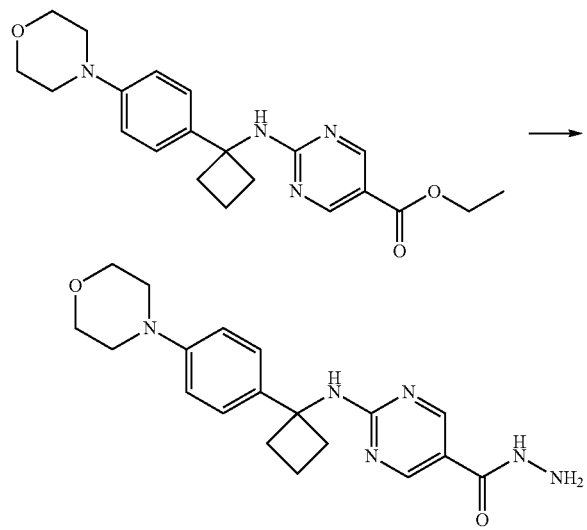

ethyl 2-((1-(4-morpholinophenyl)cyclobutyl)amino)pyrimidine-5-carboxylate (0.280 g, 0.732 mmol) and hydrazine monohydrate (0.712 mL, 14.642 mmol) were mixed at the room temperature in ethanol (3 mL) and then stirred at 100° C. for 7 hr, cooled down to the room temperature to terminate reaction. The precipitates were collected by filtration, washed by ethanol, and dried to give 2-((1-(4-morpholinophenyl)cyclobutyl)amino)pyrimidine-5-carbohydrazide as white solid (0.112 g, 41.5%).

[Step 5] N'-(2,2-difluoroacetyl)-2-((1-(4-morpholinophenyl)cyclobutyl)amino)pyrimidine-5-carbohydrazide

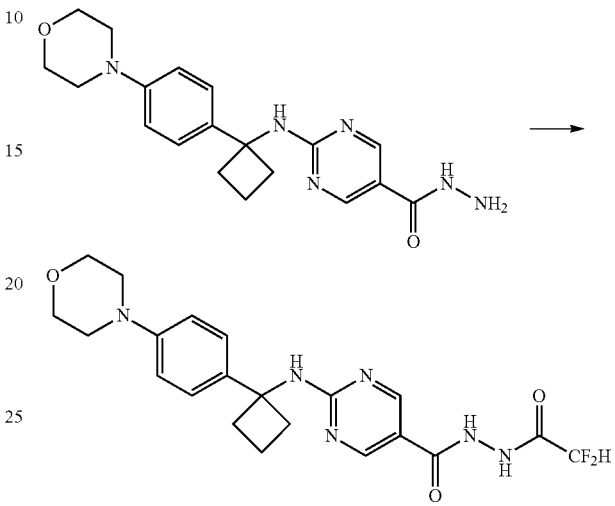

A solution of 2-((1-(4-morpholinophenyl)cyclobutyl)amino)pyrimidine-5-carbohydrazide (0.112 g, 0.304 mmol) and triethylamine (0.127 mL, 0.912 mmol) in tetrahydrofuran (5 mL) was mixed at the room temperature with 2,2-difluoroacetic anhydride (0.042 mL, 0.334 mmol), stirred at the same temperature for 18 hr, and concentrated under the reduced pressure to remove the solvent. The concentrate was purified and concentrated by column chromatography (SiO$_2$, 4 g cartridge; ethyl acetate/hexane=40% to 90%) to give N'-(2,2-difluoroacetyl)-2-((1-(4-morpholinophenyl)cyclobutyl)amino)pyrimidine-5-carbohydrazide as white solid (0.096 g, 70.7%).

[Step 6] Compound 2062

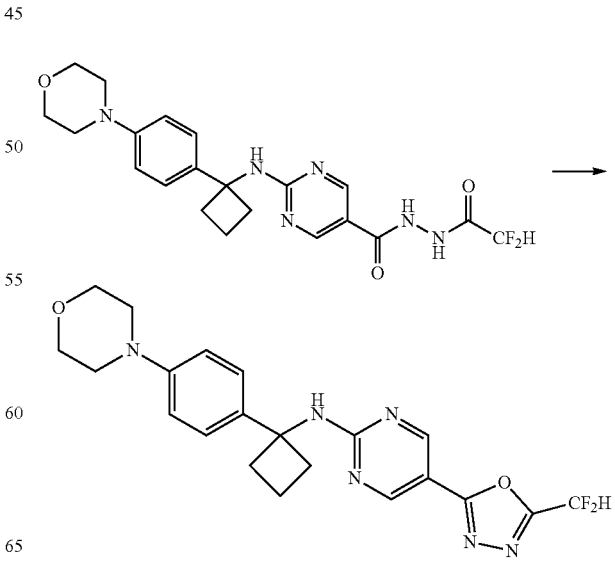

N'-(2,2-difluoroacetyl)-2-((1-(4-morpholinophenyl)cyclobutyl)amino)pyrimidine-5-carbohydrazide (0.100 g, 0.224 mmol) and 1-methoxy-N-triethylammoniosulfonylmethanimidate (Burgess reagent, 0.160 g, 0.672 mmol) were mixed at the room temperature in tetrahydrofuran (5 mL) and then stirred at 100° C. for 18 hr, and cooled down to the room temperature to terminate reaction. The reaction mixture was concentrated under the reduced pressure to remove the solvent. The concentrate was purified and concentrated by column chromatography (SiO$_2$, 4 g cartridge; ethyl acetate/hexane=10% to 40%) to give 5-(5-(difluoromethyl)-1,3,4-oxadiazol-2-yl)-N-(1-(4-morpholinophenyl)cyclobutyl)pyrimidin-2-amine as white solid (0.047 g, 49.0%).

$^1$H NMR (400 MHz, CDCl$_3$) δ 8.88 (s, 2H), 7.45 (d, J=8.8 Hz, 2H), 7.02-6.76 (m, 3H), 6.36 (s, 1H), 3.90-3.86 (m, 4H), 3.19 (t, J=4.6 Hz, 4H), 2.76-2.69 (m, 2H), 2.65-2.58 (m, 2H), 2.18-2.15 (m, 1H), 1.99-1.96 (m, 1H); LRMS (ES) m/z 429.3 (M$^+$+1).

Experimental Example: HDAC Enzyme Activity Inhibition Assays (In Vitro)

In order to examine the HDAC6 selectivity of the compounds of formula I of the present invention by HDAC1 and HDAC6 enzymatic activity inhibition assays, an experiment was performed using a conventional substance as a control.

HDAC enzyme activity was measured using a HDAC Fluorimetric Drug Discovery Kit (BML-AK511, 516, Enzo Life Science). For the HDAC1 enzyme activity test, human recombinant HDAC1 (BML-SE456) was used as an enzyme source, and Fluor de Lys®-"SIRT1 (BNL-KI177) was used as a substrate. A 5-fold dilution of the compound was seeded into a 96-well plate, and then 0.3 μg of the enzyme and 10 μM of the substrate were added to each well of the plate and allowed to react at 30° C. for 60 minutes. Then, Fluor de Lys®-Developer II (BML-KI176) was added thereto and allowed to react for 30 minutes, after which the fluorescence value (Ex 360, Em 460) was measured using a multi-plate reader (Flexstation 3, Molecular Device). The HDAC6 enzyme was tested using human recombinant HDAC6 (382180) (Calbiochem) according to the same protocol as the HDAC1 enzyme activity test method. Based on the resulting values, each IC$_{50}$ value was calculated using GraphPad Prism4.0 program.

TABLE 3

Results of HDAC enzyme activity inhibition assays

| Compound | HDAC6 | HDAC1 enzyme |
|---|---|---|
| 1524 | 0.048 | >10 |
| 1526 | 0.179 | >10 |
| 1559 | 0.03 | >10 |
| 1579 | 0.046 | >10 |
| 1580 | 0.305 | >10 |
| 1581 | 0.135 | >10 |
| 1582 | 1.25 | >10 |
| 1603 | 0.05 | >10 |
| 1604 | 0.204 | >10 |
| 1605 | 0.044 | >10 |
| 1606 | 0.168 | >10 |
| 1607 | 0.032 | >10 |
| 1608 | 0.154 | >10 |
| 1609 | 0.023 | >10 |
| 1610 | 0.151 | >10 |
| 1611 | 0.038 | >10 |
| 1612 | 0.455 | >10 |
| 1614 | 0.029 | >10 |
| 1615 | 0.022 | >10 |
| 1616 | 0.044 | >10 |
| 1617 | 0.211 | >10 |
| 1618 | 0.267 | >10 |
| 1640 | 0.028 | >10 |
| 1641 | 0.058 | >10 |
| 1642 | 0.057 | >10 |
| 1670 | 0.596 | >10 |
| 1671 | 0.044 | >10 |
| 1672 | 0.234 | >10 |
| 1673 | 0.025 | >10 |
| 1674 | 0.132 | >10 |
| 1675 | 0.039 | >10 |
| 1676 | 0.242 | >10 |
| 1677 | 0.267 | >10 |
| 1678 | 0.225 | >10 |
| 1683 | 0.021 | >10 |
| 1711 | 0.026 | >10 |
| 1712 | 0.1 | >10 |
| 1713 | 0.033 | >10 |
| 1714 | 0.138 | >10 |
| 1722 | 0.029 | >10 |
| 1723 | 0.219 | >10 |
| 1738 | 0.132 | >10 |
| 1740 | 0.062 | >10 |
| 1741 | 0.45 | >10 |
| 1742 | 0.531 | >10 |
| 1761 | 0.025 | >10 |
| 1779 | 0.134 | >10 |
| 1780 | 0.42 | >10 |
| 1817 | 0.078 | >10 |
| 1818 | 0.751 | >10 |
| 1819 | 0.07 | >10 |
| 1820 | 0.083 | >10 |
| 1821 | 0.032 | >10 |
| 1822 | 0.282 | >10 |
| 1826 | 0.12 | >10 |
| 1827 | 0.043 | >10 |
| 1828 | 0.039 | >10 |
| 1832 | 0.1 | >10 |
| 1833 | 0.75 | >10 |
| 1834 | 0.12 | >10 |
| 1835 | 1.96 | >10 |
| 1836 | 0.2 | >10 |
| 1837 | 2.52 | >10 |
| 1838 | 0.11 | >10 |
| 1913 | 0.04 | >10 |
| 1959 | 0.163 | >10 |
| 1960 | 1.23 | >10 |
| 1961 | 0.115 | >10 |
| 1962 | 0.888 | >10 |
| 1963 | 0.089 | >10 |
| 1964 | 1.85 | >10 |
| 1965 | 0.070 | >10 |
| 1966 | 1.47 | >10 |
| 2023 | 0.387 | >10 |
| 2026 | >10 | >10 |
| 2027 | 0.09 | >10 |
| 2028 | 0.302 | >10 |
| 2030 | 0.758 | >10 |
| 2035 | 0.367 | >10 |
| 2036 | 0.478 | >10 |
| 2037 | 0.397 | >10 |
| 2038 | 0.111 | >10 |
| 2040 | 0.1 | >10 |
| 2041 | 0.189 | >10 |
| 2042 | 0.173 | >10 |
| 2043 | 0.277 | >10 |
| 2044 | 1.735 | >10 |
| 2045 | 0.061 | >10 |
| 2046 | 0.329 | >10 |
| 2047 | 0.032 | >10 |
| 2048 | 0.063 | >10 |
| 2049 | 0.051 | >10 |
| 2050 | 0.026 | >10 |
| 2051 | 0.152 | >10 |
| 2052 | 0.075 | >10 |
| 2053 | 0.519 | >10 |

TABLE 3-continued

Results of HDAC enzyme activity inhibition assays

| Compound | HDAC6 | HDAC1 enzyme |
|---|---|---|
| 2054 | 0.083 | >10 |
| 2055 | 0.031 | >10 |
| 2056 | 0.035 | >10 |
| 2057 | 0.033 | >10 |
| 2058 | 0.039 | >10 |
| 2060 | 0.221 | >10 |
| 2061 | 0.043 | >10 |
| 2062 | 0.256 | >10 |

As can be seen in Table 3 above, the oxadiazole amine derivative compounds, stereoisomers thereof or pharmaceutically acceptable salts thereof according to the present disclosure showed about 8 to 454 times higher selective HDAC6 inhibitory activities in the HDAC1 and HDAC6 activity inhibition assays.

The invention claimed is:

1. An oxadiazole amine derivative compound represented by the following Formula I, a stereoisomer thereof or a pharmaceutically acceptable salt thereof:

[Formula I]

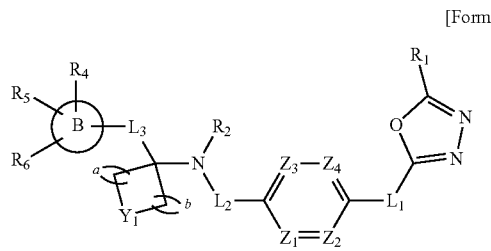

wherein $R_1$ is —$CF_2H$ or $CF_3$;
$L_1$ and $L_2$ are each independently —($C_1$-$C_2$ alkyl)- or null;
$Z_1$ to $Z_4$ are each independently N or $CR^Z$ {wherein three or more of $Z_1$ to $Z_4$ cannot be N at the same time}, wherein $R^Z$ is H, —F, —Cl, —Br, —I or —O($C_1$-$C_4$ alkyl);
$R_2$ is —H or —($C_1$-$C_4$ alkyl);
$Y_1$ is —$CH_2$—, —$NR^C$—, —O—, —C(=O)— or —S(=O)$_2$—, wherein $R^C$ is —H, —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —C(=O)—O($C_1$-$C_4$ alkyl)-aryl, —($C_1$-$C_4$ alkyl)-C(=O)—O($C_1$-$C_4$ alkyl), —($C_1$-$C_4$ alkyl)-$NR^AR^B$, —S(=O)$_2$—($C_1$-$C_4$ alkyl), aryl, —($C_1$-$C_4$ alkyl)-aryl, —($C_2$-$C_4$ alkenyl)-aryl, heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl), {wherein at least one H of the —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —C(=O)—O($C_1$-$C_4$ alkyl)-aryl, —($C_1$-$C_4$ alkyl)-C(=O)—O($C_1$-$C_4$ alkyl), —($C_1$-$C_4$ alkyl)-$NR^AR^B$, —S(=O)$_2$—($C_1$-$C_4$ alkyl), aryl, —($C_1$-$C_4$ alkyl)-aryl, ($C_2$-$C_4$ alkenyl)-aryl, heteroaryl, —($C_1$-$C_4$ alkyl)-heteroaryl, —C(=O)—($C_3$-$C_7$ cycloalkyl), —$C_2$-$C_6$ heterocycloaklyl or —($C_1$-$C_4$ alkyl)-C(=O)—($C_2$-$C_6$ heterocycloalkyl) may be substituted with —X, wherein X is a halogen};
a and b are each independently an integer of 0, 1, 2, 3 or 4 {wherein the a and b cannot all be 0};
$L_3$ is —($C_1$-$C_2$ alkyl)-, —$SO_2$—, —($C_1$-$C_2$ alkyl)-$SO_2$—, or null;

is -aryl, -heteroaryl,

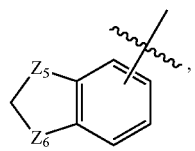

or heterocycloalkyl, wherein $Z_5$ and $Z_6$ are each independently —$CH_2$— or —O—; and
$R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, heterocycloalkyl {wherein the heterocycloalkyl may be unsubstituted or substituted with $C_1$-$C_4$ alkyl or heterocycloalkyl},

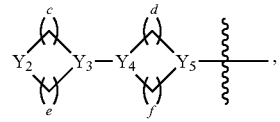

—O-aryl, —$CF_2H$, —C(=O)—($C_1$-$C_4$ alkyl), —C(=O)—O($C_1$-$C_4$ alkyl), —$NR^AR^B$, —C(=O)—$NR^AR^B$ or —S(=O)$_2$—($C_1$-$C_4$ alkyl), wherein $Y_2$ is —$CH_2$—, —$NR^C$—, —O—, —C(=O)— or —S(=O)$_2$—, $Y_3$ to $Y_5$ are each independently —CH— or —N—, and c to f are each independently an integer of 0, 1, 2, 3 or 4 {wherein c and e cannot all be 0, and d and f cannot all be 0}, wherein $R^A$ and $R^B$ are each independently —H or —($C_1$-$C_4$ alkyl) {wherein at least one H of the —($C_1$-$C_4$ alkyl) may be substituted with —X or —OH}.

2. The oxadiazole amine derivative compound represented by Formula I, stereoisomer thereof or pharmaceutically acceptable salt thereof according to claim 1,
wherein $R_1$ is —$CF_2H$ or —$CF_3$;
$L_1$ and $L_2$ are null;
$Z_1$ and $Z_3$ are N;
$Z_2$ and $Z_4$ are $CR^Z$, wherein $R^Z$ is —H, —F, —Cl, —Br, —I or —O($C_1$-$C_4$ alkyl);
$R_2$ is —H or —($C_1$-$C_4$ alkyl);
$Y_1$ is —$CH_2$— or —$NR^C$—, wherein $R^C$ is —H, or —C(=O)—O($C_1$-$C_4$ alkyl)-aryl {wherein at least one H of the —C(=O)—O($C_1$-$C_4$ alkyl)-aryl may be substituted with —X, wherein X is a halogen};
a and b are each independently an integer of 0, 1, 2 or 3 {wherein the a and b cannot all be 0};
$L_3$ is —($C_1$-$C_2$ ($C_1$-$C_2$ alkyl)-$SO_2$—, or null;

is phenyl, pyridine, benzo[d][1,3]dioxol, thiophene, pyrimidine, pyrazine or pyridazine; and $R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, piperidine, morpholino, piperazine or pyrrolidine {wherein the piperidine, morpholino, piperazine or pyrrolidine may be unsubstituted or substituted with $C_1$-$C_4$ alkyl}, or

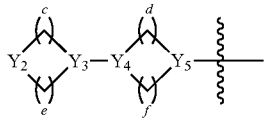

wherein $Y_2$ is —O—, $Y_3$ and $Y_5$ are —CH—, $Y_4$ is —N—, c and e are each independently an integer of 0, 1 or 2 {wherein c and e cannot all be 0}, and d and f are each independently an integer of 0, 1, 2 or 3 {wherein d and f cannot all be 0}.

3. The oxadiazole amine derivative compound represented by Formula I, stereoisomer thereof or pharmaceutically acceptable salt thereof according to claim 1, wherein the compound represented by the above Formula I is a compound represented by the following Formula II:

[Formula II]

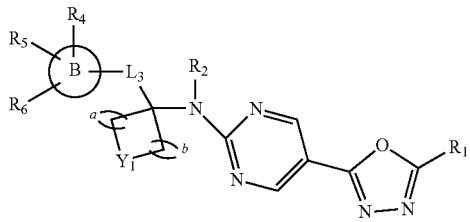

wherein $R_1$ is —$CF_2$H or —$CF_3$;
$R_2$ is —H;
$Y_1$ is —$CH_2$— or —$NR^C$—, wherein $R^C$ is —H, or —C(=O)—O($C_1$-$C_4$ alkyl)-aryl;
a and b are each independently an integer of 0, 1, 2 or 3 {wherein a and b cannot all be 0};
$L_3$ is —($C_1$-$C_2$ alkyl)-, ($C_1$-$C_2$ alkyl)-$SO_2$—, or null;

B is phenyl, pyridine, benzo[d][1,3]dioxol and thiophene; and
$R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, piperidine morpholino {wherein the piperidine may be unsubstituted or substituted with $C_1$-$C_4$ alkyl}, or

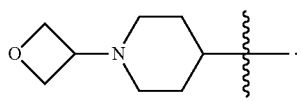 [SMILES: *C1CCN(C2COC2)CC1 ; "."]

4. The oxadiazole amine derivative compound represented by Formula II, stereoisomer thereof or pharmaceutically acceptable salt thereof according to claim 3, wherein $R_1$ is —$CF_2$H or —$CF_3$;
$R_2$ is —H;
$Y_1$ is —$CH_2$— or —$NR^c$—, wherein $R^C$ is —H, or

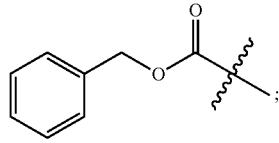 [SMILES: *C(=O)OCc1ccccc1 ; ";"]

a and b are each independently an integer of 0, 1, 2 or 3 {wherein the a and b cannot all be 0, a ring formed by $Y_1$, a and b is a 3- to 7-membered saturated cycloalkyl when $Y_1$ is —$CH_2$— or a ring formed by $Y_1$, a and b is a 3- to 7-membered saturated heterocycloalkyl containing one N when Y1 is —$NR^c$—};
$L_3$ is —$CH_2$—, —$CH_2$—$SO_2$—, or null;

B is phenyl, pyridine, benzo[d][1,3]dioxol and thiophene; and
$R_4$ to $R_6$ are each independently —H, —F, —Cl, —Br, —I, —OH, —O($C_1$-$C_4$ alkyl), —($C_1$-$C_4$ alkyl), —$CF_3$, —$OCF_3$, morpholino,

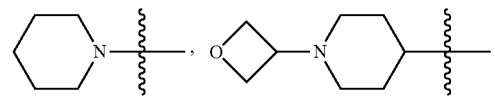 [SMILES: *N1CCCCC1 ; "," ; *C1CCN(C2COC2)CC1]

or

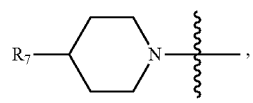

wherein $R_7$ is —H or —($C_1$-$C_4$ alkyl).

5. The oxadiazole amine derivative compound represented by formula I, stereoisomer thereof or pharmaceutically acceptable salt thereof according to claim 1, wherein the compound of Formula I is selected from the group consisting of the following compounds:
5-(5-(difluoromethyl)-1,3,4-oxadiazol-2-yl)-N-(1-phenylcyclopropyl)pyrimidin-2-amine;
N-(1-phenylcyclopropyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-phenylcyclobutyl)pyrimidin-2-amine;
5-(5-(difluoromethyl)-1,3,4-oxadiazol-2-yl)-N-(1-phenylcyclopentyl)pyrimidin-2-amine;
N-(1-phenylcyclopentyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-phenylcyclohexyl)pyrimidin-2-amine;
N-(1-phenylcyclohexyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(4-methoxyphenyl)cyclobutyl)pyrimidin-2-amine;

N-(1-(4-methoxyphenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(3-methoxyphenyl)cyclobutyl)pyrimidin-2-amine;
N-(1-(3-methoxyphenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(3-fluorophenyl)cyclobutyl)pyrimidin-2-amine;
N-(1-(3-fluorophenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(2-fluorophenyl)cyclobutyl)pyrimidin-2-amine;
N-(1-(2-fluorophenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(4-fluorophenyl)cyclobutyl)pyrimidin-2-amine;
N-(1-(4-fluorophenyl)cyclobutyl)-5-(5-(trifluoromethyl)-1,3,4-oxadiazol-2-yl)pyrimidin-2-amine;
N-(1-(2-chlorophenyl)cyclobutyl)-5-(5-(difluoromethyl)-1,3,4-oxadiazol-2-yl)pyrimidin-2-amine;
N-(1-(3-chlorophenyl)cyclobutyl)-5-(5-(difluoromethyl)-1,3,4-oxadiazol-2-yl)pyrimidin-2-amine;
N-(1-(4-chlorophenyl)cyclobutyl)-5-(5-(difluoromethyl)-1,3,4-oxadiazol-2-yl)pyrimidin-2-amine;
N-(1-(2-chlorophenyl)cyclobutyl)-5-(5-(trifluoromethyl)-1,3,4-oxadiazol-2-yl)pyrimidin-2-amine;
N-(1-(4-chlorophenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(pyridin-2-yl)cyclobutyl)pyrimidin-2-amine;
N-(1-(pyridin-2-yl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(3-(trifluoromethyl)phenyl)cyclobutyl)pyrimidin-2-amine;
5-(5-(trifluoromethyl)-1,3,4-oxadiazol-2-yl)-N-(1-(3-(trifluoromethyl)phenyl)cyclobutyl)pyrimidin-2-amine;
5-(5-(difluoromethyl)-1,3,4-oxadiazol-2-yl)-N-(1-(o-tolyl)cyclobutyl)pyrimidin-2-amine;
N-(1-(o-tolyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(m-tolyl)cyclobutyl)pyrimidin-2-amine;
N-(1-(m-tolyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(p-tolyl)cyclobutyl)pyrimidin-2-amine;
N-(1-(p-tolyl)cyclobutyl)-5-(5-(trifluoromethyl)-1,3,4-oxadiazol-2-yl)pyrimidin-2-amine;
Benzyl 4-((5-(5-(difluoromethyl)-1,3,4-oxadiazol-2-yl)pyrimidin-2-yl)amino)-4-phenylpiperidine-1-carboxylate;
5-(5-(difluoromethyl)-1,3,4-oxadiazol-2-yl)-N-(4-phenylpiperidin-4-yl)pyrimidin-2-amine;
5-(5-(difluoromethyl)-1,3,4-oxadiazol-2-yl)-N-(1-(2-fluorophenyl)cyclopropyl)pyrimidin-2-amine;
5-(5-(difluoromethyl)-1,3,4-oxadiazol-2-yl)-N-(1-(4-fluorophenyl)cyclopropyl)pyrimidin-2-amine;
N-(1-(4-fluorophenyl)cyclopropyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(3-fluorophenyl)cyclopropyl)pyrimidin-2-amine;
N-(1-(3-fluorophenyl)cyclopropyl)-5-(5-(trifluoromethyl)-1,3,4-oxadiazol-2-yl)pyrimidin-2-amine;
N-(1-(3-chloro-4-fluorophenyl)cyclopropyl)-5-(5-(difluoromethyl)-1,3,4-oxadiazol-2-yl)pyrimidin-2-amine;
N-(1-(3-chloro-4-fluorophenyl)cyclopropyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(4-(trifluoromethyl)phenyl)cyclopropyl)pyrimidin-2-amine;
5-(5-(difluoromethyl)-1,3,4-oxadiazol-2-yl)-N-(1-(3-(trifluoromethyl)phenyl)cyclopropyl)pyrimidin-2-amine;
5-(5-(trifluoromethyl)-1,3,4-oxadiazol-2-yl)-N-(1-(3-(trifluoromethyl)phenyl)cyclopropyl)pyrimidin-2-amine;
5-(5-(trifluoromethyl)-1,3,4-oxadiazol-2-yl)-N-(1-(4-(trifluoromethyl)phenyl)cyclopropyl)pyrimidin-2-amine;
3-(1-((5-(5-(difluoromethyl)-1,3,4-oxadiazol-2-yl)pyrimidin-2-yl)amino)cyclobutyl)phenol;
5-(5-(difluoromethyl)-1,3,4-oxadiazol-2-yl)-N-(1-(3,4-difluorophenyl)cyclopropyl)pyrimidin-2-amine;
N-(1-(3,4-difluorophenyl)cyclopropyl)-5-(5-(trifluoromethyl)-1,3,4-oxadiazol-2-yl)pyrimidin-2-amine;
N-(1-(3-chloro-4-fluorophenyl)cyclobutyl)-5-(5-(difluoromethyl)-1,3,4-oxadiazol-2-yl)pyrimidin-2-amine;
N-(1-(3-chloro-4-fluorophenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(3,5-difluorophenyl)cyclobutyl)pyrimidin-2-amine;
N-(1-(benzo[d][1,3]dioxol-5-yl)cyclobutyl)-5-(5-(difluoromethyl)-1,3,4-oxadiazol-2-yl)pyrimidin-2-amine;
5-(5-(difluoromethyl)-1,3,4-oxadiazol-2-yl)-N-(1-(2,5-difluorophenyl)cyclobutyl)pyrimidin-2-amine;
5-(5-(difluoromethyl)-1,3,4-oxadiazol-2-yl)-N-(1-(4-(trifluoromethoxy)phenyl)cyclobutyl)pyrimidin-2-amine;
5-(5-(difluoromethyl)-1,3,4-oxadiazol-2-yl)-N-(1-(2,4,5-trifluorophenyl)cyclobutyl)pyrimidin-2-amine;
5-(5-(difluoromethyl)-1,3,4-oxadiazol-2-yl)-N-(1-(2,3-difluorophenyl)cyclobutyl)pyrimidin-2-amine;
5-(5-(difluoromethyl)-1,3,4-oxadiazol-2-yl)-N-(1-(2,6-difluorophenyl)cyclobutyl)pyrimidin-2-amine
N-(1-(2,3-dichlorophenyl)cyclobutyl)-5-(5-(difluoromethyl)-1,3,4-oxadiazol-2-yl)pyrimidin-2-amine;
N-(1-(2,3-dichlorophenyl)cyclobutyl)-5-(5-(trifluoromethyl)-1,3,4-oxadiazol-2-yl)pyrimidin-2-amine;
N-(1-(3,4-dichlorophenyl)cyclobutyl)-5-(5-(difluoromethyl)-1,3,4-oxadiazol-2-yl)pyrimidin-2-amine;
N-(1-(3,4-dichlorophenyl)cyclobutyl)-5-(5-(trifluoromethyl)-1,3,4-oxadiazol-2-yl)pyrimidin-2-amine;
N-(1-(2,4-dichlorophenyl)cyclobutyl)-5-(5-(difluoromethyl)-1,3,4-oxadiazol-2-yl)pyrimidin-2-amine;
N-(1-(2,4-dichlorophenyl)cyclobutyl)-5-(5-(trifluoromethyl)-1,3,4-oxadiazol-2-yl)pyrimidin-2-amine;
N-(1-(2,6-dichlorophenyl)cyclobutyl)-5-(5-(difluoromethyl)-1,3,4-oxadiazol-2-yl)pyrimidin-2-amine;
5-(5-(difluoromethyl)-1,3,4-oxadiazol-2-yl)-N-(1-(pyridin-3-yl)cyclobutyl)pyrimidin-2-amine;
N-(1-(2-chloro-4-fluorophenyl)cyclobutyl)-5-(5-(difluoromethyl)-1,3,4-oxadiazol-2-yl)pyrimidin-2-amine;
N-(1-(2-chloro-4-fluorophenyl)cyclobutyl)-5-(5-(trifluoromethyl)-1,3,4-oxadiazol-2-yl)pyrimidin-2-amine;
N-(1-(2-chloro-5-fluorophenyl)cyclobutyl)-5-(5-(difluoromethyl)-1,3,4-oxadiazol-2-yl)pyrimidin-2-amine;
N-(1-(2-chloro-5-fluorophenyl)cyclobutyl)-5-(5-(trifluoromethyl)-1,3,4-oxadiazol-2-yl)pyrimidin-2-amine;
N-(1-(5-chloro-2-fluorophenyl)cyclobutyl)-5-(5-(difluoromethyl)-1, 3,4-oxadiazol-2-yl)pyrimidin-2-amine;
N-(1-(5-chloro-2-fluorophenyl)cyclobutyl)-5-(5-(trifluoromethyl)-1,3,4-oxadiazol-2-yl)pyrimidin-2-amine;
N-(1-(3-chloro-2-fluorophenyl)cyclobutyl)-5-(5-(difluoromethyl)-1,3,4-oxadiazol-2-yl)pyrimidin-2-amine;
N-(1-(3-chloro-2-fluorophenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(4-(1-(oxetan-3-yl)piperidin-4-yl)phenyl)cyclobutyl)pyrimidin-2-amine;

5-(5-(difluoromethyl)-1,3,4-oxadiazol-2-yl)-N-(1-(tosyl-methyl)cyclobutyl)pyrimidin-2-amine;
5-(5-(difluoromethyl)-1,3,4-oxadiazol-2-yl)-N-(1-(2,4-difluorophenyl)cyclobutyl)pyrimidin-2-amine;
5-(5-(difluoromethyl)-1,3,4-oxadiazol-2-yl)-N-(1-(2-(trifluoromethoxy)phenyl)cyclobutyl)pyrimidin-2-amine;
N-(1-benzylcyclobutyl)-5-(5-(difluoromethyl)-1,3,4-oxadiazol-2-yl)pyrimidin-2-amine;
N-(1-(2-(trifluoromethoxy)phenyl)cyclobutyl)-5-(5-(trifluoromethyl)-1,3,4-oxadiazol-2-yl)pyrimidin-2-amine;
N-(1-(2,4-difluorophenyl)cyclobutyl)-5-(5-(trifluoromethyl)-1,3,4-oxadiazol-2-yl)pyrimidin-2-amine;
5-(5-(difluoromethyl)-1,3,4-oxadiazol-2-yl)-N-(1-(4-(1-methylpiperidin-4-yl)phenyl)cyclobutyl)pyrimidin-2-amine;
5-(5-(difluoromethyl)-1,3,4-oxadiazol-2-yl)-N-(1-(4-(1-ethylpiperidin-4-yl)phenyl)cyclobutyl)pyrimidin-2-amine;
5-(5-(difluoromethyl)-1,3,4-oxadiazol-2-yl)-N-(1-(4-(1-isopropylpiperidin-4-yl)phenyl)cyclobutyl)pyrimidin-2-amine;
5-(5-(difluoromethyl)-1,3,4-oxadiazol-2-yl)-N-(1-(thiophen-3-yl)cyclobutyl)pyrimidin-2-amine;
5-(5-(difluoromethyl)-1,3,4-oxadiazol-2-yl)-N-(1-(thiophen-2-yl)cyclopropyl)pyrimidin-2-amine;
5-(5-(difluoromethyl)-1,3,4-oxadiazol-2-yl)-N-(1-(4-(piperidin-1-yl)phenyl)cyclobutyl)pyrimidin-2-amine;
5-(5-(difluoromethyl)-1,3,4-oxadiazol-2-yl)-N-(1-(2-(trifluoromethyl)phenyl)cyclobutyl)pyrimidin-2-amine;
5-(5-(difluoromethyl)-1,3,4-oxadiazol-2-yl)-N-(1-(4-(trifluoromethyl)phenyl)cyclobutyl)pyrimidin-2-amine;
5-(5-(trifluoromethyl)-1,3,4-oxadiazol-2-yl)-N-(1-(4-(trifluoromethyl)phenyl)cyclobutyl)pyrimidin-2-amine;
5-(5-(difluoromethyl)-1,3,4-oxadiazol-2-yl)-N-(1-(3,4-difluorophenyl)cyclobutyl)pyrimidin-2-amine;
5-(5-(difluoromethyl)-1,3,4-oxadiazol-2-yl)-N-(1-(4-fluoro-3-morpholinophenyl)cyclobutyl)pyrimidin-2-amine;
5-(5-(difluoromethyl)-1,3,4-oxadiazol-2-yl)-N-(1-(2-methoxyphenyl)cyclopropyl)pyrimidin-2-amine;
5-(5-(difluoromethyl)-1,3,4-oxadiazol-2-yl)-N-(1-(3-methoxyphenyl)cyclopropyl)pyrimidin-2-amine;
5-(5-(difluoromethyl)-1,3,4-oxadiazol-2-yl)-N-(1-(4-methoxyphenyl)cyclopropyl)pyrimidin-2-amine;
N-(1-(3-chlorophenyl)cyclopropyl)-5-(5-(difluoromethyl)-1,3,4-oxadiazol-2-yl)pyrimidin-2-amine;
N-(1-(3-chlorophenyl)cyclopropyl)-5-(5-(trifluoromethyl)-1,3,4-oxadiazol-2-yl)pyrimidin-2-amine;
N-(1-(4-chlorophenyl)cyclopropyl)-5-(5-(difluoromethyl)-1,3,4-oxadiazol-2-yl)pyrimidin-2-amine;
N-(1-(4-chlorophenyl)cyclopropyl)-5-(5-(trifluoromethyl)-1,3,4-oxadiazol-2-yl)pyrimidin-2-amine;
N-(1-(4-chloro-3-fluorophenyl)cyclopropyl)-5-(5-(difluoromethyl)-1,3,4-oxadiazol-2-yl)pyrimidin-2-amine;
5-(5-(difluoromethyl)-1,3,4-oxadiazol-2-yl)-N-(1-(o-tolyl)cyclopropyl)pyrimidin-2-amine;
N-(1-(4-chloro-2-fluorophenyl)cyclopropyl)-5-(5-(difluoromethyl)-1,3,4-oxadiazol-2-yl)pyrimidin-2-amine;
5-(5-(difluoromethyl)-1,3,4-oxadiazol-2-yl)-N-(1-(3,5-difluorophenyl)cyclopropyl)pyrimidin-2-amine;
5-(5-(difluoromethyl)-1,3,4-oxadiazol-2-yl)-N-(1-(3,4-difluorophenyl)cyclopropyl)pyrimidin-2-amine;
5-(5-(difluoromethyl)-1,3,4-oxadiazol-2-yl)-N-(1-(3-(1-(oxetan-3-yl)piperidin-4-yl)phenyl)cyclobutyl)pyrimidin-2-amine;
5-(5-(difluoromethyl)-1,3,4-oxadiazol-2-yl)-N-(1-(2,4-difluorophenyl)cyclopropyl)pyrimidin-2-amine; and
5-(5-(difluoromethyl)-1,3,4-oxadiazol-2-yl)-N-(1-(4-morpholinophenyl)cyclobutyl)pyrimidin-2-amine.

6. The oxadiazole amine derivative compound represented by Formula I, stereoisomer thereof or pharmaceutically acceptable salt thereof according to claim 5, wherein the compound of Formula I is selected from the group consisting of the following compounds:
5-(5-(difluoromethyl)-1,3,4-oxadiazol-2-yl)-N-(1-phenylcyclopropyl)pyrimidin-2-amine;
5-(5-(difluoromethyl)-1,3,4-oxadiazol-2-yl)-N-(1-phenylcyclobutyl)pyrimidin-2-amine;
5-(5-(difluoromethyl)-1,3,4-oxadiazol-2-yl)-N-(1-phenylcyclopentyl)pyrimidin-2-amine;
5-(5-(difluoromethyl)-1,3,4-oxadiazol-2-yl)-N-(1-(4-methoxyphenyl)cyclobutyl)pyrimidin-2-amine;
5-(5-(difluoromethyl)-1,3,4-oxadiazol-2-yl)-N-(1-(3-methoxyphenyl)cyclobutyl)pyrimidin-2-amine;
5-(5-(difluoromethyl)-1,3,4-oxadiazol-2-yl)-N-(1-(3-fluorophenyl)cyclobutyl)pyrimidin-2-amine;
5-(5-(difluoromethyl)-1,3,4-oxadiazol-2-yl)-N-(1-(2-fluorophenyl)cyclobutyl)pyrimidin-2-amine;
5-(5-(difluoromethyl)-1,3,4-oxadiazol-2-yl)-N-(1-(4-fluorophenyl)cyclobutyl)pyrimidin-2-amine;
N-(1-(2-chlorophenyl)cyclobutyl)-5-(5-(difluoromethyl)-1,3,4-oxadiazol-2-yl)pyrimidin-2-amine;
N-(1-(3-chlorophenyl)cyclobutyl)-5-(5-(difluoromethyl)-1,3,4-oxadiazol-2-yl)pyrimidin-2-amine;
N-(1-(4-chlorophenyl)cyclobutyl)-5-(5-(difluoromethyl)-1,3,4-oxadiazol-2-yl)pyrimidin-2-amine; and
5-(5-(difluoromethyl)-1,3,4-oxadiazol-2-yl)-N-(1-(pyridin-2-yl)cyclobutyl)pyrimidin-2-amine.

7. The oxadiazole amine derivative compound represented by Formula I, stereoisomer thereof or pharmaceutically acceptable salt thereof according to claim 6, wherein the compound of Formula I is selected from the group consisting of the following compounds:
5-(5-(difluoromethyl)-1,3,4-oxadiazol-2-yl)-N-(1-phenylcyclobutyl)pyrimidin-2-amine;
5-(5-(difluoromethyl)-1,3,4-oxadiazol-2-yl)-N-(1-(3-fluorophenyl)cyclobutyl)pyrimidin-2-amine;
5-(5-(difluoromethyl)-1,3,4-oxadiazol-2-yl)-N-(1-(2-fluorophenyl)cyclobutyl)pyrimidin-2-amine;
N-(1-(2-chlorophenyl)cyclobutyl)-5-(5-(difluoromethyl)-1,3,4-oxadiazol-2-yl)pyrimidin-2-amine;
N-(1-(3-chlorophenyl)cyclobutyl)-5-(5-(difluoromethyl)-1,3,4-oxadiazol-2-yl)pyrimidin-2-amine; and
5-(5-(difluoromethyl)-1,3,4-oxadiazol-2-yl)-N-(1-(pyridin-2-yl)cyclobutyl)pyrimidin-2-amine.

8. A pharmaceutical composition comprising a compound represented by Formula I, stereoisomer thereof or pharmaceutically acceptable salt thereof according to claim 1.

9. A pharmaceutical composition for treating histone deacetylase-mediated disease, comprising a compound represented by Formula I, stereoisomer thereof or pharmaceutically acceptable salt thereof according to claim 1.

10. The pharmaceutical composition of claim 9, wherein the histone deacetylase-mediated disease is selected from among infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities.

11. A method for treating histone deacetylase-mediated disease, comprising administering a therapeutically effective amount of a compound represented by Formula I, stereoisomer thereof or pharmaceutically acceptable salt thereof according to claim 1.

\* \* \* \* \*

UNITED STATES PATENT AND TRADEMARK OFFICE
CERTIFICATE OF CORRECTION

Page 1 of 2

PATENT NO. : 10,494,355 B2
APPLICATION NO. : 15/763972
DATED : December 3, 2019
INVENTOR(S) : Yuntae Kim et al.

It is certified that error appears in the above-identified patent and that said Letters Patent is hereby corrected as shown below:

In the Claims

Column 363, Line 38, in Claim 1:
Delete "$CF_3$;" and insert -- —$CF_3$; --, therefor.

Column 363, Line 42, in Claim 1:
Delete "H," and insert -- —H, --, therefor.

Column 363, Line 45, in Claim 1:
Delete "—$NR^C$—," and insert -- —$NR^c$—, --, therefor.

Column 363, Line 63, in Claim 1:
Delete "heterocycloaklyl" and insert -- heterocycloalkyl --, therefor.

Column 364, Line 37, in Claim 1:
Delete "—$NR^C$—," and insert -- —$NR^c$—, --, therefor.

Column 364, Line 59, in Claim 2:
Delete "—($C_1$-$C_2$" and insert -- —($C_1$-$C_2$ alkyl)—, --, therefor.

Column 365, Line 41, in Claim 3:
Delete "—$NR^C$—," and insert -- —$NR^c$—, --, therefor.

Column 365, Line 41, in Claim 3:
Delete "$R^C$" and insert -- $R^c$ --, therefor.

Column 365, Line 55, in Claim 3:
Delete "piperidine" and insert -- piperidine, --, therefor.

Signed and Sealed this
Ninth Day of June, 2020

Andrei Iancu
*Director of the United States Patent and Trademark Office*

Column 366, Line 39, in Claim 4:
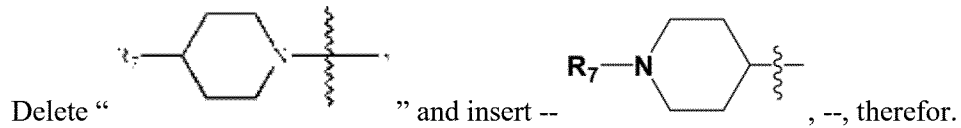
Delete " " and insert -- , --, therefor.
Column 368, Line 32, in Claim 5:
Delete "-amine" and insert -- -amine; --, therefor.
Column 368, Line 58, in Claim 5:
Delete "-1, 3,4-" and insert -- -1,3,4- --, therefor.